(12) United States Patent
Nishi et al.

(10) Patent No.: US 6,288,059 B1
(45) Date of Patent: Sep. 11, 2001

(54) ACYLATED HETERO-ALICYCLIC DERIVATIVES

(75) Inventors: Takahide Nishi, Tokyo; Takeshi Yamaguchi, Ushiku, both of (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/586,728

(22) Filed: Jun. 5, 2000

Related U.S. Application Data

(63) Continuation-in-part of application No. PCT/JP98/05500, filed on Dec. 4, 1998.

(30) Foreign Application Priority Data

Dec. 4, 1997 (JP) .................................................. 9-334608

(51) Int. Cl.$^7$ ....................... A61K 31/5377; A61P 11/06; C07D 495/10
(52) U.S. Cl. ....................... 514/233.5; 540/543; 540/544; 540/598; 544/70; 544/87; 544/58.5; 544/121; 544/130
(58) Field of Search ................... 544/70, 130; 514/233.5

(56) References Cited

FOREIGN PATENT DOCUMENTS

| 776893 A | 6/1997 | (EP) . |
|---|---|---|
| 11-43435 A | 2/1999 | (JP) . |
| WO 96/05193 A | 2/1996 | (WO) . |
| WO 96/23787 A | 8/1996 | (WO) . |
| WO 97/25322 A | 7/1997 | (WO) . |
| WO 97/27185 A | 7/1997 | (WO) . |

*Primary Examiner*—Robert W. Ramsuer
(74) *Attorney, Agent, or Firm*—Frishauf, Holtz, Goodman, Langer & Chick, P.C.

(57) ABSTRACT

A compound of formula (I), a pharmaceutically acceptable salt or ester or other derivative thereof:

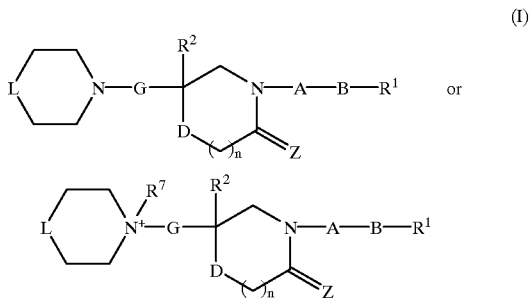

$R^1$ is optionally substituted cycloalkyl or optionally substituted saturated heterocyclic group. $R^2$ is optionally substituted aryl or optionally substituted heteroaryl. A is methylene, carbonyl or sulfonyl. B is a single bond, alkylene or alkenylene. D is oxygen or sulfur. G is alkylene or alkenylene. L is —N($R^3$)— or —C($R^4$)($R^5$)—. $R^3$ is optionally substituted aryl or optionally substituted heteroaryl. $R^4$ is H, optionally substituted aryl, optionally substituted heteroaryl, optionally substituted cycloalkyl or optionally substituted saturated heterocyclic group. $R^5$ is alkyl optionally substituted with amino, amino, optionally substituted acylamino, OH, optionally substituted hydroxyalkyl, alkoxy or —CO—$R^6$. $R^6$ is alkyl, alkoxy or amine residue. $R^4$ together with $R^5$ forms a cycloalkane ring, cycloalkene ring, or saturated heterocyclic ring. $R^7$ is alkyl. Z is two hydrogens or oxygen. n is 0, 1 or 2. These compounds have selective antagonistic activity against the $NK_2$ receptor.

52 Claims, No Drawings

ACYLATED HETERO-ALICYCLIC DERIVATIVES

This application is a continuation-in-part application of International Application PCT/JP98/05500 filed Dec. 4, 1998.

The present invention relates to compounds having selective antagonistic activity against $NK_2$ receptors.

BACKGROUND OF THE INVENTION $NK_1$ receptors, $NK_2$ receptors and $NK_3$ receptors are known to act as tachykinin receptors. With respect to tachykinin antagonists, compounds that demonstrate selective antagonistic activity on one of $NK_1$, $NK_2$ and $NK_3$ receptors, and compounds that demonstrate antagonistic activity on more than one of the sub-types of receptors (e.g. Against both $NK_1$) and $NK_2$ receptors) have been found in recent years. In the case of intending to inhibit comprehensively the action of tachykinin, it is important to use a compound that demonstrates antagonistic action against more than one of the types of receptors.

However, since it is generally predicted that the frequency of occurrence of effects other than the desired pharmacological effect increases when inhibiting the action of more than one of the types of receptors, a compound which demonstrate selective and potent antagonistic action against a specific receptor is also important.

Compounds considered to be structurally similar to the compounds of the present invention are disclosed in EP-776893, but these compounds demonstrate antagonistic action against both $NK_1$, and $NK_2$ receptors and, therefore, they should be considered to be completely different from the compounds of the present invention that selectively demonstrate antagonistic action against $NK_2$ receptors.

With respect to selective antagonistic action against $NK_2$ receptors, clinical studies on SR48968 (a compound having structural formula A shown below) have begun at present. Moreover, SR144190 (a compound having structural formula B shown below) is reported to have $NK_2$ receptor-selective antagonistic activity that is more potent than that of SR.48968 (X. Edmonds-Salt. Et al., Tachykinin in Health and Disease, Sep. 7–11, 1997 in Cairns, Australia, Abstract p. 5).

(A)

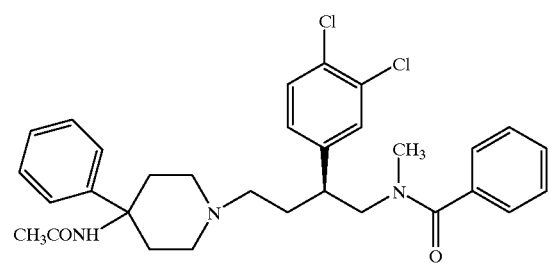

(B)

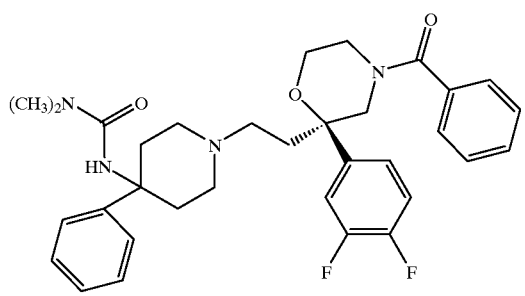

DISCLOSURE OF THE INVENTION

As a result of conducting extensive research on tachykinin antagonists, the inventors of the present invention found that novel acylated hetero-alicyclic deliveries have excellent $NK_2$-selective antagonistic activity, thereby leading to completion of the present invention.

Moreover, another object of the present invention is to provide a novel medicament containing an above-mentioned compound as an active ingredient. Examples of diseases for which this medicament can be applied include diseases of the central nervous system such as anxiety, depression, psychosis and schizophrenia; neurodegenerative diseases such as dementia of AIDS, Alzheimer's senile dementia, Alzheimer's disease, Down's syndrome, demyelinating disease, amyotrophic lateral sclerosis, neuropathy, peripheral neuropathy and neuralgia; respiratory diseases such as chronic obstructive pulmonary disease, bronchitis, pneumonia, bronchoconstriction, asthma and coughs; inflammatory diseases such as inflammatory bowel disease (IBD), psoriasis, fibrosis, arthrosteitis, degenerative arthritis and rheumatoid arthritis; eczema; allergic diseases such as rhinitis; hypersensitivity diseases such as hypersensitivity to vines; ophthalmological diseases such as conjunctivitis, vernal conjunctivitis, vernal cetarrh, destruction of the blood-aqueous humor barrier caused by various inflammatory eye diseases, elevated introcular pressure and miosis; skin diseases such as contact dermatitis, atopic dermnatitis, urticaria and other eczematoid dermatitis; addictions such as alcohol dependency; somatic diseases caused by stress; sympathetic reflex dystrophy such as hand and shoulder syndrome; dysthymia; undesirable immune reactions such as rejection of grafts, diseases relating to immunopotentiation such as systemic lupus erythematosus or immunosuppression; digestive diseases such as diseases caused by abnormalities in nerves regulating the organs, colitis, ulcerative colitis and Crohn's disease; emesis such as emesis induced by adverse effects of X-ray irradiation and chemotherapy, poisons, toxins, pregnancy, vestibular disorders, postoperative illness, gastrointestinal occlusion, reduced gastrointestinal movement, visceral pain, migraine headaches, increased intracranial pressure, reduced intracranial pressure or adverse reactions induced by administration of various medicaments; urinary bladder functional diseases such as cystitis and urinary incontinence, eosinophilia caused by collagen diseases, scleriasis or Fasciola hepatica infection; diseases caused by abnormal blood flow due to vasodilation or vasoconstriction such as angina pectoris, migraine headache and Reynauds's disease; and pain of pain nociceptive reception such as migraine headaches, headaches and toothache; and sleep apnea. The novel medicament of the present invention can particularly be used as a preventive agent or therapeutic agent for asthma and/or bronchitis, rhinitis, allergic diseases and urinary incontinence.

(1) This invention relates to a compound of the formula (I):

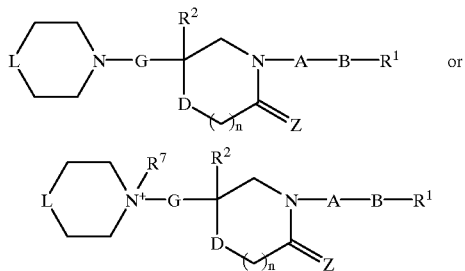

{wherein
$R^1$ represents a ($C_3$–$C_7$)cycloalkyl group, a 3- to 7-membered saturated heterocyclic group, a ($C_3$–$C_7$)cycloalkyl group substituted with 1 to 3 substituents selected from Substituent group A and Substituent group B, or a 3- to 7-membered saturated heterocyclic group substituted with 1 or 2 substituents selected from Substituent group A and Substituent group B, $R^2$ represents an aryl group, a heteroaryl group, an aryl group substituted with 1 to 3 substituents selected from Substituent group A, or a heteroaryl group substituted with 1 to 3 substituents selected from Substituent group A, A represents a methylene group, a carbonyl group or a sulfonyl group, B represents a single bond, a ($C_1$–$C_4$)alkylene group or a ($C_2$–$C_4$)alkenylene group, D represents an oxygen atom or a sulfur atom, G represents a ($C_1$–$C_4$)alkylene group or a ($C_2$–$C_4$) alkenylene group.

L represents a group of formula —N($R^3$)— or —C($R^4$)($R^5$)—

[wherein $R^3$ represents an aryl group, a heteroaryl group, an aryl group substituted with 1 to 3 substituents selected from Substituent group A, or a heteroaryl group substituted with 1 to 3 substituents selected from Substituent group A, $R^4$ represents a hydrogen atom, an aryl group, a heteroaryl group, an aryl group substituted with 1 to 3 of substituents selected from Substituent group A, or a heteroaryl group substituted with 1 to 3 substituents selected from Substituent group A, a ($C_3$–$C_7$) cycloalkyl group, a 3- to 7-membered saturated heterocyclic group, a ($C_3$–$C_7$) cycloalkyl group substituted with 1 to 3 substituents selected from Substituent group A and Substituent group B, or a 3- to 7-membered saturated heterocyclic group substituted with 1 or 2 substituents selected from Substituent group A and Substituent group B, $R^5$ represents a lower alkyl group, an amino group, an acylamino group, an acylamino lower alkyl group, an acylamino group wherein the nitrogen atom is substituted with a lower alkyl group, a hydroxy group, a hydroxy lower alkyl group wherein the oxygen atom is optionally substituted with an aralkyl group, a lower alkoxy group or a group of formula —CO—$R^6$ (wherein $R^6$ represents a lower alkyl group, a lower alkoxy group, an amine residue, an aryl group substituted with 1 to 3 substituents selected from Substituent group A, or a heteroaryl group substituted with 1 to 3 substituents selected from Substituent group A) or $R^4$ and $R^5$, together with the carbon atom to which they are attached, form a ($C_5$–$C_8$) cycloalkane ring, a ($C_5$–$C_8$) cycloalkene ring, or a 5- to 8-membered saturated heterocyclic ring (any of these rings may be optionally substituted with 1 or 2 substituents selected from Substituent group A and Substituent group B and may be optionally fused with an aryl ring, a heteroaryl ring, an aryl ring substituted with 1 to 3 substituents selected from Substituent group A or a heteroaryl ring substituted with 1 to 3 substituents selected from Substituent group A), $R^7$ represents a lower alkyl group, Z represents two hydrogen atoms or an oxygen atom, n represents 0, 1 or 2}
and a pharmaceutically acceptable salt, ester or other derivative thereof;

Substituent Group A halogen atoms, lower alkyl groups, halogeno lower alkyl groups, lower alkoxy groups, lower alkoxycarbonyl groups, carboxyl groups, hydroxy groups, lower aliphatic acyl groups, lower aliphatic acylamino groups, amino groups, and cyano groups, Substituent Group B oxo groups and thiol groups; and as substituents on a nitrogen atom, lower alkyl, aryl and aralkyl groups, which may be optionally substituted with a substituent selected from Substituent group A, lower alkanesulfonyl groups and acyl groups.

Among the compounds of formula (I), preferred compounds are: (2) compounds wherein $R^1$ is a ($C_3$–$C_6$) cycloalkyl group, a 5- or 6-membered saturated heterocyclic group, a ($C_3$–$C_6$)cycloalkyl group substituted with 1 to 3 substituents selected from Substituent group A and Substituent group B, or a 5- or 6-membered saturated heterocyclic group substituted with 1 or 2 substituents selected from Substituent group A and Substituent group B, (3) compounds wherein $R^1$ is a ($C_3$–$C_6$)cycloalkyl group, a 5- or 6-membered saturated heterocyclic group, or a 5- or 6-membered saturated heterocyclic group substituted with 1 or 2 substituents selected from Substituent group A and Substituent group B, (4) compounds wherein $R^2$ is an aryl group, or an aryl group substituted with 1 to 3 substituents selected from Substituent group A, (5) compounds wherein $R^2$ is an aryl group substituted with 1 to 3 halogen atoms, (6) compounds wherein A is a methylene group or a carbonyl group, (7) compounds wherein A is a carbonyl group and Z is two hydrogen atoms or wherein A is a methylene group and Z is an oxygen atom, (8) compounds wherein A is a carbonyl group, (9) compounds wherein B is a single bond,

(10) compounds wherein D is an oxygen atom,

(11) compounds wherein G is a ($C_1$–$C_4$)alkylene group,

(12) compounds wherein G is a ($C_2$–$C_3$)alkylene group,

(13) compounds wherein $R^3$ is a heteroaryl group, or an aryl group substituted with 1 to 3 substituents selected from Substituent group A,

(14) compounds wherein L is a group of formula —C($R^4$)($R^5$)—,

(15) compounds wherein $R^4$ and $R^5$, together with the carbon atom to which they are attached, form a ($C_5$–$C_8$) cycloalkane ring, a ($C_5$–$C_8$)cycloalkene ring, or a 5- to 8-membered saturated heterocyclic ring (any of these rings may be optionally substituted with 1 or 2 substituents selected from Substituent group A and Substituent group B and may be optionally fused with an aryl ring, a heteroaryl ring, an aryl ring substituted with 1 to 3 substituents selected from Substituent group A or a heteroaryl ring substituted with 1 to 3 substituents selected from Substituent group A),

(16) compounds wherein $R^4$ and $R^5$, together with the carbon atom to which they are attached, form a $(C_5–C_6)$ cycloalkane ring, a $(C_5–C_6)$cycloalkene ring, or a 5- or 6-membered saturated heterocyclic ring (any of these rings may be optionally substituted with 1 or 2 substituents selected from Substituent group A and Substituent group B and may be optionally fused with an aryl ring, a heteroaryl ring, an aryl ring substituted with 1 to 3 substituents selected from Substituent group A or a heteroaryl ring substituted with 1 to 3 substituents selected from Substituent group A),

(17) compounds wherein $R^4$ and $R^5$, together with the carbon atom to which they are attached form a cyclopentane ring, a cyclopentene ring, a tetrahydrothiophene ring, a tetrahydrothiophenesulfoxide ring, a tetrahydrothiophene-sulfone ring or a piperidine ring (any of these rings may be optionally substituted with 1 or 2 substituents selected from Substituent group A and Substituent group B and may be optionally fused with an aryl ring, a heteroaryl ring, an aryl ring substituted with 1 to 3 substituents selected from Substituent group A or a heteroaryl ring substituted with 1 to 3 substituents selected from Substituent group A),

(18) compounds wherein z is two hydrogen atoms,

(19) compounds wherein n is 0 or 1,

(20) compounds wherein n is 1, and a pharmaceutically acceptable salt, ester or other derivative thereof.

Moreover, compounds which include a combination of factors selected at random from each of the ten groups, which are (2) and (3); (4) and (5); (6) to (8); (9); (10); (11) and (12); (13); (14) to (17); (18); and (19) and (20), are also preferable.

Particularly preferred compounds are

(21) a compound selected from the following compounds or a pharmaceutically acceptable salt, ester or other derivative thereof:

1-{2-[(2R)-(3,4-dichlorophenyl)-4-(cyclopropanecarbonyl) morpholin-2-yl]ethyl}spiro[benzo[c]thiophene-1(3H),4'-piperidine]-(2S)-oxide, 1-{2-[(2R)-(3,4-dichlorophenyl)-4-(cyclobutanecarbonyl) morpholin-2-yl]ethyl}spiro[benzo[c]thiophene-1(3H),4'-piperidine]-(2S)-oxide, 1-{2-[(2R)-(3,4-dichlorophenyl)-4-(cyclopentanecarbonyl) morpholin-2-yl]ethyl}spiro[benzo[c]thiophene-1(3H),4'-piperidine]-(2S)-oxide.

1-{2-[(2R)-(3,4-dichlorophenyl)-4-(cyclohexanecarbonyl) morpholin-2-yl]ethyl}spiro[benzo[c]thiophene-1 (3H),4'-piperidine]-(2S)-oxide, 1-{2-[(2R)-(3,4-difluorophenyl)-4-(cyclopropanecarbonyl) morpholin-2-yl]ethyl}spiro[benzo[c]thiophene-1(3H),4'-piperidine]-(2S)-oxide, 1-{2-[(2R)-(3,4-difluorophenyl)-4-(cyclobutanecarbonyl) morpholin-2-yl]ethyl}spiro[benzo[c]thiophene-1(3H),4'-piperidine]-(2S)-oxide, 1-{2-[(2R)-(3,4-difluorophenyl)-4-(cyclopentanecarbonyl) morpholin-2-yl]ethyl}spiro[benzo[c]thiophene-1(3H),4'-piperidine]-(2S)-oxide, 1-{2-[(2R)-(3,4-difluorophenyl)-4-(cyclohexanecarbonyl) morpholin-2-yl]ethyl}spiro[benzo[c]thiophene-1(3H),4'-piperidine]-(2S)-oxide, 1-{2-[(2R)-(3,4-dichlorophenyl)-4-(cyclopropanecarbonyl) morpholin-2-yl]ethyl}spiro[((2S)-hydroxy)indane-1,4'-piperidine], 1-{2-[(2R)-(3,4-dichlorophenyl)-4-(cyclobutanecarbonyl) morpholin-2-yl]ethyl}spiro[((2S)-hydroxy)indane-1,4'-piperidine], 1-{2-[(2R)-(3,4-dichlorophenyl)-4-(cyclopentanecarbonyl) morpholin-2-yl]ethyl}spiro[((2S)-hydroxy)indane-1,4'-piperidine], 1-{2-[(2R)-(3,4-dichlorophenyl)-4-(cyclohexanecarbonyl) morpholin-2-yl]ethyl}spiro[((2S)-hydroxy)indane-1,4'-piperidine], 1-{2-[(2R)-(3,4-difluorophenyl)-4-(cyclopropanecarbonyl) morpholin-2-yl]ethyl}spiro[((2S)-hydroxy)indane-1,4'-piperidine], 1-{2-[(2R)-(3,4-difluorophenyl)-4-(cyclobutanecarbonyl) morpholin-2-yl]ethyl}spiro[((2S)-hydroxy)indane-1,4'-piperidine], 1-{2-[(2R)-(3,4-difluorophenyl)-4-(cyclopentanecarbonyl) morpholin-2-yl]ethyl}spiro[((2S)-hydroxy)indane-1,4'-piperidine], 1-{2-[(2R)-(3,4-difluorophenyl)-4-(cyclohexanecarbonyl) morpholin-2-yl]ethyl}spiro[((2S)-hydroxy)indane-1,4'-piperidine], 1-{2-[(2R)-(3,4-dichlorophenyl)-4-(cyclopropanecarbonyl) morpholin-2-yl]ethyl}-4-phenylpiperidine-4-carboxamide, and 1-{2-[(2R)-(3,4-dichlorophenyl)-4-(cyclopentanecarbonyl) morpholin-2-yl]ethyl } -4-(2-pyridyl)piperidine4-carboxamide.

In addition, the novel medicament of the present invention contains a compound or a pharmacologically acceptable salt, ester or other derivative thereof described in any group selected from the above-mentioned groups (1) to (21) as an active ingredient. It can particularly be used as a preventive or therapeutic agent of tachykinin-mediated diseases (for example, asthma and/or bronchitis, rhinitis, allergic diseases and urinary incontinence).

In the Formula (I):

The "$(C_3–C_7)$cycloalkyl group" and the $(C_3–C_7)$ cycloalkyl group of the "$(C_3–C_7)$ cycloalkyl group substituted with 1 to 3 substituents selected from Substituent group A and Substituent group B" as used in the definition of $R^1$ and $R^4$ is intended to include cyclopropyl, cyclobutyl, cyclopentyl, cyclohexyl and cycloheptyl groups. The "$(C_3–C_7)$cycloalkyl group" mentioned above may be optionally fused with an "aryl ring", "heteroaryl ring", "aryl ring substituted with 1 to 3 substituents selected from Substituent group A", or "heteroaryl ring substituted with 1 to 3 substituents selected from Substituent group A"

(The "aryl ring"and the aryl ring of the "aryl ring which may be optionally substituted with 1 to 3 substituents selected from Substituent group A" are intended to include $C_6–C_{14}$ aromatic hydrocarbon rings such as a benzene ring, an indene ring, a naphthalene ring, a phenanthrene ring and an anthracene ring, preferably a benzene ring. The "heteroaryl ring" and the heteroaryl ring of the "heteroaryl ring which may be optionally substituted with 1 to 3 substituents selected from Substituent group A" are intended to include 5- to 7- membered heteroaryl rings containing 1 to 3 sulfur, oxygen and/or nitrogen atoms such as a furan ring, a thiophene ring, a pyrrole ring, an azepine ring, a pyrazole ring, an imidazole ring, an oxazole ring, an isoxazole ring, a thiazole ring, an isothiazole ring, a 1,2,3-oxadiazole ring, a triazole ring, a tetrazole ring, a thiadiazole ring, a pyran ring, a pyridine ring, a pyridazine ring, a pyrimidine ring and a pyrazine ring; preferred heteroaryl rings include 5- to 7-membered heteroaryl rings which have at least one nitrogen atom and may optionally also have a sulfur atom or an oxygen atom, for example a pyrrole ring, an azepine ring, a pyrazole ring, an imidazole ring, an oxazole ring, an isoxazole ring, a thiazole ring, an isothiazole ring, a 1,2,3-oxadiazole ring, a triazole ring, a tetrazole ring, a thiadiazole ring, a pyridine ring, a pyridazine ring, a pyrimidine ring and a pyrazine ring; more preferred heteroaryl groups includes a pyridine ring, an imidazole ring, an oxazole ring, a pyrazine ring and a thiazole ring.) As examples of the $(C_3-C_7)$ CyCloalkyl group fused with one of those ring systems, benzocyclobutenyl, indanyl, 4,5,6,7-tetrahydroindanyl, tetrahydronaphthyl, 5,6,7,8-tetrahydroquinolyl and 5,6,7,8-tetrahydroisoquinolyl groups can be exemplified.

The "3- to 7-membered saturated heterocyclic group" and the 3- to 7-membered saturated heterocyclic group of the "3- to 7-membered saturated heterocyclic group substituted with 1 or 2 substituents selected from Substituent group A and Substituent group B" in the definition of $R^1$ and $R^4$ mean a 3- to 7-membered non-aromatic heterocyclic group containing 1 to 3 sulfur, oxygen and/or nitrogen atoms, preferably a 5- to 6-membered non-aromatic heterocyclic group containing 1 to 3 sulfur, oxygen and/or nitrogen atoms, more preferably a 5- to 6-membered non-aromatic group containing 1 or 2 sulfur, oxygen and/or nitrogen atoms. Examples of such group are pyrrolidinyl, tetrahydrofuranyl, tetrahydrothienyl, oxazolidinyl, thiazolidinyl, piperidinyl, morpholinyl, thiomorpholinyl, piperazinyl and azepinyl groups.

These groups may optionally be fused with a ring system the same as for the "aryl ring", "heteroaryl ring", "aryl ring substituted with 1 to 3 the substituents selected from Substituent group A" and "heteroaryl ring substituted with 1 to 3 the substituents selected from Substituent group A", which is described above. Examples of such a group include a 1,2,3,4-tetrahydroisoquinolyl group and the like.

Furthermore, examples of the "5- to 7-membered saturated heterocyclic group substituted with 1 or 2 substituents selected from Substituent group A and Substituent group B" include a 2-oxooxazolidinyl group, a 2-oxothiazolidinyl group and the like. The "aryl group" in the definition of $R^2$, $R^3$ and $R^4$, the "aryl group" of the "aryl group substituted with 1 to 3 substituents selected from Substituent group A" in the definition of $R^2$, $R^3$, $R^4$ and $R^6$, and the "aryl group" of the "as substituents on a nitrogen atom, aryl group which may optionally be substituted with a substituent selected from Substituent group A" in the definition of [Substituent group B] mean a $(C_5-C_{14})$aromatic hydrocarbon group such as phenyl, indenyl, naphthyl, phenanthryl and anthrathenyl groups, preferably a phenyl group.

In addition, the above-mentioned "aryl group" may be optionally fused with a $(C_3-C_{10})$ cycloalkyl group, and examples of such a group include a 5-indanyl group and the like.

The "heteroaryl group" in the definition of $R^2$, $R^3$ and $R^4$, and the "heteroaryl group" of the "heteroaryl group substituted with 1 to 3 substituents selected from Substituent group A" in the definition of $R^2$, $R^3$, $R^4$ and $R^6$ mean a 5- to 7-membered heteroaryl group containing 1 to 3 sulfur, oxygen and/or nitrogen atoms, such as furyl, thienyl, pyrrolyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl and pyrazinyl groups, preferably a 5- to 7-membered heteroaryl group containing at least one nitrogen atom and optionally containing a sulfur atom or oxygen atom, for example pyrrolyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl and pyrazinyl, and more preferably, pyridyl, imidazolyl, oxazolyl, pyrazinyl and thiazolyl.

In addition, the above-mentioned "heteroaryl group"may optionally be fused with an another ring system, and examples of such a group include indolyl, benzofuryl, benzothienyl, benzoxazolyl, benzimidazolyl, isoquinolyl, quinolyl and quinoxalyl groups and the like.

The "$(C_1-C_4)$alkylene group" in the definition of B and G means a straight or branched chain $(C_1-C_4)$alkylene group such as a methylene, methylmethylene, ethylene, propylene, trimethylene, tetramethylene, 1-methyltrimethylene, 2-methyltrimethylene and 3-methyltrimethylene.

With regard to B, a straight or branched $(C_1-C_3)$alkylene group is preferable.

With regard to G, a straight or branched $(C_1-C_3)$alkylene group is preferable, ethylene and trimethylene are more preferable, and ethylene is the most preferable.

The "$(C_2-C_4)$alkenylene group" in the definition of B and G means a straight or branched $(C_2-C_4)$alkenylene group such as ethenylene, 2-propenylene,1-methyl-2-propenylene, 2-methyl-2-propenylene, 2-ethyl-2-propenylene, and 2-butenylene, preferably, ethenylene, 2-propenylene or 3-butenylene, and more preferably, ethenylene or 2-propenylene.

The "lower alkyl group" in the definition of $R^5$, $R^6$, $R^7$ and Substituent group A]; the "lower alkyl group" of the "acylamino group wherein the nitrogen atom is substituted with a lower alkyl group" in the definition of $R^5$; the "lower alkyl group" of the "hydroxy lower alkyl group wherein the oxygen atom is optionally substituted with an aralkyl group" in the definition of $R^5$; the "lower alkyl group" of the "acylamino lower alkyl group" in the definition of $R^5$; the "lower alkyl group" of "as substituents at a nitrogen atom, lower alkyl, which may be optionally substituted with substituents selected from Substituent group A" in the definition of [Substituent group B] mean a straight or branched $(C_1-C_6)$alkyl group such as methyl, ethyl, n-propyl, isopropyl, n-butyl, isobutyl, s-butyl, tert-butyl, n-pentyl, isopentyl, 2-methylbutyl. neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl. 1,1-dimethylbutyl, 1,2-dimethylbutyl, 1,3-dimethylbutyl. 2,3-dimethylbutyl and 2-ethylbutyl. A straight or branched $(C_1-C_4)$alkyl group is more preferred.

The "acyl" of the "acylamino group", the "acyl" of the "acylamino lower alkyl group" and the "acyl" of the "acylamino group wherein the nitrogen atom is substituted with a lower alkyl group" in the definition of $R^5$; and the "acyl" of "as substituents as a nitrogen atom, acyl groups" in the definition of [Substituent group B] mean, for example, and "aliphatic acyl group" including an alkylcarbonyl group such as formyl, acetyl, propionyl, butyryl, isobutyryl, pentanoyl, pivaloyl, valeryl, isovaleryl, octanoyl, nonylcarbonyl, decylcarbonyl, 3-methylnonylcarbonyl, 8-methylnonylcarbonyl, 3-ethyloctylcarbonyl, 3,7-dimethyloctylcarbonyl, undecylcarbonyl, dodecylcarbonyl, tridecylcarbonyl, tetradecylcarbonyl, pentadecylcarbonyl, hexadecylcarbonyl, 1-methylpentadecylcarbonyl, 14-methylpentadecylcarbonyl, 13,13-dimethyltetradecylcarbonyl, heptadecylcarbonyl, 15-methylhexadecylcarbonyl, octadecylcarbonyl, 1-methylheptadecylcarbonyl, nonadecylcarbonyl, icosylcarbonyl and henicosylcarbonyl; a halogenated alkylcarbonyl group such as chloroacetyl, dichloroacetyl, trichloroacetyl and trifluoroacetyl; a lower alkoxyalkylcarbonyl group such as methoxyacetyl; and an unsaturated alkylcarbonyl group such as acrylcarbonyl, propionylcarbonyl, methacrylcarbonyl, crotonylcarbonyl, isocrotonylcarbonyl, (E)-2-methyl-2-butenoyl: an "aromatic acyl group" including an arylcarbonyl group such as benzoyl, α-naphthoyl and β-naphthoyl; a halogenated arylcarbonyl group such as 2-bromobenzoyl and 4-chlorobenzoyl; a lower alkylated arylcarbonyl group such as 2,4,6-trimethylbenzoyl and 4-toluoyl; a lower alkoxylated arylcarbonyl group such as 4-anisoyl; a nitrated arylcarbonyl group such as 4-nitrobenzoyl and 2-nitrobenzoyl; a lower alkoxycarbonylated arylcarbonyl group such as 2-(methoxycarbonyl) benzoyl; and an arylated arylcarbonyl group such as 4-phenylbenzoyl: an "alkoxycarbonyl group" including a lower alkoxycarbonyl group such as methoxycarbonyl, ethoxycarbonyl, propoxycarbonyl, butoxycarbonyl, s-butoxycarbonyl, tert-butoxycarbonyl and isobutoxycarbonyl; and a lower alkoxycarbonyl group substituted with halogen atoms or with a tri(lower alkyl)silyl group such as 2,2,2-trichloroethoxycarbonyl and 2-trimethylsilylethoxycarbonyl: an "alkenylcarbonyl group" such as vinylcarbonyl and allylcarbonyl: an "aralkylcarbonyl group" of which the aryl ring may optionally be substituted with 1 or 2 lower alkoxy or nitro groups, such as benzylcarbonyl, phenacyl, 4-methoxybenzylcarbonyl. 3,4-dimethoxybenzylcarbonyl, 2-nitrobenzylcarbonyl and 4-nitrobenzylcarbonyl: a "loweralkanesulfonyl group" such as methanesulfonyl, ethansulfonyl and 1-propanesulfonyl: a fluorinated "loweralkanesulfonyl group" such as trifluoromethanesulfonyl and pentafluoroethanesulfonyl: and an "arylsulfonyl group" such as benzenesulfonyl and p-toluensulfonyl. Among those groups, the "aliphatic acyl group", "aromatic acyl group" and "lower alkanesulfonyl group" are preferred.

The "lower alkoxy group" in the definition of $R^5$, $R^6$ and [Substituent group A] and the "lower alkoxy group" of the "lower alkoxycarbonyl group" in the definition of [Substituent group A] mean a group wherein the above-described "lower alkyl group" is attached to an oxygen atom, for example, a straight or branched chain $(C_1-C_6)$ alkoxy group such as methoxy, ethoxy, n-propoxy, isopropoxy, n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy. Preferably, it is a straight or branched chain $(C_1-C_4)$alkoxy group.

The "aralkyl group" of the "hydroxy lower alkyl group wherein the oxygen atom is optionally substituted with an aralkyl group" in the definition of $R^5$ and the "aralkyl group" of "as substituents on a nitrogen atom, lower alkyl, aryl and aralkyl groups, which may be optionally substituted with substituents selected from Substituent group A" in the definition of [Substituent group B] mean a group wherein the above-described "aryl group" is attached to the above-described "alkyl group", for example, benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl. 1-naphthylethyl, 2-naphthylethyl, 1-phenylpropyl, 2-phenylpropyl, 3-phenylpropyl. 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl. 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl. Preferably, it is a group wherein the "aryl group" moiety is a phenyl group and the "alkyl group" moiety is a $(C_1-C_4)$alkyl group. More preferably, it is a benzyl group or phenethyl group.

The "$(C_5-C_8)$cycloalkane ring" which $R^4$ and $R^5$ together with the carbon to which they are attached form means, for example, a cyclopropane ring, cyclobutane ring, cyclopentane ring, cyclohexane ring, cycloheptane ring and cyclooctane ring. Preferably, it is a $(C_5-C_6)$cycloalkane ring, and more preferably, it is a cyclopentane ring.

The "$(C_5-C_8)$cycloalkene ring" which $R^4$ and $R^5$ together with the carbon to which they are attached form means, for example, a cyclopropene ring, cyclobutene ring, cyclopentene ring, cyclohexene ring, cycloheptene ring and cyclooctene ring. Preferably, it is a $(C_5-C_6)$cycloalkene ring. More preferably, it is a cyclopentene ring.

The "5- to 8-membered saturated heterocyclic ring" of the "5- to 8-membered saturated heterocyclic ring" which $R^4$ and $R^5$ together with the carbon to which they are attached form means a 5- to 8-membered saturated heterocyclic ring containing 1 to 3 sulfur, oxygen and/or nitrogen atoms (wherein the sulfur atom may be a sulfoxide or sulfone if the ring contains a sulfur atom). Preferably, it is a 5- to 6-membered saturated heterocyclic ring containing 1 to 3 sulfur, oxygen and/or nitrogen atoms. More preferably, it is a 5-membered saturated heterocyclic ring containing 1 to 2 sulfur, oxygen and/or nitrogen atoms such as an imidazolidine ring, an oxazolidine ring, a pyrrolidine ring, a tetrahydrofuran ring, a tetrahydrothiophene ring, a tetrahydrothiophenesulfoxide ring, a tetrahydrothiophenesulfone ring and a piperidine ring.

Furthermore, the "$(C_5-C_8)$cycloalkane ring", "$(C_5-C_8)$ cycloalkene ring" and "5- to 8-membered saturated heterocyclic ring" may optionally be substituted with 1 or 2 substituents selected from Substituent group A and Substituent group B, and may optionally be fused with the above-described "aryl ring", "heteroaryl ring", "aryl ring substituted with 1 to 3 substituents selected from Substituent group A and Substituent group B" or "heteroaryl ring substituted with 1 to 3 substituents selected from Substituent group A and Substituent group B". Examples of such a group include a 4-oxo-1-phenylimidazolidine ring, a 2-oxo-3-phenyloxazolidine ring, a 3-benzyl-2-oxooxazolidine ring, a 1-methylsulfonyl-2.3-dihydroindole ring, a 1.3-dihydroisobenzofuran ring, a 1-oxo-2,3-dihydrobenzo[b] thiophene ring, a 1,3-dihydrobenzo[c]thiophene ring, a 2-oxo-1,3-dihydrobenzo[c]thiophene ring, a 2.2-dioxo-1,3-dihydrobenzo[c]thiophene ring, a 1,4-dihydro-3-isoquinolone ring, an indane ring, a 1-hydroxyindane ring, a 2-hydroxyindane ring, a 1-oxoindane ring, a 2-oxoindane ring, a 1,2-dioxoindane ring, an indene ring and the like.

The "amine residue" in the definition of $R^6$ means an amino residue which binds by its nitrogen atom, including an amino group; an amino group substituted with 1 or 2 "lower alkyl group"s, such as methylamino, ethylamino, isopropylamino, butylamino, dimethylamino, diethylamino, diisopropylamino and dibutylamino; an amino group substituted with 1 or 2 "$(C_5-C_7)$cycloalkyl group"s, such as cyclopentylamino, cyclohexylamino, dicyclopentylamino and dicyclohexylamino; a saturated cyclic amine residue containing at least one nitrogen atom in the ring, such as pyrrolidino, piperidino, piperazino, N-methylpiperazino, morpholino and thiomorpholino; an arylamino or aralkylamino group optionally substituted on the nitrogen atom with a "lower alkyl group", such as anilino, benzylamino, N-methylanilino and N-methylbenzylamino; a heteroarylamino group optionally substituted on the nitrogen atom with a "lower alkyl group", such as pyridylamino, N-methylpyridylamino and N-ethylpyridylamino; and the like. Preferably, it is an amino group; an amino group substituted with 1 or 2 "lower alkyl group"s, a saturated cyclic amine residue containing at least one nitrogen atom in the ring, such as pyrrolidino, piperidino, piperazino, N-methylpiperazino, morpholino and thiomorpholino; or an arylamino or aralkylamino group optionally substituted on the nitrogen atom with a "lower alkyl group", such as anilino, benzylarnino, N-methylanilino and N-methylbenzylamino.

The "halogen atoms" in the definition of [Substituent group A] are intended to include fluorine atoms, chlorine atoms, bromine atoms and iodine atoms, and fluorine and chlorine atoms are preferred.

The "halogeno lower alkyl groups" in the definition of [Substituent group A] means a group wherein the above-described "lower alkyl group" are substituted by the above-described "halogen atoms", such as trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl or 2,2-dibromoethyl. Among them, trifluoromethyl, 2-bromoethyl, 2-chloroethyl and 2-fluoroethyl are preferred.

The "lower aliphatic acyl groups" in the definition of [Substituent group A] and the "lower aliphatic acyl group" of the "lower aliphatic acylamino groups" in the definition of [Substituent group A] mean a $C_2$–$C_7$ aliphatic acyl group such as formyl, acetyl, propionyl, butyryl, isobutyryl, pentanoyl, pivaloyl, valeryl and isovaleryl. Among them, acetyl and propionyl are preferred.

With regard to the "aryl group substituted with 1 to 3 substituents selected from Substituent group A" in the definition of $R^2$, an aryl group substituted with 1 to 3 "halogen atoms" is preferable, and a phenyl group substituted with 1 to 3 "halogen atoms" is more preferable.

The compound (I) of the present invention can be converted into and used in the form of a "pharmaceutically acceptable salt", i.e. "salt".

Preferred examples of a salt which consists of a compound (I) of the present invention and an acid include hydrohalic acid salts such as hydrofluoric acid salts, hydrochloric acid salts, hydrobromic acid salts and hydroiodic acid salts, inorganic acid salts such as nitric acid salts, perchloric acid salts, sulfuric acid salts and phosphoric acid salts; salts with a lower alkylsulfonic acid, such as methanesulfonic acid salts, trifluoromethanesulfonic acid salts and ethanesulfonic acid salts, salts with an arylsulfonic acid, such as benzenesulfonic acid salts and p-toluenesulfonic acid salts; salts with organic acids, such as acetic acid salts, malic acid salts, furmaric acid salts, succinic acid salts, citric acid salts, tartaric acid salts, oxalic acid salts, and maleic acid salts; and salts with amino acids, such as glycine salts, lysine salts, arginine salts, ornithine salts, glutamic acid salts and aspartic acid salts.

On the other hand, preferred examples of a salt which consists of a compound (I) of the present invention and a base include salts with a metal, such as salts with an alkali metal, e.g. sodium salts, potassium salts and lithium salts, salts with an alkaline earth metal, e.g. calcium salts and magnesium salts, aluminium salts and iron salts: salts with an amine, such as inorganic salts, e.g. ammonium salts, organic salts. e.g. t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N-dibenzylethylenediamine salts, chloroprocaine salts, procaine salts, diethanolamine salts, N-benzylphenethylamine salts, piperazine salts, tetramethylammonium salts and tris(hydroxymethyl)aminomethane salts; and salts with an amino acid, such as glycine salts, lysine salts, arginine salts, ornithine salts, glutamic acid salts and aspartic acid salts.

Furthermore, a quaternary amine can be prepared from the compound (I) of the present invention by modifying the nitrogen atom of the piperidino group in its molecule with group $R^7$, the cation compound and anion (on which there is no restriction, provided that it is an anion, and a halogen ion, such as chloride ion or idoide ion, can be exemplified as such an anion) can form a salt, and such a salt is also included in the present invention.

The compound (I) of the present invention can sometimes be converted into a hydrate by absorption of water or adhesion of absorbed water when it is allowed to stand in the atomosphere, and such a hydrate is also included in the present invention.

The "ester" means a pharmaceutically acceptable ester into which the compound (I) of the present invention can be converted and it includes an "ester of a hydroxy group" and an "ester of a carboxyl group", and it includes an ester wherein the ester forming group is a "general protecting group" or a "protecting group which can be cleaved through a biological method such as hydrolysis in vivo".

The "general protecting group" means a protecting group which can be removed through a chemical method such as hydrogenolysis, hydrolysis, electrolysis and photolysis.

Preferred examples of the "general protecting group" for the "ester of a hydroxyl group" include the above-mentioned "lower aliphatic acyl group"; the above-mentioned "aromatic acyl group"; "tetrahydropyranyl or tetrahydropyrathionyl groups" such as tetrahydropyran-2-yl, 3-bromotetrahydropyran-2-yl. 4-methoxytetrahydropyran-4-yl, tetrahydrothiopyran-2-yl and 4-methoxytetrahydrothiopyran-4-yl; "silyl groups" such as tri(lower alkyl)silyl groups, e.g. trimethylsilyl, triethylsilyl, isopropyldimethylsilyl t-butyldimethylsilyl. methyldiiospropylsilyl, di-t-butylmethylsilyl and triisopropylsilyl, and tri(lower alkyl)silyl groups substituted with 1 or 2 aryl groups, e.g. diphenylmethylsilyl, diphenylbutylsilyl, diphenylisopropylsilyl and phenyldiisopropylsilyl; "alkoxymethyl groups" such as lower alkoxymethyl groups, e.g methoxymethyl, 1,1-dimethyl-1-methoxymethyl, ethoxymethyl, propoxymethyl, isopropoxymethyl, butoxymethyl and tert-butoxymethyl, lower alkoxylated lower alkoxymethyl groups, e.g. 2-methoxyethoxymethyl, and halogeno lower alkoxy methyl groups, e.g. 2,2,2-trichloroethoxymethyl and bis(2-chloroethoxy)methyl; "substituted ethyl groups" such as lower alkoxyethyl groups, e.g. 1-ethoxyethyl and 1-(isopropoxy)ethyl, and halogenoethyl groups, e.g. 2,2,2-trichloroethyl; "aralkyl groups" such as a lower alkyl group substituted with 1 to 3 aryl groups, e.g. benzyl, α-naphthylmethyl. β-naphthylmethyl, diphenylmethyl, triphenylmethyl, α-naphthyldiphenylmethyl or 9-anthrylmethyl, and a lower alkyl group substituted with 1 to 3 aryl groups which are substituted with a lower alkyl, halogeno lower alkyl, lower alkoxy or nitro group, a halogen atom or a cyano group, e.g. 4-methylbenzyl, 2,4,6-trimethylbenzyl, 3,4,5-trimethylbenzyl, 3,5-di(trifluoromethyl)benzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl; the above-mentioned "lower alkoxycarbonyl group"; and the above-mentioned "aralkyloxycarbonyl group".

Preferred examples of the "general protecting group" for the "ester of a carboxyl group" include the above-mentioned "lower alkyl group"; lower alkenyl groups such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl; lower alkynyl groups such as ethynyl 2-propynyl, 1-methyl-2-propynyl 2-methyl-2-propynyl, 2-ethyl-2-propynyl, 2-butynyl, 1-methyl-2-butynyl. 2-methyl-2-butynyl, 1-ethyl-2-butynyl. 3-butynyl, 1-methyl-3-butynyl, 2-methyl-3-butynyl, 1-ethyl-3-butynyl, 2-pentynyl, 1-methyl-2-pentynyl. 2-methyl-2-pentynyl, 3-pentynyl, 1-methyl-3-pentynyl. 2-methyl -3-pentynyl, 4-pentynyl, 1-methyl-4-pentynyl, 2-methyl-4-pentynyl. 2-hexynyl, 3-hexynyl, 4-hexynyl and 5-hexynyl; the above-mentioned "halogeno lower alkyl group"; hydroxy "lower alkyl group"s such as 2-hydroxyethyl, 2,3-dihydroxypropyl, 3-hydroxypropyl, 3,4-dihydroxybutyl and 4-hydroxybutyl; "lower aliphatic acyl"—"lower alkyl group"s such as acetyl methyl; the above-mentioned "aralkyl group"; and the above-mentioned "silyl group".

The "protecting group which can be cleaved through a biological method such as hydrolysis in vivo" means a group which is cleaved through a biological method such as hydrolysis in the human body to give a free acid compound or a salt thereof. Whether a compound is such an ester or not can be determined as follows; the compound is intravenously administered to an experimental animal such as a rat or mouse and the body fluid of the animal is thereafter studied. If the original compound or a pharmacologically acceptable salt thereof can be detected from the body fluid, the compound thus studied is such an ester.

Preferred examples of the "protecting group which can be cleaved through a biological method such as hydrolysis in vivo" for a hydroxy group include a "carbonyloxyalkyl group" such as 1-(acyloxy)"lower alkyl group"s including 1-("lower aliphatic acyl"oxy)"lower alkyl group"s, e.g. formyloxymethyl, acetoxymethyl, dimethylaminoacetoxymethyl, propionyoxymethyl, butyryloxymethyl, pivaloyloxymethyl, valeryloxymethy, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl, 1-("cycloalkyl"carbonyloxy)"lower alkyl group"s, e.g. cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl and 1-cyclohexylcarbonyloxybutyl; 1-("aromatic acyl"oxy) "lower alkyl group"s, e.g. benzoyloxymethyl; (lower alkoxycarbonyloxy)alkyl groups, e.g. methoxycarbonyloxymethyl. ethoxycarbonyloxymethyl, propoxycarbonyloxymethyl. isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl cyclohexyloxycarbonyloxy(cyclohexyl)methyl, 1-(methoxycarbonyloxy)ethyl, 1-(ethoxycarbonyloxy)ethyl, -(propoxycarbonyloxy)ethyl, 1-(isopropoxycarbonyloxy) ethyl, 1-(butoxycarbonyloxy)ethyl, 1-(isobutoxycarbonyloxy)ethyl, 1-(tert-butoxycarbonyloxy) ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 2-(methoxycarbonyloxy) ethyl, 2-(ethoxycarbonyloxy)ethyl, 2-(propoxycarbonyloxy) ethyl, 2-(isopropoxycarbonyloxy)ethyl, 2-(butoxycarbonyloxy)ethyl, 2-(isobutoxycarbonyloxy) ethyl, 2-(pentyloxycarbonyloxy)ethyl, 2-(hexyloxycarbonyloxy)ethyl, 1-(methoxycarbonyloxy) propyl, 1-(ethoxycarbonyloxy)propyl, 1-(propoxycarbonyloxy)propyl, 1-(isopropoxycarbonyloxy) propyl, 1-(butoxycarbonyloxy)propyl, 1-(isobutoxycarbonyloxy)propyl, 1-(pentyloxycarbonyloxy) propyl, 1-(hexyloxycarbonyloxy)propyl, 1-(methoxycarbonyloxy)butyl, 1-(ethoxycarbonyloxy) butyl, 1-(propoxycarbonyloxy)butyl, 1-(isopropoxycarbonyloxy)butyl, 1-(butoxycarbonyloxy) butyl, 1-(isobutoxycarbonyloxy)butyl, 1-(methoxycarbonyloxy)pentyl, 1-(ethoxycarbonyloxy) pentyl, 1-(methoxycarbonyloxy)hexyl and 1-(ethoxycarbonyloxy)hexyl; oxodioxolenylmethyl groups, e.g (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxoien-4-yl]methyl, (2-oxo -1,3-dioxolen-4-yl)methyl, (5-methyl-2-oxo-1,3-dioxolen-4-yl) methyl, (5-ethyl-2-oxo -1,3-dioxolen-4-yl)methyl, (5-propyl-2-oxo-1,3-dioxolen-4-yl)methyl, (5-isopropyl-2 -oxo-1,3-dioxolen-4-yl)methyl and (5-butyl-2-oxo-l1,3-dioxolen-4-yl)methyl: and the like: "phthalidyl group"s, e.g. phthalidyl, dimethylphthalidyl and dimethoxyphthalidyl: the above-mentioned "lower aliphatic acyl group": the above-mentioned "aromatic acyl group": "half-ester salt residues of succinic acid": "phosphate ester salt residues": "ester-forming residues of an amino acid or the like": carbamoyl groups: carbamoyl groups substituted with 1 or 2 lower alkyl groups: and "1-(acyloxy)alkyloxycarbonyl groups, e.g. pivaloyloxymethyloxycarbonyl. Among them, a "carbonyloxyalkyl group" is more preferred.

Preferred examples of the "protecting group which can be cleaved through biological method such as hydrolysis in vivo" for a carboxyl group include "alkoxy lower alkyl groups" such as a lower alkoxy lower alkyl groups, e.g. methoxymethyl, 1-ethoxyethyl, 1-methyl-1-methoxyethyl, 1-(isopropoxy)ethyl, 2-methoxyethyl, 2-ethoxyethyl, 1,1 -dimethyl-1-methoxyethyl, ethoxymethyl, n-propoxymethyl, isoproxymethyl, n-butoxymethyl or tert-butoxymethyl; (lower alkoxy lower alkoxy)alkyl groups such as 2-methoxyethoxymethyl; lower alkoxylated lower alkoxy lower alkyl groups, e.g. 2-methoxyethoxymethyl;

"aryl"oxy"lower alkyl group"s, e.g. phenoxymethyl; and halogeno lower alkoxy lower alkyl group, e.g. 2,2,2-trichloroethoxymethyl and bis(2-chloroethoxy)methyl; ""lower alkoxy"carbonyl"lower alkyl group""s, e.g. methoxycarbonylmethyl; "cyano"lower alkyl group""s e.g. cyanomethyl or 2-cyanomethyl; ""lower alkyl"thiomethyl group"s, e.g. methylthiomethyl or ethylthiomethyl; ""aryl"thiomethyl group"s, e.g. phenylthiomethyl or naphthylthiomethyl; ""lower alkyl"sulfonyl"lower alkyl groups optionally substituted with halogen atoms"", e.g. 2-methanesulfonylethyl or 2-trifluoromethanesulfonylethyl; """aryl"sulfonyl"lower alkyl group""s, e.g. 2-benzenesulfonylethyl or 2-toluenesulfonylethyl; the above-mentioned "1-(acyloxy)"lower alkyl group""s; the above-mentioned "phthalidyl group"s; the above-mentioned "aryl group"s; the above-mentioned "lower alkyl group"s; "carboxyalkyl group"s, e.g. carboxymethyl groups: and "amide-forming residues of an amino acid", e.g. phenylalanine.

Since the compound (I) of the present invention can be converted to a derivative other than the above-mentioned "pharmaceutically acceptable salt" and the above-mentioned "ester" when it has an amino group and/or carboxy group, the "other derivative" means such a derivative. The example of such a derivatitive includes amide derivatives.

The compound (I) of the present invention has some asymmetric centers and stereoisomers can exist due to R or S configuration at each asymmetric center. The present invention includes all individual isomers and a mixture of these isomers in any proportions.

MODE FOR CARRYING OUT THE INVENTION

The acylated hetero-alicyclic derivatives of the present invention can be prepared as follows.

Method A

Method A is a method to produce a compound (I) wherein Z represents two hydrogen atoms.

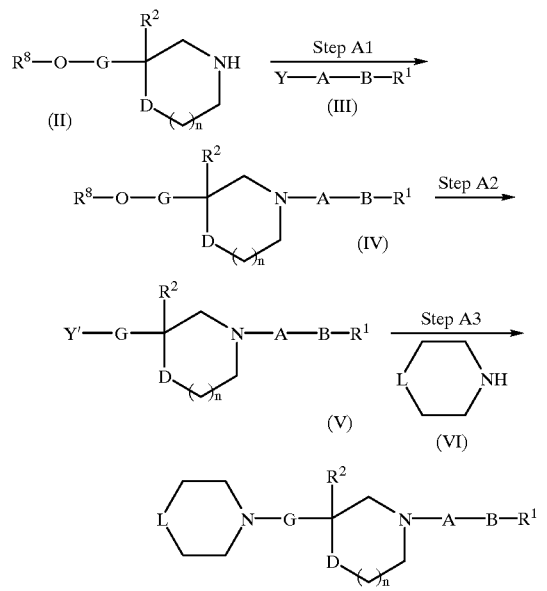

In the above scheme $R^1$, $R^2$, A, B, D, G, L and n are as defined above.

Y and Y' preferably represent, although there is no restriction provided that they are a group capable of leaving as a nucleophilic group, halogen atoms such as chlorine, bromine and iodine atoms; trihalogenomethyloxy groups such as trichloromethyloxy; lower alkanesulfonyloxy groups such as methanesulfonyloxy and ethanesulfonyloxy; halogeno lower alkanesulfonyloxy groups such as trifluoromethanesulfonyloxy and pentafluoroethanesulfonyloxy; and arylsulfonyloxy groups such as benzenesulfonyloxy, p-toluenesulfonyloxy and p-nitrobenzenesulfonyloxy. Among them, halogen atoms and lower alkanesulfonyloxy groups are more preferred.

$R^8$ represents a hydrogen atom or a hydroxyl protecting group. The hydroxyl protecting group means a "protecting group in a reaction" which can be removed through a chemical method such as hydrogenolysis, hydrolysis, electrolysis and photolysis and examples thereof include the same groups as the "general protecting group for the ester of a hydroxyl group".

Step A1 is a process, wherein a compound (II) is reacted with a compound (III) in a solvent in the presence of a base to produce a compound (IV), wherein the imino group of the compound (II) is modified with a group having formula —A—B—$R^1$ (wherein A, B and $R^1$ are as defined above.).

The solvent to be used is not particularly limited, provided that it has no adverse effect on the reaction and it can dissolve the starting materials to some extent, and preferred examples include aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethylcarbonate; ethers such as diethyl ether, diisopropyl ether, tetrahydrofuran, dioxane, dimethoxyethane and diethylene glycol dimethyl ether; ketones such as acetone, methyl ethyl ketone, methyl isobutyl ketone, isophorone and cyclohexanone; nitro compounds such as nitroethane and nitrobenzene; and nitriles such as acetonitrile and isobutyronitrile. Among them, halogenated hydrocarbons and ethers are more preferred and methylene chloride and tetrahydrofuran are most preferred.

The base to be used is not particularly limited, provide that it is one used as a base in conventional reactions. Preferred examples include organic bases such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU). Among them, triethylamine and diisopropylethylamine are more preferred.

The reaction can be carried out at a temperature of from −20° C. to 100° C., preferably from 0° C. to 20° C.

The reaction time varies depending on the reaction temperature, starting materials, reagents and solvent and is usually from 5 minutes to 24 hours, preferably 10 minutes to 12 hours.

In addition, in the case where the compound (II) is reacted with a compound (III) wherein A is carbonyl group, the process can be accomplished by conducting a reaction using a compound having the formula $R^1$—B—A—OH (wherein A, B and $R^1$ are as defined above) and a condensing agent in a solvent in the presence or absence of a base.

The examples of a "condensing agent" to be used include: (1) a combination of a phosphonate (e.g. diethyl cyanophosphate or diphenylphosphoryl azide) and a base described below;

(2) a carbodiimide (e.g. 1,3-dicyclohexylcarbodiimide, 1,3-diisopropylcarbodiimide or 1-ethyl-3-(3-dimethylaminopropyl)carbodiimide); a combination of one of the above carbodiimides and a base described below; or a combination of one of the above carbodiimides and an N-hydroxy compound (e.g. N-hydrosuccinimide, 1-hydroxybenzotriazole or N-hydroxy-5-norbornene-2,3-dicarboxyimide);
(3) a combination of a disulfide (e.g. 2,2'-dipyridyl disulfide or 2,2'-dibenzothiazolyl disulfide, etc.) and a phosphine (e.g. triphenylphosphine or tributylphosphine);
(4) a carbonate [e.g. N,N'-disuccinimidyl carbonate, di-2-pyridyl carbonate or S,S'-bis(1-phenyl-1H-tetrazol-5-yl) dithiocarbonate];
(5) a phosphinic chloride [e.g. N,N'-bis(2-oxo-3-oxazolidinyl)phosphinic chloride];
(6) an oxalate [e.g. N,N'-disuccinimidyl oxalate, N,N'-diphthalimide oxalate, N,N'-bis(5-norbornene-2,3-dicarboxyimidyl)oxalate, 1,1'-bis(benzotriazolyl)oxalate, 1,1'-bis(6-chlorobenzotriazolyl)oxalate or 1,1'-bis(6-trifluoromethylbenzotriazolyl) -oxalate];
(7) a combination of the above phosphine and an azodicarboxylate or azodicarboxamide [e.g. diethyl azodicarboxylate, 1,1'-(azodicarbonyl)dipiperidine]; or a combination of the above phosphine and a base described below;
(8) an N-lower alkyl-5-alisoxazolum-3'-sulfonate (e.g. N-ethl-5-phenylisoxazolium-3'-sulfonate);
(9) a diheteroaryldiselenide (e.g. di-2-pyridyldiselenide):
(10) an arylsulfonyltriazolide (e.g. p-nitrobenzenesulfonyltriazolide)
(11) a 2-halo-1-lower alkylpyridinium halide (e.g. 2-chloro-1-methylpyridinium iodide);
(12) an imidazoje (e.g. 1,1'-oxalyldiimidazole or N,N'-carbonyldiimidazole);
(13) a 3-lower alkyl-2-halogen-benzothiazolium fluoroborate (e.g. 3-ethyl-2-chlorobenzothiazolium fluoroborate);
(14) a 3-lower alkyl-benzothiazole-2-serone (e.g. 3-methylbenzothiazole-2-serone);
(15) a phosphate (e.g. phenyldichlorophosphate or polyphosphate);
(16) a halosulfonyl isocyanate (e.g. chlorosulfonyl isocyanate);
(17) a halosilane (e.g. trimethylsilyl chloride or triethylsilyl chloride);
(18) a combination of a lower alkanesulfonyl halide (e.g. methanesulfonyl chloride) and a base described below; and
(19) an N,N,N',N'-tetra(lower alkyl) haloformamidium chloride (e.g. N,N,N',N'-tetramethylchloroformamidium chloride).

Of these, the (1) mentioned above is more preferred.

The solvent to be used is not particularly limited, provided that it has no adverse effect on the reaction and it can dissolve the starting materials to some extent, and preferred examples include aliphatic hydrocarbons such as hexane and heptane; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate: ethers such as diethyl ether, diisopropyl ether, tetrahydrofuran, dioxane, dimethoxyethane and diethylene glycol dimethyl ether; nitriles such as acetonitrile and isobutyronitrile; and amides such as formamide, N,N-dimethylformamide, N,N-dimethylacetamide, N-methyl-2-pyrrolidone, N-methylpyrolidinone and hexamethylphosphoric triamide.

The base to be used is not particularly limited, provide that it is one used as a base in conventional reactions. Preferred examples include organic bases such as N-methylmorpholine, triethylamine, tributylamine, diisopropylethylamine, dicyclohexylamine, N-methylpiperidine, pyridine, 4-pyrrolidinopyridine, picoline, 4 -(N,N-dimethylamino)pyridine. 2,6-di(t-butyl)-4-methylpyridine. quinoline, N,N-dimethylaniline and N,N-diethylaniline.

In addition, a catalytic amount of 4-(N,N-dimethylamino) pyridine or 4-pyrrolidinopyridine can be used in combination with an other base, and in order to carry out the reaction effectively, it is possible to add a dehydrating agent such as molecular sieves, quaternary ammonium salts such as benzyltriethylarnmonium chloride and tetrabutylammonium chloride, crown ethers such as dibenzo-18-crown-6, and acid scavengers such as 3,4-dihydro-2H-pyrido[1.2-a] pyrimidine-2-one.

The reaction can be carried out at a temperature of from $-20°$ C. to $80°$ C., preferably from $0°$ C. to room temperature.

The reaction time varies depending mainly on the reaction temperature, starting materials, reagents and solvent, and is usually from 10 minutes to 3 days, preferably 30 minutes to one day.

Step A2 is a process to produce a compound (V) by removing the $R^8$ group from compound (IV), and then converting the hydroxy group, in the presence or absence of a base, to a leaving group Y'.

The removal reaction of the $R^8$ group varies depending on the nature of the group, and is carried out as shown below in a manner known to those skilled in the art.

In the case where $R^8$ is a silyl group, it can be removed by treatment with a compound forming a fluoride anion such as tetrabutylammonium fluoride, hydrogen fluoride, hydrogen fluoride-pyridine or potassium fluoride; or by treatment with an organic acid such as acetic acid, methanesulfonic acid, p-toluenesulfonic acid, trifluoroacetic acid, trifluoromethanesulfonic acid or B-bromocatecholborane, or an inorganic acid such as hydrochloric acid.

In addition, in the case of removal by the fluoride anion, the reaction may sometimes be promoted by adding an organic acid such as formic acid, acetic acid or propionic acid.

The solvent to be used is not particularly limited, provided that it has no adverse effect on the reaction and it can dissolve the starting materials to some extent, and preferred examples include ethers such as diethyl ether, diisopropyl ether. tetrahydrofuran, dioxane, dimethoxyethane and diethylene glycol dimethyl ether; nitriles such as acetonitrile and isobutyronitrile; water: organic acids such as acetic acid; and a mixture thereof.

The reaction can be carried out at a temperature of $0°$ C. to $150°$ C. (preferably from $10°$ C. to $100°$ C.) for a period of from 1 hour to 48 hours (preferably from 2 hours to 12 hours).

In the case where $R^8$ is an aralkyl or aralkyloxycarbonyl group, it can preferably be removed by contacting it with a reducing agent (preferably, catalytic hydrogenation at room temperature in the presence of a catalyst) in a solvent or by using an oxidizing agent.

The solvent to be used in the removal by catalytic hydrogenation is not particularly limited, provided that it has no adverse effect on the reaction, and preferred examples include alcohols such as methanol, ethanol and isopropanol, ethers such as diethyl ether, tetrahydrofuran and dioxane, aromatic hydrocarbons such as toluene, benzene and xylene, aliphatic hydrocarbons such as hexane and cyclohexane, esters such as ethyl acetate and propyl acetate, amides such as formamide, dimethylformamide, dimethylacetamide, N-methyl-2-pyrrolidone and hexamethylphosphoric triamide, aliphatic acids such as formic acid and acetic acid, water, or mixtures thereof. Of these, alcohols, aliphatic acids, mixtures of an alcohol and an ether, mixtures of an alcohol and water, or mixtures of an aliphatic acid and water are more preferred.

There is no particular restriction on the catalyst to be used, provided that it is usually used in a catalytic hydrogenation reaction, and preferred examples include palladium-on-carbon, palladium black, Raney nickel, platinum oxide, platinum black, rhodium-aluminium oxide, triphenylphosphine-rhodium chloride and palladium-barium sulfate.

The pressure is not particularly limited and is usually from 1 to 10 atomospheres.

The reaction time and temperature vary depending on the starting materials, solvent and catalyst but the reaction is usually carried out at a temperature of from 0° C. to 100° C. (preferably, from 20° C. to 70° C.) for a period of from 5 minutes to 48 hours (preferably, from 1 hour to 24 hours).

The solvent to be used in the removal by oxidation is not particularly limited, provided that it has no adverse effect on the reaction, and a water-containing organic solvent is preferably used.

Preferred examples of such an organic solvent include ketones such as acetone, halogenated hydrocarbons such as methylene chloride, chloroform and carbon tetrachloride, nitriles such as acetonitrile, ethers such as diethyl ether, tetrahydrofuran and dioxane, amides such as dimethylformamide, dimethylacetamide and hexamethylphosphoric triamide, and sulfoxides such as dimethylsulfoxide.

There is no particular restriction on the oxidizing agent to be used, provided that it is usually used in oxidation reactions, and preferred examples include potassium persulfate, sodium persulfate, cerium ammonium nitrate (CAN) and 2,3-dichloro-5,6-dicyano-p-benzoquinone (DDQ).

The reaction time and temperature vary depending on the starting materials, solvent and catalyst but the reaction is usually carried out at a temperature of from 0° C. to 150° C. for a period of from 10 minutes to 24 hours.

It can also be removed by an alkali metal, such as metallic lithium or metallic sodium, in liquid ammonia or an alcohol, such as methanol or ethanol at a temperature of from −78° C. to −20° C.

Furthermore, it can also be removed using aluminium chloride-sodium iodide or an alkylsilyl halide, such as trimethylsilyl iodide, in a solvent.

The solvent to be used is not particularly limited, provided that it has no adverse effect on the reaction, and nitrites such as acetonitrile, halogenated hydrocarbons such as methylene chloride or chloroform; or a mixture thereof is preferably used.

The reaction time and temperature vary depending on the starting materials and solvent but the reaction is usually carried out at a temperature of from 0° C. to 50° C. for a period of from 5 minutes to 3 days.

When a substrate in the reaction contains a sulfur atom, aluminium chloride-sodium iodide is preferably used.

In the case where $R^8$ is an aliphatic acyl group, aromatic acyl group or lower alkoxycarbonyl group, it can be removed by treatment with a base in a solvent.

The base to be used is not particularly limited, provided that it does not effect on any other part of the compound, and preferred examples include metal alkoxides such as sodium methoxide; alkali metal carbonates such as sodium carbonate, potassium carbonate and lithium carbonate; alkali metal hydroxides such as sodium hydroxide, potassium hydroxide, lithium hydroxide and barium hydroxide; and ammonia such as aqueous ammonia and concentrated ammonia-methanol.

There is no particular restriction on the solvent to be used, provided that it is usually used in hydrolysis reactions, and preferred examples include water; organic solvents such as alcohols (e.g. methanol, ethanol and n-propanol), and ethers (e.g. tetrahydrofuran and dioxane); or a mixture of water and an organic solvent described above.

The reaction time and temperature vary depending on the starting materials, solvent and the base used, but the reaction is usually carried out at a temperature of from 0° C. to 150° C. for a period of from 1 hour to 10 hours in order to inhibit side reactions.

In the case where $R^8$ is a lower alkoxymethyl group, tetrahydropyranyl group, tetrahydrothiopyranyl group, tetrahydrofuranyl group, tetrahydrothiofaranyl group or substituted ethyl group, it usually can be removed by treatment with an acid in a solvent.

The acid to be used is not particularly limited, provided that it is conventionally used as a Brønstead acid or Lewis acid, and preferred examples include Brønstead acids such as hydrogen chloride; an inorganic acid (e.g. hydrochloric acid. sulfuric acid or nitric acid); and an organic acid (e.g. acetic acid, trifluoroacetic acid, methanesulfonic acid or p-toluenesulfonic acid): and Lewis acids such as boron trifluoride. Strong acidic cation exchange resins such as Dowex 50W can also be used.

The solvent to be used is not particularly limited, provided that it has no adverse effect on the reaction and it can dissolve the starting materials to some extent, and preferable examples include aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethylcarbonate; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, tert-butanol, isoamyl alcohol, diethylene glycol, glycerin, octanol, cyclohexanol and methyl cellosolve; ketones such as acetone, methyl ethyl ketone, methyl isobutyl ketone, isophorone and cyclohexanone; water; and mixtures thereof. Of these, halogenated hydrocarbons, esters and ethers are more preferred.

The reaction temperature and time vary depending on the starting materials, solvent and the nature and concentration of the used acid, but the reaction is usually carried out at a temperature of from −10° C. to 100° C. (preferably, from −5° C. to 50° C.) for a period of from 5 minutes to 48 hours (preferably, from 30 minutes to 10 hours).

In the case where $R^8$ is an alkenyloxycarbonyl group, it can be removed by treatment with a base under reaction conditions similar to that described for the case where $R^8$ is an aliphatic acyl group, aromatic acyl group or lower alkoxycarbonyl group as mentioned above.

In addition, in the case of an allyloxycarbonyl group, a method using palladium and triphenylphosphine or bis (methylphenylphosphine)(1,5-cyclooctadiene)iridium (I) hexafluorophosphate is convenient and the reaction can be accomplished with few side reactions.

In the latter step of Step A2, the solvent to be used is not particularly limited, provided that it has no adverse effect on the reaction and it can dissolve the starting materials to some extent, and preferred examples include aromatic hydrocarbons such as benzene, toluene and xylene; halogenated hydrocarbons such as methylene chloride and chloroform; ethers such as diethyl ether, tetrahydrofuran, dioxane and dimethoxyethane; nitriles such as acetonitrile; and amides such as formamide, N,N-dimethylformamide, N,N-dimethylacetamide, N-methyl-2-pyrrolidone, N-methylpyrrolidinone and hexamethylphosphoric triamide. Of these, amides are more preferred.

The base to be used is not particularly limited, provide that it is one used as a base in conventional reactions. Preferred examples include organic bases such as N-methylmorpholine, triethylamine, tripropylamine, tributylamine, diisopropylethylamine, dicyclohexylamine, N-methylpiperidine, pyridine. 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU). Among them, triethylamine, pyridine and 4-(N,N-dimethylamino)pyridine are preferred, and, most preferably, the reaction is accomplished by using pyridine as a solvent and by adding a catalytic amount of 4-(N,N-dimethylamino)pyridine.

The reaction can be carried out at a temperature of from −20° C. to 50° C., preferably from −10° C. to 20° C.

The reaction time varies depending on the reaction temperature, starting materials, reagents and solvent and is usually from 15 minutes to 24 hours, preferably 30 minutes to 6 hours.

As for the reagent to form the leaving group Y', a corresponding halide compound is used, and the examples of such a reagent include a sulfonyl halide compound such as methanesulfonyl chloride or p-toluenesulfonyl chloride.

Step A3 is a process to produce compound (I) of the present invention by reacting a compound (V) with a compound (VI) in the presence of a base.

The solvent to be used is not particularly limited, provided that it has no adverse effect on the reaction and it can dissolve the starting materials to some extent, and preferred examples include aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; ketones such as acetone, methyl ethyl ketone, methyl isobutyl ketone, isophorone and cyclohexanone; nitro compounds such as nitroethane and nitrobenzene; nitriles such as acetonitrile and isobutylonitrile; amides such as formamide, N,N-dimethylformamide, N,N-dimethylacetamide, N-methyl-2-pyrrolidone, N-methylpyrrolidinone and hexamethylphosphoric triamide; and sulfoxides such as dimethyl sulfoxide and sulforane. Of these, amides, ethers and nitriles are preferred and amides are most preferred.

The base to be used is not particularly limited, provide that it is one used as a base in conventional reactions. Preferred examples include: a combination of a metal iodide (e.g. potassium iodide) and an inorganic base, such as an alkali metal carbonate (e.g. sodium carbonate, potassium carbonate or lithium carbonate), an alkali metal hydrogencarbonate (e.g. sodium hydrogencarbonate, potassium hydrogencarbonate or lithium hydrogencarbonate), an alkali metal hydride (e.g. lithium hydride, sodium hydride or potassium hydride), an alkali metal hydroxide (e.g. sodium hydroxide, potassium hydroxide, barium hydroxide or lithium hydroxide) or an alkali metal fluoride (e.g. sodium fluoride or potassium fluoride); or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU). Of these, a combination of a metal iodide and an inorganic base is more preferred and a combination of a metal iodide and an alkali metal hydrogencarbonate is most preferred.

The reaction can be carried out at a temperature of from 0° C. to 150° C., preferably from 20° C. to 120° C.

The reaction time varies depending on the reaction temperature, starting materials, reagents and solvents and is usually from 30 minutes to 48 hours, preferably 1 hour to 12 hours.

Method B

A compound (I) wherein n is 0 and Z is oxygen atom can be produced by Method B.

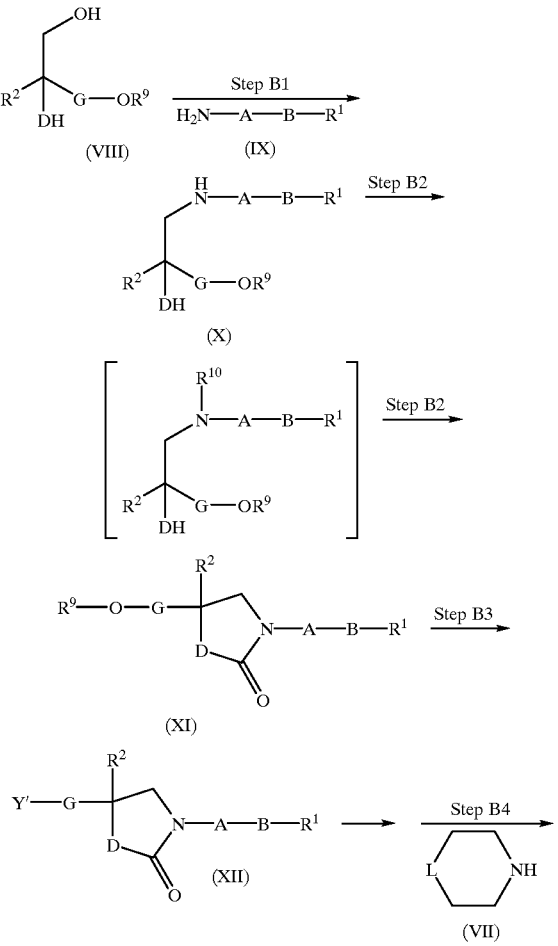

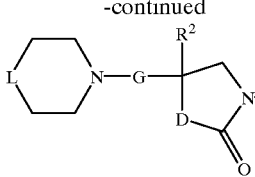
(I-b)

In the above scheme $R^1$, $R^2$, A, B, D, G, L and Y' are as defined above.

$R^9$ represents a hydroxyl protecting group as defined in the definition of $R^8$ as a "protecting group in a reaction".

$R^{10}$ represents an imino protecting group, and examples includes the above-mentioned "alipahtic acyl groups"; the above-mentioned "aromatic acyl groups"; the above-mentioned "lower alkoxycarbonyl groups"; the above-mentioned "alkenyloxycarbonyl groups"; the above-mentioned "aralkyloxycarbonyl groups"; and the above-mentioned "silyl groups". Of these, a lower alkoxycarbonyl group is more preferred and a tert-butoxycarbonyl group is most preferred.

Step B1 is a process to produce an amino compound (X) by converting the primary hydroxy group of a diol compound (VIII) to a leaving group and then by replacing the group with the amino group of an amine compound (IX).

The reaction of converting the primary hydroxy group of the diol compound (VIII) to a leaving group is carried out in a similar manner to that described in the latter step reaction of Step A2.

The latter replacement reaction is usually carried out using a metal salt in a solvent.

The solvent to be used is not particularly limited, provided that it has no adverse effect on the reaction and it can dissolve the starting materials to some extent, and preferred examples include aromatic hydrocarbons such as benzene, toluene and xylene; halogenated hydrocarbons such as methylene chloride, chloroform, carbon tetrachloride, dichloroethane, chlorobenzene and dichlorobenzene; ethers such as diethyl ether, diisopropyl ether, tetrahydrofuran, dioxane, dimethoxyethane and diethylene glycol dimethyl ether; ketones such as acetone, methyl ethyl ketone, methyl isobutyl ketone, isophorone and cyclohexanone; nitrites such as acetonitrile, propionitrile and isobutylonitrile; and amides such as formamide, N,N-dimethylformamide, N,N-dimethylacetamide, N-methyl-2-pyrrolidone, N-methylpyrrolidinone and hexamethylphosphoric triamide. Of these, nitrites are preferred and acetonitrile is most preferred.

Examples of the metal salt to be used include metal perchlorates such as lithium perchlorate, magnesium perchlorate and sodium perchlorate; metal chlorides such as calcium chloride, zinc chloride and cobalt chloride; metal tetrafluoroborates such as lithium tetrafluoroborate and potassium tetrafluoroborate; and zinc trifluoromethanesulfonate. Of these, metal perchlorates are preferred and lithium perchlorate is most preferred.

The reaction can be carried out at a temperature of from −20° C. to 150° C. preferably from room temperature to 100° C.

The reaction time varies depending on the reaction temperature, starting materials, reagents and solvents, and is usually from 30 minutes to 2 days, preferably 2 hours to 1 day.

Step B2 is a process to produce a compound (XI) by protecting the secondary amino group of the resulting amino compound (X) followed by conducting cyclization.

The protection of the secondary amino group with the $R^{10}$ group can be carried out as follows:

Method 1 a method wherein the resulting compound is reacted with 1 to 4 equivalents (preferably 2 to 3 equivalents) of a compound of formula $R^{10}$—X or with a compound of formula $R^{10}$—O—$R^{10}$ (in a case wherein $R^{10}$ is an acyl group) in a solvent in the presence or absence of a base; [wherein $R^{10}$ is as defined above and X represents a leaving group, and the leaving group is not particularly limited provide that it can usually leave as a nucleophilic group. Preferred example include halogen atoms such as chlorine, bromine and iodine; lower alkoxycarbonyloxy groups such as methoxycarbonyloxy and ethoxycarbonyloxy; halogenated alkylcarbonyloxy groups such as chloroacetyloxy, dichloroacetyloxy, trichloroacetyloxy and trifluoroacetyloxy;

lower alkanesulfonyloxy groups such as methanesulfonyloxy and ethanesulfonyloxy; halogeno lower alkanesulfonyloxy groups such as trifluoromethanesulfonyloxy and pentafluoroethanesulfonyloxy; and arylsulfonyloxy groups such as benzenesulfonyloxy, p-toluenesulfonyloxy and p-nitrobenzenesulfonyloxy. Of these, halogen atoms, halogeno lower alkanesulfonyloxy groups and arylsulfonyloxy groups are preferred.]: or Method 2 a method wherein the resulting compound is reacted with a compound of formula $R^{10}$—OH (in the case wherein $R^{10}$ is an acyl group) in a solvent in the presence or absence of the above-mentioned "condensing agent" and a catalytic amount of a base.

Method 3 particularly, in the case where $R^{10}$ is a tert-butoxycarbonyl group or benzyloxycarbonyl group, protection of the secondary amino group with the $R^{10}$ group can be carried out by reacting a reagent of tert-butoxycarbonylation or a reagent of benzyloxycarbonylation with the resulting compound in a solvent in the presence of a base.

The solvent to be used in [method 1] is not particularly limited, provided that it has no adverse effect on the reaction and it can dissolve the starting materials to some extent, and preferred examples include aliphatic hydrocarbons such as hexane and heptane; aromatic hydrocarbons such as benzene, toluene and xylene; halogenated hydrocarbons such as methylene chloride, chloroform, carbon tetrachloride. dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; nitriles such as acetonitrile and isobutyilonitrile; and amides such as formamide, N,N-dimethylformamide, N,N-dimethylacetamide, N-methyl-2-pyrrolidone, N-methylpyrrolidinone and hexamethylphosphoric triamide.

The base to be used in [method 1] is not particularly limited, provide that it is one used as a base in conventional reactions. Preferred examples include organic bases such as N-methylmorpholine, triethylamine, tributylamine, diisopropylehtylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline and N,N-diethylaniline.

In addition, a catalytic amount of 4-(N,N-dimethylamino)pyridine or 4-pyrrolidinopyridine can be used in a combination with another base. Furthermore, in order to carry out the reaction effectively, it is possible to add a quaternary ammonium salt such as benzyltriethylammonium chloride or tetrabutylammonium chloride, or a crown ether such as dibenzo-18-crown-6.

The reaction can be carried out at a temperature of from −20° C. to the refluxing temperature of the solvent used, preferably from 0° C. to room temperature.

The reaction time varies depending on the reaction temperature, starting materials, base and solvent, and is usually from 10 minutes to 3 days, preferably 1 hour to 1 day.

Examples of the compound of formula $R^{10}$—X include acyl halides such as aliphatic acyl halides (e.g. acetyl chloride, propionyl chloride, butyryl bromide, valeryl chloride and hexanoyl chloride); lower alkoxycarbonyl halides (e.g. methoxycarbonyl chloride, methoxycarbonyl bromide, ethoxycarbonyl chloride, propoxycarbonyl chloride, butoxycarbonyl chloride and hexyloxycarbonyl chloride; arylcarbonyl halides (e.g. benzoyl chloride, benzoyl bromide and naphthoyl chloride; silyl halides such as tert-butyldimethylsilyl chloride, trimethylsilyl chloride, triethylsilyl chloride, triethylsilyl bromide, triisopropylsilyl chloride, dimethylisopropylsilyl chloride, diethylisopropylsilyl chloride, tert-butyldiphenylsilyl chloride, diphenylmethylsilyl chloride and triphenylsilyl chloride; corresponding silyltrifluoromethanesulfonates; aralkyl halides such as benzyl chloride and benzyl bromide; and carbonyloxy lower alkyl halides such as pivaloyloxymethyl chloride and ethoxycarbonyloxymethyl chloride.

Examples of the compound of formula $R^{10}$—O—$R^{10}$ include aliphatic carboxylic anhydrides such as acetic anhydride, propionic anhydride, valeric anhydride or hexanoic anhydride; and mixed acid anhydrides such as the mixed anhydride of formic and acetic acids.

The solvent to be used in [method 2] is not particularly limited, provided that it has no adverse effect on the reaction and it can dissolve the starting materials to some extent, and preferred examples include aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; nitriles such as acetonitrile and isobutyilonitrile; and amides such as formamide, N,N-dimethylformamide, N,N-dimethylacetamide, N-methyl-2-pyrrolidone, N-methylpyrrolidinone and hexamethylphosphoric triamide.

The base described in the method 1 can be used in method 2 as the base.

The reaction can be carried out at a temperature of from −20° C. to 80° C., preferably from 0° C. to room temperature.

The reaction time varies depending on the reaction temperature, starting materials, base and solvent, and is usually from 10 minutes to 3 days, preferably 30 minutes to 1 day.

The solvent to be used in [method 3] is not particularly limited, provided that it has no adverse effect on the reaction and it can dissolve the starting materials to some extent, and preferred examples include aliphatic hydrocarbons such as hexane and heptane; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; nitriles such as acetonitrile and isobutylonitrile; amides such as formamide, N,N-dimethylformamide, N.N-dimethylacetamide, N-methyl-2-pyrrolidone, N-methylpyrrolidinone and hexamethylphosphoric triamide; water; and a mixture of water and one of the above-mentioned organic solvents.

The base described in the method 1 can be used in method 3 as the base.

Preferred examples of the reagent for tert-butoxycarbonylation include di-tert-butyl dicarbonate, 2-(tert-butoxycarbonyloxyimino)-2-phenylacetonitrile, tert butyl S-(4,6-dimethylpyridin-2-yl)thiolcarboxylate, 1,2,2,2-tetrachloroethyl and tert-butyl carbonate. Of these, di-tert-butyl dicarbonate is more preferred.

Preferred examples of the reagent for benzyloxycarbonylation include benzyloxycarbonyl chloride, benzyloxycarbonyl cyanide and dibenzyl dicarbonate.

The reaction can be carried out at a temperature of from −20° C. to 80° C., preferably from 0° C. to room temperature.

The reaction time varies depending on the reaction temperature, starting materials, base and solvent, and is usually from 10 minutes to 3 days, preferably 30 minutes to 1 day.

The cyclization reaction of the latter step is usually carried out in a solvent in the presence of a base.

The solvent to be used is not particularly limited, provided that it has no adverse effect on the reaction and it can dissolve the starting materials to some extent, and preferred examples include aliphatic hydrocarbons such as hexane and heptane; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; nitriles such as acetonitrile and isobutylonitrile; and amides such as formamide, N,N-dimethylformamide, N,N-dimethylacetamide, N-methyl-2-pyrrolidone, N-methylpyrrolidinone and hexamethylphosphoric triamide.

The base to be used is not particularly limited, provide that it is one used as a base in conventional reactions. Preferred examples include inorganic bases such as alkali metal carbonates (e.g. sodium carbonate, potassium carbonate and lithium carbonate; alkali metal hydrogencarbonates (e.g. sodium hydrogencarbonate, potassium hydrogencarbonate and lithium hydrogencarbonate); alkali metal hydrides (e.g. lithium hydride, sodium hydride and potassium hydride); alkali metal hydroxides (e.g. sodium hydroxide, potassium hydroxide, barium hydroxide and lithium hydroxide); and alkali metal fluorides (e.g. sodium fluoride and potassium fluoride); and alkali metal alkoxides such as sodium methoxide, sodium ethoxide, potassium methoxide, potassium ethoxide, potassium tert-butoxide and lithium methoxide. Of these, alkali metal hydrides and alkali metal alkoxides are more preferred.

The reaction can be carried out at a temperature of from −20° C. to 80° C., preferably from 0° C. to room temperature.

The reaction time varies depending on the reaction temperature, starting materials, base and solvent, and is usually from 10 minutes to 3 days, preferably 30 minutes to 1 day.

Step B3 is a process to produce a compound (XII) by deprotecting the hydroxy group of the compound (XI) and then by converting the resulting hydroxy group to a leaving group, and can be carried out in a similar manner to that described in the latter step of Step A2.

Step B4 is a process to produce a compound (I-b) of the present invention by conducting a condensation reaction between a compound (XII) and compound (VII), and can be carried out in a similar manner to that described in Step A3.

Method C

Compound (I) wherein n is 1 or 2 and Z is an oxygen atom can be produced by method C.

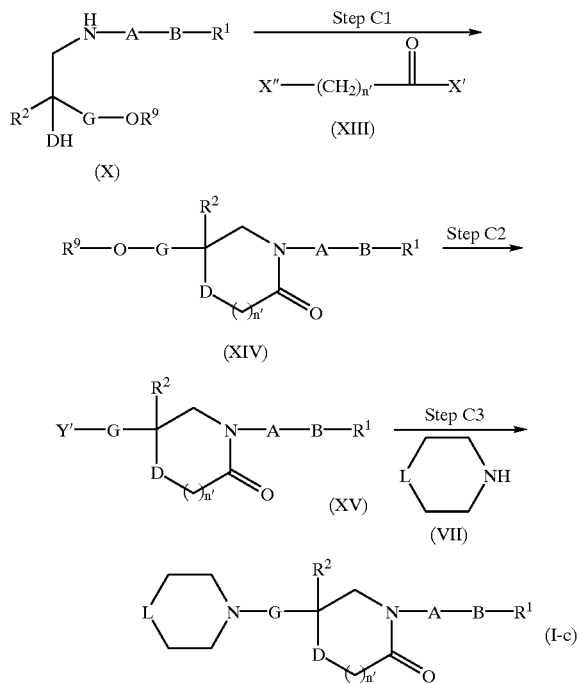

Wherein $R^1$, $R^2$, $R^9$, A, B, D, G, L and Y' are as defined above;

X and X' represent leaving groups which have the same meaning as Y' defined above; and n' represents 1 or 2.

Step C1 is a process to produce a cyclic amide compound (XIV) by reacting the secondary amine of the amino compound (X) with a compound (XIII) in a solvent in the presence of a base and then by alkylation at the DH group.

The solvent to be used in the former step is not particularly limited, provided that it has no adverse effect on the reaction and it can dissolve the starting materials to some extent, and preferred examples include aliphatic hydrocarbons such as hexane and heptane; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran dioxane, dimethoxyethane and diethylene glycol dimethyl ether; nitriles such as acetonitrile and isobutylonitrile; and amides such as formamide, N,N-dimethylformamide, N,N-dimethylacetamide, N-methyl-2-pyrrolidone, N-methylpyrrolidinone and hexamethylphosphoric triamide.

The base to be used is not particularly limited, provide that it is one used as a base in conventional reactions. Preferred examples include organic bases such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline and N,N-diethylaniline.

In addition, a catalytic amount of 4-(N,N-dimethylamino) pyridine or 4-pyrrolidinopyridine can be used in combination with another base, and in order to carry out the reaction effectively, it is possible to add a dehydrating agent such as molecular sieves, quaternary anmonium salts such as benzyltriethylammonium chloride and tetrabutylammonium chloride, crown ethers such as dibenzo-18-crown-6, and acid scavengers such as 3,4-dihydro-2H-pyrido[1,2-a] pyrimidine-2-one.

The reaction can be carried out at the temperature of from −20° C. to 80° C., preferably from 0° C. to room temperature.

The reaction time varies depending mainly on the reaction temperature, starting materials, reagent and solvent, and is usually from 10 minutes to 3 days, preferably 30 minutes to one day.

The solvent to be used in the alkylation reaction of the latter step is not particularly limited, provided that it has no adverse effect on the reaction and it can dissolve the starting materials to some extent, and preferred examples include aromatic hydrocarbons such as benzene, toluene and xylene; halogenated hydrocarbons such as methylene chloride, chloroform, carbon tetrachloride, dichloroethane, chlorobenzene and dichlorobenzene; ethers such as diethyl ether, diisopropyl ether, tetrahydrofuran, dioxane, dimethoxyethane and diethylene glycol dimethyl ether; nitriles such as acetonitrile, propionitrile and isobutylonitrile: amides such as formamide, N,N-dimethylformamide, N,N-dimethylacetamide, N-methyl-2-pyrrolidone, N-methylpyrrolidinone and hexamethylphosphoric triamide; and sulfoxides such as dimethylsulfoxide and sulfolan. Of these, ethers and amides are more preferred and tetrahydrofuran and N,N-dimethylformamide are most preferred.

The base to be used is not particularly limited, provide that it is one used as a base in conventional reactions. Preferred examples include inorganic bases such as alkali metal carbonates (e.g. sodium carbonate, potassium carbonate and lithium carbonate); alkali metal hydrogencarbonates (e.g. sodium hydrogencarbonate, potassium hydrogencarbonate and lithium hydrogencarbonate); alkali metal hydrides (e.g. lithium hydride, sodium hydride and potassium hydride); alkali metal hydroxides (e.g. sodium hydroxide, potassium hydroxide, barium hydroxide and lithium hydroxide) and alkali metal fluorides (e.g. sodium fluoride and potassium fluoride); and alkali metal alkoxides such as sodium methoxide, sodium ethoxide, potassium methoxide, potassium ethoxide, potassium tert-butoxide and lithium methoxide. Of these, alkali metal hydrides and alkali metal alkoxides are more preferred.

The reaction can be carried out at a temperature of from −20° C. to 100° C., preferably from 0° C. to 50° C.

The reaction time varies depending on the reaction temperature, starting materials, base and solvent, and is usually from 10 minutes to 24 hours, preferably 30 minutes to 12 hours.

Step C2 is a process to produce a compound (XV) of the present invention by deprotecting the hydroxy group of the compound (XIV) and then by converting the resulting hydroxy group to a leaving group, and can be carried out in a similar manner to that described in the latter step of Step A2.

Step C3 is a process to produce a compound (I-b) of the present invention by conducting a condensation reaction between the compound (XV) and compound (VII), and can be carried out in a similar manner to that described in Step A3.

After completion of each reaction described above, the desired compound is isolated from the reaction mixture in a conventional manner.

For example, it is obtained by neutralizing the reaction mixture as needed, removing the insoluble matters by filtration if any, adding organic solvents which are not miscible with each other, such as water and ethyl acetate, washing with water or the like, separating the organic layer containing the desired compound, drying it over anhydrous magnesium sulfate or the like and then distilling off the solvent.

If necessary, the desired compound thus obtained can be isolated and purified using a conventional method such as recrystallization or reprecipitation and chromatography in which a method ordinarily employed for the isolation and purification of an organic compound in combination as needed and eluting using a proper eluant. Examples of chromatography include adsorption column chromatography using a carrier such as silica gelt alumina or magnesium-silica gel type Florisil, chromatography using a synthetic adsorbent, for example, partition column chromatography using a carrier such as Sephadex LH-20 (product of Pharmacia), Amberlite XAD-11(product of Rohm & Haas) or Diaion HP-20 (product of Mitsubishi Chemical), ion exchange chromatography or normal-phasereverse-phase column chromatography (high-performance liquid chromatography) using a silica gel or alkylated silica gel.

In addition, starting materials are either commercially available or can be easily prepared by known techniques (for example EP-776893 and U.S. Pat. No. 5,641,777 and the like) from commercially available starting materials.

The novel acylated hetero-alicyclic derivatives of the present invention have excellent $NK_2$-selective antagonistic activity and have low toxicity, and thus they are usefull as a medicament. For example, they are useful as a preventive and therapeutic agent for diseases of the central nervous system such as anxiety, depression, psychosis and schizophrenia; sleep apnea; neurodegenerative diseases such as dementia of AIDS, Alzheimer's senile dementia, Alzheimer's disease, Down's syndrome, demyelinating disease, amyotrophic lateral sclerosis, neuropathy, peripheral neuropathy and neuralgia; respiratory diseases such as chronic obstructive pulmonary disease, bronchitis, pneumonia, bronchoconstriction, asthma and coughs; inflammatory diseases such as inflammatory bowel disease (IBD), psoriasis, fibrosis, arthrosteitis, degenerative arthritis and rheumatoid arthritis; eczema; allergic diseases such as rhinitis; hypersensitivity diseases such as hypersensitivity to vines; ophthalmological diseases such as conjunctivitis, vernal conjunctivitis, vernal cetarrh, destruction of the blood-aqueous humor barrier caused by various inflammatory eye diseases, elevated intraocular pressure and miosis; skin diseases such as contact dermatitis, atopic dermatitis, urticaria and other eczematoid dermatitis; addictions such as alcohol dependency; somatic diseases caused by stress; sympathetic reflex dystrophy such as hand and shoulder syndrome; dysthymia; undesirable immune reactions such as rejection of grafts, diseases relating to immunopotentiation such as systemic lupus erythematosus or immunosuppression; digestive diseases such as diseases caused by abnormalities in nerves regulating the organs, colitis. ulcerative colitis and Crohn's disease; emesis such as emesis induced by adverse effects of X-ray irradiation and chemotherapy, poisons, toxins, pregnancy, vestibular disorders, postoperative illness, gastrointestinal occlusion, reduced gastrointestinal movement, visceral pain, migraine headaches, increased intracranial pressure, reduced intracranial pressure or adverse reactions induced by administration of various medicaments; urinary bladder functional diseases such as cystitis and urinary incontinence; eosinophilia caused by collagen diseases, scleriasis or Fasciola hepatica infection; diseases caused by abnormal blood flow due to vasodilation or vasoconstriction such as angina pectoris, migraine headaches and Reynauds's disease; and pain of pain nociceptive reception such as migraine headaches, headaches and toothaches.

The administration route of compound (I) of the present invention includes oral administration in the form of tablets, capsules, granules powders or syrups; parenteral administration in the form of injections or suppositories; inhalation sprays, skin patches, etc. These formulations can be prepared by a known method using carriers such as excipients (e.g. organic excipients including sugar derivatives, such as lactose, sucrose, glucose, mannitol or sorbitol; starch derivatives, such as corn starch, potato starch, α-starch, dextrin or carboxymethyl starch; cellulose derivatives, such as crystalline cellulose, low-substituted hydroxypropylcellulose, hydroxypropylmethylcellulose, carboxymethylcellulose, calcium carboxymethylcellulose or internally cross-linked carboxymethylcellulose sodium; gum arabic; dextran and pullulan; and inorganic excipients including silicate derivatives, such as light anhydrous silicic acid, synthetic aluminium silicate or magnesium aluminate metasilicate; phosphates, such as calcium phosphate: carbonates, such as calcium carbonate; and sulfates, such as calcium sulfate), lubricants (e.g. stearic acid and metal stearates such as calcium stearate and magnesium stearate; talc; colloidal silica; waxes, such as bee gum and spermaciti; boric acid; adipic acid; sulfates, such as sodium sulfate, glycol; fumaric acid; sodium benzoate; DL-leucine; sodium salts of aliphatic acids; laurylsulfates, such as sodium laurylsulfate and magnesium laurylsulfate; silicic acids, such as anhydrous silicic acid and silicate hydrate; and the starch derivatives described above), binders (e.g. polyvinyl pyrrolidone, macrogol and the same compounds as those of the above excipients), disintegrators (e.g. the same compounds as those of the above excipients and chemically modified starch-celluloses, such as croscarmellose sodium, carboxymethylstarch sodium and cross-linked polyvinylpyrrolidone), stabilizers (e.g. paraoxybenzoates, such as methylparaben and propylparaben; alcohols, such as chlorobutanol, benzyl alcohol and phenethyl alcohol; benzalkonium chloride; phenols, such as phenol and cresol;

thimerosal; dehydroacetic acid; and sorbic acid), corrigents (e.g. normally used sweetening agents, sour agents and perfumes) and diluents.

The dosage of compound (I) will vary depending on the conditions of the disease, age of the patient (human or mammal) and administration route. A suitable single unit dose of a compound of (I) is from 0.01 mg/kg body weight (preferably 0.1 mg/kg body weight), as the lower limit, to 100 mg/kg body weight (preferably 50 mg/kg body weight), as the upper limit, for oral administration. For intravenous administration, it is from 0.01 mg body weight (preferably 0.05 mg/kg body weight), as the lower limit, to 100 mg/kg body weight (preferably 50 mg /kg body weight), as the upper limit. It is desired to administer the above once or several times per day depending on the conditions of the disease.

The present invention provides pharmaceutical compositions comprising an effective amount of the compound (I) and/or a pharmaceutically acceptable salt or ester or other derivative thereof. The present invention also provides a method to prevent or treat the diseases and conditions identified in this specification.

The following examples, reference examples, formulation examples and test examples are intended to further illustrate the present invention and are not intended to limit the scope of this invention in any way.

EXAMPLES

Example 1

1-{2-[(2R)-(3,4-dichlorophenyl)-4-(cyclobutanecarbonyl)morpholin-2-yl]ethyl }spiro[benzo[c]thiophene-1(3H),4'-piperidine]-(2S)-oxide

Example 1(a)

2-[(2R)-(3,4-dichlorophenyl)-4-(cyclobutanecarbonyl)morpholin-2-yl]ethanol

Water soluble carbodiimide hydrochloride (WSC.HCl, 166 mg, 0.87 mmol), 1-hydroxybenzotriazole (117 mg, 0.87 mnol) and triethylamine (0.15 ml. 1.09 mmol), in turn, were added to a solution of cyclobutanecarboxylic acid (80 mg, 0.80 mmol) in methylene chloride (5 ml) at 0° C. under a nitrogen atmosphere, and 2-[(2R)-(3,4-dichlorophenyl)morpholin-2-yl]ethanol (200 mg, 0.72 mmol), which was obtained in Reference example 1, was added to this. The mixture was stirred at room temperature for 6 hours. The reaction mixture was washed with a saturated aqueous solution of sodium hydrogencarbonate and with a saturated aqueous solution of sodium chloride solution in turn. The organic layer was dried over anhydrous magnesium sulfate and then the solvent was distilled off under reduced pressure. The residue was purified by silica gel thin layer chromatography using n-hexane/ethyl acetate=¼ as a developing solvent to afford the desired compound (254 mg, 98%) as a white amorphous solid.

Nuclear magnetic resonance spectrum (270 MHz, CDCl$_3$)δ ppm 7.59(1H,bs), 7.44(1H,d,J=8.4 Hz), 7.29(1H, bd,J=8.4 Hz), 4.55(1H,d,J=13.9 Hz), 3.71–3.80(1H,m), 3.32–3.62(6H,m), 3.09–3.22(1H,m), 2.28–2.42(1H,m), 1.79–2.18(8H,m).

Infrared spectrum ν max cm$^{-1}$(CHCl$_3$): 3624, 2954, 1640, 1441.

Mass spectrometric analysis (FAB) m/z: 358((M+H)$^+$).

Example 1(b)

2-[(2R)-(3,4-dichlorophenyl)-4-(cyclobutanecarbonyl)morpholin-2-yl]ethanol methanesulfonate Methanesulfonyl chloride (0.071 ml, 0.92 mmol) and 4-dimethylaminopyridine (catalytic amount) were added to a solution of 2-[(2R)-(3,4-dichlorophenyl)-4-(cyclobutanecarbonyl)morpholin-2-yl]ethanol (219 mg, 0.61 mmol), which was prepared in Example 1(a), in pyridine (2 ml) with ice-cooling under a nitrogen atmosphere. The mixture was stirred at the same temperature for 30 minutes. The reaction mixture was acidified with ice-cooled hydrochloric acid (10%) and extracted with ethyl acetate. The organic layer was washed with a saturated aqueous solution of sodium chloride and dried over anhydrous magnesium sulfate. The ethyl acetate was distilled off under reduced pressure. The residue was purified by silica gel thin layer chromatography using n-hexane/ethyl acetate=¼ as a developing solvent to afford the desired compound (255 mg, 96%) as a white amorphous solid.

Nuclear magnetic resonance spectrum (270 MHz, CDCl$_3$)δ ppm: 7.57(1H,bs), 7.46(1H,d,J=8.5 Hz), 7.20–7.30 (1H,m), 3.14–4.31(9H,m), 2.93(3H,s), 2.26–2.42(2H,m), 1.82–2.22(6H,m).

Infrared spectrum ν max cm$^{-1}$(CHCl$_3$): 2971, 1641, 1440.

Mass spectrometric analysis (FAB) m/z: 436((M+H)$^+$).

Example 1(c)

1-{2-[(2R)-(3,4-dichlorophenyl)-4-(cyclobutanecarbonyl)morpholin-2-yl]ethyl}spiro[benzo[c]thiophene-1(3H), 4'-piperidine]-(2S)-oxide 2-[(2R)-(3,4-dichlorophenyl)-4-(cyclobutanecarbonyl)morpholin-2-yl]ethanol methanesulfonate (114 mg, 0.26 mmol), which was prepared in Example 1(b), spiro[benzo[c]thiophene-1(3H),4'-piperidine]-(2S)-oxide hydrochloride (74 mg, 0.29 mmol), sodium hydrogencarbonate (66 mg, 0.78 mmol) and potassium iodide (65 mg, 0.39 mmol) were suspended in anhydrous dimethylformamide (2 ml), and this was stirred at 80° C. under a nitrogen atmosphere for 8 hours. To the reaction mixture, water was added and it was extracted with ethyl acetate. The organic layer was washed with a saturated aqueous solution of sodium chloride and dried over anhydrous magnesium sulfate. The solvent was distilled off under reduced pressure.

The residue was purified by silica gel thin layer chromatography using methylene chloride/methanol =10/1 as a developing solvent to give the title compound (111 mg, 76%) as a white crystalline solid.

Melting point: 99–101° C.

$[\alpha]_D^{24}$+65.4° (c=0.54, Chloroform)

Nuclear magnetic resonance spectrum (400 MHz, CDCl$_3$) δppm: 7.22–7.59(7H,m), 4.52(1H,d,J=13.8 Hz), 4.31(1H,d, J=16.8 Hz), 3.99(1H,d,J=16.8 Hz), 3.13–3.83(6H,m), 2.72–296(2H,m), 2.02–2.45(11H,m), 1.82–1.99(4H,m), 1.52–1.56(1H,m).

Infrared spectrum ν]max cm$^{-1}$(KBr): 3432, 2949, 1643, 1436.

Mass spectrometric analysis (FAB) m/z: 561((M+H)$^+$)

Elemental analysis (%): for $C_{29}H_{34}N_2O_3SCl_2.0.5H_2O$

Calculated: C;61.04,H;6.18,N;4.90,S;5.61,Cl;12.43

Found: C;61.75,H;6.40,N;4.86,S;5.52,Cl;11.72.

Example 2

1-{2-[(2R)-(3,4-dichlorophenyl)-4-(cyclopropanecarbonyl)morpholin-2-yl]ethyl}spiro[benzo[c]thiophene-1(3H),4'-piperidine]-(2S)-oxide

Example 2(a)

2-[(2R)-(3,4-dichlorophenyl)-4-(cyclopropanecarbonyl)morpholin-2-yl]ethanol

The desired compound (230 mg, 92%) was obtained as a white amorphous solid, according to the procedures described in Example 1(a) using cyclopropanecarboxylic acid (69 mg, 0.80 mmol) and 2-[(2R)-(3,4-dichlorophenyl) morpholin-2-yl]ethanol (200 mg, 0.72 mmol).

Nuclear magnetic resonance spectrum (270 MHz, CDCl$_3$)δ ppm: 7.58(1H,bs), 7.43(1H,d,J=8.7 Hz), 7.28(1H, bd,J=8.7 Hz), 4.54(1H,d,J=13.9 Hz), 3.5–3.9(8H,m), 1.9–2.2(2H,m), 1.5–1.7(1H,bs), 0.7–1.0(4H,m).

Infrared spectrum ν max cm–$^1$ (CHCl$_3$): 3623, 2968, 1732, 1637, 1471.

Mass spectrometric analysis (FAB) m/z: 344((M+H)$^+$).

Example 2(b)

2-[(2R)-(3,4-dichlorophenyl)-4-(cyclopropanecarbonyl)morpholin-2-yl]ethanol methanesulfonate The desired compound (257 mg, 95%) was obtained as a white amorphous solid, according to the procedures described in Example 1 (b) using 2-[(2R)-(3,4-dichlorophenyl)-4-(cyclopropanecarbonyl)morpholin-2-yl] ethanol (220 mg, 0.64 mmol).

Nuclear magnetic resonance spectrum (270 MHz, CDCl$_3$)δ ppm: 7.57(1H,bs), 7.45(1H,d,J=7.9 Hz), 7.25–7.32 (1H,m), 3.48–4.30(8H,m), 2.93(3H,s), 2.09–2.49(2H,m), 0.65–1.12(4H,m).

Infrared spectrum ν max cm$^{-1}$(CHCl$_3$): 2973, 1731, 1678, 1471.

Mass spectrometric analysis (FAB) m/z: 422((M+H)$^+$).

Example 2(c)

1-{2-[(2R)-(3,4-dichlorophenyl)-4-(cyclopropanecarbonyl)morpholin-2-yl]ethyl}spiro [benzo[c]thiophene-1(3H),4'-piperidine]-(2S)-oxide The desired compound (63 mg, 45%) was obtained as white crystals, according to the procedures described in Example 1 (c) using 2-[(2R)-(3,4-dichlorophenyl)-4-(cyclopropanecarbonyl)morpholin-2-yl]ethanol methanesulfonate (109 mg, 0.26 mmol) and spiro[benzo[c] thiophene-1(3H),4'-piperidine]-(2S)-oxide hydrochloride (71 mg, 0.28 mmol).

Melting point: 96–99° C.

[α]$_D^{24}$+56.7° (c=0.30, chloroform)

Nuclear magnetic resonance spectrum (400 MHz, CDCl$_3$)δ ppm: 7.23–7.59(7H,m), 4.31(1H,d,J=16.8 Hz), 3.99(1H,d,J=16.8 Hz), 3.44–4.52(5H,m), 2.73–2.96(2H,m), 1.52–2.40(12H,m), 0.75–1.15(4H,m).

Infrared spectrum ν max cm$^{-1}$(KBr): 3414, 2922, 1639, 1470.

Mass spectrometric analysis (FAB) m/z: 547((M+H)$^+$).

Elemental analysis (%): for C$_{28}$H$_{32}$N$_2$O$_3$SCl$_2$.0.5H$_2$O:

Calculated: C;60.42,H;5.98,N;5.03,S;5.76,Cl;12.74

Found: C;60.92,H;6.32,N;4.84,S;5.71,Cl;12.35.

Example 3

1-{2-[(2R)-(3,4-dichlorophenyl)-4-(cyclopentanecarbonyl)morpholin-2-yl]ethyl}spiro [benzo[c]thiophene-1(3H),4'-piperidine]-(2S)-oxide

Example 3(a)

2-[(2R)-(3,4-dichlorophenyl)-4-(cyclopentanecarbonyl)morpholin-2-yl]ethanol

The desired compound (389 mg, 96%) was obtained as a white amorphous solid, according to the procedures described in Example 1(a) using cyclopentanecarboxylic acid (186 mg, 1.63 mmol) and 2-[(2R)-(3,4-dichlorophenyl) morpholin-2-yl]ethanol (300 mg, 1.09 mmol).

Nuclear magnetic resonance spectrum (400 MHz, CDCl$_3$)δ ppm: 7.59(1H,d,J=20 Hz), 7.43(1H,d,J=8.4 Hz), 7.28(1H,dd,J=8.4 and 2.0 Hz), 4.62(1H,d,J=13.9 Hz), 3.3–3.9(7H,m), 3.37(1H,d,J=13.9 Hz), 2.78(1H,m), 1.4–2.1 (9H,m).

Infrared spectrum ν max cm$^{-1}$(CHCl$_3$): 3622, 2960, 1732, 1637, 1440.

Mass spectrometric analysis (FAB) m/z: 372((M+H)$^+$).

Example 3(b)

2-[(2R)-(3,4-dichlorophenyl)-4-(cyclopentanecarbonyl)morpholin-2-yl ]ethanol methanesulfonate The desired compound (435 mg, 95%) was obtained as a white amorphous solid, according to the procedures described in Example 1(b) using 2-[(2R)-(3,4-dichlorophenyl)-4-(cyclopentanecarbonyl)morpholin-2-yl] ethanol (380 mg, 1.02 mmol).

Nuclear magnetic resonance spectrurm (400 MHz, CDCl$_3$)δ ppm: 7.57(1H,d,J=2.0 Hz), 7.45(1H,d,J=8.4 Hz), 7.27(1H,dd,J=8.4 and 2.0 Hz),4.38(1H,d,J=3.9 Hz), 4.19–4.25(1H,m), 3.94–4.00(1H,m), 3.74–3.79(1H,m), 3.45–3.62(4H,m), 2.89–2.94(4H,m), 2.79(1H,m), 2.27–2.34 (1H,m), 2.13–2.21(1H,m), 1.53–1.91(7H,m).

Infrared spectrum ν max cm$^{-1}$(CHCl$_3$): 2964, 1640, 1440, 1362,1175.

Mass spectrometric analysis (FAB) m/z: 450((M+H)$^+$).

Example 3(c)

1-{2-[(2R)-(3,4-dichlorophenyl)-4-(cycipentanecarbonyl)morpholin-2-yl]ethyl}spiro [benzo[c]thiophene-1(3H),4'-piperidine]-(2S)-oxide The desired compound (132 mg, 49%) was obtained as white crystals. according to the procedures described in Example 1(c) using 2-[(2R)-(3,4-dichlorophenyl)-4-(cyclopentanecarbonyl)morpholin-2-yl]ethanol methanesulfonate (210 mg, 0.47 mmol) and spiro[benzo[c] thiophene-1(3H),4'-piperidine]-(2S)-oxide hydrochloride (144 mg, 0.56 mmol).

Melting point: 99–100° C.

[α]$_D^{24}$+55.0° (c=0.50, chloroform)

Nuclear magnetic resonance spectrum (400 MHz, CDCl$_3$)δ ppm: 7.55–7.59(1H,m), 7.41–7.48(1H,m), 7.20–7.36(5H m), 4.59(1H,d,J=13.8 Hz), 4.31(1H,d,J=16.8 Hz), 3.98(1H,d,J=16.8 Hz), 3.43–3.82(4H,m), 3.36(1H,d,J= 13.8 Hz), 2.89–2.94(1H,m), 2.73–2.84(2H,m), 2.17–2.43 (6H,m), 2.04–2.15(1H,m), 1.48–1.99(11H,m).

Infrared spectrum ν max cm$^{-1}$(KBr): 3441, 2952, 1640, 1435, 1227.

Mass spectrometric analysis (FAB) m/z: 575((M+H)$^+$).

Elemental analysis (%): for C$_{30}$H$_{36}$N$_2$O$_3$SCl$_2$.0.5H$_2$O:

Calculated: C;61.63,H;6.38,N;4.79,S;5.49,Cl;12.13

Found: C;61.46,H;6.28,N;4.69,S;5.40,Cl;11.57.

Example 4

1-{2-[(2R)-(3,4-dichlorophenyl)-4-(cyclohexanecarbonyl)morpholin-2-yl]ethyl}spiro [benzo[c]thiophene-1(3H),4'-piperidine]-(2S)-oxide

Example 4(a)

2-[(2R)-(3,4-dichlorophenyl)-4-(cyclohexanecarbonyl)morpholin-2-yl]ethanol

The desired compound (405 mg, 96%) was obtained as a white amorphous solid, according to the procedures described in Example 1(a) using cyclohexanecarboxylic acid (147 mg, 1.15 mmol) and 2-[(2R)-(3,4-dichlorophenyl) morpholin-2-yl]ethanol (300 mg, 1.09 mmol).

Nuclear magnetic resonance spectrum (400 MHz, $CDCl_3$)δ ppm: 7.58(1H,d,J=20 Hz), 7.42(1H,d,J=8.0 Hz), 7.28(1H,m), 4.63(1H,d,J=14.0 Hz), 3.40–3.93(6H,m), 3.34 (1H,d,J=14.0 Hz), 1.15–2.55(13H,m).

Infrared spectrum ν max $cm^{-1}$($CHCl_3$): 3623, 3536, 2936, 2858, 1711, 1634.

Mass spectrometric analysis (FAB) m/z: 386((M+H)$^+$).

Example 4(b)

2-[(2R)-(3,4-dichlorophenyl)-4-(cyclohexanecarbonyl)morpholin-2-yl]ethanol methanesulfonate The desired compound (450 mg, 94%) was obtained as a white amorphous solid, according to the procedures described in Example 1(b) using 2-[(2R)-(3,4-dichlorophenyl)-4-(cyclohexanecarbonyl)morpholin-2-yl] ethanol (400 mg, 1.04 mmol).

Nuclear magnetic resonance spectrum (400 MHz. $CDCl_3$)δ ppm: 7.56(1H,d,J=2.0 Hz), 7.44(1H,d,J=8.0 Hz), 7.26(1H,dd,J=8.0 and 2.0 Hz), 4.39(1H,d,J=14.0 Hz), 4.22 (1H,m), 3.97(1H,dt,J=10.0 and 7.0 Hz), 3.77(1H,dt,J=12.0 and 4.0 Hz), 3.60(1H,m), 3.48(1H,m), 3.43(1H,d,J=14.0 Hz), 2.94(3H,s), 2.12–2.60(3H,m), 1.15–1.85(10H,m).

Infrared spectrum ν max $cm^{-1}$($CHCl_3$): 2936, 2858, 1634.

Mass spectrometric analysis (FAB) m/z: 464((M+H)$^+$).

Example 4(c)

1-{2-[(2R)-(3,4-dichlorophenyl)-4-(cyclohexanecarbonyl)morpholin-2-yl]ethyl}spiro [benzo[c]thiophene-1(3H),4'-piperidine]-(2S)-oxide The desired compound (168 mg, 70%) was obtained as white crystals, according to the procedures described in Example 1(c) using 2-[(2R)-(3,4-dichlorophenyl)-4-(cyclohexanecarbonyl)morpholin-2-yl]ethanol methanesulfonate (190 mg, 0.41 mmol) and spiro[benzo[c] thiophene-1(3H),4'-piperidine]-(2S)-oxide hydrochloride (127 mg, 0.49 mmol).

Melting point: 119–123° C.

$[\alpha]_D^{24}$+50.1° (c=0.44, chloroform)

Nuclear magnetic resonance spectrum (400 MHz, $CDCl_3$)δ ppm: 7.25–7.60(7H,m), 4.60(1H,d,J=14.0 Hz), 4.30(1H,d,J=17.0 Hz), 3.99(1H,d,J=17.0 Hz), 3.40–3.90 (4H,m), 3.32(1H,d,J=14.0 Hz), 2.94(1H,m), 2.74(1H,m), 1.15–2.60(21H,m).

Infrared spectrum ν max $cm^{-1}$(KBr): 3438, 2928, 2855, 1642.

Mass spectrometric analysis (FAB) mlz: 589((M+H)$^+$).

Elemental analysis (%): for $C_{31}H_{38}N_2O_3SCl_2$.0.2$H_2O$: Calculated C;62.96,H;6.51,N;4.74,S;5.42,Cl;11.99
Found: C;62.80,H;6.69,N;4.65,S;5.39,Cl;12.07.

Example 5

1-{2-[(2R)-(3,4-dichlorophenyl)-4-(cyclopropanecarbonyl)morpholin-2-yl]ethyl}-4-phenylpiperidine-4-carboxamide The desired compound (93 mg, 69%) was obtained as white crystals, according to the procedures described in Example 1(c) using 2-[(2R)-(3,4-dichlorophenyl)-4-(cyclopropanecarbonyl)morpholin-2-yl]ethanol methanesulfonate (107 mg, 0.25 mmol) and 4-phenylpiperidine carboxamide hydrochloride (67 mg, 0.30 mmol).

Melting point: 94–96° C.

$[\alpha]_D^{23}$+39.60(c=0.54, methanol)

Nuclear magnetic resonance spectrum (400 MHz, $CDCl_3$)δ ppm: 7.22–7.55(8H, m), 5.17(2H, s), 1.85–4.43 (19H, m), 0.65–1.15(4H, m).

Infrared spectrum ν max $cm^{-1}$(KBr): 3350,2927, 1676, 1633,1470.

Mass spectrometric analysis (FAB) m/z: 530((M+H)$^+$).

Elemental analysis (%): for $C_{28}H_{33}N_3O_3Cl_2$.0.5$H_2O$:
Calculated: C;62.34,H; 6.35, N;7.79, Cl;13.14
Found: C;62.40, H:6.54, N;7.47, Cl;13.81.

Example 6

1-{2-[(2R)-(3,4-dichlorophenyl)-4-(cyclopentanecarbonyl)morpholin-2-yl]ethyl}-4-(2-pyridyl)piperidine-4-carboxamide The desired compound (129 mg, 69%) was obtained as white crystals, according to the procedures described in Example 1(c) using 2-[(2R)-(3,4-dichlorophenyl)-4-(cyclopentanecarbonyl)morpholin-2-yl]ethanol methanesulfonate (150 mg, 0.33 mmol) and 4-(2-pyridyl)piperidin-4-carboxamide dihydrochloride (102 mg, 0.37 mmol).

Melting point: 189–190° C.

$[\alpha]_D^{23}$+43.3° (c=0.53, methanol)

Nuclear magnetic resonance spectrum (400 MHz, $CDCl_3$)δ ppm: 8.57(1H,d,J=4.7 Hz), 7.15–7.68(6H,m), 6.40 (1H,br.s), 5.14(1H,br.s), 4.57(1H,d,J=13.5 Hz), 3.20–3.95 (5H,m), 1.45–2.98(21H,m).

Infrared spectrum ν max $cm^{-1}$(KBr): 3412.2953,1679, 1639, 1468,1433.

Mass spectrometric analysis (FAB) m/z: 559((M+H)$^+$)

Elemental analysis (%): for $C_{29}H_{36}N_4O_3Cl_2$:
Calculated: C;62.25,H; 6.49, N;10.01, Cl;12.67
Found: C;62.06,H; 6.43, N;9.89, Cl; 12.67

Example 7

N,N-Dimethyl-1-{2-[(2R)-(3,4-dichlorophenyl)-4-(cyclopentanecarbonyl)morpholin-2-yl]ethyl}-4-(cyclohexyl)piperidine-4-carboxamide The desired compound (152 mg, 77%) was obtained as white crystals, according to the procedures described in Example 1(c) using 2-[(2R)-(3,4-dichlorophenyl)-4-(cyclopentanecarbonyl)morpholin-2-yl]ethanol methanesulfonate (150 mg, 0.33 mmol) and N,N-dimethyl-4-(cyclohexyl)piperidine-4-carboxamide hydrochloride (101 mg, 0.37 mmol).

Melting point: 98–102° C.

$[\alpha]_D^{23}$+40.90(c=0.52, methanol)

Nuclear magnetic resonance spectrum (400 MHz, $CDCl_3$)δ ppm: 7.21–7.53(3H,m), 4.53(1H,d,J=13.8 Hz), 2.60–3.95(8H,m), 3.02(6H,s), 1.40–2.35(22H,m), 1.00–1.35 (7H,m).

Infrared spectrum ν max $cm^{-1}$(KBr): 3441, 2932, 2855, 1630, 1450.

Mass spectrometric analysis (FAB) m/z: 591((M+H)$^+$)

Elemental analysis (%): for $C_{32}H_{47}N_3O_3Cl_2$.0.5$H_2O$:
Calculated: C;63.88,H; 8.04, N;6.98, Cl; 11.79
Found: C:64.06,H; 7.97, N;6.84, Cl11.72

Example 8

1-{2-[(2R)-(3,4-dichlorophenyl)-4-(cyclopentanecarbonyl)morpholin-2-yl]ethyl}spiro [((2S)-hydroxy)indane-1,4'-piperidine]

The desired compound (817 mg, 78%) was obtained as white crystals, according to the procedure described in Example 1(c) using 2-[(2R)-(3,4-dichlorophenyl)-4-(cyclopentanecarbonyl)morpholin-2-yl]ethanol methanesulfonate (850 mg, 1.89 mmol) and [((2S)-hydroxy)indane-1,4'-piperidine] hydrochloride (497 mg, 2.08 mmol).

Melting point: 192–193° C.

$[\alpha]_D^{23}$+63.1° (c=0.52, methanol)

Nuclear magnetic resonance spectrum (400 MHz, $CDCl_3$)δ ppm: 7.16–7.58(7H,m), 4.60(1H,d,J=13.6 Hz), 4.40(1H,d,J=3.3 Hz), 3.24–3.98(7H,m), 2.64–3.01(4H,m), 1.42–2.43(18H,m).

Infrared spectrum ν max $cm^{-1}$(KBr): 3423, 2949, 1640, 1434.

Mass spectrometric analysis (FAB) m/z: 557((M+H)$^+$)

Elemental analysis (%): for $C_{31}H_{38}N_2O_3Cl_2$:
Calculated: C;66.78,H; 6.87, N;5.02, Cl;12.72
Found: C;66.77,H; 6.79, N;5.07, Cl;12.41.

Example 9

1-{2-[(2R)-(3,4-dichlorophenyl)-4-(L-prolyl)morpholin-2-yl]ethyl}spiro[((2S) -hydroxy)indane-1,4'-piperidine] dihydrochloride Example 9(a)

2-[(2R)-(3,4-dichlorophenyl)-4-(N-t-butoxycarbonyl-L-prolyl)morpholin-2-yl]ethanol The desired compound (314 mg, 92%) was obtained as a white amorphous solid, according to the procedures described in Example 1(a) using 2-[(2R)-(3,4-dichlorophenyl)morpholin-2-yl]ethanol (200 mg, 0.72 mmol) and N-t-butoxycarbonyl-L-proline (171 mg, 0.80 mmol).

Nuclear magnetic resonance spectrum (270 MHz, $CDCl_3$)δ ppm: 7.20–7.62(3H,m), 3.98–4.94(2H,m), 3.10–3.91(9H,m), 1.55–2.25(7H,m), 1.46(3H,s), 1.38(3H,s), 1.14(3H,s).

Infrared spectrum ν max $cm^{-1}$(KBr): 3442, 2975,2876, 1695, 1401.

Mass spectrometric analysis (FAB) m/z: 473((M+H)$^+$)

Example 9(b)

2-[(2R)-(3,4-dichlorophenyl)-4-(N-t-butoxycarbonyl-L-prolyl)morpholin-2-yl]ethanol methanesulfonate The desired compound (313 mg, 94%) was obtained as a white amorphous solid, according to the procedures described in Example 1(b) using 2-[(2R)-(3,4-dichlorophenyl)-4-(N-t-butoxycarbonyl-L-prolyl)morpholin-2-yl]ethanol (286 mg, 0.60 mmol).

Nuclear magnetic resonance spectrum (270 MHz, $CDCl_3$)δ ppm: 7.20–7.60(3H,m), 4.10–4.77(2H,m), 3.30–4.00(9H,m), 2.93(3H,s), 1.75–2.40(6H,m), 1.46(3H,s), 1.40(3H,s), 1.16(3H,s).

Infrared spectrum ν max $cm^{-1}$(KBr): 2976, 1695, 1659, 1401, 1359, 1175.

Mass spectrometric analysis (FAB) m/z: 551 ((M+H)$^+$)

Example 9(c)

1-{2-[(2R)-(3,4-dichlorophenyl)-4-(N-t-butoxycarbonyl-L-prolyl)morpholin-2-yl]ethyl}spiro[((2S)-hydroxy)indane-1,4'-piperidine]

The desired compound (175 mg, 73%) was obtained as white crystals, according to the procedures described in Example 1(c) using 2-[(2R)-(3,4-dichlorophenyl)-4-(N-t-butoxycarbonyl-L-prolyl)morpholin- 2-yl]ethanol methanesulfonate (200 mg, 0.36 mmol) and [((2S)-hydroxy)indane-1,4'-piperidine] hydrochloride (95 mg, 0.40 mmol).

Melting point: 108–110° C.

$[\alpha]_D^{24}$+21.5° (c=0.52, methanol)

Nuclear magnetic resonance spectrum (400 MHz, $CDCl_3$)δ ppm: 7.20–7.62(7H,m), 4.30–4.84(3Hm), 3.20–3.98(10H,m), 1.58–2.90(16H,m), 1.46(3H,s), 1.40 (3H,s), 1.17(3H,s).

Infrared spectrum ν max $cm^{-1}$(KBr): 3442, 2928, 1696, 1661, 1400.

Mass spectrometric analysis (FAB) o/z: 658((M+H)$^+$)

Elemental analysis (%): for $C_{35}H_{45}N_3O_5Cl_2 \cdot 0.5H_2O$:
Calculated: C;62.96,H; 6.94, N;6.29, Cl;10.62
Found: C;63.09,H; 7.10, N;6.27, Cl;10.50.

Example 9(d)

1-{2-[(2R)-(3,4-dichlorophenyl)4-(L-prolyl)morpholin-2yl]ethyl}spiro[((2S)-hydroxy)indane-1,4'-piperidine] dihydrochloride A dioxane solution of hydrogen chloride (4N, 1.5 ml) was added to a solution of 1-{2-[(2R)-(3,4-dichlorophenyl)-4-(N-t-butoxycarbonyl-L-prolyl)morpholin-2-yl]ethyl}spiro[((2S)-hydroxy)indane-1,4'-piperidine], which was prepared in Example 9(c), (131 mg, 0.20 mmol) in ethanol (2 ml) with ice-cooling. The solution was stirred at room temperature for 3 hours. The solvent was distilled off under reduced pressure. To the residue, diethyl ether was added. After distillation to dryness, the desired compound (127 mg, 100%) was obtained as white crystals.

Melting point: 290–294° C.

$[\alpha]_D^{23}$+24.7° (c=0.52, methanol)

Nuclear magnetic resonance spectrum (400 MHz, DMSO-$d_6$)δ ppm: 9.83–11.20(2H,m), 8.45–8.63(3H,m), 7.43–7.98(3H,m), 7.05–7.25(4H,m), 3.60–5.05(8H,m), 2.85–3.58(8H,m), 1.48–2.80(13H,m).

Infrared spectrum ν max $cm^{-1}$(KBr): 3350, 2925, 2677, 2574, 165,1476.

Mass spectrometric analysis (FAB) m/z: 558((M+H)$^+$, free form)

Elemental analysis (%): for $C_{30}H_{37}N_3O_3Cl_2 \cdot 2HCl \cdot 0.5H_2O$:
Calculated: C;56.26,H; 6.29, N;6.56, Cl;22.14
Found: C;56.02,H; 6.31, N;6.55, Cl;21.94.

Example 10

1-{2-[(2R)-(3,4-dichlorophenyl)-4-(4-piperidinecarbonyl)morpholin-2-yl]ethyl}spiro[((2S)-hydroxy)indane-1,4'-piperidine] dihydrochloride Example 10(a)

2-[(2R)-(3,4-dichlorophenyl)-4-(N-t-butoxycarbonyl-4-piperidinecarbonyl)morpholin-2-yl]ethanol The desired compound (226 mg, 85%) was obtained as an amorphous solid, according to the procedures described in Example 1(a) using 2-[(2R)-(3,4-dichlorophenyl)morpholin-2-yl]ethanol (150 mg, 0.54 mmol) and N-t-butoxycarbonyl-4-piperidinecarboxylic acid (137 mg, 0.60 mmol).

Nuclear magnetic resonance spectrum (270 MHz, $CDCl_3$)δ ppm: 7.57(1H,d,J=1.9 Hz), 7.43(1H,d,J=8.5 Hz), 7.26(1H,dd,J=8.5,1.9 Hz), 4.69(1H,d,J=14.2 Hz), 3.99–4.22 (2H,m), 3.73–3.85(1H,m), 3.40–3.64(5H,m), 3.32(1H,d,J=14.2 Hz), 2.60–2.82(2H,m), 2.45–2.58(1H,m), 1.88–2.12 (2H,m), 1.50–1.85(3H,m), 1.45(9H,s), 1.30–1.50(2H,m).

Infrared spectrum ν max cm$^{-1}$(KBr): 3447, 2930, 1690, 1640, 1427.

Mass spectrometric analysis (FAB) m/z: 487((M+H)$^+$)

Example 10(b)

2-[(2R)-(3,4-dichorophenyl)-4-(N-t-butoxycarbonyl-4-piperidinecarbonyl)morpholin-2-yl]ethanol methanesulfonate The desired compound (216 mg, 93%) was obtained as a white amorphous solid, according to the procedures described in Example 1(b) using 2-[(2R)-(3,4-dichlorophenyl)-4-(N-t-butoxycarbonyl-4-piperidinecarbonyl)morpholin-2-yl]ethanol (200 mg, 0.41 mmol).

Nuclear magnetic resonance spectrum (270 MHz, CDCl$_3$)δ ppm: 7.55(1H,d,J=1.8 Hz), 7.45(1H,d,J=8.3 Hz), 7.26(1H,dd,J=8.3,1.8 Hz), 4.43(1H,d,J=13.9 Hz), 3.43(1H, d,J=13.9 Hz), 3.40–4.30(8H,m), 2.94(3H,s), 2.60–2.82(2H, m), 2.45–2.60(1H,m), 2.10–2.35(2H,m), 1.50–1.80(2H,m), 1.46(9H,s), 1.35–1.50(2H,m).

Infrared spectrum ν max cm$^{-1}$(KBr): 2974,2932, 1689, 1642, 1175.

Mass spectrometric analysis (FAB) m/z: 565((M+H)$^+$)

Example 10(c)

1-{2-[(2R)-(3,4-dichlorophenyl)-4-(N-t-butoxycarbonyl-4-piperidinecarbonyl) morpholin-2-yl]ethyl}spiro[((2S)-hydroxy)indane-1,4'-piperidine]

The desired compound (193 mg, 83%) was obtained as white crystals, according to the procedures described in Example 1(c) using 2-[(2R)-(3,4-dichlorophenyl)-4-(N-t-butoxycarbonyl-4-piperidinecarbonyl)morpholin-2-yl] ethanol methanesulfonate (195 mg, 0.35 mmol) and [((2S)-hydroxy)indane-1,4'-piperidine] hydrochloride (91 mg, 0.38 mmol).

Melting point: 105–107° C.

[α]$_D^{23}$+59.0° (c=0.53, methanol)

Nuclear magnetic resonance spectrum (400 MHz, CDCl$_3$)δ ppm: 7.56(1H,d,J=1.7 Hz), 7.42(1H,d,J=8.5 Hz), 7.20–7.30(5H,m), 3.20–4.75(8H,m), 2.45–2.90(6H,m), 1.46 (9H,s), 1.35–2.40(15H,m).

Infrared spectrum ν max cm$^{-1}$(KBr): 3448,2926,1693, 1644,1426,1169.

Mass spectrometric analysis (FAB) m/z: 672((M+H)$^+$)

Elemental analysis (%): for C$_{36}$H$_{47}$N$_3$O$_5$Cl$_2$.0.3H$_2$O:

Calculated: C;63.77,H; 7.08, N;6.20, Cl; 10.46

Found: C;63.81,H; 7.04, N;6.05, Cl;10.56.

Example 10(d)

1-{2-[(2R)-(3,4-dichlorophenyl)-4-(4-piperidinecarbonyl)morpholin-2-yl]ethyl}spiro [((2S)-hydroxy)indane-1,4'-piperidine] dihydrochloride The desired compound (141 mg, 100%) was obtained as white crystals, according to the procedures described in Example 9(c) using 1-{2-[(2R)-(3,4-dichlorophenyl)-4-(N-t-butoxycarbonyl-4-piperidinecarbonyl)morpholin-2-yl] ethyl}spiro[((2S)-hydroxy)indane-1,4'-piperidine] (147 mg, 0.22 mmol).

Melting point: 216–220° C.

[α]$_D^{23}$+45.6° (c=0.53, methanol)

Nuclear magnetic resonance spectrum (400 MHz, DMSO-d$_6$)δ ppm: 10.40–11.93(1H,m), 8.60–9.27(1H,m), 7.40–7.90(3H,m), 7.05–7.25(4H,m), 4.99(1H,br,s), 2.40–4.43(22H,m), 2.12–2.40(2H,m), 1.75–2.12(4H,m), 1.48–1.75(3H,m).

Infrared spectrum ν max cm$^{-1}$(KBr): 3381, 2933, 2712, 1636, 1457.

Mass spectrometric analysis (FAB) m/z: 572((M+H)$^+$, free form)

Elemental analysis (%): for C$_{31}$H$_{39}$N$_3$O$_3$Cl$_2$.2HCl.1.5H$_2$O:

Calculated: C;55.36,H; 6.59, N;6.25, Cl;21.09

Found: C;55.65,H; 6.89, N;6.19, Cl;20.70.

Example 11

1-{2-[(2R)-(3,4-dichlorophenyl)-4-(2-oxo-(4R)-thiazolidinecarbonyl)morpholin-2-yl]ethyl}spiro [((2S)-hydroxy)indane-1,4'-piperidine]

Example 11(a)

2-[(2R)-(3,4-dichlorophenyl)-4-(2-oxo-(4R)-thiazolidinecarbonyl)morpholin-2-yl]ethanol The desired compound (92 mg, 31 %) was obtained as a white solid, according to the procedures described in Example 1(a) using 2-oxo-(4R)-thiazolidinecarboxylic acid (107 mg, 0.724 mmol) and 2-[(2R)-(3,4-dichlorophenyl) morpholin-2-yl]ethanol (200 mg, 0.724 mmol).

Nuclear magnetic resonance spectrum (270 MHz, CDCl$_3$)δ ppm 7.53(1H,d,J=2.0 Hz), 7.46(1H,d,J=8.3 Hz), 7.28(1H, J=8.3,2.0 Hz), 5.85(1H,br,s), 4.53–4.81(2H,m), 3.28–3.91 (9H,m), 1.93–2.10(2H,m)

Infrared spectrum ν max cm$^{-1}$(KBr): 3251, 1680, 1470, 1375, 1239, 1092.

Mass spectrometric analysis (FAB) m/z: 405((M+H)$^+$)

Example 11(b)

2-[(2R)-(3,4-dichlorophenyl)-4-(2-oxo-(4R)-thiazolidinecarbonyl)morpholin-2-yl]ethanol methanesulfonate The desired compound (62 mg, 61 %) was obtained as a white solid. according to the procedures described in Example 1(b) using 2-[(2R)-(3,4-dichlorophenyl)-4-(2-oxo-(4R)-thiazolidinecarbonyl)morpholin-2-yl]ethanol (85 mg, 0.21 mmol).

Nuclear magnetic resonance spectrum (270 MHz, CDCl$_3$)δ ppm: 7.56(1H,d,J=1.9 Hz), 7.48(1H,d,J=8.3 Hz), 7.27(1H,J=8.3,1.9 Hz), 5.78(1H,br.s), 4.18–4.66(3H,m), 3.37–3.96(8H,m), 2.96(3H,s), 2.13–2.32(2H,m)

Infrared spectrum ν max cm$^{-1}$(KBr): 2934, 1687, 1468, 1352,1241, 1174, 1095.

Mass spectrometric analysis (FAB) m/z: 483((M+H)$^+$)

Example 11(c)

1-{2-[(2R)-(3,4-dichlorophenyl)-4-(2-oxo-(4R)-thiazolidinecarbonyl)morpholin-2-yl]ethyl}spiro [((2S)-hydroxy)indane-1,4'-piperidine]

The desired compound (32 mg, 44%) was obtained as white solid, according to the procedures described in Example 1(c) using $^2$-[(2R)-(3,4-dichlorophenyl)-4-(2-oxo-(4R)-thiazolidinecarbonyl)morpholin-2-yl]ethanol methanesulfonate (60 mg, 0.124 mmol) and [((2S)-hydroxy) indane-1,4'-piperidine] hydrochloride (31 mg, 0.130 mmol).

Melting point: 155–156° C.

$[\alpha]_D^{23}$+41.6° (c=0.38, methanol)

Nuclear magnetic resonance spectrum (400 MHz, CDCl$_3$)δ ppm: 7.57(1H,d,J=2.1 Hz), 7.44(1H,d,J=8.3 Hz), 7.14–7.29(5H,m), 5.68 (1H,br.s), 4.32–4.76(3H,m), 3.22–3.85(8H,m), 2.57–2.83(3H,m), 1.41–2.43(11H,m)

Infrared spectrum ν max cm$^{-1}$(KBr): 3400, 2924, 1683, 1472, 1238, 1090, 759.

Mass spectrometric analysis (FAB) m/z: 590 ((M+H)$^+$)

Elemental analysis (%): for $C_{29}H_{33}N_3O_4SCl_2 \cdot H_2O$:

Calculated: C;57.23,H; 5.80. N;6.90, Cl;11.65, S;5.27

Found: C;56.54,H; 5.73, N;6.53, Cl; 11.48, S;5.61

Example 12

1-{2-[4-(cyclohexylmethyl)-(2R)-(3,4-dichlorophenyl)-5-oxomorpholin-2-yl]ethyl}spiro[((2S)-hydroxy)indane-1,4'-piperidine]

Example 12(a)

(2R)-(3,4-dichlorophenyl)-4-(triphenylmethoxy)butan-1,2-diol (DHQD)$_2$PHAL (85 mg, 0.11 mmol), potassium ferricyanide (10.75g, 32.7 mmol) and potassium carbonate (4.51 g, 32.7 mmol) were added to a mixture of t-butanol (200 ml) and water (200 ml). To the mixture, osmium tetraoxide (55 μl (0.02 mmol) of a 0.393 M toluene solution) was added and then 3-(3,4-dichlorophenyl)-3-buten-1-ol triphenylmethylether (5.00 g, 10.9 mmol) was added. This mixture was stirred at room temperature for 3 days. After addition of sodium sulfite (15 g) to the reaction mixture, the mixture was stirred at room temperature for 1 hour. The reaction mixture was extracted with ethyl acetate. The organic layer was dried over anhydrous magnesium sulfate and then the solvent was distilled off under reduced pressure. The residue was purified by flash chromatography on a silica gel column using n-hexane/ethyl acetate=50/1–2/1 as an eluant to afford the title compound (3.56 g, 66%) as white crystals.

Nuclear magnetic resonance spectrum (270 MHz, CDCl$_3$)δ ppm: 7.43(1H,d,J=2.0 Hz), 7.19–7.39(16H,m), 7.03(1H,dd,J=8.5,2.0 Hz), 4.69(1H,s), 3.48–3.66(2H,m), 3.34–3.45(1H,m), 2.94(1H,m), 2.49(1H,m), 2.32(1H,m), 1.92(1H,m)

Infrared spectrum ν max cm$^{-1}$(KBr): 3446, 3059, 2932, 1449, 1062.

Mass spectrometric analysis (FAB) m/z: 515((M+Na)$^+$)

Example 12(b)

4-(triphenylmethoxy)-(2R)-(3,4-dichlorophenyl)-1-[N-(chloroacetyl)-N-(cyclohexylmethyl)amino]-2-butanol p-Toluenesulfonyl chloride (2.03g, 10.7 mmol) was added to a solution of (2R)-(3,4-dichlorophenyl)-4-(triphenylmethoxy)butan-1,2-diol (3.51 g, 7.11 mmol), which was prepared in Example 12(a), in pyridine (17 ml). The mixture was stirred at room temperature overnight. To the reaction mixture, water was added and it was extracted with ethyl acetate. The organic layer was dried over anhydrous magnesium sulfate and then the solvent was distilled off under reduced pressure. The residue was dissolved in acetonitrile (50 ml) and lithium perchlorate trihydrate (3.42 g. 21.3 mmol) and cyclohexylmethylamine (2.78 ml, 21.3 mmol) were added to the solution. The mixture was stirred at 100° C. overnight. Ethyl acetate was added to the reaction mixture and it was washed with a saturated aqueous solution of sodium chloride. The organic layer was dried over anhydrous magnesium sulfate and then the solvent was distilled off under reduced pressure. A half of the residue by weight was dissolved in methylene chloride (30 ml). To this solution, triethylamine (2.48 ml, 17.8 mmol) and chloroacetyl chloride (1.42 ml, 17.8 mmol) were added with ice-cooling. The mixture was stirred at 0° C. for 1 hour. To the reaction mixture, methylene chloride was added, the organic layer was washed with water and then with a saturated aquoeus solution of sodium chloride and was dried over anhydrous magnesium sulfate. After distillation under reduced pressure, the resulting residue was purified by flash chromatography on a silica gel column using n-hexane/ethyl acetate=20/1–10/1 as an eluant to afford the title compound (1.49 g, 63%).

Nuclear magnetic resonance spectrum (270 MHz, CDCl$_3$)δ ppm: 6.98–7.62(18H,m), 4.84 and 4.99(total 1H, each br.s), 3.97–4.38(3H,m), 2.81–3.72(5H,m), 1.93–2.37 (2H,m), 1.40–1.80(6H,m), 1.10–1.30(3H,m), 0.75–1.00(2H, m)

Infrared spectrum ν max cm$^{-1}$(KBr): 3455, 2926, 2853, 1649, 1469,1449, 1073, 1029.

Mass spectrometric analysis (FAB) m/z: 664((M+H)$^+$)

Example 12(c)

2-[4-(cyclohexylmethyl)-(2R)-(3,4-dichlorophenyl)-3-oxomorpholin-2-yl]ethanol triphenylmethylether Sodium hydride (127 mg, (3.18 mmol) of a 60% suspension in oil) was added to a solution of 4-(triphenylmethoxy)-(2R)-(3,4-dichlorophenyl)-1-[N-(chloroacetyl)-N-(cyclohexylmethyl)amino]-2-butanol (1.41 g, 2.12 mmol), which was prepered in Example 12(b), in dimethylformamide (15 ml) with ice-cooling. The mixture was stirred at room temperature overnight. The reaction mixture was poured into ice-water and then it was extracted with ethyl acetate. The organic layer was dried over anhydrous magnesium sulfate and then the solvent was distilled off under reduced pressure. The residue was purified by flash chromatography on a silica gel column using n-hexane/ethyl acetate=10/1–5/1 as an eluant to afford the title compound (1.08 g, 81%).

Nuclear magnetic resonance spectrum (270 MHz, CDCl$_3$)δ ppm: 7.19–7.35(17H,m), 6.89(1H,dd,J=8.4,2.2 Hz), 4.13(1H,d,J=17.0 Hz), 3.88(1H,d,J=17.0 Hz), 3.80(1H, d,J=13.4 Hz), 3.70(1H,d,J=13.4 Hz), 3.39(1H,dd,J=13.4,7.0 Hz), 3.18(1H,m), 3.02(1H,dd,J=13.4,7.3 Hz), 2.67(1H,m), 2.13–2.24(2H,m), 1.10–1.80(9H,m), 0.85–1.08(2H,m)

Infrared spectrum ν max cm$^{-1}$(KBr): 2924, 2852, 1664, 1490, 1449.

Mass spectrometric analysis (FAB) m/z: 628((M+H)$^+$)

Example 12(d)

2-[4-(cyclohexylmethyl)-(2R)-(3,4-dichlorophenyl)-3-oxomorpholin-2-yl]ethanol methanesulfonate A solution of hydrogen chloride in dioxane (4N, 4.1 ml) was added to a solution of 2-[4-(cyclohexylmethyl)-(2R)-(3,4-dichlorophenyl)-3-oxomorpholin-2-yl]ethanol triphenylmethylether (1.04 g, 1.65 mmol), which was prepered in Example 12(c), in ethanol (10 ml) with ice-cooling. The mixture was stirred at room temperature for 1 hour. To the reaction mixture, water was added and then it was extracted with ethyl acetate. The organic layer was washed with a saturated aqueous solution of sodium chloride and was then dried over anhydrous magnesium sulfate. After the solvent was distilled off under reduced pressure, the residue was purified by flash chromatography on a silica gel column using n-hexane/ethyl acetate=10/1–0/1 as the eluant to afford the alcohol derivative (440 mg, 69%). The alcohol derivative (418 mg, 1.08 mmol) was dissolved in methylene chloride (10 ml), and triethylamine (0.23 ml, 1.62 mmol) and methanesulfonyl chloride (0.10 ml, 1.30 mmol) were added to the solution. The mixture was stirred at room temperature for 2 days. Methylene chloride was added to the reaction mixture, this was washed with water and then with a saturated aqueous solution of sodium chloride, and the organic layer was dried over anhydrous magnesium sulfate. After the solvent was distilled off under reduced pressure, the residue was purified by flash chromatography on a silica gel column using n-hexane/ethyl acetate=1/1–1/3 as an eluant to afford the title compound (500 mg, 99%).

Nuclear magnetic resonance spectrum (270 MHz, $CDCl_3$)δ ppm: 7.49(1H,d,J=8.4 Hz), 7.46(1H,d.J=2.1 Hz), 7.20(1H,dd.J=8.4,2.1 Hz), 4.27(1H,d,J=17.0 Hz), 4.23(1H, m), 4.15(1H,d.J=17.0 Hz), 4.00(1H,ddd,J=10.5,7.3,7.3 Hz), 3.69(1H,d.J=13.2Hz), 3.61(1H,d,J=13.2Hz), 3.28(1H,dd, 13.6,7.0 Hz), 3.22(1H,dd.J=13.6,7.7 Hz), 2.92(3H,s), 2.40 (1H,ddd,J=14.6,6.4,6.4 Hz), 2.26(1H,ddd,J=14.6,7.3,7.3 Hz), 1.46–1.78(6H,m), 1.12–1.29(3H,m), 0.88–1.04(2H,m)

Infrared spectrum ν max $cm^{-1}$(neat): 2926,2853,1657, 1474, 1450,1356,1176.

Mass spectrometric analysis (EI) m/z: 463($M^+$)

Example 12(e)

1-{2-[4-(cyclohexylmethyl)-(2R)-(3,4-dichlorophenyl)-5-oxomorpholin-2-yl]ethyl}spiro [((2S)-hydroxy)indane-1,4'-piperidine]

The desired compound (94 mg, 76%) was obtained as white crystals, according to the procedures described in Example 1(c) using 2-[4-(cyclohexylmethyl)-(2R)-(3,4-dichlorophenyl)-3-oxomorpholin-2-yl]ethanol methanesulfonate (100 mg, 0.22 mmol) and [((2S)-hydroxy)indane-1,4'-piperidine] hydrochloride (57 mg, 0.24 mmol).

Melting point: 84–86° C.

$[\alpha]_D^{23}$+35.80 (c=0.52, methanol)

Nuclear magnetic resonance spectrum (400 MHz, $CDCl_3$)δ ppm: 7.47(1H,d,J=2.1 Hz), 7.47(1H,d,J=8.5 Hz), 7.17–7.24(5H,m), 4.41(1H,dd,J–5.2,1.8 Hz), 4.24(1H,d,J= 17.0 Hz), 4.12(1H,d,J=17.0 Hz), 3.78(1H,d,J=12.9 Hz), 3.58 (1H,d,J=12.9 Hz), 3.23–3.31(3H,m), 2.55–2.87(3H,m), 1.45–2.40(17H,m), 1.15–1.32(3H,m), 0.91–1.08(2H,m)

Infrared spectrum ν max $cm^{-1}$(KBr): 3417,2924,2851, 1654, 1474,1450.11381.

Mass spectrometric analysis (FAB) m/z: 571 (($M+H)^+$)

Elemental analysis (%): for $C_{32}H_{40}N_2O_3Cl_2$.0.3$H_2O$:

Calculated: C;66.61,H; 7.09, N;4.86, Cl;12.29

Found: C;66.89,H; 6.85, N:4.83. Cl;11.83

Example 13

1-{2-[3-(cyclohexylmethyl)-(5R)-(3,4-dichlorophenyl)-2-oxooxazolidin-5-yl]ethyl}spiro [((2S)-hydroxy)indane-1,4'-piperidine]

Example 13(a)

2-[3-(cyclohexylmethyl)-(5R)-(3,4-dichlorophenyl)-2-oxooxazolidin-5-yl]ethanol triphenylmethylether p-Toluenesulfonyl chloride (2.03g, 10.7 mmol) was added to a solution of (2R)-(3,4-dichlorophenyl)-4-(triphenylmethoxy)butan-1,2-diol (3.51 g, 7.11 mmol), which was prepered in Example 12(a), in pyridine (17 ml). The mixture was stirred at room temperature overnight. To the reaction mixture, water was added and then this was extracted with ethyl acetate. The organic layer was dried over anydrous magnesium sulfate and the solvent was distilled off under reduced pressure. The residue was dissolved in acetonitrile (50 ml), and lithium perchlorate trihydrate (3.42 g. 21.3 mmol) and cyclohexylmethylamine (2.78 ml, 21.3 mmol) were added to the solution. The mixture was stirred at 100° C. overnight. Ethyl acetate was added to the reaction mixture, this was washed with a saturated aqueous solution of sodium chloride, and the solvent was distilled off under reduced pressure. A half of the resulting residue by weight was dissolved in methylene chloride (30 ml), and triethylamine (2.48 ml, 17.8 mmol) and di-t-butyldicarbonate (3.88 g, 17.8 mmol) were added to the solution with ice-cooling. The mixture was stirred at room temperature overnight. To the reaction mixture, methylene chloride was added, this was washed with water, and the organic layer was dried over anhydrous magnesium sulfate. After the solvent was distilled off, the resulting residue was dissolved in dimethylformamide (30 ml). To the solution, sodium hydride (213 mg (5.34 mmol) of a 60% suspension in oil) was added with ice-cooling. The mixture was stirred at room temperature for 4 hours. The reaction mixture was poured into ice-water and this was extracted with ethyl acetate. The organic layer was washed with a saturated aqueous solution of sodium chloride and was dried over anhydrous magnesium sulfate. After the solvent was distilled off, the residue was purified by flash chromatography on a silica gel column using n-hexane/ethyl acetate= 20/1–5/1 as an eluant to afford the title compound (1.76 g, 81%).

Nuclear magnetic resonance spectrum (400 MHz. $CDCl_3$)δ ppm: 7.21–7.37(17H,m), 7.04(1H,dd,J=8.3,2.3 Hz), 3.90(1H.d,J=8.8 Hz), 3.53(1H,d,J=8.8Hz), 3.31(1H, ddd,J=10.9,5.4,5.4 Hz), 3.07(1H,dd,J=13.9,7.3 Hz), 2.93–3.00(2H,m), 2.29(1H,ddd,J=14.0,7.0,7.0 Hz), 2.15 (1H.ddd,J=14.0,5.4,5.4 Hz), 1.44–1.76(6H,m), 1.07–1.22 (3H,m), 0.84–0.99(2H,m)

Infrared spectrum ν max $cm^1$(KBr): 3059, 2924, 2852, 1759, 1449, 1265, 1064.

Mass spectrometric analysis (FAB) m/z: 612(($M-H)^+$)

Example 13(b)

2-[3-(cyclohexylmethyl)-(5R)-(3,4-dichlorophenyl)-2-oxooxazolidin-5-yl]ethanol methanesulfonate An alcohol derivative (930 mg, 91%) was prepared according to the procedures described in Example 12(d) using 2-[3-(cyclohexylmethyl)-(5R)-(3,4-dichlorophenyl)-2-oxooxazolidin-5-yl]ethanol triphenylmethylether (1.69 g, 2.75 mmol) and a solution of hydrogen chloride in dioxane (4N, 6.9 ml). The alcohol derivative (880 mg, 2.36 mmol) was dissolved in methylene chloride (18 ml), and triethylamine (0.50 ml, 3.55 mmol) and methanesulfonyl chloride (0.22 ml, 2.84 mmol) were added to the solution. The mixture was stirred at room temperature overnight. To the reaction mixture, methylene chloride was added, and this was washed with water and then with a saturated aqueous solution of sodium chloride. The organic layer was dried over anhydrous magnesium sulfate and the solvent was distilled off under reduced pressure. The residue was purified by flash chromatography on a silica gel column using n-hexane/ethyl acetate=4/1–1/1 as an eluant to afford the title compound (1.03 g, 97%).

Nuclear magnetic resonance spectrum (400 MHz, $CDCl_3$)δ ppm: 7.52(1H,d,J=8.4 Hz), 7.51(1H,d,J=2.3 Hz), 7.22(1H,dd,J=8.4,2.3 Hz), 4.33(1H,ddd,J=10.7,6.7,6.7 Hz), 4.10(1H,ddd,J=10.7,6.9,6.9 Hz), 3.79(1H,d,J=8.9 Hz), 3.59 (1H,d,J=8.9 Hz), 3.13(1H,dd,J=13.9,7.3 Hz), 3.05(1H,dd,J=13.9,7.1 Hz), 2.94(3H,s), 2.48–2.54(2H,m), 1.48–1.78(6H,m), 1.12–1.28(3H,m), 0.86–1.02(2H,m)

Infrared spectrum ν max cm$^{-1}$(CHCl$_3$): 2927, 2856, 1757, 1365, 1264, 1176.

Mass spectrometric analysis (FAB) m/z: 450((M+H)$^+$)

Example 13(c)

1-{2-[3-(cyclohexylmethyl)-(5R)-(3,4-dichlorophenyl)-2-oxooxazolidin-5-yl]ethyl}spiro[((2 S)-hydroxy)indane-1,4'-piperidine]

The desired compound (85 mg, 69%) was obtained as white crystals, according to the procedures described in Example 1(c) using 2-[3-(cyclohexylmethyl)-(5R)-(3,4-dichlorophenyl)-2-oxooxazolidin-5-yl]ethanol methanesulfonate (100 mg, 0.22 mmol) and [((2S)-hydroxy)indane-1,4'-piperidine)]hydrochloride (58 mg, 0.24 mmol).

Melting point: 67–69° C. $[\alpha]_D^{24}$-2.2° (c 0.50, methanol)

Nuclear magnetic resonance spectrum (400 MHz, CDCl$_3$)δ ppm: 7.50(1H,d,J=2.2 Hz), 7.48(1H,d,J=8.4 Hz), 7.16–7.23(5H,m), 4.43(1H,dd,=5.4,2.0 Hz), 3.80(1H,d,J=8.8 Hz), 3.56(1H,d,J=8.8 Hz), 3.28(1H,dd,J=16.6,5.4 Hz), 3.14(1H,dd,J=13.9,7.4 Hz), 3.02(1H,dd,J=13.9,6.8 Hz), 2.82(1H,dd,J=16.6,2.0 Hz), 2.15–2.90(8H,m), 1.47–2.10(11H,m), 1.10–1.30(3H,m), 0.85–1.02(2H,m)

Infrared spectrum ν max c$^{-1}$(KBr): 3437, 2924, 2852, 1752, 1475, 1449, 1268.

Mass spectrometric analysis (FAB) onlz: 557((M+H)$^+$)

Elemental analysis (%): for C$_{31}$, H$_{38}$N$_2$O$_3$Cl$_2$.0.5H$_2$O:

Calculated: C;65.72,H; 6.94, N;4.94, Cl;12.51

Found: C;65.75,H; 6.70, N;5.20, Cl;12.72.

The following compounds listed in Table 1 can be prepared in a similar manner to those described in the above examples.

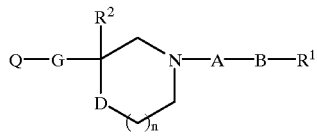

(I-1)

In "Table 1", each substituent (which is set forth as "sub." in the table) represents the following group.

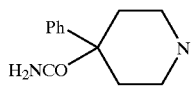
sub.1

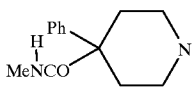
sub.2

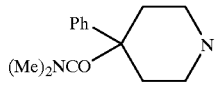
sub.3

-continued

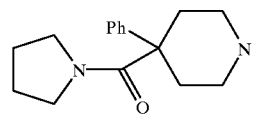
sub.4

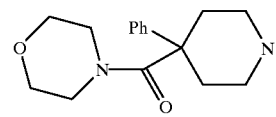
sub.5

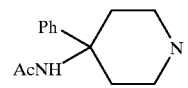
sub.6

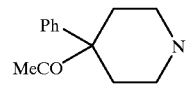
sub.7

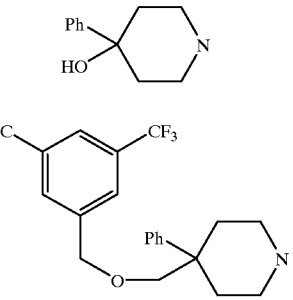
sub.8

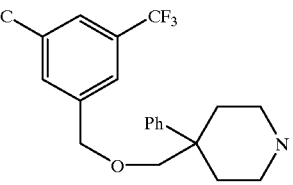
sub.9

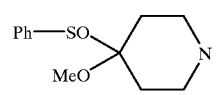
sub.10

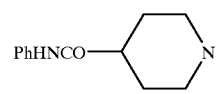
sub.11

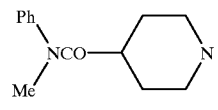
sub.12

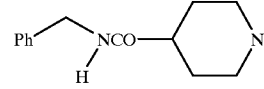
sub.13

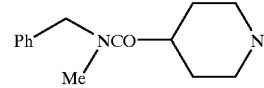
sub.14

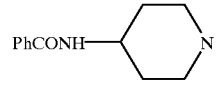
sub.15

sub.16

| | |
|---|---|
| sub.17 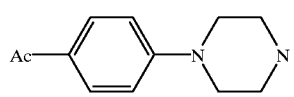 | sub.26 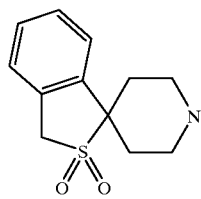 |
| sub.18 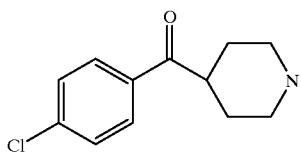 | sub.27 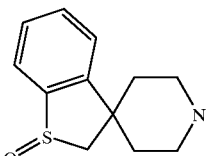 |
| sub.19 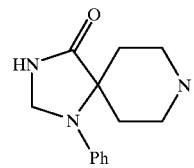 | sub.28 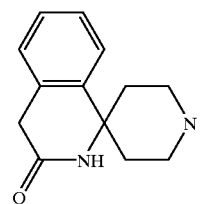 |
| sub.20 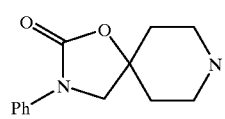 | sub.29 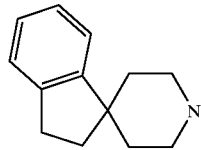 |
| sub.21 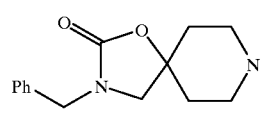 | sub.30 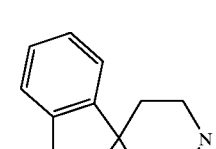 |
| sub.22 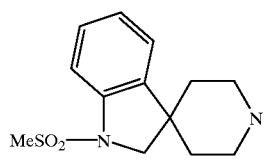 | sub.31 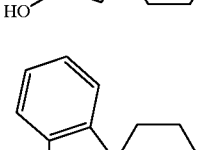 |
| sub.23 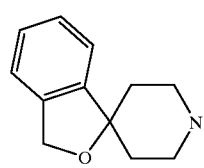 | sub.32 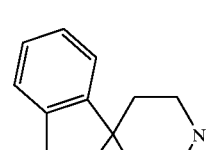 |
| sub.24 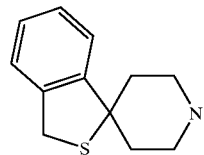 | sub.33 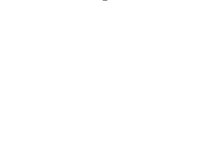 |
| sub.25 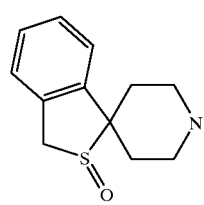 | | sub.34

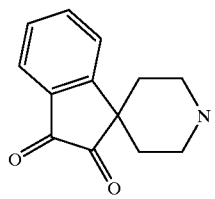

sub.35

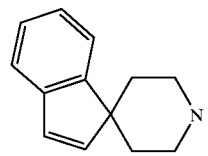

The following abbreviations are used in Table 1. Ph phenyl ; Me methyl ; Ac : acetyl ; cPr: cyclopropyl cBu :cyclobutyl; cPn : cyclopentyl ; chex : cyclohexyl cHep : cycloheptyl ; Pyrd :pyrrolidinyl ; Oxa : oxazolidinyl Thi : thiazolidinyl ; OOxa : 2-oxooxazolidinyl; OThi :2-oxothiazolidinyl ; Pip : piperidinyl; Mor: morpholinyl Thmor :thiomorpholinyl; Piz : piperazinyl; Aze :azepinyl.

TABLE 1

| Exemplification compound number | $R^1$ | $R^2$ | A | B | N | D | G | Q |
|---|---|---|---|---|---|---|---|---|
| 1 | cPr | 3,4-diClPh | CO | single bond | 1 | O | $CH_2CH_2$ | sub. 1 |
| 2 | cBu | 3,4-diClPh | CO | single bond | 1 | O | $CH_2CH_2$ | sub. 1 |
| 3 | cPn | 3,4-diClPh | CO | single bond | 1 | O | $CH_2CH_2$ | sub. 1 |
| 4 | cHex | 3,4-diClPh | CO | single bond | 1 | O | $CH_2CH_2$ | sub. 1 |
| 5 | cHep | 3,4-diClPh | CO | single bond | 1 | O | $CH_2CH_2$ | sub. 1 |
| 6 | 2-Pyrd | 3,4-diClPh | CO | single bond | 1 | O | $CH_2CH_2$ | sub. 1 |
| 7 | 3-Pyrd | 3,4-diClPh | CO | single bond | 1 | O | $CH_2CH_2$ | sub. 1 |
| 8 | 4-Oxa | 3,4-diClPh | CO | single bond | 1 | O | $CH_2CH_2$ | sub. 1 |
| 9 | 5-Oxa | 3,4-diClPh | CO | single bond | 1 | O | $CH_2CH_2$ | sub. 1 |
| 10 | 4-Thi | 3,4-diClPh | CO | single bond | 1 | O | $CH_2CH_2$ | sub. 1 |
| 11 | 5-Thi | 3,4-diClPh | CO | single bond | 1 | O | $CH_2CH_2$ | sub. 1 |
| 12 | 4-OOxa | 3,4-diClPh | CO | single bond | 1 | O | $CH_2CH_2$ | sub. 1 |
| 13 | 5-OOxa | 3,4-diClPh | CO | single bond | 1 | O | $CH_2CH_2$ | sub. 1 |
| 14 | 4-OThi | 3,4-diClPh | CO | single bond | 1 | O | $CH_2CH_2$ | sub. 1 |
| 15 | 5-OThi | 3,4-diClPh | CO | single bond | 1 | O | $CH_2CH_2$ | sub. 1 |
| 16 | 2-Pip | 3,4-diClPh | CO | single bond | 1 | O | $CH_2CH_2$ | sub. 1 |
| 17 | 3-Pip | 3,4-diClPh | CO | single bond | 1 | O | $CH_2CH_2$ | sub. 1 |
| 18 | 4-Pip | 3,4-diClPh | CO | single bond | 1 | O | $CH_2CH_2$ | sub. 1 |
| 19 | 2-Mor | 3,4-diClPh | CO | single bond | 1 | O | $CH_2CH_2$ | sub. 1 |
| 20 | 3-Mor | 3,4-diClPh | CO | single bond | 1 | O | $CH_2CH_2$ | sub. 1 |
| 21 | 4-Mor | 3,4-diClPh | CO | single bond | 1 | O | $CH_2CH_2$ | sub. 1 |
| 22 | 2-Thmor | 3,4-diClPh | CO | single bond | 1 | O | $CH_2CH_2$ | sub. 1 |
| 23 | 3-Thmor | 3,4-diClPh | CO | single bond | 1 | O | $CH_2CH_2$ | sub. 1 |
| 24 | 4-Thmor | 3,4-diClPh | CO | single bond | 1 | O | $CH_2CH_2$ | sub. 1 |
| 25 | 2-Piz | 3,4-diClPh | CO | single bond | 1 | O | $CH_2CH_2$ | sub. 1 |
| 26 | 3-Piz | 3,4-diClPh | CO | single bond | 1 | O | $CH_2CH_2$ | sub. 1 |
| 27 | 4-Piz | 3,4-diClPh | CO | single bond | 1 | O | $CH_2CH_2$ | sub. 1 |
| 28 | 2-Aze | 3,4-diClPh | CO | single bond | 1 | O | $CH_2CH_2$ | sub. 1 |
| 29 | 3-Aze | 3,4-diClPh | CO | single bond | 1 | O | $CH_2CH_2$ | sub. 1 |
| 30 | 4-Aze | 3,4-diClPh | CO | single bond | 1 | O | $CH_2CH_2$ | sub. 1 |
| 31 | cPr | 3,4-diClPh | CO | single bond | 1 | O | $CH_2CH_2$ | sub. 2 |
| 32 | cBu | 3,4-diClPh | CO | single bond | 1 | O | $CH_2CH_2$ | sub. 2 |
| 33 | cPn | 3,4-diClPh | CO | single bond | 1 | O | $CH_2CH_2$ | sub. 2 |
| 34 | cHex | 3,4-diClPh | CO | single bond | 1 | O | $CH_2CH_2$ | sub. 2 |
| 35 | cHep | 3,4-diClPh | CO | single bond | 1 | O | $CH_2CH_2$ | sub. 2 |
| 36 | 2-Pyrd | 3,4-diClPh | CO | single bond | 1 | O | $CH_2CH_2$ | sub. 2 |
| 37 | 3-Pyrd | 3,4-diClPh | CO | single bond | 1 | O | $CH_2CH_2$ | sub. 2 |
| 38 | 4-Oxa | 3,4-diClPh | CO | single bond | 1 | O | $CH_2CH_2$ | sub. 2 |
| 39 | 5-Oxa | 3,4-diClPh | CO | single bond | 1 | O | $CH_2CH_2$ | sub. 2 |
| 40 | 4-Thi | 3,4-diClPh | CO | single bond | 1 | O | $CH_2CH_2$ | sub. 2 |
| 41 | 5-Thi | 3,4-diClPh | CO | single bond | 1 | O | $CH_2CH_2$ | sub. 2 |
| 42 | 4-OOxa | 3,4-diClPh | CO | single bond | 1 | O | $CH_2CH_2$ | sub. 2 |
| 43 | 5-OOxa | 3,4-diClPh | CO | single bond | 1 | O | $CH_2CH_2$ | sub. 2 |
| 44 | 4-OThi | 3,4-diClPh | CO | single bond | 1 | O | $CH_2CH_2$ | sub. 2 |
| 45 | 5-OThi | 3,4-diClPh | CO | single bond | 1 | O | $CH_2CH_2$ | sub. 2 |
| 46 | 2-Pip | 3,4-diClPh | CO | single bond | 1 | O | $CH_2CH_2$ | sub. 2 |
| 47 | 3-Pip | 3,4-diClPh | CO | single bond | 1 | O | $CH_2CH_2$ | sub. 2 |
| 48 | 4-Pip | 3,4-diClPh | CO | single bond | 1 | O | $CH_2CH_2$ | sub. 2 |
| 49 | 2-Mor | 3,4-diClPh | CO | single bond | 1 | O | $CH_2CH_2$ | sub. 2 |
| 50 | 3-Mor | 3,4-diClPh | CO | single bond | 1 | O | $CH_2CH_2$ | sub. 2 |
| 51 | 4-Mor | 3,4-diClPh | CO | single bond | 1 | O | $CH_2CH_2$ | sub. 2 |
| 52 | 2-Thmor | 3,4-diClPh | CO | single bond | 1 | O | $CH_2CH_2$ | sub. 2 |
| 53 | 3-Thmor | 3,4-diClPh | CO | single bond | 1 | O | $CH_2CH_2$ | sub. 2 |
| 54 | 4-Thmor | 3,4-diClPh | CO | single bond | 1 | O | $CH_2CH_2$ | sub. 2 |
| 55 | 2-Piz | 3,4-diClPh | CO | single bond | 1 | O | $CH_2CH_2$ | sub. 2 |
| 56 | 3-Piz | 3,4-diClPh | CO | single bond | 1 | O | $CH_2CH_2$ | sub. 2 |

TABLE 1-continued

| Exemplification compound number | R¹ | R² | A | B | N | D | G | Q |
|---|---|---|---|---|---|---|---|---|
| 57 | 4-Piz | 3,4-diClPh | CO | single bond | 1 | O | CH$_2$CH$_2$ | sub. 2 |
| 58 | 2-Aze | 3,4-diClPh | CO | single bond | 1 | O | CH$_2$CH$_2$ | sub. 2 |
| 59 | 3-Aze | 3,4-diClPh | CO | single bond | 1 | O | CH$_2$CH$_2$ | sub. 2 |
| 60 | 4-Aze | 3,4-diClPh | CO | single bond | 1 | O | CH$_2$CH$_2$ | sub. 2 |
| 61 | cPr | 3,4-diClPh | CO | single bond | 1 | O | CH$_2$CH$_2$ | sub. 3 |
| 62 | cBu | 3,4-diClPh | CO | single bond | 1 | O | CH$_2$CH$_2$ | sub. 3 |
| 63 | cPn | 3,4-diClPh | CO | single bond | 1 | O | CH$_2$CH$_2$ | sub. 3 |
| 64 | cHex | 3,4-diClPh | CO | single bond | 1 | O | CH$_2$CH$_2$ | sub. 3 |
| 65 | cHep | 3,4-diClPh | CO | single bond | 1 | O | CH$_2$CH$_2$ | sub. 3 |
| 66 | 2-Pyrd | 3,4-diClPh | CO | single bond | 1 | O | CH$_2$CH$_2$ | sub. 3 |
| 67 | 3-Pyrd | 3,4-diClPh | CO | single bond | 1 | O | CH$_2$CH$_2$ | sub. 3 |
| 68 | 4-Oxa | 3,4-diClPh | CO | single bond | 1 | O | CH$_2$CH$_2$ | sub. 3 |
| 69 | 5-Oxa | 3,4-diClPh | CO | single bond | 1 | O | CH$_2$CH$_2$ | sub. 3 |
| 70 | 4-Thi | 3,4-diClPh | CO | single bond | 1 | O | CH$_2$CH$_2$ | sub. 3 |
| 71 | 5-Thi | 3,4-diClPh | CO | single bond | 1 | O | CH$_2$CH$_2$ | sub. 3 |
| 72 | 4-OOxa | 3,4-diClPh | CO | single bond | 1 | O | CH$_2$CH$_2$ | sub. 3 |
| 73 | 5-OOxa | 3,4-diClPh | CO | single bond | 1 | O | CH$_2$CH$_2$ | sub. 3 |
| 74 | 4-OThi | 3,4-diClPh | CO | single bond | 1 | O | CH$_2$CH$_2$ | sub. 3 |
| 75 | 5-OThi | 3,4-diClPh | CO | single bond | 1 | O | CH$_2$CH$_2$ | sub. 3 |
| 76 | 2-Pip | 3,4-diClPh | CO | single bond | 1 | O | CH$_2$CH$_2$ | sub. 3 |
| 77 | 3-Pip | 3,4-diClPh | CO | single bond | 1 | O | CH$_2$CH$_2$ | sub. 3 |
| 78 | 4-Pip | 3,4-diClPh | CO | single bond | 1 | O | CH$_2$CH$_2$ | sub. 3 |
| 79 | 2-Mor | 3,4-diClPh | CO | single bond | 1 | O | CH$_2$CH$_2$ | sub. 3 |
| 80 | 3-Mor | 3,4-diClPh | CO | single bond | 1 | O | CH$_2$CH$_2$ | sub. 3 |
| 81 | 4-Mor | 3,4-diClPh | CO | single bond | 1 | O | CH$_2$CH$_2$ | sub. 3 |
| 82 | 2-Thmor | 3,4-diClPh | CO | single bond | 1 | O | CH$_2$CH$_2$ | sub. 3 |
| 83 | 3-Thmor | 3,4-diClPh | CO | single bond | 1 | O | CH$_2$CH$_2$ | sub. 3 |
| 84 | 4-Thmor | 3,4-diClPh | CO | single bond | 1 | O | CH$_2$CH$_2$ | sub. 3 |
| 85 | 2-Piz | 3,4-diClPh | CO | single bond | 1 | O | CH$_2$CH$_2$ | sub. 3 |
| 86 | 3-Piz | 3,4-diClPh | CO | single bond | 1 | O | CH$_2$CH$_2$ | sub. 3 |
| 87 | 4-Piz | 3,4-diClPh | CO | single bond | 1 | O | CH$_2$CH$_2$ | sub. 3 |
| 88 | 2-Aze | 3,4-diClPh | CO | single bond | 1 | O | CH$_2$CH$_2$ | sub. 3 |
| 89 | 3-Aze | 3,4-diClPh | CO | single bond | 1 | O | CH$_2$CH$_2$ | sub. 3 |
| 90 | 4-Aze | 3,4-diClPh | CO | single bond | 1 | O | CH$_2$CH$_2$ | sub. 3 |
| 91 | cPr | 3,4-diClPh | CO | single bond | 1 | O | CH$_2$CH$_2$ | sub. 4 |
| 92 | cBu | 3,4-diClPh | CO | single bond | 1 | O | CH$_2$CH$_2$ | sub. 4 |
| 93 | cPn | 3,4-diClPh | CO | single bond | 1 | O | CH$_2$CH$_2$ | sub. 4 |
| 94 | cHex | 3,4-diClPh | CO | single bond | 1 | O | CH$_2$CH$_2$ | sub. 4 |
| 95 | cHep | 3,4-diClPh | CO | single bond | 1 | O | CH$_2$CH$_2$ | sub. 4 |
| 96 | 2-Pyrd | 3,4-diClPh | CO | single bond | 1 | O | CH$_2$CH$_2$ | sub. 4 |
| 97 | 3-Pyrd | 3,4-diClPh | CO | single bond | 1 | O | CH$_2$CH$_2$ | sub. 4 |
| 98 | 4-Oxa | 3,4-diClPh | CO | single bond | 1 | O | CH$_2$CH$_2$ | sub. 4 |
| 99 | 5-Oxa | 3,4-diClPh | CO | single bond | 1 | O | CH$_2$CH$_2$ | sub. 4 |
| 100 | 4-Thi | 3,4-diClPh | CO | single bond | 1 | O | CH$_2$CH$_2$ | sub. 4 |
| 101 | 5-Thi | 3,4-diClPh | CO | single bond | 1 | O | CH$_2$CH$_2$ | sub. 4 |
| 102 | 4-OOxa | 3,4-diClPh | CO | single bond | 1 | O | CH$_2$CH$_2$ | sub. 4 |
| 103 | 5-OOxa | 3,4-diClPh | CO | single bond | 1 | O | CH$_2$CH$_2$ | sub. 4 |
| 104 | 4-OThi | 3,4-diClPh | CO | single bond | 1 | O | CH$_2$CH$_2$ | sub. 4 |
| 105 | 5-OThi | 3,4-diClPh | CO | single bond | 1 | O | CH$_2$CH$_2$ | sub. 4 |
| 106 | 2-Pip | 3,4-diClPh | CO | single bond | 1 | O | CH$_2$CH$_2$ | sub. 4 |
| 107 | 3-Pip | 3,4-diClPh | CO | single bond | 1 | O | CH$_2$CH$_2$ | sub. 4 |
| 108 | 4-Pip | 3,4-diClPh | CO | single bond | 1 | O | CH$_2$CH$_2$ | sub. 4 |
| 109 | 2-Mor | 3,4-diClPh | CO | single bond | 1 | O | CH$_2$CH$_2$ | sub. 4 |
| 110 | 3-Mor | 3,4-diClPh | CO | single bond | 1 | O | CH$_2$CH$_2$ | sub. 4 |
| 111 | 4-Mor | 3,4-diClPh | CO | single bond | 1 | O | CH$_2$CH$_2$ | sub. 4 |
| 112 | 2-Thmor | 3,4-diClPh | CO | single bond | 1 | O | CH$_2$CH$_2$ | sub. 4 |
| 113 | 3-Thmor | 3,4-diClPh | CO | single bond | 1 | O | CH$_2$CH$_2$ | sub. 4 |
| 114 | 4-Thmor | 3,4-diClPh | CO | single bond | 1 | O | CH$_2$CH$_2$ | sub. 4 |
| 115 | 2-Piz | 3,4-diClPh | CO | single bond | 1 | O | CH$_2$CH$_2$ | sub. 4 |
| 116 | 3-Piz | 3,4-diClPh | CO | single bond | 1 | O | CH$_2$CH$_2$ | sub. 4 |
| 117 | 4-Piz | 3,4-diClPh | CO | single bond | 1 | O | CH$_2$CH$_2$ | sub. 4 |
| 118 | 2-Aze | 3,4-diClPh | CO | single bond | 1 | O | CH$_2$CH$_2$ | sub. 4 |
| 119 | 3-Aze | 3,4-diClPh | CO | single bond | 1 | O | CH$_2$CH$_2$ | sub. 4 |
| 120 | 4-Aze | 3,4-diClPh | CO | single bond | 1 | O | CH$_2$CH$_2$ | sub. 4 |
| 121 | cPr | 3,4-diClPh | CO | single bond | 1 | O | CH$_2$CH$_2$ | sub. 5 |
| 122 | cBu | 3,4-diClPh | CO | single bond | 1 | O | CH$_2$CH$_2$ | sub. 5 |
| 123 | cPn | 3,4-diClPh | CO | single bond | 1 | O | CH$_2$CH$_2$ | sub. 5 |
| 124 | cHex | 3,4-diClPh | CO | single bond | 1 | O | CH$_2$CH$_2$ | sub. 5 |
| 125 | cHep | 3,4-diClPh | CO | single bond | 1 | O | CH$_2$CH$_2$ | sub. 5 |
| 126 | 2-Pyrd | 3,4-diClPh | CO | single bond | 1 | O | CH$_2$CH$_2$ | sub. 5 |
| 127 | 3-Pyrd | 3,4-diClPh | CO | single bond | 1 | O | CH$_2$CH$_2$ | sub. 5 |
| 128 | 4-Oxa | 3,4-diClPh | CO | single bond | 1 | O | CH$_2$CH$_2$ | sub. 5 |
| 129 | 5-Oxa | 3,4-diClPh | CO | single bond | 1 | O | CH$_2$CH$_2$ | sub. 5 |
| 130 | 4-Thi | 3,4-diClPh | CO | single bond | 1 | O | CH$_2$CH$_2$ | sub. 5 |
| 131 | 5-Thi | 3,4-diClPh | CO | single bond | 1 | O | CH$_2$CH$_2$ | sub. 5 |
| 132 | 4-OOxa | 3,4-diClPh | CO | single bond | 1 | O | CH$_2$CH$_2$ | sub. 5 |

TABLE 1-continued

| Exemplification compound number | R¹ | R² | A | B | N | D | G | Q |
|---|---|---|---|---|---|---|---|---|
| 133 | 5-OOxa | 3,4-diClPh | CO | single bond | 1 | O | CH₂CH₂ | sub. 5 |
| 134 | 4-OThi | 3,4-diClPh | CO | single bond | 1 | O | CH₂CH₂ | sub. 5 |
| 135 | 5-OThi | 3,4-diClPh | CO | single bond | 1 | O | CH₂CH₂ | sub. 5 |
| 136 | 2-Pip | 3,4-diClPh | CO | single bond | 1 | O | CH₂CH₂ | sub. 5 |
| 137 | 3-Pip | 3,4-diClPh | CO | single bond | 1 | O | CH₂CH₂ | sub. 5 |
| 138 | 4-Pip | 3,4-diClPh | CO | single bond | 1 | O | CH₂CH₂ | sub. 5 |
| 139 | 2-Mor | 3,4-diClPh | CO | single bond | 1 | O | CH₂CH₂ | sub. 5 |
| 140 | 3-Mor | 3,4-diClPh | CO | single bond | 1 | O | CH₂CH₂ | sub. 5 |
| 141 | 4-Mor | 3,4-diClPh | CO | single bond | 1 | O | CH₂CH₂ | sub. 5 |
| 142 | 2-Thmor | 3,4-diClPh | CO | single bond | 1 | O | CH₂CH₂ | sub. 5 |
| 143 | 3-Thmor | 3,4-diClPh | CO | single bond | 1 | O | CH₂CH₂ | sub. 5 |
| 144 | 4-Thmor | 3,4-diClPh | CO | single bond | 1 | O | CH₂CH₂ | sub. 5 |
| 145 | 2-Piz | 3,4-diClPh | CO | single bond | 1 | O | CH₂CH₂ | sub. 5 |
| 146 | 3-Piz | 3,4-diClPh | CO | single bond | 1 | O | CH₂CH₂ | sub. 5 |
| 147 | 4-Piz | 3,4-diClPh | CO | single bond | 1 | O | CH₂CH₂ | sub. 5 |
| 148 | 2-Aze | 3,4-diClPh | CO | single bond | 1 | O | CH₂CH₂ | sub. 5 |
| 149 | 3-Aze | 3,4-diClPh | CO | single bond | 1 | O | CH₂CH₂ | sub. 5 |
| 150 | 4-Aze | 3,4-diClPh | CO | single bond | 1 | O | CH₂CH₂ | sub. 5 |
| 151 | cPr | 3,4-diClPh | CO | single bond | 1 | O | CH₂CH₂ | sub. 6 |
| 152 | cBu | 3,4-diClPh | CO | single bond | 1 | O | CH₂CH₂ | sub. 6 |
| 153 | cPn | 3,4-diClPh | CO | single bond | 1 | O | CH₂CH₂ | sub. 6 |
| 154 | cHex | 3,4-diClPh | CO | single bond | 1 | O | CH₂CH₂ | sub. 6 |
| 155 | cHep | 3,4-diClPh | CO | single bond | 1 | O | CH₂CH₂ | sub. 6 |
| 156 | 2-Pyrd | 3,4-diClPh | CO | single bond | 1 | O | CH₂CH₂ | sub. 6 |
| 157 | 3-Pyrd | 3,4-diClPh | CO | single bond | 1 | O | CH₂CH₂ | sub. 6 |
| 158 | 4-Oxa | 3,4-diClPh | CO | single bond | 1 | O | CH₂CH₂ | sub. 6 |
| 159 | 5-Oxa | 3,4-diClPh | CO | single bond | 1 | O | CH₂CH₂ | sub. 6 |
| 160 | 4-Thi | 3,4-diClPh | CO | single bond | 1 | O | CH₂CH₂ | sub. 6 |
| 161 | 5-Thi | 3,4-diClPh | CO | single bond | 1 | O | CH₂CH₂ | sub. 6 |
| 162 | 4-OOxa | 3,4-diClPh | CO | single bond | 1 | O | CH₂CH₂ | sub. 6 |
| 163 | 5-OOxa | 3,4-diClPh | CO | single bond | 1 | O | CH₂CH₂ | sub. 6 |
| 164 | 4-OThi | 3,4-diClPh | CO | single bond | 1 | O | CH₂CH₂ | sub. 6 |
| 165 | 5-OThi | 3,4-diClPh | CO | single bond | 1 | O | CH₂CH₂ | sub. 6 |
| 166 | 2-Pip | 3,4-diClPh | CO | single bond | 1 | O | CH₂CH₂ | sub. 6 |
| 167 | 3-Pip | 3,4-diClPh | CO | single bond | 1 | O | CH₂CH₂ | sub. 6 |
| 168 | 4-Pip | 3,4-diClPh | CO | single bond | 1 | O | CH₂CH₂ | sub. 6 |
| 169 | 2-Mor | 3,4-diClPh | CO | single bond | 1 | O | CH₂CH₂ | sub. 6 |
| 170 | 3-Mor | 3,4-diClPh | CO | single bond | 1 | O | CH₂CH₂ | sub. 6 |
| 171 | 4-Mor | 3,4-diClPh | CO | single bond | 1 | O | CH₂CH₂ | sub. 6 |
| 172 | 2-Thmor | 3,4-diClPh | CO | single bond | 1 | O | CH₂CH₂ | sub. 6 |
| 173 | 3-Thmor | 3,4-diClPh | CO | single bond | 1 | O | CH₂CH₂ | sub. 6 |
| 174 | 4-Thmor | 3,4-diClPh | CO | single bond | 1 | O | CH₂CH₂ | sub. 6 |
| 175 | 2-Piz | 3,4-diClPh | CO | single bond | 1 | O | CH₂CH₂ | sub. 6 |
| 176 | 3-Piz | 3,4-diClPh | CO | single bond | 1 | O | CH₂CH₂ | sub. 6 |
| 177 | 4-Piz | 3,4-diClPh | CO | single bond | 1 | O | CH₂CH₂ | sub. 6 |
| 178 | 2-Aze | 3,4-diClPh | CO | single bond | 1 | O | CH₂CH₂ | sub. 6 |
| 179 | 3-Aze | 3,4-diClPh | CO | single bond | 1 | O | CH₂CH₂ | sub. 6 |
| 180 | 4-Aze | 3,4-diClPh | CO | single bond | 1 | O | CH₂CH₂ | sub. 6 |
| 181 | cPr | 3,4-diClPh | CO | single bond | 1 | O | CH₂CH₂ | sub. 7 |
| 182 | cBu | 3,4-diClPh | CO | single bond | 1 | O | CH₂CH₂ | sub. 7 |
| 183 | cPn | 3,4-diClPh | CO | single bond | 1 | O | CH₂CH₂ | sub. 7 |
| 184 | cHex | 3,4-diClPh | CO | single bond | 1 | O | CH₂CH₂ | sub. 7 |
| 185 | cHep | 3,4-diClPh | CO | single bond | 1 | O | CH₂CH₂ | sub. 7 |
| 186 | 2-Pyrd | 3,4-diClPh | CO | single bond | 1 | O | CH₂CH₂ | sub. 7 |
| 187 | 3-Pyrd | 3,4-diClPh | CO | single bond | 1 | O | CH₂CH₂ | sub. 7 |
| 188 | 4-Oxa | 3,4-diClPh | CO | single bond | 1 | O | CH₂CH₂ | sub. 7 |
| 189 | 5-Oxa | 3,4-diClPh | CO | single bond | 1 | O | CH₂CH₂ | sub. 7 |
| 190 | 4-Thi | 3,4-diClPh | CO | single bond | 1 | O | CH₂CH₂ | sub. 7 |
| 191 | 5-Thi | 3,4-diClPh | CO | single bond | 1 | O | CH₂CH₂ | sub. 7 |
| 192 | 4-OOxa | 3,4-diClPh | CO | single bond | 1 | O | CH₂CH₂ | sub. 7 |
| 193 | 5-OOxa | 3,4-diClPh | CO | single bond | 1 | O | CH₂CH₂ | sub. 7 |
| 194 | 4-OThi | 3,4-diClPh | CO | single bond | 1 | O | CH₂CH₂ | sub. 7 |
| 195 | 5-OThi | 3,4-diClPh | CO | single bond | 1 | O | CH₂CH₂ | sub. 7 |
| 196 | 2-Pip | 3,4-diClPh | CO | single bond | 1 | O | CH₂CH₂ | sub. 7 |
| 197 | 3-Pip | 3,4-diClPh | CO | single bond | 1 | O | CH₂CH₂ | sub. 7 |
| 198 | 4-Pip | 3,4-diClPh | CO | single bond | 1 | O | CH₂CH₂ | sub. 7 |
| 199 | 2-Mor | 3,4-diClPh | CO | single bond | 1 | O | CH₂CH₂ | sub. 7 |
| 200 | 3-Mor | 3,4-diClPh | CO | single bond | 1 | O | CH₂CH₂ | sub. 7 |
| 201 | 4-Mor | 3,4-diClPh | CO | single bond | 1 | O | CH₂CH₂ | sub. 7 |
| 202 | 2-Thmor | 3,4-diClPh | CO | single bond | 1 | O | CH₂CH₂ | sub. 7 |
| 203 | 3-Thmor | 3,4-diClPh | CO | single bond | 1 | O | CH₂CH₂ | sub. 7 |
| 204 | 4-Thmor | 3,4-diClPh | CO | single bond | 1 | O | CH₂CH₂ | sub. 7 |
| 205 | 2-Piz | 3,4-diClPh | CO | single bond | 1 | O | CH₂CH₂ | sub. 7 |
| 206 | 3-Piz | 3,4-diClPh | CO | single bond | 1 | O | CH₂CH₂ | sub. 7 |
| 207 | 4-Piz | 3,4-diClPh | CO | single bond | 1 | O | CH₂CH₂ | sub. 7 |
| 208 | 2-Aze | 3,4-diClPh | CO | single bond | 1 | O | CH₂CH₂ | sub. 7 |

TABLE 1-continued

| Exemplification compound number | R¹ | R² | A | B | N | D | G | Q |
|---|---|---|---|---|---|---|---|---|
| 209 | 3-Aze | 3,4-diClPh | CO | single bond | 1 | O | CH₂CH₂ | sub. 7 |
| 210 | 4-Aze | 3,4-diClPh | CO | single bond | 1 | O | CH₂CH₂ | sub. 7 |
| 211 | cPr | 3,4-diClPh | CO | single bond | 1 | O | CH₂CH₂ | sub. 8 |
| 212 | cBu | 3,4-diClPh | CO | single bond | 1 | O | CH₂CH₂ | sub. 8 |
| 213 | cPn | 3,4-diClPh | CO | single bond | 1 | O | CH₂CH₂ | sub. 8 |
| 214 | cHex | 3,4-diClPh | CO | single bond | 1 | O | CH₂CH₂ | sub. 8 |
| 215 | cHep | 3,4-diClPh | CO | single bond | 1 | O | CH₂CH₂ | sub. 8 |
| 216 | 2-Pyrd | 3,4-diClPh | CO | single bond | 1 | O | CH₂CH₂ | sub. 8 |
| 217 | 3-Pyrd | 3,4-diClPh | CO | single bond | 1 | O | CH₂CH₂ | sub. 8 |
| 218 | 4-Oxa | 3,4-diClPh | CO | single bond | 1 | O | CH₂CH₂ | sub. 8 |
| 219 | 5-Oxa | 3,4-diClPh | CO | single bond | 1 | O | CH₂CH₂ | sub. 8 |
| 220 | 4-Thi | 3,4-diClPh | CO | single bond | 1 | O | CH₂CH₂ | sub. 8 |
| 221 | 5-Thi | 3,4-diClPh | CO | single bond | 1 | O | CH₂CH₂ | sub. 8 |
| 222 | 4-OOxa | 3,4-diClPh | CO | single bond | 1 | O | CH₂CH₂ | sub. 8 |
| 223 | 5-OOxa | 3,4-diClPh | CO | single bond | 1 | O | CH₂CH₂ | sub. 8 |
| 224 | 4-OThi | 3,4-diClPh | CO | single bond | 1 | O | CH₂CH₂ | sub. 8 |
| 225 | 5-OThi | 3,4-diClPh | CO | single bond | 1 | O | CH₂CH₂ | sub. 8 |
| 226 | 2-Pip | 3,4-diClPh | CO | single bond | 1 | O | CH₂CH₂ | sub. 8 |
| 227 | 3-Pip | 3,4-diClPh | CO | single bond | 1 | O | CH₂CH₂ | sub. 8 |
| 228 | 4-Pip | 3,4-diClPh | CO | single bond | 1 | O | CH₂CH₂ | sub. 8 |
| 229 | 2-Mor | 3,4-diClPh | CO | single bond | 1 | O | CH₂CH₂ | sub. 8 |
| 230 | 3-Mor | 3,4-diClPh | CO | single bond | 1 | O | CH₂CH₂ | sub. 8 |
| 231 | 4-Mor | 3,4-diClPh | CO | single bond | 1 | O | CH₂CH₂ | sub. 8 |
| 232 | 2-Thmor | 3,4-diClPh | CO | single bond | 1 | O | CH₂CH₂ | sub. 8 |
| 233 | 3-Thmor | 3,4-diClPh | CO | single bond | 1 | O | CH₂CH₂ | sub. 8 |
| 234 | 4-Thmor | 3,4-diClPh | CO | single bond | 1 | O | CH₂CH₂ | sub. 8 |
| 235 | 2-Piz | 3,4-diClPh | CO | single bond | 1 | O | CH₂CH₂ | sub. 8 |
| 236 | 3-Piz | 3,4-diClPh | CO | single bond | 1 | O | CH₂CH₂ | sub. 8 |
| 237 | 4-Piz | 3,4-diClPh | CO | single bond | 1 | O | CH₂CH₂ | sub. 8 |
| 238 | 2-Aze | 3,4-diClPh | CO | single bond | 1 | O | CH₂CH₂ | sub. 8 |
| 239 | 3-Aze | 3,4-diClPh | CO | single bond | 1 | O | CH₂CH₂ | sub. 8 |
| 240 | 4-Aze | 3,4-diClPh | CO | single bond | 1 | O | CH₂CH₂ | sub. 8 |
| 241 | cPr | 3,4-diClPh | CO | single bond | 1 | O | CH₂CH₂ | sub. 9 |
| 242 | cBu | 3,4-diClPh | CO | single bond | 1 | O | CH₂CH₂ | sub. 9 |
| 243 | cPn | 3,4-diClPh | CO | single bond | 1 | O | CH₂CH₂ | sub. 9 |
| 244 | cHex | 3,4-diClPh | CO | single bond | 1 | O | CH₂CH₂ | sub. 9 |
| 245 | cHep | 3,4-diClPh | CO | single bond | 1 | O | CH₂CH₂ | sub. 9 |
| 246 | 2-Pyrd | 3,4-diClPh | CO | single bond | 1 | O | CH₂CH₂ | sub. 9 |
| 247 | 3-Pyrd | 3,4-diClPh | CO | single bond | 1 | O | CH₂CH₂ | sub. 9 |
| 248 | 4-Oxa | 3,4-diClPh | CO | single bond | 1 | O | CH₂CH₂ | sub. 9 |
| 249 | 5-Oxa | 3,4-diClPh | CO | single bond | 1 | O | CH₂CH₂ | sub. 9 |
| 250 | 4-Thi | 3,4-diClPh | CO | single bond | 1 | O | CH₂CH₂ | sub. 9 |
| 251 | 5-Thi | 3,4-diClPh | CO | single bond | 1 | O | CH₂CH₂ | sub. 9 |
| 252 | 4-OOxa | 3,4-diClPh | CO | single bond | 1 | O | CH₂CH₂ | sub. 9 |
| 253 | 5-OOxa | 3,4-diClPh | CO | single bond | 1 | O | CH₂CH₂ | sub. 9 |
| 254 | 4-OThi | 3,4-diClPh | CO | single bond | 1 | O | CH₂CH₂ | sub. 9 |
| 255 | 5-OThi | 3,4-diClPh | CO | single bond | 1 | O | CH₂CH₂ | sub. 9 |
| 256 | 2-Pip | 3,4-diClPh | CO | single bond | 1 | O | CH₂CH₂ | sub. 9 |
| 257 | 3-Pip | 3,4-diClPh | CO | single bond | 1 | O | CH₂CH₂ | sub. 9 |
| 258 | 4-Pip | 3,4-diClPh | CO | single bond | 1 | O | CH₂CH₂ | sub. 9 |
| 259 | 2-Mor | 3,4-diClPh | CO | single bond | 1 | O | CH₂CH₂ | sub. 9 |
| 260 | 3-Mor | 3,4-diClPh | CO | single bond | 1 | O | CH₂CH₂ | sub. 9 |
| 261 | 4-Mor | 3,4-diClPh | CO | single bond | 1 | O | CH₂CH₂ | sub. 9 |
| 262 | 2-Thmor | 3,4-diClPh | CO | single bond | 1 | O | CH₂CH₂ | sub. 9 |
| 263 | 3-Thmor | 3,4-diClPh | CO | single bond | 1 | O | CH₂CH₂ | sub. 9 |
| 264 | 4-Thmor | 3,4-diClPh | CO | single bond | 1 | O | CH₂CH₂ | sub. 9 |
| 265 | 2-Piz | 3,4-diClPh | CO | single bond | 1 | O | CH₂CH₂ | sub. 9 |
| 266 | 3-Piz | 3,4-diClPh | CO | single bond | 1 | O | CH₂CH₂ | sub. 9 |
| 267 | 4-Piz | 3,4-diClPh | CO | single bond | 1 | O | CH₂CH₂ | sub. 9 |
| 268 | 2-Aze | 3,4-diClPh | CO | single bond | 1 | O | CH₂CH₂ | sub. 9 |
| 269 | 3-Aze | 3,4-diClPh | CO | single bond | 1 | O | CH₂CH₂ | sub. 9 |
| 270 | 4-Aze | 3,4-diClPh | CO | single bond | 1 | O | CH₂CH₂ | sub. 9 |
| 271 | cPr | 3,4-diClPh | CO | single bond | 1 | O | CH₂CH₂ | sub. 10 |
| 272 | cBu | 3,4-diClPh | CO | single bond | 1 | O | CH₂CH₂ | sub. 10 |
| 273 | cPn | 3,4-diClPh | CO | single bond | 1 | O | CH₂CH₂ | sub. 10 |
| 274 | cHex | 3,4-diClPh | CO | single bond | 1 | O | CH₂CH₂ | sub. 10 |
| 275 | cHep | 3,4-diClPh | CO | single bond | 1 | O | CH₂CH₂ | sub. 10 |
| 276 | 2-Pyrd | 3,4-diClPh | CO | single bond | 1 | O | CH₂CH₂ | sub. 10 |
| 277 | 3-Pyrd | 3,4-diClPh | CO | single bond | 1 | O | CH₂CH₂ | sub. 10 |
| 278 | 4-Oxa | 3,4-diClPh | CO | single bond | 1 | O | CH₂CH₂ | sub. 10 |
| 279 | 5-Oxa | 3,4-diClPh | CO | single bond | 1 | O | CH₂CH₂ | sub. 10 |
| 280 | 4-Thi | 3,4-diClPh | CO | single bond | 1 | O | CH₂CH₂ | sub. 10 |
| 281 | 5-Thi | 3,4-diClPh | CO | single bond | 1 | O | CH₂CH₂ | sub. 10 |
| 282 | 4-OOxa | 3,4-diClPh | CO | single bond | 1 | O | CH₂CH₂ | sub. 10 |
| 283 | 5-OOxa | 3,4-diClPh | CO | single bond | 1 | O | CH₂CH₂ | sub. 10 |
| 284 | 4-OThi | 3,4-diClPh | CO | single bond | 1 | O | CH₂CH₂ | sub. 10 |

TABLE 1-continued

| Exemplification compound number | R¹ | R² | A | B | N | D | G | Q |
|---|---|---|---|---|---|---|---|---|
| 285 | 5-OThi | 3,4-diClPh | CO | single bond | 1 | O | $CH_2CH_2$ | sub. 10 |
| 286 | 2-Pip | 3,4-diClPh | CO | single bond | 1 | O | $CH_2CH_2$ | sub. 10 |
| 287 | 3-Pip | 3,4-diClPh | CO | single bond | 1 | O | $CH_2CH_2$ | sub. 10 |
| 288 | 4-Pip | 3,4-diClPh | CO | single bond | 1 | O | $CH_2CH_2$ | sub. 10 |
| 289 | 2-Mor | 3,4-diClPh | CO | single bond | 1 | O | $CH_2CH_2$ | sub. 10 |
| 290 | 3-Mor | 3,4-diClPh | CO | single bond | 1 | O | $CH_2CH_2$ | sub. 10 |
| 291 | 4-Mor | 3,4-diClPh | CO | single bond | 1 | O | $CH_2CH_2$ | sub. 10 |
| 292 | 2-Thmor | 3,4-diClPh | CO | single bond | 1 | O | $CH_2CH_2$ | sub. 10 |
| 293 | 3-Thmor | 3,4-diClPh | CO | single bond | 1 | O | $CH_2CH_2$ | sub. 10 |
| 294 | 4-Thmor | 3,4-diClPh | CO | single bond | 1 | O | $CH_2CH_2$ | sub. 10 |
| 295 | 2-Piz | 3,4-diClPh | CO | single bond | 1 | O | $CH_2CH_2$ | sub. 10 |
| 296 | 3-Piz | 3,4-diClPh | CO | single bond | 1 | O | $CH_2CH_2$ | sub. 10 |
| 297 | 4-Piz | 3,4-diClPh | CO | single bond | 1 | O | $CH_2CH_2$ | sub. 10 |
| 298 | 2-Aze | 3,4-diClPh | CO | single bond | 1 | O | $CH_2CH_2$ | sub. 10 |
| 299 | 3-Aze | 3,4-diClPh | CO | single bond | 1 | O | $CH_2CH_2$ | sub. 10 |
| 300 | 4-Aze | 3,4-diClPh | CO | single bond | 1 | O | $CH_2CH_2$ | sub. 10 |
| 301 | cPr | 3,4-diClPh | CO | single bond | 1 | O | $CH_2CH_2$ | sub. 11 |
| 302 | cBu | 3,4-diClPh | CO | single bond | 1 | O | $CH_2CH_2$ | sub. 11 |
| 303 | cPn | 3,4-diClPh | CO | single bond | 1 | O | $CH_2CH_2$ | sub. 11 |
| 304 | cHex | 3,4-diClPh | CO | single bond | 1 | O | $CH_2CH_2$ | sub. 11 |
| 305 | cHep | 3,4-diClPh | CO | single bond | 1 | O | $CH_2CH_2$ | sub. 11 |
| 306 | 2-Pyrd | 3,4-diClPh | CO | single bond | 1 | O | $CH_2CH_2$ | sub. 11 |
| 307 | 3-Pyrd | 3,4-diClPh | CO | single bond | 1 | O | $CH_2CH_2$ | sub. 11 |
| 308 | 4-Oxa | 3,4-diClPh | CO | single bond | 1 | O | $CH_2CH_2$ | sub. 11 |
| 309 | 5-Oxa | 3,4-diClPh | CO | single bond | 1 | O | $CH_2CH_2$ | sub. 11 |
| 310 | 4-Thi | 3,4-diClPh | CO | single bond | 1 | O | $CH_2CH_2$ | sub. 11 |
| 311 | 5-Thi | 3,4-diClPh | CO | single bond | 1 | O | $CH_2CH_2$ | sub. 11 |
| 312 | 4-OOxa | 3,4-diClPh | CO | single bond | 1 | O | $CH_2CH_2$ | sub. 11 |
| 313 | 5-OOxa | 3,4-diClPh | CO | single bond | 1 | O | $CH_2CH_2$ | sub. 11 |
| 314 | 4-OThi | 3,4-diClPh | CO | single bond | 1 | O | $CH_2CH_2$ | sub. 11 |
| 315 | 5-OThi | 3,4-diClPh | CO | single bond | 1 | O | $CH_2CH_2$ | sub. 11 |
| 316 | 2-Pip | 3,4-diClPh | CO | single bond | 1 | O | $CH_2CH_2$ | sub. 11 |
| 317 | 3-Pip | 3,4-diClPh | CO | single bond | 1 | O | $CH_2CH_2$ | sub. 11 |
| 318 | 4-Pip | 3,4-diClPh | CO | single bond | 1 | O | $CH_2CH_2$ | sub. 11 |
| 319 | 2-Mor | 3,4-diClPh | CO | single bond | 1 | O | $CH_2CH_2$ | sub. 11 |
| 320 | 3-Mor | 3,4-diClPh | CO | single bond | 1 | O | $CH_2CH_2$ | sub. 11 |
| 321 | 4-Mor | 3,4-diClPh | CO | single bond | 1 | O | $CH_2CH_2$ | sub. 11 |
| 322 | 2-Thmor | 3,4-diClPh | CO | single bond | 1 | O | $CH_2CH_2$ | sub. 11 |
| 323 | 3-Thmor | 3,4-diClPh | CO | single bond | 1 | O | $CH_2CH_2$ | sub. 11 |
| 324 | 4-Thmor | 3,4-diClPh | CO | single bond | 1 | O | $CH_2CH_2$ | sub. 11 |
| 325 | 2-Piz | 3,4-diClPh | CO | single bond | 1 | O | $CH_2CH_2$ | sub. 11 |
| 326 | 3-Piz | 3,4-diClPh | CO | single bond | 1 | O | $CH_2CH_2$ | sub. 11 |
| 327 | 4-Piz | 3,4-diClPh | CO | single bond | 1 | O | $CH_2CH_2$ | sub. 11 |
| 328 | 2-Aze | 3,4-diClPh | CO | single bond | 1 | O | $CH_2CH_2$ | sub. 11 |
| 329 | 3-Aze | 3,4-diClPh | CO | single bond | 1 | O | $CH_2CH_2$ | sub. 11 |
| 330 | 4-Aze | 3,4-diClPh | CO | single bond | 1 | O | $CH_2CH_2$ | sub. 11 |
| 331 | cPr | 3,4-diClPh | CO | single bond | 1 | O | $CH_2CH_2$ | sub. 12 |
| 332 | cBu | 3,4-diClPh | CO | single bond | 1 | O | $CH_2CH_2$ | sub. 12 |
| 333 | cPn | 3,4-diClPh | CO | single bond | 1 | O | $CH_2CH_2$ | sub. 12 |
| 334 | cHex | 3,4-diClPh | CO | single bond | 1 | O | $CH_2CH_2$ | sub. 12 |
| 335 | cHep | 3,4-diClPh | CO | single bond | 1 | O | $CH_2CH_2$ | sub. 12 |
| 336 | 2-Pyrd | 3,4-diClPh | CO | single bond | 1 | O | $CH_2CH_2$ | sub. 12 |
| 337 | 3-Pyrd | 3,4-diClPh | CO | single bond | 1 | O | $CH_2CH_2$ | sub. 12 |
| 338 | 4-Oxa | 3,4-diClPh | CO | single bond | 1 | O | $CH_2CH_2$ | sub. 12 |
| 339 | 5-Oxa | 3,4-diClPh | CO | single bond | 1 | O | $CH_2CH_2$ | sub. 12 |
| 340 | 4-Thi | 3,4-diClPh | CO | single bond | 1 | O | $CH_2CH_2$ | sub. 12 |
| 341 | 5-Thi | 3,4-diClPh | CO | single bond | 1 | O | $CH_2CH_2$ | sub. 12 |
| 342 | 4-OOxa | 3,4-diClPh | CO | single bond | 1 | O | $CH_2CH_2$ | sub. 12 |
| 343 | 5-OOxa | 3,4-diClPh | CO | single bond | 1 | O | $CH_2CH_2$ | sub. 12 |
| 344 | 4-OThi | 3,4-diClPh | CO | single bond | 1 | O | $CH_2CH_2$ | sub. 12 |
| 345 | 5-OThi | 3,4-diClPh | CO | single bond | 1 | O | $CH_2CH_2$ | sub. 12 |
| 346 | 2-Pip | 3,4-diClPh | CO | single bond | 1 | O | $CH_2CH_2$ | sub. 12 |
| 347 | 3-Pip | 3,4-diClPh | CO | single bond | 1 | O | $CH_2CH_2$ | sub. 12 |
| 348 | 4-Pip | 3,4-diClPh | CO | single bond | 1 | O | $CH_2CH_2$ | sub. 12 |
| 349 | 2-Mor | 3,4-diClPh | CO | single bond | 1 | O | $CH_2CH_2$ | sub. 12 |
| 350 | 3-Mor | 3,4-diClPh | CO | single bond | 1 | O | $CH_2CH_2$ | sub. 12 |
| 351 | 4-Mor | 3,4-diClPh | CO | single bond | 1 | O | $CH_2CH_2$ | sub. 12 |
| 352 | 2-Thmor | 3,4-diClPh | CO | single bond | 1 | O | $CH_2CH_2$ | sub. 12 |
| 353 | 3-Thmor | 3,4-diClPh | CO | single bond | 1 | O | $CH_2CH_2$ | sub. 12 |
| 354 | 4-Thmor | 3,4-diClPh | CO | single bond | 1 | O | $CH_2CH_2$ | sub. 12 |
| 355 | 2-Piz | 3,4-diClPh | CO | single bond | 1 | O | $CH_2CH_2$ | sub. 12 |
| 356 | 3-Piz | 3,4-diClPh | CO | single bond | 1 | O | $CH_2CH_2$ | sub. 12 |
| 357 | 4-Piz | 3,4-diClPh | CO | single bond | 1 | O | $CH_2CH_2$ | sub. 12 |
| 358 | 2-Aze | 3,4-diClPh | CO | single bond | 1 | O | $CH_2CH_2$ | sub. 12 |
| 359 | 3-Aze | 3,4-diClPh | CO | single bond | 1 | O | $CH_2CH_2$ | sub. 12 |
| 360 | 4-Aze | 3,4-diClPh | CO | single bond | 1 | O | $CH_2CH_2$ | sub. 12 |

TABLE 1-continued

| Exemplification compound number | R¹ | R² | A | B | N | D | G | Q |
|---|---|---|---|---|---|---|---|---|
| 361 | cPr | 3,4-diClPh | CO | single bond | 1 | O | CH₂CH₂ | sub. 13 |
| 362 | cBu | 3,4-diClPh | CO | single bond | 1 | O | CH₂CH₂ | sub. 13 |
| 363 | cPn | 3,4-diClPh | CO | single bond | 1 | O | CH₂CH₂ | sub. 13 |
| 364 | cHex | 3,4-diClPh | CO | single bond | 1 | O | CH₂CH₂ | sub. 13 |
| 365 | cHep | 3,4-diClPh | CO | single bond | 1 | O | CH₂CH₂ | sub. 13 |
| 366 | 2-Pyrd | 3,4-diClPh | CO | single bond | 1 | O | CH₂CH₂ | sub. 13 |
| 367 | 3-Pyrd | 3,4-diClPh | CO | single bond | 1 | O | CH₂CH₂ | sub. 13 |
| 368 | 4-Oxa | 3,4-diClPh | CO | single bond | 1 | O | CH₂CH₂ | sub. 13 |
| 369 | 5-Oxa | 3,4-diClPh | CO | single bond | 1 | O | CH₂CH₂ | sub. 13 |
| 370 | 4-Thi | 3,4-diClPh | CO | single bond | 1 | O | CH₂CH₂ | sub. 13 |
| 371 | 5-Thi | 3,4-diClPh | CO | single bond | 1 | O | CH₂CH₂ | sub. 13 |
| 372 | 4-OOxa | 3,4-diClPh | CO | single bond | 1 | O | CH₂CH₂ | sub. 13 |
| 373 | 5-OOxa | 3,4-diClPh | CO | single bond | 1 | O | CH₂CH₂ | sub. 13 |
| 374 | 4-OThi | 3,4-diClPh | CO | single bond | 1 | O | CH₂CH₂ | sub. 13 |
| 375 | 5-OThi | 3,4-diClPh | CO | single bond | 1 | O | CH₂CH₂ | sub. 13 |
| 376 | 2-Pip | 3,4-diClPh | CO | single bond | 1 | O | CH₂CH₂ | sub. 13 |
| 377 | 3-Pip | 3,4-diClPh | CO | single bond | 1 | O | CH₂CH₂ | sub. 13 |
| 378 | 4-Pip | 3,4-diClPh | CO | single bond | 1 | O | CH₂CH₂ | sub. 13 |
| 379 | 2-Mor | 3,4-diClPh | CO | single bond | 1 | O | CH₂CH₂ | sub. 13 |
| 380 | 3-Mor | 3,4-diClPh | CO | single bond | 1 | O | CH₂CH₂ | sub. 13 |
| 381 | 4-Mor | 3,4-diClPh | CO | single bond | 1 | O | CH₂CH₂ | sub. 13 |
| 382 | 2-Thmor | 3,4-diClPh | CO | single bond | 1 | O | CH₂CH₂ | sub. 13 |
| 383 | 3-Thmor | 3,4-diClPh | CO | single bond | 1 | O | CH₂CH₂ | sub. 13 |
| 384 | 4-Thmor | 3,4-diClPh | CO | single bond | 1 | O | CH₂CH₂ | sub. 13 |
| 385 | 2-Piz | 3,4-diClPh | CO | single bond | 1 | O | CH₂CH₂ | sub. 13 |
| 386 | 3-Piz | 3,4-diClPh | CO | single bond | 1 | O | CH₂CH₂ | sub. 13 |
| 387 | 4-Piz | 3,4-diClPh | CO | single bond | 1 | O | CH₂CH₂ | sub. 13 |
| 388 | 2-Aze | 3,4-diClPh | CO | single bond | 1 | O | CH₂CH₂ | sub. 13 |
| 389 | 3-Aze | 3,4-diClPh | CO | single bond | 1 | O | CH₂CH₂ | sub. 13 |
| 390 | 4-Aze | 3,4-diClPh | CO | single bond | 1 | O | CH₂CH₂ | sub. 13 |
| 391 | cPr | 3,4-diClPh | CO | single bond | 1 | O | CH₂CH₂ | sub. 14 |
| 392 | cBu | 3,4-diClPh | CO | single bond | 1 | O | CH₂CH₂ | sub. 14 |
| 393 | cPn | 3,4-diClPh | CO | single bond | 1 | O | CH₂CH₂ | sub. 14 |
| 394 | cHex | 3,4-diClPh | CO | single bond | 1 | O | CH₂CH₂ | sub. 14 |
| 395 | cHep | 3,4-diClPh | CO | single bond | 1 | O | CH₂CH₂ | sub. 14 |
| 396 | 2-Pyrd | 3,4-diClPh | CO | single bond | 1 | O | CH₂CH₂ | sub. 14 |
| 397 | 3-Pyrd | 3,4-diClPh | CO | single bond | 1 | O | CH₂CH₂ | sub. 14 |
| 398 | 4-Oxa | 3,4-diClPh | CO | single bond | 1 | O | CH₂CH₂ | sub. 14 |
| 399 | 5-Oxa | 3,4-diClPh | CO | single bond | 1 | O | CH₂CH₂ | sub. 14 |
| 400 | 4-Thi | 3,4-diClPh | CO | single bond | 1 | O | CH₂CH₂ | sub. 14 |
| 401 | 5-Thi | 3,4-diClPh | CO | single bond | 1 | O | CH₂CH₂ | sub. 14 |
| 402 | 4-OOxa | 3,4-diClPh | CO | single bond | 1 | O | CH₂CH₂ | sub. 14 |
| 403 | 5-OOxa | 3,4-diClPh | CO | single bond | 1 | O | CH₂CH₂ | sub. 14 |
| 404 | 4-OThi | 3,4-diClPh | CO | single bond | 1 | O | CH₂CH₂ | sub. 14 |
| 405 | 5-OThi | 3,4-diClPh | CO | single bond | 1 | O | CH₂CH₂ | sub. 14 |
| 406 | 2-Pip | 3,4-diClPh | CO | single bond | 1 | O | CH₂CH₂ | sub. 14 |
| 407 | 3-Pip | 3,4-diClPh | CO | single bond | 1 | O | CH₂CH₂ | sub. 14 |
| 408 | 4-Pip | 3,4-diClPh | CO | single bond | 1 | O | CH₂CH₂ | sub. 14 |
| 409 | 2-Mor | 3,4-diClPh | CO | single bond | 1 | O | CH₂CH₂ | sub. 14 |
| 410 | 3-Mor | 3,4-diClPh | CO | single bond | 1 | O | CH₂CH₂ | sub. 14 |
| 411 | 4-Mor | 3,4-diClPh | CO | single bond | 1 | O | CH₂CH₂ | sub. 14 |
| 412 | 2-Thmor | 3,4-diClPh | CO | single bond | 1 | O | CH₂CH₂ | sub. 14 |
| 413 | 3-Thmor | 3,4-diClPh | CO | single bond | 1 | O | CH₂CH₂ | sub. 14 |
| 414 | 4-Thmor | 3,4-diClPh | CO | single bond | 1 | O | CH₂CH₂ | sub. 14 |
| 415 | 2-Piz | 3,4-diClPh | CO | single bond | 1 | O | CH₂CH₂ | sub. 14 |
| 416 | 3-Piz | 3,4-diClPh | CO | single bond | 1 | O | CH₂CH₂ | sub. 14 |
| 417 | 4-Piz | 3,4-diClPh | CO | single bond | 1 | O | CH₂CH₂ | sub. 14 |
| 418 | 2-Aze | 3,4-diClPh | CO | single bond | 1 | O | CH₂CH₂ | sub. 14 |
| 419 | 3-Aze | 3,4-diClPh | CO | single bond | 1 | O | CH₂CH₂ | sub. 14 |
| 420 | 4-Aze | 3,4-diClPh | CO | single bond | 1 | O | CH₂CH₂ | sub. 14 |
| 421 | cPr | 3,4-diClPh | CO | single bond | 1 | O | CH₂CH₂ | sub. 15 |
| 422 | cBu | 3,4-diClPh | CO | single bond | 1 | O | CH₂CH₂ | sub. 15 |
| 423 | cPn | 3,4-diClPh | CO | single bond | 1 | O | CH₂CH₂ | sub. 15 |
| 424 | cHex | 3,4-diClPh | CO | single bond | 1 | O | CH₂CH₂ | sub. 15 |
| 425 | cHep | 3,4-diClPh | CO | single bond | 1 | O | CH₂CH₂ | sub. 15 |
| 426 | 2-Pyrd | 3,4-diClPh | CO | single bond | 1 | O | CH₂CH₂ | sub. 15 |
| 427 | 3-Pyrd | 3,4-diClPh | CO | single bond | 1 | O | CH₂CH₂ | sub. 15 |
| 428 | 4-Oxa | 3,4-diClPh | CO | single bond | 1 | O | CH₂CH₂ | sub. 15 |
| 429 | 5-Oxa | 3,4-diClPh | CO | single bond | 1 | O | CH₂CH₂ | sub. 15 |
| 430 | 4-Thi | 3,4-diClPh | CO | single bond | 1 | O | CH₂CH₂ | sub. 15 |
| 431 | 5-Thi | 3,4-diClPh | CO | single bond | 1 | O | CH₂CH₂ | sub. 15 |
| 432 | 4-OOxa | 3,4-diClPh | CO | single bond | 1 | O | CH₂CH₂ | sub. 15 |
| 433 | 5-OOxa | 3,4-diClPh | CO | single bond | 1 | O | CH₂CH₂ | sub. 15 |
| 434 | 4-OThi | 3,4-diClPh | CO | single bond | 1 | O | CH₂CH₂ | sub. 15 |
| 435 | 5-OThi | 3,4-diClPh | CO | single bond | 1 | O | CH₂CH₂ | sub. 15 |
| 436 | 2-Pip | 3,4-diClPh | CO | single bond | 1 | O | CH₂CH₂ | sub. 15 |

TABLE 1-continued

| Exemplification compound number | R¹ | R² | A | B | N | D | G | Q |
|---|---|---|---|---|---|---|---|---|
| 437 | 3-Pip | 3,4-diClPh | CO | single bond | 1 | O | $CH_2CH_2$ | sub. 15 |
| 438 | 4-Pip | 3,4-diClPh | CO | single bond | 1 | O | $CH_2CH_2$ | sub. 15 |
| 439 | 2-Mor | 3,4-diClPh | CO | single bond | 1 | O | $CH_2CH_2$ | sub. 15 |
| 440 | 3-Mor | 3,4-diClPh | CO | single bond | 1 | O | $CH_2CH_2$ | sub. 15 |
| 441 | 4-Mor | 3,4-diClPh | CO | single bond | 1 | O | $CH_2CH_2$ | sub. 15 |
| 442 | 2-Thmor | 3,4-diClPh | CO | single bond | 1 | O | $CH_2CH_2$ | sub. 15 |
| 443 | 3-Thmor | 3,4-diClPh | CO | single bond | 1 | O | $CH_2CH_2$ | sub. 15 |
| 444 | 4-Thmor | 3,4-diClPh | CO | single bond | 1 | O | $CH_2CH_2$ | sub. 15 |
| 445 | 2-Piz | 3,4-diClPh | CO | single bond | 1 | O | $CH_2CH_2$ | sub. 15 |
| 446 | 3-Piz | 3,4-diClPh | CO | single bond | 1 | O | $CH_2CH_2$ | sub. 15 |
| 447 | 4-Piz | 3,4-diClPh | CO | single bond | 1 | O | $CH_2CH_2$ | sub. 15 |
| 448 | 2-Aze | 3,4-diClPh | CO | single bond | 1 | O | $CH_2CH_2$ | sub. 15 |
| 449 | 3-Aze | 3,4-diClPh | CO | single bond | 1 | O | $CH_2CH_2$ | sub. 15 |
| 450 | 4-Aze | 3,4-diClPh | CO | single bond | 1 | O | $CH_2CH_2$ | sub. 15 |
| 451 | cPr | 3,4-diClPh | CO | single bond | 1 | O | $CH_2CH_2$ | sub. 16 |
| 452 | cBu | 3,4-diClPh | CO | single bond | 1 | O | $CH_2CH_2$ | sub. 16 |
| 453 | cPn | 3,4-diClPh | CO | single bond | 1 | O | $CH_2CH_2$ | sub. 16 |
| 454 | cHex | 3,4-diClPh | CO | single bond | 1 | O | $CH_2CH_2$ | sub. 16 |
| 455 | cHep | 3,4-diClPh | CO | single bond | 1 | O | $CH_2CH_2$ | sub. 16 |
| 456 | 2-Pyrd | 3,4-diClPh | CO | single bond | 1 | O | $CH_2CH_2$ | sub. 16 |
| 457 | 3-Pyrd | 3,4-diClPh | CO | single bond | 1 | O | $CH_2CH_2$ | sub. 16 |
| 458 | 4-Oxa | 3,4-diClPh | CO | single bond | 1 | O | $CH_2CH_2$ | sub. 16 |
| 459 | 5-Oxa | 3,4-diClPh | CO | single bond | 1 | O | $CH_2CH_2$ | sub. 16 |
| 460 | 4-Thi | 3,4-diClPh | CO | single bond | 1 | O | $CH_2CH_2$ | sub. 16 |
| 461 | 5-Thi | 3,4-diClPh | CO | single bond | 1 | O | $CH_2CH_2$ | sub. 16 |
| 462 | 4-OOxa | 3,4-diClPh | CO | single bond | 1 | O | $CH_2CH_2$ | sub. 16 |
| 463 | 5-OOxa | 3,4-diClPh | CO | single bond | 1 | O | $CH_2CH_2$ | sub. 16 |
| 464 | 4-OThi | 3,4-diClPh | CO | single bond | 1 | O | $CH_2CH_2$ | sub. 16 |
| 465 | 5-OThi | 3,4-diClPh | CO | single bond | 1 | O | $CH_2CH_2$ | sub. 16 |
| 466 | 2-Pip | 3,4-diClPh | CO | single bond | 1 | O | $CH_2CH_2$ | sub. 16 |
| 467 | 3-Pip | 3,4-diClPh | CO | single bond | 1 | O | $CH_2CH_2$ | sub. 16 |
| 468 | 4-Pip | 3,4-diClPh | CO | single bond | 1 | O | $CH_2CH_2$ | sub. 16 |
| 469 | 2-Mor | 3,4-diClPh | CO | single bond | 1 | O | $CH_2CH_2$ | sub. 16 |
| 470 | 3-Mor | 3,4-diClPh | CO | single bond | 1 | O | $CH_2CH_2$ | sub. 16 |
| 471 | 4-Mor | 3,4-diClPh | CO | single bond | 1 | O | $CH_2CH_2$ | sub. 16 |
| 472 | 2-Thmor | 3,4-diClPh | CO | single bond | 1 | O | $CH_2CH_2$ | sub. 16 |
| 473 | 3-Thmor | 3,4-diClPh | CO | single bond | 1 | O | $CH_2CH_2$ | sub. 16 |
| 474 | 4-Thmor | 3,4-diClPh | CO | single bond | 1 | O | $CH_2CH_2$ | sub. 16 |
| 475 | 2-Piz | 3,4-diClPh | CO | single bond | 1 | O | $CH_2CH_2$ | sub. 16 |
| 476 | 3-Piz | 3,4-diClPh | CO | single bond | 1 | O | $CH_2CH_2$ | sub. 16 |
| 477 | 4-Piz | 3,4-diClPh | CO | single bond | 1 | O | $CH_2CH_2$ | sub. 16 |
| 478 | 2-Aze | 3,4-diClPh | CO | single bond | 1 | O | $CH_2CH_2$ | sub. 16 |
| 479 | 3-Aze | 3,4-diClPh | CO | single bond | 1 | O | $CH_2CH_2$ | sub. 16 |
| 480 | 4-Aze | 3,4-diClPh | CO | single bond | 1 | O | $CH_2CH_2$ | sub. 16 |
| 481 | cPr | 3,4-diClPh | CO | single bond | 1 | O | $CH_2CH_2$ | sub. 17 |
| 482 | cBu | 3,4-diClPh | CO | single bond | 1 | O | $CH_2CH_2$ | sub. 17 |
| 483 | cPn | 3,4-diClPh | CO | single bond | 1 | O | $CH_2CH_2$ | sub. 17 |
| 484 | cHex | 3,4-diClPh | CO | single bond | 1 | O | $CH_2CH_2$ | sub. 17 |
| 485 | cHep | 3,4-diClPh | CO | single bond | 1 | O | $CH_2CH_2$ | sub. 17 |
| 486 | 2-Pyrd | 3,4-diClPh | CO | single bond | 1 | O | $CH_2CH_2$ | sub. 17 |
| 487 | 3-Pyrd | 3,4-diClPh | CO | single bond | 1 | O | $CH_2CH_2$ | sub. 17 |
| 488 | 4-Oxa | 3,4-diClPh | CO | single bond | 1 | O | $CH_2CH_2$ | sub. 17 |
| 489 | 5-Oxa | 3,4-diClPh | CO | single bond | 1 | O | $CH_2CH_2$ | sub. 17 |
| 490 | 4-Thi | 3,4-diClPh | CO | single bond | 1 | O | $CH_2CH_2$ | sub. 17 |
| 491 | 5-Thi | 3,4-diClPh | CO | single bond | 1 | O | $CH_2CH_2$ | sub. 17 |
| 492 | 4-OOxa | 3,4-diClPh | CO | single bond | 1 | O | $CH_2CH_2$ | sub. 17 |
| 493 | 5-OOxa | 3,4-diClPh | CO | single bond | 1 | O | $CH_2CH_2$ | sub. 17 |
| 494 | 4-OThi | 3,4-diClPh | CO | single bond | 1 | O | $CH_2CH_2$ | sub. 17 |
| 495 | 5-OThi | 3,4-diClPh | CO | single bond | 1 | O | $CH_2CH_2$ | sub. 17 |
| 496 | 2-Pip | 3,4-diClPh | CO | single bond | 1 | O | $CH_2CH_2$ | sub. 17 |
| 497 | 3-Pip | 3,4-diClPh | CO | single bond | 1 | O | $CH_2CH_2$ | sub. 17 |
| 498 | 4-Pip | 3,4-diClPh | CO | single bond | 1 | O | $CH_2CH_2$ | sub. 17 |
| 499 | 2-Mor | 3,4-diClPh | CO | single bond | 1 | O | $CH_2CH_2$ | sub. 17 |
| 500 | 3-Mor | 3,4-diClPh | CO | single bond | 1 | O | $CH_2CH_2$ | sub. 17 |
| 501 | 4-Mor | 3,4-diClPh | CO | single bond | 1 | O | $CH_2CH_2$ | sub. 17 |
| 502 | 2-Thmor | 3,4-diClPh | CO | single bond | 1 | O | $CH_2CH_2$ | sub. 17 |
| 503 | 3-Thmor | 3,4-diClPh | CO | single bond | 1 | O | $CH_2CH_2$ | sub. 17 |
| 504 | 4-Thmor | 3,4-diClPh | CO | single bond | 1 | O | $CH_2CH_2$ | sub. 17 |
| 505 | 2-Piz | 3,4-diClPh | CO | single bond | 1 | O | $CH_2CH_2$ | sub. 17 |
| 506 | 3-Piz | 3,4-diClPh | CO | single bond | 1 | O | $CH_2CH_2$ | sub. 17 |
| 507 | 4-Piz | 3,4-diClPh | CO | single bond | 1 | O | $CH_2CH_2$ | sub. 17 |
| 508 | 2-Aze | 3,4-diClPh | CO | single bond | 1 | O | $CH_2CH_2$ | sub. 17 |
| 509 | 3-Aze | 3,4-diClPh | CO | single bond | 1 | O | $CH_2CH_2$ | sub. 17 |
| 510 | 4-Aze | 3,4-diClPh | CO | single bond | 1 | O | $CH_2CH_2$ | sub. 17 |
| 511 | cPr | 3,4-diClPh | CO | single bond | 1 | O | $CH_2CH_2$ | sub. 18 |
| 512 | cBu | 3,4-diClPh | CO | single bond | 1 | O | $CH_2CH_2$ | sub. 18 |

TABLE 1-continued

| Exemplification compound number | R¹ | R² | A | B | N | D | G | Q |
|---|---|---|---|---|---|---|---|---|
| 513 | cPn | 3,4-diClPh | CO | single bond | 1 | O | $CH_2CH_2$ | sub. 18 |
| 514 | cHex | 3,4-diClPh | CO | single bond | 1 | O | $CH_2CH_2$ | sub. 18 |
| 515 | cHep | 3,4-diClPh | CO | single bond | 1 | O | $CH_2CH_2$ | sub. 18 |
| 516 | 2-Pyrd | 3,4-diClPh | CO | single bond | 1 | O | $CH_2CH_2$ | sub. 18 |
| 517 | 3-Pyrd | 3,4-diClPh | CO | single bond | 1 | O | $CH_2CH_2$ | sub. 18 |
| 518 | 4-Oxa | 3,4-diClPh | CO | single bond | 1 | O | $CH_2CH_2$ | sub. 18 |
| 519 | 5-Oxa | 3,4-diClPh | CO | single bond | 1 | O | $CH_2CH_2$ | sub. 18 |
| 520 | 4-Thi | 3,4-diClPh | CO | single bond | 1 | O | $CH_2CH_2$ | sub. 18 |
| 521 | 5-Thi | 3,4-diClPh | CO | single bond | 1 | O | $CH_2CH_2$ | sub. 18 |
| 522 | 4-OOxa | 3,4-diClPh | CO | single bond | 1 | O | $CH_2CH_2$ | sub. 18 |
| 523 | 5-OOxa | 3,4-diClPh | CO | single bond | 1 | O | $CH_2CH_2$ | sub. 18 |
| 524 | 4-OThi | 3,4-diClPh | CO | single bond | 1 | O | $CH_2CH_2$ | sub. 18 |
| 525 | 5-OThi | 3,4-diClPh | CO | single bond | 1 | O | $CH_2CH_2$ | sub. 18 |
| 526 | 2-Pip | 3,4-diClPh | CO | single bond | 1 | O | $CH_2CH_2$ | sub. 18 |
| 527 | 3-Pip | 3,4-diClPh | CO | single bond | 1 | O | $CH_2CH_2$ | sub. 18 |
| 528 | 4-Pip | 3,4-diClPh | CO | single bond | 1 | O | $CH_2CH_2$ | sub. 18 |
| 529 | 2-Mor | 3,4-diClPh | CO | single bond | 1 | O | $CH_2CH_2$ | sub. 18 |
| 530 | 3-Mor | 3,4-diClPh | CO | single bond | 1 | O | $CH_2CH_2$ | sub. 18 |
| 531 | 4-Mor | 3,4-diClPh | CO | single bond | 1 | O | $CH_2CH_2$ | sub. 18 |
| 532 | 2-Thmor | 3,4-diClPh | CO | single bond | 1 | O | $CH_2CH_2$ | sub. 18 |
| 533 | 3-Thmor | 3,4-diClPh | CO | single bond | 1 | O | $CH_2CH_2$ | sub. 18 |
| 534 | 4-Thmor | 3,4-diClPh | CO | single bond | 1 | O | $CH_2CH_2$ | sub. 18 |
| 535 | 2-Piz | 3,4-diClPh | CO | single bond | 1 | O | $CH_2CH_2$ | sub. 18 |
| 536 | 3-Piz | 3,4-diClPh | CO | single bond | 1 | O | $CH_2CH_2$ | sub. 18 |
| 537 | 4-Piz | 3,4-diClPh | CO | single bond | 1 | O | $CH_2CH_2$ | sub. 18 |
| 538 | 2-Aze | 3,4-diClPh | CO | single bond | 1 | O | $CH_2CH_2$ | sub. 18 |
| 539 | 3-Aze | 3,4-diClPh | CO | single bond | 1 | O | $CH_2CH_2$ | sub. 18 |
| 540 | 4-Aze | 3,4-diClPh | CO | single bond | 1 | O | $CH_2CH_2$ | sub. 18 |
| 541 | cPr | 3,4-diClPh | CO | single bond | 1 | O | $CH_2CH_2$ | sub. 19 |
| 542 | cBu | 3,4-diClPh | CO | single bond | 1 | O | $CH_2CH_2$ | sub. 19 |
| 543 | cPn | 3,4-diClPh | CO | single bond | 1 | O | $CH_2CH_2$ | sub. 19 |
| 544 | cHex | 3,4-diClPh | CO | single bond | 1 | O | $CH_2CH_2$ | sub. 19 |
| 545 | cHep | 3,4-diClPh | CO | single bond | 1 | O | $CH_2CH_2$ | sub. 19 |
| 546 | 2-Pyrd | 3,4-diClPh | CO | single bond | 1 | O | $CH_2CH_2$ | sub. 19 |
| 547 | 3-Pyrd | 3,4-diClPh | CO | single bond | 1 | O | $CH_2CH_2$ | sub. 19 |
| 548 | 4-Oxa | 3,4-diClPh | CO | single bond | 1 | O | $CH_2CH_2$ | sub. 19 |
| 549 | 5-Oxa | 3,4-diClPh | CO | single bond | 1 | O | $CH_2CH_2$ | sub. 19 |
| 550 | 4-Thi | 3,4-diClPh | CO | single bond | 1 | O | $CH_2CH_2$ | sub. 19 |
| 551 | 5-Thi | 3,4-diClPh | CO | single bond | 1 | O | $CH_2CH_2$ | sub. 19 |
| 552 | 4-OOxa | 3,4-diClPh | CO | single bond | 1 | O | $CH_2CH_2$ | sub. 19 |
| 553 | 5-OOxa | 3,4-diClPh | CO | single bond | 1 | O | $CH_2CH_2$ | sub. 19 |
| 554 | 4-OThi | 3,4-diClPh | CO | single bond | 1 | O | $CH_2CH_2$ | sub. 19 |
| 555 | 5-OThi | 3,4-diClPh | CO | single bond | 1 | O | $CH_2CH_2$ | sub. 19 |
| 556 | 2-Pip | 3,4-diClPh | CO | single bond | 1 | O | $CH_2CH_2$ | sub. 19 |
| 557 | 3-Pip | 3,4-diClPh | CO | single bond | 1 | O | $CH_2CH_2$ | sub. 19 |
| 558 | 4-Pip | 3,4-diClPh | CO | single bond | 1 | O | $CH_2CH_2$ | sub. 19 |
| 559 | 2-Mor | 3,4-diClPh | CO | single bond | 1 | O | $CH_2CH_2$ | sub. 19 |
| 560 | 3-Mor | 3,4-diClPh | CO | single bond | 1 | O | $CH_2CH_2$ | sub. 19 |
| 561 | 4-Mor | 3,4-diClPh | CO | single bond | 1 | O | $CH_2CH_2$ | sub. 19 |
| 562 | 2-Thmor | 3,4-diClPh | CO | single bond | 1 | O | $CH_2CH_2$ | sub. 19 |
| 563 | 3-Thmor | 3,4-diClPh | CO | single bond | 1 | O | $CH_2CH_2$ | sub. 19 |
| 564 | 4-Thmor | 3,4-diClPh | CO | single bond | 1 | O | $CH_2CH_2$ | sub. 19 |
| 565 | 2-Piz | 3,4-diClPh | CO | single bond | 1 | O | $CH_2CH_2$ | sub. 19 |
| 566 | 3-Piz | 3,4-diClPh | CO | single bond | 1 | O | $CH_2CH_2$ | sub. 19 |
| 567 | 4-Piz | 3,4-diClPh | CO | single bond | 1 | O | $CH_2CH_2$ | sub. 19 |
| 568 | 2-Aze | 3,4-diClPh | CO | single bond | 1 | O | $CH_2CH_2$ | sub. 19 |
| 569 | 3-Aze | 3,4-diClPh | CO | single bond | 1 | O | $CH_2CH_2$ | sub. 19 |
| 570 | 4-Aze | 3,4-diClPh | CO | single bond | 1 | O | $CH_2CH_2$ | sub. 19 |
| 571 | cPr | 3,4-diClPh | CO | single bond | 1 | O | $CH_2CH_2$ | sub. 20 |
| 572 | cBu | 3,4-diClPh | CO | single bond | 1 | O | $CH_2CH_2$ | sub. 20 |
| 573 | cPn | 3,4-diClPh | CO | single bond | 1 | O | $CH_2CH_2$ | sub. 20 |
| 574 | cHex | 3,4-diClPh | CO | single bond | 1 | O | $CH_2CH_2$ | sub. 20 |
| 575 | cHep | 3,4-diClPh | CO | single bond | 1 | O | $CH_2CH_2$ | sub. 20 |
| 576 | 2-Pyrd | 3,4-diClPh | CO | single bond | 1 | O | $CH_2CH_2$ | sub. 20 |
| 577 | 3-Pyrd | 3,4-diClPh | CO | single bond | 1 | O | $CH_2CH_2$ | sub. 20 |
| 578 | 4-Oxa | 3,4-diClPh | CO | single bond | 1 | O | $CH_2CH_2$ | sub. 20 |
| 579 | 5-Oxa | 3,4-diClPh | CO | single bond | 1 | O | $CH_2CH_2$ | sub. 20 |
| 580 | 4-Thi | 3,4-diClPh | CO | single bond | 1 | O | $CH_2CH_2$ | sub. 20 |
| 581 | 5-Thi | 3,4-diClPh | CO | single bond | 1 | O | $CH_2CH_2$ | sub. 20 |
| 582 | 4-OOxa | 3,4-diClPh | CO | single bond | 1 | O | $CH_2CH_2$ | sub. 20 |
| 583 | 5-OOxa | 3,4-diClPh | CO | single bond | 1 | O | $CH_2CH_2$ | sub. 20 |
| 584 | 4-OThi | 3,4-diClPh | CO | single bond | 1 | O | $CH_2CH_2$ | sub. 20 |
| 585 | 5-OThi | 3,4-diClPh | CO | single bond | 1 | O | $CH_2CH_2$ | sub. 20 |
| 586 | 2-Pip | 3,4-diClPh | CO | single bond | 1 | O | $CH_2CH_2$ | sub. 20 |
| 587 | 3-Pip | 3,4-diClPh | CO | single bond | 1 | O | $CH_2CH_2$ | sub. 20 |
| 588 | 4-Pip | 3,4-diClPh | CO | single bond | 1 | O | $CH_2CH_2$ | sub. 20 |

TABLE 1-continued

| Exemplification compound number | R¹ | R² | A | B | N | D | G | Q |
|---|---|---|---|---|---|---|---|---|
| 589 | 2-Mor | 3,4-diClPh | CO | single bond | 1 | O | $CH_2CH_2$ | sub. 20 |
| 590 | 3-Mor | 3,4-diClPh | CO | single bond | 1 | O | $CH_2CH_2$ | sub. 20 |
| 591 | 4-Mor | 3,4-diClPh | CO | single bond | 1 | O | $CH_2CH_2$ | sub. 20 |
| 592 | 2-Thmor | 3,4-diClPh | CO | single bond | 1 | O | $CH_2CH_2$ | sub. 20 |
| 593 | 3-Thmor | 3,4-diClPh | CO | single bond | 1 | O | $CH_2CH_2$ | sub. 20 |
| 594 | 4-Thmor | 3,4-diClPh | CO | single bond | 1 | O | $CH_2CH_2$ | sub. 20 |
| 595 | 2-Piz | 3,4-diClPh | CO | single bond | 1 | O | $CH_2CH_2$ | sub. 20 |
| 596 | 3-Piz | 3,4-diClPh | CO | single bond | 1 | O | $CH_2CH_2$ | sub. 20 |
| 597 | 4-Piz | 3,4-diClPh | CO | single bond | 1 | O | $CH_2CH_2$ | sub. 20 |
| 598 | 2-Aze | 3,4-diClPh | CO | single bond | 1 | O | $CH_2CH_2$ | sub. 20 |
| 599 | 3-Aze | 3,4-diClPh | CO | single bond | 1 | O | $CH_2CH_2$ | sub. 20 |
| 600 | 4-Aze | 3,4-diClPh | CO | single bond | 1 | O | $CH_2CH_2$ | sub. 20 |
| 601 | cPr | 3,4-diClPh | CO | single bond | 1 | O | $CH_2CH_2$ | sub. 21 |
| 602 | cBu | 3,4-diClPh | CO | single bond | 1 | O | $CH_2CH_2$ | sub. 21 |
| 603 | cPn | 3,4-diClPh | CO | single bond | 1 | O | $CH_2CH_2$ | sub. 21 |
| 604 | cHex | 3,4-diClPh | CO | single bond | 1 | O | $CH_2CH_2$ | sub. 21 |
| 605 | cHep | 3,4-diClPh | CO | single bond | 1 | O | $CH_2CH_2$ | sub. 21 |
| 606 | 2-Pyrd | 3,4-diClPh | CO | single bond | 1 | O | $CH_2CH_2$ | sub. 21 |
| 607 | 3-Pyrd | 3,4-diClPh | CO | single bond | 1 | O | $CH_2CH_2$ | sub. 21 |
| 608 | 4-Oxa | 3,4-diClPh | CO | single bond | 1 | O | $CH_2CH_2$ | sub. 21 |
| 609 | 5-Oxa | 3,4-diClPh | CO | single bond | 1 | O | $CH_2CH_2$ | sub. 21 |
| 610 | 4-Thi | 3,4-diClPh | CO | single bond | 1 | O | $CH_2CH_2$ | sub. 21 |
| 611 | 5-Thi | 3,4-diClPh | CO | single bond | 1 | O | $CH_2CH_2$ | sub. 21 |
| 612 | 4-OOxa | 3,4-diClPh | CO | single bond | 1 | O | $CH_2CH_2$ | sub. 21 |
| 613 | 5-OOxa | 3,4-diClPh | CO | single bond | 1 | O | $CH_2CH_2$ | sub. 21 |
| 614 | 4-OThi | 3,4-diClPh | CO | single bond | 1 | O | $CH_2CH_2$ | sub. 21 |
| 615 | 5-OThi | 3,4-diClPh | CO | single bond | 1 | O | $CH_2CH_2$ | sub. 21 |
| 616 | 2-Pip | 3,4-diClPh | CO | single bond | 1 | O | $CH_2CH_2$ | sub. 21 |
| 617 | 3-Pip | 3,4-diClPh | CO | single bond | 1 | O | $CH_2CH_2$ | sub. 21 |
| 618 | 4-Pip | 3,4-diClPh | CO | single bond | 1 | O | $CH_2CH_2$ | sub. 21 |
| 619 | 2-Mor | 3,4-diClPh | CO | single bond | 1 | O | $CH_2CH_2$ | sub. 21 |
| 620 | 3-Mor | 3,4-diClPh | CO | single bond | 1 | O | $CH_2CH_2$ | sub. 21 |
| 621 | 4-Mor | 3,4-diClPh | CO | single bond | 1 | O | $CH_2CH_2$ | sub. 21 |
| 622 | 2-Thmor | 3,4-diClPh | CO | single bond | 1 | O | $CH_2CH_2$ | sub. 21 |
| 623 | 3-Thmor | 3,4-diClPh | CO | single bond | 1 | O | $CH_2CH_2$ | sub. 21 |
| 624 | 4-Thmor | 3,4-diClPh | CO | single bond | 1 | O | $CH_2CH_2$ | sub. 21 |
| 625 | 2-Piz | 3,4-diClPh | CO | single bond | 1 | O | $CH_2CH_2$ | sub. 21 |
| 626 | 3-Piz | 3,4-diClPh | CO | single bond | 1 | O | $CH_2CH_2$ | sub. 21 |
| 627 | 4-Piz | 3,4-diClPh | CO | single bond | 1 | O | $CH_2CH_2$ | sub. 21 |
| 628 | 2-Aze | 3,4-diClPh | CO | single bond | 1 | O | $CH_2CH_2$ | sub. 21 |
| 629 | 3-Aze | 3,4-diClPh | CO | single bond | 1 | O | $CH_2CH_2$ | sub. 21 |
| 630 | 4-Aze | 3,4-diClPh | CO | single bond | 1 | O | $CH_2CH_2$ | sub. 21 |
| 631 | cPr | 3,4-diClPh | CO | single bond | 1 | O | $CH_2CH_2$ | sub. 22 |
| 632 | cBu | 3,4-diClPh | CO | single bond | 1 | O | $CH_2CH_2$ | sub. 22 |
| 633 | cPn | 3,4-diClPh | CO | single bond | 1 | O | $CH_2CH_2$ | sub. 22 |
| 634 | cHex | 3,4-diClPh | CO | single bond | 1 | O | $CH_2CH_2$ | sub. 22 |
| 635 | cHep | 3,4-diClPh | CO | single bond | 1 | O | $CH_2CH_2$ | sub. 22 |
| 636 | 2-Pyrd | 3,4-diClPh | CO | single bond | 1 | O | $CH_2CH_2$ | sub. 22 |
| 637 | 3-Pyrd | 3,4-diClPh | CO | single bond | 1 | O | $CH_2CH_2$ | sub. 22 |
| 638 | 4-Oxa | 3,4-diClPh | CO | single bond | 1 | O | $CH_2CH_2$ | sub. 22 |
| 639 | 5-Oxa | 3,4-diClPh | CO | single bond | 1 | O | $CH_2CH_2$ | sub. 22 |
| 640 | 4-Thi | 3,4-diClPh | CO | single bond | 1 | O | $CH_2CH_2$ | sub. 22 |
| 641 | 5-Thi | 3,4-diClPh | CO | single bond | 1 | O | $CH_2CH_2$ | sub. 22 |
| 642 | 4-OOxa | 3,4-diClPh | CO | single bond | 1 | O | $CH_2CH_2$ | sub. 22 |
| 643 | 5-OOxa | 3,4-diClPh | CO | single bond | 1 | O | $CH_2CH_2$ | sub. 22 |
| 644 | 4-OThi | 3,4-diClPh | CO | single bond | 1 | O | $CH_2CH_2$ | sub. 22 |
| 645 | 5-OThi | 3,4-diClPh | CO | single bond | 1 | O | $CH_2CH_2$ | sub. 22 |
| 646 | 2-Pip | 3,4-diClPh | CO | single bond | 1 | O | $CH_2CH_2$ | sub. 22 |
| 647 | 3-Pip | 3,4-diClPh | CO | single bond | 1 | O | $CH_2CH_2$ | sub. 22 |
| 648 | 4-Pip | 3,4-diClPh | CO | single bond | 1 | O | $CH_2CH_2$ | sub. 22 |
| 649 | 2-Mor | 3,4-diClPh | CO | single bond | 1 | O | $CH_2CH_2$ | sub. 22 |
| 650 | 3-Mor | 3,4-diClPh | CO | single bond | 1 | O | $CH_2CH_2$ | sub. 22 |
| 651 | 4-Mor | 3,4-diClPh | CO | single bond | 1 | O | $CH_2CH_2$ | sub. 22 |
| 652 | 2-Thmor | 3,4-diClPh | CO | single bond | 1 | O | $CH_2CH_2$ | sub. 22 |
| 653 | 3-Thmor | 3,4-diClPh | CO | single bond | 1 | O | $CH_2CH_2$ | sub. 22 |
| 654 | 4-Thmor | 3,4-diClPh | CO | single bond | 1 | O | $CH_2CH_2$ | sub. 22 |
| 655 | 2-Piz | 3,4-diClPh | CO | single bond | 1 | O | $CH_2CH_2$ | sub. 22 |
| 656 | 3-Piz | 3,4-diClPh | CO | single bond | 1 | O | $CH_2CH_2$ | sub. 22 |
| 657 | 4-Piz | 3,4-diClPh | CO | single bond | 1 | O | $CH_2CH_2$ | sub. 22 |
| 658 | 2-Aze | 3,4-diClPh | CO | single bond | 1 | O | $CH_2CH_2$ | sub. 22 |
| 659 | 3-Aze | 3,4-diClPh | CO | single bond | 1 | O | $CH_2CH_2$ | sub. 22 |
| 660 | 4-Aze | 3,4-diClPh | CO | single bond | 1 | O | $CH_2CH_2$ | sub. 22 |
| 661 | cPr | 3,4-diClPh | CO | single bond | 1 | O | $CH_2CH_2$ | sub. 23 |
| 662 | cBu | 3,4-diClPh | CO | single bond | 1 | O | $CH_2CH_2$ | sub. 23 |
| 663 | cPn | 3,4-diClPh | CO | single bond | 1 | O | $CH_2CH_2$ | sub. 23 |
| 664 | cHex | 3,4-diClPh | CO | single bond | 1 | O | $CH_2CH_2$ | sub. 23 |

TABLE 1-continued

| Exemplification compound number | R¹ | R² | A | B | N | D | G | Q |
|---|---|---|---|---|---|---|---|---|
| 665 | cHep | 3,4-diClPh | CO | single bond | 1 | O | $CH_2CH_2$ | sub. 23 |
| 666 | 2-Pyrd | 3,4-diClPh | CO | single bond | 1 | O | $CH_2CH_2$ | sub. 23 |
| 667 | 3-Pyrd | 3,4-diClPh | CO | single bond | 1 | O | $CH_2CH_2$ | sub. 23 |
| 668 | 4-Oxa | 3,4-diClPh | CO | single bond | 1 | O | $CH_2CH_2$ | sub. 23 |
| 669 | 5-Oxa | 3,4-diClPh | CO | single bond | 1 | O | $CH_2CH_2$ | sub. 23 |
| 670 | 4-Thi | 3,4-diClPh | CO | single bond | 1 | O | $CH_2CH_2$ | sub. 23 |
| 671 | 5-Thi | 3,4-diClPh | CO | single bond | 1 | O | $CH_2CH_2$ | sub. 23 |
| 672 | 4-OOxa | 3,4-diClPh | CO | single bond | 1 | O | $CH_2CH_2$ | sub. 23 |
| 673 | 5-OOxa | 3,4-diClPh | CO | single bond | 1 | O | $CH_2CH_2$ | sub. 23 |
| 674 | 4-OThi | 3,4-diClPh | CO | single bond | 1 | O | $CH_2CH_2$ | sub. 23 |
| 675 | 5-OThi | 3,4-diClPh | CO | single bond | 1 | O | $CH_2CH_2$ | sub. 23 |
| 676 | 2-Pip | 3,4-diClPh | CO | single bond | 1 | O | $CH_2CH_2$ | sub. 23 |
| 677 | 3-Pip | 3,4-diClPh | CO | single bond | 1 | O | $CH_2CH_2$ | sub. 23 |
| 678 | 4-Pip | 3,4-diClPh | CO | single bond | 1 | O | $CH_2CH_2$ | sub. 23 |
| 679 | 2-Mor | 3,4-diClPh | CO | single bond | 1 | O | $CH_2CH_2$ | sub. 23 |
| 680 | 3-Mor | 3,4-diClPh | CO | single bond | 1 | O | $CH_2CH_2$ | sub. 23 |
| 681 | 4-Mor | 3,4-diClPh | CO | single bond | 1 | O | $CH_2CH_2$ | sub. 23 |
| 682 | 2-Thmor | 3,4-diClPh | CO | single bond | 1 | O | $CH_2CH_2$ | sub. 23 |
| 683 | 3-Thmor | 3,4-diClPh | CO | single bond | 1 | O | $CH_2CH_2$ | sub. 23 |
| 684 | 4-Thmor | 3,4-diClPh | CO | single bond | 1 | O | $CH_2CH_2$ | sub. 23 |
| 685 | 2-Piz | 3,4-diClPh | CO | single bond | 1 | O | $CH_2CH_2$ | sub. 23 |
| 686 | 3-Piz | 3,4-diClPh | CO | single bond | 1 | O | $CH_2CH_2$ | sub. 23 |
| 687 | 4-Piz | 3,4-diClPh | CO | single bond | 1 | O | $CH_2CH_2$ | sub. 23 |
| 688 | 2-Aze | 3,4-diClPh | CO | single bond | 1 | O | $CH_2CH_2$ | sub. 23 |
| 689 | 3-Aze | 3,4-diClPh | CO | single bond | 1 | O | $CH_2CH_2$ | sub. 23 |
| 690 | 4-Aze | 3,4-diClPh | CO | single bond | 1 | O | $CH_2CH_2$ | sub. 23 |
| 691 | cPr | 3,4-diClPh | CO | single bond | 1 | O | $CH_2CH_2$ | sub. 24 |
| 692 | cBu | 3,4-diClPh | CO | single bond | 1 | O | $CH_2CH_2$ | sub. 24 |
| 693 | cPn | 3,4-diClPh | CO | single bond | 1 | O | $CH_2CH_2$ | sub. 24 |
| 694 | cHex | 3,4-diClPh | CO | single bond | 1 | O | $CH_2CH_2$ | sub. 24 |
| 695 | cHep | 3,4-diClPh | CO | single bond | 1 | O | $CH_2CH_2$ | sub. 24 |
| 696 | 2-Pyrd | 3,4-diClPh | CO | single bond | 1 | O | $CH_2CH_2$ | sub. 24 |
| 697 | 3-Pyrd | 3,4-diClPh | CO | single bond | 1 | O | $CH_2CH_2$ | sub. 24 |
| 698 | 4-Oxa | 3,4-diClPh | CO | single bond | 1 | O | $CH_2CH_2$ | sub. 24 |
| 699 | 5-Oxa | 3,4-diClPh | CO | single bond | 1 | O | $CH_2CH_2$ | sub. 24 |
| 700 | 4-Thi | 3,4-diClPh | CO | single bond | 1 | O | $CH_2CH_2$ | sub. 24 |
| 701 | 5-Thi | 3,4-diClPh | CO | single bond | 1 | O | $CH_2CH_2$ | sub. 24 |
| 702 | 4-OOxa | 3,4-diClPh | CO | single bond | 1 | O | $CH_2CH_2$ | sub. 24 |
| 703 | 5-OOxa | 3,4-diClPh | CO | single bond | 1 | O | $CH_2CH_2$ | sub. 24 |
| 704 | 4-OThi | 3,4-diClPh | CO | single bond | 1 | O | $CH_2CH_2$ | sub. 24 |
| 705 | 5-OThi | 3,4-diClPh | CO | single bond | 1 | O | $CH_2CH_2$ | sub. 24 |
| 706 | 2-Pip | 3,4-diClPh | CO | single bond | 1 | O | $CH_2CH_2$ | sub. 24 |
| 707 | 3-Pip | 3,4-diClPh | CO | single bond | 1 | O | $CH_2CH_2$ | sub. 24 |
| 708 | 4-Pip | 3,4-diClPh | CO | single bond | 1 | O | $CH_2CH_2$ | sub. 24 |
| 709 | 2-Mor | 3,4-diClPh | CO | single bond | 1 | O | $CH_2CH_2$ | sub. 24 |
| 710 | 3-Mor | 3,4-diClPh | CO | single bond | 1 | O | $CH_2CH_2$ | sub. 24 |
| 711 | 4-Mor | 3,4-diClPh | CO | single bond | 1 | O | $CH_2CH_2$ | sub. 24 |
| 712 | 2-Thmor | 3,4-diClPh | CO | single bond | 1 | O | $CH_2CH_2$ | sub. 24 |
| 713 | 3-Thmor | 3,4-diClPh | CO | single bond | 1 | O | $CH_2CH_2$ | sub. 24 |
| 714 | 4-Thmor | 3,4-diClPh | CO | single bond | 1 | O | $CH_2CH_2$ | sub. 24 |
| 715 | 2-Piz | 3,4-diClPh | CO | single bond | 1 | O | $CH_2CH_2$ | sub. 24 |
| 716 | 3-Piz | 3,4-diClPh | CO | single bond | 1 | O | $CH_2CH_2$ | sub. 24 |
| 717 | 4-Piz | 3,4-diClPh | CO | single bond | 1 | O | $CH_2CH_2$ | sub. 24 |
| 718 | 2-Aze | 3,4-diClPh | CO | single bond | 1 | O | $CH_2CH_2$ | sub. 24 |
| 719 | 3-Aze | 3,4-diClPh | CO | single bond | 1 | O | $CH_2CH_2$ | sub. 24 |
| 720 | 4-Aze | 3,4-diClPh | CO | single bond | 1 | O | $CH_2CH_2$ | sub. 24 |
| 721 | cPr | 3,4-diClPh | CO | single bond | 1 | O | $CH_2CH_2$ | sub. 25 |
| 722 | cBu | 3,4-diClPh | CO | single bond | 1 | O | $CH_2CH_2$ | sub. 25 |
| 723 | cPn | 3,4-diClPh | CO | single bond | 1 | O | $CH_2CH_2$ | sub. 25 |
| 724 | cHex | 3,4-diClPh | CO | single bond | 1 | O | $CH_2CH_2$ | sub. 25 |
| 725 | cHep | 3,4-diClPh | CO | single bond | 1 | O | $CH_2CH_2$ | sub. 25 |
| 726 | 2-Pyrd | 3,4-diClPh | CO | single bond | 1 | O | $CH_2CH_2$ | sub. 25 |
| 727 | 3-Pyrd | 3,4-diClPh | CO | single bond | 1 | O | $CH_2CH_2$ | sub. 25 |
| 728 | 4-Oxa | 3,4-diClPh | CO | single bond | 1 | O | $CH_2CH_2$ | sub. 25 |
| 729 | 5-Oxa | 3,4-diClPh | CO | single bond | 1 | O | $CH_2CH_2$ | sub. 25 |
| 730 | 4-Thi | 3,4-diClPh | CO | single bond | 1 | O | $CH_2CH_2$ | sub. 25 |
| 731 | 5-Thi | 3,4-diClPh | CO | single bond | 1 | O | $CH_2CH_2$ | sub. 25 |
| 732 | 4-OOxa | 3,4-diClPh | CO | single bond | 1 | O | $CH_2CH_2$ | sub. 25 |
| 733 | 5-OOxa | 3,4-diClPh | CO | single bond | 1 | O | $CH_2CH_2$ | sub. 25 |
| 734 | 4-OThi | 3,4-diClPh | CO | single bond | 1 | O | $CH_2CH_2$ | sub. 25 |
| 735 | 5-OThi | 3,4-diClPh | CO | single bond | 1 | O | $CH_2CH_2$ | sub. 25 |
| 736 | 2-Pip | 3,4-diClPh | CO | single bond | 1 | O | $CH_2CH_2$ | sub. 25 |
| 737 | 3-Pip | 3,4-diClPh | CO | single bond | 1 | O | $CH_2CH_2$ | sub. 25 |
| 738 | 4-Pip | 3,4-diClPh | CO | single bond | 1 | O | $CH_2CH_2$ | sub. 25 |
| 739 | 2-Mor | 3,4-diClPh | CO | single bond | 1 | O | $CH_2CH_2$ | sub. 25 |
| 740 | 3-Mor | 3,4-diClPh | CO | single bond | 1 | O | $CH_2CH_2$ | sub. 25 |

TABLE 1-continued

| Exemplification compound number | R¹ | R² | A | B | N | D | G | Q |
|---|---|---|---|---|---|---|---|---|
| 741 | 4-Mor | 3,4-diClPh | CO | single bond | 1 | O | CH₂CH₂ | sub. 25 |
| 742 | 2-Thmor | 3,4-diClPh | CO | single bond | 1 | O | CH₂CH₂ | sub. 25 |
| 743 | 3-Thmor | 3,4-diClPh | CO | single bond | 1 | O | CH₂CH₂ | sub. 25 |
| 744 | 4-Thmor | 3,4-diClPh | CO | single bond | 1 | O | CH₂CH₂ | sub. 25 |
| 745 | 2-Piz | 3,4-diClPh | CO | single bond | 1 | O | CH₂CH₂ | sub. 25 |
| 746 | 3-Piz | 3,4-diClPh | CO | single bond | 1 | O | CH₂CH₂ | sub. 25 |
| 747 | 4-Piz | 3,4-diClPh | CO | single bond | 1 | O | CH₂CH₂ | sub. 25 |
| 748 | 2-Aze | 3,4-diClPh | CO | single bond | 1 | O | CH₂CH₂ | sub. 25 |
| 749 | 3-Aze | 3,4-diClPh | CO | single bond | 1 | O | CH₂CH₂ | sub. 25 |
| 750 | 4-Aze | 3,4-diClPh | CO | single bond | 1 | O | CH₂CH₂ | sub. 25 |
| 751 | cPr | 3,4-diClPh | CO | single bond | 1 | O | CH₂CH₂ | sub. 26 |
| 752 | cBu | 3,4-diClPh | CO | single bond | 1 | O | CH₂CH₂ | sub. 26 |
| 753 | cPn | 3,4-diClPh | CO | single bond | 1 | O | CH₂CH₂ | sub. 26 |
| 754 | cHex | 3,4-diClPh | CO | single bond | 1 | O | CH₂CH₂ | sub. 26 |
| 755 | cHep | 3,4-diClPh | CO | single bond | 1 | O | CH₂CH₂ | sub. 26 |
| 756 | 2-Pyrd | 3,4-diClPh | CO | single bond | 1 | O | CH₂CH₂ | sub. 26 |
| 757 | 3-Pyrd | 3,4-diClPh | CO | single bond | 1 | O | CH₂CH₂ | sub. 26 |
| 758 | 4-Oxa | 3,4-diClPh | CO | single bond | 1 | O | CH₂CH₂ | sub. 26 |
| 759 | 5-Oxa | 3,4-diClPh | CO | single bond | 1 | O | CH₂CH₂ | sub. 26 |
| 760 | 4-Thi | 3,4-diClPh | CO | single bond | 1 | O | CH₂CH₂ | sub. 26 |
| 761 | 5-Thi | 3,4-diClPh | CO | single bond | 1 | O | CH₂CH₂ | sub. 26 |
| 762 | 4-OOxa | 3,4-diClPh | CO | single bond | 1 | O | CH₂CH₂ | sub. 26 |
| 763 | 5-OOxa | 3,4-diClPh | CO | single bond | 1 | O | CH₂CH₂ | sub. 26 |
| 764 | 4-OThi | 3,4-diClPh | CO | single bond | 1 | O | CH₂CH₂ | sub. 26 |
| 765 | 5-OThi | 3,4-diClPh | CO | single bond | 1 | O | CH₂CH₂ | sub. 26 |
| 766 | 2-Pip | 3,4-diClPh | CO | single bond | 1 | O | CH₂CH₂ | sub. 26 |
| 767 | 3-Pip | 3,4-diClPh | CO | single bond | 1 | O | CH₂CH₂ | sub. 26 |
| 768 | 4-Pip | 3,4-diClPh | CO | single bond | 1 | O | CH₂CH₂ | sub. 26 |
| 769 | 2-Mor | 3,4-diClPh | CO | single bond | 1 | O | CH₂CH₂ | sub. 26 |
| 770 | 3-Mor | 3,4-diClPh | CO | single bond | 1 | O | CH₂CH₂ | sub. 26 |
| 771 | 4-Mor | 3,4-diClPh | CO | single bond | 1 | O | CH₂CH₂ | sub. 26 |
| 772 | 2-Thmor | 3,4-diClPh | CO | single bond | 1 | O | CH₂CH₂ | sub. 26 |
| 773 | 3-Thmor | 3,4-diClPh | CO | single bond | 1 | O | CH₂CH₂ | sub. 26 |
| 774 | 4-Thmor | 3,4-diClPh | CO | single bond | 1 | O | CH₂CH₂ | sub. 26 |
| 775 | 2-Piz | 3,4-diClPh | CO | single bond | 1 | O | CH₂CH₂ | sub. 26 |
| 776 | 3-Piz | 3,4-diClPh | CO | single bond | 1 | O | CH₂CH₂ | sub. 26 |
| 777 | 4-Piz | 3,4-diClPh | CO | single bond | 1 | O | CH₂CH₂ | sub. 26 |
| 778 | 2-Aze | 3,4-diClPh | CO | single bond | 1 | O | CH₂CH₂ | sub. 26 |
| 779 | 3-Aze | 3,4-diClPh | CO | single bond | 1 | O | CH₂CH₂ | sub. 26 |
| 780 | 4-Aze | 3,4-diClPh | CO | single bond | 1 | O | CH₂CH₂ | sub. 26 |
| 781 | cPr | 3,4-diClPh | CO | single bond | 1 | O | CH₂CH₂ | sub. 27 |
| 782 | cBu | 3,4-diClPh | CO | single bond | 1 | O | CH₂CH₂ | sub. 27 |
| 783 | cPn | 3,4-diClPh | CO | single bond | 1 | O | CH₂CH₂ | sub. 27 |
| 784 | cHex | 3,4-diClPh | CO | single bond | 1 | O | CH₂CH₂ | sub. 27 |
| 785 | cHep | 3,4-diClPh | CO | single bond | 1 | O | CH₂CH₂ | sub. 27 |
| 786 | 2-Pyrd | 3,4-diClPh | CO | single bond | 1 | O | CH₂CH₂ | sub. 27 |
| 787 | 3-Pyrd | 3,4-diClPh | CO | single bond | 1 | O | CH₂CH₂ | sub. 27 |
| 788 | 4-Oxa | 3,4-diClPh | CO | single bond | 1 | O | CH₂CH₂ | sub. 27 |
| 789 | 5-Oxa | 3,4-diClPh | CO | single bond | 1 | O | CH₂CH₂ | sub. 27 |
| 790 | 4-Thi | 3,4-diClPh | CO | single bond | 1 | O | CH₂CH₂ | sub. 27 |
| 791 | 5-Thi | 3,4-diClPh | CO | single bond | 1 | O | CH₂CH₂ | sub. 27 |
| 792 | 4-OOxa | 3,4-diClPh | CO | single bond | 1 | O | CH₂CH₂ | sub. 27 |
| 793 | 5-OOxa | 3,4-diClPh | CO | single bond | 1 | O | CH₂CH₂ | sub. 27 |
| 794 | 4-OThi | 3,4-diClPh | CO | single bond | 1 | O | CH₂CH₂ | sub. 27 |
| 795 | 5-OThi | 3,4-diClPh | CO | single bond | 1 | O | CH₂CH₂ | sub. 27 |
| 796 | 2-Pip | 3,4-diClPh | CO | single bond | 1 | O | CH₂CH₂ | sub. 27 |
| 797 | 3-Pip | 3,4-diClPh | CO | single bond | 1 | O | CH₂CH₂ | sub. 27 |
| 798 | 4-Pip | 3,4-diClPh | CO | single bond | 1 | O | CH₂CH₂ | sub. 27 |
| 799 | 2-Mor | 3,4-diClPh | CO | single bond | 1 | O | CH₂CH₂ | sub. 27 |
| 800 | 3-Mor | 3,4-diClPh | CO | single bond | 1 | O | CH₂CH₂ | sub. 27 |
| 801 | 4-Mor | 3,4-diClPh | CO | single bond | 1 | O | CH₂CH₂ | sub. 27 |
| 802 | 2-Thmor | 3,4-diClPh | CO | single bond | 1 | O | CH₂CH₂ | sub. 27 |
| 803 | 3-Thmor | 3,4-diClPh | CO | single bond | 1 | O | CH₂CH₂ | sub. 27 |
| 804 | 4-Thmor | 3,4-diClPh | CO | single bond | 1 | O | CH₂CH₂ | sub. 27 |
| 805 | 2-Piz | 3,4-diClPh | CO | single bond | 1 | O | CH₂CH₂ | sub. 27 |
| 806 | 3-Piz | 3,4-diClPh | CO | single bond | 1 | O | CH₂CH₂ | sub. 27 |
| 807 | 4-Piz | 3,4-diClPh | CO | single bond | 1 | O | CH₂CH₂ | sub. 27 |
| 808 | 2-Aze | 3,4-diClPh | CO | single bond | 1 | O | CH₂CH₂ | sub. 27 |
| 809 | 3-Aze | 3,4-diClPh | CO | single bond | 1 | O | CH₂CH₂ | sub. 27 |
| 810 | 4-Aze | 3,4-diClPh | CO | single bond | 1 | O | CH₂CH₂ | sub. 27 |
| 811 | cPr | 3,4-diClPh | CO | single bond | 1 | O | CH₂CH₂ | sub. 28 |
| 812 | cBu | 3,4-diClPh | CO | single bond | 1 | O | CH₂CH₂ | sub. 28 |
| 813 | cPn | 3,4-diClPh | CO | single bond | 1 | O | CH₂CH₂ | sub. 28 |
| 814 | cHex | 3,4-diClPh | CO | single bond | 1 | O | CH₂CH₂ | sub. 28 |
| 815 | cHep | 3,4-diClPh | CO | single bond | 1 | O | CH₂CH₂ | sub. 28 |
| 816 | 2-Pyrd | 3,4-diClPh | CO | single bond | 1 | O | CH₂CH₂ | sub. 28 |

TABLE 1-continued

| Exemplification compound number | R¹ | R² | A | B | N | D | G | Q |
|---|---|---|---|---|---|---|---|---|
| 817 | 3-Pyrd | 3,4-diClPh | CO | single bond | 1 | O | $CH_2CH_2$ | sub. 28 |
| 818 | 4-Oxa | 3,4-diClPh | CO | single bond | 1 | O | $CH_2CH_2$ | sub. 28 |
| 819 | 5-Oxa | 3,4-diClPh | CO | single bond | 1 | O | $CH_2CH_2$ | sub. 28 |
| 820 | 4-Thi | 3,4-diClPh | CO | single bond | 1 | O | $CH_2CH_2$ | sub. 28 |
| 821 | 5-Thi | 3,4-diClPh | CO | single bond | 1 | O | $CH_2CH_2$ | sub. 28 |
| 822 | 4-OOxa | 3,4-diClPh | CO | single bond | 1 | O | $CH_2CH_2$ | sub. 28 |
| 823 | 5-OOxa | 3,4-diClPh | CO | single bond | 1 | O | $CH_2CH_2$ | sub. 28 |
| 824 | 4-OThi | 3,4-diClPh | CO | single bond | 1 | O | $CH_2CH_2$ | sub. 28 |
| 825 | 5-OThi | 3,4-diClPh | CO | single bond | 1 | O | $CH_2CH_2$ | sub. 28 |
| 826 | 2-Pip | 3,4-diClPh | CO | single bond | 1 | O | $CH_2CH_2$ | sub. 28 |
| 827 | 3-Pip | 3,4-diClPh | CO | single bond | 1 | O | $CH_2CH_2$ | sub. 28 |
| 828 | 4-Pip | 3,4-diClPh | CO | single bond | 1 | O | $CH_2CH_2$ | sub. 28 |
| 829 | 2-Mor | 3,4-diClPh | CO | single bond | 1 | O | $CH_2CH_2$ | sub. 28 |
| 830 | 3-Mor | 3,4-diClPh | CO | single bond | 1 | O | $CH_2CH_2$ | sub. 28 |
| 831 | 4-Mor | 3,4-diClPh | CO | single bond | 1 | O | $CH_2CH_2$ | sub. 28 |
| 832 | 2-Thmor | 3,4-diClPh | CO | single bond | 1 | O | $CH_2CH_2$ | sub. 28 |
| 833 | 3-Thmor | 3,4-diClPh | CO | single bond | 1 | O | $CH_2CH_2$ | sub. 28 |
| 834 | 4-Thmor | 3,4-diClPh | CO | single bond | 1 | O | $CH_2CH_2$ | sub. 28 |
| 835 | 2-Piz | 3,4-diClPh | CO | single bond | 1 | O | $CH_2CH_2$ | sub. 28 |
| 836 | 3-Piz | 3,4-diClPh | CO | single bond | 1 | O | $CH_2CH_2$ | sub. 28 |
| 837 | 4-Piz | 3,4-diClPh | CO | single bond | 1 | O | $CH_2CH_2$ | sub. 28 |
| 838 | 2-Aze | 3,4-diClPh | CO | single bond | 1 | O | $CH_2CH_2$ | sub. 28 |
| 839 | 3-Aze | 3,4-diClPh | CO | single bond | 1 | O | $CH_2CH_2$ | sub. 28 |
| 840 | 4-Aze | 3,4-diClPh | CO | single bond | 1 | O | $CH_2CH_2$ | sub. 28 |
| 841 | cPr | 3,4-diClPh | CO | single bond | 1 | O | $CH_2CH_2$ | sub. 29 |
| 842 | cBu | 3,4-diClPh | CO | single bond | 1 | O | $CH_2CH_2$ | sub. 29 |
| 843 | cPn | 3,4-diClPh | CO | single bond | 1 | O | $CH_2CH_2$ | sub. 29 |
| 844 | cHex | 3,4-diClPh | CO | single bond | 1 | O | $CH_2CH_2$ | sub. 29 |
| 845 | cHep | 3,4-diClPh | CO | single bond | 1 | O | $CH_2CH_2$ | sub. 29 |
| 846 | 2-Pyrd | 3,4-diClPh | CO | single bond | 1 | O | $CH_2CH_2$ | sub. 29 |
| 847 | 3-Pyrd | 3,4-diClPh | CO | single bond | 1 | O | $CH_2CH_2$ | sub. 29 |
| 848 | 4-Oxa | 3,4-diClPh | CO | single bond | 1 | O | $CH_2CH_2$ | sub. 29 |
| 849 | 5-Oxa | 3,4-diClPh | CO | single bond | 1 | O | $CH_2CH_2$ | sub. 29 |
| 850 | 4-Thi | 3,4-diClPh | CO | single bond | 1 | O | $CH_2CH_2$ | sub. 29 |
| 851 | 5-Thi | 3,4-diClPh | CO | single bond | 1 | O | $CH_2CH_2$ | sub. 29 |
| 852 | 4-OOxa | 3,4-diClPh | CO | single bond | 1 | O | $CH_2CH_2$ | sub. 29 |
| 853 | 5-OOxa | 3,4-diClPh | CO | single bond | 1 | O | $CH_2CH_2$ | sub. 29 |
| 854 | 4-OThi | 3,4-diClPh | CO | single bond | 1 | O | $CH_2CH_2$ | sub. 29 |
| 855 | 5-OThi | 3,4-diClPh | CO | single bond | 1 | O | $CH_2CH_2$ | sub. 29 |
| 856 | 2-Pip | 3,4-diClPh | CO | single bond | 1 | O | $CH_2CH_2$ | sub. 29 |
| 857 | 3-Pip | 3,4-diClPh | CO | single bond | 1 | O | $CH_2CH_2$ | sub. 29 |
| 858 | 4-Pip | 3,4-diClPh | CO | single bond | 1 | O | $CH_2CH_2$ | sub. 29 |
| 859 | 2-Mor | 3,4-diClPh | CO | single bond | 1 | O | $CH_2CH_2$ | sub. 29 |
| 860 | 3-Mor | 3,4-diClPh | CO | single bond | 1 | O | $CH_2CH_2$ | sub. 29 |
| 861 | 4-Mor | 3,4-diClPh | CO | single bond | 1 | O | $CH_2CH_2$ | sub. 29 |
| 862 | 2-Thmor | 3,4-diClPh | CO | single bond | 1 | O | $CH_2CH_2$ | sub. 29 |
| 863 | 3-Thmor | 3,4-diClPh | CO | single bond | 1 | O | $CH_2CH_2$ | sub. 29 |
| 864 | 4-Thmor | 3,4-diClPh | CO | single bond | 1 | O | $CH_2CH_2$ | sub. 29 |
| 865 | 2-Piz | 3,4-diClPh | CO | single bond | 1 | O | $CH_2CH_2$ | sub. 29 |
| 866 | 3-Piz | 3,4-diClPh | CO | single bond | 1 | O | $CH_2CH_2$ | sub. 29 |
| 867 | 4-Piz | 3,4-diClPh | CO | single bond | 1 | O | $CH_2CH_2$ | sub. 29 |
| 868 | 2-Aze | 3,4-diClPh | CO | single bond | 1 | O | $CH_2CH_2$ | sub. 29 |
| 869 | 3-Aze | 3,4-diClPh | CO | single bond | 1 | O | $CH_2CH_2$ | sub. 29 |
| 870 | 4-Aze | 3,4-diClPh | CO | single bond | 1 | O | $CH_2CH_2$ | sub. 29 |
| 871 | cPr | 3,4-diClPh | CO | single bond | 1 | O | $CH_2CH_2$ | sub. 30 |
| 872 | cBu | 3,4-diClPh | CO | single bond | 1 | O | $CH_2CH_2$ | sub. 30 |
| 873 | cPn | 3,4-diClPh | CO | single bond | 1 | O | $CH_2CH_2$ | sub. 30 |
| 874 | cHex | 3,4-diClPh | CO | single bond | 1 | O | $CH_2CH_2$ | sub. 30 |
| 875 | cHep | 3,4-diClPh | CO | single bond | 1 | O | $CH_2CH_2$ | sub. 30 |
| 876 | 2-Pyrd | 3,4-diClPh | CO | single bond | 1 | O | $CH_2CH_2$ | sub. 30 |
| 877 | 3-Pyrd | 3,4-diClPh | CO | single bond | 1 | O | $CH_2CH_2$ | sub. 30 |
| 878 | 4-Oxa | 3,4-diClPh | CO | single bond | 1 | O | $CH_2CH_2$ | sub. 30 |
| 879 | 5-Oxa | 3,4-diClPh | CO | single bond | 1 | O | $CH_2CH_2$ | sub. 30 |
| 880 | 4-Thi | 3,4-diClPh | CO | single bond | 1 | O | $CH_2CH_2$ | sub. 30 |
| 881 | 5-Thi | 3,4-diClPh | CO | single bond | 1 | O | $CH_2CH_2$ | sub. 30 |
| 882 | 4-OOxa | 3,4-diClPh | CO | single bond | 1 | O | $CH_2CH_2$ | sub. 30 |
| 883 | 5-OOxa | 3,4-diClPh | CO | single bond | 1 | O | $CH_2CH_2$ | sub. 30 |
| 884 | 4-OThi | 3,4-diClPh | CO | single bond | 1 | O | $CH_2CH_2$ | sub. 30 |
| 885 | 5-OThi | 3,4-diClPh | CO | single bond | 1 | O | $CH_2CH_2$ | sub. 30 |
| 886 | 2-Pip | 3,4-diClPh | CO | single bond | 1 | O | $CH_2CH_2$ | sub. 30 |
| 887 | 3-Pip | 3,4-diClPh | CO | single bond | 1 | O | $CH_2CH_2$ | sub. 30 |
| 888 | 4-Pip | 3,4-diClPh | CO | single bond | 1 | O | $CH_2CH_2$ | sub. 30 |
| 889 | 2-Mor | 3,4-diClPh | CO | single bond | 1 | O | $CH_2CH_2$ | sub. 30 |
| 890 | 3-Mor | 3,4-diClPh | CO | single bond | 1 | O | $CH_2CH_2$ | sub. 30 |
| 891 | 4-Mor | 3,4-diClPh | CO | single bond | 1 | O | $CH_2CH_2$ | sub. 30 |
| 892 | 2-Thmor | 3,4-diClPh | CO | single bond | 1 | O | $CH_2CH_2$ | sub. 30 |

TABLE 1-continued

| Exemplification compound number | R¹ | R² | A | B | N | D | G | Q |
|---|---|---|---|---|---|---|---|---|
| 893 | 3-Thmor | 3,4-diClPh | CO | single bond | 1 | O | CH₂CH₂ | sub. 30 |
| 894 | 4-Thmor | 3,4-diClPh | CO | single bond | 1 | O | CH₂CH₂ | sub. 30 |
| 895 | 2-Piz | 3,4-diClPh | CO | single bond | 1 | O | CH₂CH₂ | sub. 30 |
| 896 | 3-Piz | 3,4-diClPh | CO | single bond | 1 | O | CH₂CH₂ | sub. 30 |
| 897 | 4-Piz | 3,4-diClPh | CO | single bond | 1 | O | CH₂CH₂ | sub. 30 |
| 898 | 2-Aze | 3,4-diClPh | CO | single bond | 1 | O | CH₂CH₂ | sub. 30 |
| 899 | 3-Aze | 3,4-diClPh | CO | single bond | 1 | O | CH₂CH₂ | sub. 30 |
| 900 | 4-Aze | 3,4-diClPh | CO | single bond | 1 | O | CH₂CH₂ | sub. 30 |
| 901 | cPr | 3,4-diClPh | CO | single bond | 1 | O | CH₂CH₂ | sub. 31 |
| 902 | cBu | 3,4-diClPh | CO | single bond | 1 | O | CH₂CH₂ | sub. 31 |
| 903 | cPn | 3,4-diClPh | CO | single bond | 1 | O | CH₂CH₂ | sub. 31 |
| 904 | cHex | 3,4-diClPh | CO | single bond | 1 | O | CH₂CH₂ | sub. 31 |
| 905 | cHep | 3,4-diClPh | CO | single bond | 1 | O | CH₂CH₂ | sub. 31 |
| 906 | 2-Pyrd | 3,4-diClPh | CO | single bond | 1 | O | CH₂CH₂ | sub. 31 |
| 907 | 3-Pyrd | 3,4-diClPh | CO | single bond | 1 | O | CH₂CH₂ | sub. 31 |
| 908 | 4-Oxa | 3,4-diClPh | CO | single bond | 1 | O | CH₂CH₂ | sub. 31 |
| 909 | 5-Oxa | 3,4-diClPh | CO | single bond | 1 | O | CH₂CH₂ | sub. 31 |
| 910 | 4-Thi | 3,4-diClPh | CO | single bond | 1 | O | CH₂CH₂ | sub. 31 |
| 911 | 5-Thi | 3,4-diClPh | CO | single bond | 1 | O | CH₂CH₂ | sub. 31 |
| 912 | 4-OOxa | 3,4-diClPh | CO | single bond | 1 | O | CH₂CH₂ | sub. 31 |
| 913 | 5-OOxa | 3,4-diClPh | CO | single bond | 1 | O | CH₂CH₂ | sub. 31 |
| 914 | 4-OThi | 3,4-diClPh | CO | single bond | 1 | O | CH₂CH₂ | sub. 31 |
| 915 | 5-OThi | 3,4-diClPh | CO | single bond | 1 | O | CH₂CH₂ | sub. 31 |
| 916 | 2-Pip | 3,4-diClPh | CO | single bond | 1 | O | CH₂CH₂ | sub. 31 |
| 917 | 3-Pip | 3,4-diClPh | CO | single bond | 1 | O | CH₂CH₂ | sub. 31 |
| 918 | 4-Pip | 3,4-diClPh | CO | single bond | 1 | O | CH₂CH₂ | sub. 31 |
| 919 | 2-Mor | 3,4-diClPh | CO | single bond | 1 | O | CH₂CH₂ | sub. 31 |
| 920 | 3-Mor | 3,4-diClPh | CO | single bond | 1 | O | CH₂CH₂ | sub. 31 |
| 921 | 4-Mor | 3,4-diClPh | CO | single bond | 1 | O | CH₂CH₂ | sub. 31 |
| 922 | 2-Thmor | 3,4-diClPh | CO | single bond | 1 | O | CH₂CH₂ | sub. 31 |
| 923 | 3-Thmor | 3,4-diClPh | CO | single bond | 1 | O | CH₂CH₂ | sub. 31 |
| 924 | 4-Thmor | 3,4-diClPh | CO | single bond | 1 | O | CH₂CH₂ | sub. 31 |
| 925 | 2-Piz | 3,4-diClPh | CO | single bond | 1 | O | CH₂CH₂ | sub. 31 |
| 926 | 3-Piz | 3,4-diClPh | CO | single bond | 1 | O | CH₂CH₂ | sub. 31 |
| 927 | 4-Piz | 3,4-diClPh | CO | single bond | 1 | O | CH₂CH₂ | sub. 31 |
| 928 | 2-Aze | 3,4-diClPh | CO | single bond | 1 | O | CH₂CH₂ | sub. 31 |
| 929 | 3-Aze | 3,4-diClPh | CO | single bond | 1 | O | CH₂CH₂ | sub. 31 |
| 930 | 4-Aze | 3,4-diClPh | CO | single bond | 1 | O | CH₂CH₂ | sub. 31 |
| 931 | cPr | 3,4-diClPh | CO | single bond | 1 | O | CH₂CH₂ | sub. 32 |
| 932 | cBu | 3,4-diClPh | CO | single bond | 1 | O | CH₂CH₂ | sub. 32 |
| 933 | cPn | 3,4-diClPh | CO | single bond | 1 | O | CH₂CH₂ | sub. 32 |
| 934 | cHex | 3,4-diClPh | CO | single bond | 1 | O | CH₂CH₂ | sub. 32 |
| 935 | cHep | 3,4-diClPh | CO | single bond | 1 | O | CH₂CH₂ | sub. 32 |
| 936 | 2-Pyrd | 3,4-diClPh | CO | single bond | 1 | O | CH₂CH₂ | sub. 32 |
| 937 | 3-Pyrd | 3,4-diClPh | CO | single bond | 1 | O | CH₂CH₂ | sub. 32 |
| 938 | 4-Oxa | 3,4-diClPh | CO | single bond | 1 | O | CH₂CH₂ | sub. 32 |
| 939 | 5-Oxa | 3,4-diClPh | CO | single bond | 1 | O | CH₂CH₂ | sub. 32 |
| 940 | 4-Thi | 3,4-diClPh | CO | single bond | 1 | O | CH₂CH₂ | sub. 32 |
| 941 | 5-Thi | 3,4-diClPh | CO | single bond | 1 | O | CH₂CH₂ | sub. 32 |
| 942 | 4-OOxa | 3,4-diClPh | CO | single bond | 1 | O | CH₂CH₂ | sub. 32 |
| 943 | 5-OOxa | 3,4-diClPh | CO | single bond | 1 | O | CH₂CH₂ | sub. 32 |
| 944 | 4-OThi | 3,4-diClPh | CO | single bond | 1 | O | CH₂CH₂ | sub. 32 |
| 945 | 5-OThi | 3,4-diClPh | CO | single bond | 1 | O | CH₂CH₂ | sub. 32 |
| 946 | 2-Pip | 3,4-diClPh | CO | single bond | 1 | O | CH₂CH₂ | sub. 32 |
| 947 | 3-Pip | 3,4-diClPh | CO | single bond | 1 | O | CH₂CH₂ | sub. 32 |
| 948 | 4-Pip | 3,4-diClPh | CO | single bond | 1 | O | CH₂CH₂ | sub. 32 |
| 949 | 2-Mor | 3,4-diClPh | CO | single bond | 1 | O | CH₂CH₂ | sub. 32 |
| 950 | 3-Mor | 3,4-diClPh | CO | single bond | 1 | O | CH₂CH₂ | sub. 32 |
| 951 | 4-Mor | 3,4-diClPh | CO | single bond | 1 | O | CH₂CH₂ | sub. 32 |
| 952 | 2-Thmor | 3,4-diClPh | CO | single bond | 1 | O | CH₂CH₂ | sub. 32 |
| 953 | 3-Thmor | 3,4-diClPh | CO | single bond | 1 | O | CH₂CH₂ | sub. 32 |
| 954 | 4-Thmor | 3,4-diClPh | CO | single bond | 1 | O | CH₂CH₂ | sub. 32 |
| 955 | 2-Piz | 3,4-diClPh | CO | single bond | 1 | O | CH₂CH₂ | sub. 32 |
| 956 | 3-Piz | 3,4-diClPh | CO | single bond | 1 | O | CH₂CH₂ | sub. 32 |
| 957 | 4-Piz | 3,4-diClPh | CO | single bond | 1 | O | CH₂CH₂ | sub. 32 |
| 958 | 2-Aze | 3,4-diClPh | CO | single bond | 1 | O | CH₂CH₂ | sub. 32 |
| 959 | 3-Aze | 3,4-diClPh | CO | single bond | 1 | O | CH₂CH₂ | sub. 32 |
| 960 | 4-Aze | 3,4-diClPh | CO | single bond | 1 | O | CH₂CH₂ | sub. 32 |
| 961 | cPr | 3,4-diClPh | CO | single bond | 1 | O | CH₂CH₂ | sub. 33 |
| 962 | cBu | 3,4-diClPh | CO | single bond | 1 | O | CH₂CH₂ | sub. 33 |
| 963 | cPn | 3,4-diClPh | CO | single bond | 1 | O | CH₂CH₂ | sub. 33 |
| 964 | cHex | 3,4-diClPh | CO | single bond | 1 | O | CH₂CH₂ | sub. 33 |
| 965 | cHep | 3,4-diClPh | CO | single bond | 1 | O | CH₂CH₂ | sub. 33 |
| 966 | 2-Pyrd | 3,4-diClPh | CO | single bond | 1 | O | CH₂CH₂ | sub. 33 |
| 967 | 3-Pyrd | 3,4-diClPh | CO | single bond | 1 | O | CH₂CH₂ | sub. 33 |
| 968 | 4-Oxa | 3,4-diClPh | CO | single bond | 1 | O | CH₂CH₂ | sub. 33 |

TABLE 1-continued

| Exemplification compound number | R¹ | R² | A | B | N | D | G | Q |
|---|---|---|---|---|---|---|---|---|
| 969 | 5-Oxa | 3,4-diClPh | CO | single bond | 1 | O | CH₂CH₂ | sub. 33 |
| 970 | 4-Thi | 3,4-diClPh | CO | single bond | 1 | O | CH₂CH₂ | sub. 33 |
| 971 | 5-Thi | 3,4-diClPh | CO | single bond | 1 | O | CH₂CH₂ | sub. 33 |
| 972 | 4-OOxa | 3,4-diClPh | CO | single bond | 1 | O | CH₂CH₂ | sub. 33 |
| 973 | 5-OOxa | 3,4-diClPh | CO | single bond | 1 | O | CH₂CH₂ | sub. 33 |
| 974 | 4-OThi | 3,4-diClPh | CO | single bond | 1 | O | CH₂CH₂ | sub. 33 |
| 975 | 5-OThi | 3,4-diClPh | CO | single bond | 1 | O | CH₂CH₂ | sub. 33 |
| 976 | 2-Pip | 3,4-diClPh | CO | single bond | 1 | O | CH₂CH₂ | sub. 33 |
| 977 | 3-Pip | 3,4-diClPh | CO | single bond | 1 | O | CH₂CH₂ | sub. 33 |
| 978 | 4-Pip | 3,4-diClPh | CO | single bond | 1 | O | CH₂CH₂ | sub. 33 |
| 979 | 2-Mor | 3,4-diClPh | CO | single bond | 1 | O | CH₂CH₂ | sub. 33 |
| 980 | 3-Mor | 3,4-diClPh | CO | single bond | 1 | O | CH₂CH₂ | sub. 33 |
| 981 | 4-Mor | 3,4-diClPh | CO | single bond | 1 | O | CH₂CH₂ | sub. 33 |
| 982 | 2-Thmor | 3,4-diClPh | CO | single bond | 1 | O | CH₂CH₂ | sub. 33 |
| 983 | 3-Thmor | 3,4-diClPh | CO | single bond | 1 | O | CH₂CH₂ | sub. 33 |
| 984 | 4-Thmor | 3,4-diClPh | CO | single bond | 1 | O | CH₂CH₂ | sub. 33 |
| 985 | 2-Piz | 3,4-diClPh | CO | single bond | 1 | O | CH₂CH₂ | sub. 33 |
| 986 | 3-Piz | 3,4-diClPh | CO | single bond | 1 | O | CH₂CH₂ | sub. 33 |
| 987 | 4-Piz | 3,4-diClPh | CO | single bond | 1 | O | CH₂CH₂ | sub. 33 |
| 988 | 2-Aze | 3,4-diClPh | CO | single bond | 1 | O | CH₂CH₂ | sub. 33 |
| 989 | 3-Aze | 3,4-diClPh | CO | single bond | 1 | O | CH₂CH₂ | sub. 33 |
| 990 | 4-Aze | 3,4-diClPh | CO | single bond | 1 | O | CH₂CH₂ | sub. 33 |
| 991 | cPr | 3,4-diClPh | CO | single bond | 1 | O | CH₂CH₂ | sub. 34 |
| 992 | cBu | 3,4-diClPh | CO | single bond | 1 | O | CH₂CH₂ | sub. 34 |
| 993 | cPn | 3,4-diClPh | CO | single bond | 1 | O | CH₂CH₂ | sub. 34 |
| 994 | cHex | 3,4-diClPh | CO | single bond | 1 | O | CH₂CH₂ | sub. 34 |
| 995 | cHep | 3,4-diClPh | CO | single bond | 1 | O | CH₂CH₂ | sub. 34 |
| 996 | 2-Pyrd | 3,4-diClPh | CO | single bond | 1 | O | CH₂CH₂ | sub. 34 |
| 997 | 3-Pyrd | 3,4-diClPh | CO | single bond | 1 | O | CH₂CH₂ | sub. 34 |
| 998 | 4-Oxa | 3,4-diClPh | CO | single bond | 1 | O | CH₂CH₂ | sub. 34 |
| 999 | 5-Oxa | 3,4-diClPh | CO | single bond | 1 | O | CH₂CH₂ | sub. 34 |
| 1000 | 4-Thi | 3,4-diClPh | CO | single bond | 1 | O | CH₂CH₂ | sub. 34 |
| 1001 | 5-Thi | 3,4-diClPh | CO | single bond | 1 | O | CH₂CH₂ | sub. 34 |
| 1002 | 4-OOxa | 3,4-diClPh | CO | single bond | 1 | O | CH₂CH₂ | sub. 34 |
| 1003 | 5-OOxa | 3,4-diClPh | CO | single bond | 1 | O | CH₂CH₂ | sub. 34 |
| 1004 | 4-OThi | 3,4-diClPh | CO | single bond | 1 | O | CH₂CH₂ | sub. 34 |
| 1005 | 5-OThi | 3,4-diClPh | CO | single bond | 1 | O | CH₂CH₂ | sub. 34 |
| 1006 | 2-Pip | 3,4-diClPh | CO | single bond | 1 | O | CH₂CH₂ | sub. 34 |
| 1007 | 3-Pip | 3,4-diClPh | CO | single bond | 1 | O | CH₂CH₂ | sub. 34 |
| 1008 | 4-Pip | 3,4-diClPh | CO | single bond | 1 | O | CH₂CH₂ | sub. 34 |
| 1009 | 2-Mor | 3,4-diClPh | CO | single bond | 1 | O | CH₂CH₂ | sub. 34 |
| 1010 | 3-Mor | 3,4-diClPh | CO | single bond | 1 | O | CH₂CH₂ | sub. 34 |
| 1011 | 4-Mor | 3,4-diClPh | CO | single bond | 1 | O | CH₂CH₂ | sub. 34 |
| 1012 | 2-Thmor | 3,4-diClPh | CO | single bond | 1 | O | CH₂CH₂ | sub. 34 |
| 1013 | 3-Thmor | 3,4-diClPh | CO | single bond | 1 | O | CH₂CH₂ | sub. 34 |
| 1014 | 4-Thmor | 3,4-diClPh | CO | single bond | 1 | O | CH₂CH₂ | sub. 34 |
| 1015 | 2-Piz | 3,4-diClPh | CO | single bond | 1 | O | CH₂CH₂ | sub. 34 |
| 1016 | 3-Piz | 3,4-diClPh | CO | single bond | 1 | O | CH₂CH₂ | sub. 34 |
| 1017 | 4-Piz | 3,4-diClPh | CO | single bond | 1 | O | CH₂CH₂ | sub. 34 |
| 1018 | 2-Aze | 3,4-diClPh | CO | single bond | 1 | O | CH₂CH₂ | sub. 34 |
| 1019 | 3-Aze | 3,4-diClPh | CO | single bond | 1 | O | CH₂CH₂ | sub. 34 |
| 1020 | 4-Aze | 3,4-diClPh | CO | single bond | 1 | O | CH₂CH₂ | sub. 34 |
| 1021 | cPr | 3,4-diClPh | CO | single bond | 1 | O | CH₂CH₂ | sub. 35 |
| 1022 | cBu | 3,4-diClPh | CO | single bond | 1 | O | CH₂CH₂ | sub. 35 |
| 1023 | cPn | 3,4-diClPh | CO | single bond | 1 | O | CH₂CH₂ | sub. 35 |
| 1024 | cHex | 3,4-diClPh | CO | single bond | 1 | O | CH₂CH₂ | sub. 35 |
| 1025 | cHep | 3,4-diClPh | CO | single bond | 1 | O | CH₂CH₂ | sub. 35 |
| 1026 | 2-Pyrd | 3,4-diClPh | CO | single bond | 1 | O | CH₂CH₂ | sub. 35 |
| 1027 | 3-Pyrd | 3,4-diClPh | CO | single bond | 1 | O | CH₂CH₂ | sub. 35 |
| 1028 | 4-Oxa | 3,4-diClPh | CO | single bond | 1 | O | CH₂CH₂ | sub. 35 |
| 1029 | 5-Oxa | 3,4-diClPh | CO | single bond | 1 | O | CH₂CH₂ | sub. 35 |
| 1030 | 4-Thi | 3,4-diClPh | CO | single bond | 1 | O | CH₂CH₂ | sub. 35 |
| 1031 | 5-Thi | 3,4-diClPh | CO | single bond | 1 | O | CH₂CH₂ | sub. 35 |
| 1032 | 4-OOxa | 3,4-diClPh | CO | single bond | 1 | O | CH₂CH₂ | sub. 35 |
| 1033 | 5-OOxa | 3,4-diClPh | CO | single bond | 1 | O | CH₂CH₂ | sub. 35 |
| 1034 | 4-OThi | 3,4-diClPh | CO | single bond | 1 | O | CH₂CH₂ | sub. 35 |
| 1035 | 5-OThi | 3,4-diClPh | CO | single bond | 1 | O | CH₂CH₂ | sub. 35 |
| 1036 | 2-Pip | 3,4-diClPh | CO | single bond | 1 | O | CH₂CH₂ | sub. 35 |
| 1037 | 3-Pip | 3,4-diClPh | CO | single bond | 1 | O | CH₂CH₂ | sub. 35 |
| 1038 | 4-Pip | 3,4-diClPh | CO | single bond | 1 | O | CH₂CH₂ | sub. 35 |
| 1039 | 2-Mor | 3,4-diClPh | CO | single bond | 1 | O | CH₂CH₂ | sub. 35 |
| 1040 | 3-Mor | 3,4-diClPh | CO | single bond | 1 | O | CH₂CH₂ | sub. 35 |
| 1041 | 4-Mor | 3,4-diClPh | CO | single bond | 1 | O | CH₂CH₂ | sub. 35 |
| 1042 | 2-Thmor | 3,4-diClPh | CO | single bond | 1 | O | CH₂CH₂ | sub. 35 |
| 1043 | 3-Thmor | 3,4-diClPh | CO | single bond | 1 | O | CH₂CH₂ | sub. 35 |
| 1044 | 4-Thmor | 3,4-diClPh | CO | single bond | 1 | O | CH₂CH₂ | sub. 35 |

TABLE 1-continued

| Exemplification compound number | R¹ | R² | A | B | N | D | G | Q |
|---|---|---|---|---|---|---|---|---|
| 1045 | 2-Piz | 3,4-diClPh | CO | single bond | 1 | O | CH₂CH₂ | sub. 35 |
| 1046 | 3-Piz | 3,4-diClPh | CO | single bond | 1 | O | CH₂CH₂ | sub. 35 |
| 1047 | 4-Piz | 3,4-diClPh | CO | single bond | 1 | O | CH₂CH₂ | sub. 35 |
| 1048 | 2-Aze | 3,4-diClPh | CO | single bond | 1 | O | CH₂CH₂ | sub. 35 |
| 1049 | 3-Aze | 3,4-diClPh | CO | single bond | 1 | O | CH₂CH₂ | sub. 35 |
| 1050 | 4-Aze | 3,4-diClPh | CO | single bond | 1 | O | CH₂CH₂ | sub. 35 |
| 1051 | cPr | 3,4-diClPh | CO | single bond | 2 | O | CH₂CH₂ | sub. 1 |
| 1052 | cBu | 3,4-diClPh | CO | single bond | 2 | O | CH₂CH₂ | sub. 1 |
| 1053 | cPn | 3,4-diClPh | CO | single bond | 2 | O | CH₂CH₂ | sub. 1 |
| 1054 | cHex | 3,4-diClPh | CO | single bond | 2 | O | CH₂CH₂ | sub. 1 |
| 1055 | cHep | 3,4-diClPh | CO | single bond | 2 | O | CH₂CH₂ | sub. 1 |
| 1056 | 2-Pyrd | 3,4-diClPh | CO | single bond | 2 | O | CH₂CH₂ | sub. 1 |
| 1057 | 3-Pyrd | 3,4-diClPh | CO | single bond | 2 | O | CH₂CH₂ | sub. 1 |
| 1058 | 4-Oxa | 3,4-diClPh | CO | single bond | 2 | O | CH₂CH₂ | sub. 1 |
| 1059 | 5-Oxa | 3,4-diClPh | CO | single bond | 2 | O | CH₂CH₂ | sub. 1 |
| 1060 | 4-Thi | 3,4-diClPh | CO | single bond | 2 | O | CH₂CH₂ | sub. 1 |
| 1061 | 5-Thi | 3,4-diClPh | CO | single bond | 2 | O | CH₂CH₂ | sub. 1 |
| 1062 | 4-OOxa | 3,4-diClPh | CO | single bond | 2 | O | CH₂CH₂ | sub. 1 |
| 1063 | 5-OOxa | 3,4-diClPh | CO | single bond | 2 | O | CH₂CH₂ | sub. 1 |
| 1064 | 4-OThi | 3,4-diClPh | CO | single bond | 2 | O | CH₂CH₂ | sub. 1 |
| 1065 | 5-OThi | 3,4-diClPh | CO | single bond | 2 | O | CH₂CH₂ | sub. 1 |
| 1066 | 2-Pip | 3,4-diClPh | CO | single bond | 2 | O | CH₂CH₂ | sub. 1 |
| 1067 | 3-Pip | 3,4-diClPh | CO | single bond | 2 | O | CH₂CH₂ | sub. 1 |
| 1068 | 4-Pip | 3,4-diClPh | CO | single bond | 2 | O | CH₂CH₂ | sub. 1 |
| 1069 | 2-Mor | 3,4-diClPh | CO | single bond | 2 | O | CH₂CH₂ | sub. 1 |
| 1070 | 3-Mor | 3,4-diClPh | CO | single bond | 2 | O | CH₂CH₂ | sub. 1 |
| 1071 | 4-Mor | 3,4-diClPh | CO | single bond | 2 | O | CH₂CH₂ | sub. 1 |
| 1072 | 2-Thmor | 3,4-diClPh | CO | single bond | 2 | O | CH₂CH₂ | sub. 1 |
| 1073 | 3-Thmor | 3,4-diClPh | CO | single bond | 2 | O | CH₂CH₂ | sub. 1 |
| 1074 | 4-Thmor | 3,4-diClPh | CO | single bond | 2 | O | CH₂CH₂ | sub. 1 |
| 1075 | 2-Piz | 3,4-diClPh | CO | single bond | 2 | O | CH₂CH₂ | sub. 1 |
| 1076 | 3-Piz | 3,4-diClPh | CO | single bond | 2 | O | CH₂CH₂ | sub. 1 |
| 1077 | 4-Piz | 3,4-diClPh | CO | single bond | 2 | O | CH₂CH₂ | sub. 1 |
| 1078 | 2-Aze | 3,4-diClPh | CO | single bond | 2 | O | CH₂CH₂ | sub. 1 |
| 1079 | 3-Aze | 3,4-diClPh | CO | single bond | 2 | O | CH₂CH₂ | sub. 1 |
| 1080 | 4-Aze | 3,4-diClPh | CO | single bond | 2 | O | CH₂CH₂ | sub. 1 |
| 1081 | cPr | 3,4-diClPh | CO | single bond | 2 | O | CH₂CH₂ | sub. 2 |
| 1082 | cBu | 3,4-diClPh | CO | single bond | 2 | O | CH₂CH₂ | sub. 2 |
| 1083 | cPn | 3,4-diClPh | CO | single bond | 2 | O | CH₂CH₂ | sub. 2 |
| 1084 | cHex | 3,4-diClPh | CO | single bond | 2 | O | CH₂CH₂ | sub. 2 |
| 1085 | cHep | 3,4-diClPh | CO | single bond | 2 | O | CH₂CH₂ | sub. 2 |
| 1086 | 2-Pyrd | 3,4-diClPh | CO | single bond | 2 | O | CH₂CH₂ | sub. 2 |
| 1087 | 3-Pyrd | 3,4-diClPh | CO | single bond | 2 | O | CH₂CH₂ | sub. 2 |
| 1088 | 4-Oxa | 3,4-diClPh | CO | single bond | 2 | O | CH₂CH₂ | sub. 2 |
| 1089 | 5-Oxa | 3,4-diClPh | CO | single bond | 2 | O | CH₂CH₂ | sub. 2 |
| 1090 | 4-Thi | 3,4-diClPh | CO | single bond | 2 | O | CH₂CH₂ | sub. 2 |
| 1091 | 5-Thi | 3,4-diClPh | CO | single bond | 2 | O | CH₂CH₂ | sub. 2 |
| 1092 | 4-OOxa | 3,4-diClPh | CO | single bond | 2 | O | CH₂CH₂ | sub. 2 |
| 1093 | 5-OOxa | 3,4-diClPh | CO | single bond | 2 | O | CH₂CH₂ | sub. 2 |
| 1094 | 4-OThi | 3,4-diClPh | CO | single bond | 2 | O | CH₂CH₂ | sub. 2 |
| 1095 | 5-OThi | 3,4-diClPh | CO | single bond | 2 | O | CH₂CH₂ | sub. 2 |
| 1096 | 2-Pip | 3,4-diClPh | CO | single bond | 2 | O | CH₂CH₂ | sub. 2 |
| 1097 | 3-Pip | 3,4-diClPh | CO | single bond | 2 | O | CH₂CH₂ | sub. 2 |
| 1098 | 4-Pip | 3,4-diClPh | CO | single bond | 2 | O | CH₂CH₂ | sub. 2 |
| 1099 | 2-Mor | 3,4-diClPh | CO | single bond | 2 | O | CH₂CH₂ | sub. 2 |
| 1100 | 3-Mor | 3,4-diClPh | CO | single bond | 2 | O | CH₂CH₂ | sub. 2 |
| 1101 | 4-Mor | 3,4-diClPh | CO | single bond | 2 | O | CH₂CH₂ | sub. 2 |
| 1102 | 2-Thmor | 3,4-diClPh | CO | single bond | 2 | O | CH₂CH₂ | sub. 2 |
| 1103 | 3-Thmor | 3,4-diClPh | CO | single bond | 2 | O | CH₂CH₂ | sub. 2 |
| 1104 | 4-Thmor | 3,4-diClPh | CO | single bond | 2 | O | CH₂CH₂ | sub. 2 |
| 1105 | 2-Piz | 3,4-diClPh | CO | single bond | 2 | O | CH₂CH₂ | sub. 2 |
| 1106 | 3-Piz | 3,4-diClPh | CO | single bond | 2 | O | CH₂CH₂ | sub. 2 |
| 1107 | 4-Piz | 3,4-diClPh | CO | single bond | 2 | O | CH₂CH₂ | sub. 2 |
| 1108 | 2-Aze | 3,4-diClPh | CO | single bond | 2 | O | CH₂CH₂ | sub. 2 |
| 1109 | 3-Aze | 3,4-diClPh | CO | single bond | 2 | O | CH₂CH₂ | sub. 2 |
| 1110 | 4-Aze | 3,4-diClPh | CO | single bond | 2 | O | CH₂CH₂ | sub. 2 |
| 1111 | cPr | 3,4-diClPh | CO | single bond | 2 | O | CH₂CH₂ | sub. 3 |
| 1112 | cBu | 3,4-diClPh | CO | single bond | 2 | O | CH₂CH₂ | sub. 3 |
| 1113 | cPn | 3,4-diClPh | CO | single bond | 2 | O | CH₂CH₂ | sub. 3 |
| 1114 | cHex | 3,4-diClPh | CO | single bond | 2 | O | CH₂CH₂ | sub. 3 |
| 1115 | cHep | 3,4-diClPh | CO | single bond | 2 | O | CH₂CH₂ | sub. 3 |
| 1116 | 2-Pyrd | 3,4-diClPh | CO | single bond | 2 | O | CH₂CH₂ | sub. 3 |
| 1117 | 3-Pyrd | 3,4-diClPh | CO | single bond | 2 | O | CH₂CH₂ | sub. 3 |
| 1118 | 4-Oxa | 3,4-diClPh | CO | single bond | 2 | O | CH₂CH₂ | sub. 3 |
| 1119 | 5-Oxa | 3,4-diClPh | CO | single bond | 2 | O | CH₂CH₂ | sub. 3 |
| 1120 | 4-Thi | 3,4-diClPh | CO | single bond | 2 | O | CH₂CH₂ | sub. 3 |

TABLE 1-continued

| Exemplification compound number | R¹ | R² | A | B | N | D | G | Q |
|---|---|---|---|---|---|---|---|---|
| 1121 | 5-Thi | 3,4-diClPh | CO | single bond | 2 | O | $CH_2CH_2$ | sub. 3 |
| 1122 | 4-OOxa | 3,4-diClPh | CO | single bond | 2 | O | $CH_2CH_2$ | sub. 3 |
| 1123 | 5-OOxa | 3,4-diClPh | CO | single bond | 2 | O | $CH_2CH_2$ | sub. 3 |
| 1124 | 4-OThi | 3,4-diClPh | CO | single bond | 2 | O | $CH_2CH_2$ | sub. 3 |
| 1125 | 5-OThi | 3,4-diClPh | CO | single bond | 2 | O | $CH_2CH_2$ | sub. 3 |
| 1126 | 2-Pip | 3,4-diClPh | CO | single bond | 2 | O | $CH_2CH_2$ | sub. 3 |
| 1127 | 3-Pip | 3,4-diClPh | CO | single bond | 2 | O | $CH_2CH_2$ | sub. 3 |
| 1128 | 4-Pip | 3,4-diClPh | CO | single bond | 2 | O | $CH_2CH_2$ | sub. 3 |
| 1129 | 2-Mor | 3,4-diClPh | CO | single bond | 2 | O | $CH_2CH_2$ | sub. 3 |
| 1130 | 3-Mor | 3,4-diClPh | CO | single bond | 2 | O | $CH_2CH_2$ | sub. 3 |
| 1131 | 4-Mor | 3,4-diClPh | CO | single bond | 2 | O | $CH_2CH_2$ | sub. 3 |
| 1132 | 2-Thmor | 3,4-diClPh | CO | single bond | 2 | O | $CH_2CH_2$ | sub. 3 |
| 1133 | 3-Thmor | 3,4-diClPh | CO | single bond | 2 | O | $CH_2CH_2$ | sub. 3 |
| 1134 | 4-Thmor | 3,4-diClPh | CO | single bond | 2 | O | $CH_2CH_2$ | sub. 3 |
| 1135 | 2-Piz | 3,4-diClPh | CO | single bond | 2 | O | $CH_2CH_2$ | sub. 3 |
| 1136 | 3-Piz | 3,4-diClPh | CO | single bond | 2 | O | $CH_2CH_2$ | sub. 3 |
| 1137 | 4-Piz | 3,4-diClPh | CO | single bond | 2 | O | $CH_2CH_2$ | sub. 3 |
| 1138 | 2-Aze | 3,4-diClPh | CO | single bond | 2 | O | $CH_2CH_2$ | sub. 3 |
| 1139 | 3-Aze | 3,4-diClPh | CO | single bond | 2 | O | $CH_2CH_2$ | sub. 3 |
| 1140 | 4-Aze | 3,4-diClPh | CO | single bond | 2 | O | $CH_2CH_2$ | sub. 3 |
| 1141 | cPr | 3,4-diClPh | CO | single bond | 2 | O | $CH_2CH_2$ | sub. 4 |
| 1142 | cBu | 3,4-diClPh | CO | single bond | 2 | O | $CH_2CH_2$ | sub. 4 |
| 1143 | cPn | 3,4-diClPh | CO | single bond | 2 | O | $CH_2CH_2$ | sub. 4 |
| 1144 | cHex | 3,4-diClPh | CO | single bond | 2 | O | $CH_2CH_2$ | sub. 4 |
| 1145 | cHep | 3,4-diClPh | CO | single bond | 2 | O | $CH_2CH_2$ | sub. 4 |
| 1146 | 2-Pyrd | 3,4-diClPh | CO | single bond | 2 | O | $CH_2CH_2$ | sub. 4 |
| 1147 | 3-Pyrd | 3,4-diClPh | CO | single bond | 2 | O | $CH_2CH_2$ | sub. 4 |
| 1148 | 4-Oxa | 3,4-diClPh | CO | single bond | 2 | O | $CH_2CH_2$ | sub. 4 |
| 1149 | 5-Oxa | 3,4-diClPh | CO | single bond | 2 | O | $CH_2CH_2$ | sub. 4 |
| 1150 | 4-Thi | 3,4-diClPh | CO | single bond | 2 | O | $CH_2CH_2$ | sub. 4 |
| 1151 | 5-Thi | 3,4-diClPh | CO | single bond | 2 | O | $CH_2CH_2$ | sub. 4 |
| 1152 | 4-OOxa | 3,4-diClPh | CO | single bond | 2 | O | $CH_2CH_2$ | sub. 4 |
| 1153 | 5-OOxa | 3,4-diClPh | CO | single bond | 2 | O | $CH_2CH_2$ | sub. 4 |
| 1154 | 4-OThi | 3,4-diClPh | CO | single bond | 2 | O | $CH_2CH_2$ | sub. 4 |
| 1155 | 5-OThi | 3,4-diClPh | CO | single bond | 2 | O | $CH_2CH_2$ | sub. 4 |
| 1156 | 2-Pip | 3,4-diClPh | CO | single bond | 2 | O | $CH_2CH_2$ | sub. 4 |
| 1157 | 3-Pip | 3,4-diClPh | CO | single bond | 2 | O | $CH_2CH_2$ | sub. 4 |
| 1158 | 4-Pip | 3,4-diClPh | CO | single bond | 2 | O | $CH_2CH_2$ | sub. 4 |
| 1159 | 2-Mor | 3,4-diClPh | CO | single bond | 2 | O | $CH_2CH_2$ | sub. 4 |
| 1160 | 3-Mor | 3,4-diClPh | CO | single bond | 2 | O | $CH_2CH_2$ | sub. 4 |
| 1161 | 4-Mor | 3,4-diClPh | CO | single bond | 2 | O | $CH_2CH_2$ | sub. 4 |
| 1162 | 2-Thmor | 3,4-diClPh | CO | single bond | 2 | O | $CH_2CH_2$ | sub. 4 |
| 1163 | 3-Thmor | 3,4-diClPh | CO | single bond | 2 | O | $CH_2CH_2$ | sub. 4 |
| 1164 | 4-Thmor | 3,4-diClPh | CO | single bond | 2 | O | $CH_2CH_2$ | sub. 4 |
| 1165 | 2-Piz | 3,4-diClPh | CO | single bond | 2 | O | $CH_2CH_2$ | sub. 4 |
| 1166 | 3-Piz | 3,4-diClPh | CO | single bond | 2 | O | $CH_2CH_2$ | sub. 4 |
| 1167 | 4-Piz | 3,4-diClPh | CO | single bond | 2 | O | $CH_2CH_2$ | sub. 4 |
| 1168 | 2-Aze | 3,4-diClPh | CO | single bond | 2 | O | $CH_2CH_2$ | sub. 4 |
| 1169 | 3-Aze | 3,4-diClPh | CO | single bond | 2 | O | $CH_2CH_2$ | sub. 4 |
| 1170 | 4-Aze | 3,4-diClPh | CO | single bond | 2 | O | $CH_2CH_2$ | sub. 4 |
| 1171 | cPr | 3,4-diClPh | CO | single bond | 2 | O | $CH_2CH_2$ | sub. 5 |
| 1172 | cBu | 3,4-diClPh | CO | single bond | 2 | O | $CH_2CH_2$ | sub. 5 |
| 1173 | cPn | 3,4-diClPh | CO | single bond | 2 | O | $CH_2CH_2$ | sub. 5 |
| 1174 | cHex | 3,4-diClPh | CO | single bond | 2 | O | $CH_2CH_2$ | sub. 5 |
| 1175 | cHep | 3,4-diClPh | CO | single bond | 2 | O | $CH_2CH_2$ | sub. 5 |
| 1176 | 2-Pyrd | 3,4-diClPh | CO | single bond | 2 | O | $CH_2CH_2$ | sub. 5 |
| 1177 | 3-Pyrd | 3,4-diClPh | CO | single bond | 2 | O | $CH_2CH_2$ | sub. 5 |
| 1178 | 4-Oxa | 3,4-diClPh | CO | single bond | 2 | O | $CH_2CH_2$ | sub. 5 |
| 1179 | 5-Oxa | 3,4-diClPh | CO | single bond | 2 | O | $CH_2CH_2$ | sub. 5 |
| 1180 | 4-Thi | 3,4-diClPh | CO | single bond | 2 | O | $CH_2CH_2$ | sub. 5 |
| 1181 | 5-Thi | 3,4-diClPh | CO | single bond | 2 | O | $CH_2CH_2$ | sub. 5 |
| 1182 | 4-OOxa | 3,4-diClPh | CO | single bond | 2 | O | $CH_2CH_2$ | sub. 5 |
| 1183 | 5-OOxa | 3,4-diClPh | CO | single bond | 2 | O | $CH_2CH_2$ | sub. 5 |
| 1184 | 4-OThi | 3,4-diClPh | CO | single bond | 2 | O | $CH_2CH_2$ | sub. 5 |
| 1185 | 5-OThi | 3,4-diClPh | CO | single bond | 2 | O | $CH_2CH_2$ | sub. 5 |
| 1186 | 2-Pip | 3,4-diClPh | CO | single bond | 2 | O | $CH_2CH_2$ | sub. 5 |
| 1187 | 3-Pip | 3,4-diClPh | CO | single bond | 2 | O | $CH_2CH_2$ | sub. 5 |
| 1188 | 4-Pip | 3,4-diClPh | CO | single bond | 2 | O | $CH_2CH_2$ | sub. 5 |
| 1189 | 2-Mor | 3,4-diClPh | CO | single bond | 2 | O | $CH_2CH_2$ | sub. 5 |
| 1190 | 3-Mor | 3,4-diClPh | CO | single bond | 2 | O | $CH_2CH_2$ | sub. 5 |
| 1191 | 4-Mor | 3,4-diClPh | CO | single bond | 2 | O | $CH_2CH_2$ | sub. 5 |
| 1192 | 2-Thmor | 3,4-diClPh | CO | single bond | 2 | O | $CH_2CH_2$ | sub. 5 |
| 1193 | 3-Thmor | 3,4-diClPh | CO | single bond | 2 | O | $CH_2CH_2$ | sub. 5 |
| 1194 | 4-Thmor | 3,4-diClPh | CO | single bond | 2 | O | $CH_2CH_2$ | sub. 5 |
| 1195 | 2-Piz | 3,4-diClPh | CO | single bond | 2 | O | $CH_2CH_2$ | sub. 5 |
| 1196 | 3-Piz | 3,4-diClPh | CO | single bond | 2 | O | $CH_2CH_2$ | sub. 5 |

TABLE 1-continued

| Exemplification compound number | R¹ | R² | A | B | N | D | G | Q |
|---|---|---|---|---|---|---|---|---|
| 1197 | 4-Piz | 3,4-diClPh | CO | single bond | 2 | O | $CH_2CH_2$ | sub. 5 |
| 1198 | 2-Aze | 3,4-diClPh | CO | single bond | 2 | O | $CH_2CH_2$ | sub. 5 |
| 1199 | 3-Aze | 3,4-diClPh | CO | single bond | 2 | O | $CH_2CH_2$ | sub. 5 |
| 1200 | 4-Aze | 3,4-diClPh | CO | single bond | 2 | O | $CH_2CH_2$ | sub. 5 |
| 1201 | cPr | 3,4-diClPh | CO | single bond | 2 | O | $CH_2CH_2$ | sub. 6 |
| 1202 | cBu | 3,4-diClPh | CO | single bond | 2 | O | $CH_2CH_2$ | sub. 6 |
| 1203 | cPn | 3,4-diClPh | CO | single bond | 2 | O | $CH_2CH_2$ | sub. 6 |
| 1204 | cHex | 3,4-diClPh | CO | single bond | 2 | O | $CH_2CH_2$ | sub. 6 |
| 1205 | cHep | 3,4-diClPh | CO | single bond | 2 | O | $CH_2CH_2$ | sub. 6 |
| 1206 | 2-Pyrd | 3,4-diClPh | CO | single bond | 2 | O | $CH_2CH_2$ | sub. 6 |
| 1207 | 3-Pyrd | 3,4-diClPh | CO | single bond | 2 | O | $CH_2CH_2$ | sub. 6 |
| 1208 | 4-Oxa | 3,4-diClPh | CO | single bond | 2 | O | $CH_2CH_2$ | sub. 6 |
| 1209 | 5-Oxa | 3,4-diClPh | CO | single bond | 2 | O | $CH_2CH_2$ | sub. 6 |
| 1210 | 4-Thi | 3,4-diClPh | CO | single bond | 2 | O | $CH_2CH_2$ | sub. 6 |
| 1211 | 5-Thi | 3,4-diClPh | CO | single bond | 2 | O | $CH_2CH_2$ | sub. 6 |
| 1212 | 4-OOxa | 3,4-diClPh | CO | single bond | 2 | O | $CH_2CH_2$ | sub. 6 |
| 1213 | 5-OOxa | 3,4-diClPh | CO | single bond | 2 | O | $CH_2CH_2$ | sub. 6 |
| 1214 | 4-OThi | 3,4-diClPh | CO | single bond | 2 | O | $CH_2CH_2$ | sub. 6 |
| 1215 | 5-OThi | 3,4-diClPh | CO | single bond | 2 | O | $CH_2CH_2$ | sub. 6 |
| 1216 | 2-Pip | 3,4-diClPh | CO | single bond | 2 | O | $CH_2CH_2$ | sub. 6 |
| 1217 | 3-Pip | 3,4-diClPh | CO | single bond | 2 | O | $CH_2CH_2$ | sub. 6 |
| 1218 | 4-Pip | 3,4-diClPh | CO | single bond | 2 | O | $CH_2CH_2$ | sub. 6 |
| 1219 | 2-Mor | 3,4-diClPh | CO | single bond | 2 | O | $CH_2CH_2$ | sub. 6 |
| 1220 | 3-Mor | 3,4-diClPh | CO | single bond | 2 | O | $CH_2CH_2$ | sub. 6 |
| 1221 | 4-Mor | 3,4-diClPh | CO | single bond | 2 | O | $CH_2CH_2$ | sub. 6 |
| 1222 | 2-Thmor | 3,4-diClPh | CO | single bond | 2 | O | $CH_2CH_2$ | sub. 6 |
| 1223 | 3-Thmor | 3,4-diClPh | CO | single bond | 2 | O | $CH_2CH_2$ | sub. 6 |
| 1224 | 4-Thmor | 3,4-diClPh | CO | single bond | 2 | O | $CH_2CH_2$ | sub. 6 |
| 1225 | 2-Piz | 3,4-diClPh | CO | single bond | 2 | O | $CH_2CH_2$ | sub. 6 |
| 1226 | 3-Piz | 3,4-diClPh | CO | single bond | 2 | O | $CH_2CH_2$ | sub. 6 |
| 1227 | 4-Piz | 3,4-diClPh | CO | single bond | 2 | O | $CH_2CH_2$ | sub. 6 |
| 1228 | 2-Aze | 3,4-diClPh | CO | single bond | 2 | O | $CH_2CH_2$ | sub. 6 |
| 1229 | 3-Aze | 3,4-diClPh | CO | single bond | 2 | O | $CH_2CH_2$ | sub. 6 |
| 1230 | 4-Aze | 3,4-diClPh | CO | single bond | 2 | O | $CH_2CH_2$ | sub. 6 |
| 1231 | cPr | 3,4-diClPh | CO | single bond | 2 | O | $CH_2CH_2$ | sub. 7 |
| 1232 | cBu | 3,4-diClPh | CO | single bond | 2 | O | $CH_2CH_2$ | sub. 7 |
| 1233 | cPn | 3,4-diClPh | CO | single bond | 2 | O | $CH_2CH_2$ | sub. 7 |
| 1234 | cHex | 3,4-diClPh | CO | single bond | 2 | O | $CH_2CH_2$ | sub. 7 |
| 1235 | cHep | 3,4-diClPh | CO | single bond | 2 | O | $CH_2CH_2$ | sub. 7 |
| 1236 | 2-Pyrd | 3,4-diClPh | CO | single bond | 2 | O | $CH_2CH_2$ | sub. 7 |
| 1237 | 3-Pyrd | 3,4-diClPh | CO | single bond | 2 | O | $CH_2CH_2$ | sub. 7 |
| 1238 | 4-Oxa | 3,4-diClPh | CO | single bond | 2 | O | $CH_2CH_2$ | sub. 7 |
| 1239 | 5-Oxa | 3,4-diClPh | CO | single bond | 2 | O | $CH_2CH_2$ | sub. 7 |
| 1240 | 4-Thi | 3,4-diClPh | CO | single bond | 2 | O | $CH_2CH_2$ | sub. 7 |
| 1241 | 5-Thi | 3,4-diClPh | CO | single bond | 2 | O | $CH_2CH_2$ | sub. 7 |
| 1242 | 4-OOxa | 3,4-diClPh | CO | single bond | 2 | O | $CH_2CH_2$ | sub. 7 |
| 1243 | 5-OOxa | 3,4-diClPh | CO | single bond | 2 | O | $CH_2CH_2$ | sub. 7 |
| 1244 | 4-OThi | 3,4-diClPh | CO | single bond | 2 | O | $CH_2CH_2$ | sub. 7 |
| 1245 | 5-OThi | 3,4-diClPh | CO | single bond | 2 | O | $CH_2CH_2$ | sub. 7 |
| 1246 | 2-Pip | 3,4-diClPh | CO | single bond | 2 | O | $CH_2CH_2$ | sub. 7 |
| 1247 | 3-Pip | 3,4-diClPh | CO | single bond | 2 | O | $CH_2CH_2$ | sub. 7 |
| 1248 | 4-Pip | 3,4-diClPh | CO | single bond | 2 | O | $CH_2CH_2$ | sub. 7 |
| 1249 | 2-Mor | 3,4-diClPh | CO | single bond | 2 | O | $CH_2CH_2$ | sub. 7 |
| 1250 | 3-Mor | 3,4-diClPh | CO | single bond | 2 | O | $CH_2CH_2$ | sub. 7 |
| 1251 | 4-Mor | 3,4-diClPh | CO | single bond | 2 | O | $CH_2CH_2$ | sub. 7 |
| 1252 | 2-Thmor | 3,4-diClPh | CO | single bond | 2 | O | $CH_2CH_2$ | sub. 7 |
| 1253 | 3-Thmor | 3,4-diClPh | CO | single bond | 2 | O | $CH_2CH_2$ | sub. 7 |
| 1254 | 4-Thmor | 3,4-diClPh | CO | single bond | 2 | O | $CH_2CH_2$ | sub. 7 |
| 1255 | 2-Piz | 3,4-diClPh | CO | single bond | 2 | O | $CH_2CH_2$ | sub. 7 |
| 1256 | 3-Piz | 3,4-diClPh | CO | single bond | 2 | O | $CH_2CH_2$ | sub. 7 |
| 1257 | 4-Piz | 3,4-diClPh | CO | single bond | 2 | O | $CH_2CH_2$ | sub. 7 |
| 1258 | 2-Aze | 3,4-diClPh | CO | single bond | 2 | O | $CH_2CH_2$ | sub. 7 |
| 1259 | 3-Aze | 3,4-diClPh | CO | single bond | 2 | O | $CH_2CH_2$ | sub. 7 |
| 1260 | 4-Aze | 3,4-diClPh | CO | single bond | 2 | O | $CH_2CH_2$ | sub. 7 |
| 1261 | cPr | 3,4-diClPh | CO | single bond | 2 | O | $CH_2CH_2$ | sub. 8 |
| 1262 | cBu | 3,4-diClPh | CO | single bond | 2 | O | $CH_2CH_2$ | sub. 8 |
| 1263 | cPn | 3,4-diClPh | CO | single bond | 2 | O | $CH_2CH_2$ | sub. 8 |
| 1264 | cHex | 3,4-diClPh | CO | single bond | 2 | O | $CH_2CH_2$ | sub. 8 |
| 1265 | cHep | 3,4-diClPh | CO | single bond | 2 | O | $CH_2CH_2$ | sub. 8 |
| 1266 | 2-Pyrd | 3,4-diClPh | CO | single bond | 2 | O | $CH_2CH_2$ | sub. 8 |
| 1267 | 3-Pyrd | 3,4-diClPh | CO | single bond | 2 | O | $CH_2CH_2$ | sub. 8 |
| 1268 | 4-Oxa | 3,4-diClPh | CO | single bond | 2 | O | $CH_2CH_2$ | sub. 8 |
| 1269 | 5-Oxa | 3,4-diClPh | CO | single bond | 2 | O | $CH_2CH_2$ | sub. 8 |
| 1270 | 4-Thi | 3,4-diClPh | CO | single bond | 2 | O | $CH_2CH_2$ | sub. 8 |
| 1271 | 5-Thi | 3,4-diClPh | CO | single bond | 2 | O | $CH_2CH_2$ | sub. 8 |
| 1272 | 4-OOxa | 3,4-diClPh | CO | single bond | 2 | O | $CH_2CH_2$ | sub. 8 |

TABLE 1-continued

| Exemplification compound number | R¹ | R² | A | B | N | D | G | Q |
|---|---|---|---|---|---|---|---|---|
| 1273 | 5-OOxa | 3,4-diClPh | CO | single bond | 2 | O | $CH_2CH_2$ | sub. 8 |
| 1274 | 4-OThi | 3,4-diClPh | CO | single bond | 2 | O | $CH_2CH_2$ | sub. 8 |
| 1275 | 5-OThi | 3,4-diClPh | CO | single bond | 2 | O | $CH_2CH_2$ | sub. 8 |
| 1276 | 2-Pip | 3,4-diClPh | CO | single bond | 2 | O | $CH_2CH_2$ | sub. 8 |
| 1277 | 3-Pip | 3,4-diClPh | CO | single bond | 2 | O | $CH_2CH_2$ | sub. 8 |
| 1278 | 4-Pip | 3,4-diClPh | CO | single bond | 2 | O | $CH_2CH_2$ | sub. 8 |
| 1279 | 2-Mor | 3,4-diClPh | CO | single bond | 2 | O | $CH_2CH_2$ | sub. 8 |
| 1280 | 3-Mor | 3,4-diClPh | CO | single bond | 2 | O | $CH_2CH_2$ | sub. 8 |
| 1281 | 4-Mor | 3,4-diClPh | CO | single bond | 2 | O | $CH_2CH_2$ | sub. 8 |
| 1282 | 2-Thmor | 3,4-diClPh | CO | single bond | 2 | O | $CH_2CH_2$ | sub. 8 |
| 1283 | 3-Thmor | 3,4-diClPh | CO | single bond | 2 | O | $CH_2CH_2$ | sub. 8 |
| 1284 | 4-Thmor | 3,4-diClPh | CO | single bond | 2 | O | $CH_2CH_2$ | sub. 8 |
| 1285 | 2-Piz | 3,4-diClPh | CO | single bond | 2 | O | $CH_2CH_2$ | sub. 8 |
| 1286 | 3-Piz | 3,4-diClPh | CO | single bond | 2 | O | $CH_2CH_2$ | sub. 8 |
| 1287 | 4-Piz | 3,4-diClPh | CO | single bond | 2 | O | $CH_2CH_2$ | sub. 8 |
| 1288 | 2-Aze | 3,4-diClPh | CO | single bond | 2 | O | $CH_2CH_2$ | sub. 8 |
| 1289 | 3-Aze | 3,4-diClPh | CO | single bond | 2 | O | $CH_2CH_2$ | sub. 8 |
| 1290 | 4-Aze | 3,4-diClPh | CO | single bond | 2 | O | $CH_2CH_2$ | sub. 8 |
| 1291 | cPr | 3,4-diClPh | CO | single bond | 2 | O | $CH_2CH_2$ | sub. 9 |
| 1292 | cBu | 3,4-diClPh | CO | single bond | 2 | O | $CH_2CH_2$ | sub. 9 |
| 1293 | cPn | 3,4-diClPh | CO | single bond | 2 | O | $CH_2CH_2$ | sub. 9 |
| 1294 | cHex | 3,4-diClPh | CO | single bond | 2 | O | $CH_2CH_2$ | sub. 9 |
| 1295 | cHep | 3,4-diClPh | CO | single bond | 2 | O | $CH_2CH_2$ | sub. 9 |
| 1296 | 2-Pyrd | 3,4-diClPh | CO | single bond | 2 | O | $CH_2CH_2$ | sub. 9 |
| 1297 | 3-Pyrd | 3,4-diClPh | CO | single bond | 2 | O | $CH_2CH_2$ | sub. 9 |
| 1298 | 4-Oxa | 3,4-diClPh | CO | single bond | 2 | O | $CH_2CH_2$ | sub. 9 |
| 1299 | 5-Oxa | 3,4-diClPh | CO | single bond | 2 | O | $CH_2CH_2$ | sub. 9 |
| 1300 | 4-Thi | 3,4-diClPh | CO | single bond | 2 | O | $CH_2CH_2$ | sub. 9 |
| 1301 | 5-Thi | 3,4-diClPh | CO | single bond | 2 | O | $CH_2CH_2$ | sub. 9 |
| 1302 | 4-OOxa | 3,4-diClPh | CO | single bond | 2 | O | $CH_2CH_2$ | sub. 9 |
| 1303 | 5-OOxa | 3,4-diClPh | CO | single bond | 2 | O | $CH_2CH_2$ | sub. 9 |
| 1304 | 4-OThi | 3,4-diClPh | CO | single bond | 2 | O | $CH_2CH_2$ | sub. 9 |
| 1305 | 5-OThi | 3,4-diClPh | CO | single bond | 2 | O | $CH_2CH_2$ | sub. 9 |
| 1306 | 2-Pip | 3,4-diClPh | CO | single bond | 2 | O | $CH_2CH_2$ | sub. 9 |
| 1307 | 3-Pip | 3,4-diClPh | CO | single bond | 2 | O | $CH_2CH_2$ | sub. 9 |
| 1308 | 4-Pip | 3,4-diClPh | CO | single bond | 2 | O | $CH_2CH_2$ | sub. 9 |
| 1309 | 2-Mor | 3,4-diClPh | CO | single bond | 2 | O | $CH_2CH_2$ | sub. 9 |
| 1310 | 3-Mor | 3,4-diClPh | CO | single bond | 2 | O | $CH_2CH_2$ | sub. 9 |
| 1311 | 4-Mor | 3,4-diClPh | CO | single bond | 2 | O | $CH_2CH_2$ | sub. 9 |
| 1312 | 2-Thmor | 3,4-diClPh | CO | single bond | 2 | O | $CH_2CH_2$ | sub. 9 |
| 1313 | 3-Thmor | 3,4-diClPh | CO | single bond | 2 | O | $CH_2CH_2$ | sub. 9 |
| 1314 | 4-Thmor | 3,4-diClPh | CO | single bond | 2 | O | $CH_2CH_2$ | sub. 9 |
| 1315 | 2-Piz | 3,4-diClPh | CO | single bond | 2 | O | $CH_2CH_2$ | sub. 9 |
| 1316 | 3-Piz | 3,4-diClPh | CO | single bond | 2 | O | $CH_2CH_2$ | sub. 9 |
| 1317 | 4-Piz | 3,4-diClPh | CO | single bond | 2 | O | $CH_2CH_2$ | sub. 9 |
| 1318 | 2-Aze | 3,4-diClPh | CO | single bond | 2 | O | $CH_2CH_2$ | sub. 9 |
| 1319 | 3-Aze | 3,4-diClPh | CO | single bond | 2 | O | $CH_2CH_2$ | sub. 9 |
| 1320 | 4-Aze | 3,4-diClPh | CO | single bond | 2 | O | $CH_2CH_2$ | sub. 9 |
| 1321 | cPr | 3,4-diClPh | CO | single bond | 2 | O | $CH_2CH_2$ | sub. 10 |
| 1322 | cBu | 3,4-diClPh | CO | single bond | 2 | O | $CH_2CH_2$ | sub. 10 |
| 1323 | cPn | 3,4-diClPh | CO | single bond | 2 | O | $CH_2CH_2$ | sub. 10 |
| 1324 | cHex | 3,4-diClPh | CO | single bond | 2 | O | $CH_2CH_2$ | sub. 10 |
| 1325 | cHep | 3,4-diClPh | CO | single bond | 2 | O | $CH_2CH_2$ | sub. 10 |
| 1326 | 2-Pyrd | 3,4-diClPh | CO | single bond | 2 | O | $CH_2CH_2$ | sub. 10 |
| 1327 | 3-Pyrd | 3,4-diClPh | CO | single bond | 2 | O | $CH_2CH_2$ | sub. 10 |
| 1328 | 4-Oxa | 3,4-diClPh | CO | single bond | 2 | O | $CH_2CH_2$ | sub. 10 |
| 1329 | 5-Oxa | 3,4-diClPh | CO | single bond | 2 | O | $CH_2CH_2$ | sub. 10 |
| 1330 | 4-Thi | 3,4-diClPh | CO | single bond | 2 | O | $CH_2CH_2$ | sub. 10 |
| 1331 | 5-Thi | 3,4-diClPh | CO | single bond | 2 | O | $CH_2CH_2$ | sub. 10 |
| 1332 | 4-OOxa | 3,4-diClPh | CO | single bond | 2 | O | $CH_2CH_2$ | sub. 10 |
| 1333 | 5-OOxa | 3,4-diClPh | CO | single bond | 2 | O | $CH_2CH_2$ | sub. 10 |
| 1334 | 4-OThi | 3,4-diClPh | CO | single bond | 2 | O | $CH_2CH_2$ | sub. 10 |
| 1335 | 5-OThi | 3,4-diClPh | CO | single bond | 2 | O | $CH_2CH_2$ | sub. 10 |
| 1336 | 2-Pip | 3,4-diClPh | CO | single bond | 2 | O | $CH_2CH_2$ | sub. 10 |
| 1337 | 3-Pip | 3,4-diClPh | CO | single bond | 2 | O | $CH_2CH_2$ | sub. 10 |
| 1338 | 4-Pip | 3,4-diClPh | CO | single bond | 2 | O | $CH_2CH_2$ | sub. 10 |
| 1339 | 2-Mor | 3,4-diClPh | CO | single bond | 2 | O | $CH_2CH_2$ | sub. 10 |
| 1340 | 3-Mor | 3,4-diClPh | CO | single bond | 2 | O | $CH_2CH_2$ | sub. 10 |
| 1341 | 4-Mor | 3,4-diClPh | CO | single bond | 2 | O | $CH_2CH_2$ | sub. 10 |
| 1342 | 2-Thmor | 3,4-diClPh | CO | single bond | 2 | O | $CH_2CH_2$ | sub. 10 |
| 1343 | 3-Thmor | 3,4-diClPh | CO | single bond | 2 | O | $CH_2CH_2$ | sub. 10 |
| 1344 | 4-Thmor | 3,4-diClPh | CO | single bond | 2 | O | $CH_2CH_2$ | sub. 10 |
| 1345 | 2-Piz | 3,4-diClPh | CO | single bond | 2 | O | $CH_2CH_2$ | sub. 10 |
| 1346 | 3-Piz | 3,4-diClPh | CO | single bond | 2 | O | $CH_2CH_2$ | sub. 10 |
| 1347 | 4-Piz | 3,4-diClPh | CO | single bond | 2 | O | $CH_2CH_2$ | sub. 10 |
| 1348 | 2-Aze | 3,4-diClPh | CO | single bond | 2 | O | $CH_2CH_2$ | sub. 10 |

TABLE 1-continued

| Exemplification compound number | R¹ | R² | A | B | N | D | G | Q |
|---|---|---|---|---|---|---|---|---|
| 1349 | 3-Aze | 3,4-diClPh | CO | single bond | 2 | O | CH₂CH₂ | sub. 10 |
| 1350 | 4-Aze | 3,4-diClPh | CO | single bond | 2 | O | CH₂CH₂ | sub. 10 |
| 1351 | cPr | 3,4-diClPh | CO | single bond | 2 | O | CH₂CH₂ | sub. 11 |
| 1352 | cBu | 3,4-diClPh | CO | single bond | 2 | O | CH₂CH₂ | sub. 11 |
| 1353 | cPn | 3,4-diClPh | CO | single bond | 2 | O | CH₂CH₂ | sub. 11 |
| 1354 | cHex | 3,4-diClPh | CO | single bond | 2 | O | CH₂CH₂ | sub. 11 |
| 1355 | cHep | 3,4-diClPh | CO | single bond | 2 | O | CH₂CH₂ | sub. 11 |
| 1356 | 2-Pyrd | 3,4-diClPh | CO | single bond | 2 | O | CH₂CH₂ | sub. 11 |
| 1357 | 3-Pyrd | 3,4-diClPh | CO | single bond | 2 | O | CH₂CH₂ | sub. 11 |
| 1358 | 4-Oxa | 3,4-diClPh | CO | single bond | 2 | O | CH₂CH₂ | sub. 11 |
| 1359 | 5-Oxa | 3,4-diClPh | CO | single bond | 2 | O | CH₂CH₂ | sub. 11 |
| 1360 | 4-Thi | 3,4-diClPh | CO | single bond | 2 | O | CH₂CH₂ | sub. 11 |
| 1361 | 5-Thi | 3,4-diClPh | CO | single bond | 2 | O | CH₂CH₂ | sub. 11 |
| 1362 | 4-OOxa | 3,4-diClPh | CO | single bond | 2 | O | CH₂CH₂ | sub. 11 |
| 1363 | 5-OOxa | 3,4-diClPh | CO | single bond | 2 | O | CH₂CH₂ | sub. 11 |
| 1364 | 4-OThi | 3,4-diClPh | CO | single bond | 2 | O | CH₂CH₂ | sub. 11 |
| 1365 | 5-OThi | 3,4-diClPh | CO | single bond | 2 | O | CH₂CH₂ | sub. 11 |
| 1366 | 2-Pip | 3,4-diClPh | CO | single bond | 2 | O | CH₂CH₂ | sub. 11 |
| 1367 | 3-Pip | 3,4-diClPh | CO | single bond | 2 | O | CH₂CH₂ | sub. 11 |
| 1368 | 4-Pip | 3,4-diClPh | CO | single bond | 2 | O | CH₂CH₂ | sub. 11 |
| 1369 | 2-Mor | 3,4-diClPh | CO | single bond | 2 | O | CH₂CH₂ | sub. 11 |
| 1370 | 3-Mor | 3,4-diClPh | CO | single bond | 2 | O | CH₂CH₂ | sub. 11 |
| 1371 | 4-Mor | 3,4-diClPh | CO | single bond | 2 | O | CH₂CH₂ | sub. 11 |
| 1372 | 2-Thmor | 3,4-diClPh | CO | single bond | 2 | O | CH₂CH₂ | sub. 11 |
| 1373 | 3-Thmor | 3,4-diClPh | CO | single bond | 2 | O | CH₂CH₂ | sub. 11 |
| 1374 | 4-Thmor | 3,4-diClPh | CO | single bond | 2 | O | CH₂CH₂ | sub. 11 |
| 1375 | 2-Piz | 3,4-diClPh | CO | single bond | 2 | O | CH₂CH₂ | sub. 11 |
| 1376 | 3-Piz | 3,4-diClPh | CO | single bond | 2 | O | CH₂CH₂ | sub. 11 |
| 1377 | 4-Piz | 3,4-diClPh | CO | single bond | 2 | O | CH₂CH₂ | sub. 11 |
| 1378 | 2-Aze | 3,4-diClPh | CO | single bond | 2 | O | CH₂CH₂ | sub. 11 |
| 1379 | 3-Aze | 3,4-diClPh | CO | single bond | 2 | O | CH₂CH₂ | sub. 11 |
| 1380 | 4-Aze | 3,4-diClPh | CO | single bond | 2 | O | CH₂CH₂ | sub. 11 |
| 1381 | cPr | 3,4-diClPh | CO | single bond | 2 | O | CH₂CH₂ | sub. 12 |
| 1382 | cBu | 3,4-diClPh | CO | single bond | 2 | O | CH₂CH₂ | sub. 12 |
| 1383 | cPn | 3,4-diClPh | CO | single bond | 2 | O | CH₂CH₂ | sub. 12 |
| 1384 | cHex | 3,4-diClPh | CO | single bond | 2 | O | CH₂CH₂ | sub. 12 |
| 1385 | cHep | 3,4-diClPh | CO | single bond | 2 | O | CH₂CH₂ | sub. 12 |
| 1386 | 2-Pyrd | 3,4-diClPh | CO | single bond | 2 | O | CH₂CH₂ | sub. 12 |
| 1387 | 3-Pyrd | 3,4-diClPh | CO | single bond | 2 | O | CH₂CH₂ | sub. 12 |
| 1388 | 4-Oxa | 3,4-diClPh | CO | single bond | 2 | O | CH₂CH₂ | sub. 12 |
| 1389 | 5-Oxa | 3,4-diClPh | CO | single bond | 2 | O | CH₂CH₂ | sub. 12 |
| 1390 | 4-Thi | 3,4-diClPh | CO | single bond | 2 | O | CH₂CH₂ | sub. 12 |
| 1391 | 5-Thi | 3,4-diClPh | CO | single bond | 2 | O | CH₂CH₂ | sub. 12 |
| 1392 | 4-OOxa | 3,4-diClPh | CO | single bond | 2 | O | CH₂CH₂ | sub. 12 |
| 1393 | 5-OOxa | 3,4-diClPh | CO | single bond | 2 | O | CH₂CH₂ | sub. 12 |
| 1394 | 4-OThi | 3,4-diClPh | CO | single bond | 2 | O | CH₂CH₂ | sub. 12 |
| 1395 | 5-OThi | 3,4-diClPh | CO | single bond | 2 | O | CH₂CH₂ | sub. 12 |
| 1396 | 2-Pip | 3,4-diClPh | CO | single bond | 2 | O | CH₂CH₂ | sub. 12 |
| 1397 | 3-Pip | 3,4-diClPh | CO | single bond | 2 | O | CH₂CH₂ | sub. 12 |
| 1398 | 4-Pip | 3,4-diClPh | CO | single bond | 2 | O | CH₂CH₂ | sub. 12 |
| 1399 | 2-Mor | 3,4-diClPh | CO | single bond | 2 | O | CH₂CH₂ | sub. 12 |
| 1400 | 3-Mor | 3,4-diClPh | CO | single bond | 2 | O | CH₂CH₂ | sub. 12 |
| 1401 | 4-Mor | 3,4-diClPh | CO | single bond | 2 | O | CH₂CH₂ | sub. 12 |
| 1402 | 2-Thmor | 3,4-diClPh | CO | single bond | 2 | O | CH₂CH₂ | sub. 12 |
| 1403 | 3-Thmor | 3,4-diClPh | CO | single bond | 2 | O | CH₂CH₂ | sub. 12 |
| 1404 | 4-Thmor | 3,4-diClPh | CO | single bond | 2 | O | CH₂CH₂ | sub. 12 |
| 1405 | 2-Piz | 3,4-diClPh | CO | single bond | 2 | O | CH₂CH₂ | sub. 12 |
| 1406 | 3-Piz | 3,4-diClPh | CO | single bond | 2 | O | CH₂CH₂ | sub. 12 |
| 1407 | 4-Piz | 3,4-diClPh | CO | single bond | 2 | O | CH₂CH₂ | sub. 12 |
| 1408 | 2-Aze | 3,4-diClPh | CO | single bond | 2 | O | CH₂CH₂ | sub. 12 |
| 1409 | 3-Aze | 3,4-diClPh | CO | single bond | 2 | O | CH₂CH₂ | sub. 12 |
| 1410 | 4-Aze | 3,4-diClPh | CO | single bond | 2 | O | CH₂CH₂ | sub. 12 |
| 1411 | cPr | 3,4-diClPh | CO | single bond | 2 | O | CH₂CH₂ | sub. 13 |
| 1412 | cBu | 3,4-diClPh | CO | single bond | 2 | O | CH₂CH₂ | sub. 13 |
| 1413 | cPn | 3,4-diClPh | CO | single bond | 2 | O | CH₂CH₂ | sub. 13 |
| 1414 | cHex | 3,4-diClPh | CO | single bond | 2 | O | CH₂CH₂ | sub. 13 |
| 1415 | cHep | 3,4-diClPh | CO | single bond | 2 | O | CH₂CH₂ | sub. 13 |
| 1416 | 2-Pyrd | 3,4-diClPh | CO | single bond | 2 | O | CH₂CH₂ | sub. 13 |
| 1417 | 3-Pyrd | 3,4-diClPh | CO | single bond | 2 | O | CH₂CH₂ | sub. 13 |
| 1418 | 4-Oxa | 3,4-diClPh | CO | single bond | 2 | O | CH₂CH₂ | sub. 13 |
| 1419 | 5-Oxa | 3,4-diClPh | CO | single bond | 2 | O | CH₂CH₂ | sub. 13 |
| 1420 | 4-Thi | 3,4-diClPh | CO | single bond | 2 | O | CH₂CH₂ | sub. 13 |
| 1421 | 5-Thi | 3,4-diClPh | CO | single bond | 2 | O | CH₂CH₂ | sub. 13 |
| 1422 | 4-OOxa | 3,4-diClPh | CO | single bond | 2 | O | CH₂CH₂ | sub. 13 |
| 1423 | 5-OOxa | 3,4-diClPh | CO | single bond | 2 | O | CH₂CH₂ | sub. 13 |
| 1424 | 4-OThi | 3,4-diClPh | CO | single bond | 2 | O | CH₂CH₂ | sub. 13 |

TABLE 1-continued

| Exemplification compound number | R¹ | R² | A | B | N | D | G | Q |
|---|---|---|---|---|---|---|---|---|
| 1425 | 5-OThi | 3,4-diClPh | CO | single bond | 2 | O | $CH_2CH_2$ | sub. 13 |
| 1426 | 2-Pip | 3,4-diClPh | CO | single bond | 2 | O | $CH_2CH_2$ | sub. 13 |
| 1427 | 3-Pip | 3,4-diClPh | CO | single bond | 2 | O | $CH_2CH_2$ | sub. 13 |
| 1428 | 4-Pip | 3,4-diClPh | CO | single bond | 2 | O | $CH_2CH_2$ | sub. 13 |
| 1429 | 2-Mor | 3,4-diClPh | CO | single bond | 2 | O | $CH_2CH_2$ | sub. 13 |
| 1430 | 3-Mor | 3,4-diClPh | CO | single bond | 2 | O | $CH_2CH_2$ | sub. 13 |
| 1431 | 4-Mor | 3,4-diClPh | CO | single bond | 2 | O | $CH_2CH_2$ | sub. 13 |
| 1432 | 2-Thmor | 3,4-diClPh | CO | single bond | 2 | O | $CH_2CH_2$ | sub. 13 |
| 1433 | 3-Thmor | 3,4-diClPh | CO | single bond | 2 | O | $CH_2CH_2$ | sub. 13 |
| 1434 | 4-Thmor | 3,4-diClPh | CO | single bond | 2 | O | $CH_2CH_2$ | sub. 13 |
| 1435 | 2-Piz | 3,4-diClPh | CO | single bond | 2 | O | $CH_2CH_2$ | sub. 13 |
| 1436 | 3-Piz | 3,4-diClPh | CO | single bond | 2 | O | $CH_2CH_2$ | sub. 13 |
| 1437 | 4-Piz | 3,4-diClPh | CO | single bond | 2 | O | $CH_2CH_2$ | sub. 13 |
| 1438 | 2-Aze | 3,4-diClPh | CO | single bond | 2 | O | $CH_2CH_2$ | sub. 13 |
| 1439 | 3-Aze | 3,4-diClPh | CO | single bond | 2 | O | $CH_2CH_2$ | sub. 13 |
| 1440 | 4-Aze | 3,4-diClPh | CO | single bond | 2 | O | $CH_2CH_2$ | sub. 13 |
| 1441 | cPr | 3,4-diClPh | CO | single bond | 2 | O | $CH_2CH_2$ | sub. 14 |
| 1442 | cBu | 3,4-diClPh | CO | single bond | 2 | O | $CH_2CH_2$ | sub. 14 |
| 1443 | cPn | 3,4-diClPh | CO | single bond | 2 | O | $CH_2CH_2$ | sub. 14 |
| 1444 | cHex | 3,4-diClPh | CO | single bond | 2 | O | $CH_2CH_2$ | sub. 14 |
| 1445 | cHep | 3,4-diClPh | CO | single bond | 2 | O | $CH_2CH_2$ | sub. 14 |
| 1446 | 2-Pyrd | 3,4-diClPh | CO | single bond | 2 | O | $CH_2CH_2$ | sub. 14 |
| 1447 | 3-Pyrd | 3,4-diClPh | CO | single bond | 2 | O | $CH_2CH_2$ | sub. 14 |
| 1448 | 4-Oxa | 3,4-diClPh | CO | single bond | 2 | O | $CH_2CH_2$ | sub. 14 |
| 1449 | 5-Oxa | 3,4-diClPh | CO | single bond | 2 | O | $CH_2CH_2$ | sub. 14 |
| 1450 | 4-Thi | 3,4-diClPh | CO | single bond | 2 | O | $CH_2CH_2$ | sub. 14 |
| 1451 | 5-Thi | 3,4-diClPh | CO | single bond | 2 | O | $CH_2CH_2$ | sub. 14 |
| 1452 | 4-OOxa | 3,4-diClPh | CO | single bond | 2 | O | $CH_2CH_2$ | sub. 14 |
| 1453 | 5-OOxa | 3,4-diClPh | CO | single bond | 2 | O | $CH_2CH_2$ | sub. 14 |
| 1454 | 4-OThi | 3,4-diClPh | CO | single bond | 2 | O | $CH_2CH_2$ | sub. 14 |
| 1455 | 5-OThi | 3,4-diClPh | CO | single bond | 2 | O | $CH_2CH_2$ | sub. 14 |
| 1456 | 2-Pip | 3,4-diClPh | CO | single bond | 2 | O | $CH_2CH_2$ | sub. 14 |
| 1457 | 3-Pip | 3,4-diClPh | CO | single bond | 2 | O | $CH_2CH_2$ | sub. 14 |
| 1458 | 4-Pip | 3,4-diClPh | CO | single bond | 2 | O | $CH_2CH_2$ | sub. 14 |
| 1459 | 2-Mor | 3,4-diClPh | CO | single bond | 2 | O | $CH_2CH_2$ | sub. 14 |
| 1460 | 3-Mor | 3,4-diClPh | CO | single bond | 2 | O | $CH_2CH_2$ | sub. 14 |
| 1461 | 4-Mor | 3,4-diClPh | CO | single bond | 2 | O | $CH_2CH_2$ | sub. 14 |
| 1462 | 2-Thmor | 3,4-diClPh | CO | single bond | 2 | O | $CH_2CH_2$ | sub. 14 |
| 1463 | 3-Thmor | 3,4-diClPh | CO | single bond | 2 | O | $CH_2CH_2$ | sub. 14 |
| 1464 | 4-Thmor | 3,4-diClPh | CO | single bond | 2 | O | $CH_2CH_2$ | sub. 14 |
| 1465 | 2-Piz | 3,4-diClPh | CO | single bond | 2 | O | $CH_2CH_2$ | sub. 14 |
| 1466 | 3-Piz | 3,4-diClPh | CO | single bond | 2 | O | $CH_2CH_2$ | sub. 14 |
| 1467 | 4-Piz | 3,4-diClPh | CO | single bond | 2 | O | $CH_2CH_2$ | sub. 14 |
| 1468 | 2-Aze | 3,4-diClPh | CO | single bond | 2 | O | $CH_2CH_2$ | sub. 14 |
| 1469 | 3-Aze | 3,4-diClPh | CO | single bond | 2 | O | $CH_2CH_2$ | sub. 14 |
| 1470 | 4-Aze | 3,4-diClPh | CO | single bond | 2 | O | $CH_2CH_2$ | sub. 14 |
| 1471 | cPr | 3,4-diClPh | CO | single bond | 2 | O | $CH_2CH_2$ | sub. 15 |
| 1472 | cBu | 3,4-diClPh | CO | single bond | 2 | O | $CH_2CH_2$ | sub. 15 |
| 1473 | cPn | 3,4-diClPh | CO | single bond | 2 | O | $CH_2CH_2$ | sub. 15 |
| 1474 | cHex | 3,4-diClPh | CO | single bond | 2 | O | $CH_2CH_2$ | sub. 15 |
| 1475 | cHep | 3,4-diClPh | CO | single bond | 2 | O | $CH_2CH_2$ | sub. 15 |
| 1476 | 2-Pyrd | 3,4-diClPh | CO | single bond | 2 | O | $CH_2CH_2$ | sub. 15 |
| 1477 | 3-Pyrd | 3,4-diClPh | CO | single bond | 2 | O | $CH_2CH_2$ | sub. 15 |
| 1478 | 4-Oxa | 3,4-diClPh | CO | single bond | 2 | O | $CH_2CH_2$ | sub. 15 |
| 1479 | 5-Oxa | 3,4-diClPh | CO | single bond | 2 | O | $CH_2CH_2$ | sub. 15 |
| 1480 | 4-Thi | 3,4-diClPh | CO | single bond | 2 | O | $CH_2CH_2$ | sub. 15 |
| 1481 | 5-Thi | 3,4-diClPh | CO | single bond | 2 | O | $CH_2CH_2$ | sub. 15 |
| 1482 | 4-OOxa | 3,4-diClPh | CO | single bond | 2 | O | $CH_2CH_2$ | sub. 15 |
| 1483 | 5-OOxa | 3,4-diClPh | CO | single bond | 2 | O | $CH_2CH_2$ | sub. 15 |
| 1484 | 4-OThi | 3,4-diClPh | CO | single bond | 2 | O | $CH_2CH_2$ | sub. 15 |
| 1485 | 5-OThi | 3,4-diClPh | CO | single bond | 2 | O | $CH_2CH_2$ | sub. 15 |
| 1486 | 2-Pip | 3,4-diClPh | CO | single bond | 2 | O | $CH_2CH_2$ | sub. 15 |
| 1487 | 3-Pip | 3,4-diClPh | CO | single bond | 2 | O | $CH_2CH_2$ | sub. 15 |
| 1488 | 4-Pip | 3,4-diClPh | CO | single bond | 2 | O | $CH_2CH_2$ | sub. 15 |
| 1489 | 2-Mor | 3,4-diClPh | CO | single bond | 2 | O | $CH_2CH_2$ | sub. 15 |
| 1490 | 3-Mor | 3,4-diClPh | CO | single bond | 2 | O | $CH_2CH_2$ | sub. 15 |
| 1491 | 4-Mor | 3,4-diClPh | CO | single bond | 2 | O | $CH_2CH_2$ | sub. 15 |
| 1492 | 2-Thmor | 3,4-diClPh | CO | single bond | 2 | O | $CH_2CH_2$ | sub. 15 |
| 1493 | 3-Thmor | 3,4-diClPh | CO | single bond | 2 | O | $CH_2CH_2$ | sub. 15 |
| 1494 | 4-Thmor | 3,4-diClPh | CO | single bond | 2 | O | $CH_2CH_2$ | sub. 15 |
| 1495 | 2-Piz | 3,4-diClPh | CO | single bond | 2 | O | $CH_2CH_2$ | sub. 15 |
| 1496 | 3-Piz | 3,4-diClPh | CO | single bond | 2 | O | $CH_2CH_2$ | sub. 15 |
| 1497 | 4-Piz | 3,4-diClPh | CO | single bond | 2 | O | $CH_2CH_2$ | sub. 15 |
| 1498 | 2-Aze | 3,4-diClPh | CO | single bond | 2 | O | $CH_2CH_2$ | sub. 15 |
| 1499 | 3-Aze | 3,4-diClPh | CO | single bond | 2 | O | $CH_2CH_2$ | sub. 15 |
| 1500 | 4-Aze | 3,4-diClPh | CO | single bond | 2 | O | $CH_2CH_2$ | sub. 15 |

TABLE 1-continued

| Exemplification compound number | R¹ | R² | A | B | N | D | G | Q |
|---|---|---|---|---|---|---|---|---|
| 1501 | cPr | 3,4-diClPh | CO | single bond | 2 | O | CH₂CH₂ | sub. 16 |
| 1502 | cBu | 3,4-diClPh | CO | single bond | 2 | O | CH₂CH₂ | sub. 16 |
| 1503 | cPn | 3,4-diClPh | CO | single bond | 2 | O | CH₂CH₂ | sub. 16 |
| 1504 | cHex | 3,4-diClPh | CO | single bond | 2 | O | CH₂CH₂ | sub. 16 |
| 1505 | cHep | 3,4-diClPh | CO | single bond | 2 | O | CH₂CH₂ | sub. 16 |
| 1506 | 2-Pyrd | 3,4-diClPh | CO | single bond | 2 | O | CH₂CH₂ | sub. 16 |
| 1507 | 3-Pyrd | 3,4-diClPh | CO | single bond | 2 | O | CH₂CH₂ | sub. 16 |
| 1508 | 4-Oxa | 3,4-diClPh | CO | single bond | 2 | O | CH₂CH₂ | sub. 16 |
| 1509 | 5-Oxa | 3,4-diClPh | CO | single bond | 2 | O | CH₂CH₂ | sub. 16 |
| 1510 | 4-Thi | 3,4-diClPh | CO | single bond | 2 | O | CH₂CH₂ | sub. 16 |
| 1511 | 5-Thi | 3,4-diClPh | CO | single bond | 2 | O | CH₂CH₂ | sub. 16 |
| 1512 | 4-OOxa | 3,4-diClPh | CO | single bond | 2 | O | CH₂CH₂ | sub. 16 |
| 1513 | 5-OOxa | 3,4-diClPh | CO | single bond | 2 | O | CH₂CH₂ | sub. 16 |
| 1514 | 4-OThi | 3,4-diClPh | CO | single bond | 2 | O | CH₂CH₂ | sub. 16 |
| 1515 | 5-OThi | 3,4-diClPh | CO | single bond | 2 | O | CH₂CH₂ | sub. 16 |
| 1516 | 2-Pip | 3,4-diClPh | CO | single bond | 2 | O | CH₂CH₂ | sub. 16 |
| 1517 | 3-Pip | 3,4-diClPh | CO | single bond | 2 | O | CH₂CH₂ | sub. 16 |
| 1518 | 4-Pip | 3,4-diClPh | CO | single bond | 2 | O | CH₂CH₂ | sub. 16 |
| 1519 | 2-Mor | 3,4-diClPh | CO | single bond | 2 | O | CH₂CH₂ | sub. 16 |
| 1520 | 3-Mor | 3,4-diClPh | CO | single bond | 2 | O | CH₂CH₂ | sub. 16 |
| 1521 | 4-Mor | 3,4-diClPh | CO | single bond | 2 | O | CH₂CH₂ | sub. 16 |
| 1522 | 2-Thmor | 3,4-diClPh | CO | single bond | 2 | O | CH₂CH₂ | sub. 16 |
| 1523 | 3-Thmor | 3,4-diClPh | CO | single bond | 2 | O | CH₂CH₂ | sub. 16 |
| 1524 | 4-Thmor | 3,4-diClPh | CO | single bond | 2 | O | CH₂CH₂ | sub. 16 |
| 1525 | 2-Piz | 3,4-diClPh | CO | single bond | 2 | O | CH₂CH₂ | sub. 16 |
| 1526 | 3-Piz | 3,4-diClPh | CO | single bond | 2 | O | CH₂CH₂ | sub. 16 |
| 1527 | 4-Piz | 3,4-diClPh | CO | single bond | 2 | O | CH₂CH₂ | sub. 16 |
| 1528 | 2-Aze | 3,4-diClPh | CO | single bond | 2 | O | CH₂CH₂ | sub. 16 |
| 1529 | 3-Aze | 3,4-diClPh | CO | single bond | 2 | O | CH₂CH₂ | sub. 16 |
| 1530 | 4-Aze | 3,4-diClPh | CO | single bond | 2 | O | CH₂CH₂ | sub. 16 |
| 1531 | cPr | 3,4-diClPh | CO | single bond | 2 | O | CH₂CH₂ | sub. 17 |
| 1532 | cBu | 3,4-diClPh | CO | single bond | 2 | O | CH₂CH₂ | sub. 17 |
| 1533 | cPn | 3,4-diClPh | CO | single bond | 2 | O | CH₂CH₂ | sub. 17 |
| 1534 | cHex | 3,4-diClPh | CO | single bond | 2 | O | CH₂CH₂ | sub. 17 |
| 1535 | cHep | 3,4-diClPh | CO | single bond | 2 | O | CH₂CH₂ | sub. 17 |
| 1536 | 2-Pyrd | 3,4-diClPh | CO | single bond | 2 | O | CH₂CH₂ | sub. 17 |
| 1537 | 3-Pyrd | 3,4-diClPh | CO | single bond | 2 | O | CH₂CH₂ | sub. 17 |
| 1538 | 4-Oxa | 3,4-diClPh | CO | single bond | 2 | O | CH₂CH₂ | sub. 17 |
| 1539 | 5-Oxa | 3,4-diClPh | CO | single bond | 2 | O | CH₂CH₂ | sub. 17 |
| 1540 | 4-Thi | 3,4-diClPh | CO | single bond | 2 | O | CH₂CH₂ | sub. 17 |
| 1541 | 5-Thi | 3,4-diClPh | CO | single bond | 2 | O | CH₂CH₂ | sub. 17 |
| 1542 | 4-OOxa | 3,4-diClPh | CO | single bond | 2 | O | CH₂CH₂ | sub. 17 |
| 1543 | 5-OOxa | 3,4-diClPh | CO | single bond | 2 | O | CH₂CH₂ | sub. 17 |
| 1544 | 4-OThi | 3,4-diClPh | CO | single bond | 2 | O | CH₂CH₂ | sub. 17 |
| 1545 | 5-OThi | 3,4-diClPh | CO | single bond | 2 | O | CH₂CH₂ | sub. 17 |
| 1546 | 2-Pip | 3,4-diClPh | CO | single bond | 2 | O | CH₂CH₂ | sub. 17 |
| 1547 | 3-Pip | 3,4-diClPh | CO | single bond | 2 | O | CH₂CH₂ | sub. 17 |
| 1548 | 4-Pip | 3,4-diClPh | CO | single bond | 2 | O | CH₂CH₂ | sub. 17 |
| 1549 | 2-Mor | 3,4-diClPh | CO | single bond | 2 | O | CH₂CH₂ | sub. 17 |
| 1550 | 3-Mor | 3,4-diClPh | CO | single bond | 2 | O | CH₂CH₂ | sub. 17 |
| 1551 | 4-Mor | 3,4-diClPh | CO | single bond | 2 | O | CH₂CH₂ | sub. 17 |
| 1552 | 2-Thmor | 3,4-diClPh | CO | single bond | 2 | O | CH₂CH₂ | sub. 17 |
| 1553 | 3-Thmor | 3,4-diClPh | CO | single bond | 2 | O | CH₂CH₂ | sub. 17 |
| 1554 | 4-Thmor | 3,4-diClPh | CO | single bond | 2 | O | CH₂CH₂ | sub. 17 |
| 1555 | 2-Piz | 3,4-diClPh | CO | single bond | 2 | O | CH₂CH₂ | sub. 17 |
| 1556 | 3-Piz | 3,4-diClPh | CO | single bond | 2 | O | CH₂CH₂ | sub. 17 |
| 1557 | 4-Piz | 3,4-diClPh | CO | single bond | 2 | O | CH₂CH₂ | sub. 17 |
| 1558 | 2-Aze | 3,4-diClPh | CO | single bond | 2 | O | CH₂CH₂ | sub. 17 |
| 1559 | 3-Aze | 3,4-diClPh | CO | single bond | 2 | O | CH₂CH₂ | sub. 17 |
| 1560 | 4-Aze | 3,4-diClPh | CO | single bond | 2 | O | CH₂CH₂ | sub. 17 |
| 1561 | cPr | 3,4-diClPh | CO | single bond | 2 | O | CH₂CH₂ | sub. 18 |
| 1562 | cBu | 3,4-diClPh | CO | single bond | 2 | O | CH₂CH₂ | sub. 18 |
| 1563 | cPn | 3,4-diClPh | CO | single bond | 2 | O | CH₂CH₂ | sub. 18 |
| 1564 | cHex | 3,4-diClPh | CO | single bond | 2 | O | CH₂CH₂ | sub. 18 |
| 1565 | cHep | 3,4-diClPh | CO | single bond | 2 | O | CH₂CH₂ | sub. 18 |
| 1566 | 2-Pyrd | 3,4-diClPh | CO | single bond | 2 | O | CH₂CH₂ | sub. 18 |
| 1567 | 3-Pyrd | 3,4-diClPh | CO | single bond | 2 | O | CH₂CH₂ | sub. 18 |
| 1568 | 4-Oxa | 3,4-diClPh | CO | single bond | 2 | O | CH₂CH₂ | sub. 18 |
| 1569 | 5-Oxa | 3,4-diClPh | CO | single bond | 2 | O | CH₂CH₂ | sub. 18 |
| 1570 | 4-Thi | 3,4-diClPh | CO | single bond | 2 | O | CH₂CH₂ | sub. 18 |
| 1571 | 5-Thi | 3,4-diClPh | CO | single bond | 2 | O | CH₂CH₂ | sub. 18 |
| 1572 | 4-OOxa | 3,4-diClPh | CO | single bond | 2 | O | CH₂CH₂ | sub. 18 |
| 1573 | 5-OOxa | 3,4-diClPh | CO | single bond | 2 | O | CH₂CH₂ | sub. 18 |
| 1574 | 4-OThi | 3,4-diClPh | CO | single bond | 2 | O | CH₂CH₂ | sub. 18 |
| 1575 | 5-OThi | 3,4-diClPh | CO | single bond | 2 | O | CH₂CH₂ | sub. 18 |
| 1576 | 2-Pip | 3,4-diClPh | CO | single bond | 2 | O | CH₂CH₂ | sub. 18 |

TABLE 1-continued

| Exemplification compound number | R¹ | R² | A | B | N | D | G | Q |
|---|---|---|---|---|---|---|---|---|
| 1577 | 3-Pip | 3,4-diClPh | CO | single bond | 2 | O | $CH_2CH_2$ | sub. 18 |
| 1578 | 4-Pip | 3,4-diClPh | CO | single bond | 2 | O | $CH_2CH_2$ | sub. 18 |
| 1579 | 2-Mor | 3,4-diClPh | CO | single bond | 2 | O | $CH_2CH_2$ | sub. 18 |
| 1580 | 3-Mor | 3,4-diClPh | CO | single bond | 2 | O | $CH_2CH_2$ | sub. 18 |
| 1581 | 4-Mor | 3,4-diClPh | CO | single bond | 2 | O | $CH_2CH_2$ | sub. 18 |
| 1582 | 2-Thmor | 3,4-diClPh | CO | single bond | 2 | O | $CH_2CH_2$ | sub. 18 |
| 1583 | 3-Thmor | 3,4-diClPh | CO | single bond | 2 | O | $CH_2CH_2$ | sub. 18 |
| 1584 | 4-Thmor | 3,4-diClPh | CO | single bond | 2 | O | $CH_2CH_2$ | sub. 18 |
| 1585 | 2-Piz | 3,4-diClPh | CO | single bond | 2 | O | $CH_2CH_2$ | sub. 18 |
| 1586 | 3-Piz | 3,4-diClPh | CO | single bond | 2 | O | $CH_2CH_2$ | sub. 18 |
| 1587 | 4-Piz | 3,4-diClPh | CO | single bond | 2 | O | $CH_2CH_2$ | sub. 18 |
| 1588 | 2-Aze | 3,4-diClPh | CO | single bond | 2 | O | $CH_2CH_2$ | sub. 18 |
| 1589 | 3-Aze | 3,4-diClPh | CO | single bond | 2 | O | $CH_2CH_2$ | sub. 18 |
| 1590 | 4-Aze | 3,4-diClPh | CO | single bond | 2 | O | $CH_2CH_2$ | sub. 18 |
| 1591 | cPr | 3,4-diClPh | CO | single bond | 2 | O | $CH_2CH_2$ | sub. 19 |
| 1592 | cBu | 3,4-diClPh | CO | single bond | 2 | O | $CH_2CH_2$ | sub. 19 |
| 1593 | cPn | 3,4-diClPh | CO | single bond | 2 | O | $CH_2CH_2$ | sub. 19 |
| 1594 | cHex | 3,4-diClPh | CO | single bond | 2 | O | $CH_2CH_2$ | sub. 19 |
| 1595 | cHep | 3,4-diClPh | CO | single bond | 2 | O | $CH_2CH_2$ | sub. 19 |
| 1596 | 2-Pyrd | 3,4-diClPh | CO | single bond | 2 | O | $CH_2CH_2$ | sub. 19 |
| 1597 | 3-Pyrd | 3,4-diClPh | CO | single bond | 2 | O | $CH_2CH_2$ | sub. 19 |
| 1598 | 4-Oxa | 3,4-diClPh | CO | single bond | 2 | O | $CH_2CH_2$ | sub. 19 |
| 1599 | 5-Oxa | 3,4-diClPh | CO | single bond | 2 | O | $CH_2CH_2$ | sub. 19 |
| 1600 | 4-Thi | 3,4-diClPh | CO | single bond | 2 | O | $CH_2CH_2$ | sub. 19 |
| 1601 | 5-Thi | 3,4-diClPh | CO | single bond | 2 | O | $CH_2CH_2$ | sub. 19 |
| 1602 | 4-OOxa | 3,4-diClPh | CO | single bond | 2 | O | $CH_2CH_2$ | sub. 19 |
| 1603 | 5-OOxa | 3,4-diClPh | CO | single bond | 2 | O | $CH_2CH_2$ | sub. 19 |
| 1604 | 4-OThi | 3,4-diClPh | CO | single bond | 2 | O | $CH_2CH_2$ | sub. 19 |
| 1605 | 5-OThi | 3,4-diClPh | CO | single bond | 2 | O | $CH_2CH_2$ | sub. 19 |
| 1606 | 2-Pip | 3,4-diClPh | CO | single bond | 2 | O | $CH_2CH_2$ | sub. 19 |
| 1607 | 3-Pip | 3,4-diClPh | CO | single bond | 2 | O | $CH_2CH_2$ | sub. 19 |
| 1608 | 4-Pip | 3,4-diClPh | CO | single bond | 2 | O | $CH_2CH_2$ | sub. 19 |
| 1609 | 2-Mor | 3,4-diClPh | CO | single bond | 2 | O | $CH_2CH_2$ | sub. 19 |
| 1610 | 3-Mor | 3,4-diClPh | CO | single bond | 2 | O | $CH_2CH_2$ | sub. 19 |
| 1611 | 4-Mor | 3,4-diClPh | CO | single bond | 2 | O | $CH_2CH_2$ | sub. 19 |
| 1612 | 2-Thmor | 3,4-diClPh | CO | single bond | 2 | O | $CH_2CH_2$ | sub. 19 |
| 1613 | 3-Thmor | 3,4-diClPh | CO | single bond | 2 | O | $CH_2CH_2$ | sub. 19 |
| 1614 | 4-Thmor | 3,4-diClPh | CO | single bond | 2 | O | $CH_2CH_2$ | sub. 19 |
| 1615 | 2-Piz | 3,4-diClPh | CO | single bond | 2 | O | $CH_2CH_2$ | sub. 19 |
| 1616 | 3-Piz | 3,4-diClPh | CO | single bond | 2 | O | $CH_2CH_2$ | sub. 19 |
| 1617 | 4-Piz | 3,4-diClPh | CO | single bond | 2 | O | $CH_2CH_2$ | sub. 19 |
| 1618 | 2-Aze | 3,4-diClPh | CO | single bond | 2 | O | $CH_2CH_2$ | sub. 19 |
| 1619 | 3-Aze | 3,4-diClPh | CO | single bond | 2 | O | $CH_2CH_2$ | sub. 19 |
| 1620 | 4-Aze | 3,4-diClPh | CO | single bond | 2 | O | $CH_2CH_2$ | sub. 19 |
| 1621 | cPr | 3,4-diClPh | CO | single bond | 2 | O | $CH_2CH_2$ | sub. 20 |
| 1622 | cBu | 3,4-diClPh | CO | single bond | 2 | O | $CH_2CH_2$ | sub. 20 |
| 1623 | cPn | 3,4-diClPh | CO | single bond | 2 | O | $CH_2CH_2$ | sub. 20 |
| 1624 | cHex | 3,4-diClPh | CO | single bond | 2 | O | $CH_2CH_2$ | sub. 20 |
| 1625 | cHep | 3,4-diClPh | CO | single bond | 2 | O | $CH_2CH_2$ | sub. 20 |
| 1626 | 2-Pyrd | 3,4-diClPh | CO | single bond | 2 | O | $CH_2CH_2$ | sub. 20 |
| 1627 | 3-Pyrd | 3,4-diClPh | CO | single bond | 2 | O | $CH_2CH_2$ | sub. 20 |
| 1628 | 4-Oxa | 3,4-diClPh | CO | single bond | 2 | O | $CH_2CH_2$ | sub. 20 |
| 1629 | 5-Oxa | 3,4-diClPh | CO | single bond | 2 | O | $CH_2CH_2$ | sub. 20 |
| 1630 | 4-Thi | 3,4-diClPh | CO | single bond | 2 | O | $CH_2CH_2$ | sub. 20 |
| 1631 | 5-Thi | 3,4-diClPh | CO | single bond | 2 | O | $CH_2CH_2$ | sub. 20 |
| 1632 | 4-OOxa | 3,4-diClPh | CO | single bond | 2 | O | $CH_2CH_2$ | sub. 20 |
| 1633 | 5-OOxa | 3,4-diClPh | CO | single bond | 2 | O | $CH_2CH_2$ | sub. 20 |
| 1634 | 4-OThi | 3,4-diClPh | CO | single bond | 2 | O | $CH_2CH_2$ | sub. 20 |
| 1635 | 5-OThi | 3,4-diClPh | CO | single bond | 2 | O | $CH_2CH_2$ | sub. 20 |
| 1636 | 2-Pip | 3,4-diClPh | CO | single bond | 2 | O | $CH_2CH_2$ | sub. 20 |
| 1637 | 3-Pip | 3,4-diClPh | CO | single bond | 2 | O | $CH_2CH_2$ | sub. 20 |
| 1638 | 4-Pip | 3,4-diClPh | CO | single bond | 2 | O | $CH_2CH_2$ | sub. 20 |
| 1639 | 2-Mor | 3,4-diClPh | CO | single bond | 2 | O | $CH_2CH_2$ | sub. 20 |
| 1640 | 3-Mor | 3,4-diClPh | CO | single bond | 2 | O | $CH_2CH_2$ | sub. 20 |
| 1641 | 4-Mor | 3,4-diClPh | CO | single bond | 2 | O | $CH_2CH_2$ | sub. 20 |
| 1642 | 2-Thmor | 3,4-diClPh | CO | single bond | 2 | O | $CH_2CH_2$ | sub. 20 |
| 1643 | 3-Thmor | 3,4-diClPh | CO | single bond | 2 | O | $CH_2CH_2$ | sub. 20 |
| 1644 | 4-Thmor | 3,4-diClPh | CO | single bond | 2 | O | $CH_2CH_2$ | sub. 20 |
| 1645 | 2-Piz | 3,4-diClPh | CO | single bond | 2 | O | $CH_2CH_2$ | sub. 20 |
| 1646 | 3-Piz | 3,4-diClPh | CO | single bond | 2 | O | $CH_2CH_2$ | sub. 20 |
| 1647 | 4-Piz | 3,4-diClPh | CO | single bond | 2 | O | $CH_2CH_2$ | sub. 20 |
| 1648 | 2-Aze | 3,4-diClPh | CO | single bond | 2 | O | $CH_2CH_2$ | sub. 20 |
| 1649 | 3-Aze | 3,4-diClPh | CO | single bond | 2 | O | $CH_2CH_2$ | sub. 20 |
| 1650 | 4-Aze | 3,4-diClPh | CO | single bond | 2 | O | $CH_2CH_2$ | sub. 20 |
| 1651 | cPr | 3,4-diClPh | CO | single bond | 2 | O | $CH_2CH_2$ | sub. 21 |
| 1652 | cBu | 3,4-diClPh | CO | single bond | 2 | O | $CH_2CH_2$ | sub. 21 |

TABLE 1-continued

| Exemplification compound number | R¹ | R² | A | B | N | D | G | Q |
|---|---|---|---|---|---|---|---|---|
| 1653 | cPn | 3,4-diClPh | CO | single bond | 2 | O | CH₂CH₂ | sub. 21 |
| 1654 | cHex | 3,4-diClPh | CO | single bond | 2 | O | CH₂CH₂ | sub. 21 |
| 1655 | cHep | 3,4-diClPh | CO | single bond | 2 | O | CH₂CH₂ | sub. 21 |
| 1656 | 2-Pyrd | 3,4-diClPh | CO | single bond | 2 | O | CH₂CH₂ | sub. 21 |
| 1657 | 3-Pyrd | 3,4-diClPh | CO | single bond | 2 | O | CH₂CH₂ | sub. 21 |
| 1658 | 4-Oxa | 3,4-diClPh | CO | single bond | 2 | O | CH₂CH₂ | sub. 21 |
| 1659 | 5-Oxa | 3,4-diClPh | CO | single bond | 2 | O | CH₂CH₂ | sub. 21 |
| 1660 | 4-Thi | 3,4-diClPh | CO | single bond | 2 | O | CH₂CH₂ | sub. 21 |
| 1661 | 5-Thi | 3,4-diClPh | CO | single bond | 2 | O | CH₂CH₂ | sub. 21 |
| 1662 | 4-OOxa | 3,4-diClPh | CO | single bond | 2 | O | CH₂CH₂ | sub. 21 |
| 1663 | 5-OOxa | 3,4-diClPh | CO | single bond | 2 | O | CH₂CH₂ | sub. 21 |
| 1664 | 4-OThi | 3,4-diClPh | CO | single bond | 2 | O | CH₂CH₂ | sub. 21 |
| 1665 | 5-OThi | 3,4-diClPh | CO | single bond | 2 | O | CH₂CH₂ | sub. 21 |
| 1666 | 2-Pip | 3,4-diClPh | CO | single bond | 2 | O | CH₂CH₂ | sub. 21 |
| 1667 | 3-Pip | 3,4-diClPh | CO | single bond | 2 | O | CH₂CH₂ | sub. 21 |
| 1668 | 4-Pip | 3,4-diClPh | CO | single bond | 2 | O | CH₂CH₂ | sub. 21 |
| 1669 | 2-Mor | 3,4-diClPh | CO | single bond | 2 | O | CH₂CH₂ | sub. 21 |
| 1670 | 3-Mor | 3,4-diClPh | CO | single bond | 2 | O | CH₂CH₂ | sub. 21 |
| 1671 | 4-Mor | 3,4-diClPh | CO | single bond | 2 | O | CH₂CH₂ | sub. 21 |
| 1672 | 2-Thmor | 3,4-diClPh | CO | single bond | 2 | O | CH₂CH₂ | sub. 21 |
| 1673 | 3-Thmor | 3,4-diClPh | CO | single bond | 2 | O | CH₂CH₂ | sub. 21 |
| 1674 | 4-Thmor | 3,4-diClPh | CO | single bond | 2 | O | CH₂CH₂ | sub. 21 |
| 1675 | 2-Piz | 3,4-diClPh | CO | single bond | 2 | O | CH₂CH₂ | sub. 21 |
| 1676 | 3-Piz | 3,4-diClPh | CO | single bond | 2 | O | CH₂CH₂ | sub. 21 |
| 1677 | 4-Piz | 3,4-diClPh | CO | single bond | 2 | O | CH₂CH₂ | sub. 21 |
| 1678 | 2-Aze | 3,4-diClPh | CO | single bond | 2 | O | CH₂CH₂ | sub. 21 |
| 1679 | 3-Aze | 3,4-diClPh | CO | single bond | 2 | O | CH₂CH₂ | sub. 21 |
| 1680 | 4-Aze | 3,4-diClPh | CO | single bond | 2 | O | CH₂CH₂ | sub. 21 |
| 1681 | cPr | 3,4-diClPh | CO | single bond | 2 | O | CH₂CH₂ | sub. 22 |
| 1682 | cBu | 3,4-diClPh | CO | single bond | 2 | O | CH₂CH₂ | sub. 22 |
| 1683 | cPn | 3,4-diClPh | CO | single bond | 2 | O | CH₂CH₂ | sub. 22 |
| 1684 | cHex | 3,4-diClPh | CO | single bond | 2 | O | CH₂CH₂ | sub. 22 |
| 1685 | cHep | 3,4-diClPh | CO | single bond | 2 | O | CH₂CH₂ | sub. 22 |
| 1686 | 2-Pyrd | 3,4-diClPh | CO | single bond | 2 | O | CH₂CH₂ | sub. 22 |
| 1687 | 3-Pyrd | 3,4-diClPh | CO | single bond | 2 | O | CH₂CH₂ | sub. 22 |
| 1688 | 4-Oxa | 3,4-diClPh | CO | single bond | 2 | O | CH₂CH₂ | sub. 22 |
| 1689 | 5-Oxa | 3,4-diClPh | CO | single bond | 2 | O | CH₂CH₂ | sub. 22 |
| 1690 | 4-Thi | 3,4-diClPh | CO | single bond | 2 | O | CH₂CH₂ | sub. 22 |
| 1691 | 5-Thi | 3,4-diClPh | CO | single bond | 2 | O | CH₂CH₂ | sub. 22 |
| 1692 | 4-OOxa | 3,4-diClPh | CO | single bond | 2 | O | CH₂CH₂ | sub. 22 |
| 1693 | 5-OOxa | 3,4-diClPh | CO | single bond | 2 | O | CH₂CH₂ | sub. 22 |
| 1694 | 4-OThi | 3,4-diClPh | CO | single bond | 2 | O | CH₂CH₂ | sub. 22 |
| 1695 | 5-OThi | 3,4-diClPh | CO | single bond | 2 | O | CH₂CH₂ | sub. 22 |
| 1696 | 2-Pip | 3,4-diClPh | CO | single bond | 2 | O | CH₂CH₂ | sub. 22 |
| 1697 | 3-Pip | 3,4-diClPh | CO | single bond | 2 | O | CH₂CH₂ | sub. 22 |
| 1698 | 4-Pip | 3,4-diClPh | CO | single bond | 2 | O | CH₂CH₂ | sub. 22 |
| 1699 | 2-Mor | 3,4-diClPh | CO | single bond | 2 | O | CH₂CH₂ | sub. 22 |
| 1700 | 3-Mor | 3,4-diClPh | CO | single bond | 2 | O | CH₂CH₂ | sub. 22 |
| 1701 | 4-Mor | 3,4-diClPh | CO | single bond | 2 | O | CH₂CH₂ | sub. 22 |
| 1702 | 2-Thmor | 3,4-diClPh | CO | single bond | 2 | O | CH₂CH₂ | sub. 22 |
| 1703 | 3-Thmor | 3,4-diClPh | CO | single bond | 2 | O | CH₂CH₂ | sub. 22 |
| 1704 | 4-Thmor | 3,4-diClPh | CO | single bond | 2 | O | CH₂CH₂ | sub. 22 |
| 1705 | 2-Piz | 3,4-diClPh | CO | single bond | 2 | O | CH₂CH₂ | sub. 22 |
| 1706 | 3-Piz | 3,4-diClPh | CO | single bond | 2 | O | CH₂CH₂ | sub. 22 |
| 1707 | 4-Piz | 3,4-diClPh | CO | single bond | 2 | O | CH₂CH₂ | sub. 22 |
| 1708 | 2-Aze | 3,4-diClPh | CO | single bond | 2 | O | CH₂CH₂ | sub. 22 |
| 1709 | 3-Aze | 3,4-diClPh | CO | single bond | 2 | O | CH₂CH₂ | sub. 22 |
| 1710 | 4-Aze | 3,4-diClPh | CO | single bond | 2 | O | CH₂CH₂ | sub. 22 |
| 1711 | cPr | 3,4-diClPh | CO | single bond | 2 | O | CH₂CH₂ | sub. 23 |
| 1712 | cBu | 3,4-diClPh | CO | single bond | 2 | O | CH₂CH₂ | sub. 23 |
| 1713 | cPn | 3,4-diClPh | CO | single bond | 2 | O | CH₂CH₂ | sub. 23 |
| 1714 | cHex | 3,4-diClPh | CO | single bond | 2 | O | CH₂CH₂ | sub. 23 |
| 1715 | cHep | 3,4-diClPh | CO | single bond | 2 | O | CH₂CH₂ | sub. 23 |
| 1716 | 2-Pyrd | 3,4-diClPh | CO | single bond | 2 | O | CH₂CH₂ | sub. 23 |
| 1717 | 3-Pyrd | 3,4-diClPh | CO | single bond | 2 | O | CH₂CH₂ | sub. 23 |
| 1718 | 4-Oxa | 3,4-diClPh | CO | single bond | 2 | O | CH₂CH₂ | sub. 23 |
| 1719 | 5-Oxa | 3,4-diClPh | CO | single bond | 2 | O | CH₂CH₂ | sub. 23 |
| 1720 | 4-Thi | 3,4-diClPh | CO | single bond | 2 | O | CH₂CH₂ | sub. 23 |
| 1721 | 5-Thi | 3,4-diClPh | CO | single bond | 2 | O | CH₂CH₂ | sub. 23 |
| 1722 | 4-OOxa | 3,4-diClPh | CO | single bond | 2 | O | CH₂CH₂ | sub. 23 |
| 1723 | 5-OOxa | 3,4-diClPh | CO | single bond | 2 | O | CH₂CH₂ | sub. 23 |
| 1724 | 4-OThi | 3,4-diClPh | CO | single bond | 2 | O | CH₂CH₂ | sub. 23 |
| 1725 | 5-OThi | 3,4-diClPh | CO | single bond | 2 | O | CH₂CH₂ | sub. 23 |
| 1726 | 2-Pip | 3,4-diClPh | CO | single bond | 2 | O | CH₂CH₂ | sub. 23 |
| 1727 | 3-Pip | 3,4-diClPh | CO | single bond | 2 | O | CH₂CH₂ | sub. 23 |
| 1728 | 4-Pip | 3,4-diClPh | CO | single bond | 2 | O | CH₂CH₂ | sub. 23 |

TABLE 1-continued

| Exemplification compound number | R¹ | R² | A | B | N | D | G | Q |
|---|---|---|---|---|---|---|---|---|
| 1729 | 2-Mor | 3,4-diClPh | CO | single bond | 2 | O | $CH_2CH_2$ | sub. 23 |
| 1730 | 3-Mor | 3,4-diClPh | CO | single bond | 2 | O | $CH_2CH_2$ | sub. 23 |
| 1731 | 4-Mor | 3,4-diClPh | CO | single bond | 2 | O | $CH_2CH_2$ | sub. 23 |
| 1732 | 2-Thmor | 3,4-diClPh | CO | single bond | 2 | O | $CH_2CH_2$ | sub. 23 |
| 1733 | 3-Thmor | 3,4-diClPh | CO | single bond | 2 | O | $CH_2CH_2$ | sub. 23 |
| 1734 | 4-Thmor | 3,4-diClPh | CO | single bond | 2 | O | $CH_2CH_2$ | sub. 23 |
| 1735 | 2-Piz | 3,4-diClPh | CO | single bond | 2 | O | $CH_2CH_2$ | sub. 23 |
| 1736 | 3-Piz | 3,4-diClPh | CO | single bond | 2 | O | $CH_2CH_2$ | sub. 23 |
| 1737 | 4-Piz | 3,4-diClPh | CO | single bond | 2 | O | $CH_2CH_2$ | sub. 23 |
| 1738 | 2-Aze | 3,4-diClPh | CO | single bond | 2 | O | $CH_2CH_2$ | sub. 23 |
| 1739 | 3-Aze | 3,4-diClPh | CO | single bond | 2 | O | $CH_2CH_2$ | sub. 23 |
| 1740 | 4-Aze | 3,4-diClPh | CO | single bond | 2 | O | $CH_2CH_2$ | sub. 23 |
| 1741 | cPr | 3,4-diClPh | CO | single bond | 2 | O | $CH_2CH_2$ | sub. 24 |
| 1742 | cBu | 3,4-diClPh | CO | single bond | 2 | O | $CH_2CH_2$ | sub. 24 |
| 1743 | cPn | 3,4-diClPh | CO | single bond | 2 | O | $CH_2CH_2$ | sub. 24 |
| 1744 | cHex | 3,4-diClPh | CO | single bond | 2 | O | $CH_2CH_2$ | sub. 24 |
| 1745 | cHep | 3,4-diClPh | CO | single bond | 2 | O | $CH_2CH_2$ | sub. 24 |
| 1746 | 2-Pyrd | 3,4-diClPh | CO | single bond | 2 | O | $CH_2CH_2$ | sub. 24 |
| 1747 | 3-Pyrd | 3,4-diClPh | CO | single bond | 2 | O | $CH_2CH_2$ | sub. 24 |
| 1748 | 4-Oxa | 3,4-diClPh | CO | single bond | 2 | O | $CH_2CH_2$ | sub. 24 |
| 1749 | 5-Oxa | 3,4-diClPh | CO | single bond | 2 | O | $CH_2CH_2$ | sub. 24 |
| 1750 | 4-Thi | 3,4-diClPh | CO | single bond | 2 | O | $CH_2CH_2$ | sub. 24 |
| 1751 | 5-Thi | 3,4-diClPh | CO | single bond | 2 | O | $CH_2CH_2$ | sub. 24 |
| 1752 | 4-OOxa | 3,4-diClPh | CO | single bond | 2 | O | $CH_2CH_2$ | sub. 24 |
| 1753 | 5-OOxa | 3,4-diClPh | CO | single bond | 2 | O | $CH_2CH_2$ | sub. 24 |
| 1754 | 4-OThi | 3,4-diClPh | CO | single bond | 2 | O | $CH_2CH_2$ | sub. 24 |
| 1755 | 5-OThi | 3,4-diClPh | CO | single bond | 2 | O | $CH_2CH_2$ | sub. 24 |
| 1756 | 2-Pip | 3,4-diClPh | CO | single bond | 2 | O | $CH_2CH_2$ | sub. 24 |
| 1757 | 3-Pip | 3,4-diClPh | CO | single bond | 2 | O | $CH_2CH_2$ | sub. 24 |
| 1758 | 4-Pip | 3,4-diClPh | CO | single bond | 2 | O | $CH_2CH_2$ | sub. 24 |
| 1759 | 2-Mor | 3,4-diClPh | CO | single bond | 2 | O | $CH_2CH_2$ | sub. 24 |
| 1760 | 3-Mor | 3,4-diClPh | CO | single bond | 2 | O | $CH_2CH_2$ | sub. 24 |
| 1761 | 4-Mor | 3,4-diClPh | CO | single bond | 2 | O | $CH_2CH_2$ | sub. 24 |
| 1762 | 2-Thmor | 3,4-diClPh | CO | single bond | 2 | O | $CH_2CH_2$ | sub. 24 |
| 1763 | 3-Thmor | 3,4-diClPh | CO | single bond | 2 | O | $CH_2CH_2$ | sub. 24 |
| 1764 | 4-Thmor | 3,4-diClPh | CO | single bond | 2 | O | $CH_2CH_2$ | sub. 24 |
| 1765 | 2-Piz | 3,4-diClPh | CO | single bond | 2 | O | $CH_2CH_2$ | sub. 24 |
| 1766 | 3-Piz | 3,4-diClPh | CO | single bond | 2 | O | $CH_2CH_2$ | sub. 24 |
| 1767 | 4-Piz | 3,4-diClPh | CO | single bond | 2 | O | $CH_2CH_2$ | sub. 24 |
| 1768 | 2-Aze | 3,4-diClPh | CO | single bond | 2 | O | $CH_2CH_2$ | sub. 24 |
| 1769 | 3-Aze | 3,4-diClPh | CO | single bond | 2 | O | $CH_2CH_2$ | sub. 24 |
| 1770 | 4-Aze | 3,4-diClPh | CO | single bond | 2 | O | $CH_2CH_2$ | sub. 24 |
| 1771 | cPr | 3,4-diClPh | CO | single bond | 2 | O | $CH_2CH_2$ | sub. 25 |
| 1772 | cBu | 3,4-diClPh | CO | single bond | 2 | O | $CH_2CH_2$ | sub. 25 |
| 1773 | cPn | 3,4-diClPh | CO | single bond | 2 | O | $CH_2CH_2$ | sub. 25 |
| 1774 | cHex | 3,4-diClPh | CO | single bond | 2 | O | $CH_2CH_2$ | sub. 25 |
| 1775 | cHep | 3,4-diClPh | CO | single bond | 2 | O | $CH_2CH_2$ | sub. 25 |
| 1776 | 2-Pyrd | 3,4-diClPh | CO | single bond | 2 | O | $CH_2CH_2$ | sub. 25 |
| 1777 | 3-Pyrd | 3,4-diClPh | CO | single bond | 2 | O | $CH_2CH_2$ | sub. 25 |
| 1778 | 4-Oxa | 3,4-diClPh | CO | single bond | 2 | O | $CH_2CH_2$ | sub. 25 |
| 1779 | 5-Oxa | 3,4-diClPh | CO | single bond | 2 | O | $CH_2CH_2$ | sub. 25 |
| 1780 | 4-Thi | 3,4-diClPh | CO | single bond | 2 | O | $CH_2CH_2$ | sub. 25 |
| 1781 | 5-Thi | 3,4-diClPh | CO | single bond | 2 | O | $CH_2CH_2$ | sub. 25 |
| 1782 | 4-OOxa | 3,4-diClPh | CO | single bond | 2 | O | $CH_2CH_2$ | sub. 25 |
| 1783 | 5-OOxa | 3,4-diClPh | CO | single bond | 2 | O | $CH_2CH_2$ | sub. 25 |
| 1784 | 4-OThi | 3,4-diClPh | CO | single bond | 2 | O | $CH_2CH_2$ | sub. 25 |
| 1785 | 5-OThi | 3,4-diClPh | CO | single bond | 2 | O | $CH_2CH_2$ | sub. 25 |
| 1786 | 2-Pip | 3,4-diClPh | CO | single bond | 2 | O | $CH_2CH_2$ | sub. 25 |
| 1787 | 3-Pip | 3,4-diClPh | CO | single bond | 2 | O | $CH_2CH_2$ | sub. 25 |
| 1788 | 4-Pip | 3,4-diClPh | CO | single bond | 2 | O | $CH_2CH_2$ | sub. 25 |
| 1789 | 2-Mor | 3,4-diClPh | CO | single bond | 2 | O | $CH_2CH_2$ | sub. 25 |
| 1790 | 3-Mor | 3,4-diClPh | CO | single bond | 2 | O | $CH_2CH_2$ | sub. 25 |
| 1791 | 4-Mor | 3,4-diClPh | CO | single bond | 2 | O | $CH_2CH_2$ | sub. 25 |
| 1792 | 2-Thmor | 3,4-diClPh | CO | single bond | 2 | O | $CH_2CH_2$ | sub. 25 |
| 1793 | 3-Thmor | 3,4-diClPh | CO | single bond | 2 | O | $CH_2CH_2$ | sub. 25 |
| 1794 | 4-Thmor | 3,4-diClPh | CO | single bond | 2 | O | $CH_2CH_2$ | sub. 25 |
| 1795 | 2-Piz | 3,4-diClPh | CO | single bond | 2 | O | $CH_2CH_2$ | sub. 25 |
| 1796 | 3-Piz | 3,4-diClPh | CO | single bond | 2 | O | $CH_2CH_2$ | sub. 25 |
| 1797 | 4-Piz | 3,4-diClPh | CO | single bond | 2 | O | $CH_2CH_2$ | sub. 25 |
| 1798 | 2-Aze | 3,4-diClPh | CO | single bond | 2 | O | $CH_2CH_2$ | sub. 25 |
| 1799 | 3-Aze | 3,4-diClPh | CO | single bond | 2 | O | $CH_2CH_2$ | sub. 25 |
| 1800 | 4-Aze | 3,4-diClPh | CO | single bond | 2 | O | $CH_2CH_2$ | sub. 25 |
| 1801 | cPr | 3,4-diClPh | CO | single bond | 2 | O | $CH_2CH_2$ | sub. 26 |
| 1802 | cBu | 3,4-diClPh | CO | single bond | 2 | O | $CH_2CH_2$ | sub. 26 |
| 1803 | cPn | 3,4-diClPh | CO | single bond | 2 | O | $CH_2CH_2$ | sub. 26 |
| 1804 | cHex | 3,4-diClPh | CO | single bond | 2 | O | $CH_2CH_2$ | sub. 26 |

TABLE 1-continued

| Exemplification compound number | R¹ | R² | A | B | N | D | G | Q |
|---|---|---|---|---|---|---|---|---|
| 1805 | cHep | 3,4-diClPh | CO | single bond | 2 | O | $CH_2CH_2$ | sub. 26 |
| 1806 | 2-Pyrd | 3,4-diClPh | CO | single bond | 2 | O | $CH_2CH_2$ | sub. 26 |
| 1807 | 3-Pyrd | 3,4-diClPh | CO | single bond | 2 | O | $CH_2CH_2$ | sub. 26 |
| 1808 | 4-Oxa | 3,4-diClPh | CO | single bond | 2 | O | $CH_2CH_2$ | sub. 26 |
| 1809 | 5-Oxa | 3,4-diClPh | CO | single bond | 2 | O | $CH_2CH_2$ | sub. 26 |
| 1810 | 4-Thi | 3,4-diClPh | CO | single bond | 2 | O | $CH_2CH_2$ | sub. 26 |
| 1811 | 5-Thi | 3,4-diClPh | CO | single bond | 2 | O | $CH_2CH_2$ | sub. 26 |
| 1812 | 4-OOxa | 3,4-diClPh | CO | single bond | 2 | O | $CH_2CH_2$ | sub. 26 |
| 1813 | 5-OOxa | 3,4-diClPh | CO | single bond | 2 | O | $CH_2CH_2$ | sub. 26 |
| 1814 | 4-OThi | 3,4-diClPh | CO | single bond | 2 | O | $CH_2CH_2$ | sub. 26 |
| 1815 | 5-OThi | 3,4-diClPh | CO | single bond | 2 | O | $CH_2CH_2$ | sub. 26 |
| 1816 | 2-Pip | 3,4-diClPh | CO | single bond | 2 | O | $CH_2CH_2$ | sub. 26 |
| 1817 | 3-Pip | 3,4-diClPh | CO | single bond | 2 | O | $CH_2CH_2$ | sub. 26 |
| 1818 | 4-Pip | 3,4-diClPh | CO | single bond | 2 | O | $CH_2CH_2$ | sub. 26 |
| 1819 | 2-Mor | 3,4-diClPh | CO | single bond | 2 | O | $CH_2CH_2$ | sub. 26 |
| 1820 | 3-Mor | 3,4-diClPh | CO | single bond | 2 | O | $CH_2CH_2$ | sub. 26 |
| 1821 | 4-Mor | 3,4-diClPh | CO | single bond | 2 | O | $CH_2CH_2$ | sub. 26 |
| 1822 | 2-Thmor | 3,4-diClPh | CO | single bond | 2 | O | $CH_2CH_2$ | sub. 26 |
| 1823 | 3-Thmor | 3,4-diClPh | CO | single bond | 2 | O | $CH_2CH_2$ | sub. 26 |
| 1824 | 4-Thmor | 3,4-diClPh | CO | single bond | 2 | O | $CH_2CH_2$ | sub. 26 |
| 1825 | 2-Piz | 3,4-diClPh | CO | single bond | 2 | O | $CH_2CH_2$ | sub. 26 |
| 1826 | 3-Piz | 3,4-diClPh | CO | single bond | 2 | O | $CH_2CH_2$ | sub. 26 |
| 1827 | 4-Piz | 3,4-diClPh | CO | single bond | 2 | O | $CH_2CH_2$ | sub. 26 |
| 1828 | 2-Aze | 3,4-diClPh | CO | single bond | 2 | O | $CH_2CH_2$ | sub. 26 |
| 1829 | 3-Aze | 3,4-diClPh | CO | single bond | 2 | O | $CH_2CH_2$ | sub. 26 |
| 1830 | 4-Aze | 3,4-diClPh | CO | single bond | 2 | O | $CH_2CH_2$ | sub. 26 |
| 1831 | cPr | 3,4-diClPh | CO | single bond | 2 | O | $CH_2CH_2$ | sub. 27 |
| 1832 | cBu | 3,4-diClPh | CO | single bond | 2 | O | $CH_2CH_2$ | sub. 27 |
| 1833 | cPn | 3,4-diClPh | CO | single bond | 2 | O | $CH_2CH_2$ | sub. 27 |
| 1834 | cHex | 3,4-diClPh | CO | single bond | 2 | O | $CH_2CH_2$ | sub. 27 |
| 1835 | cHep | 3,4-diClPh | CO | single bond | 2 | O | $CH_2CH_2$ | sub. 27 |
| 1836 | 2-Pyrd | 3,4-diClPh | CO | single bond | 2 | O | $CH_2CH_2$ | sub. 27 |
| 1837 | 3-Pyrd | 3,4-diClPh | CO | single bond | 2 | O | $CH_2CH_2$ | sub. 27 |
| 1838 | 4-Oxa | 3,4-diClPh | CO | single bond | 2 | O | $CH_2CH_2$ | sub. 27 |
| 1839 | 5-Oxa | 3,4-diClPh | CO | single bond | 2 | O | $CH_2CH_2$ | sub. 27 |
| 1840 | 4-Thi | 3,4-diClPh | CO | single bond | 2 | O | $CH_2CH_2$ | sub. 27 |
| 1841 | 5-Thi | 3,4-diClPh | CO | single bond | 2 | O | $CH_2CH_2$ | sub. 27 |
| 1842 | 4-OOxa | 3,4-diClPh | CO | single bond | 2 | O | $CH_2CH_2$ | sub. 27 |
| 1843 | 5-OOxa | 3,4-diClPh | CO | single bond | 2 | O | $CH_2CH_2$ | sub. 27 |
| 1844 | 4-OThi | 3,4-diClPh | CO | single bond | 2 | O | $CH_2CH_2$ | sub. 27 |
| 1845 | 5-OThi | 3,4-diClPh | CO | single bond | 2 | O | $CH_2CH_2$ | sub. 27 |
| 1846 | 2-Pip | 3,4-diClPh | CO | single bond | 2 | O | $CH_2CH_2$ | sub. 27 |
| 1847 | 3-Pip | 3,4-diClPh | CO | single bond | 2 | O | $CH_2CH_2$ | sub. 27 |
| 1848 | 4-Pip | 3,4-diClPh | CO | single bond | 2 | O | $CH_2CH_2$ | sub. 27 |
| 1849 | 2-Mor | 3,4-diClPh | CO | single bond | 2 | O | $CH_2CH_2$ | sub. 27 |
| 1850 | 3-Mor | 3,4-diClPh | CO | single bond | 2 | O | $CH_2CH_2$ | sub. 27 |
| 1851 | 4-Mor | 3,4-diClPh | CO | single bond | 2 | O | $CH_2CH_2$ | sub. 27 |
| 1852 | 2-Thmor | 3,4-diClPh | CO | single bond | 2 | O | $CH_2CH_2$ | sub. 27 |
| 1853 | 3-Thmor | 3,4-diClPh | CO | single bond | 2 | O | $CH_2CH_2$ | sub. 27 |
| 1854 | 4-Thmor | 3,4-diClPh | CO | single bond | 2 | O | $CH_2CH_2$ | sub. 27 |
| 1855 | 2-Piz | 3,4-diClPh | CO | single bond | 2 | O | $CH_2CH_2$ | sub. 27 |
| 1856 | 3-Piz | 3,4-diClPh | CO | single bond | 2 | O | $CH_2CH_2$ | sub. 27 |
| 1857 | 4-Piz | 3,4-diClPh | CO | single bond | 2 | O | $CH_2CH_2$ | sub. 27 |
| 1858 | 2-Aze | 3,4-diClPh | CO | single bond | 2 | O | $CH_2CH_2$ | sub. 27 |
| 1859 | 3-Aze | 3,4-diClPh | CO | single bond | 2 | O | $CH_2CH_2$ | sub. 27 |
| 1860 | 4-Aze | 3,4-diClPh | CO | single bond | 2 | O | $CH_2CH_2$ | sub. 27 |
| 1861 | cPr | 3,4-diClPh | CO | single bond | 2 | O | $CH_2CH_2$ | sub. 28 |
| 1862 | cBu | 3,4-diClPh | CO | single bond | 2 | O | $CH_2CH_2$ | sub. 28 |
| 1863 | cPn | 3,4-diClPh | CO | single bond | 2 | O | $CH_2CH_2$ | sub. 28 |
| 1864 | cHex | 3,4-diClPh | CO | single bond | 2 | O | $CH_2CH_2$ | sub. 28 |
| 1865 | cHep | 3,4-diClPh | CO | single bond | 2 | O | $CH_2CH_2$ | sub. 28 |
| 1866 | 2-Pyrd | 3,4-diClPh | CO | single bond | 2 | O | $CH_2CH_2$ | sub. 28 |
| 1867 | 3-Pyrd | 3,4-diClPh | CO | single bond | 2 | O | $CH_2CH_2$ | sub. 28 |
| 1868 | 4-Oxa | 3,4-diClPh | CO | single bond | 2 | O | $CH_2CH_2$ | sub. 28 |
| 1869 | 5-Oxa | 3,4-diClPh | CO | single bond | 2 | O | $CH_2CH_2$ | sub. 28 |
| 1870 | 4-Thi | 3,4-diClPh | CO | single bond | 2 | O | $CH_2CH_2$ | sub. 28 |
| 1871 | 5-Thi | 3,4-diClPh | CO | single bond | 2 | O | $CH_2CH_2$ | sub. 28 |
| 1872 | 4-OOxa | 3,4-diClPh | CO | single bond | 2 | O | $CH_2CH_2$ | sub. 28 |
| 1873 | 5-OOxa | 3,4-diClPh | CO | single bond | 2 | O | $CH_2CH_2$ | sub. 28 |
| 1874 | 4-OThi | 3,4-diClPh | CO | single bond | 2 | O | $CH_2CH_2$ | sub. 28 |
| 1875 | 5-OThi | 3,4-diClPh | CO | single bond | 2 | O | $CH_2CH_2$ | sub. 28 |
| 1876 | 2-Pip | 3,4-diClPh | CO | single bond | 2 | O | $CH_2CH_2$ | sub. 28 |
| 1877 | 3-Pip | 3,4-diClPh | CO | single bond | 2 | O | $CH_2CH_2$ | sub. 28 |
| 1878 | 4-Pip | 3,4-diClPh | CO | single bond | 2 | O | $CH_2CH_2$ | sub. 28 |
| 1879 | 2-Mor | 3,4-diClPh | CO | single bond | 2 | O | $CH_2CH_2$ | sub. 28 |
| 1880 | 3-Mor | 3,4-diClPh | CO | single bond | 2 | O | $CH_2CH_2$ | sub. 28 |

TABLE 1-continued

| Exemplification compound number | R¹ | R² | A | B | N | D | G | Q |
|---|---|---|---|---|---|---|---|---|
| 1881 | 4-Mor | 3,4-diClPh | CO | single bond | 2 | O | $CH_2CH_2$ | sub. 28 |
| 1882 | 2-Thmor | 3,4-diClPh | CO | single bond | 2 | O | $CH_2CH_2$ | sub. 28 |
| 1883 | 3-Thmor | 3,4-diClPh | CO | single bond | 2 | O | $CH_2CH_2$ | sub. 28 |
| 1884 | 4-Thmor | 3,4-diClPh | CO | single bond | 2 | O | $CH_2CH_2$ | sub. 28 |
| 1885 | 2-Piz | 3,4-diClPh | CO | single bond | 2 | O | $CH_2CH_2$ | sub. 28 |
| 1886 | 3-Piz | 3,4-diClPh | CO | single bond | 2 | O | $CH_2CH_2$ | sub. 28 |
| 1887 | 4-Piz | 3,4-diClPh | CO | single bond | 2 | O | $CH_2CH_2$ | sub. 28 |
| 1888 | 2-Aze | 3,4-diClPh | CO | single bond | 2 | O | $CH_2CH_2$ | sub. 28 |
| 1889 | 3-Aze | 3,4-diClPh | CO | single bond | 2 | O | $CH_2CH_2$ | sub. 28 |
| 1890 | 4-Aze | 3,4-diClPh | CO | single bond | 2 | O | $CH_2CH_2$ | sub. 28 |
| 1891 | cPr | 3,4-diClPh | CO | single bond | 2 | O | $CH_2CH_2$ | sub. 29 |
| 1892 | cBu | 3,4-diClPh | CO | single bond | 2 | O | $CH_2CH_2$ | sub. 29 |
| 1893 | cPn | 3,4-diClPh | CO | single bond | 2 | O | $CH_2CH_2$ | sub. 29 |
| 1894 | cHex | 3,4-diClPh | CO | single bond | 2 | O | $CH_2CH_2$ | sub. 29 |
| 1895 | cHep | 3,4-diClPh | CO | single bond | 2 | O | $CH_2CH_2$ | sub. 29 |
| 1896 | 2-Pyrd | 3,4-diClPh | CO | single bond | 2 | O | $CH_2CH_2$ | sub. 29 |
| 1897 | 3-Pyrd | 3,4-diClPh | CO | single bond | 2 | O | $CH_2CH_2$ | sub. 29 |
| 1898 | 4-Oxa | 3,4-diClPh | CO | single bond | 2 | O | $CH_2CH_2$ | sub. 29 |
| 1899 | 5-Oxa | 3,4-diClPh | CO | single bond | 2 | O | $CH_2CH_2$ | sub. 29 |
| 1900 | 4-Thi | 3,4-diClPh | CO | single bond | 2 | O | $CH_2CH_2$ | sub. 29 |
| 1901 | 5-Thi | 3,4-diClPh | CO | single bond | 2 | O | $CH_2CH_2$ | sub. 29 |
| 1902 | 4-OOxa | 3,4-diClPh | CO | single bond | 2 | O | $CH_2CH_2$ | sub. 29 |
| 1903 | 5-OOxa | 3,4-diClPh | CO | single bond | 2 | O | $CH_2CH_2$ | sub. 29 |
| 1904 | 4-OThi | 3,4-diClPh | CO | single bond | 2 | O | $CH_2CH_2$ | sub. 29 |
| 1905 | 5-OThi | 3,4-diClPh | CO | single bond | 2 | O | $CH_2CH_2$ | sub. 29 |
| 1906 | 2-Pip | 3,4-diClPh | CO | single bond | 2 | O | $CH_2CH_2$ | sub. 29 |
| 1907 | 3-Pip | 3,4-diClPh | CO | single bond | 2 | O | $CH_2CH_2$ | sub. 29 |
| 1908 | 4-Pip | 3,4-diClPh | CO | single bond | 2 | O | $CH_2CH_2$ | sub. 29 |
| 1909 | 2-Mor | 3,4-diClPh | CO | single bond | 2 | O | $CH_2CH_2$ | sub. 29 |
| 1910 | 3-Mor | 3,4-diClPh | CO | single bond | 2 | O | $CH_2CH_2$ | sub. 29 |
| 1911 | 4-Mor | 3,4-diClPh | CO | single bond | 2 | O | $CH_2CH_2$ | sub. 29 |
| 1912 | 2-Thmor | 3,4-diClPh | CO | single bond | 2 | O | $CH_2CH_2$ | sub. 29 |
| 1913 | 3-Thmor | 3,4-diClPh | CO | single bond | 2 | O | $CH_2CH_2$ | sub. 29 |
| 1914 | 4-Thmor | 3,4-diClPh | CO | single bond | 2 | O | $CH_2CH_2$ | sub. 29 |
| 1915 | 2-Piz | 3,4-diClPh | CO | single bond | 2 | O | $CH_2CH_2$ | sub. 29 |
| 1916 | 3-Piz | 3,4-diClPh | CO | single bond | 2 | O | $CH_2CH_2$ | sub. 29 |
| 1917 | 4-Piz | 3,4-diClPh | CO | single bond | 2 | O | $CH_2CH_2$ | sub. 29 |
| 1918 | 2-Aze | 3,4-diClPh | CO | single bond | 2 | O | $CH_2CH_2$ | sub. 29 |
| 1919 | 3-Aze | 3,4-diClPh | CO | single bond | 2 | O | $CH_2CH_2$ | sub. 29 |
| 1920 | 4-Aze | 3,4-diClPh | CO | single bond | 2 | O | $CH_2CH_2$ | sub. 29 |
| 1921 | cPr | 3,4-diClPh | CO | single bond | 2 | O | $CH_2CH_2$ | sub. 30 |
| 1922 | cBu | 3,4-diClPh | CO | single bond | 2 | O | $CH_2CH_2$ | sub. 30 |
| 1923 | cPn | 3,4-diClPh | CO | single bond | 2 | O | $CH_2CH_2$ | sub. 30 |
| 1924 | cHex | 3,4-diClPh | CO | single bond | 2 | O | $CH_2CH_2$ | sub. 30 |
| 1925 | cHep | 3,4-diClPh | CO | single bond | 2 | O | $CH_2CH_2$ | sub. 30 |
| 1926 | 2-Pyrd | 3,4-diClPh | CO | single bond | 2 | O | $CH_2CH_2$ | sub. 30 |
| 1927 | 3-Pyrd | 3,4-diClPh | CO | single bond | 2 | O | $CH_2CH_2$ | sub. 30 |
| 1928 | 4-Oxa | 3,4-diClPh | CO | single bond | 2 | O | $CH_2CH_2$ | sub. 30 |
| 1929 | 5-Oxa | 3,4-diClPh | CO | single bond | 2 | O | $CH_2CH_2$ | sub. 30 |
| 1930 | 4-Thi | 3,4-diClPh | CO | single bond | 2 | O | $CH_2CH_2$ | sub. 30 |
| 1931 | 5-Thi | 3,4-diClPh | CO | single bond | 2 | O | $CH_2CH_2$ | sub. 30 |
| 1932 | 4-OOxa | 3,4-diClPh | CO | single bond | 2 | O | $CH_2CH_2$ | sub. 30 |
| 1933 | 5-OOxa | 3,4-diClPh | CO | single bond | 2 | O | $CH_2CH_2$ | sub. 30 |
| 1934 | 4-OThi | 3,4-diClPh | CO | single bond | 2 | O | $CH_2CH_2$ | sub. 30 |
| 1935 | 5-OThi | 3,4-diClPh | CO | single bond | 2 | O | $CH_2CH_2$ | sub. 30 |
| 1936 | 2-Pip | 3,4-diClPh | CO | single bond | 2 | O | $CH_2CH_2$ | sub. 30 |
| 1937 | 3-Pip | 3,4-diClPh | CO | single bond | 2 | O | $CH_2CH_2$ | sub. 30 |
| 1938 | 4-Pip | 3,4-diClPh | CO | single bond | 2 | O | $CH_2CH_2$ | sub. 30 |
| 1939 | 2-Mor | 3,4-diClPh | CO | single bond | 2 | O | $CH_2CH_2$ | sub. 30 |
| 1940 | 3-Mor | 3,4-diClPh | CO | single bond | 2 | O | $CH_2CH_2$ | sub. 30 |
| 1941 | 4-Mor | 3,4-diClPh | CO | single bond | 2 | O | $CH_2CH_2$ | sub. 30 |
| 1942 | 2-Thmor | 3,4-diClPh | CO | single bond | 2 | O | $CH_2CH_2$ | sub. 30 |
| 1943 | 3-Thmor | 3,4-diClPh | CO | single bond | 2 | O | $CH_2CH_2$ | sub. 30 |
| 1944 | 4-Thmor | 3,4-diClPh | CO | single bond | 2 | O | $CH_2CH_2$ | sub. 30 |
| 1945 | 2-Piz | 3,4-diClPh | CO | single bond | 2 | O | $CH_2CH_2$ | sub. 30 |
| 1946 | 3-Piz | 3,4-diClPh | CO | single bond | 2 | O | $CH_2CH_2$ | sub. 30 |
| 1947 | 4-Piz | 3,4-diClPh | CO | single bond | 2 | O | $CH_2CH_2$ | sub. 30 |
| 1948 | 2-Aze | 3,4-diClPh | CO | single bond | 2 | O | $CH_2CH_2$ | sub. 30 |
| 1949 | 3-Aze | 3,4-diClPh | CO | single bond | 2 | O | $CH_2CH_2$ | sub. 30 |
| 1950 | 4-Aze | 3,4-diClPh | CO | single bond | 2 | O | $CH_2CH_2$ | sub. 30 |
| 1951 | cPr | 3,4-diClPh | CO | single bond | 2 | O | $CH_2CH_2$ | sub. 31 |
| 1952 | cBu | 3,4-diClPh | CO | single bond | 2 | O | $CH_2CH_2$ | sub. 31 |
| 1953 | cPn | 3,4-diClPh | CO | single bond | 2 | O | $CH_2CH_2$ | sub. 31 |
| 1954 | cHex | 3,4-diClPh | CO | single bond | 2 | O | $CH_2CH_2$ | sub. 31 |
| 1955 | cHep | 3,4-diClPh | CO | single bond | 2 | O | $CH_2CH_2$ | sub. 31 |
| 1956 | 2-Pyrd | 3,4-diClPh | CO | single bond | 2 | O | $CH_2CH_2$ | sub. 31 |

TABLE 1-continued

| Exemplification compound number | R¹ | R² | A | B | N | D | G | Q |
|---|---|---|---|---|---|---|---|---|
| 1957 | 3-Pyrd | 3,4-diClPh | CO | single bond | 2 | O | CH$_2$CH$_2$ | sub. 31 |
| 1958 | 4-Oxa | 3,4-diClPh | CO | single bond | 2 | O | CH$_2$CH$_2$ | sub. 31 |
| 1959 | 5-Oxa | 3,4-diClPh | CO | single bond | 2 | O | CH$_2$CH$_2$ | sub. 31 |
| 1960 | 4-Thi | 3,4-diClPh | CO | single bond | 2 | O | CH$_2$CH$_2$ | sub. 31 |
| 1961 | 5-Thi | 3,4-diClPh | CO | single bond | 2 | O | CH$_2$CH$_2$ | sub. 31 |
| 1962 | 4-OOxa | 3,4-diClPh | CO | single bond | 2 | O | CH$_2$CH$_2$ | sub. 31 |
| 1963 | 5-OOxa | 3,4-diClPh | CO | single bond | 2 | O | CH$_2$CH$_2$ | sub. 31 |
| 1964 | 4-OThi | 3,4-diClPh | CO | single bond | 2 | O | CH$_2$CH$_2$ | sub. 31 |
| 1965 | 5-OThi | 3,4-diClPh | CO | single bond | 2 | O | CH$_2$CH$_2$ | sub. 31 |
| 1966 | 2-Pip | 3,4-diClPh | CO | single bond | 2 | O | CH$_2$CH$_2$ | sub. 31 |
| 1967 | 3-Pip | 3,4-diClPh | CO | single bond | 2 | O | CH$_2$CH$_2$ | sub. 31 |
| 1968 | 4-Pip | 3,4-diClPh | CO | single bond | 2 | O | CH$_2$CH$_2$ | sub. 31 |
| 1969 | 2-Mor | 3,4-diClPh | CO | single bond | 2 | O | CH$_2$CH$_2$ | sub. 31 |
| 1970 | 3-Mor | 3,4-diClPh | CO | single bond | 2 | O | CH$_2$CH$_2$ | sub. 31 |
| 1971 | 4-Mor | 3,4-diClPh | CO | single bond | 2 | O | CH$_2$CH$_2$ | sub. 31 |
| 1972 | 2-Thmor | 3,4-diClPh | CO | single bond | 2 | O | CH$_2$CH$_2$ | sub. 31 |
| 1973 | 3-Thmor | 3,4-diClPh | CO | single bond | 2 | O | CH$_2$CH$_2$ | sub. 31 |
| 1974 | 4-Thmor | 3,4-diClPh | CO | single bond | 2 | O | CH$_2$CH$_2$ | sub. 31 |
| 1975 | 2-Piz | 3,4-diClPh | CO | single bond | 2 | O | CH$_2$CH$_2$ | sub. 31 |
| 1976 | 3-Piz | 3,4-diClPh | CO | single bond | 2 | O | CH$_2$CH$_2$ | sub. 31 |
| 1977 | 4-Piz | 3,4-diClPh | CO | single bond | 2 | O | CH$_2$CH$_2$ | sub. 31 |
| 1978 | 2-Aze | 3,4-diClPh | CO | single bond | 2 | O | CH$_2$CH$_2$ | sub. 31 |
| 1979 | 3-Aze | 3,4-diClPh | CO | single bond | 2 | O | CH$_2$CH$_2$ | sub. 31 |
| 1980 | 4-Aze | 3,4-diClPh | CO | single bond | 2 | O | CH$_2$CH$_2$ | sub. 31 |
| 1981 | cPr | 3,4-diClPh | CO | single bond | 2 | O | CH$_2$CH$_2$ | sub. 32 |
| 1982 | cBu | 3,4-diClPh | CO | single bond | 2 | O | CH$_2$CH$_2$ | sub. 32 |
| 1983 | cPn | 3,4-diClPh | CO | single bond | 2 | O | CH$_2$CH$_2$ | sub. 32 |
| 1984 | cHex | 3,4-diClPh | CO | single bond | 2 | O | CH$_2$CH$_2$ | sub. 32 |
| 1985 | cHep | 3,4-diClPh | CO | single bond | 2 | O | CH$_2$CH$_2$ | sub. 32 |
| 1986 | 2-Pyrd | 3,4-diClPh | CO | single bond | 2 | O | CH$_2$CH$_2$ | sub. 32 |
| 1987 | 3-Pyrd | 3,4-diClPh | CO | single bond | 2 | O | CH$_2$CH$_2$ | sub. 32 |
| 1988 | 4-Oxa | 3,4-diClPh | CO | single bond | 2 | O | CH$_2$CH$_2$ | sub. 32 |
| 1989 | 5-Oxa | 3,4-diClPh | CO | single bond | 2 | O | CH$_2$CH$_2$ | sub. 32 |
| 1990 | 4-Thi | 3,4-diClPh | CO | single bond | 2 | O | CH$_2$CH$_2$ | sub. 32 |
| 1991 | 5-Thi | 3,4-diClPh | CO | single bond | 2 | O | CH$_2$CH$_2$ | sub. 32 |
| 1992 | 4-OOxa | 3,4-diClPh | CO | single bond | 2 | O | CH$_2$CH$_2$ | sub. 32 |
| 1993 | 5-OOxa | 3,4-diClPh | CO | single bond | 2 | O | CH$_2$CH$_2$ | sub. 32 |
| 1994 | 4-OThi | 3,4-diClPh | CO | single bond | 2 | O | CH$_2$CH$_2$ | sub. 32 |
| 1995 | 5-OThi | 3,4-diClPh | CO | single bond | 2 | O | CH$_2$CH$_2$ | sub. 32 |
| 1996 | 2-Pip | 3,4-diClPh | CO | single bond | 2 | O | CH$_2$CH$_2$ | sub. 32 |
| 1997 | 3-Pip | 3,4-diClPh | CO | single bond | 2 | O | CH$_2$CH$_2$ | sub. 32 |
| 1998 | 4-Pip | 3,4-diClPh | CO | single bond | 2 | O | CH$_2$CH$_2$ | sub. 32 |
| 1999 | 2-Mor | 3,4-diClPh | CO | single bond | 2 | O | CH$_2$CH$_2$ | sub. 32 |
| 2000 | 3-Mor | 3,4-diClPh | CO | single bond | 2 | O | CH$_2$CH$_2$ | sub. 32 |
| 2001 | 4-Mor | 3,4-diClPh | CO | single bond | 2 | O | CH$_2$CH$_2$ | sub. 32 |
| 2002 | 2-Thmor | 3,4-diClPh | CO | single bond | 2 | O | CH$_2$CH$_2$ | sub. 32 |
| 2003 | 3-Thmor | 3,4-diClPh | CO | single bond | 2 | O | CH$_2$CH$_2$ | sub. 32 |
| 2004 | 4-Thmor | 3,4-diClPh | CO | single bond | 2 | O | CH$_2$CH$_2$ | sub. 32 |
| 2005 | 2-Piz | 3,4-diClPh | CO | single bond | 2 | O | CH$_2$CH$_2$ | sub. 32 |
| 2006 | 3-Piz | 3,4-diClPh | CO | single bond | 2 | O | CH$_2$CH$_2$ | sub. 32 |
| 2007 | 4-Piz | 3,4-diClPh | CO | single bond | 2 | O | CH$_2$CH$_2$ | sub. 32 |
| 2008 | 2-Aze | 3,4-diClPh | CO | single bond | 2 | O | CH$_2$CH$_2$ | sub. 32 |
| 2009 | 3-Aze | 3,4-diClPh | CO | single bond | 2 | O | CH$_2$CH$_2$ | sub. 32 |
| 2010 | 4-Aze | 3,4-diClPh | CO | single bond | 2 | O | CH$_2$CH$_2$ | sub. 32 |
| 2011 | cPr | 3,4-diClPh | CO | single bond | 2 | O | CH$_2$CH$_2$ | sub. 33 |
| 2012 | cBu | 3,4-diClPh | CO | single bond | 2 | O | CH$_2$CH$_2$ | sub. 33 |
| 2013 | cPn | 3,4-diClPh | CO | single bond | 2 | O | CH$_2$CH$_2$ | sub. 33 |
| 2014 | cHex | 3,4-diClPh | CO | single bond | 2 | O | CH$_2$CH$_2$ | sub. 33 |
| 2015 | cHep | 3,4-diClPh | CO | single bond | 2 | O | CH$_2$CH$_2$ | sub. 33 |
| 2016 | 2-Pyrd | 3,4-diClPh | CO | single bond | 2 | O | CH$_2$CH$_2$ | sub. 33 |
| 2017 | 3-Pyrd | 3,4-diClPh | CO | single bond | 2 | O | CH$_2$CH$_2$ | sub. 33 |
| 2018 | 4-Oxa | 3,4-diClPh | CO | single bond | 2 | O | CH$_2$CH$_2$ | sub. 33 |
| 2019 | 5-Oxa | 3,4-diClPh | CO | single bond | 2 | O | CH$_2$CH$_2$ | sub. 33 |
| 2020 | 4-Thi | 3,4-diClPh | CO | single bond | 2 | O | CH$_2$CH$_2$ | sub. 33 |
| 2021 | 5-Thi | 3,4-diClPh | CO | single bond | 2 | O | CH$_2$CH$_2$ | sub. 33 |
| 2022 | 4-OOxa | 3,4-diClPh | CO | single bond | 2 | O | CH$_2$CH$_2$ | sub. 33 |
| 2023 | 5-OOxa | 3,4-diClPh | CO | single bond | 2 | O | CH$_2$CH$_2$ | sub. 33 |
| 2024 | 4-OThi | 3,4-diClPh | CO | single bond | 2 | O | CH$_2$CH$_2$ | sub. 33 |
| 2025 | 5-OThi | 3,4-diClPh | CO | single bond | 2 | O | CH$_2$CH$_2$ | sub. 33 |
| 2026 | 2-Pip | 3,4-diClPh | CO | single bond | 2 | O | CH$_2$CH$_2$ | sub. 33 |
| 2027 | 3-Pip | 3,4-diClPh | CO | single bond | 2 | O | CH$_2$CH$_2$ | sub. 33 |
| 2028 | 4-Pip | 3,4-diClPh | CO | single bond | 2 | O | CH$_2$CH$_2$ | sub. 33 |
| 2029 | 2-Mor | 3,4-diClPh | CO | single bond | 2 | O | CH$_2$CH$_2$ | sub. 33 |
| 2030 | 3-Mor | 3,4-diClPh | CO | single bond | 2 | O | CH$_2$CH$_2$ | sub. 33 |
| 2031 | 4-Mor | 3,4-diClPh | CO | single bond | 2 | O | CH$_2$CH$_2$ | sub. 33 |
| 2032 | 2-Thmor | 3,4-diClPh | CO | single bond | 2 | O | CH$_2$CH$_2$ | sub. 33 |

TABLE 1-continued

| Exemplification compound number | R¹ | R² | A | B | N | D | G | Q |
|---|---|---|---|---|---|---|---|---|
| 2033 | 3-Thmor | 3,4-diClPh | CO | single bond | 2 | O | $CH_2CH_2$ | sub. 33 |
| 2034 | 4-Thmor | 3,4-diClPh | CO | single bond | 2 | O | $CH_2CH_2$ | sub. 33 |
| 2035 | 2-Piz | 3,4-diClPh | CO | single bond | 2 | O | $CH_2CH_2$ | sub. 33 |
| 2036 | 3-Piz | 3,4-diClPh | CO | single bond | 2 | O | $CH_2CH_2$ | sub. 33 |
| 2037 | 4-Piz | 3,4-diClPh | CO | single bond | 2 | O | $CH_2CH_2$ | sub. 33 |
| 2038 | 2-Aze | 3,4-diClPh | CO | single bond | 2 | O | $CH_2CH_2$ | sub. 33 |
| 2039 | 3-Aze | 3,4-diClPh | CO | single bond | 2 | O | $CH_2CH_2$ | sub. 33 |
| 2040 | 4-Aze | 3,4-diClPh | CO | single bond | 2 | O | $CH_2CH_2$ | sub. 33 |
| 2041 | cPr | 3,4-diClPh | CO | single bond | 2 | O | $CH_2CH_2$ | sub. 34 |
| 2042 | cBu | 3,4-diClPh | CO | single bond | 2 | O | $CH_2CH_2$ | sub. 34 |
| 2043 | cPn | 3,4-diClPh | CO | single bond | 2 | O | $CH_2CH_2$ | sub. 34 |
| 2044 | cHex | 3,4-diClPh | CO | single bond | 2 | O | $CH_2CH_2$ | sub. 34 |
| 2045 | cHep | 3,4-diClPh | CO | single bond | 2 | O | $CH_2CH_2$ | sub. 34 |
| 2046 | 2-Pyrd | 3,4-diClPh | CO | single bond | 2 | O | $CH_2CH_2$ | sub. 34 |
| 2047 | 3-Pyrd | 3,4-diClPh | CO | single bond | 2 | O | $CH_2CH_2$ | sub. 34 |
| 2048 | 4-Oxa | 3,4-diClPh | CO | single bond | 2 | O | $CH_2CH_2$ | sub. 34 |
| 2049 | 5-Oxa | 3,4-diClPh | CO | single bond | 2 | O | $CH_2CH_2$ | sub. 34 |
| 2050 | 4-Thi | 3,4-diClPh | CO | single bond | 2 | O | $CH_2CH_2$ | sub. 34 |
| 2051 | 5-Thi | 3,4-diClPh | CO | single bond | 2 | O | $CH_2CH_2$ | sub. 34 |
| 2052 | 4-OOxa | 3,4-diClPh | CO | single bond | 2 | O | $CH_2CH_2$ | sub. 34 |
| 2053 | 5-OOxa | 3,4-diClPh | CO | single bond | 2 | O | $CH_2CH_2$ | sub. 34 |
| 2054 | 4-OThi | 3,4-diClPh | CO | single bond | 2 | O | $CH_2CH_2$ | sub. 34 |
| 2055 | 5-OThi | 3,4-diClPh | CO | single bond | 2 | O | $CH_2CH_2$ | sub. 34 |
| 2056 | 2-Pip | 3,4-diClPh | CO | single bond | 2 | O | $CH_2CH_2$ | sub. 34 |
| 2057 | 3-Pip | 3,4-diClPh | CO | single bond | 2 | O | $CH_2CH_2$ | sub. 34 |
| 2058 | 4-Pip | 3,4-diClPh | CO | single bond | 2 | O | $CH_2CH_2$ | sub. 34 |
| 2059 | 2-Mor | 3,4-diClPh | CO | single bond | 2 | O | $CH_2CH_2$ | sub. 34 |
| 2060 | 3-Mor | 3,4-diClPh | CO | single bond | 2 | O | $CH_2CH_2$ | sub. 34 |
| 2061 | 4-Mor | 3,4-diClPh | CO | single bond | 2 | O | $CH_2CH_2$ | sub. 34 |
| 2062 | 2-Thmor | 3,4-diClPh | CO | single bond | 2 | O | $CH_2CH_2$ | sub. 34 |
| 2063 | 3-Thmor | 3,4-diClPh | CO | single bond | 2 | O | $CH_2CH_2$ | sub. 34 |
| 2064 | 4-Thmor | 3,4-diClPh | CO | single bond | 2 | O | $CH_2CH_2$ | sub. 34 |
| 2065 | 2-Piz | 3,4-diClPh | CO | single bond | 2 | O | $CH_2CH_2$ | sub. 34 |
| 2066 | 3-Piz | 3,4-diClPh | CO | single bond | 2 | O | $CH_2CH_2$ | sub. 34 |
| 2067 | 4-Piz | 3,4-diClPh | CO | single bond | 2 | O | $CH_2CH_2$ | sub. 34 |
| 2068 | 2-Aze | 3,4-diClPh | CO | single bond | 2 | O | $CH_2CH_2$ | sub. 34 |
| 2069 | 3-Aze | 3,4-diClPh | CO | single bond | 2 | O | $CH_2CH_2$ | sub. 34 |
| 2070 | 4-Aze | 3,4-diClPh | CO | single bond | 2 | O | $CH_2CH_2$ | sub. 34 |
| 2071 | cPr | 3,4-diClPh | CO | single bond | 2 | O | $CH_2CH_2$ | sub. 35 |
| 2072 | cBu | 3,4-diClPh | CO | single bond | 2 | O | $CH_2CH_2$ | sub. 35 |
| 2073 | cPn | 3,4-diClPh | CO | single bond | 2 | O | $CH_2CH_2$ | sub. 35 |
| 2074 | cHex | 3,4-diClPh | CO | single bond | 2 | O | $CH_2CH_2$ | sub. 35 |
| 2075 | cHep | 3,4-diClPh | CO | single bond | 2 | O | $CH_2CH_2$ | sub. 35 |
| 2076 | 2-Pyrd | 3,4-diClPh | CO | single bond | 2 | O | $CH_2CH_2$ | sub. 35 |
| 2077 | 3-Pyrd | 3,4-diClPh | CO | single bond | 2 | O | $CH_2CH_2$ | sub. 35 |
| 2078 | 4-Oxa | 3,4-diClPh | CO | single bond | 2 | O | $CH_2CH_2$ | sub. 35 |
| 2079 | 5-Oxa | 3,4-diClPh | CO | single bond | 2 | O | $CH_2CH_2$ | sub. 35 |
| 2080 | 4-Thi | 3,4-diClPh | CO | single bond | 2 | O | $CH_2CH_2$ | sub. 35 |
| 2081 | 5-Thi | 3,4-diClPh | CO | single bond | 2 | O | $CH_2CH_2$ | sub. 35 |
| 2082 | 4-OOxa | 3,4-diClPh | CO | single bond | 2 | O | $CH_2CH_2$ | sub. 35 |
| 2083 | 5-OOxa | 3,4-diClPh | CO | single bond | 2 | O | $CH_2CH_2$ | sub. 35 |
| 2084 | 4-OThi | 3,4-diClPh | CO | single bond | 2 | O | $CH_2CH_2$ | sub. 35 |
| 2085 | 5-OThi | 3,4-diClPh | CO | single bond | 2 | O | $CH_2CH_2$ | sub. 35 |
| 2086 | 2-Pip | 3,4-diClPh | CO | single bond | 2 | O | $CH_2CH_2$ | sub. 35 |
| 2087 | 3-Pip | 3,4-diClPh | CO | single bond | 2 | O | $CH_2CH_2$ | sub. 35 |
| 2088 | 4-Pip | 3,4-diClPh | CO | single bond | 2 | O | $CH_2CH_2$ | sub. 35 |
| 2089 | 2-Mor | 3,4-diClPh | CO | single bond | 2 | O | $CH_2CH_2$ | sub. 35 |
| 2090 | 3-Mor | 3,4-diClPh | CO | single bond | 2 | O | $CH_2CH_2$ | sub. 35 |
| 2091 | 4-Mor | 3,4-diClPh | CO | single bond | 2 | O | $CH_2CH_2$ | sub. 35 |
| 2092 | 2-Thmor | 3,4-diClPh | CO | single bond | 2 | O | $CH_2CH_2$ | sub. 35 |
| 2093 | 3-Thmor | 3,4-diClPh | CO | single bond | 2 | O | $CH_2CH_2$ | sub. 35 |
| 2094 | 4-Thmor | 3,4-diClPh | CO | single bond | 2 | O | $CH_2CH_2$ | sub. 35 |
| 2095 | 2-Piz | 3,4-diClPh | CO | single bond | 2 | O | $CH_2CH_2$ | sub. 35 |
| 2096 | 3-Piz | 3,4-diClPh | CO | single bond | 2 | O | $CH_2CH_2$ | sub. 35 |
| 2097 | 4-Piz | 3,4-diClPh | CO | single bond | 2 | O | $CH_2CH_2$ | sub. 35 |
| 2098 | 2-Aze | 3,4-diClPh | CO | single bond | 2 | O | $CH_2CH_2$ | sub. 35 |
| 2099 | 3-Aze | 3,4-diClPh | CO | single bond | 2 | O | $CH_2CH_2$ | sub. 35 |
| 2100 | 4-Aze | 3,4-diClPh | CO | single bond | 2 | O | $CH_2CH_2$ | sub. 35 |
| 2101 | cPr | 4-ClPh | CO | single bond | 2 | O | $CH_2CH_2$ | sub. 1 |
| 2102 | cBu | 4-ClPh | CO | single bond | 2 | O | $CH_2CH_2$ | sub. 1 |
| 2103 | cPn | 4-ClPh | CO | single bond | 2 | O | $CH_2CH_2$ | sub. 1 |
| 2104 | cHex | 4-ClPh | CO | single bond | 2 | O | $CH_2CH_2$ | sub. 1 |
| 2105 | cHep | 4-ClPh | CO | single bond | 2 | O | $CH_2CH_2$ | sub. 1 |
| 2106 | 2-Pyrd | 4-ClPh | CO | single bond | 2 | O | $CH_2CH_2$ | sub. 1 |
| 2107 | 3-Pyrd | 4-ClPh | CO | single bond | 2 | O | $CH_2CH_2$ | sub. 1 |
| 2108 | 4-Oxa | 4-ClPh | CO | single bond | 2 | O | $CH_2CH_2$ | sub. 1 |

TABLE 1-continued

| Exemplification compound number | R¹ | R² | A | B | N | D | G | Q |
|---|---|---|---|---|---|---|---|---|
| 2109 | 5-Oxa | 4-ClPh | CO | single bond | 2 | O | $CH_2CH_2$ | sub. 1 |
| 2110 | 4-Thi | 4-ClPh | CO | single bond | 2 | O | $CH_2CH_2$ | sub. 1 |
| 2111 | 5-Thi | 4-ClPh | CO | single bond | 2 | O | $CH_2CH_2$ | sub. 1 |
| 2112 | 4-OOxa | 4-ClPh | CO | single bond | 2 | O | $CH_2CH_2$ | sub. 1 |
| 2113 | 5-OOxa | 4-ClPh | CO | single bond | 2 | O | $CH_2CH_2$ | sub. 1 |
| 2114 | 4-OThi | 4-ClPh | CO | single bond | 2 | O | $CH_2CH_2$ | sub. 1 |
| 2115 | 5-OThi | 4-ClPh | CO | single bond | 2 | O | $CH_2CH_2$ | sub. 1 |
| 2116 | 2-Pip | 4-ClPh | CO | single bond | 2 | O | $CH_2CH_2$ | sub. 1 |
| 2117 | 3-Pip | 4-ClPh | CO | single bond | 2 | O | $CH_2CH_2$ | sub. 1 |
| 2118 | 4-Pip | 4-ClPh | CO | single bond | 2 | O | $CH_2CH_2$ | sub. 1 |
| 2119 | 2-Mor | 4-ClPh | CO | single bond | 2 | O | $CH_2CH_2$ | sub. 1 |
| 2120 | 3-Mor | 4-ClPh | CO | single bond | 2 | O | $CH_2CH_2$ | sub. 1 |
| 2121 | 4-Mor | 4-ClPh | CO | single bond | 2 | O | $CH_2CH_2$ | sub. 1 |
| 2122 | 2-Thmor | 4-ClPh | CO | single bond | 2 | O | $CH_2CH_2$ | sub. 1 |
| 2123 | 3-Thmor | 4-ClPh | CO | single bond | 2 | O | $CH_2CH_2$ | sub. 1 |
| 2124 | 4-Thmor | 4-ClPh | CO | single bond | 2 | O | $CH_2CH_2$ | sub. 1 |
| 2125 | 2-Piz | 4-ClPh | CO | single bond | 2 | O | $CH_2CH_2$ | sub. 1 |
| 2126 | 3-Piz | 4-ClPh | CO | single bond | 2 | O | $CH_2CH_2$ | sub. 1 |
| 2127 | 4-Piz | 4-ClPh | CO | single bond | 2 | O | $CH_2CH_2$ | sub. 1 |
| 2128 | 2-Aze | 4-ClPh | CO | single bond | 2 | O | $CH_2CH_2$ | sub. 1 |
| 2129 | 3-Aze | 4-ClPh | CO | single bond | 2 | O | $CH_2CH_2$ | sub. 1 |
| 2130 | 4-Aze | 4-ClPh | CO | single bond | 2 | O | $CH_2CH_2$ | sub. 1 |
| 2131 | cPr | 4-ClPh | CO | single bond | 2 | O | $CH_2CH_2$ | sub. 2 |
| 2132 | cBu | 4-ClPh | CO | single bond | 2 | O | $CH_2CH_2$ | sub. 2 |
| 2133 | cPn | 4-ClPh | CO | single bond | 2 | O | $CH_2CH_2$ | sub. 2 |
| 2134 | cHex | 4-ClPh | CO | single bond | 2 | O | $CH_2CH_2$ | sub. 2 |
| 2135 | cHep | 4-ClPh | CO | single bond | 2 | O | $CH_2CH_2$ | sub. 2 |
| 2136 | 2-Pyrd | 4-ClPh | CO | single bond | 2 | O | $CH_2CH_2$ | sub. 2 |
| 2137 | 3-Pyrd | 4-ClPh | CO | single bond | 2 | O | $CH_2CH_2$ | sub. 2 |
| 2138 | 4-Oxa | 4-ClPh | CO | single bond | 2 | O | $CH_2CH_2$ | sub. 2 |
| 2139 | 5-Oxa | 4-ClPh | CO | single bond | 2 | O | $CH_2CH_2$ | sub. 2 |
| 2140 | 4-Thi | 4-ClPh | CO | single bond | 2 | O | $CH_2CH_2$ | sub. 2 |
| 2141 | 5-Thi | 4-ClPh | CO | single bond | 2 | O | $CH_2CH_2$ | sub. 2 |
| 2142 | 4-OOxa | 4-ClPh | CO | single bond | 2 | O | $CH_2CH_2$ | sub. 2 |
| 2143 | 5-OOxa | 4-ClPh | CO | single bond | 2 | O | $CH_2CH_2$ | sub. 2 |
| 2144 | 4-OThi | 4-ClPh | CO | single bond | 2 | O | $CH_2CH_2$ | sub. 2 |
| 2145 | 5-OThi | 4-ClPh | CO | single bond | 2 | O | $CH_2CH_2$ | sub. 2 |
| 2146 | 2-Pip | 4-ClPh | CO | single bond | 2 | O | $CH_2CH_2$ | sub. 2 |
| 2147 | 3-Pip | 4-ClPh | CO | single bond | 2 | O | $CH_2CH_2$ | sub. 2 |
| 2148 | 4-Pip | 4-ClPh | CO | single bond | 2 | O | $CH_2CH_2$ | sub. 2 |
| 2149 | 2-Mor | 4-ClPh | CO | single bond | 2 | O | $CH_2CH_2$ | sub. 2 |
| 2150 | 3-Mor | 4-ClPh | CO | single bond | 2 | O | $CH_2CH_2$ | sub. 2 |
| 2151 | 4-Mor | 4-ClPh | CO | single bond | 2 | O | $CH_2CH_2$ | sub. 2 |
| 2152 | 2-Thmor | 4-ClPh | CO | single bond | 2 | O | $CH_2CH_2$ | sub. 2 |
| 2153 | 3-Thmor | 4-ClPh | CO | single bond | 2 | O | $CH_2CH_2$ | sub. 2 |
| 2154 | 4-Thmor | 4-ClPh | CO | single bond | 2 | O | $CH_2CH_2$ | sub. 2 |
| 2155 | 2-Piz | 4-ClPh | CO | single bond | 2 | O | $CH_2CH_2$ | sub. 2 |
| 2156 | 3-Piz | 4-ClPh | CO | single bond | 2 | O | $CH_2CH_2$ | sub. 2 |
| 2157 | 4-Piz | 4-ClPh | CO | single bond | 2 | O | $CH_2CH_2$ | sub. 2 |
| 2158 | 2-Aze | 4-ClPh | CO | single bond | 2 | O | $CH_2CH_2$ | sub. 2 |
| 2159 | 3-Aze | 4-ClPh | CO | single bond | 2 | O | $CH_2CH_2$ | sub. 2 |
| 2160 | 4-Aze | 4-ClPh | CO | single bond | 2 | O | $CH_2CH_2$ | sub. 2 |
| 2161 | cPr | 4-ClPh | CO | single bond | 2 | O | $CH_2CH_2$ | sub. 3 |
| 2162 | cBu | 4-ClPh | CO | single bond | 2 | O | $CH_2CH_2$ | sub. 3 |
| 2163 | cPn | 4-ClPh | CO | single bond | 2 | O | $CH_2CH_2$ | sub. 3 |
| 2164 | cHex | 4-ClPh | CO | single bond | 2 | O | $CH_2CH_2$ | sub. 3 |
| 2165 | cHep | 4-ClPh | CO | single bond | 2 | O | $CH_2CH_2$ | sub. 3 |
| 2166 | 2-Pyrd | 4-ClPh | CO | single bond | 2 | O | $CH_2CH_2$ | sub. 3 |
| 2167 | 3-Pyrd | 4-ClPh | CO | single bond | 2 | O | $CH_2CH_2$ | sub. 3 |
| 2168 | 4-Oxa | 4-ClPh | CO | single bond | 2 | O | $CH_2CH_2$ | sub. 3 |
| 2169 | 5-Oxa | 4-ClPh | CO | single bond | 2 | O | $CH_2CH_2$ | sub. 3 |
| 2170 | 4-Thi | 4-ClPh | CO | single bond | 2 | O | $CH_2CH_2$ | sub. 3 |
| 2171 | 5-Thi | 4-ClPh | CO | single bond | 2 | O | $CH_2CH_2$ | sub. 3 |
| 2172 | 4-OOxa | 4-ClPh | CO | single bond | 2 | O | $CH_2CH_2$ | sub. 3 |
| 2173 | 5-OOxa | 4-ClPh | CO | single bond | 2 | O | $CH_2CH_2$ | sub. 3 |
| 2174 | 4-OThi | 4-ClPh | CO | single bond | 2 | O | $CH_2CH_2$ | sub. 3 |
| 2175 | 5-OThi | 4-ClPh | CO | single bond | 2 | O | $CH_2CH_2$ | sub. 3 |
| 2176 | 2-Pip | 4-ClPh | CO | single bond | 2 | O | $CH_2CH_2$ | sub. 3 |
| 2177 | 3-Pip | 4-ClPh | CO | single bond | 2 | O | $CH_2CH_2$ | sub. 3 |
| 2178 | 4-Pip | 4-ClPh | CO | single bond | 2 | O | $CH_2CH_2$ | sub. 3 |
| 2179 | 2-Mor | 4-ClPh | CO | single bond | 2 | O | $CH_2CH_2$ | sub. 3 |
| 2180 | 3-Mor | 4-ClPh | CO | single bond | 2 | O | $CH_2CH_2$ | sub. 3 |
| 2181 | 4-Mor | 4-ClPh | CO | single bond | 2 | O | $CH_2CH_2$ | sub. 3 |
| 2182 | 2-Thmor | 4-ClPh | CO | single bond | 2 | O | $CH_2CH_2$ | sub. 3 |
| 2183 | 3-Thmor | 4-ClPh | CO | single bond | 2 | O | $CH_2CH_2$ | sub. 3 |
| 2184 | 4-Thmor | 4-ClPh | CO | single bond | 2 | O | $CH_2CH_2$ | sub. 3 |

TABLE 1-continued

| Exemplification compound number | R¹ | R² | A | B | N | D | G | Q |
|---|---|---|---|---|---|---|---|---|
| 2185 | 2-Piz | 4-ClPh | CO | single bond | 2 | O | $CH_2CH_2$ | sub. 3 |
| 2186 | 3-Piz | 4-ClPh | CO | single bond | 2 | O | $CH_2CH_2$ | sub. 3 |
| 2187 | 4-Piz | 4-ClPh | CO | single bond | 2 | O | $CH_2CH_2$ | sub. 3 |
| 2188 | 2-Aze | 4-ClPh | CO | single bond | 2 | O | $CH_2CH_2$ | sub. 3 |
| 2189 | 3-Aze | 4-ClPh | CO | single bond | 2 | O | $CH_2CH_2$ | sub. 3 |
| 2190 | 4-Aze | 4-ClPh | CO | single bond | 2 | O | $CH_2CH_2$ | sub. 3 |
| 2191 | cPr | 4-ClPh | CO | single bond | 2 | O | $CH_2CH_2$ | sub. 4 |
| 2192 | cBu | 4-ClPh | CO | single bond | 2 | O | $CH_2CH_2$ | sub. 4 |
| 2193 | cPn | 4-ClPh | CO | single bond | 2 | O | $CH_2CH_2$ | sub. 4 |
| 2194 | cHex | 4-ClPh | CO | single bond | 2 | O | $CH_2CH_2$ | sub. 4 |
| 2195 | cHep | 4-ClPh | CO | single bond | 2 | O | $CH_2CH_2$ | sub. 4 |
| 2196 | 2-Pyrd | 4-ClPh | CO | single bond | 2 | O | $CH_2CH_2$ | sub. 4 |
| 2197 | 3-Pyrd | 4-ClPh | CO | single bond | 2 | O | $CH_2CH_2$ | sub. 4 |
| 2198 | 4-Oxa | 4-ClPh | CO | single bond | 2 | O | $CH_2CH_2$ | sub. 4 |
| 2199 | 5-Oxa | 4-ClPh | CO | single bond | 2 | O | $CH_2CH_2$ | sub. 4 |
| 2200 | 4-Thi | 4-ClPh | CO | single bond | 2 | O | $CH_2CH_2$ | sub. 4 |
| 2201 | 5-Thi | 4-ClPh | CO | single bond | 2 | O | $CH_2CH_2$ | sub. 4 |
| 2202 | 4-OOxa | 4-ClPh | CO | single bond | 2 | O | $CH_2CH_2$ | sub. 4 |
| 2203 | 5-OOxa | 4-ClPh | CO | single bond | 2 | O | $CH_2CH_2$ | sub. 4 |
| 2204 | 4-OThi | 4-ClPh | CO | single bond | 2 | O | $CH_2CH_2$ | sub. 4 |
| 2205 | 5-OThi | 4-ClPh | CO | single bond | 2 | O | $CH_2CH_2$ | sub. 4 |
| 2206 | 2-Pip | 4-ClPh | CO | single bond | 2 | O | $CH_2CH_2$ | sub. 4 |
| 2207 | 3-Pip | 4-ClPh | CO | single bond | 2 | O | $CH_2CH_2$ | sub. 4 |
| 2208 | 4-Pip | 4-ClPh | CO | single bond | 2 | O | $CH_2CH_2$ | sub. 4 |
| 2209 | 2-Mor | 4-ClPh | CO | single bond | 2 | O | $CH_2CH_2$ | sub. 4 |
| 2210 | 3-Mor | 4-ClPh | CO | single bond | 2 | O | $CH_2CH_2$ | sub. 4 |
| 2211 | 4-Mor | 4-ClPh | CO | single bond | 2 | O | $CH_2CH_2$ | sub. 4 |
| 2212 | 2-Thmor | 4-ClPh | CO | single bond | 2 | O | $CH_2CH_2$ | sub. 4 |
| 2213 | 3-Thmor | 4-ClPh | CO | single bond | 2 | O | $CH_2CH_2$ | sub. 4 |
| 2214 | 4-Thmor | 4-ClPh | CO | single bond | 2 | O | $CH_2CH_2$ | sub. 4 |
| 2215 | 2-Piz | 4-ClPh | CO | single bond | 2 | O | $CH_2CH_2$ | sub. 4 |
| 2216 | 3-Piz | 4-ClPh | CO | single bond | 2 | O | $CH_2CH_2$ | sub. 4 |
| 2217 | 4-Piz | 4-ClPh | CO | single bond | 2 | O | $CH_2CH_2$ | sub. 4 |
| 2218 | 2-Aze | 4-ClPh | CO | single bond | 2 | O | $CH_2CH_2$ | sub. 4 |
| 2219 | 3-Aze | 4-ClPh | CO | single bond | 2 | O | $CH_2CH_2$ | sub. 4 |
| 2220 | 4-Aze | 4-ClPh | CO | single bond | 2 | O | $CH_2CH_2$ | sub. 4 |
| 2221 | cPr | 4-ClPh | CO | single bond | 2 | O | $CH_2CH_2$ | sub. 5 |
| 2222 | cBu | 4-ClPh | CO | single bond | 2 | O | $CH_2CH_2$ | sub. 5 |
| 2223 | cPn | 4-ClPh | CO | single bond | 2 | O | $CH_2CH_2$ | sub. 5 |
| 2224 | cHex | 4-ClPh | CO | single bond | 2 | O | $CH_2CH_2$ | sub. 5 |
| 2225 | cHep | 4-ClPh | CO | single bond | 2 | O | $CH_2CH_2$ | sub. 5 |
| 2226 | 2-Pyrd | 4-ClPh | CO | single bond | 2 | O | $CH_2CH_2$ | sub. 5 |
| 2227 | 3-Pyrd | 4-ClPh | CO | single bond | 2 | O | $CH_2CH_2$ | sub. 5 |
| 2228 | 4-Oxa | 4-ClPh | CO | single bond | 2 | O | $CH_2CH_2$ | sub. 5 |
| 2229 | 5-Oxa | 4-ClPh | CO | single bond | 2 | O | $CH_2CH_2$ | sub. 5 |
| 2230 | 4-Thi | 4-ClPh | CO | single bond | 2 | O | $CH_2CH_2$ | sub. 5 |
| 2231 | 5-Thi | 4-ClPh | CO | single bond | 2 | O | $CH_2CH_2$ | sub. 5 |
| 2232 | 4-OOxa | 4-ClPh | CO | single bond | 2 | O | $CH_2CH_2$ | sub. 5 |
| 2233 | 5-OOxa | 4-ClPh | CO | single bond | 2 | O | $CH_2CH_2$ | sub. 5 |
| 2234 | 4-OThi | 4-ClPh | CO | single bond | 2 | O | $CH_2CH_2$ | sub. 5 |
| 2235 | 5-OThi | 4-ClPh | CO | single bond | 2 | O | $CH_2CH_2$ | sub. 5 |
| 2236 | 2-Pip | 4-ClPh | CO | single bond | 2 | O | $CH_2CH_2$ | sub. 5 |
| 2237 | 3-Pip | 4-ClPh | CO | single bond | 2 | O | $CH_2CH_2$ | sub. 5 |
| 2238 | 4-Pip | 4-ClPh | CO | single bond | 2 | O | $CH_2CH_2$ | sub. 5 |
| 2239 | 2-Mor | 4-ClPh | CO | single bond | 2 | O | $CH_2CH_2$ | sub. 5 |
| 2240 | 3-Mor | 4-ClPh | CO | single bond | 2 | O | $CH_2CH_2$ | sub. 5 |
| 2241 | 4-Mor | 4-ClPh | CO | single bond | 2 | O | $CH_2CH_2$ | sub. 5 |
| 2242 | 2-Thmor | 4-ClPh | CO | single bond | 2 | O | $CH_2CH_2$ | sub. 5 |
| 2243 | 3-Thmor | 4-ClPh | CO | single bond | 2 | O | $CH_2CH_2$ | sub. 5 |
| 2244 | 4-Thmor | 4-ClPh | CO | single bond | 2 | O | $CH_2CH_2$ | sub. 5 |
| 2245 | 2-Piz | 4-ClPh | CO | single bond | 2 | O | $CH_2CH_2$ | sub. 5 |
| 2246 | 3-Piz | 4-ClPh | CO | single bond | 2 | O | $CH_2CH_2$ | sub. 5 |
| 2247 | 4-Piz | 4-ClPh | CO | single bond | 2 | O | $CH_2CH_2$ | sub. 5 |
| 2248 | 2-Aze | 4-ClPh | CO | single bond | 2 | O | $CH_2CH_2$ | sub. 5 |
| 2249 | 3-Aze | 4-ClPh | CO | single bond | 2 | O | $CH_2CH_2$ | sub. 5 |
| 2250 | 4-Aze | 4-ClPh | CO | single bond | 2 | O | $CH_2CH_2$ | sub. 5 |
| 2251 | cPr | 4-ClPh | CO | single bond | 2 | O | $CH_2CH_2$ | sub. 6 |
| 2252 | cBu | 4-ClPh | CO | single bond | 2 | O | $CH_2CH_2$ | sub. 6 |
| 2253 | cPn | 4-ClPh | CO | single bond | 2 | O | $CH_2CH_2$ | sub. 6 |
| 2254 | cHex | 4-ClPh | CO | single bond | 2 | O | $CH_2CH_2$ | sub. 6 |
| 2255 | cHep | 4-ClPh | CO | single bond | 2 | O | $CH_2CH_2$ | sub. 6 |
| 2256 | 2-Pyrd | 4-ClPh | CO | single bond | 2 | O | $CH_2CH_2$ | sub. 6 |
| 2257 | 3-Pyrd | 4-ClPh | CO | single bond | 2 | O | $CH_2CH_2$ | sub. 6 |
| 2258 | 4-Oxa | 4-ClPh | CO | single bond | 2 | O | $CH_2CH_2$ | sub. 6 |
| 2259 | 5-Oxa | 4-ClPh | CO | single bond | 2 | O | $CH_2CH_2$ | sub. 6 |
| 2260 | 4-Thi | 4-ClPh | CO | single bond | 2 | O | $CH_2CH_2$ | sub. 6 |

TABLE 1-continued

| Exemplification compound number | R¹ | R² | A | B | N | D | G | Q |
|---|---|---|---|---|---|---|---|---|
| 2261 | 5-Thi | 4-ClPh | CO | single bond | 2 | O | $CH_2CH_2$ | sub. 6 |
| 2262 | 4-OOxa | 4-ClPh | CO | single bond | 2 | O | $CH_2CH_2$ | sub. 6 |
| 2263 | 5-OOxa | 4-ClPh | CO | single bond | 2 | O | $CH_2CH_2$ | sub. 6 |
| 2264 | 4-OThi | 4-ClPh | CO | single bond | 2 | O | $CH_2CH_2$ | sub. 6 |
| 2265 | 5-OThi | 4-ClPh | CO | single bond | 2 | O | $CH_2CH_2$ | sub. 6 |
| 2266 | 2-Pip | 4-ClPh | CO | single bond | 2 | O | $CH_2CH_2$ | sub. 6 |
| 2267 | 3-Pip | 4-ClPh | CO | single bond | 2 | O | $CH_2CH_2$ | sub. 6 |
| 2268 | 4-Pip | 4-ClPh | CO | single bond | 2 | O | $CH_2CH_2$ | sub. 6 |
| 2269 | 2-Mor | 4-ClPh | CO | single bond | 2 | O | $CH_2CH_2$ | sub. 6 |
| 2270 | 3-Mor | 4-ClPh | CO | single bond | 2 | O | $CH_2CH_2$ | sub. 6 |
| 2271 | 4-Mor | 4-ClPh | CO | single bond | 2 | O | $CH_2CH_2$ | sub. 6 |
| 2272 | 2-Thmor | 4-ClPh | CO | single bond | 2 | O | $CH_2CH_2$ | sub. 6 |
| 2273 | 3-Thmor | 4-ClPh | CO | single bond | 2 | O | $CH_2CH_2$ | sub. 6 |
| 2274 | 4-Thmor | 4-ClPh | CO | single bond | 2 | O | $CH_2CH_2$ | sub. 6 |
| 2275 | 2-Piz | 4-ClPh | CO | single bond | 2 | O | $CH_2CH_2$ | sub. 6 |
| 2276 | 3-Piz | 4-ClPh | CO | single bond | 2 | O | $CH_2CH_2$ | sub. 6 |
| 2277 | 4-Piz | 4-ClPh | CO | single bond | 2 | O | $CH_2CH_2$ | sub. 6 |
| 2278 | 2-Aze | 4-ClPh | CO | single bond | 2 | O | $CH_2CH_2$ | sub. 6 |
| 2279 | 3-Aze | 4-ClPh | CO | single bond | 2 | O | $CH_2CH_2$ | sub. 6 |
| 2280 | 4-Aze | 4-ClPh | CO | single bond | 2 | O | $CH_2CH_2$ | sub. 6 |
| 2281 | cPr | 4-ClPh | CO | single bond | 2 | O | $CH_2CH_2$ | sub. 7 |
| 2282 | cBu | 4-ClPh | CO | single bond | 2 | O | $CH_2CH_2$ | sub. 7 |
| 2283 | cPn | 4-ClPh | CO | single bond | 2 | O | $CH_2CH_2$ | sub. 7 |
| 2284 | cHex | 4-ClPh | CO | single bond | 2 | O | $CH_2CH_2$ | sub. 7 |
| 2285 | cHep | 4-ClPh | CO | single bond | 2 | O | $CH_2CH_2$ | sub. 7 |
| 2286 | 2-Pyrd | 4-ClPh | CO | single bond | 2 | O | $CH_2CH_2$ | sub. 7 |
| 2287 | 3-Pyrd | 4-ClPh | CO | single bond | 2 | O | $CH_2CH_2$ | sub. 7 |
| 2288 | 4-Oxa | 4-ClPh | CO | single bond | 2 | O | $CH_2CH_2$ | sub. 7 |
| 2289 | 5-Oxa | 4-ClPh | CO | single bond | 2 | O | $CH_2CH_2$ | sub. 7 |
| 2290 | 4-Thi | 4-ClPh | CO | single bond | 2 | O | $CH_2CH_2$ | sub. 7 |
| 2291 | 5-Thi | 4-ClPh | CO | single bond | 2 | O | $CH_2CH_2$ | sub. 7 |
| 2292 | 4-OOxa | 4-ClPh | CO | single bond | 2 | O | $CH_2CH_2$ | sub. 7 |
| 2293 | 5-OOxa | 4-ClPh | CO | single bond | 2 | O | $CH_2CH_2$ | sub. 7 |
| 2294 | 4-OThi | 4-ClPh | CO | single bond | 2 | O | $CH_2CH_2$ | sub. 7 |
| 2295 | 5-OThi | 4-ClPh | CO | single bond | 2 | O | $CH_2CH_2$ | sub. 7 |
| 2296 | 2-Pip | 4-ClPh | CO | single bond | 2 | O | $CH_2CH_2$ | sub. 7 |
| 2297 | 3-Pip | 4-ClPh | CO | single bond | 2 | O | $CH_2CH_2$ | sub. 7 |
| 2298 | 4-Pip | 4-ClPh | CO | single bond | 2 | O | $CH_2CH_2$ | sub. 7 |
| 2299 | 2-Mor | 4-ClPh | CO | single bond | 2 | O | $CH_2CH_2$ | sub. 7 |
| 2300 | 3-Mor | 4-ClPh | CO | single bond | 2 | O | $CH_2CH_2$ | sub. 7 |
| 2301 | 4-Mor | 4-ClPh | CO | single bond | 2 | O | $CH_2CH_2$ | sub. 7 |
| 2302 | 2-Thmor | 4-ClPh | CO | single bond | 2 | O | $CH_2CH_2$ | sub. 7 |
| 2303 | 3-Thmor | 4-ClPh | CO | single bond | 2 | O | $CH_2CH_2$ | sub. 7 |
| 2304 | 4-Thmor | 4-ClPh | CO | single bond | 2 | O | $CH_2CH_2$ | sub. 7 |
| 2305 | 2-Piz | 4-ClPh | CO | single bond | 2 | O | $CH_2CH_2$ | sub. 7 |
| 2306 | 3-Piz | 4-ClPh | CO | single bond | 2 | O | $CH_2CH_2$ | sub. 7 |
| 2307 | 4-Piz | 4-ClPh | CO | single bond | 2 | O | $CH_2CH_2$ | sub. 7 |
| 2308 | 2-Aze | 4-ClPh | CO | single bond | 2 | O | $CH_2CH_2$ | sub. 7 |
| 2309 | 3-Aze | 4-ClPh | CO | single bond | 2 | O | $CH_2CH_2$ | sub. 7 |
| 2310 | 4-Aze | 4-ClPh | CO | single bond | 2 | O | $CH_2CH_2$ | sub. 7 |
| 2311 | cPr | 4-ClPh | CO | single bond | 2 | O | $CH_2CH_2$ | sub. 8 |
| 2312 | cBu | 4-ClPh | CO | single bond | 2 | O | $CH_2CH_2$ | sub. 8 |
| 2313 | cPn | 4-ClPh | CO | single bond | 2 | O | $CH_2CH_2$ | sub. 8 |
| 2314 | cHex | 4-ClPh | CO | single bond | 2 | O | $CH_2CH_2$ | sub. 8 |
| 2315 | cHep | 4-ClPh | CO | single bond | 2 | O | $CH_2CH_2$ | sub. 8 |
| 2316 | 2-Pyrd | 4-ClPh | CO | single bond | 2 | O | $CH_2CH_2$ | sub. 8 |
| 2317 | 3-Pyrd | 4-ClPh | CO | single bond | 2 | O | $CH_2CH_2$ | sub. 8 |
| 2318 | 4-Oxa | 4-ClPh | CO | single bond | 2 | O | $CH_2CH_2$ | sub. 8 |
| 2319 | 5-Oxa | 4-ClPh | CO | single bond | 2 | O | $CH_2CH_2$ | sub. 8 |
| 2320 | 4-Thi | 4-ClPh | CO | single bond | 2 | O | $CH_2CH_2$ | sub. 8 |
| 2321 | 5-Thi | 4-ClPh | CO | single bond | 2 | O | $CH_2CH_2$ | sub. 8 |
| 2322 | 4-OOxa | 4-ClPh | CO | single bond | 2 | O | $CH_2CH_2$ | sub. 8 |
| 2323 | 5-OOxa | 4-ClPh | CO | single bond | 2 | O | $CH_2CH_2$ | sub. 8 |
| 2324 | 4-OThi | 4-ClPh | CO | single bond | 2 | O | $CH_2CH_2$ | sub. 8 |
| 2325 | 5-OThi | 4-ClPh | CO | single bond | 2 | O | $CH_2CH_2$ | sub. 8 |
| 2326 | 2-Pip | 4-ClPh | CO | single bond | 2 | O | $CH_2CH_2$ | sub. 8 |
| 2327 | 3-Pip | 4-ClPh | CO | single bond | 2 | O | $CH_2CH_2$ | sub. 8 |
| 2328 | 4-Pip | 4-ClPh | CO | single bond | 2 | O | $CH_2CH_2$ | sub. 8 |
| 2329 | 2-Mor | 4-ClPh | CO | single bond | 2 | O | $CH_2CH_2$ | sub. 8 |
| 2330 | 3-Mor | 4-ClPh | CO | single bond | 2 | O | $CH_2CH_2$ | sub. 8 |
| 2331 | 4-Mor | 4-ClPh | CO | single bond | 2 | O | $CH_2CH_2$ | sub. 8 |
| 2332 | 2-Thmor | 4-ClPh | CO | single bond | 2 | O | $CH_2CH_2$ | sub. 8 |
| 2333 | 3-Thmor | 4-ClPh | CO | single bond | 2 | O | $CH_2CH_2$ | sub. 8 |
| 2334 | 4-Thmor | 4-ClPh | CO | single bond | 2 | O | $CH_2CH_2$ | sub. 8 |
| 2335 | 2-Piz | 4-ClPh | CO | single bond | 2 | O | $CH_2CH_2$ | sub. 8 |
| 2336 | 3-Piz | 4-ClPh | CO | single bond | 2 | O | $CH_2CH_2$ | sub. 8 |

TABLE 1-continued

| Exemplification compound number | R¹ | R² | A | B | N | D | G | Q |
|---|---|---|---|---|---|---|---|---|
| 2337 | 4-Piz | 4-ClPh | CO | single bond | 2 | O | $CH_2CH_2$ | sub. 8 |
| 2338 | 2-Aze | 4-ClPh | CO | single bond | 2 | O | $CH_2CH_2$ | sub. 8 |
| 2339 | 3-Aze | 4-ClPh | CO | single bond | 2 | O | $CH_2CH_2$ | sub. 8 |
| 2340 | 4-Aze | 4-ClPh | CO | single bond | 2 | O | $CH_2CH_2$ | sub. 8 |
| 2341 | cPr | 4-ClPh | CO | single bond | 2 | O | $CH_2CH_2$ | sub. 9 |
| 2342 | cBu | 4-ClPh | CO | single bond | 2 | O | $CH_2CH_2$ | sub. 9 |
| 2343 | cPn | 4-ClPh | CO | single bond | 2 | O | $CH_2CH_2$ | sub. 9 |
| 2344 | cHex | 4-ClPh | CO | single bond | 2 | O | $CH_2CH_2$ | sub. 9 |
| 2345 | cHep | 4-ClPh | CO | single bond | 2 | O | $CH_2CH_2$ | sub. 9 |
| 2346 | 2-Pyrd | 4-ClPh | CO | single bond | 2 | O | $CH_2CH_2$ | sub. 9 |
| 2347 | 3-Pyrd | 4-ClPh | CO | single bond | 2 | O | $CH_2CH_2$ | sub. 9 |
| 2348 | 4-Oxa | 4-ClPh | CO | single bond | 2 | O | $CH_2CH_2$ | sub. 9 |
| 2349 | 5-Oxa | 4-ClPh | CO | single bond | 2 | O | $CH_2CH_2$ | sub. 9 |
| 2350 | 4-Thi | 4-ClPh | CO | single bond | 2 | O | $CH_2CH_2$ | sub. 9 |
| 2351 | 5-Thi | 4-ClPh | CO | single bond | 2 | O | $CH_2CH_2$ | sub. 9 |
| 2352 | 4-OOxa | 4-ClPh | CO | single bond | 2 | O | $CH_2CH_2$ | sub. 9 |
| 2353 | 5-OOxa | 4-ClPh | CO | single bond | 2 | O | $CH_2CH_2$ | sub. 9 |
| 2354 | 4-OThi | 4-ClPh | CO | single bond | 2 | O | $CH_2CH_2$ | sub. 9 |
| 2355 | 5-OThi | 4-ClPh | CO | single bond | 2 | O | $CH_2CH_2$ | sub. 9 |
| 2356 | 2-Pip | 4-ClPh | CO | single bond | 2 | O | $CH_2CH_2$ | sub. 9 |
| 2357 | 3-Pip | 4-ClPh | CO | single bond | 2 | O | $CH_2CH_2$ | sub. 9 |
| 2358 | 4-Pip | 4-ClPh | CO | single bond | 2 | O | $CH_2CH_2$ | sub. 9 |
| 2359 | 2-Mor | 4-ClPh | CO | single bond | 2 | O | $CH_2CH_2$ | sub. 9 |
| 2360 | 3-Mor | 4-ClPh | CO | single bond | 2 | O | $CH_2CH_2$ | sub. 9 |
| 2361 | 4-Mor | 4-ClPh | CO | single bond | 2 | O | $CH_2CH_2$ | sub. 9 |
| 2362 | 2-Thmor | 4-ClPh | CO | single bond | 2 | O | $CH_2CH_2$ | sub. 9 |
| 2363 | 3-Thmor | 4-ClPh | CO | single bond | 2 | O | $CH_2CH_2$ | sub. 9 |
| 2364 | 4-Thmor | 4-ClPh | CO | single bond | 2 | O | $CH_2CH_2$ | sub. 9 |
| 2365 | 2-Piz | 4-ClPh | CO | single bond | 2 | O | $CH_2CH_2$ | sub. 9 |
| 2366 | 3-Piz | 4-ClPh | CO | single bond | 2 | O | $CH_2CH_2$ | sub. 9 |
| 2367 | 4-Piz | 4-ClPh | CO | single bond | 2 | O | $CH_2CH_2$ | sub. 9 |
| 2368 | 2-Aze | 4-ClPh | CO | single bond | 2 | O | $CH_2CH_2$ | sub. 9 |
| 2369 | 3-Aze | 4-ClPh | CO | single bond | 2 | O | $CH_2CH_2$ | sub. 9 |
| 2370 | 4-Aze | 4-ClPh | CO | single bond | 2 | O | $CH_2CH_2$ | sub. 9 |
| 2371 | cPr | 4-ClPh | CO | single bond | 2 | O | $CH_2CH_2$ | sub. 10 |
| 2372 | cBu | 4-ClPh | CO | single bond | 2 | O | $CH_2CH_2$ | sub. 10 |
| 2373 | cPn | 4-ClPh | CO | single bond | 2 | O | $CH_2CH_2$ | sub. 10 |
| 2374 | cHex | 4-ClPh | CO | single bond | 2 | O | $CH_2CH_2$ | sub. 10 |
| 2375 | cHep | 4-ClPh | CO | single bond | 2 | O | $CH_2CH_2$ | sub. 10 |
| 2376 | 2-Pyrd | 4-ClPh | CO | single bond | 2 | O | $CH_2CH_2$ | sub. 10 |
| 2377 | 3-Pyrd | 4-ClPh | CO | single bond | 2 | O | $CH_2CH_2$ | sub. 10 |
| 2378 | 4-Oxa | 4-ClPh | CO | single bond | 2 | O | $CH_2CH_2$ | sub. 10 |
| 2379 | 5-Oxa | 4-ClPh | CO | single bond | 2 | O | $CH_2CH_2$ | sub. 10 |
| 2380 | 4-Thi | 4-ClPh | CO | single bond | 2 | O | $CH_2CH_2$ | sub. 10 |
| 2381 | 5-Thi | 4-ClPh | CO | single bond | 2 | O | $CH_2CH_2$ | sub. 10 |
| 2382 | 4-OOxa | 4-ClPh | CO | single bond | 2 | O | $CH_2CH_2$ | sub. 10 |
| 2383 | 5-OOxa | 4-ClPh | CO | single bond | 2 | O | $CH_2CH_2$ | sub. 10 |
| 2384 | 4-OThi | 4-ClPh | CO | single bond | 2 | O | $CH_2CH_2$ | sub. 10 |
| 2385 | 5-OThi | 4-ClPh | CO | single bond | 2 | O | $CH_2CH_2$ | sub. 10 |
| 2386 | 2-Pip | 4-ClPh | CO | single bond | 2 | O | $CH_2CH_2$ | sub. 10 |
| 2387 | 3-Pip | 4-ClPh | CO | single bond | 2 | O | $CH_2CH_2$ | sub. 10 |
| 2388 | 4-Pip | 4-ClPh | CO | single bond | 2 | O | $CH_2CH_2$ | sub. 10 |
| 2389 | 2-Mor | 4-ClPh | CO | single bond | 2 | O | $CH_2CH_2$ | sub. 10 |
| 2390 | 3-Mor | 4-ClPh | CO | single bond | 2 | O | $CH_2CH_2$ | sub. 10 |
| 2391 | 4-Mor | 4-ClPh | CO | single bond | 2 | O | $CH_2CH_2$ | sub. 10 |
| 2392 | 2-Thmor | 4-ClPh | CO | single bond | 2 | O | $CH_2CH_2$ | sub. 10 |
| 2393 | 3-Thmor | 4-ClPh | CO | single bond | 2 | O | $CH_2CH_2$ | sub. 10 |
| 2394 | 4-Thmor | 4-ClPh | CO | single bond | 2 | O | $CH_2CH_2$ | sub. 10 |
| 2395 | 2-Piz | 4-ClPh | CO | single bond | 2 | O | $CH_2CH_2$ | sub. 10 |
| 2396 | 3-Piz | 4-ClPh | CO | single bond | 2 | O | $CH_2CH_2$ | sub. 10 |
| 2397 | 4-Piz | 4-ClPh | CO | single bond | 2 | O | $CH_2CH_2$ | sub. 10 |
| 2398 | 2-Aze | 4-ClPh | CO | single bond | 2 | O | $CH_2CH_2$ | sub. 10 |
| 2399 | 3-Aze | 4-ClPh | CO | single bond | 2 | O | $CH_2CH_2$ | sub. 10 |
| 2400 | 4-Aze | 4-ClPh | CO | single bond | 2 | O | $CH_2CH_2$ | sub. 10 |
| 2401 | cPr | 4-ClPh | CO | single bond | 2 | O | $CH_2CH_2$ | sub. 11 |
| 2402 | cBu | 4-ClPh | CO | single bond | 2 | O | $CH_2CH_2$ | sub. 11 |
| 2403 | cPn | 4-ClPh | CO | single bond | 2 | O | $CH_2CH_2$ | sub. 11 |
| 2404 | cHex | 4-ClPh | CO | single bond | 2 | O | $CH_2CH_2$ | sub. 11 |
| 2405 | cHep | 4-ClPh | CO | single bond | 2 | O | $CH_2CH_2$ | sub. 11 |
| 2406 | 2-Pyrd | 4-ClPh | CO | single bond | 2 | O | $CH_2CH_2$ | sub. 11 |
| 2407 | 3-Pyrd | 4-ClPh | CO | single bond | 2 | O | $CH_2CH_2$ | sub. 11 |
| 2408 | 4-Oxa | 4-ClPh | CO | single bond | 2 | O | $CH_2CH_2$ | sub. 11 |
| 2409 | 5-Oxa | 4-ClPh | CO | single bond | 2 | O | $CH_2CH_2$ | sub. 11 |
| 2410 | 4-Thi | 4-ClPh | CO | single bond | 2 | O | $CH_2CH_2$ | sub. 11 |
| 2411 | 5-Thi | 4-ClPh | CO | single bond | 2 | O | $CH_2CH_2$ | sub. 11 |
| 2412 | 4-OOxa | 4-ClPh | CO | single bond | 2 | O | $CH_2CH_2$ | sub. 11 |

TABLE 1-continued

| Exemplification compound number | R¹ | R² | A | B | N | D | G | Q |
|---|---|---|---|---|---|---|---|---|
| 2413 | 5-OOxa | 4-ClPh | CO | single bond | 2 | O | $CH_2CH_2$ | sub. 11 |
| 2414 | 4-OThi | 4-ClPh | CO | single bond | 2 | O | $CH_2CH_2$ | sub. 11 |
| 2415 | 5-OThi | 4-ClPh | CO | single bond | 2 | O | $CH_2CH_2$ | sub. 11 |
| 2416 | 2-Pip | 4-ClPh | CO | single bond | 2 | O | $CH_2CH_2$ | sub. 11 |
| 2417 | 3-Pip | 4-ClPh | CO | single bond | 2 | O | $CH_2CH_2$ | sub. 11 |
| 2418 | 4-Pip | 4-ClPh | CO | single bond | 2 | O | $CH_2CH_2$ | sub. 11 |
| 2419 | 2-Mor | 4-ClPh | CO | single bond | 2 | O | $CH_2CH_2$ | sub. 11 |
| 2420 | 3-Mor | 4-ClPh | CO | single bond | 2 | O | $CH_2CH_2$ | sub. 11 |
| 2421 | 4-Mor | 4-ClPh | CO | single bond | 2 | O | $CH_2CH_2$ | sub. 11 |
| 2422 | 2-Thmor | 4-ClPh | CO | single bond | 2 | O | $CH_2CH_2$ | sub. 11 |
| 2423 | 3-Thmor | 4-ClPh | CO | single bond | 2 | O | $CH_2CH_2$ | sub. 11 |
| 2424 | 4-Thmor | 4-ClPh | CO | single bond | 2 | O | $CH_2CH_2$ | sub. 11 |
| 2425 | 2-Piz | 4-ClPh | CO | single bond | 2 | O | $CH_2CH_2$ | sub. 11 |
| 2426 | 3-Piz | 4-ClPh | CO | single bond | 2 | O | $CH_2CH_2$ | sub. 11 |
| 2427 | 4-Piz | 4-ClPh | CO | single bond | 2 | O | $CH_2CH_2$ | sub. 11 |
| 2428 | 2-Aze | 4-ClPh | CO | single bond | 2 | O | $CH_2CH_2$ | sub. 11 |
| 2429 | 3-Aze | 4-ClPh | CO | single bond | 2 | O | $CH_2CH_2$ | sub. 11 |
| 2430 | 4-Aze | 4-ClPh | CO | single bond | 2 | O | $CH_2CH_2$ | sub. 11 |
| 2431 | cPr | 4-ClPh | CO | single bond | 2 | O | $CH_2CH_2$ | sub. 12 |
| 2432 | cBu | 4-ClPh | CO | single bond | 2 | O | $CH_2CH_2$ | sub. 12 |
| 2433 | cPn | 4-ClPh | CO | single bond | 2 | O | $CH_2CH_2$ | sub. 12 |
| 2434 | cHex | 4-ClPh | CO | single bond | 2 | O | $CH_2CH_2$ | sub. 12 |
| 2435 | cHep | 4-ClPh | CO | single bond | 2 | O | $CH_2CH_2$ | sub. 12 |
| 2436 | 2-Pyrd | 4-ClPh | CO | single bond | 2 | O | $CH_2CH_2$ | sub. 12 |
| 2437 | 3-Pyrd | 4-ClPh | CO | single bond | 2 | O | $CH_2CH_2$ | sub. 12 |
| 2438 | 4-Oxa | 4-ClPh | CO | single bond | 2 | O | $CH_2CH_2$ | sub. 12 |
| 2439 | 5-Oxa | 4-ClPh | CO | single bond | 2 | O | $CH_2CH_2$ | sub. 12 |
| 2440 | 4-Thi | 4-ClPh | CO | single bond | 2 | O | $CH_2CH_2$ | sub. 12 |
| 2441 | 5-Thi | 4-ClPh | CO | single bond | 2 | O | $CH_2CH_2$ | sub. 12 |
| 2442 | 4-OOxa | 4-ClPh | CO | single bond | 2 | O | $CH_2CH_2$ | sub. 12 |
| 2443 | 5-OOxa | 4-ClPh | CO | single bond | 2 | O | $CH_2CH_2$ | sub. 12 |
| 2444 | 4-OThi | 4-ClPh | CO | single bond | 2 | O | $CH_2CH_2$ | sub. 12 |
| 2445 | 5-OThi | 4-ClPh | CO | single bond | 2 | O | $CH_2CH_2$ | sub. 12 |
| 2446 | 2-Pip | 4-ClPh | CO | single bond | 2 | O | $CH_2CH_2$ | sub. 12 |
| 2447 | 3-Pip | 4-ClPh | CO | single bond | 2 | O | $CH_2CH_2$ | sub. 12 |
| 2448 | 4-Pip | 4-ClPh | CO | single bond | 2 | O | $CH_2CH_2$ | sub. 12 |
| 2449 | 2-Mor | 4-ClPh | CO | single bond | 2 | O | $CH_2CH_2$ | sub. 12 |
| 2450 | 3-Mor | 4-ClPh | CO | single bond | 2 | O | $CH_2CH_2$ | sub. 12 |
| 2451 | 4-Mor | 4-ClPh | CO | single bond | 2 | O | $CH_2CH_2$ | sub. 12 |
| 2452 | 2-Thmor | 4-ClPh | CO | single bond | 2 | O | $CH_2CH_2$ | sub. 12 |
| 2453 | 3-Thmor | 4-ClPh | CO | single bond | 2 | O | $CH_2CH_2$ | sub. 12 |
| 2454 | 4-Thmor | 4-ClPh | CO | single bond | 2 | O | $CH_2CH_2$ | sub. 12 |
| 2455 | 2-Piz | 4-ClPh | CO | single bond | 2 | O | $CH_2CH_2$ | sub. 12 |
| 2456 | 3-Piz | 4-ClPh | CO | single bond | 2 | O | $CH_2CH_2$ | sub. 12 |
| 2457 | 4-Piz | 4-ClPh | CO | single bond | 2 | O | $CH_2CH_2$ | sub. 12 |
| 2458 | 2-Aze | 4-ClPh | CO | single bond | 2 | O | $CH_2CH_2$ | sub. 12 |
| 2459 | 3-Aze | 4-ClPh | CO | single bond | 2 | O | $CH_2CH_2$ | sub. 12 |
| 2460 | 4-Aze | 4-ClPh | CO | single bond | 2 | O | $CH_2CH_2$ | sub. 12 |
| 2461 | cPr | 4-ClPh | CO | single bond | 2 | O | $CH_2CH_2$ | sub. 13 |
| 2462 | cBu | 4-ClPh | CO | single bond | 2 | O | $CH_2CH_2$ | sub. 13 |
| 2463 | cPn | 4-ClPh | CO | single bond | 2 | O | $CH_2CH_2$ | sub. 13 |
| 2464 | cHex | 4-ClPh | CO | single bond | 2 | O | $CH_2CH_2$ | sub. 13 |
| 2465 | cHep | 4-ClPh | CO | single bond | 2 | O | $CH_2CH_2$ | sub. 13 |
| 2466 | 2-Pyrd | 4-ClPh | CO | single bond | 2 | O | $CH_2CH_2$ | sub. 13 |
| 2467 | 3-Pyrd | 4-ClPh | CO | single bond | 2 | O | $CH_2CH_2$ | sub. 13 |
| 2468 | 4-Oxa | 4-ClPh | CO | single bond | 2 | O | $CH_2CH_2$ | sub. 13 |
| 2469 | 5-Oxa | 4-ClPh | CO | single bond | 2 | O | $CH_2CH_2$ | sub. 13 |
| 2470 | 4-Thi | 4-ClPh | CO | single bond | 2 | O | $CH_2CH_2$ | sub. 13 |
| 2471 | 5-Thi | 4-ClPh | CO | single bond | 2 | O | $CH_2CH_2$ | sub. 13 |
| 2472 | 4-OOxa | 4-ClPh | CO | single bond | 2 | O | $CH_2CH_2$ | sub. 13 |
| 2473 | 5-OOxa | 4-ClPh | CO | single bond | 2 | O | $CH_2CH_2$ | sub. 13 |
| 2474 | 4-OThi | 4-ClPh | CO | single bond | 2 | O | $CH_2CH_2$ | sub. 13 |
| 2475 | 5-OThi | 4-ClPh | CO | single bond | 2 | O | $CH_2CH_2$ | sub. 13 |
| 2476 | 2-Pip | 4-ClPh | CO | single bond | 2 | O | $CH_2CH_2$ | sub. 13 |
| 2477 | 3-Pip | 4-ClPh | CO | single bond | 2 | O | $CH_2CH_2$ | sub. 13 |
| 2478 | 4-Pip | 4-ClPh | CO | single bond | 2 | O | $CH_2CH_2$ | sub. 13 |
| 2479 | 2-Mor | 4-ClPh | CO | single bond | 2 | O | $CH_2CH_2$ | sub. 13 |
| 2480 | 3-Mor | 4-ClPh | CO | single bond | 2 | O | $CH_2CH_2$ | sub. 13 |
| 2481 | 4-Mor | 4-ClPh | CO | single bond | 2 | O | $CH_2CH_2$ | sub. 13 |
| 2482 | 2-Thmor | 4-ClPh | CO | single bond | 2 | O | $CH_2CH_2$ | sub. 13 |
| 2483 | 3-Thmor | 4-ClPh | CO | single bond | 2 | O | $CH_2CH_2$ | sub. 13 |
| 2484 | 4-Thmor | 4-ClPh | CO | single bond | 2 | O | $CH_2CH_2$ | sub. 13 |
| 2485 | 2-Piz | 4-ClPh | CO | single bond | 2 | O | $CH_2CH_2$ | sub. 13 |
| 2486 | 3-Piz | 4-ClPh | CO | single bond | 2 | O | $CH_2CH_2$ | sub. 13 |
| 2487 | 4-Piz | 4-ClPh | CO | single bond | 2 | O | $CH_2CH_2$ | sub. 13 |
| 2488 | 2-Aze | 4-ClPh | CO | single bond | 2 | O | $CH_2CH_2$ | sub. 13 |

TABLE 1-continued

| Exemplification compound number | R¹ | R² | A | B | N | D | G | Q |
|---|---|---|---|---|---|---|---|---|
| 2489 | 3-Aze | 4-ClPh | CO | single bond | 2 | O | CH₂CH₂ | sub. 13 |
| 2490 | 4-Aze | 4-ClPh | CO | single bond | 2 | O | CH₂CH₂ | sub. 13 |
| 2491 | cPr | 4-ClPh | CO | single bond | 2 | O | CH₂CH₂ | sub. 14 |
| 2492 | cBu | 4-ClPh | CO | single bond | 2 | O | CH₂CH₂ | sub. 14 |
| 2493 | cPn | 4-ClPh | CO | single bond | 2 | O | CH₂CH₂ | sub. 14 |
| 2494 | cHex | 4-ClPh | CO | single bond | 2 | O | CH₂CH₂ | sub. 14 |
| 2495 | cHep | 4-ClPh | CO | single bond | 2 | O | CH₂CH₂ | sub. 14 |
| 2496 | 2-Pyrd | 4-ClPh | CO | single bond | 2 | O | CH₂CH₂ | sub. 14 |
| 2497 | 3-Pyrd | 4-ClPh | CO | single bond | 2 | O | CH₂CH₂ | sub. 14 |
| 2498 | 4-Oxa | 4-ClPh | CO | single bond | 2 | O | CH₂CH₂ | sub. 14 |
| 2499 | 5-Oxa | 4-ClPh | CO | single bond | 2 | O | CH₂CH₂ | sub. 14 |
| 2500 | 4-Thi | 4-ClPh | CO | single bond | 2 | O | CH₂CH₂ | sub. 14 |
| 2501 | 5-Thi | 4-ClPh | CO | single bond | 2 | O | CH₂CH₂ | sub. 14 |
| 2502 | 4-OOxa | 4-ClPh | CO | single bond | 2 | O | CH₂CH₂ | sub. 14 |
| 2503 | 5-OOxa | 4-ClPh | CO | single bond | 2 | O | CH₂CH₂ | sub. 14 |
| 2504 | 4-OThi | 4-ClPh | CO | single bond | 2 | O | CH₂CH₂ | sub. 14 |
| 2505 | 5-OThi | 4-ClPh | CO | single bond | 2 | O | CH₂CH₂ | sub. 14 |
| 2506 | 2-Pip | 4-ClPh | CO | single bond | 2 | O | CH₂CH₂ | sub. 14 |
| 2507 | 3-Pip | 4-ClPh | CO | single bond | 2 | O | CH₂CH₂ | sub. 14 |
| 2508 | 4-Pip | 4-ClPh | CO | single bond | 2 | O | CH₂CH₂ | sub. 14 |
| 2509 | 2-Mor | 4-ClPh | CO | single bond | 2 | O | CH₂CH₂ | sub. 14 |
| 2510 | 3-Mor | 4-ClPh | CO | single bond | 2 | O | CH₂CH₂ | sub. 14 |
| 2511 | 4-Mor | 4-ClPh | CO | single bond | 2 | O | CH₂CH₂ | sub. 14 |
| 2512 | 2-Thmor | 4-ClPh | CO | single bond | 2 | O | CH₂CH₂ | sub. 14 |
| 2513 | 3-Thmor | 4-ClPh | CO | single bond | 2 | O | CH₂CH₂ | sub. 14 |
| 2514 | 4-Thmor | 4-ClPh | CO | single bond | 2 | O | CH₂CH₂ | sub. 14 |
| 2515 | 2-Piz | 4-ClPh | CO | single bond | 2 | O | CH₂CH₂ | sub. 14 |
| 2516 | 3-Piz | 4-ClPh | CO | single bond | 2 | O | CH₂CH₂ | sub. 14 |
| 2517 | 4-Piz | 4-ClPh | CO | single bond | 2 | O | CH₂CH₂ | sub. 14 |
| 2518 | 2-Aze | 4-ClPh | CO | single bond | 2 | O | CH₂CH₂ | sub. 14 |
| 2519 | 3-Aze | 4-ClPh | CO | single bond | 2 | O | CH₂CH₂ | sub. 14 |
| 2520 | 4-Aze | 4-ClPh | CO | single bond | 2 | O | CH₂CH₂ | sub. 14 |
| 2521 | cPr | 4-ClPh | CO | single bond | 2 | O | CH₂CH₂ | sub. 15 |
| 2522 | cBu | 4-ClPh | CO | single bond | 2 | O | CH₂CH₂ | sub. 15 |
| 2523 | cPn | 4-ClPh | CO | single bond | 2 | O | CH₂CH₂ | sub. 15 |
| 2524 | cHex | 4-ClPh | CO | single bond | 2 | O | CH₂CH₂ | sub. 15 |
| 2525 | cHep | 4-ClPh | CO | single bond | 2 | O | CH₂CH₂ | sub. 15 |
| 2526 | 2-Pyrd | 4-ClPh | CO | single bond | 2 | O | CH₂CH₂ | sub. 15 |
| 2527 | 3-Pyrd | 4-ClPh | CO | single bond | 2 | O | CH₂CH₂ | sub. 15 |
| 2528 | 4-Oxa | 4-ClPh | CO | single bond | 2 | O | CH₂CH₂ | sub. 15 |
| 2529 | 5-Oxa | 4-ClPh | CO | single bond | 2 | O | CH₂CH₂ | sub. 15 |
| 2530 | 4-Thi | 4-ClPh | CO | single bond | 2 | O | CH₂CH₂ | sub. 15 |
| 2531 | 5-Thi | 4-ClPh | CO | single bond | 2 | O | CH₂CH₂ | sub. 15 |
| 2532 | 4-OOxa | 4-ClPh | CO | single bond | 2 | O | CH₂CH₂ | sub. 15 |
| 2533 | 5-OOxa | 4-ClPh | CO | single bond | 2 | O | CH₂CH₂ | sub. 15 |
| 2534 | 4-OThi | 4-ClPh | CO | single bond | 2 | O | CH₂CH₂ | sub. 15 |
| 2535 | 5-OThi | 4-ClPh | CO | single bond | 2 | O | CH₂CH₂ | sub. 15 |
| 2536 | 2-Pip | 4-ClPh | CO | single bond | 2 | O | CH₂CH₂ | sub. 15 |
| 2537 | 3-Pip | 4-ClPh | CO | single bond | 2 | O | CH₂CH₂ | sub. 15 |
| 2538 | 4-Pip | 4-ClPh | CO | single bond | 2 | O | CH₂CH₂ | sub. 15 |
| 2539 | 2-Mor | 4-ClPh | CO | single bond | 2 | O | CH₂CH₂ | sub. 15 |
| 2540 | 3-Mor | 4-ClPh | CO | single bond | 2 | O | CH₂CH₂ | sub. 15 |
| 2541 | 4-Mor | 4-ClPh | CO | single bond | 2 | O | CH₂CH₂ | sub. 15 |
| 2542 | 2-Thmor | 4-ClPh | CO | single bond | 2 | O | CH₂CH₂ | sub. 15 |
| 2543 | 3-Thmor | 4-ClPh | CO | single bond | 2 | O | CH₂CH₂ | sub. 15 |
| 2544 | 4-Thmor | 4-ClPh | CO | single bond | 2 | O | CH₂CH₂ | sub. 15 |
| 2545 | 2-Piz | 4-ClPh | CO | single bond | 2 | O | CH₂CH₂ | sub. 15 |
| 2546 | 3-Piz | 4-ClPh | CO | single bond | 2 | O | CH₂CH₂ | sub. 15 |
| 2547 | 4-Piz | 4-ClPh | CO | single bond | 2 | O | CH₂CH₂ | sub. 15 |
| 2548 | 2-Aze | 4-ClPh | CO | single bond | 2 | O | CH₂CH₂ | sub. 15 |
| 2549 | 3-Aze | 4-ClPh | CO | single bond | 2 | O | CH₂CH₂ | sub. 15 |
| 2550 | 4-Aze | 4-ClPh | CO | single bond | 2 | O | CH₂CH₂ | sub. 15 |
| 2551 | cPr | 4-ClPh | CO | single bond | 2 | O | CH₂CH₂ | sub. 16 |
| 2552 | cBu | 4-ClPh | CO | single bond | 2 | O | CH₂CH₂ | sub. 16 |
| 2553 | cPn | 4-ClPh | CO | single bond | 2 | O | CH₂CH₂ | sub. 16 |
| 2554 | cHex | 4-ClPh | CO | single bond | 2 | O | CH₂CH₂ | sub. 16 |
| 2555 | cHep | 4-ClPh | CO | single bond | 2 | O | CH₂CH₂ | sub. 16 |
| 2556 | 2-Pyrd | 4-ClPh | CO | single bond | 2 | O | CH₂CH₂ | sub. 16 |
| 2557 | 3-Pyrd | 4-ClPh | CO | single bond | 2 | O | CH₂CH₂ | sub. 16 |
| 2558 | 4-Oxa | 4-ClPh | CO | single bond | 2 | O | CH₂CH₂ | sub. 16 |
| 2559 | 5-Oxa | 4-ClPh | CO | single bond | 2 | O | CH₂CH₂ | sub. 16 |
| 2560 | 4-Thi | 4-ClPh | CO | single bond | 2 | O | CH₂CH₂ | sub. 16 |
| 2561 | 5-Thi | 4-ClPh | CO | single bond | 2 | O | CH₂CH₂ | sub. 16 |
| 2562 | 4-OOxa | 4-ClPh | CO | single bond | 2 | O | CH₂CH₂ | sub. 16 |
| 2563 | 5-OOxa | 4-ClPh | CO | single bond | 2 | O | CH₂CH₂ | sub. 16 |
| 2564 | 4-OThi | 4-ClPh | CO | single bond | 2 | O | CH₂CH₂ | sub. 16 |

TABLE 1-continued

| Exemplification compound number | R¹ | R² | A | B | N | D | G | Q |
|---|---|---|---|---|---|---|---|---|
| 2565 | 5-OThi | 4-ClPh | CO | single bond | 2 | O | $CH_2CH_2$ | sub. 16 |
| 2566 | 2-Pip | 4-ClPh | CO | single bond | 2 | O | $CH_2CH_2$ | sub. 16 |
| 2567 | 3-Pip | 4-ClPh | CO | single bond | 2 | O | $CH_2CH_2$ | sub. 16 |
| 2568 | 4-Pip | 4-ClPh | CO | single bond | 2 | O | $CH_2CH_2$ | sub. 16 |
| 2569 | 2-Mor | 4-ClPh | CO | single bond | 2 | O | $CH_2CH_2$ | sub. 16 |
| 2570 | 3-Mor | 4-ClPh | CO | single bond | 2 | O | $CH_2CH_2$ | sub. 16 |
| 2571 | 4-Mor | 4-ClPh | CO | single bond | 2 | O | $CH_2CH_2$ | sub. 16 |
| 2572 | 2-Thmor | 4-ClPh | CO | single bond | 2 | O | $CH_2CH_2$ | sub. 16 |
| 2573 | 3-Thmor | 4-ClPh | CO | single bond | 2 | O | $CH_2CH_2$ | sub. 16 |
| 2574 | 4-Thmor | 4-ClPh | CO | single bond | 2 | O | $CH_2CH_2$ | sub. 16 |
| 2575 | 2-Piz | 4-ClPh | CO | single bond | 2 | O | $CH_2CH_2$ | sub. 16 |
| 2576 | 3-Piz | 4-ClPh | CO | single bond | 2 | O | $CH_2CH_2$ | sub. 16 |
| 2577 | 4-Piz | 4-ClPh | CO | single bond | 2 | O | $CH_2CH_2$ | sub. 16 |
| 2578 | 2-Aze | 4-ClPh | CO | single bond | 2 | O | $CH_2CH_2$ | sub. 16 |
| 2579 | 3-Aze | 4-ClPh | CO | single bond | 2 | O | $CH_2CH_2$ | sub. 16 |
| 2580 | 4-Aze | 4-ClPh | CO | single bond | 2 | O | $CH_2CH_2$ | sub. 16 |
| 2581 | cPr | 4-ClPh | CO | single bond | 2 | O | $CH_2CH_2$ | sub. 17 |
| 2582 | cBu | 4-ClPh | CO | single bond | 2 | O | $CH_2CH_2$ | sub. 17 |
| 2583 | cPn | 4-ClPh | CO | single bond | 2 | O | $CH_2CH_2$ | sub. 17 |
| 2584 | cHex | 4-ClPh | CO | single bond | 2 | O | $CH_2CH_2$ | sub. 17 |
| 2585 | cHep | 4-ClPh | CO | single bond | 2 | O | $CH_2CH_2$ | sub. 17 |
| 2586 | 2-Pyrd | 4-ClPh | CO | single bond | 2 | O | $CH_2CH_2$ | sub. 17 |
| 2587 | 3-Pyrd | 4-ClPh | CO | single bond | 2 | O | $CH_2CH_2$ | sub. 17 |
| 2588 | 4-Oxa | 4-ClPh | CO | single bond | 2 | O | $CH_2CH_2$ | sub. 17 |
| 2589 | 5-Oxa | 4-ClPh | CO | single bond | 2 | O | $CH_2CH_2$ | sub. 17 |
| 2590 | 4-Thi | 4-ClPh | CO | single bond | 2 | O | $CH_2CH_2$ | sub. 17 |
| 2591 | 5-Thi | 4-ClPh | CO | single bond | 2 | O | $CH_2CH_2$ | sub. 17 |
| 2592 | 4-OOxa | 4-ClPh | CO | single bond | 2 | O | $CH_2CH_2$ | sub. 17 |
| 2593 | 5-OOxa | 4-ClPh | CO | single bond | 2 | O | $CH_2CH_2$ | sub. 17 |
| 2594 | 4-OThi | 4-ClPh | CO | single bond | 2 | O | $CH_2CH_2$ | sub. 17 |
| 2595 | 5-OThi | 4-ClPh | CO | single bond | 2 | O | $CH_2CH_2$ | sub. 17 |
| 2596 | 2-Pip | 4-ClPh | CO | single bond | 2 | O | $CH_2CH_2$ | sub. 17 |
| 2597 | 3-Pip | 4-ClPh | CO | single bond | 2 | O | $CH_2CH_2$ | sub. 17 |
| 2598 | 4-Pip | 4-ClPh | CO | single bond | 2 | O | $CH_2CH_2$ | sub. 17 |
| 2599 | 2-Mor | 4-ClPh | CO | single bond | 2 | O | $CH_2CH_2$ | sub. 17 |
| 2600 | 3-Mor | 4-ClPh | CO | single bond | 2 | O | $CH_2CH_2$ | sub. 17 |
| 2601 | 4-Mor | 4-ClPh | CO | single bond | 2 | O | $CH_2CH_2$ | sub. 17 |
| 2602 | 2-Thmor | 4-ClPh | CO | single bond | 2 | O | $CH_2CH_2$ | sub. 17 |
| 2603 | 3-Thmor | 4-ClPh | CO | single bond | 2 | O | $CH_2CH_2$ | sub. 17 |
| 2604 | 4-Thmor | 4-ClPh | CO | single bond | 2 | O | $CH_2CH_2$ | sub. 17 |
| 2605 | 2-Piz | 4-ClPh | CO | single bond | 2 | O | $CH_2CH_2$ | sub. 17 |
| 2606 | 3-Piz | 4-ClPh | CO | single bond | 2 | O | $CH_2CH_2$ | sub. 17 |
| 2607 | 4-Piz | 4-ClPh | CO | single bond | 2 | O | $CH_2CH_2$ | sub. 17 |
| 2608 | 2-Aze | 4-ClPh | CO | single bond | 2 | O | $CH_2CH_2$ | sub. 17 |
| 2609 | 3-Aze | 4-ClPh | CO | single bond | 2 | O | $CH_2CH_2$ | sub. 17 |
| 2610 | 4-Aze | 4-ClPh | CO | single bond | 2 | O | $CH_2CH_2$ | sub. 17 |
| 2611 | cPr | 4-ClPh | CO | single bond | 2 | O | $CH_2CH_2$ | sub. 18 |
| 2612 | cBu | 4-ClPh | CO | single bond | 2 | O | $CH_2CH_2$ | sub. 18 |
| 2613 | cPn | 4-ClPh | CO | single bond | 2 | O | $CH_2CH_2$ | sub. 18 |
| 2614 | cHex | 4-ClPh | CO | single bond | 2 | O | $CH_2CH_2$ | sub. 18 |
| 2615 | cHep | 4-ClPh | CO | single bond | 2 | O | $CH_2CH_2$ | sub. 18 |
| 2616 | 2-Pyrd | 4-ClPh | CO | single bond | 2 | O | $CH_2CH_2$ | sub. 18 |
| 2617 | 3-Pyrd | 4-ClPh | CO | single bond | 2 | O | $CH_2CH_2$ | sub. 18 |
| 2618 | 4-Oxa | 4-ClPh | CO | single bond | 2 | O | $CH_2CH_2$ | sub. 18 |
| 2619 | 5-Oxa | 4-ClPh | CO | single bond | 2 | O | $CH_2CH_2$ | sub. 18 |
| 2620 | 4-Thi | 4-ClPh | CO | single bond | 2 | O | $CH_2CH_2$ | sub. 18 |
| 2621 | 5-Thi | 4-ClPh | CO | single bond | 2 | O | $CH_2CH_2$ | sub. 18 |
| 2622 | 4-OOxa | 4-ClPh | CO | single bond | 2 | O | $CH_2CH_2$ | sub. 18 |
| 2623 | 5-OOxa | 4-ClPh | CO | single bond | 2 | O | $CH_2CH_2$ | sub. 18 |
| 2624 | 4-OThi | 4-ClPh | CO | single bond | 2 | O | $CH_2CH_2$ | sub. 18 |
| 2625 | 5-OThi | 4-ClPh | CO | single bond | 2 | O | $CH_2CH_2$ | sub. 18 |
| 2626 | 2-Pip | 4-ClPh | CO | single bond | 2 | O | $CH_2CH_2$ | sub. 18 |
| 2627 | 3-Pip | 4-ClPh | CO | single bond | 2 | O | $CH_2CH_2$ | sub. 18 |
| 2628 | 4-Pip | 4-ClPh | CO | single bond | 2 | O | $CH_2CH_2$ | sub. 18 |
| 2629 | 2-Mor | 4-ClPh | CO | single bond | 2 | O | $CH_2CH_2$ | sub. 18 |
| 2630 | 3-Mor | 4-ClPh | CO | single bond | 2 | O | $CH_2CH_2$ | sub. 18 |
| 2631 | 4-Mor | 4-ClPh | CO | single bond | 2 | O | $CH_2CH_2$ | sub. 18 |
| 2632 | 2-Thmor | 4-ClPh | CO | single bond | 2 | O | $CH_2CH_2$ | sub. 18 |
| 2633 | 3-Thmor | 4-ClPh | CO | single bond | 2 | O | $CH_2CH_2$ | sub. 18 |
| 2634 | 4-Thmor | 4-ClPh | CO | single bond | 2 | O | $CH_2CH_2$ | sub. 18 |
| 2635 | 2-Piz | 4-ClPh | CO | single bond | 2 | O | $CH_2CH_2$ | sub. 18 |
| 2636 | 3-Piz | 4-ClPh | CO | single bond | 2 | O | $CH_2CH_2$ | sub. 18 |
| 2637 | 4-Piz | 4-ClPh | CO | single bond | 2 | O | $CH_2CH_2$ | sub. 18 |
| 2638 | 2-Aze | 4-ClPh | CO | single bond | 2 | O | $CH_2CH_2$ | sub. 18 |
| 2639 | 3-Aze | 4-ClPh | CO | single bond | 2 | O | $CH_2CH_2$ | sub. 18 |
| 2640 | 4-Aze | 4-ClPh | CO | single bond | 2 | O | $CH_2CH_2$ | sub. 18 |

TABLE 1-continued

| Exemplification compound number | R¹ | R² | A | B | N | D | G | Q |
|---|---|---|---|---|---|---|---|---|
| 2641 | cPr | 4-ClPh | CO | single bond | 2 | O | $CH_2CH_2$ | sub. 19 |
| 2642 | cBu | 4-ClPh | CO | single bond | 2 | O | $CH_2CH_2$ | sub. 19 |
| 2643 | cPn | 4-ClPh | CO | single bond | 2 | O | $CH_2CH_2$ | sub. 19 |
| 2644 | cHex | 4-ClPh | CO | single bond | 2 | O | $CH_2CH_2$ | sub. 19 |
| 2645 | cHep | 4-ClPh | CO | single bond | 2 | O | $CH_2CH_2$ | sub. 19 |
| 2646 | 2-Pyrd | 4-ClPh | CO | single bond | 2 | O | $CH_2CH_2$ | sub. 19 |
| 2647 | 3-Pyrd | 4-ClPh | CO | single bond | 2 | O | $CH_2CH_2$ | sub. 19 |
| 2648 | 4-Oxa | 4-ClPh | CO | single bond | 2 | O | $CH_2CH_2$ | sub. 19 |
| 2649 | 5-Oxa | 4-ClPh | CO | single bond | 2 | O | $CH_2CH_2$ | sub. 19 |
| 2650 | 4-Thi | 4-ClPh | CO | single bond | 2 | O | $CH_2CH_2$ | sub. 19 |
| 2651 | 5-Thi | 4-ClPh | CO | single bond | 2 | O | $CH_2CH_2$ | sub. 19 |
| 2652 | 4-OOxa | 4-ClPh | CO | single bond | 2 | O | $CH_2CH_2$ | sub. 19 |
| 2653 | 5-OOxa | 4-ClPh | CO | single bond | 2 | O | $CH_2CH_2$ | sub. 19 |
| 2654 | 4-OThi | 4-ClPh | CO | single bond | 2 | O | $CH_2CH_2$ | sub. 19 |
| 2655 | 5-OThi | 4-ClPh | CO | single bond | 2 | O | $CH_2CH_2$ | sub. 19 |
| 2656 | 2-Pip | 4-ClPh | CO | single bond | 2 | O | $CH_2CH_2$ | sub. 19 |
| 2657 | 3-Pip | 4-ClPh | CO | single bond | 2 | O | $CH_2CH_2$ | sub. 19 |
| 2658 | 4-Pip | 4-ClPh | CO | single bond | 2 | O | $CH_2CH_2$ | sub. 19 |
| 2659 | 2-Mor | 4-ClPh | CO | single bond | 2 | O | $CH_2CH_2$ | sub. 19 |
| 2660 | 3-Mor | 4-ClPh | CO | single bond | 2 | O | $CH_2CH_2$ | sub. 19 |
| 2661 | 4-Mor | 4-ClPh | CO | single bond | 2 | O | $CH_2CH_2$ | sub. 19 |
| 2662 | 2-Thmor | 4-ClPh | CO | single bond | 2 | O | $CH_2CH_2$ | sub. 19 |
| 2663 | 3-Thmor | 4-ClPh | CO | single bond | 2 | O | $CH_2CH_2$ | sub. 19 |
| 2664 | 4-Thmor | 4-ClPh | CO | single bond | 2 | O | $CH_2CH_2$ | sub. 19 |
| 2665 | 2-Piz | 4-ClPh | CO | single bond | 2 | O | $CH_2CH_2$ | sub. 19 |
| 2666 | 3-Piz | 4-ClPh | CO | single bond | 2 | O | $CH_2CH_2$ | sub. 19 |
| 2667 | 4-Piz | 4-ClPh | CO | single bond | 2 | O | $CH_2CH_2$ | sub. 19 |
| 2668 | 2-Aze | 4-ClPh | CO | single bond | 2 | O | $CH_2CH_2$ | sub. 19 |
| 2669 | 3-Aze | 4-ClPh | CO | single bond | 2 | O | $CH_2CH_2$ | sub. 19 |
| 2670 | 4-Aze | 4-ClPh | CO | single bond | 2 | O | $CH_2CH_2$ | sub. 19 |
| 2671 | cPr | 4-ClPh | CO | single bond | 2 | O | $CH_2CH_2$ | sub. 20 |
| 2672 | cBu | 4-ClPh | CO | single bond | 2 | O | $CH_2CH_2$ | sub. 20 |
| 2673 | cPn | 4-ClPh | CO | single bond | 2 | O | $CH_2CH_2$ | sub. 20 |
| 2674 | cHex | 4-ClPh | CO | single bond | 2 | O | $CH_2CH_2$ | sub. 20 |
| 2675 | cHep | 4-ClPh | CO | single bond | 2 | O | $CH_2CH_2$ | sub. 20 |
| 2676 | 2-Pyrd | 4-ClPh | CO | single bond | 2 | O | $CH_2CH_2$ | sub. 20 |
| 2677 | 3-Pyrd | 4-ClPh | CO | single bond | 2 | O | $CH_2CH_2$ | sub. 20 |
| 2678 | 4-Oxa | 4-ClPh | CO | single bond | 2 | O | $CH_2CH_2$ | sub. 20 |
| 2679 | 5-Oxa | 4-ClPh | CO | single bond | 2 | O | $CH_2CH_2$ | sub. 20 |
| 2680 | 4-Thi | 4-ClPh | CO | single bond | 2 | O | $CH_2CH_2$ | sub. 20 |
| 2681 | 5-Thi | 4-ClPh | CO | single bond | 2 | O | $CH_2CH_2$ | sub. 20 |
| 2682 | 4-OOxa | 4-ClPh | CO | single bond | 2 | O | $CH_2CH_2$ | sub. 20 |
| 2683 | 5-OOxa | 4-ClPh | CO | single bond | 2 | O | $CH_2CH_2$ | sub. 20 |
| 2684 | 4-OThi | 4-ClPh | CO | single bond | 2 | O | $CH_2CH_2$ | sub. 20 |
| 2685 | 5-OThi | 4-ClPh | CO | single bond | 2 | O | $CH_2CH_2$ | sub. 20 |
| 2686 | 2-Pip | 4-ClPh | CO | single bond | 2 | O | $CH_2CH_2$ | sub. 20 |
| 2687 | 3-Pip | 4-ClPh | CO | single bond | 2 | O | $CH_2CH_2$ | sub. 20 |
| 2688 | 4-Pip | 4-ClPh | CO | single bond | 2 | O | $CH_2CH_2$ | sub. 20 |
| 2689 | 2-Mor | 4-ClPh | CO | single bond | 2 | O | $CH_2CH_2$ | sub. 20 |
| 2690 | 3-Mor | 4-ClPh | CO | single bond | 2 | O | $CH_2CH_2$ | sub. 20 |
| 2691 | 4-Mor | 4-ClPh | CO | single bond | 2 | O | $CH_2CH_2$ | sub. 20 |
| 2692 | 2-Thmor | 4-ClPh | CO | single bond | 2 | O | $CH_2CH_2$ | sub. 20 |
| 2693 | 3-Thmor | 4-ClPh | CO | single bond | 2 | O | $CH_2CH_2$ | sub. 20 |
| 2694 | 4-Thmor | 4-ClPh | CO | single bond | 2 | O | $CH_2CH_2$ | sub. 20 |
| 2695 | 2-Piz | 4-ClPh | CO | single bond | 2 | O | $CH_2CH_2$ | sub. 20 |
| 2696 | 3-Piz | 4-ClPh | CO | single bond | 2 | O | $CH_2CH_2$ | sub. 20 |
| 2697 | 4-Piz | 4-ClPh | CO | single bond | 2 | O | $CH_2CH_2$ | sub. 20 |
| 2698 | 2-Aze | 4-ClPh | CO | single bond | 2 | O | $CH_2CH_2$ | sub. 20 |
| 2699 | 3-Aze | 4-ClPh | CO | single bond | 2 | O | $CH_2CH_2$ | sub. 20 |
| 2700 | 4-Aze | 4-ClPh | CO | single bond | 2 | O | $CH_2CH_2$ | sub. 20 |
| 2701 | cPr | 4-ClPh | CO | single bond | 2 | O | $CH_2CH_2$ | sub. 21 |
| 2702 | cBu | 4-ClPh | CO | single bond | 2 | O | $CH_2CH_2$ | sub. 21 |
| 2703 | cPn | 4-ClPh | CO | single bond | 2 | O | $CH_2CH_2$ | sub. 21 |
| 2704 | cHex | 4-ClPh | CO | single bond | 2 | O | $CH_2CH_2$ | sub. 21 |
| 2705 | cHep | 4-ClPh | CO | single bond | 2 | O | $CH_2CH_2$ | sub. 21 |
| 2706 | 2-Pyrd | 4-ClPh | CO | single bond | 2 | O | $CH_2CH_2$ | sub. 21 |
| 2707 | 3-Pyrd | 4-ClPh | CO | single bond | 2 | O | $CH_2CH_2$ | sub. 21 |
| 2708 | 4-Oxa | 4-ClPh | CO | single bond | 2 | O | $CH_2CH_2$ | sub. 21 |
| 2709 | 5-Oxa | 4-ClPh | CO | single bond | 2 | O | $CH_2CH_2$ | sub. 21 |
| 2710 | 4-Thi | 4-ClPh | CO | single bond | 2 | O | $CH_2CH_2$ | sub. 21 |
| 2711 | 5-Thi | 4-ClPh | CO | single bond | 2 | O | $CH_2CH_2$ | sub. 21 |
| 2712 | 4-OOxa | 4-ClPh | CO | single bond | 2 | O | $CH_2CH_2$ | sub. 21 |
| 2713 | 5-OOxa | 4-ClPh | CO | single bond | 2 | O | $CH_2CH_2$ | sub. 21 |
| 2714 | 4-OThi | 4-ClPh | CO | single bond | 2 | O | $CH_2CH_2$ | sub. 21 |
| 2715 | 5-OThi | 4-ClPh | CO | single bond | 2 | O | $CH_2CH_2$ | sub. 21 |
| 2716 | 2-Pip | 4-ClPh | CO | single bond | 2 | O | $CH_2CH_2$ | sub. 21 |

TABLE 1-continued

| Exemplification compound number | R¹ | R² | A | B | N | D | G | Q |
|---|---|---|---|---|---|---|---|---|
| 2717 | 3-Pip | 4-ClPh | CO | single bond | 2 | O | $CH_2CH_2$ | sub. 21 |
| 2718 | 4-Pip | 4-ClPh | CO | single bond | 2 | O | $CH_2CH_2$ | sub. 21 |
| 2719 | 2-Mor | 4-ClPh | CO | single bond | 2 | O | $CH_2CH_2$ | sub. 21 |
| 2720 | 3-Mor | 4-ClPh | CO | single bond | 2 | O | $CH_2CH_2$ | sub. 21 |
| 2721 | 4-Mor | 4-ClPh | CO | single bond | 2 | O | $CH_2CH_2$ | sub. 21 |
| 2722 | 2-Thmor | 4-ClPh | CO | single bond | 2 | O | $CH_2CH_2$ | sub. 21 |
| 2723 | 3-Thmor | 4-ClPh | CO | single bond | 2 | O | $CH_2CH_2$ | sub. 21 |
| 2724 | 4-Thmor | 4-ClPh | CO | single bond | 2 | O | $CH_2CH_2$ | sub. 21 |
| 2725 | 2-Piz | 4-ClPh | CO | single bond | 2 | O | $CH_2CH_2$ | sub. 21 |
| 2726 | 3-Piz | 4-ClPh | CO | single bond | 2 | O | $CH_2CH_2$ | sub. 21 |
| 2727 | 4-Piz | 4-ClPh | CO | single bond | 2 | O | $CH_2CH_2$ | sub. 21 |
| 2728 | 2-Aze | 4-ClPh | CO | single bond | 2 | O | $CH_2CH_2$ | sub. 21 |
| 2729 | 3-Aze | 4-ClPh | CO | single bond | 2 | O | $CH_2CH_2$ | sub. 21 |
| 2730 | 4-Aze | 4-ClPh | CO | single bond | 2 | O | $CH_2CH_2$ | sub. 21 |
| 2731 | cPr | 4-ClPh | CO | single bond | 2 | O | $CH_2CH_2$ | sub. 22 |
| 2732 | cBu | 4-ClPh | CO | single bond | 2 | O | $CH_2CH_2$ | sub. 22 |
| 2733 | cPn | 4-ClPh | CO | single bond | 2 | O | $CH_2CH_2$ | sub. 22 |
| 2734 | cHex | 4-ClPh | CO | single bond | 2 | O | $CH_2CH_2$ | sub. 22 |
| 2735 | cHep | 4-ClPh | CO | single bond | 2 | O | $CH_2CH_2$ | sub. 22 |
| 2736 | 2-Pyrd | 4-ClPh | CO | single bond | 2 | O | $CH_2CH_2$ | sub. 22 |
| 2737 | 3-Pyrd | 4-ClPh | CO | single bond | 2 | O | $CH_2CH_2$ | sub. 22 |
| 2738 | 4-Oxa | 4-ClPh | CO | single bond | 2 | O | $CH_2CH_2$ | sub. 22 |
| 2739 | 5-Oxa | 4-ClPh | CO | single bond | 2 | O | $CH_2CH_2$ | sub. 22 |
| 2740 | 4-Thi | 4-ClPh | CO | single bond | 2 | O | $CH_2CH_2$ | sub. 22 |
| 2741 | 5-Thi | 4-ClPh | CO | single bond | 2 | O | $CH_2CH_2$ | sub. 22 |
| 2742 | 4-OOxa | 4-ClPh | CO | single bond | 2 | O | $CH_2CH_2$ | sub. 22 |
| 2743 | 5-OOxa | 4-ClPh | CO | single bond | 2 | O | $CH_2CH_2$ | sub. 22 |
| 2744 | 4-OThi | 4-ClPh | CO | single bond | 2 | O | $CH_2CH_2$ | sub. 22 |
| 2745 | 5-OThi | 4-ClPh | CO | single bond | 2 | O | $CH_2CH_2$ | sub. 22 |
| 2746 | 2-Pip | 4-ClPh | CO | single bond | 2 | O | $CH_2CH_2$ | sub. 22 |
| 2747 | 3-Pip | 4-ClPh | CO | single bond | 2 | O | $CH_2CH_2$ | sub. 22 |
| 2748 | 4-Pip | 4-ClPh | CO | single bond | 2 | O | $CH_2CH_2$ | sub. 22 |
| 2749 | 2-Mor | 4-ClPh | CO | single bond | 2 | O | $CH_2CH_2$ | sub. 22 |
| 2750 | 3-Mor | 4-ClPh | CO | single bond | 2 | O | $CH_2CH_2$ | sub. 22 |
| 2751 | 4-Mor | 4-ClPh | CO | single bond | 2 | O | $CH_2CH_2$ | sub. 22 |
| 2752 | 2-Thmor | 4-ClPh | CO | single bond | 2 | O | $CH_2CH_2$ | sub. 22 |
| 2753 | 3-Thmor | 4-ClPh | CO | single bond | 2 | O | $CH_2CH_2$ | sub. 22 |
| 2754 | 4-Thmor | 4-ClPh | CO | single bond | 2 | O | $CH_2CH_2$ | sub. 22 |
| 2755 | 2-Piz | 4-ClPh | CO | single bond | 2 | O | $CH_2CH_2$ | sub. 22 |
| 2756 | 3-Piz | 4-ClPh | CO | single bond | 2 | O | $CH_2CH_2$ | sub. 22 |
| 2757 | 4-Piz | 4-ClPh | CO | single bond | 2 | O | $CH_2CH_2$ | sub. 22 |
| 2758 | 2-Aze | 4-ClPh | CO | single bond | 2 | O | $CH_2CH_2$ | sub. 22 |
| 2759 | 3-Aze | 4-ClPh | CO | single bond | 2 | O | $CH_2CH_2$ | sub. 22 |
| 2760 | 4-Aze | 4-ClPh | CO | single bond | 2 | O | $CH_2CH_2$ | sub. 22 |
| 2761 | cPr | 4-ClPh | CO | single bond | 2 | O | $CH_2CH_2$ | sub. 23 |
| 2762 | cBu | 4-ClPh | CO | single bond | 2 | O | $CH_2CH_2$ | sub. 23 |
| 2763 | cPn | 4-ClPh | CO | single bond | 2 | O | $CH_2CH_2$ | sub. 23 |
| 2764 | cHex | 4-ClPh | CO | single bond | 2 | O | $CH_2CH_2$ | sub. 23 |
| 2765 | cHep | 4-ClPh | CO | single bond | 2 | O | $CH_2CH_2$ | sub. 23 |
| 2766 | 2-Pyrd | 4-ClPh | CO | single bond | 2 | O | $CH_2CH_2$ | sub. 23 |
| 2767 | 3-Pyrd | 4-ClPh | CO | single bond | 2 | O | $CH_2CH_2$ | sub. 23 |
| 2768 | 4-Oxa | 4-ClPh | CO | single bond | 2 | O | $CH_2CH_2$ | sub. 23 |
| 2769 | 5-Oxa | 4-ClPh | CO | single bond | 2 | O | $CH_2CH_2$ | sub. 23 |
| 2770 | 4-Thi | 4-ClPh | CO | single bond | 2 | O | $CH_2CH_2$ | sub. 23 |
| 2771 | 5-Thi | 4-ClPh | CO | single bond | 2 | O | $CH_2CH_2$ | sub. 23 |
| 2772 | 4-OOxa | 4-ClPh | CO | single bond | 2 | O | $CH_2CH_2$ | sub. 23 |
| 2773 | 5-OOxa | 4-ClPh | CO | single bond | 2 | O | $CH_2CH_2$ | sub. 23 |
| 2774 | 4-OThi | 4-ClPh | CO | single bond | 2 | O | $CH_2CH_2$ | sub. 23 |
| 2775 | 5-OThi | 4-ClPh | CO | single bond | 2 | O | $CH_2CH_2$ | sub. 23 |
| 2776 | 2-Pip | 4-ClPh | CO | single bond | 2 | O | $CH_2CH_2$ | sub. 23 |
| 2777 | 3-Pip | 4-ClPh | CO | single bond | 2 | O | $CH_2CH_2$ | sub. 23 |
| 2778 | 4-Pip | 4-ClPh | CO | single bond | 2 | O | $CH_2CH_2$ | sub. 23 |
| 2779 | 2-Mor | 4-ClPh | CO | single bond | 2 | O | $CH_2CH_2$ | sub. 23 |
| 2780 | 3-Mor | 4-ClPh | CO | single bond | 2 | O | $CH_2CH_2$ | sub. 23 |
| 2781 | 4-Mor | 4-ClPh | CO | single bond | 2 | O | $CH_2CH_2$ | sub. 23 |
| 2782 | 2-Thmor | 4-ClPh | CO | single bond | 2 | O | $CH_2CH_2$ | sub. 23 |
| 2783 | 3-Thmor | 4-ClPh | CO | single bond | 2 | O | $CH_2CH_2$ | sub. 23 |
| 2784 | 4-Thmor | 4-ClPh | CO | single bond | 2 | O | $CH_2CH_2$ | sub. 23 |
| 2785 | 2-Piz | 4-ClPh | CO | single bond | 2 | O | $CH_2CH_2$ | sub. 23 |
| 2786 | 3-Piz | 4-ClPh | CO | single bond | 2 | O | $CH_2CH_2$ | sub. 23 |
| 2787 | 4-Piz | 4-ClPh | CO | single bond | 2 | O | $CH_2CH_2$ | sub. 23 |
| 2788 | 2-Aze | 4-ClPh | CO | single bond | 2 | O | $CH_2CH_2$ | sub. 23 |
| 2789 | 3-Aze | 4-ClPh | CO | single bond | 2 | O | $CH_2CH_2$ | sub. 23 |
| 2790 | 4-Aze | 4-ClPh | CO | single bond | 2 | O | $CH_2CH_2$ | sub. 23 |
| 2791 | cPr | 4-ClPh | CO | single bond | 2 | O | $CH_2CH_2$ | sub. 24 |
| 2792 | cBu | 4-ClPh | CO | single bond | 2 | O | $CH_2CH_2$ | sub. 24 |

TABLE 1-continued

| Exemplification compound number | R¹ | R² | A | B | N | D | G | Q |
|---|---|---|---|---|---|---|---|---|
| 2793 | cPn | 4-ClPh | CO | single bond | 2 | O | CH₂CH₂ | sub. 24 |
| 2794 | cHex | 4-ClPh | CO | single bond | 2 | O | CH₂CH₂ | sub. 24 |
| 2795 | cHep | 4-ClPh | CO | single bond | 2 | O | CH₂CH₂ | sub. 24 |
| 2796 | 2-Pyrd | 4-ClPh | CO | single bond | 2 | O | CH₂CH₂ | sub. 24 |
| 2797 | 3-Pyrd | 4-ClPh | CO | single bond | 2 | O | CH₂CH₂ | sub. 24 |
| 2798 | 4-Oxa | 4-ClPh | CO | single bond | 2 | O | CH₂CH₂ | sub. 24 |
| 2799 | 5-Oxa | 4-ClPh | CO | single bond | 2 | O | CH₂CH₂ | sub. 24 |
| 2800 | 4-Thi | 4-ClPh | CO | single bond | 2 | O | CH₂CH₂ | sub. 24 |
| 2801 | 5-Thi | 4-ClPh | CO | single bond | 2 | O | CH₂CH₂ | sub. 24 |
| 2802 | 4-OOxa | 4-ClPh | CO | single bond | 2 | O | CH₂CH₂ | sub. 24 |
| 2803 | 5-OOxa | 4-ClPh | CO | single bond | 2 | O | CH₂CH₂ | sub. 24 |
| 2804 | 4-OThi | 4-ClPh | CO | single bond | 2 | O | CH₂CH₂ | sub. 24 |
| 2805 | 5-OThi | 4-ClPh | CO | single bond | 2 | O | CH₂CH₂ | sub. 24 |
| 2806 | 2-Pip | 4-ClPh | CO | single bond | 2 | O | CH₂CH₂ | sub. 24 |
| 2807 | 3-Pip | 4-ClPh | CO | single bond | 2 | O | CH₂CH₂ | sub. 24 |
| 2808 | 4-Pip | 4-ClPh | CO | single bond | 2 | O | CH₂CH₂ | sub. 24 |
| 2809 | 2-Mor | 4-ClPh | CO | single bond | 2 | O | CH₂CH₂ | sub. 24 |
| 2810 | 3-Mor | 4-ClPh | CO | single bond | 2 | O | CH₂CH₂ | sub. 24 |
| 2811 | 4-Mor | 4-ClPh | CO | single bond | 2 | O | CH₂CH₂ | sub. 24 |
| 2812 | 2-Thmor | 4-ClPh | CO | single bond | 2 | O | CH₂CH₂ | sub. 24 |
| 2813 | 3-Thmor | 4-ClPh | CO | single bond | 2 | O | CH₂CH₂ | sub. 24 |
| 2814 | 4-Thmor | 4-ClPh | CO | single bond | 2 | O | CH₂CH₂ | sub. 24 |
| 2815 | 2-Piz | 4-ClPh | CO | single bond | 2 | O | CH₂CH₂ | sub. 24 |
| 2816 | 3-Piz | 4-ClPh | CO | single bond | 2 | O | CH₂CH₂ | sub. 24 |
| 2817 | 4-Piz | 4-ClPh | CO | single bond | 2 | O | CH₂CH₂ | sub. 24 |
| 2818 | 2-Aze | 4-ClPh | CO | single bond | 2 | O | CH₂CH₂ | sub. 24 |
| 2819 | 3-Aze | 4-ClPh | CO | single bond | 2 | O | CH₂CH₂ | sub. 24 |
| 2820 | 4-Aze | 4-ClPh | CO | single bond | 2 | O | CH₂CH₂ | sub. 24 |
| 2821 | cPr | 4-ClPh | CO | single bond | 2 | O | CH₂CH₂ | sub. 25 |
| 2822 | cBu | 4-ClPh | CO | single bond | 2 | O | CH₂CH₂ | sub. 25 |
| 2823 | cPn | 4-ClPh | CO | single bond | 2 | O | CH₂CH₂ | sub. 25 |
| 2824 | cHex | 4-ClPh | CO | single bond | 2 | O | CH₂CH₂ | sub. 25 |
| 2825 | cHep | 4-ClPh | CO | single bond | 2 | O | CH₂CH₂ | sub. 25 |
| 2826 | 2-Pyrd | 4-ClPh | CO | single bond | 2 | O | CH₂CH₂ | sub. 25 |
| 2827 | 3-Pyrd | 4-ClPh | CO | single bond | 2 | O | CH₂CH₂ | sub. 25 |
| 2828 | 4-Oxa | 4-ClPh | CO | single bond | 2 | O | CH₂CH₂ | sub. 25 |
| 2829 | 5-Oxa | 4-ClPh | CO | single bond | 2 | O | CH₂CH₂ | sub. 25 |
| 2830 | 4-Thi | 4-ClPh | CO | single bond | 2 | O | CH₂CH₂ | sub. 25 |
| 2831 | 5-Thi | 4-ClPh | CO | single bond | 2 | O | CH₂CH₂ | sub. 25 |
| 2832 | 4-OOxa | 4-ClPh | CO | single bond | 2 | O | CH₂CH₂ | sub. 25 |
| 2833 | 5-OOxa | 4-ClPh | CO | single bond | 2 | O | CH₂CH₂ | sub. 25 |
| 2834 | 4-OThi | 4-ClPh | CO | single bond | 2 | O | CH₂CH₂ | sub. 25 |
| 2835 | 5-OThi | 4-ClPh | CO | single bond | 2 | O | CH₂CH₂ | sub. 25 |
| 2836 | 2-Pip | 4-ClPh | CO | single bond | 2 | O | CH₂CH₂ | sub. 25 |
| 2837 | 3-Pip | 4-ClPh | CO | single bond | 2 | O | CH₂CH₂ | sub. 25 |
| 2838 | 4-Pip | 4-ClPh | CO | single bond | 2 | O | CH₂CH₂ | sub. 25 |
| 2839 | 2-Mor | 4-ClPh | CO | single bond | 2 | O | CH₂CH₂ | sub. 25 |
| 2840 | 3-Mor | 4-ClPh | CO | single bond | 2 | O | CH₂CH₂ | sub. 25 |
| 2841 | 4-Mor | 4-ClPh | CO | single bond | 2 | O | CH₂CH₂ | sub. 25 |
| 2842 | 2-Thmor | 4-ClPh | CO | single bond | 2 | O | CH₂CH₂ | sub. 25 |
| 2843 | 3-Thmor | 4-ClPh | CO | single bond | 2 | O | CH₂CH₂ | sub. 25 |
| 2844 | 4-Thmor | 4-ClPh | CO | single bond | 2 | O | CH₂CH₂ | sub. 25 |
| 2845 | 2-Piz | 4-ClPh | CO | single bond | 2 | O | CH₂CH₂ | sub. 25 |
| 2846 | 3-Piz | 4-ClPh | CO | single bond | 2 | O | CH₂CH₂ | sub. 25 |
| 2847 | 4-Piz | 4-ClPh | CO | single bond | 2 | O | CH₂CH₂ | sub. 25 |
| 2848 | 2-Aze | 4-ClPh | CO | single bond | 2 | O | CH₂CH₂ | sub. 25 |
| 2849 | 3-Aze | 4-ClPh | CO | single bond | 2 | O | CH₂CH₂ | sub. 25 |
| 2850 | 4-Aze | 4-ClPh | CO | single bond | 2 | O | CH₂CH₂ | sub. 25 |
| 2851 | cPr | 4-ClPh | CO | single bond | 2 | O | CH₂CH₂ | sub. 26 |
| 2852 | cBu | 4-ClPh | CO | single bond | 2 | O | CH₂CH₂ | sub. 26 |
| 2853 | cPn | 4-ClPh | CO | single bond | 2 | O | CH₂CH₂ | sub. 26 |
| 2854 | cHex | 4-ClPh | CO | single bond | 2 | O | CH₂CH₂ | sub. 26 |
| 2855 | cHep | 4-ClPh | CO | single bond | 2 | O | CH₂CH₂ | sub. 26 |
| 2856 | 2-Pyrd | 4-ClPh | CO | single bond | 2 | O | CH₂CH₂ | sub. 26 |
| 2857 | 3-Pyrd | 4-ClPh | CO | single bond | 2 | O | CH₂CH₂ | sub. 26 |
| 2858 | 4-Oxa | 4-ClPh | CO | single bond | 2 | O | CH₂CH₂ | sub. 26 |
| 2859 | 5-Oxa | 4-ClPh | CO | single bond | 2 | O | CH₂CH₂ | sub. 26 |
| 2860 | 4-Thi | 4-ClPh | CO | single bond | 2 | O | CH₂CH₂ | sub. 26 |
| 2861 | 5-Thi | 4-ClPh | CO | single bond | 2 | O | CH₂CH₂ | sub. 26 |
| 2862 | 4-OOxa | 4-ClPh | CO | single bond | 2 | O | CH₂CH₂ | sub. 26 |
| 2863 | 5-OOxa | 4-ClPh | CO | single bond | 2 | O | CH₂CH₂ | sub. 26 |
| 2864 | 4-OThi | 4-ClPh | CO | single bond | 2 | O | CH₂CH₂ | sub. 26 |
| 2865 | 5-OThi | 4-ClPh | CO | single bond | 2 | O | CH₂CH₂ | sub. 26 |
| 2866 | 2-Pip | 4-ClPh | CO | single bond | 2 | O | CH₂CH₂ | sub. 26 |
| 2867 | 3-Pip | 4-ClPh | CO | single bond | 2 | O | CH₂CH₂ | sub. 26 |
| 2868 | 4-Pip | 4-ClPh | CO | single bond | 2 | O | CH₂CH₂ | sub. 26 |

TABLE 1-continued

| Exemplification compound number | R¹ | R² | A | B | N | D | G | Q |
|---|---|---|---|---|---|---|---|---|
| 2869 | 2-Mor | 4-ClPh | CO | single bond | 2 | O | $CH_2CH_2$ | sub. 26 |
| 2870 | 3-Mor | 4-ClPh | CO | single bond | 2 | O | $CH_2CH_2$ | sub. 26 |
| 2871 | 4-Mor | 4-ClPh | CO | single bond | 2 | O | $CH_2CH_2$ | sub. 26 |
| 2872 | 2-Thmor | 4-ClPh | CO | single bond | 2 | O | $CH_2CH_2$ | sub. 26 |
| 2873 | 3-Thmor | 4-ClPh | CO | single bond | 2 | O | $CH_2CH_2$ | sub. 26 |
| 2874 | 4-Thmor | 4-ClPh | CO | single bond | 2 | O | $CH_2CH_2$ | sub. 26 |
| 2875 | 2-Piz | 4-ClPh | CO | single bond | 2 | O | $CH_2CH_2$ | sub. 26 |
| 2876 | 3-Piz | 4-ClPh | CO | single bond | 2 | O | $CH_2CH_2$ | sub. 26 |
| 2877 | 4-Piz | 4-ClPh | CO | single bond | 2 | O | $CH_2CH_2$ | sub. 26 |
| 2878 | 2-Aze | 4-ClPh | CO | single bond | 2 | O | $CH_2CH_2$ | sub. 26 |
| 2879 | 3-Aze | 4-ClPh | CO | single bond | 2 | O | $CH_2CH_2$ | sub. 26 |
| 2880 | 4-Aze | 4-ClPh | CO | single bond | 2 | O | $CH_2CH_2$ | sub. 26 |
| 2881 | cPr | 4-ClPh | CO | single bond | 2 | O | $CH_2CH_2$ | sub. 27 |
| 2882 | cBu | 4-ClPh | CO | single bond | 2 | O | $CH_2CH_2$ | sub. 27 |
| 2883 | cPn | 4-ClPh | CO | single bond | 2 | O | $CH_2CH_2$ | sub. 27 |
| 2884 | cHex | 4-ClPh | CO | single bond | 2 | O | $CH_2CH_2$ | sub. 27 |
| 2885 | cHep | 4-ClPh | CO | single bond | 2 | O | $CH_2CH_2$ | sub. 27 |
| 2886 | 2-Pyrd | 4-ClPh | CO | single bond | 2 | O | $CH_2CH_2$ | sub. 27 |
| 2887 | 3-Pyrd | 4-ClPh | CO | single bond | 2 | O | $CH_2CH_2$ | sub. 27 |
| 2888 | 4-Oxa | 4-ClPh | CO | single bond | 2 | O | $CH_2CH_2$ | sub. 27 |
| 2889 | 5-Oxa | 4-ClPh | CO | single bond | 2 | O | $CH_2CH_2$ | sub. 27 |
| 2890 | 4-Thi | 4-ClPh | CO | single bond | 2 | O | $CH_2CH_2$ | sub. 27 |
| 2891 | 5-Thi | 4-ClPh | CO | single bond | 2 | O | $CH_2CH_2$ | sub. 27 |
| 2892 | 4-OOxa | 4-ClPh | CO | single bond | 2 | O | $CH_2CH_2$ | sub. 27 |
| 2893 | 5-OOxa | 4-ClPh | CO | single bond | 2 | O | $CH_2CH_2$ | sub. 27 |
| 2894 | 4-OThi | 4-ClPh | CO | single bond | 2 | O | $CH_2CH_2$ | sub. 27 |
| 2895 | 5-OThi | 4-ClPh | CO | single bond | 2 | O | $CH_2CH_2$ | sub. 27 |
| 2896 | 2-Pip | 4-ClPh | CO | single bond | 2 | O | $CH_2CH_2$ | sub. 27 |
| 2897 | 3-Pip | 4-ClPh | CO | single bond | 2 | O | $CH_2CH_2$ | sub. 27 |
| 2898 | 4-Pip | 4-ClPh | CO | single bond | 2 | O | $CH_2CH_2$ | sub. 27 |
| 2899 | 2-Mor | 4-ClPh | CO | single bond | 2 | O | $CH_2CH_2$ | sub. 27 |
| 2900 | 3-Mor | 4-ClPh | CO | single bond | 2 | O | $CH_2CH_2$ | sub. 27 |
| 2901 | 4-Mor | 4-ClPh | CO | single bond | 2 | O | $CH_2CH_2$ | sub. 27 |
| 2902 | 2-Thmor | 4-ClPh | CO | single bond | 2 | O | $CH_2CH_2$ | sub. 27 |
| 2903 | 3-Thmor | 4-ClPh | CO | single bond | 2 | O | $CH_2CH_2$ | sub. 27 |
| 2904 | 4-Thmor | 4-ClPh | CO | single bond | 2 | O | $CH_2CH_2$ | sub. 27 |
| 2905 | 2-Piz | 4-ClPh | CO | single bond | 2 | O | $CH_2CH_2$ | sub. 27 |
| 2906 | 3-Piz | 4-ClPh | CO | single bond | 2 | O | $CH_2CH_2$ | sub. 27 |
| 2907 | 4-Piz | 4-ClPh | CO | single bond | 2 | O | $CH_2CH_2$ | sub. 27 |
| 2908 | 2-Aze | 4-ClPh | CO | single bond | 2 | O | $CH_2CH_2$ | sub. 27 |
| 2909 | 3-Aze | 4-ClPh | CO | single bond | 2 | O | $CH_2CH_2$ | sub. 27 |
| 2910 | 4-Aze | 4-ClPh | CO | single bond | 2 | O | $CH_2CH_2$ | sub. 27 |
| 2911 | cPr | 4-ClPh | CO | single bond | 2 | O | $CH_2CH_2$ | sub. 28 |
| 2912 | cBu | 4-ClPh | CO | single bond | 2 | O | $CH_2CH_2$ | sub. 28 |
| 2913 | cPn | 4-ClPh | CO | single bond | 2 | O | $CH_2CH_2$ | sub. 28 |
| 2914 | cHex | 4-ClPh | CO | single bond | 2 | O | $CH_2CH_2$ | sub. 28 |
| 2915 | cHep | 4-ClPh | CO | single bond | 2 | O | $CH_2CH_2$ | sub. 28 |
| 2916 | 2-Pyrd | 4-ClPh | CO | single bond | 2 | O | $CH_2CH_2$ | sub. 28 |
| 2917 | 3-Pyrd | 4-ClPh | CO | single bond | 2 | O | $CH_2CH_2$ | sub. 28 |
| 2918 | 4-Oxa | 4-ClPh | CO | single bond | 2 | O | $CH_2CH_2$ | sub. 28 |
| 2919 | 5-Oxa | 4-ClPh | CO | single bond | 2 | O | $CH_2CH_2$ | sub. 28 |
| 2920 | 4-Thi | 4-ClPh | CO | single bond | 2 | O | $CH_2CH_2$ | sub. 28 |
| 2921 | 5-Thi | 4-ClPh | CO | single bond | 2 | O | $CH_2CH_2$ | sub. 28 |
| 2922 | 4-OOxa | 4-ClPh | CO | single bond | 2 | O | $CH_2CH_2$ | sub. 28 |
| 2923 | 5-OOxa | 4-ClPh | CO | single bond | 2 | O | $CH_2CH_2$ | sub. 28 |
| 2924 | 4-OThi | 4-ClPh | CO | single bond | 2 | O | $CH_2CH_2$ | sub. 28 |
| 2925 | 5-OThi | 4-ClPh | CO | single bond | 2 | O | $CH_2CH_2$ | sub. 28 |
| 2926 | 2-Pip | 4-ClPh | CO | single bond | 2 | O | $CH_2CH_2$ | sub. 28 |
| 2927 | 3-Pip | 4-ClPh | CO | single bond | 2 | O | $CH_2CH_2$ | sub. 28 |
| 2928 | 4-Pip | 4-ClPh | CO | single bond | 2 | O | $CH_2CH_2$ | sub. 28 |
| 2929 | 2-Mor | 4-ClPh | CO | single bond | 2 | O | $CH_2CH_2$ | sub. 28 |
| 2930 | 3-Mor | 4-ClPh | CO | single bond | 2 | O | $CH_2CH_2$ | sub. 28 |
| 2931 | 4-Mor | 4-ClPh | CO | single bond | 2 | O | $CH_2CH_2$ | sub. 28 |
| 2932 | 2-Thmor | 4-ClPh | CO | single bond | 2 | O | $CH_2CH_2$ | sub. 28 |
| 2933 | 3-Thmor | 4-ClPh | CO | single bond | 2 | O | $CH_2CH_2$ | sub. 28 |
| 2934 | 4-Thmor | 4-ClPh | CO | single bond | 2 | O | $CH_2CH_2$ | sub. 28 |
| 2935 | 2-Piz | 4-ClPh | CO | single bond | 2 | O | $CH_2CH_2$ | sub. 28 |
| 2936 | 3-Piz | 4-ClPh | CO | single bond | 2 | O | $CH_2CH_2$ | sub. 28 |
| 2937 | 4-Piz | 4-ClPh | CO | single bond | 2 | O | $CH_2CH_2$ | sub. 28 |
| 2938 | 2-Aze | 4-ClPh | CO | single bond | 2 | O | $CH_2CH_2$ | sub. 28 |
| 2939 | 3-Aze | 4-ClPh | CO | single bond | 2 | O | $CH_2CH_2$ | sub. 28 |
| 2940 | 4-Aze | 4-ClPh | CO | single bond | 2 | O | $CH_2CH_2$ | sub. 28 |
| 2941 | cPr | 4-ClPh | CO | single bond | 2 | O | $CH_2CH_2$ | sub. 29 |
| 2942 | cBu | 4-ClPh | CO | single bond | 2 | O | $CH_2CH_2$ | sub. 29 |
| 2943 | cPn | 4-ClPh | CO | single bond | 2 | O | $CH_2CH_2$ | sub. 29 |
| 2944 | cHex | 4-ClPh | CO | single bond | 2 | O | $CH_2CH_2$ | sub. 29 |

TABLE 1-continued

| Exemplification compound number | R¹ | R² | A | B | N | D | G | Q |
|---|---|---|---|---|---|---|---|---|
| 2945 | cHep | 4-ClPh | CO | single bond | 2 | O | CH$_2$CH$_2$ | sub. 29 |
| 2946 | 2-Pyrd | 4-ClPh | CO | single bond | 2 | O | CH$_2$CH$_2$ | sub. 29 |
| 2947 | 3-Pyrd | 4-ClPh | CO | single bond | 2 | O | CH$_2$CH$_2$ | sub. 29 |
| 2948 | 4-Oxa | 4-ClPh | CO | single bond | 2 | O | CH$_2$CH$_2$ | sub. 29 |
| 2949 | 5-Oxa | 4-ClPh | CO | single bond | 2 | O | CH$_2$CH$_2$ | sub. 29 |
| 2950 | 4-Thi | 4-ClPh | CO | single bond | 2 | O | CH$_2$CH$_2$ | sub. 29 |
| 2951 | 5-Thi | 4-ClPh | CO | single bond | 2 | O | CH$_2$CH$_2$ | sub. 29 |
| 2952 | 4-OOxa | 4-ClPh | CO | single bond | 2 | O | CH$_2$CH$_2$ | sub. 29 |
| 2953 | 5-OOxa | 4-ClPh | CO | single bond | 2 | O | CH$_2$CH$_2$ | sub. 29 |
| 2954 | 4-OThi | 4-ClPh | CO | single bond | 2 | O | CH$_2$CH$_2$ | sub. 29 |
| 2955 | 5-OThi | 4-ClPh | CO | single bond | 2 | O | CH$_2$CH$_2$ | sub. 29 |
| 2956 | 2-Pip | 4-ClPh | CO | single bond | 2 | O | CH$_2$CH$_2$ | sub. 29 |
| 2957 | 3-Pip | 4-ClPh | CO | single bond | 2 | O | CH$_2$CH$_2$ | sub. 29 |
| 2958 | 4-Pip | 4-ClPh | CO | single bond | 2 | O | CH$_2$CH$_2$ | sub. 29 |
| 2959 | 2-Mor | 4-ClPh | CO | single bond | 2 | O | CH$_2$CH$_2$ | sub. 29 |
| 2960 | 3-Mor | 4-ClPh | CO | single bond | 2 | O | CH$_2$CH$_2$ | sub. 29 |
| 2961 | 4-Mor | 4-ClPh | CO | single bond | 2 | O | CH$_2$CH$_2$ | sub. 29 |
| 2962 | 2-Thmor | 4-ClPh | CO | single bond | 2 | O | CH$_2$CH$_2$ | sub. 29 |
| 2963 | 3-Thmor | 4-ClPh | CO | single bond | 2 | O | CH$_2$CH$_2$ | sub. 29 |
| 2964 | 4-Thmor | 4-ClPh | CO | single bond | 2 | O | CH$_2$CH$_2$ | sub. 29 |
| 2965 | 2-Piz | 4-ClPh | CO | single bond | 2 | O | CH$_2$CH$_2$ | sub. 29 |
| 2966 | 3-Piz | 4-ClPh | CO | single bond | 2 | O | CH$_2$CH$_2$ | sub. 29 |
| 2967 | 4-Piz | 4-ClPh | CO | single bond | 2 | O | CH$_2$CH$_2$ | sub. 29 |
| 2968 | 2-Aze | 4-ClPh | CO | single bond | 2 | O | CH$_2$CH$_2$ | sub. 29 |
| 2969 | 3-Aze | 4-ClPh | CO | single bond | 2 | O | CH$_2$CH$_2$ | sub. 29 |
| 2970 | 4-Aze | 4-ClPh | CO | single bond | 2 | O | CH$_2$CH$_2$ | sub. 29 |
| 2971 | cPr | 4-ClPh | CO | single bond | 2 | O | CH$_2$CH$_2$ | sub. 30 |
| 2972 | cBu | 4-ClPh | CO | single bond | 2 | O | CH$_2$CH$_2$ | sub. 30 |
| 2973 | cPn | 4-ClPh | CO | single bond | 2 | O | CH$_2$CH$_2$ | sub. 30 |
| 2974 | cHex | 4-ClPh | CO | single bond | 2 | O | CH$_2$CH$_2$ | sub. 30 |
| 2975 | cHep | 4-ClPh | CO | single bond | 2 | O | CH$_2$CH$_2$ | sub. 30 |
| 2976 | 2-Pyrd | 4-ClPh | CO | single bond | 2 | O | CH$_2$CH$_2$ | sub. 30 |
| 2977 | 3-Pyrd | 4-ClPh | CO | single bond | 2 | O | CH$_2$CH$_2$ | sub. 30 |
| 2978 | 4-Oxa | 4-ClPh | CO | single bond | 2 | O | CH$_2$CH$_2$ | sub. 30 |
| 2979 | 5-Oxa | 4-ClPh | CO | single bond | 2 | O | CH$_2$CH$_2$ | sub. 30 |
| 2980 | 4-Thi | 4-ClPh | CO | single bond | 2 | O | CH$_2$CH$_2$ | sub. 30 |
| 2981 | 5-Thi | 4-ClPh | CO | single bond | 2 | O | CH$_2$CH$_2$ | sub. 30 |
| 2982 | 4-OOxa | 4-ClPh | CO | single bond | 2 | O | CH$_2$CH$_2$ | sub. 30 |
| 2983 | 5-OOxa | 4-ClPh | CO | single bond | 2 | O | CH$_2$CH$_2$ | sub. 30 |
| 2984 | 4-OThi | 4-ClPh | CO | single bond | 2 | O | CH$_2$CH$_2$ | sub. 30 |
| 2985 | 5-OThi | 4-ClPh | CO | single bond | 2 | O | CH$_2$CH$_2$ | sub. 30 |
| 2986 | 2-Pip | 4-ClPh | CO | single bond | 2 | O | CH$_2$CH$_2$ | sub. 30 |
| 2987 | 3-Pip | 4-ClPh | CO | single bond | 2 | O | CH$_2$CH$_2$ | sub. 30 |
| 2988 | 4-Pip | 4-ClPh | CO | single bond | 2 | O | CH$_2$CH$_2$ | sub. 30 |
| 2989 | 2-Mor | 4-ClPh | CO | single bond | 2 | O | CH$_2$CH$_2$ | sub. 30 |
| 2990 | 3-Mor | 4-ClPh | CO | single bond | 2 | O | CH$_2$CH$_2$ | sub. 30 |
| 2991 | 4-Mor | 4-ClPh | CO | single bond | 2 | O | CH$_2$CH$_2$ | sub. 30 |
| 2992 | 2-Thmor | 4-ClPh | CO | single bond | 2 | O | CH$_2$CH$_2$ | sub. 30 |
| 2993 | 3-Thmor | 4-ClPh | CO | single bond | 2 | O | CH$_2$CH$_2$ | sub. 30 |
| 2994 | 4-Thmor | 4-ClPh | CO | single bond | 2 | O | CH$_2$CH$_2$ | sub. 30 |
| 2995 | 2-Piz | 4-ClPh | CO | single bond | 2 | O | CH$_2$CH$_2$ | sub. 30 |
| 2996 | 3-Piz | 4-ClPh | CO | single bond | 2 | O | CH$_2$CH$_2$ | sub. 30 |
| 2997 | 4-Piz | 4-ClPh | CO | single bond | 2 | O | CH$_2$CH$_2$ | sub. 30 |
| 2998 | 2-Aze | 4-ClPh | CO | single bond | 2 | O | CH$_2$CH$_2$ | sub. 30 |
| 2999 | 3-Aze | 4-ClPh | CO | single bond | 2 | O | CH$_2$CH$_2$ | sub. 30 |
| 3000 | 4-Aze | 4-ClPh | CO | single bond | 2 | O | CH$_2$CH$_2$ | sub. 30 |
| 3001 | cPr | 4-ClPh | CO | single bond | 2 | O | CH$_2$CH$_2$ | sub. 31 |
| 3002 | cBu | 4-ClPh | CO | single bond | 2 | O | CH$_2$CH$_2$ | sub. 31 |
| 3003 | cPn | 4-ClPh | CO | single bond | 2 | O | CH$_2$CH$_2$ | sub. 31 |
| 3004 | cHex | 4-ClPh | CO | single bond | 2 | O | CH$_2$CH$_2$ | sub. 31 |
| 3005 | cHep | 4-ClPh | CO | single bond | 2 | O | CH$_2$CH$_2$ | sub. 31 |
| 3006 | 2-Pyrd | 4-ClPh | CO | single bond | 2 | O | CH$_2$CH$_2$ | sub. 31 |
| 3007 | 3-Pyrd | 4-ClPh | CO | single bond | 2 | O | CH$_2$CH$_2$ | sub. 31 |
| 3008 | 4-Oxa | 4-ClPh | CO | single bond | 2 | O | CH$_2$CH$_2$ | sub. 31 |
| 3009 | 5-Oxa | 4-ClPh | CO | single bond | 2 | O | CH$_2$CH$_2$ | sub. 31 |
| 3010 | 4-Thi | 4-ClPh | CO | single bond | 2 | O | CH$_2$CH$_2$ | sub. 31 |
| 3011 | 5-Thi | 4-ClPh | CO | single bond | 2 | O | CH$_2$CH$_2$ | sub. 31 |
| 3012 | 4-OOxa | 4-ClPh | CO | single bond | 2 | O | CH$_2$CH$_2$ | sub. 31 |
| 3013 | 5-OOxa | 4-ClPh | CO | single bond | 2 | O | CH$_2$CH$_2$ | sub. 31 |
| 3014 | 4-OThi | 4-ClPh | CO | single bond | 2 | O | CH$_2$CH$_2$ | sub. 31 |
| 3015 | 5-OThi | 4-ClPh | CO | single bond | 2 | O | CH$_2$CH$_2$ | sub. 31 |
| 3016 | 2-Pip | 4-ClPh | CO | single bond | 2 | O | CH$_2$CH$_2$ | sub. 31 |
| 3017 | 3-Pip | 4-ClPh | CO | single bond | 2 | O | CH$_2$CH$_2$ | sub. 31 |
| 3018 | 4-Pip | 4-ClPh | CO | single bond | 2 | O | CH$_2$CH$_2$ | sub. 31 |
| 3019 | 2-Mor | 4-ClPh | CO | single bond | 2 | O | CH$_2$CH$_2$ | sub. 31 |
| 3020 | 3-Mor | 4-ClPh | CO | single bond | 2 | O | CH$_2$CH$_2$ | sub. 31 |

TABLE 1-continued

| Exemplification compound number | R¹ | R² | A | B | N | D | G | Q |
|---|---|---|---|---|---|---|---|---|
| 3021 | 4-Mor | 4-ClPh | CO | single bond | 2 | O | $CH_2CH_2$ | sub. 31 |
| 3022 | 2-Thmor | 4-ClPh | CO | single bond | 2 | O | $CH_2CH_2$ | sub. 31 |
| 3023 | 3-Thmor | 4-ClPh | CO | single bond | 2 | O | $CH_2CH_2$ | sub. 31 |
| 3024 | 4-Thmor | 4-ClPh | CO | single bond | 2 | O | $CH_2CH_2$ | sub. 31 |
| 3025 | 2-Piz | 4-ClPh | CO | single bond | 2 | O | $CH_2CH_2$ | sub. 31 |
| 3026 | 3-Piz | 4-ClPh | CO | single bond | 2 | O | $CH_2CH_2$ | sub. 31 |
| 3027 | 4-Piz | 4-ClPh | CO | single bond | 2 | O | $CH_2CH_2$ | sub. 31 |
| 3028 | 2-Aze | 4-ClPh | CO | single bond | 2 | O | $CH_2CH_2$ | sub. 31 |
| 3029 | 3-Aze | 4-ClPh | CO | single bond | 2 | O | $CH_2CH_2$ | sub. 31 |
| 3030 | 4-Aze | 4-ClPh | CO | single bond | 2 | O | $CH_2CH_2$ | sub. 31 |
| 3031 | cPr | 4-ClPh | CO | single bond | 2 | O | $CH_2CH_2$ | sub. 32 |
| 3032 | cBu | 4-ClPh | CO | single bond | 2 | O | $CH_2CH_2$ | sub. 32 |
| 3033 | cPn | 4-ClPh | CO | single bond | 2 | O | $CH_2CH_2$ | sub. 32 |
| 3034 | cHex | 4-ClPh | CO | single bond | 2 | O | $CH_2CH_2$ | sub. 32 |
| 3035 | cHep | 4-ClPh | CO | single bond | 2 | O | $CH_2CH_2$ | sub. 32 |
| 3036 | 2-Pyrd | 4-ClPh | CO | single bond | 2 | O | $CH_2CH_2$ | sub. 32 |
| 3037 | 3-Pyrd | 4-ClPh | CO | single bond | 2 | O | $CH_2CH_2$ | sub. 32 |
| 3038 | 4-Oxa | 4-ClPh | CO | single bond | 2 | O | $CH_2CH_2$ | sub. 32 |
| 3039 | 5-Oxa | 4-ClPh | CO | single bond | 2 | O | $CH_2CH_2$ | sub. 32 |
| 3040 | 4-Thi | 4-ClPh | CO | single bond | 2 | O | $CH_2CH_2$ | sub. 32 |
| 3041 | 5-Thi | 4-ClPh | CO | single bond | 2 | O | $CH_2CH_2$ | sub. 32 |
| 3042 | 4-OOxa | 4-ClPh | CO | single bond | 2 | O | $CH_2CH_2$ | sub. 32 |
| 3043 | 5-OOxa | 4-ClPh | CO | single bond | 2 | O | $CH_2CH_2$ | sub. 32 |
| 3044 | 4-OThi | 4-ClPh | CO | single bond | 2 | O | $CH_2CH_2$ | sub. 32 |
| 3045 | 5-OThi | 4-ClPh | CO | single bond | 2 | O | $CH_2CH_2$ | sub. 32 |
| 3046 | 2-Pip | 4-ClPh | CO | single bond | 2 | O | $CH_2CH_2$ | sub. 32 |
| 3047 | 3-Pip | 4-ClPh | CO | single bond | 2 | O | $CH_2CH_2$ | sub. 32 |
| 3048 | 4-Pip | 4-ClPh | CO | single bond | 2 | O | $CH_2CH_2$ | sub. 32 |
| 3049 | 2-Mor | 4-ClPh | CO | single bond | 2 | O | $CH_2CH_2$ | sub. 32 |
| 3050 | 3-Mor | 4-ClPh | CO | single bond | 2 | O | $CH_2CH_2$ | sub. 32 |
| 3051 | 4-Mor | 4-ClPh | CO | single bond | 2 | O | $CH_2CH_2$ | sub. 32 |
| 3052 | 2-Thmor | 4-ClPh | CO | single bond | 2 | O | $CH_2CH_2$ | sub. 32 |
| 3053 | 3-Thmor | 4-ClPh | CO | single bond | 2 | O | $CH_2CH_2$ | sub. 32 |
| 3054 | 4-Thmor | 4-ClPh | CO | single bond | 2 | O | $CH_2CH_2$ | sub. 32 |
| 3055 | 2-Piz | 4-ClPh | CO | single bond | 2 | O | $CH_2CH_2$ | sub. 32 |
| 3056 | 3-Piz | 4-ClPh | CO | single bond | 2 | O | $CH_2CH_2$ | sub. 32 |
| 3057 | 4-Piz | 4-ClPh | CO | single bond | 2 | O | $CH_2CH_2$ | sub. 32 |
| 3058 | 2-Aze | 4-ClPh | CO | single bond | 2 | O | $CH_2CH_2$ | sub. 32 |
| 3059 | 3-Aze | 4-ClPh | CO | single bond | 2 | O | $CH_2CH_2$ | sub. 32 |
| 3060 | 4-Aze | 4-ClPh | CO | single bond | 2 | O | $CH_2CH_2$ | sub. 32 |
| 3061 | cPr | 4-ClPh | CO | single bond | 2 | O | $CH_2CH_2$ | sub. 33 |
| 3062 | cBu | 4-ClPh | CO | single bond | 2 | O | $CH_2CH_2$ | sub. 33 |
| 3063 | cPn | 4-ClPh | CO | single bond | 2 | O | $CH_2CH_2$ | sub. 33 |
| 3064 | cHex | 4-ClPh | CO | single bond | 2 | O | $CH_2CH_2$ | sub. 33 |
| 3065 | cHep | 4-ClPh | CO | single bond | 2 | O | $CH_2CH_2$ | sub. 33 |
| 3066 | 2-Pyrd | 4-ClPh | CO | single bond | 2 | O | $CH_2CH_2$ | sub. 33 |
| 3067 | 3-Pyrd | 4-ClPh | CO | single bond | 2 | O | $CH_2CH_2$ | sub. 33 |
| 3068 | 4-Oxa | 4-ClPh | CO | single bond | 2 | O | $CH_2CH_2$ | sub. 33 |
| 3069 | 5-Oxa | 4-ClPh | CO | single bond | 2 | O | $CH_2CH_2$ | sub. 33 |
| 3070 | 4-Thi | 4-ClPh | CO | single bond | 2 | O | $CH_2CH_2$ | sub. 33 |
| 3071 | 5-Thi | 4-ClPh | CO | single bond | 2 | O | $CH_2CH_2$ | sub. 33 |
| 3072 | 4-OOxa | 4-ClPh | CO | single bond | 2 | O | $CH_2CH_2$ | sub. 33 |
| 3073 | 5-OOxa | 4-ClPh | CO | single bond | 2 | O | $CH_2CH_2$ | sub. 33 |
| 3074 | 4-OThi | 4-ClPh | CO | single bond | 2 | O | $CH_2CH_2$ | sub. 33 |
| 3075 | 5-OThi | 4-ClPh | CO | single bond | 2 | O | $CH_2CH_2$ | sub. 33 |
| 3076 | 2-Pip | 4-ClPh | CO | single bond | 2 | O | $CH_2CH_2$ | sub. 33 |
| 3077 | 3-Pip | 4-ClPh | CO | single bond | 2 | O | $CH_2CH_2$ | sub. 33 |
| 3078 | 4-Pip | 4-ClPh | CO | single bond | 2 | O | $CH_2CH_2$ | sub. 33 |
| 3079 | 2-Mor | 4-ClPh | CO | single bond | 2 | O | $CH_2CH_2$ | sub. 33 |
| 3080 | 3-Mor | 4-ClPh | CO | single bond | 2 | O | $CH_2CH_2$ | sub. 33 |
| 3081 | 4-Mor | 4-ClPh | CO | single bond | 2 | O | $CH_2CH_2$ | sub. 33 |
| 3082 | 2-Thmor | 4-ClPh | CO | single bond | 2 | O | $CH_2CH_2$ | sub. 33 |
| 3083 | 3-Thmor | 4-ClPh | CO | single bond | 2 | O | $CH_2CH_2$ | sub. 33 |
| 3084 | 4-Thmor | 4-ClPh | CO | single bond | 2 | O | $CH_2CH_2$ | sub. 33 |
| 3085 | 2-Piz | 4-ClPh | CO | single bond | 2 | O | $CH_2CH_2$ | sub. 33 |
| 3086 | 3-Piz | 4-ClPh | CO | single bond | 2 | O | $CH_2CH_2$ | sub. 33 |
| 3087 | 4-Piz | 4-ClPh | CO | single bond | 2 | O | $CH_2CH_2$ | sub. 33 |
| 3088 | 2-Aze | 4-ClPh | CO | single bond | 2 | O | $CH_2CH_2$ | sub. 33 |
| 3089 | 3-Aze | 4-ClPh | CO | single bond | 2 | O | $CH_2CH_2$ | sub. 33 |
| 3090 | 4-Aze | 4-ClPh | CO | single bond | 2 | O | $CH_2CH_2$ | sub. 33 |
| 3091 | cPr | 4-ClPh | CO | single bond | 2 | O | $CH_2CH_2$ | sub. 34 |
| 3092 | cBu | 4-ClPh | CO | single bond | 2 | O | $CH_2CH_2$ | sub. 34 |
| 3093 | cPn | 4-ClPh | CO | single bond | 2 | O | $CH_2CH_2$ | sub. 34 |
| 3094 | cHex | 4-ClPh | CO | single bond | 2 | O | $CH_2CH_2$ | sub. 34 |
| 3095 | cHep | 4-ClPh | CO | single bond | 2 | O | $CH_2CH_2$ | sub. 34 |
| 3096 | 2-Pyrd | 4-ClPh | CO | single bond | 2 | O | $CH_2CH_2$ | sub. 34 |

TABLE 1-continued

| Exemplification compound number | R¹ | R² | A | B | N | D | G | Q |
|---|---|---|---|---|---|---|---|---|
| 3097 | 3-Pyrd | 4-ClPh | CO | single bond | 2 | O | $CH_2CH_2$ | sub. 34 |
| 3098 | 4-Oxa | 4-ClPh | CO | single bond | 2 | O | $CH_2CH_2$ | sub. 34 |
| 3099 | 5-Oxa | 4-ClPh | CO | single bond | 2 | O | $CH_2CH_2$ | sub. 34 |
| 3100 | 4-Thi | 4-ClPh | CO | single bond | 2 | O | $CH_2CH_2$ | sub. 34 |
| 3101 | 5-Thi | 4-ClPh | CO | single bond | 2 | O | $CH_2CH_2$ | sub. 34 |
| 3102 | 4-OOxa | 4-ClPh | CO | single bond | 2 | O | $CH_2CH_2$ | sub. 34 |
| 3103 | 5-OOxa | 4-ClPh | CO | single bond | 2 | O | $CH_2CH_2$ | sub. 34 |
| 3104 | 4-OThi | 4-ClPh | CO | single bond | 2 | O | $CH_2CH_2$ | sub. 34 |
| 3105 | 5-OThi | 4-ClPh | CO | single bond | 2 | O | $CH_2CH_2$ | sub. 34 |
| 3106 | 2-Pip | 4-ClPh | CO | single bond | 2 | O | $CH_2CH_2$ | sub. 34 |
| 3107 | 3-Pip | 4-ClPh | CO | single bond | 2 | O | $CH_2CH_2$ | sub. 34 |
| 3108 | 4-Pip | 4-ClPh | CO | single bond | 2 | O | $CH_2CH_2$ | sub. 34 |
| 3109 | 2-Mor | 4-ClPh | CO | single bond | 2 | O | $CH_2CH_2$ | sub. 34 |
| 3110 | 3-Mor | 4-ClPh | CO | single bond | 2 | O | $CH_2CH_2$ | sub. 34 |
| 3111 | 4-Mor | 4-ClPh | CO | single bond | 2 | O | $CH_2CH_2$ | sub. 34 |
| 3112 | 2-Thmor | 4-ClPh | CO | single bond | 2 | O | $CH_2CH_2$ | sub. 34 |
| 3113 | 3-Thmor | 4-ClPh | CO | single bond | 2 | O | $CH_2CH_2$ | sub. 34 |
| 3114 | 4-Thmor | 4-ClPh | CO | single bond | 2 | O | $CH_2CH_2$ | sub. 34 |
| 3115 | 2-Piz | 4-ClPh | CO | single bond | 2 | O | $CH_2CH_2$ | sub. 34 |
| 3116 | 3-Piz | 4-ClPh | CO | single bond | 2 | O | $CH_2CH_2$ | sub. 34 |
| 3117 | 4-Piz | 4-ClPh | CO | single bond | 2 | O | $CH_2CH_2$ | sub. 34 |
| 3118 | 2-Aze | 4-ClPh | CO | single bond | 2 | O | $CH_2CH_2$ | sub. 34 |
| 3119 | 3-Aze | 4-ClPh | CO | single bond | 2 | O | $CH_2CH_2$ | sub. 34 |
| 3120 | 4-Aze | 4-ClPh | CO | single bond | 2 | O | $CH_2CH_2$ | sub. 34 |
| 3121 | cPr | 4-ClPh | CO | single bond | 2 | O | $CH_2CH_2$ | sub. 35 |
| 3122 | cBu | 4-ClPh | CO | single bond | 2 | O | $CH_2CH_2$ | sub. 35 |
| 3123 | cPn | 4-ClPh | CO | single bond | 2 | O | $CH_2CH_2$ | sub. 35 |
| 3124 | cHex | 4-ClPh | CO | single bond | 2 | O | $CH_2CH_2$ | sub. 35 |
| 3125 | cHep | 4-ClPh | CO | single bond | 2 | O | $CH_2CH_2$ | sub. 35 |
| 3126 | 2-Pyrd | 4-ClPh | CO | single bond | 2 | O | $CH_2CH_2$ | sub. 35 |
| 3127 | 3-Pyrd | 4-ClPh | CO | single bond | 2 | O | $CH_2CH_2$ | sub. 35 |
| 3128 | 4-Oxa | 4-ClPh | CO | single bond | 2 | O | $CH_2CH_2$ | sub. 35 |
| 3129 | 5-Oxa | 4-ClPh | CO | single bond | 2 | O | $CH_2CH_2$ | sub. 35 |
| 3130 | 4-Thi | 4-ClPh | CO | single bond | 2 | O | $CH_2CH_2$ | sub. 35 |
| 3131 | 5-Thi | 4-ClPh | CO | single bond | 2 | O | $CH_2CH_2$ | sub. 35 |
| 3132 | 4-OOxa | 4-ClPh | CO | single bond | 2 | O | $CH_2CH_2$ | sub. 35 |
| 3133 | 5-OOxa | 4-ClPh | CO | single bond | 2 | O | $CH_2CH_2$ | sub. 35 |
| 3134 | 4-OThi | 4-ClPh | CO | single bond | 2 | O | $CH_2CH_2$ | sub. 35 |
| 3135 | 5-OThi | 4-ClPh | CO | single bond | 2 | O | $CH_2CH_2$ | sub. 35 |
| 3136 | 2-Pip | 4-ClPh | CO | single bond | 2 | O | $CH_2CH_2$ | sub. 35 |
| 3137 | 3-Pip | 4-ClPh | CO | single bond | 2 | O | $CH_2CH_2$ | sub. 35 |
| 3138 | 4-Pip | 4-ClPh | CO | single bond | 2 | O | $CH_2CH_2$ | sub. 35 |
| 3139 | 2-Mor | 4-ClPh | CO | single bond | 2 | O | $CH_2CH_2$ | sub. 35 |
| 3140 | 3-Mor | 4-ClPh | CO | single bond | 2 | O | $CH_2CH_2$ | sub. 35 |
| 3141 | 4-Mor | 4-ClPh | CO | single bond | 2 | O | $CH_2CH_2$ | sub. 35 |
| 3142 | 2-Thmor | 4-ClPh | CO | single bond | 2 | O | $CH_2CH_2$ | sub. 35 |
| 3143 | 3-Thmor | 4-ClPh | CO | single bond | 2 | O | $CH_2CH_2$ | sub. 35 |
| 3144 | 4-Thmor | 4-ClPh | CO | single bond | 2 | O | $CH_2CH_2$ | sub. 35 |
| 3145 | 2-Piz | 4-ClPh | CO | single bond | 2 | O | $CH_2CH_2$ | sub. 35 |
| 3146 | 3-Piz | 4-ClPh | CO | single bond | 2 | O | $CH_2CH_2$ | sub. 35 |
| 3147 | 4-Piz | 4-ClPh | CO | single bond | 2 | O | $CH_2CH_2$ | sub. 35 |
| 3148 | 2-Aze | 4-ClPh | CO | single bond | 2 | O | $CH_2CH_2$ | sub. 35 |
| 3149 | 3-Aze | 4-ClPh | CO | single bond | 2 | O | $CH_2CH_2$ | sub. 35 |
| 3150 | 4-Aze | 4-ClPh | CO | single bond | 2 | O | $CH_2CH_2$ | sub. 35 |
| 3151 | cPr | 3,4-diFPh | CO | single bond | 2 | O | $CH_2CH_2$ | sub. 1 |
| 3152 | cBu | 3,4-diFPh | CO | single bond | 2 | O | $CH_2CH_2$ | sub. 1 |
| 3153 | cPn | 3,4-diFPh | CO | single bond | 2 | O | $CH_2CH_2$ | sub. 1 |
| 3154 | cHex | 3,4-diFPh | CO | single bond | 2 | O | $CH_2CH_2$ | sub. 1 |
| 3155 | cHep | 3,4-diFPh | CO | single bond | 2 | O | $CH_2CH_2$ | sub. 1 |
| 3156 | 2-Pyrd | 3,4-diFPh | CO | single bond | 2 | O | $CH_2CH_2$ | sub. 1 |
| 3157 | 3-Pyrd | 3,4-diFPh | CO | single bond | 2 | O | $CH_2CH_2$ | sub. 1 |
| 3158 | 4-Oxa | 3,4-diFPh | CO | single bond | 2 | O | $CH_2CH_2$ | sub. 1 |
| 3159 | 5-Oxa | 3,4-diFPh | CO | single bond | 2 | O | $CH_2CH_2$ | sub. 1 |
| 3160 | 4-Thi | 3,4-diFPh | CO | single bond | 2 | O | $CH_2CH_2$ | sub. 1 |
| 3161 | 5-Thi | 3,4-diFPh | CO | single bond | 2 | O | $CH_2CH_2$ | sub. 1 |
| 3162 | 4-OOxa | 3,4-diFPh | CO | single bond | 2 | O | $CH_2CH_2$ | sub. 1 |
| 3163 | 5-OOxa | 3,4-diFPh | CO | single bond | 2 | O | $CH_2CH_2$ | sub. 1 |
| 3164 | 4-OThi | 3,4-diFPh | CO | single bond | 2 | O | $CH_2CH_2$ | sub. 1 |
| 3165 | 5-OThi | 3,4-diFPh | CO | single bond | 2 | O | $CH_2CH_2$ | sub. 1 |
| 3166 | 2-Pip | 3,4-diFPh | CO | single bond | 2 | O | $CH_2CH_2$ | sub. 1 |
| 3167 | 3-Pip | 3,4-diFPh | CO | single bond | 2 | O | $CH_2CH_2$ | sub. 1 |
| 3168 | 4-Pip | 3,4-diFPh | CO | single bond | 2 | O | $CH_2CH_2$ | sub. 1 |
| 3169 | 2-Mor | 3,4-diFPh | CO | single bond | 2 | O | $CH_2CH_2$ | sub. 1 |
| 3170 | 3-Mor | 3,4-diFPh | CO | single bond | 2 | O | $CH_2CH_2$ | sub. 1 |
| 3171 | 4-Mor | 3,4-diFPh | CO | single bond | 2 | O | $CH_2CH_2$ | sub. 1 |
| 3172 | 2-Thmor | 3,4-diFPh | CO | single bond | 2 | O | $CH_2CH_2$ | sub. 1 |

TABLE 1-continued

| Exemplification compound number | R¹ | R² | A | B | N | D | G | Q |
|---|---|---|---|---|---|---|---|---|
| 3173 | 3-Thmor | 3,4-diFPh | CO | single bond | 2 | O | CH₂CH₂ | sub. 1 |
| 3174 | 4-Thmor | 3,4-diFPh | CO | single bond | 2 | O | CH₂CH₂ | sub. 1 |
| 3175 | 2-Piz | 3,4-diFPh | CO | single bond | 2 | O | CH₂CH₂ | sub. 1 |
| 3176 | 3-Piz | 3,4-diFPh | CO | single bond | 2 | O | CH₂CH₂ | sub. 1 |
| 3177 | 4-Piz | 3,4-diFPh | CO | single bond | 2 | O | CH₂CH₂ | sub. 1 |
| 3178 | 2-Aze | 3,4-diFPh | CO | single bond | 2 | O | CH₂CH₂ | sub. 1 |
| 3179 | 3-Aze | 3,4-diFPh | CO | single bond | 2 | O | CH₂CH₂ | sub. 1 |
| 3180 | 4-Aze | 3,4-diFPh | CO | single bond | 2 | O | CH₂CH₂ | sub. 1 |
| 3181 | cPr | 3,4-diFPh | CO | single bond | 2 | O | CH₂CH₂ | sub. 2 |
| 3182 | cBu | 3,4-diFPh | CO | single bond | 2 | O | CH₂CH₂ | sub. 2 |
| 3183 | cPn | 3,4-diFPh | CO | single bond | 2 | O | CH₂CH₂ | sub. 2 |
| 3184 | cHex | 3,4-diFPh | CO | single bond | 2 | O | CH₂CH₂ | sub. 2 |
| 3185 | cHep | 3,4-diFPh | CO | single bond | 2 | O | CH₂CH₂ | sub. 2 |
| 3186 | 2-Pyrd | 3,4-diFPh | CO | single bond | 2 | O | CH₂CH₂ | sub. 2 |
| 3187 | 3-Pyrd | 3,4-diFPh | CO | single bond | 2 | O | CH₂CH₂ | sub. 2 |
| 3188 | 4-Oxa | 3,4-diFPh | CO | single bond | 2 | O | CH₂CH₂ | sub. 2 |
| 3189 | 5-Oxa | 3,4-diFPh | CO | single bond | 2 | O | CH₂CH₂ | sub. 2 |
| 3190 | 4-Thi | 3,4-diFPh | CO | single bond | 2 | O | CH₂CH₂ | sub. 2 |
| 3191 | 5-Thi | 3,4-diFPh | CO | single bond | 2 | O | CH₂CH₂ | sub. 2 |
| 3192 | 4-OOxa | 3,4-diFPh | CO | single bond | 2 | O | CH₂CH₂ | sub. 2 |
| 3193 | 5-OOxa | 3,4-diFPh | CO | single bond | 2 | O | CH₂CH₂ | sub. 2 |
| 3194 | 4-OThi | 3,4-diFPh | CO | single bond | 2 | O | CH₂CH₂ | sub. 2 |
| 3195 | 5-OThi | 3,4-diFPh | CO | single bond | 2 | O | CH₂CH₂ | sub. 2 |
| 3196 | 2-Pip | 3,4-diFPh | CO | single bond | 2 | O | CH₂CH₂ | sub. 2 |
| 3197 | 3-Pip | 3,4-diFPh | CO | single bond | 2 | O | CH₂CH₂ | sub. 2 |
| 3198 | 4-Pip | 3,4-diFPh | CO | single bond | 2 | O | CH₂CH₂ | sub. 2 |
| 3199 | 2-Mor | 3,4-diFPh | CO | single bond | 2 | O | CH₂CH₂ | sub. 2 |
| 3200 | 3-Mor | 3,4-diFPh | CO | single bond | 2 | O | CH₂CH₂ | sub. 2 |
| 3201 | 4-Mor | 3,4-diFPh | CO | single bond | 2 | O | CH₂CH₂ | sub. 2 |
| 3202 | 2-Thmor | 3,4-diFPh | CO | single bond | 2 | O | CH₂CH₂ | sub. 2 |
| 3203 | 3-Thmor | 3,4-diFPh | CO | single bond | 2 | O | CH₂CH₂ | sub. 2 |
| 3204 | 4-Thmor | 3,4-diFPh | CO | single bond | 2 | O | CH₂CH₂ | sub. 2 |
| 3205 | 2-Piz | 3,4-diFPh | CO | single bond | 2 | O | CH₂CH₂ | sub. 2 |
| 3206 | 3-Piz | 3,4-diFPh | CO | single bond | 2 | O | CH₂CH₂ | sub. 2 |
| 3207 | 4-Piz | 3,4-diFPh | CO | single bond | 2 | O | CH₂CH₂ | sub. 2 |
| 3208 | 2-Aze | 3,4-diFPh | CO | single bond | 2 | O | CH₂CH₂ | sub. 2 |
| 3209 | 3-Aze | 3,4-diFPh | CO | single bond | 2 | O | CH₂CH₂ | sub. 2 |
| 3210 | 4-Aze | 3,4-diFPh | CO | single bond | 2 | O | CH₂CH₂ | sub. 2 |
| 3211 | cPr | 3,4-diFPh | CO | single bond | 2 | O | CH₂CH₂ | sub. 3 |
| 3212 | cBu | 3,4-diFPh | CO | single bond | 2 | O | CH₂CH₂ | sub. 3 |
| 3213 | cPn | 3,4-diFPh | CO | single bond | 2 | O | CH₂CH₂ | sub. 3 |
| 3214 | cHex | 3,4-diFPh | CO | single bond | 2 | O | CH₂CH₂ | sub. 3 |
| 3215 | cHep | 3,4-diFPh | CO | single bond | 2 | O | CH₂CH₂ | sub. 3 |
| 3216 | 2-Pyrd | 3,4-diFPh | CO | single bond | 2 | O | CH₂CH₂ | sub. 3 |
| 3217 | 3-Pyrd | 3,4-diFPh | CO | single bond | 2 | O | CH₂CH₂ | sub. 3 |
| 3218 | 4-Oxa | 3,4-diFPh | CO | single bond | 2 | O | CH₂CH₂ | sub. 3 |
| 3219 | 5-Oxa | 3,4-diFPh | CO | single bond | 2 | O | CH₂CH₂ | sub. 3 |
| 3220 | 4-Thi | 3,4-diFPh | CO | single bond | 2 | O | CH₂CH₂ | sub. 3 |
| 3221 | 5-Thi | 3,4-diFPh | CO | single bond | 2 | O | CH₂CH₂ | sub. 3 |
| 3222 | 4-OOxa | 3,4-diFPh | CO | single bond | 2 | O | CH₂CH₂ | sub. 3 |
| 3223 | 5-OOxa | 3,4-diFPh | CO | single bond | 2 | O | CH₂CH₂ | sub. 3 |
| 3224 | 4-OThi | 3,4-diFPh | CO | single bond | 2 | O | CH₂CH₂ | sub. 3 |
| 3225 | 5-OThi | 3,4-diFPh | CO | single bond | 2 | O | CH₂CH₂ | sub. 3 |
| 3226 | 2-Pip | 3,4-diFPh | CO | single bond | 2 | O | CH₂CH₂ | sub. 3 |
| 3227 | 3-Pip | 3,4-diFPh | CO | single bond | 2 | O | CH₂CH₂ | sub. 3 |
| 3228 | 4-Pip | 3,4-diFPh | CO | single bond | 2 | O | CH₂CH₂ | sub. 3 |
| 3229 | 2-Mor | 3,4-diFPh | CO | single bond | 2 | O | CH₂CH₂ | sub. 3 |
| 3230 | 3-Mor | 3,4-diFPh | CO | single bond | 2 | O | CH₂CH₂ | sub. 3 |
| 3231 | 4-Mor | 3,4-diFPh | CO | single bond | 2 | O | CH₂CH₂ | sub. 3 |
| 3232 | 2-Thmor | 3,4-diFPh | CO | single bond | 2 | O | CH₂CH₂ | sub. 3 |
| 3233 | 3-Thmor | 3,4-diFPh | CO | single bond | 2 | O | CH₂CH₂ | sub. 3 |
| 3234 | 4-Thmor | 3,4-diFPh | CO | single bond | 2 | O | CH₂CH₂ | sub. 3 |
| 3235 | 2-Piz | 3,4-diFPh | CO | single bond | 2 | O | CH₂CH₂ | sub. 3 |
| 3236 | 3-Piz | 3,4-diFPh | CO | single bond | 2 | O | CH₂CH₂ | sub. 3 |
| 3237 | 4-Piz | 3,4-diFPh | CO | single bond | 2 | O | CH₂CH₂ | sub. 3 |
| 3238 | 2-Aze | 3,4-diFPh | CO | single bond | 2 | O | CH₂CH₂ | sub. 3 |
| 3239 | 3-Aze | 3,4-diFPh | CO | single bond | 2 | O | CH₂CH₂ | sub. 3 |
| 3240 | 4-Aze | 3,4-diFPh | CO | single bond | 2 | O | CH₂CH₂ | sub. 3 |
| 3241 | cPr | 3,4-diFPh | CO | single bond | 2 | O | CH₂CH₂ | sub. 4 |
| 3242 | cBu | 3,4-diFPh | CO | single bond | 2 | O | CH₂CH₂ | sub. 4 |
| 3243 | cPn | 3,4-diFPh | CO | single bond | 2 | O | CH₂CH₂ | sub. 4 |
| 3244 | cHex | 3,4-diFPh | CO | single bond | 2 | O | CH₂CH₂ | sub. 4 |
| 3245 | cHep | 3,4-diFPh | CO | single bond | 2 | O | CH₂CH₂ | sub. 4 |
| 3246 | 2-Pyrd | 3,4-diFPh | CO | single bond | 2 | O | CH₂CH₂ | sub. 4 |
| 3247 | 3-Pyrd | 3,4-diFPh | CO | single bond | 2 | O | CH₂CH₂ | sub. 4 |
| 3248 | 4-Oxa | 3,4-diFPh | CO | single bond | 2 | O | CH₂CH₂ | sub. 4 |

TABLE 1-continued

| Exemplification compound number | R¹ | R² | A | B | N | D | G | Q |
|---|---|---|---|---|---|---|---|---|
| 3249 | 5-Oxa | 3,4-diFPh | CO | single bond | 2 | O | $CH_2CH_2$ | sub. 4 |
| 3250 | 4-Thi | 3,4-diFPh | CO | single bond | 2 | O | $CH_2CH_2$ | sub. 4 |
| 3251 | 5-Thi | 3,4-diFPh | CO | single bond | 2 | O | $CH_2CH_2$ | sub. 4 |
| 3252 | 4-OOxa | 3,4-diFPh | CO | single bond | 2 | O | $CH_2CH_2$ | sub. 4 |
| 3253 | 5-OOxa | 3,4-diFPh | CO | single bond | 2 | O | $CH_2CH_2$ | sub. 4 |
| 3254 | 4-OThi | 3,4-diFPh | CO | single bond | 2 | O | $CH_2CH_2$ | sub. 4 |
| 3255 | 5-OThi | 3,4-diFPh | CO | single bond | 2 | O | $CH_2CH_2$ | sub. 4 |
| 3256 | 2-Pip | 3,4-diFPh | CO | single bond | 2 | O | $CH_2CH_2$ | sub. 4 |
| 3257 | 3-Pip | 3,4-diFPh | CO | single bond | 2 | O | $CH_2CH_2$ | sub. 4 |
| 3258 | 4-Pip | 3,4-diFPh | CO | single bond | 2 | O | $CH_2CH_2$ | sub. 4 |
| 3259 | 2-Mor | 3,4-diFPh | CO | single bond | 2 | O | $CH_2CH_2$ | sub. 4 |
| 3260 | 3-Mor | 3,4-diFPh | CO | single bond | 2 | O | $CH_2CH_2$ | sub. 4 |
| 3261 | 4-Mor | 3,4-diFPh | CO | single bond | 2 | O | $CH_2CH_2$ | sub. 4 |
| 3262 | 2-Thmor | 3,4-diFPh | CO | single bond | 2 | O | $CH_2CH_2$ | sub. 4 |
| 3263 | 3-Thmor | 3,4-diFPh | CO | single bond | 2 | O | $CH_2CH_2$ | sub. 4 |
| 3264 | 4-Thmor | 3,4-diFPh | CO | single bond | 2 | O | $CH_2CH_2$ | sub. 4 |
| 3265 | 2-Piz | 3,4-diFPh | CO | single bond | 2 | O | $CH_2CH_2$ | sub. 4 |
| 3266 | 3-Piz | 3,4-diFPh | CO | single bond | 2 | O | $CH_2CH_2$ | sub. 4 |
| 3267 | 4-Piz | 3,4-diFPh | CO | single bond | 2 | O | $CH_2CH_2$ | sub. 4 |
| 3268 | 2-Aze | 3,4-diFPh | CO | single bond | 2 | O | $CH_2CH_2$ | sub. 4 |
| 3269 | 3-Aze | 3,4-diFPh | CO | single bond | 2 | O | $CH_2CH_2$ | sub. 4 |
| 3270 | 4-Aze | 3,4-diFPh | CO | single bond | 2 | O | $CH_2CH_2$ | sub. 4 |
| 3271 | cPr | 3,4-diFPh | CO | single bond | 2 | O | $CH_2CH_2$ | sub. 5 |
| 3272 | cBu | 3,4-diFPh | CO | single bond | 2 | O | $CH_2CH_2$ | sub. 5 |
| 3273 | cPn | 3,4-diFPh | CO | single bond | 2 | O | $CH_2CH_2$ | sub. 5 |
| 3274 | cHex | 3,4-diFPh | CO | single bond | 2 | O | $CH_2CH_2$ | sub. 5 |
| 3275 | cHep | 3,4-diFPh | CO | single bond | 2 | O | $CH_2CH_2$ | sub. 5 |
| 3276 | 2-Pyrd | 3,4-diFPh | CO | single bond | 2 | O | $CH_2CH_2$ | sub. 5 |
| 3277 | 3-Pyrd | 3,4-diFPh | CO | single bond | 2 | O | $CH_2CH_2$ | sub. 5 |
| 3278 | 4-Oxa | 3,4-diFPh | CO | single bond | 2 | O | $CH_2CH_2$ | sub. 5 |
| 3279 | 5-Oxa | 3,4-diFPh | CO | single bond | 2 | O | $CH_2CH_2$ | sub. 5 |
| 3280 | 4-Thi | 3,4-diFPh | CO | single bond | 2 | O | $CH_2CH_2$ | sub. 5 |
| 3281 | 5-Thi | 3,4-diFPh | CO | single bond | 2 | O | $CH_2CH_2$ | sub. 5 |
| 3282 | 4-OOxa | 3,4-diFPh | CO | single bond | 2 | O | $CH_2CH_2$ | sub. 5 |
| 3283 | 5-OOxa | 3,4-diFPh | CO | single bond | 2 | O | $CH_2CH_2$ | sub. 5 |
| 3284 | 4-OThi | 3,4-diFPh | CO | single bond | 2 | O | $CH_2CH_2$ | sub. 5 |
| 3285 | 5-OThi | 3,4-diFPh | CO | single bond | 2 | O | $CH_2CH_2$ | sub. 5 |
| 3286 | 2-Pip | 3,4-diFPh | CO | single bond | 2 | O | $CH_2CH_2$ | sub. 5 |
| 3287 | 3-Pip | 3,4-diFPh | CO | single bond | 2 | O | $CH_2CH_2$ | sub. 5 |
| 3288 | 4-Pip | 3,4-diFPh | CO | single bond | 2 | O | $CH_2CH_2$ | sub. 5 |
| 3289 | 2-Mor | 3,4-diFPh | CO | single bond | 2 | O | $CH_2CH_2$ | sub. 5 |
| 3290 | 3-Mor | 3,4-diFPh | CO | single bond | 2 | O | $CH_2CH_2$ | sub. 5 |
| 3291 | 4-Mor | 3,4-diFPh | CO | single bond | 2 | O | $CH_2CH_2$ | sub. 5 |
| 3292 | 2-Thmor | 3,4-diFPh | CO | single bond | 2 | O | $CH_2CH_2$ | sub. 5 |
| 3293 | 3-Thmor | 3,4-diFPh | CO | single bond | 2 | O | $CH_2CH_2$ | sub. 5 |
| 3294 | 4-Thmor | 3,4-diFPh | CO | single bond | 2 | O | $CH_2CH_2$ | sub. 5 |
| 3295 | 2-Piz | 3,4-diFPh | CO | single bond | 2 | O | $CH_2CH_2$ | sub. 5 |
| 3296 | 3-Piz | 3,4-diFPh | CO | single bond | 2 | O | $CH_2CH_2$ | sub. 5 |
| 3297 | 4-Piz | 3,4-diFPh | CO | single bond | 2 | O | $CH_2CH_2$ | sub. 5 |
| 3298 | 2-Aze | 3,4-diFPh | CO | single bond | 2 | O | $CH_2CH_2$ | sub. 5 |
| 3299 | 3-Aze | 3,4-diFPh | CO | single bond | 2 | O | $CH_2CH_2$ | sub. 5 |
| 3300 | 4-Aze | 3,4-diFPh | CO | single bond | 2 | O | $CH_2CH_2$ | sub. 5 |
| 3301 | cPr | 3,4-diFPh | CO | single bond | 2 | O | $CH_2CH_2$ | sub. 6 |
| 3302 | cBu | 3,4-diFPh | CO | single bond | 2 | O | $CH_2CH_2$ | sub. 6 |
| 3303 | cPn | 3,4-diFPh | CO | single bond | 2 | O | $CH_2CH_2$ | sub. 6 |
| 3304 | cHex | 3,4-diFPh | CO | single bond | 2 | O | $CH_2CH_2$ | sub. 6 |
| 3305 | cHep | 3,4-diFPh | CO | single bond | 2 | O | $CH_2CH_2$ | sub. 6 |
| 3306 | 2-Pyrd | 3,4-diFPh | CO | single bond | 2 | O | $CH_2CH_2$ | sub. 6 |
| 3307 | 3-Pyrd | 3,4-diFPh | CO | single bond | 2 | O | $CH_2CH_2$ | sub. 6 |
| 3308 | 4-Oxa | 3,4-diFPh | CO | single bond | 2 | O | $CH_2CH_2$ | sub. 6 |
| 3309 | 5-Oxa | 3,4-diFPh | CO | single bond | 2 | O | $CH_2CH_2$ | sub. 6 |
| 3310 | 4-Thi | 3,4-diFPh | CO | single bond | 2 | O | $CH_2CH_2$ | sub. 6 |
| 3311 | 5-Thi | 3,4-diFPh | CO | single bond | 2 | O | $CH_2CH_2$ | sub. 6 |
| 3312 | 4-OOxa | 3,4-diFPh | CO | single bond | 2 | O | $CH_2CH_2$ | sub. 6 |
| 3313 | 5-OOxa | 3,4-diFPh | CO | single bond | 2 | O | $CH_2CH_2$ | sub. 6 |
| 3314 | 4-OThi | 3,4-diFPh | CO | single bond | 2 | O | $CH_2CH_2$ | sub. 6 |
| 3315 | 5-OThi | 3,4-diFPh | CO | single bond | 2 | O | $CH_2CH_2$ | sub. 6 |
| 3316 | 2-Pip | 3,4-diFPh | CO | single bond | 2 | O | $CH_2CH_2$ | sub. 6 |
| 3317 | 3-Pip | 3,4-diFPh | CO | single bond | 2 | O | $CH_2CH_2$ | sub. 6 |
| 3318 | 4-Pip | 3,4-diFPh | CO | single bond | 2 | O | $CH_2CH_2$ | sub. 6 |
| 3319 | 2-Mor | 3,4-diFPh | CO | single bond | 2 | O | $CH_2CH_2$ | sub. 6 |
| 3320 | 3-Mor | 3,4-diFPh | CO | single bond | 2 | O | $CH_2CH_2$ | sub. 6 |
| 3321 | 4-Mor | 3,4-diFPh | CO | single bond | 2 | O | $CH_2CH_2$ | sub. 6 |
| 3322 | 2-Thmor | 3,4-diFPh | CO | single bond | 2 | O | $CH_2CH_2$ | sub. 6 |
| 3323 | 3-Thmor | 3,4-diFPh | CO | single bond | 2 | O | $CH_2CH_2$ | sub. 6 |
| 3324 | 4-Thmor | 3,4-diFPh | CO | single bond | 2 | O | $CH_2CH_2$ | sub. 6 |

TABLE 1-continued

| Exemplification compound number | R¹ | R² | A | B | N | D | G | Q |
|---|---|---|---|---|---|---|---|---|
| 3325 | 2-Piz | 3,4-diFPh | CO | single bond | 2 | O | CH₂CH₂ | sub. 6 |
| 3326 | 3-Piz | 3,4-diFPh | CO | single bond | 2 | O | CH₂CH₂ | sub. 6 |
| 3327 | 4-Piz | 3,4-diFPh | CO | single bond | 2 | O | CH₂CH₂ | sub. 6 |
| 3328 | 2-Aze | 3,4-diFPh | CO | single bond | 2 | O | CH₂CH₂ | sub. 6 |
| 3329 | 3-Aze | 3,4-diFPh | CO | single bond | 2 | O | CH₂CH₂ | sub. 6 |
| 3330 | 4-Aze | 3,4-diFPh | CO | single bond | 2 | O | CH₂CH₂ | sub. 6 |
| 3331 | cPr | 3,4-diFPh | CO | single bond | 2 | O | CH₂CH₂ | sub. 7 |
| 3332 | cBu | 3,4-diFPh | CO | single bond | 2 | O | CH₂CH₂ | sub. 7 |
| 3333 | cPn | 3,4-diFPh | CO | single bond | 2 | O | CH₂CH₂ | sub. 7 |
| 3334 | cHex | 3,4-diFPh | CO | single bond | 2 | O | CH₂CH₂ | sub. 7 |
| 3335 | cHep | 3,4-diFPh | CO | single bond | 2 | O | CH₂CH₂ | sub. 7 |
| 3336 | 2-Pyrd | 3,4-diFPh | CO | single bond | 2 | O | CH₂CH₂ | sub. 7 |
| 3337 | 3-Pyrd | 3,4-diFPh | CO | single bond | 2 | O | CH₂CH₂ | sub. 7 |
| 3338 | 4-Oxa | 3,4-diFPh | CO | single bond | 2 | O | CH₂CH₂ | sub. 7 |
| 3339 | 5-Oxa | 3,4-diFPh | CO | single bond | 2 | O | CH₂CH₂ | sub. 7 |
| 3340 | 4-Thi | 3,4-diFPh | CO | single bond | 2 | O | CH₂CH₂ | sub. 7 |
| 3341 | 5-Thi | 3,4-diFPh | CO | single bond | 2 | O | CH₂CH₂ | sub. 7 |
| 3342 | 4-OOxa | 3,4-diFPh | CO | single bond | 2 | O | CH₂CH₂ | sub. 7 |
| 3343 | 5-OOxa | 3,4-diFPh | CO | single bond | 2 | O | CH₂CH₂ | sub. 7 |
| 3344 | 4-OThi | 3,4-diFPh | CO | single bond | 2 | O | CH₂CH₂ | sub. 7 |
| 3345 | 5-OThi | 3,4-diFPh | CO | single bond | 2 | O | CH₂CH₂ | sub. 7 |
| 3346 | 2-Pip | 3,4-diFPh | CO | single bond | 2 | O | CH₂CH₂ | sub. 7 |
| 3347 | 3-Pip | 3,4-diFPh | CO | single bond | 2 | O | CH₂CH₂ | sub. 7 |
| 3348 | 4-Pip | 3,4-diFPh | CO | single bond | 2 | O | CH₂CH₂ | sub. 7 |
| 3349 | 2-Mor | 3,4-diFPh | CO | single bond | 2 | O | CH₂CH₂ | sub. 7 |
| 3350 | 3-Mor | 3,4-diFPh | CO | single bond | 2 | O | CH₂CH₂ | sub. 7 |
| 3351 | 4-Mor | 3,4-diFPh | CO | single bond | 2 | O | CH₂CH₂ | sub. 7 |
| 3352 | 2-Thmor | 3,4-diFPh | CO | single bond | 2 | O | CH₂CH₂ | sub. 7 |
| 3353 | 3-Thmor | 3,4-diFPh | CO | single bond | 2 | O | CH₂CH₂ | sub. 7 |
| 3354 | 4-Thmor | 3,4-diFPh | CO | single bond | 2 | O | CH₂CH₂ | sub. 7 |
| 3355 | 2-Piz | 3,4-diFPh | CO | single bond | 2 | O | CH₂CH₂ | sub. 7 |
| 3356 | 3-Piz | 3,4-diFPh | CO | single bond | 2 | O | CH₂CH₂ | sub. 7 |
| 3357 | 4-Piz | 3,4-diFPh | CO | single bond | 2 | O | CH₂CH₂ | sub. 7 |
| 3358 | 2-Aze | 3,4-diFPh | CO | single bond | 2 | O | CH₂CH₂ | sub. 7 |
| 3359 | 3-Aze | 3,4-diFPh | CO | single bond | 2 | O | CH₂CH₂ | sub. 7 |
| 3360 | 4-Aze | 3,4-diFPh | CO | single bond | 2 | O | CH₂CH₂ | sub. 7 |
| 3361 | cPr | 3,4-diFPh | CO | single bond | 2 | O | CH₂CH₂ | sub. 8 |
| 3362 | cBu | 3,4-diFPh | CO | single bond | 2 | O | CH₂CH₂ | sub. 8 |
| 3363 | cPn | 3,4-diFPh | CO | single bond | 2 | O | CH₂CH₂ | sub. 8 |
| 3364 | cHex | 3,4-diFPh | CO | single bond | 2 | O | CH₂CH₂ | sub. 8 |
| 3365 | cHep | 3,4-diFPh | CO | single bond | 2 | O | CH₂CH₂ | sub. 8 |
| 3366 | 2-Pyrd | 3,4-diFPh | CO | single bond | 2 | O | CH₂CH₂ | sub. 8 |
| 3367 | 3-Pyrd | 3,4-diFPh | CO | single bond | 2 | O | CH₂CH₂ | sub. 8 |
| 3368 | 4-Oxa | 3,4-diFPh | CO | single bond | 2 | O | CH₂CH₂ | sub. 8 |
| 3369 | 5-Oxa | 3,4-diFPh | CO | single bond | 2 | O | CH₂CH₂ | sub. 8 |
| 3370 | 4-Thi | 3,4-diFPh | CO | single bond | 2 | O | CH₂CH₂ | sub. 8 |
| 3371 | 5-Thi | 3,4-diFPh | CO | single bond | 2 | O | CH₂CH₂ | sub. 8 |
| 3372 | 4-OOxa | 3,4-diFPh | CO | single bond | 2 | O | CH₂CH₂ | sub. 8 |
| 3373 | 5-OOxa | 3,4-diFPh | CO | single bond | 2 | O | CH₂CH₂ | sub. 8 |
| 3374 | 4-OThi | 3,4-diFPh | CO | single bond | 2 | O | CH₂CH₂ | sub. 8 |
| 3375 | 5-OThi | 3,4-diFPh | CO | single bond | 2 | O | CH₂CH₂ | sub. 8 |
| 3376 | 2-Pip | 3,4-diFPh | CO | single bond | 2 | O | CH₂CH₂ | sub. 8 |
| 3377 | 3-Pip | 3,4-diFPh | CO | single bond | 2 | O | CH₂CH₂ | sub. 8 |
| 3378 | 4-Pip | 3,4-diFPh | CO | single bond | 2 | O | CH₂CH₂ | sub. 8 |
| 3379 | 2-Mor | 3,4-diFPh | CO | single bond | 2 | O | CH₂CH₂ | sub. 8 |
| 3380 | 3-Mor | 3,4-diFPh | CO | single bond | 2 | O | CH₂CH₂ | sub. 8 |
| 3381 | 4-Mor | 3,4-diFPh | CO | single bond | 2 | O | CH₂CH₂ | sub. 8 |
| 3382 | 2-Thmor | 3,4-diFPh | CO | single bond | 2 | O | CH₂CH₂ | sub. 8 |
| 3383 | 3-Thmor | 3,4-diFPh | CO | single bond | 2 | O | CH₂CH₂ | sub. 8 |
| 3384 | 4-Thmor | 3,4-diFPh | CO | single bond | 2 | O | CH₂CH₂ | sub. 8 |
| 3385 | 2-Piz | 3,4-diFPh | CO | single bond | 2 | O | CH₂CH₂ | sub. 8 |
| 3386 | 3-Piz | 3,4-diFPh | CO | single bond | 2 | O | CH₂CH₂ | sub. 8 |
| 3387 | 4-Piz | 3,4-diFPh | CO | single bond | 2 | O | CH₂CH₂ | sub. 8 |
| 3388 | 2-Aze | 3,4-diFPh | CO | single bond | 2 | O | CH₂CH₂ | sub. 8 |
| 3389 | 3-Aze | 3,4-diFPh | CO | single bond | 2 | O | CH₂CH₂ | sub. 8 |
| 3390 | 4-Aze | 3,4-diFPh | CO | single bond | 2 | O | CH₂CH₂ | sub. 8 |
| 3391 | cPr | 3,4-diFPh | CO | single bond | 2 | O | CH₂CH₂ | sub. 9 |
| 3392 | cBu | 3,4-diFPh | CO | single bond | 2 | O | CH₂CH₂ | sub. 9 |
| 3393 | cPn | 3,4-diFPh | CO | single bond | 2 | O | CH₂CH₂ | sub. 9 |
| 3394 | cHex | 3,4-diFPh | CO | single bond | 2 | O | CH₂CH₂ | sub. 9 |
| 3395 | cHep | 3,4-diFPh | CO | single bond | 2 | O | CH₂CH₂ | sub. 9 |
| 3396 | 2-Pyrd | 3,4-diFPh | CO | single bond | 2 | O | CH₂CH₂ | sub. 9 |
| 3397 | 3-Pyrd | 3,4-diFPh | CO | single bond | 2 | O | CH₂CH₂ | sub. 9 |
| 3398 | 4-Oxa | 3,4-diFPh | CO | single bond | 2 | O | CH₂CH₂ | sub. 9 |
| 3399 | 5-Oxa | 3,4-diFPh | CO | single bond | 2 | O | CH₂CH₂ | sub. 9 |
| 3400 | 4-Thi | 3,4-diFPh | CO | single bond | 2 | O | CH₂CH₂ | sub. 9 |

TABLE 1-continued

| Exemplification compound number | R¹ | R² | A | B | N | D | G | Q |
|---|---|---|---|---|---|---|---|---|
| 3401 | 5-Thi | 3,4-diFPh | CO | single bond | 2 | O | $CH_2CH_2$ | sub. 9 |
| 3402 | 4-OOxa | 3,4-diFPh | CO | single bond | 2 | O | $CH_2CH_2$ | sub. 9 |
| 3403 | 5-OOxa | 3,4-diFPh | CO | single bond | 2 | O | $CH_2CH_2$ | sub. 9 |
| 3404 | 4-OThi | 3,4-diFPh | CO | single bond | 2 | O | $CH_2CH_2$ | sub. 9 |
| 3405 | 5-OThi | 3,4-diFPh | CO | single bond | 2 | O | $CH_2CH_2$ | sub. 9 |
| 3406 | 2-Pip | 3,4-diFPh | CO | single bond | 2 | O | $CH_2CH_2$ | sub. 9 |
| 3407 | 3-Pip | 3,4-diFPh | CO | single bond | 2 | O | $CH_2CH_2$ | sub. 9 |
| 3408 | 4-Pip | 3,4-diFPh | CO | single bond | 2 | O | $CH_2CH_2$ | sub. 9 |
| 3409 | 2-Mor | 3,4-diFPh | CO | single bond | 2 | O | $CH_2CH_2$ | sub. 9 |
| 3410 | 3-Mor | 3,4-diFPh | CO | single bond | 2 | O | $CH_2CH_2$ | sub. 9 |
| 3411 | 4-Mor | 3,4-diFPh | CO | single bond | 2 | O | $CH_2CH_2$ | sub. 9 |
| 3412 | 2-Thmor | 3,4-diFPh | CO | single bond | 2 | O | $CH_2CH_2$ | sub. 9 |
| 3413 | 3-Thmor | 3,4-diFPh | CO | single bond | 2 | O | $CH_2CH_2$ | sub. 9 |
| 3414 | 4-Thmor | 3,4-diFPh | CO | single bond | 2 | O | $CH_2CH_2$ | sub. 9 |
| 3415 | 2-Piz | 3,4-diFPh | CO | single bond | 2 | O | $CH_2CH_2$ | sub. 9 |
| 3416 | 3-Piz | 3,4-diFPh | CO | single bond | 2 | O | $CH_2CH_2$ | sub. 9 |
| 3417 | 4-Piz | 3,4-diFPh | CO | single bond | 2 | O | $CH_2CH_2$ | sub. 9 |
| 3418 | 2-Aze | 3,4-diFPh | CO | single bond | 2 | O | $CH_2CH_2$ | sub. 9 |
| 3419 | 3-Aze | 3,4-diFPh | CO | single bond | 2 | O | $CH_2CH_2$ | sub. 9 |
| 3420 | 4-Aze | 3,4-diFPh | CO | single bond | 2 | O | $CH_2CH_2$ | sub. 9 |
| 3421 | cPr | 3,4-diFPh | CO | single bond | 2 | O | $CH_2CH_2$ | sub. 10 |
| 3422 | cBu | 3,4-diFPh | CO | single bond | 2 | O | $CH_2CH_2$ | sub. 10 |
| 3423 | cPn | 3,4-diFPh | CO | single bond | 2 | O | $CH_2CH_2$ | sub. 10 |
| 3424 | cHex | 3,4-diFPh | CO | single bond | 2 | O | $CH_2CH_2$ | sub. 10 |
| 3425 | cHep | 3,4-diFPh | CO | single bond | 2 | O | $CH_2CH_2$ | sub. 10 |
| 3426 | 2-Pyrd | 3,4-diFPh | CO | single bond | 2 | O | $CH_2CH_2$ | sub. 10 |
| 3427 | 3-Pyrd | 3,4-diFPh | CO | single bond | 2 | O | $CH_2CH_2$ | sub. 10 |
| 3428 | 4-Oxa | 3,4-diFPh | CO | single bond | 2 | O | $CH_2CH_2$ | sub. 10 |
| 3429 | 5-Oxa | 3,4-diFPh | CO | single bond | 2 | O | $CH_2CH_2$ | sub. 10 |
| 3430 | 4-Thi | 3,4-diFPh | CO | single bond | 2 | O | $CH_2CH_2$ | sub. 10 |
| 3431 | 5-Thi | 3,4-diFPh | CO | single bond | 2 | O | $CH_2CH_2$ | sub. 10 |
| 3432 | 4-OOxa | 3,4-diFPh | CO | single bond | 2 | O | $CH_2CH_2$ | sub. 10 |
| 3433 | 5-OOxa | 3,4-diFPh | CO | single bond | 2 | O | $CH_2CH_2$ | sub. 10 |
| 3434 | 4-OThi | 3,4-diFPh | CO | single bond | 2 | O | $CH_2CH_2$ | sub. 10 |
| 3435 | 5-OThi | 3,4-diFPh | CO | single bond | 2 | O | $CH_2CH_2$ | sub. 10 |
| 3436 | 2-Pip | 3,4-diFPh | CO | single bond | 2 | O | $CH_2CH_2$ | sub. 10 |
| 3437 | 3-Pip | 3,4-diFPh | CO | single bond | 2 | O | $CH_2CH_2$ | sub. 10 |
| 3438 | 4-Pip | 3,4-diFPh | CO | single bond | 2 | O | $CH_2CH_2$ | sub. 10 |
| 3439 | 2-Mor | 3,4-diFPh | CO | single bond | 2 | O | $CH_2CH_2$ | sub. 10 |
| 3440 | 3-Mor | 3,4-diFPh | CO | single bond | 2 | O | $CH_2CH_2$ | sub. 10 |
| 3441 | 4-Mor | 3,4-diFPh | CO | single bond | 2 | O | $CH_2CH_2$ | sub. 10 |
| 3442 | 2-Thmor | 3,4-diFPh | CO | single bond | 2 | O | $CH_2CH_2$ | sub. 10 |
| 3443 | 3-Thmor | 3,4-diFPh | CO | single bond | 2 | O | $CH_2CH_2$ | sub. 10 |
| 3444 | 4-Thmor | 3,4-diFPh | CO | single bond | 2 | O | $CH_2CH_2$ | sub. 10 |
| 3445 | 2-Piz | 3,4-diFPh | CO | single bond | 2 | O | $CH_2CH_2$ | sub. 10 |
| 3446 | 3-Piz | 3,4-diFPh | CO | single bond | 2 | O | $CH_2CH_2$ | sub. 10 |
| 3447 | 4-Piz | 3,4-diFPh | CO | single bond | 2 | O | $CH_2CH_2$ | sub. 10 |
| 3448 | 2-Aze | 3,4-diFPh | CO | single bond | 2 | O | $CH_2CH_2$ | sub. 10 |
| 3449 | 3-Aze | 3,4-diFPh | CO | single bond | 2 | O | $CH_2CH_2$ | sub. 10 |
| 3450 | 4-Aze | 3,4-diFPh | CO | single bond | 2 | O | $CH_2CH_2$ | sub. 10 |
| 3451 | cPr | 3,4-diFPh | CO | single bond | 2 | O | $CH_2CH_2$ | sub. 11 |
| 3452 | cBu | 3,4-diFPh | CO | single bond | 2 | O | $CH_2CH_2$ | sub. 11 |
| 3453 | cPn | 3,4-diFPh | CO | single bond | 2 | O | $CH_2CH_2$ | sub. 11 |
| 3454 | cHex | 3,4-diFPh | CO | single bond | 2 | O | $CH_2CH_2$ | sub. 11 |
| 3455 | cHep | 3,4-diFPh | CO | single bond | 2 | O | $CH_2CH_2$ | sub. 11 |
| 3456 | 2-Pyrd | 3,4-diFPh | CO | single bond | 2 | O | $CH_2CH_2$ | sub. 11 |
| 3457 | 3-Pyrd | 3,4-diFPh | CO | single bond | 2 | O | $CH_2CH_2$ | sub. 11 |
| 3458 | 4-Oxa | 3,4-diFPh | CO | single bond | 2 | O | $CH_2CH_2$ | sub. 11 |
| 3459 | 5-Oxa | 3,4-diFPh | CO | single bond | 2 | O | $CH_2CH_2$ | sub. 11 |
| 3460 | 4-Thi | 3,4-diFPh | CO | single bond | 2 | O | $CH_2CH_2$ | sub. 11 |
| 3461 | 5-Thi | 3,4-diFPh | CO | single bond | 2 | O | $CH_2CH_2$ | sub. 11 |
| 3462 | 4-OOxa | 3,4-diFPh | CO | single bond | 2 | O | $CH_2CH_2$ | sub. 11 |
| 3463 | 5-OOxa | 3,4-diFPh | CO | single bond | 2 | O | $CH_2CH_2$ | sub. 11 |
| 3464 | 4-OThi | 3,4-diFPh | CO | single bond | 2 | O | $CH_2CH_2$ | sub. 11 |
| 3465 | 5-OThi | 3,4-diFPh | CO | single bond | 2 | O | $CH_2CH_2$ | sub. 11 |
| 3466 | 2-Pip | 3,4-diFPh | CO | single bond | 2 | O | $CH_2CH_2$ | sub. 11 |
| 3467 | 3-Pip | 3,4-diFPh | CO | single bond | 2 | O | $CH_2CH_2$ | sub. 11 |
| 3468 | 4-Pip | 3,4-diFPh | CO | single bond | 2 | O | $CH_2CH_2$ | sub. 11 |
| 3469 | 2-Mor | 3,4-diFPh | CO | single bond | 2 | O | $CH_2CH_2$ | sub. 11 |
| 3470 | 3-Mor | 3,4-diFPh | CO | single bond | 2 | O | $CH_2CH_2$ | sub. 11 |
| 3471 | 4-Mor | 3,4-diFPh | CO | single bond | 2 | O | $CH_2CH_2$ | sub. 11 |
| 3472 | 2-Thmor | 3,4-diFPh | CO | single bond | 2 | O | $CH_2CH_2$ | sub. 11 |
| 3473 | 3-Thmor | 3,4-diFPh | CO | single bond | 2 | O | $CH_2CH_2$ | sub. 11 |
| 3474 | 4-Thmor | 3,4-diFPh | CO | single bond | 2 | O | $CH_2CH_2$ | sub. 11 |
| 3475 | 2-Piz | 3,4-diFPh | CO | single bond | 2 | O | $CH_2CH_2$ | sub. 11 |
| 3476 | 3-Piz | 3,4-diFPh | CO | single bond | 2 | O | $CH_2CH_2$ | sub. 11 |

TABLE 1-continued

| Exemplification compound number | R¹ | R² | A | B | N | D | G | Q |
|---|---|---|---|---|---|---|---|---|
| 3477 | 4-Piz | 3,4-diFPh | CO | single bond | 2 | O | CH₂CH₂ | sub. 11 |
| 3478 | 2-Aze | 3,4-diFPh | CO | single bond | 2 | O | CH₂CH₂ | sub. 11 |
| 3479 | 3-Aze | 3,4-diFPh | CO | single bond | 2 | O | CH₂CH₂ | sub. 11 |
| 3480 | 4-Aze | 3,4-diFPh | CO | single bond | 2 | O | CH₂CH₂ | sub. 11 |
| 3481 | cPr | 3,4-diFPh | CO | single bond | 2 | O | CH₂CH₂ | sub. 12 |
| 3482 | cBu | 3,4-diFPh | CO | single bond | 2 | O | CH₂CH₂ | sub. 12 |
| 3483 | cPn | 3,4-diFPh | CO | single bond | 2 | O | CH₂CH₂ | sub. 12 |
| 3484 | cHex | 3,4-diFPh | CO | single bond | 2 | O | CH₂CH₂ | sub. 12 |
| 3485 | cHep | 3,4-diFPh | CO | single bond | 2 | O | CH₂CH₂ | sub. 12 |
| 3486 | 2-Pyrd | 3,4-diFPh | CO | single bond | 2 | O | CH₂CH₂ | sub. 12 |
| 3487 | 3-Pyrd | 3,4-diFPh | CO | single bond | 2 | O | CH₂CH₂ | sub. 12 |
| 3488 | 4-Oxa | 3,4-diFPh | CO | single bond | 2 | O | CH₂CH₂ | sub. 12 |
| 3489 | 5-Oxa | 3,4-diFPh | CO | single bond | 2 | O | CH₂CH₂ | sub. 12 |
| 3490 | 4-Thi | 3,4-diFPh | CO | single bond | 2 | O | CH₂CH₂ | sub. 12 |
| 3491 | 5-Thi | 3,4-diFPh | CO | single bond | 2 | O | CH₂CH₂ | sub. 12 |
| 3492 | 4-OOxa | 3,4-diFPh | CO | single bond | 2 | O | CH₂CH₂ | sub. 12 |
| 3493 | 5-OOxa | 3,4-diFPh | CO | single bond | 2 | O | CH₂CH₂ | sub. 12 |
| 3494 | 4-OThi | 3,4-diFPh | CO | single bond | 2 | O | CH₂CH₂ | sub. 12 |
| 3495 | 5-OThi | 3,4-diFPh | CO | single bond | 2 | O | CH₂CH₂ | sub. 12 |
| 3496 | 2-Pip | 3,4-diFPh | CO | single bond | 2 | O | CH₂CH₂ | sub. 12 |
| 3497 | 3-Pip | 3,4-diFPh | CO | single bond | 2 | O | CH₂CH₂ | sub. 12 |
| 3498 | 4-Pip | 3,4-diFPh | CO | single bond | 2 | O | CH₂CH₂ | sub. 12 |
| 3499 | 2-Mor | 3,4-diFPh | CO | single bond | 2 | O | CH₂CH₂ | sub. 12 |
| 3500 | 3-Mor | 3,4-diFPh | CO | single bond | 2 | O | CH₂CH₂ | sub. 12 |
| 3501 | 4-Mor | 3,4-diFPh | CO | single bond | 2 | O | CH₂CH₂ | sub. 12 |
| 3502 | 2-Thmor | 3,4-diFPh | CO | single bond | 2 | O | CH₂CH₂ | sub. 12 |
| 3503 | 3-Thmor | 3,4-diFPh | CO | single bond | 2 | O | CH₂CH₂ | sub. 12 |
| 3504 | 4-Thmor | 3,4-diFPh | CO | single bond | 2 | O | CH₂CH₂ | sub. 12 |
| 3505 | 2-Piz | 3,4-diFPh | CO | single bond | 2 | O | CH₂CH₂ | sub. 12 |
| 3506 | 3-Piz | 3,4-diFPh | CO | single bond | 2 | O | CH₂CH₂ | sub. 12 |
| 3507 | 4-Piz | 3,4-diFPh | CO | single bond | 2 | O | CH₂CH₂ | sub. 12 |
| 3508 | 2-Aze | 3,4-diFPh | CO | single bond | 2 | O | CH₂CH₂ | sub. 12 |
| 3509 | 3-Aze | 3,4-diFPh | CO | single bond | 2 | O | CH₂CH₂ | sub. 12 |
| 3510 | 4-Aze | 3,4-diFPh | CO | single bond | 2 | O | CH₂CH₂ | sub. 12 |
| 3511 | cPr | 3,4-diFPh | CO | single bond | 2 | O | CH₂CH₂ | sub. 13 |
| 3512 | cBu | 3,4-diFPh | CO | single bond | 2 | O | CH₂CH₂ | sub. 13 |
| 3513 | cPn | 3,4-diFPh | CO | single bond | 2 | O | CH₂CH₂ | sub. 13 |
| 3514 | cHex | 3,4-diFPh | CO | single bond | 2 | O | CH₂CH₂ | sub. 13 |
| 3515 | cHep | 3,4-diFPh | CO | single bond | 2 | O | CH₂CH₂ | sub. 13 |
| 3516 | 2-Pyrd | 3,4-diFPh | CO | single bond | 2 | O | CH₂CH₂ | sub. 13 |
| 3517 | 3-Pyrd | 3,4-diFPh | CO | single bond | 2 | O | CH₂CH₂ | sub. 13 |
| 3518 | 4-Oxa | 3,4-diFPh | CO | single bond | 2 | O | CH₂CH₂ | sub. 13 |
| 3519 | 5-Oxa | 3,4-diFPh | CO | single bond | 2 | O | CH₂CH₂ | sub. 13 |
| 3520 | 4-Thi | 3,4-diFPh | CO | single bond | 2 | O | CH₂CH₂ | sub. 13 |
| 3521 | 5-Thi | 3,4-diFPh | CO | single bond | 2 | O | CH₂CH₂ | sub. 13 |
| 3522 | 4-OOxa | 3,4-diFPh | CO | single bond | 2 | O | CH₂CH₂ | sub. 13 |
| 3523 | 5-OOxa | 3,4-diFPh | CO | single bond | 2 | O | CH₂CH₂ | sub. 13 |
| 3524 | 4-OThi | 3,4-diFPh | CO | single bond | 2 | O | CH₂CH₂ | sub. 13 |
| 3525 | 5-OThi | 3,4-diFPh | CO | single bond | 2 | O | CH₂CH₂ | sub. 13 |
| 3526 | 2-Pip | 3,4-diFPh | CO | single bond | 2 | O | CH₂CH₂ | sub. 13 |
| 3527 | 3-Pip | 3,4-diFPh | CO | single bond | 2 | O | CH₂CH₂ | sub. 13 |
| 3528 | 4-Pip | 3,4-diFPh | CO | single bond | 2 | O | CH₂CH₂ | sub. 13 |
| 3529 | 2-Mor | 3,4-diFPh | CO | single bond | 2 | O | CH₂CH₂ | sub. 13 |
| 3530 | 3-Mor | 3,4-diFPh | CO | single bond | 2 | O | CH₂CH₂ | sub. 13 |
| 3531 | 4-Mor | 3,4-diFPh | CO | single bond | 2 | O | CH₂CH₂ | sub. 13 |
| 3532 | 2-Thmor | 3,4-diFPh | CO | single bond | 2 | O | CH₂CH₂ | sub. 13 |
| 3533 | 3-Thmor | 3,4-diFPh | CO | single bond | 2 | O | CH₂CH₂ | sub. 13 |
| 3534 | 4-Thmor | 3,4-diFPh | CO | single bond | 2 | O | CH₂CH₂ | sub. 13 |
| 3535 | 2-Piz | 3,4-diFPh | CO | single bond | 2 | O | CH₂CH₂ | sub. 13 |
| 3536 | 3-Piz | 3,4-diFPh | CO | single bond | 2 | O | CH₂CH₂ | sub. 13 |
| 3537 | 4-Piz | 3,4-diFPh | CO | single bond | 2 | O | CH₂CH₂ | sub. 13 |
| 3538 | 2-Aze | 3,4-diFPh | CO | single bond | 2 | O | CH₂CH₂ | sub. 13 |
| 3539 | 3-Aze | 3,4-diFPh | CO | single bond | 2 | O | CH₂CH₂ | sub. 13 |
| 3540 | 4-Aze | 3,4-diFPh | CO | single bond | 2 | O | CH₂CH₂ | sub. 13 |
| 3541 | cPr | 3,4-diFPh | CO | single bond | 2 | O | CH₂CH₂ | sub. 14 |
| 3542 | cBu | 3,4-diFPh | CO | single bond | 2 | O | CH₂CH₂ | sub. 14 |
| 3543 | cPn | 3,4-diFPh | CO | single bond | 2 | O | CH₂CH₂ | sub. 14 |
| 3544 | cHex | 3,4-diFPh | CO | single bond | 2 | O | CH₂CH₂ | sub. 14 |
| 3545 | cHep | 3,4-diFPh | CO | single bond | 2 | O | CH₂CH₂ | sub. 14 |
| 3546 | 2-Pyrd | 3,4-diFPh | CO | single bond | 2 | O | CH₂CH₂ | sub. 14 |
| 3547 | 3-Pyrd | 3,4-diFPh | CO | single bond | 2 | O | CH₂CH₂ | sub. 14 |
| 3548 | 4-Oxa | 3,4-diFPh | CO | single bond | 2 | O | CH₂CH₂ | sub. 14 |
| 3549 | 5-Oxa | 3,4-diFPh | CO | single bond | 2 | O | CH₂CH₂ | sub. 14 |
| 3550 | 4-Thi | 3,4-diFPh | CO | single bond | 2 | O | CH₂CH₂ | sub. 14 |
| 3551 | 5-Thi | 3,4-diFPh | CO | single bond | 2 | O | CH₂CH₂ | sub. 14 |
| 3552 | 4-OOxa | 3,4-diFPh | CO | single bond | 2 | O | CH₂CH₂ | sub. 14 |

TABLE 1-continued

| Exemplification compound number | R¹ | R² | A | B | N | D | G | Q |
|---|---|---|---|---|---|---|---|---|
| 3553 | 5-OOxa | 3,4-diFPh | CO | single bond | 2 | O | CH₂CH₂ | sub. 14 |
| 3554 | 4-OThi | 3,4-diFPh | CO | single bond | 2 | O | CH₂CH₂ | sub. 14 |
| 3555 | 5-OThi | 3,4-diFPh | CO | single bond | 2 | O | CH₂CH₂ | sub. 14 |
| 3556 | 2-Pip | 3,4-diFPh | CO | single bond | 2 | O | CH₂CH₂ | sub. 14 |
| 3557 | 3-Pip | 3,4-diFPh | CO | single bond | 2 | O | CH₂CH₂ | sub. 14 |
| 3558 | 4-Pip | 3,4-diFPh | CO | single bond | 2 | O | CH₂CH₂ | sub. 14 |
| 3559 | 2-Mor | 3,4-diFPh | CO | single bond | 2 | O | CH₂CH₂ | sub. 14 |
| 3560 | 3-Mor | 3,4-diFPh | CO | single bond | 2 | O | CH₂CH₂ | sub. 14 |
| 3561 | 4-Mor | 3,4-diFPh | CO | single bond | 2 | O | CH₂CH₂ | sub. 14 |
| 3562 | 2-Thmor | 3,4-diFPh | CO | single bond | 2 | O | CH₂CH₂ | sub. 14 |
| 3563 | 3-Thmor | 3,4-diFPh | CO | single bond | 2 | O | CH₂CH₂ | sub. 14 |
| 3564 | 4-Thmor | 3,4-diFPh | CO | single bond | 2 | O | CH₂CH₂ | sub. 14 |
| 3565 | 2-Piz | 3,4-diFPh | CO | single bond | 2 | O | CH₂CH₂ | sub. 14 |
| 3566 | 3-Piz | 3,4-diFPh | CO | single bond | 2 | O | CH₂CH₂ | sub. 14 |
| 3567 | 4-Piz | 3,4-diFPh | CO | single bond | 2 | O | CH₂CH₂ | sub. 14 |
| 3568 | 2-Aze | 3,4-diFPh | CO | single bond | 2 | O | CH₂CH₂ | sub. 14 |
| 3569 | 3-Aze | 3,4-diFPh | CO | single bond | 2 | O | CH₂CH₂ | sub. 14 |
| 3570 | 4-Aze | 3,4-diFPh | CO | single bond | 2 | O | CH₂CH₂ | sub. 14 |
| 3571 | cPr | 3,4-diFPh | CO | single bond | 2 | O | CH₂CH₂ | sub. 15 |
| 3572 | cBu | 3,4-diFPh | CO | single bond | 2 | O | CH₂CH₂ | sub. 15 |
| 3573 | cPn | 3,4-diFPh | CO | single bond | 2 | O | CH₂CH₂ | sub. 15 |
| 3574 | cHex | 3,4-diFPh | CO | single bond | 2 | O | CH₂CH₂ | sub. 15 |
| 3575 | cHep | 3,4-diFPh | CO | single bond | 2 | O | CH₂CH₂ | sub. 15 |
| 3576 | 2-Pyrd | 3,4-diFPh | CO | single bond | 2 | O | CH₂CH₂ | sub. 15 |
| 3577 | 3-Pyrd | 3,4-diFPh | CO | single bond | 2 | O | CH₂CH₂ | sub. 15 |
| 3578 | 4-Oxa | 3,4-diFPh | CO | single bond | 2 | O | CH₂CH₂ | sub. 15 |
| 3579 | 5-Oxa | 3,4-diFPh | CO | single bond | 2 | O | CH₂CH₂ | sub. 15 |
| 3580 | 4-Thi | 3,4-diFPh | CO | single bond | 2 | O | CH₂CH₂ | sub. 15 |
| 3581 | 5-Thi | 3,4-diFPh | CO | single bond | 2 | O | CH₂CH₂ | sub. 15 |
| 3582 | 4-OOxa | 3,4-diFPh | CO | single bond | 2 | O | CH₂CH₂ | sub. 15 |
| 3583 | 5-OOxa | 3,4-diFPh | CO | single bond | 2 | O | CH₂CH₂ | sub. 15 |
| 3584 | 4-OThi | 3,4-diFPh | CO | single bond | 2 | O | CH₂CH₂ | sub. 15 |
| 3585 | 5-OThi | 3,4-diFPh | CO | single bond | 2 | O | CH₂CH₂ | sub. 15 |
| 3586 | 2-Pip | 3,4-diFPh | CO | single bond | 2 | O | CH₂CH₂ | sub. 15 |
| 3587 | 3-Pip | 3,4-diFPh | CO | single bond | 2 | O | CH₂CH₂ | sub. 15 |
| 3588 | 4-Pip | 3,4-diFPh | CO | single bond | 2 | O | CH₂CH₂ | sub. 15 |
| 3589 | 2-Mor | 3,4-diFPh | CO | single bond | 2 | O | CH₂CH₂ | sub. 15 |
| 3590 | 3-Mor | 3,4-diFPh | CO | single bond | 2 | O | CH₂CH₂ | sub. 15 |
| 3591 | 4-Mor | 3,4-diFPh | CO | single bond | 2 | O | CH₂CH₂ | sub. 15 |
| 3592 | 2-Thmor | 3,4-diFPh | CO | single bond | 2 | O | CH₂CH₂ | sub. 15 |
| 3593 | 3-Thmor | 3,4-diFPh | CO | single bond | 2 | O | CH₂CH₂ | sub. 15 |
| 3594 | 4-Thmor | 3,4-diFPh | CO | single bond | 2 | O | CH₂CH₂ | sub. 15 |
| 3595 | 2-Piz | 3,4-diFPh | CO | single bond | 2 | O | CH₂CH₂ | sub. 15 |
| 3596 | 3-Piz | 3,4-diFPh | CO | single bond | 2 | O | CH₂CH₂ | sub. 15 |
| 3597 | 4-Piz | 3,4-diFPh | CO | single bond | 2 | O | CH₂CH₂ | sub. 15 |
| 3598 | 2-Aze | 3,4-diFPh | CO | single bond | 2 | O | CH₂CH₂ | sub. 15 |
| 3599 | 3-Aze | 3,4-diFPh | CO | single bond | 2 | O | CH₂CH₂ | sub. 15 |
| 3600 | 4-Aze | 3,4-diFPh | CO | single bond | 2 | O | CH₂CH₂ | sub. 15 |
| 3601 | cPr | 3,4-diFPh | CO | single bond | 2 | O | CH₂CH₂ | sub. 16 |
| 3602 | cBu | 3,4-diFPh | CO | single bond | 2 | O | CH₂CH₂ | sub. 16 |
| 3603 | cPn | 3,4-diFPh | CO | single bond | 2 | O | CH₂CH₂ | sub. 16 |
| 3604 | cHex | 3,4-diFPh | CO | single bond | 2 | O | CH₂CH₂ | sub. 16 |
| 3605 | cHep | 3,4-diFPh | CO | single bond | 2 | O | CH₂CH₂ | sub. 16 |
| 3606 | 2-Pyrd | 3,4-diFPh | CO | single bond | 2 | O | CH₂CH₂ | sub. 16 |
| 3607 | 3-Pyrd | 3,4-diFPh | CO | single bond | 2 | O | CH₂CH₂ | sub. 16 |
| 3608 | 4-Oxa | 3,4-diFPh | CO | single bond | 2 | O | CH₂CH₂ | sub. 16 |
| 3609 | 5-Oxa | 3,4-diFPh | CO | single bond | 2 | O | CH₂CH₂ | sub. 16 |
| 3610 | 4-Thi | 3,4-diFPh | CO | single bond | 2 | O | CH₂CH₂ | sub. 16 |
| 3611 | 5-Thi | 3,4-diFPh | CO | single bond | 2 | O | CH₂CH₂ | sub. 16 |
| 3612 | 4-OOxa | 3,4-diFPh | CO | single bond | 2 | O | CH₂CH₂ | sub. 16 |
| 3613 | 5-OOxa | 3,4-diFPh | CO | single bond | 2 | O | CH₂CH₂ | sub. 16 |
| 3614 | 4-OThi | 3,4-diFPh | CO | single bond | 2 | O | CH₂CH₂ | sub. 16 |
| 3615 | 5-OThi | 3,4-diFPh | CO | single bond | 2 | O | CH₂CH₂ | sub. 16 |
| 3616 | 2-Pip | 3,4-diFPh | CO | single bond | 2 | O | CH₂CH₂ | sub. 16 |
| 3617 | 3-Pip | 3,4-diFPh | CO | single bond | 2 | O | CH₂CH₂ | sub. 16 |
| 3618 | 4-Pip | 3,4-diFPh | CO | single bond | 2 | O | CH₂CH₂ | sub. 16 |
| 3619 | 2-Mor | 3,4-diFPh | CO | single bond | 2 | O | CH₂CH₂ | sub. 16 |
| 3620 | 3-Mor | 3,4-diFPh | CO | single bond | 2 | O | CH₂CH₂ | sub. 16 |
| 3621 | 4-Mor | 3,4-diFPh | CO | single bond | 2 | O | CH₂CH₂ | sub. 16 |
| 3622 | 2-Thmor | 3,4-diFPh | CO | single bond | 2 | O | CH₂CH₂ | sub. 16 |
| 3623 | 3-Thmor | 3,4-diFPh | CO | single bond | 2 | O | CH₂CH₂ | sub. 16 |
| 3624 | 4-Thmor | 3,4-diFPh | CO | single bond | 2 | O | CH₂CH₂ | sub. 16 |
| 3625 | 2-Piz | 3,4-diFPh | CO | single bond | 2 | O | CH₂CH₂ | sub. 16 |
| 3626 | 3-Piz | 3,4-diFPh | CO | single bond | 2 | O | CH₂CH₂ | sub. 16 |
| 3627 | 4-Piz | 3,4-diFPh | CO | single bond | 2 | O | CH₂CH₂ | sub. 16 |
| 3628 | 2-Aze | 3,4-diFPh | CO | single bond | 2 | O | CH₂CH₂ | sub. 16 |

TABLE 1-continued

| Exemplification compound number | R¹ | R² | A | B | N | D | G | Q |
|---|---|---|---|---|---|---|---|---|
| 3629 | 3-Aze | 3,4-diFPh | CO | single bond | 2 | O | CH₂CH₂ | sub. 16 |
| 3630 | 4-Aze | 3,4-diFPh | CO | single bond | 2 | O | CH₂CH₂ | sub. 16 |
| 3631 | cPr | 3,4-diFPh | CO | single bond | 2 | O | CH₂CH₂ | sub. 17 |
| 3632 | cBu | 3,4-diFPh | CO | single bond | 2 | O | CH₂CH₂ | sub. 17 |
| 3633 | cPn | 3,4-diFPh | CO | single bond | 2 | O | CH₂CH₂ | sub. 17 |
| 3634 | cHex | 3,4-diFPh | CO | single bond | 2 | O | CH₂CH₂ | sub. 17 |
| 3635 | cHep | 3,4-diFPh | CO | single bond | 2 | O | CH₂CH₂ | sub. 17 |
| 3636 | 2-Pyrd | 3,4-diFPh | CO | single bond | 2 | O | CH₂CH₂ | sub. 17 |
| 3637 | 3-Pyrd | 3,4-diFPh | CO | single bond | 2 | O | CH₂CH₂ | sub. 17 |
| 3638 | 4-Oxa | 3,4-diFPh | CO | single bond | 2 | O | CH₂CH₂ | sub. 17 |
| 3639 | 5-Oxa | 3,4-diFPh | CO | single bond | 2 | O | CH₂CH₂ | sub. 17 |
| 3640 | 4-Thi | 3,4-diFPh | CO | single bond | 2 | O | CH₂CH₂ | sub. 17 |
| 3641 | 5-Thi | 3,4-diFPh | CO | single bond | 2 | O | CH₂CH₂ | sub. 17 |
| 3642 | 4-OOxa | 3,4-diFPh | CO | single bond | 2 | O | CH₂CH₂ | sub. 17 |
| 3643 | 5-OOxa | 3,4-diFPh | CO | single bond | 2 | O | CH₂CH₂ | sub. 17 |
| 3644 | 4-OThi | 3,4-diFPh | CO | single bond | 2 | O | CH₂CH₂ | sub. 17 |
| 3645 | 5-OThi | 3,4-diFPh | CO | single bond | 2 | O | CH₂CH₂ | sub. 17 |
| 3646 | 2-Pip | 3,4-diFPh | CO | single bond | 2 | O | CH₂CH₂ | sub. 17 |
| 3647 | 3-Pip | 3,4-diFPh | CO | single bond | 2 | O | CH₂CH₂ | sub. 17 |
| 3648 | 4-Pip | 3,4-diFPh | CO | single bond | 2 | O | CH₂CH₂ | sub. 17 |
| 3649 | 2-Mor | 3,4-diFPh | CO | single bond | 2 | O | CH₂CH₂ | sub. 17 |
| 3650 | 3-Mor | 3,4-diFPh | CO | single bond | 2 | O | CH₂CH₂ | sub. 17 |
| 3651 | 4-Mor | 3,4-diFPh | CO | single bond | 2 | O | CH₂CH₂ | sub. 17 |
| 3652 | 2-Thmor | 3,4-diFPh | CO | single bond | 2 | O | CH₂CH₂ | sub. 17 |
| 3653 | 3-Thmor | 3,4-diFPh | CO | single bond | 2 | O | CH₂CH₂ | sub. 17 |
| 3654 | 4-Thmor | 3,4-diFPh | CO | single bond | 2 | O | CH₂CH₂ | sub. 17 |
| 3655 | 2-Piz | 3,4-diFPh | CO | single bond | 2 | O | CH₂CH₂ | sub. 17 |
| 3656 | 3-Piz | 3,4-diFPh | CO | single bond | 2 | O | CH₂CH₂ | sub. 17 |
| 3657 | 4-Piz | 3,4-diFPh | CO | single bond | 2 | O | CH₂CH₂ | sub. 17 |
| 3658 | 2-Aze | 3,4-diFPh | CO | single bond | 2 | O | CH₂CH₂ | sub. 17 |
| 3659 | 3-Aze | 3,4-diFPh | CO | single bond | 2 | O | CH₂CH₂ | sub. 17 |
| 3660 | 4-Aze | 3,4-diFPh | CO | single bond | 2 | O | CH₂CH₂ | sub. 17 |
| 3661 | cPr | 3,4-diFPh | CO | single bond | 2 | O | CH₂CH₂ | sub. 18 |
| 3662 | cBu | 3,4-diFPh | CO | single bond | 2 | O | CH₂CH₂ | sub. 18 |
| 3663 | cPn | 3,4-diFPh | CO | single bond | 2 | O | CH₂CH₂ | sub. 18 |
| 3664 | cHex | 3,4-diFPh | CO | single bond | 2 | O | CH₂CH₂ | sub. 18 |
| 3665 | cHep | 3,4-diFPh | CO | single bond | 2 | O | CH₂CH₂ | sub. 18 |
| 3666 | 2-Pyrd | 3,4-diFPh | CO | single bond | 2 | O | CH₂CH₂ | sub. 18 |
| 3667 | 3-Pyrd | 3,4-diFPh | CO | single bond | 2 | O | CH₂CH₂ | sub. 18 |
| 3668 | 4-Oxa | 3,4-diFPh | CO | single bond | 2 | O | CH₂CH₂ | sub. 18 |
| 3669 | 5-Oxa | 3,4-diFPh | CO | single bond | 2 | O | CH₂CH₂ | sub. 18 |
| 3670 | 4-Thi | 3,4-diFPh | CO | single bond | 2 | O | CH₂CH₂ | sub. 18 |
| 3671 | 5-Thi | 3,4-diFPh | CO | single bond | 2 | O | CH₂CH₂ | sub. 18 |
| 3672 | 4-OOxa | 3,4-diFPh | CO | single bond | 2 | O | CH₂CH₂ | sub. 18 |
| 3673 | 5-OOxa | 3,4-diFPh | CO | single bond | 2 | O | CH₂CH₂ | sub. 18 |
| 3674 | 4-OThi | 3,4-diFPh | CO | single bond | 2 | O | CH₂CH₂ | sub. 18 |
| 3675 | 5-OThi | 3,4-diFPh | CO | single bond | 2 | O | CH₂CH₂ | sub. 18 |
| 3676 | 2-Pip | 3,4-diFPh | CO | single bond | 2 | O | CH₂CH₂ | sub. 18 |
| 3677 | 3-Pip | 3,4-diFPh | CO | single bond | 2 | O | CH₂CH₂ | sub. 18 |
| 3678 | 4-Pip | 3,4-diFPh | CO | single bond | 2 | O | CH₂CH₂ | sub. 18 |
| 3679 | 2-Mor | 3,4-diFPh | CO | single bond | 2 | O | CH₂CH₂ | sub. 18 |
| 3680 | 3-Mor | 3,4-diFPh | CO | single bond | 2 | O | CH₂CH₂ | sub. 18 |
| 3681 | 4-Mor | 3,4-diFPh | CO | single bond | 2 | O | CH₂CH₂ | sub. 18 |
| 3682 | 2-Thmor | 3,4-diFPh | CO | single bond | 2 | O | CH₂CH₂ | sub. 18 |
| 3683 | 3-Thmor | 3,4-diFPh | CO | single bond | 2 | O | CH₂CH₂ | sub. 18 |
| 3684 | 4-Thmor | 3,4-diFPh | CO | single bond | 2 | O | CH₂CH₂ | sub. 18 |
| 3685 | 2-Piz | 3,4-diFPh | CO | single bond | 2 | O | CH₂CH₂ | sub. 18 |
| 3686 | 3-Piz | 3,4-diFPh | CO | single bond | 2 | O | CH₂CH₂ | sub. 18 |
| 3687 | 4-Piz | 3,4-diFPh | CO | single bond | 2 | O | CH₂CH₂ | sub. 18 |
| 3688 | 2-Aze | 3,4-diFPh | CO | single bond | 2 | O | CH₂CH₂ | sub. 18 |
| 3689 | 3-Aze | 3,4-diFPh | CO | single bond | 2 | O | CH₂CH₂ | sub. 18 |
| 3690 | 4-Aze | 3,4-diFPh | CO | single bond | 2 | O | CH₂CH₂ | sub. 18 |
| 3691 | cPr | 3,4-diFPh | CO | single bond | 2 | O | CH₂CH₂ | sub. 19 |
| 3692 | cBu | 3,4-diFPh | CO | single bond | 2 | O | CH₂CH₂ | sub. 19 |
| 3693 | cPn | 3,4-diFPh | CO | single bond | 2 | O | CH₂CH₂ | sub. 19 |
| 3694 | cHex | 3,4-diFPh | CO | single bond | 2 | O | CH₂CH₂ | sub. 19 |
| 3695 | cHep | 3,4-diFPh | CO | single bond | 2 | O | CH₂CH₂ | sub. 19 |
| 3696 | 2-Pyrd | 3,4-diFPh | CO | single bond | 2 | O | CH₂CH₂ | sub. 19 |
| 3697 | 3-Pyrd | 3,4-diFPh | CO | single bond | 2 | O | CH₂CH₂ | sub. 19 |
| 3698 | 4-Oxa | 3,4-diFPh | CO | single bond | 2 | O | CH₂CH₂ | sub. 19 |
| 3699 | 5-Oxa | 3,4-diFPh | CO | single bond | 2 | O | CH₂CH₂ | sub. 19 |
| 3700 | 4-Thi | 3,4-diFPh | CO | single bond | 2 | O | CH₂CH₂ | sub. 19 |
| 3701 | 5-Thi | 3,4-diFPh | CO | single bond | 2 | O | CH₂CH₂ | sub. 19 |
| 3702 | 4-OOxa | 3,4-diFPh | CO | single bond | 2 | O | CH₂CH₂ | sub. 19 |
| 3703 | 5-OOxa | 3,4-diFPh | CO | single bond | 2 | O | CH₂CH₂ | sub. 19 |
| 3704 | 4-OThi | 3,4-diFPh | CO | single bond | 2 | O | CH₂CH₂ | sub. 19 |

TABLE 1-continued

| Exemplification compound number | R¹ | R² | A | B | N | D | G | Q |
|---|---|---|---|---|---|---|---|---|
| 3705 | 5-OThi | 3,4-diFPh | CO | single bond | 2 | O | CH₂CH₂ | sub. 19 |
| 3706 | 2-Pip | 3,4-diFPh | CO | single bond | 2 | O | CH₂CH₂ | sub. 19 |
| 3707 | 3-Pip | 3,4-diFPh | CO | single bond | 2 | O | CH₂CH₂ | sub. 19 |
| 3708 | 4-Pip | 3,4-diFPh | CO | single bond | 2 | O | CH₂CH₂ | sub. 19 |
| 3709 | 2-Mor | 3,4-diFPh | CO | single bond | 2 | O | CH₂CH₂ | sub. 19 |
| 3710 | 3-Mor | 3,4-diFPh | CO | single bond | 2 | O | CH₂CH₂ | sub. 19 |
| 3711 | 4-Mor | 3,4-diFPh | CO | single bond | 2 | O | CH₂CH₂ | sub. 19 |
| 3712 | 2-Thmor | 3,4-diFPh | CO | single bond | 2 | O | CH₂CH₂ | sub. 19 |
| 3713 | 3-Thmor | 3,4-diFPh | CO | single bond | 2 | O | CH₂CH₂ | sub. 19 |
| 3714 | 4-Thmor | 3,4-diFPh | CO | single bond | 2 | O | CH₂CH₂ | sub. 19 |
| 3715 | 2-Piz | 3,4-diFPh | CO | single bond | 2 | O | CH₂CH₂ | sub. 19 |
| 3716 | 3-Piz | 3,4-diFPh | CO | single bond | 2 | O | CH₂CH₂ | sub. 19 |
| 3717 | 4-Piz | 3,4-diFPh | CO | single bond | 2 | O | CH₂CH₂ | sub. 19 |
| 3718 | 2-Aze | 3,4-diFPh | CO | single bond | 2 | O | CH₂CH₂ | sub. 19 |
| 3719 | 3-Aze | 3,4-diFPh | CO | single bond | 2 | O | CH₂CH₂ | sub. 19 |
| 3720 | 4-Aze | 3,4-diFPh | CO | single bond | 2 | O | CH₂CH₂ | sub. 19 |
| 3721 | cPr | 3,4-diFPh | CO | single bond | 2 | O | CH₂CH₂ | sub. 20 |
| 3722 | cBu | 3,4-diFPh | CO | single bond | 2 | O | CH₂CH₂ | sub. 20 |
| 3723 | cPn | 3,4-diFPh | CO | single bond | 2 | O | CH₂CH₂ | sub. 20 |
| 3724 | cHex | 3,4-diFPh | CO | single bond | 2 | O | CH₂CH₂ | sub. 20 |
| 3725 | cHep | 3,4-diFPh | CO | single bond | 2 | O | CH₂CH₂ | sub. 20 |
| 3726 | 2-Pyrd | 3,4-diFPh | CO | single bond | 2 | O | CH₂CH₂ | sub. 20 |
| 3727 | 3-Pyrd | 3,4-diFPh | CO | single bond | 2 | O | CH₂CH₂ | sub. 20 |
| 3728 | 4-Oxa | 3,4-diFPh | CO | single bond | 2 | O | CH₂CH₂ | sub. 20 |
| 3729 | 5-Oxa | 3,4-diFPh | CO | single bond | 2 | O | CH₂CH₂ | sub. 20 |
| 3730 | 4-Thi | 3,4-diFPh | CO | single bond | 2 | O | CH₂CH₂ | sub. 20 |
| 3731 | 5-Thi | 3,4-diFPh | CO | single bond | 2 | O | CH₂CH₂ | sub. 20 |
| 3732 | 4-OOxa | 3,4-diFPh | CO | single bond | 2 | O | CH₂CH₂ | sub. 20 |
| 3733 | 5-OOxa | 3,4-diFPh | CO | single bond | 2 | O | CH₂CH₂ | sub. 20 |
| 3734 | 4-OThi | 3,4-diFPh | CO | single bond | 2 | O | CH₂CH₂ | sub. 20 |
| 3735 | 5-OThi | 3,4-diFPh | CO | single bond | 2 | O | CH₂CH₂ | sub. 20 |
| 3736 | 2-Pip | 3,4-diFPh | CO | single bond | 2 | O | CH₂CH₂ | sub. 20 |
| 3737 | 3-Pip | 3,4-diFPh | CO | single bond | 2 | O | CH₂CH₂ | sub. 20 |
| 3738 | 4-Pip | 3,4-diFPh | CO | single bond | 2 | O | CH₂CH₂ | sub. 20 |
| 3739 | 2-Mor | 3,4-diFPh | CO | single bond | 2 | O | CH₂CH₂ | sub. 20 |
| 3740 | 3-Mor | 3,4-diFPh | CO | single bond | 2 | O | CH₂CH₂ | sub. 20 |
| 3741 | 4-Mor | 3,4-diFPh | CO | single bond | 2 | O | CH₂CH₂ | sub. 20 |
| 3742 | 2-Thmor | 3,4-diFPh | CO | single bond | 2 | O | CH₂CH₂ | sub. 20 |
| 3743 | 3-Thmor | 3,4-diFPh | CO | single bond | 2 | O | CH₂CH₂ | sub. 20 |
| 3744 | 4-Thmor | 3,4-diFPh | CO | single bond | 2 | O | CH₂CH₂ | sub. 20 |
| 3745 | 2-Piz | 3,4-diFPh | CO | single bond | 2 | O | CH₂CH₂ | sub. 20 |
| 3746 | 3-Piz | 3,4-diFPh | CO | single bond | 2 | O | CH₂CH₂ | sub. 20 |
| 3747 | 4-Piz | 3,4-diFPh | CO | single bond | 2 | O | CH₂CH₂ | sub. 20 |
| 3748 | 2-Aze | 3,4-diFPh | CO | single bond | 2 | O | CH₂CH₂ | sub. 20 |
| 3749 | 3-Aze | 3,4-diFPh | CO | single bond | 2 | O | CH₂CH₂ | sub. 20 |
| 3750 | 4-Aze | 3,4-diFPh | CO | single bond | 2 | O | CH₂CH₂ | sub. 20 |
| 3751 | cPr | 3,4-diFPh | CO | single bond | 2 | O | CH₂CH₂ | sub. 21 |
| 3752 | cBu | 3,4-diFPh | CO | single bond | 2 | O | CH₂CH₂ | sub. 21 |
| 3753 | cPn | 3,4-diFPh | CO | single bond | 2 | O | CH₂CH₂ | sub. 21 |
| 3754 | cHex | 3,4-diFPh | CO | single bond | 2 | O | CH₂CH₂ | sub. 21 |
| 3755 | cHep | 3,4-diFPh | CO | single bond | 2 | O | CH₂CH₂ | sub. 21 |
| 3756 | 2-Pyrd | 3,4-diFPh | CO | single bond | 2 | O | CH₂CH₂ | sub. 21 |
| 3757 | 3-Pyrd | 3,4-diFPh | CO | single bond | 2 | O | CH₂CH₂ | sub. 21 |
| 3758 | 4-Oxa | 3,4-diFPh | CO | single bond | 2 | O | CH₂CH₂ | sub. 21 |
| 3759 | 5-Oxa | 3,4-diFPh | CO | single bond | 2 | O | CH₂CH₂ | sub. 21 |
| 3760 | 4-Thi | 3,4-diFPh | CO | single bond | 2 | O | CH₂CH₂ | sub. 21 |
| 3761 | 5-Thi | 3,4-diFPh | CO | single bond | 2 | O | CH₂CH₂ | sub. 21 |
| 3762 | 4-OOxa | 3,4-diFPh | CO | single bond | 2 | O | CH₂CH₂ | sub. 21 |
| 3763 | 5-OOxa | 3,4-diFPh | CO | single bond | 2 | O | CH₂CH₂ | sub. 21 |
| 3764 | 4-OThi | 3,4-diFPh | CO | single bond | 2 | O | CH₂CH₂ | sub. 21 |
| 3765 | 5-OThi | 3,4-diFPh | CO | single bond | 2 | O | CH₂CH₂ | sub. 21 |
| 3766 | 2-Pip | 3,4-diFPh | CO | single bond | 2 | O | CH₂CH₂ | sub. 21 |
| 3767 | 3-Pip | 3,4-diFPh | CO | single bond | 2 | O | CH₂CH₂ | sub. 21 |
| 3768 | 4-Pip | 3,4-diFPh | CO | single bond | 2 | O | CH₂CH₂ | sub. 21 |
| 3769 | 2-Mor | 3,4-diFPh | CO | single bond | 2 | O | CH₂CH₂ | sub. 21 |
| 3770 | 3-Mor | 3,4-diFPh | CO | single bond | 2 | O | CH₂CH₂ | sub. 21 |
| 3771 | 4-Mor | 3,4-diFPh | CO | single bond | 2 | O | CH₂CH₂ | sub. 21 |
| 3772 | 2-Thmor | 3,4-diFPh | CO | single bond | 2 | O | CH₂CH₂ | sub. 21 |
| 3773 | 3-Thmor | 3,4-diFPh | CO | single bond | 2 | O | CH₂CH₂ | sub. 21 |
| 3774 | 4-Thmor | 3,4-diFPh | CO | single bond | 2 | O | CH₂CH₂ | sub. 21 |
| 3775 | 2-Piz | 3,4-diFPh | CO | single bond | 2 | O | CH₂CH₂ | sub. 21 |
| 3776 | 3-Piz | 3,4-diFPh | CO | single bond | 2 | O | CH₂CH₂ | sub. 21 |
| 3777 | 4-Piz | 3,4-diFPh | CO | single bond | 2 | O | CH₂CH₂ | sub. 21 |
| 3778 | 2-Aze | 3,4-diFPh | CO | single bond | 2 | O | CH₂CH₂ | sub. 21 |
| 3779 | 3-Aze | 3,4-diFPh | CO | single bond | 2 | O | CH₂CH₂ | sub. 21 |
| 3780 | 4-Aze | 3,4-diFPh | CO | single bond | 2 | O | CH₂CH₂ | sub. 21 |

TABLE 1-continued

| Exemplification compound number | R¹ | R² | A | B | N | D | G | Q |
|---|---|---|---|---|---|---|---|---|
| 3781 | cPr | 3,4-diFPh | CO | single bond | 2 | O | $CH_2CH_2$ | sub. 22 |
| 3782 | cBu | 3,4-diFPh | CO | single bond | 2 | O | $CH_2CH_2$ | sub. 22 |
| 3783 | cPn | 3,4-diFPh | CO | single bond | 2 | O | $CH_2CH_2$ | sub. 22 |
| 3784 | cHex | 3,4-diFPh | CO | single bond | 2 | O | $CH_2CH_2$ | sub. 22 |
| 3785 | cHep | 3,4-diFPh | CO | single bond | 2 | O | $CH_2CH_2$ | sub. 22 |
| 3786 | 2-Pyrd | 3,4-diFPh | CO | single bond | 2 | O | $CH_2CH_2$ | sub. 22 |
| 3787 | 3-Pyrd | 3,4-diFPh | CO | single bond | 2 | O | $CH_2CH_2$ | sub. 22 |
| 3788 | 4-Oxa | 3,4-diFPh | CO | single bond | 2 | O | $CH_2CH_2$ | sub. 22 |
| 3789 | 5-Oxa | 3,4-diFPh | CO | single bond | 2 | O | $CH_2CH_2$ | sub. 22 |
| 3790 | 4-Thi | 3,4-diFPh | CO | single bond | 2 | O | $CH_2CH_2$ | sub. 22 |
| 3791 | 5-Thi | 3,4-diFPh | CO | single bond | 2 | O | $CH_2CH_2$ | sub. 22 |
| 3792 | 4-OOxa | 3,4-diFPh | CO | single bond | 2 | O | $CH_2CH_2$ | sub. 22 |
| 3793 | 5-OOxa | 3,4-diFPh | CO | single bond | 2 | O | $CH_2CH_2$ | sub. 22 |
| 3794 | 4-OThi | 3,4-diFPh | CO | single bond | 2 | O | $CH_2CH_2$ | sub. 22 |
| 3795 | 5-OThi | 3,4-diFPh | CO | single bond | 2 | O | $CH_2CH_2$ | sub. 22 |
| 3796 | 2-Pip | 3,4-diFPh | CO | single bond | 2 | O | $CH_2CH_2$ | sub. 22 |
| 3797 | 3-Pip | 3,4-diFPh | CO | single bond | 2 | O | $CH_2CH_2$ | sub. 22 |
| 3798 | 4-Pip | 3,4-diFPh | CO | single bond | 2 | O | $CH_2CH_2$ | sub. 22 |
| 3799 | 2-Mor | 3,4-diFPh | CO | single bond | 2 | O | $CH_2CH_2$ | sub. 22 |
| 3800 | 3-Mor | 3,4-diFPh | CO | single bond | 2 | O | $CH_2CH_2$ | sub. 22 |
| 3801 | 4-Mor | 3,4-diFPh | CO | single bond | 2 | O | $CH_2CH_2$ | sub. 22 |
| 3802 | 2-Thmor | 3,4-diFPh | CO | single bond | 2 | O | $CH_2CH_2$ | sub. 22 |
| 3803 | 3-Thmor | 3,4-diFPh | CO | single bond | 2 | O | $CH_2CH_2$ | sub. 22 |
| 3804 | 4-Thmor | 3,4-diFPh | CO | single bond | 2 | O | $CH_2CH_2$ | sub. 22 |
| 3805 | 2-Piz | 3,4-diFPh | CO | single bond | 2 | O | $CH_2CH_2$ | sub. 22 |
| 3806 | 3-Piz | 3,4-diFPh | CO | single bond | 2 | O | $CH_2CH_2$ | sub. 22 |
| 3807 | 4-Piz | 3,4-diFPh | CO | single bond | 2 | O | $CH_2CH_2$ | sub. 22 |
| 3808 | 2-Aze | 3,4-diFPh | CO | single bond | 2 | O | $CH_2CH_2$ | sub. 22 |
| 3809 | 3-Aze | 3,4-diFPh | CO | single bond | 2 | O | $CH_2CH_2$ | sub. 22 |
| 3810 | 4-Aze | 3,4-diFPh | CO | single bond | 2 | O | $CH_2CH_2$ | sub. 22 |
| 3811 | cPr | 3,4-diFPh | CO | single bond | 2 | O | $CH_2CH_2$ | sub. 23 |
| 3812 | cBu | 3,4-diFPh | CO | single bond | 2 | O | $CH_2CH_2$ | sub. 23 |
| 3813 | cPn | 3,4-diFPh | CO | single bond | 2 | O | $CH_2CH_2$ | sub. 23 |
| 3814 | cHex | 3,4-diFPh | CO | single bond | 2 | O | $CH_2CH_2$ | sub. 23 |
| 3815 | cHep | 3,4-diFPh | CO | single bond | 2 | O | $CH_2CH_2$ | sub. 23 |
| 3816 | 2-Pyrd | 3,4-diFPh | CO | single bond | 2 | O | $CH_2CH_2$ | sub. 23 |
| 3817 | 3-Pyrd | 3,4-diFPh | CO | single bond | 2 | O | $CH_2CH_2$ | sub. 23 |
| 3818 | 4-Oxa | 3,4-diFPh | CO | single bond | 2 | O | $CH_2CH_2$ | sub. 23 |
| 3819 | 5-Oxa | 3,4-diFPh | CO | single bond | 2 | O | $CH_2CH_2$ | sub. 23 |
| 3820 | 4-Thi | 3,4-diFPh | CO | single bond | 2 | O | $CH_2CH_2$ | sub. 23 |
| 3821 | 5-Thi | 3,4-diFPh | CO | single bond | 2 | O | $CH_2CH_2$ | sub. 23 |
| 3822 | 4-OOxa | 3,4-diFPh | CO | single bond | 2 | O | $CH_2CH_2$ | sub. 23 |
| 3823 | 5-OOxa | 3,4-diFPh | CO | single bond | 2 | O | $CH_2CH_2$ | sub. 23 |
| 3824 | 4-OThi | 3,4-diFPh | CO | single bond | 2 | O | $CH_2CH_2$ | sub. 23 |
| 3825 | 5-OThi | 3,4-diFPh | CO | single bond | 2 | O | $CH_2CH_2$ | sub. 23 |
| 3826 | 2-Pip | 3,4-diFPh | CO | single bond | 2 | O | $CH_2CH_2$ | sub. 23 |
| 3827 | 3-Pip | 3,4-diFPh | CO | single bond | 2 | O | $CH_2CH_2$ | sub. 23 |
| 3828 | 4-Pip | 3,4-diFPh | CO | single bond | 2 | O | $CH_2CH_2$ | sub. 23 |
| 3829 | 2-Mor | 3,4-diFPh | CO | single bond | 2 | O | $CH_2CH_2$ | sub. 23 |
| 3830 | 3-Mor | 3,4-diFPh | CO | single bond | 2 | O | $CH_2CH_2$ | sub. 23 |
| 3831 | 4-Mor | 3,4-diFPh | CO | single bond | 2 | O | $CH_2CH_2$ | sub. 23 |
| 3832 | 2-Thmor | 3,4-diFPh | CO | single bond | 2 | O | $CH_2CH_2$ | sub. 23 |
| 3833 | 3-Thmor | 3,4-diFPh | CO | single bond | 2 | O | $CH_2CH_2$ | sub. 23 |
| 3834 | 4-Thmor | 3,4-diFPh | CO | single bond | 2 | O | $CH_2CH_2$ | sub. 23 |
| 3835 | 2-Piz | 3,4-diFPh | CO | single bond | 2 | O | $CH_2CH_2$ | sub. 23 |
| 3836 | 3-Piz | 3,4-diFPh | CO | single bond | 2 | O | $CH_2CH_2$ | sub. 23 |
| 3837 | 4-Piz | 3,4-diFPh | CO | single bond | 2 | O | $CH_2CH_2$ | sub. 23 |
| 3838 | 2-Aze | 3,4-diFPh | CO | single bond | 2 | O | $CH_2CH_2$ | sub. 23 |
| 3839 | 3-Aze | 3,4-diFPh | CO | single bond | 2 | O | $CH_2CH_2$ | sub. 23 |
| 3840 | 4-Aze | 3,4-diFPh | CO | single bond | 2 | O | $CH_2CH_2$ | sub. 23 |
| 3841 | cPr | 3,4-diFPh | CO | single bond | 2 | O | $CH_2CH_2$ | sub. 24 |
| 3842 | cBu | 3,4-diFPh | CO | single bond | 2 | O | $CH_2CH_2$ | sub. 24 |
| 3843 | cPn | 3,4-diFPh | CO | single bond | 2 | O | $CH_2CH_2$ | sub. 24 |
| 3844 | cHex | 3,4-diFPh | CO | single bond | 2 | O | $CH_2CH_2$ | sub. 24 |
| 3845 | cHep | 3,4-diFPh | CO | single bond | 2 | O | $CH_2CH_2$ | sub. 24 |
| 3846 | 2-Pyrd | 3,4-diFPh | CO | single bond | 2 | O | $CH_2CH_2$ | sub. 24 |
| 3847 | 3-Pyrd | 3,4-diFPh | CO | single bond | 2 | O | $CH_2CH_2$ | sub. 24 |
| 3848 | 4-Oxa | 3,4-diFPh | CO | single bond | 2 | O | $CH_2CH_2$ | sub. 24 |
| 3849 | 5-Oxa | 3,4-diFPh | CO | single bond | 2 | O | $CH_2CH_2$ | sub. 24 |
| 3850 | 4-Thi | 3,4-diFPh | CO | single bond | 2 | O | $CH_2CH_2$ | sub. 24 |
| 3851 | 5-Thi | 3,4-diFPh | CO | single bond | 2 | O | $CH_2CH_2$ | sub. 24 |
| 3852 | 4-OOxa | 3,4-diFPh | CO | single bond | 2 | O | $CH_2CH_2$ | sub. 24 |
| 3853 | 5-OOxa | 3,4-diFPh | CO | single bond | 2 | O | $CH_2CH_2$ | sub. 24 |
| 3854 | 4-OThi | 3,4-diFPh | CO | single bond | 2 | O | $CH_2CH_2$ | sub. 24 |
| 3855 | 5-OThi | 3,4-diFPh | CO | single bond | 2 | O | $CH_2CH_2$ | sub. 24 |
| 3856 | 2-Pip | 3,4-diFPh | CO | single bond | 2 | O | $CH_2CH_2$ | sub. 24 |

TABLE 1-continued

| Exemplification compound number | R¹ | R² | A | B | N | D | G | Q |
|---|---|---|---|---|---|---|---|---|
| 3857 | 3-Pip | 3,4-diFPh | CO | single bond | 2 | O | CH₂CH₂ | sub. 24 |
| 3858 | 4-Pip | 3,4-diFPh | CO | single bond | 2 | O | CH₂CH₂ | sub. 24 |
| 3859 | 2-Mor | 3,4-diFPh | CO | single bond | 2 | O | CH₂CH₂ | sub. 24 |
| 3860 | 3-Mor | 3,4-diFPh | CO | single bond | 2 | O | CH₂CH₂ | sub. 24 |
| 3861 | 4-Mor | 3,4-diFPh | CO | single bond | 2 | O | CH₂CH₂ | sub. 24 |
| 3862 | 2-Thmor | 3,4-diFPh | CO | single bond | 2 | O | CH₂CH₂ | sub. 24 |
| 3863 | 3-Thmor | 3,4-diFPh | CO | single bond | 2 | O | CH₂CH₂ | sub. 24 |
| 3864 | 4-Thmor | 3,4-diFPh | CO | single bond | 2 | O | CH₂CH₂ | sub. 24 |
| 3865 | 2-Piz | 3,4-diFPh | CO | single bond | 2 | O | CH₂CH₂ | sub. 24 |
| 3866 | 3-Piz | 3,4-diFPh | CO | single bond | 2 | O | CH₂CH₂ | sub. 24 |
| 3867 | 4-Piz | 3,4-diFPh | CO | single bond | 2 | O | CH₂CH₂ | sub. 24 |
| 3868 | 2-Aze | 3,4-diFPh | CO | single bond | 2 | O | CH₂CH₂ | sub. 24 |
| 3869 | 3-Aze | 3,4-diFPh | CO | single bond | 2 | O | CH₂CH₂ | sub. 24 |
| 3870 | 4-Aze | 3,4-diFPh | CO | single bond | 2 | O | CH₂CH₂ | sub. 24 |
| 3871 | cPr | 3,4-diFPh | CO | single bond | 2 | O | CH₂CH₂ | sub. 25 |
| 3872 | cBu | 3,4-diFPh | CO | single bond | 2 | O | CH₂CH₂ | sub. 25 |
| 3873 | cPn | 3,4-diFPh | CO | single bond | 2 | O | CH₂CH₂ | sub. 25 |
| 3874 | cHex | 3,4-diFPh | CO | single bond | 2 | O | CH₂CH₂ | sub. 25 |
| 3875 | cHep | 3,4-diFPh | CO | single bond | 2 | O | CH₂CH₂ | sub. 25 |
| 3876 | 2-Pyrd | 3,4-diFPh | CO | single bond | 2 | O | CH₂CH₂ | sub. 25 |
| 3877 | 3-Pyrd | 3,4-diFPh | CO | single bond | 2 | O | CH₂CH₂ | sub. 25 |
| 3878 | 4-Oxa | 3,4-diFPh | CO | single bond | 2 | O | CH₂CH₂ | sub. 25 |
| 3879 | 5-Oxa | 3,4-diFPh | CO | single bond | 2 | O | CH₂CH₂ | sub. 25 |
| 3880 | 4-Thi | 3,4-diFPh | CO | single bond | 2 | O | CH₂CH₂ | sub. 25 |
| 3881 | 5-Thi | 3,4-diFPh | CO | single bond | 2 | O | CH₂CH₂ | sub. 25 |
| 3882 | 4-OOxa | 3,4-diFPh | CO | single bond | 2 | O | CH₂CH₂ | sub. 25 |
| 3883 | 5-OOxa | 3,4-diFPh | CO | single bond | 2 | O | CH₂CH₂ | sub. 25 |
| 3884 | 4-OThi | 3,4-diFPh | CO | single bond | 2 | O | CH₂CH₂ | sub. 25 |
| 3885 | 5-OThi | 3,4-diFPh | CO | single bond | 2 | O | CH₂CH₂ | sub. 25 |
| 3886 | 2-Pip | 3,4-diFPh | CO | single bond | 2 | O | CH₂CH₂ | sub. 25 |
| 3887 | 3-Pip | 3,4-diFPh | CO | single bond | 2 | O | CH₂CH₂ | sub. 25 |
| 3888 | 4-Pip | 3,4-diFPh | CO | single bond | 2 | O | CH₂CH₂ | sub. 25 |
| 3889 | 2-Mor | 3,4-diFPh | CO | single bond | 2 | O | CH₂CH₂ | sub. 25 |
| 3890 | 3-Mor | 3,4-diFPh | CO | single bond | 2 | O | CH₂CH₂ | sub. 25 |
| 3891 | 4-Mor | 3,4-diFPh | CO | single bond | 2 | O | CH₂CH₂ | sub. 25 |
| 3892 | 2-Thmor | 3,4-diFPh | CO | single bond | 2 | O | CH₂CH₂ | sub. 25 |
| 3893 | 3-Thmor | 3,4-diFPh | CO | single bond | 2 | O | CH₂CH₂ | sub. 25 |
| 3894 | 4-Thmor | 3,4-diFPh | CO | single bond | 2 | O | CH₂CH₂ | sub. 25 |
| 3895 | 2-Piz | 3,4-diFPh | CO | single bond | 2 | O | CH₂CH₂ | sub. 25 |
| 3896 | 3-Piz | 3,4-diFPh | CO | single bond | 2 | O | CH₂CH₂ | sub. 25 |
| 3897 | 4-Piz | 3,4-diFPh | CO | single bond | 2 | O | CH₂CH₂ | sub. 25 |
| 3898 | 2-Aze | 3,4-diFPh | CO | single bond | 2 | O | CH₂CH₂ | sub. 25 |
| 3899 | 3-Aze | 3,4-diFPh | CO | single bond | 2 | O | CH₂CH₂ | sub. 25 |
| 3900 | 4-Aze | 3,4-diFPh | CO | single bond | 2 | O | CH₂CH₂ | sub. 25 |
| 3901 | cPr | 3,4-diFPh | CO | single bond | 2 | O | CH₂CH₂ | sub. 26 |
| 3902 | cBu | 3,4-diFPh | CO | single bond | 2 | O | CH₂CH₂ | sub. 26 |
| 3903 | cPn | 3,4-diFPh | CO | single bond | 2 | O | CH₂CH₂ | sub. 26 |
| 3904 | cHex | 3,4-diFPh | CO | single bond | 2 | O | CH₂CH₂ | sub. 26 |
| 3905 | cHep | 3,4-diFPh | CO | single bond | 2 | O | CH₂CH₂ | sub. 26 |
| 3906 | 2-Pyrd | 3,4-diFPh | CO | single bond | 2 | O | CH₂CH₂ | sub. 26 |
| 3907 | 3-Pyrd | 3,4-diFPh | CO | single bond | 2 | O | CH₂CH₂ | sub. 26 |
| 3908 | 4-Oxa | 3,4-diFPh | CO | single bond | 2 | O | CH₂CH₂ | sub. 26 |
| 3909 | 5-Oxa | 3,4-diFPh | CO | single bond | 2 | O | CH₂CH₂ | sub. 26 |
| 3910 | 4-Thi | 3,4-diFPh | CO | single bond | 2 | O | CH₂CH₂ | sub. 26 |
| 3911 | 5-Thi | 3,4-diFPh | CO | single bond | 2 | O | CH₂CH₂ | sub. 26 |
| 3912 | 4-OOxa | 3,4-diFPh | CO | single bond | 2 | O | CH₂CH₂ | sub. 26 |
| 3913 | 5-OOxa | 3,4-diFPh | CO | single bond | 2 | O | CH₂CH₂ | sub. 26 |
| 3914 | 4-OThi | 3,4-diFPh | CO | single bond | 2 | O | CH₂CH₂ | sub. 26 |
| 3915 | 5-OThi | 3,4-diFPh | CO | single bond | 2 | O | CH₂CH₂ | sub. 26 |
| 3916 | 2-Pip | 3,4-diFPh | CO | single bond | 2 | O | CH₂CH₂ | sub. 26 |
| 3917 | 3-Pip | 3,4-diFPh | CO | single bond | 2 | O | CH₂CH₂ | sub. 26 |
| 3918 | 4-Pip | 3,4-diFPh | CO | single bond | 2 | O | CH₂CH₂ | sub. 26 |
| 3919 | 2-Mor | 3,4-diFPh | CO | single bond | 2 | O | CH₂CH₂ | sub. 26 |
| 3920 | 3-Mor | 3,4-diFPh | CO | single bond | 2 | O | CH₂CH₂ | sub. 26 |
| 3921 | 4-Mor | 3,4-diFPh | CO | single bond | 2 | O | CH₂CH₂ | sub. 26 |
| 3922 | 2-Thmor | 3,4-diFPh | CO | single bond | 2 | O | CH₂CH₂ | sub. 26 |
| 3923 | 3-Thmor | 3,4-diFPh | CO | single bond | 2 | O | CH₂CH₂ | sub. 26 |
| 3924 | 4-Thmor | 3,4-diFPh | CO | single bond | 2 | O | CH₂CH₂ | sub. 26 |
| 3925 | 2-Piz | 3,4-diFPh | CO | single bond | 2 | O | CH₂CH₂ | sub. 26 |
| 3926 | 3-Piz | 3,4-diFPh | CO | single bond | 2 | O | CH₂CH₂ | sub. 26 |
| 3927 | 4-Piz | 3,4-diFPh | CO | single bond | 2 | O | CH₂CH₂ | sub. 26 |
| 3928 | 2-Aze | 3,4-diFPh | CO | single bond | 2 | O | CH₂CH₂ | sub. 26 |
| 3929 | 3-Aze | 3,4-diFPh | CO | single bond | 2 | O | CH₂CH₂ | sub. 26 |
| 3930 | 4-Aze | 3,4-diFPh | CO | single bond | 2 | O | CH₂CH₂ | sub. 26 |
| 3931 | cPr | 3,4-diFPh | CO | single bond | 2 | O | CH₂CH₂ | sub. 27 |
| 3932 | cBu | 3,4-diFPh | CO | single bond | 2 | O | CH₂CH₂ | sub. 27 |

TABLE 1-continued

| Exemplification compound number | R¹ | R² | A | B | N | D | G | Q |
|---|---|---|---|---|---|---|---|---|
| 3933 | cPn | 3,4-diFPh | CO | single bond | 2 | O | $CH_2CH_2$ | sub. 27 |
| 3934 | cHex | 3,4-diFPh | CO | single bond | 2 | O | $CH_2CH_2$ | sub. 27 |
| 3935 | cHep | 3,4-diFPh | CO | single bond | 2 | O | $CH_2CH_2$ | sub. 27 |
| 3936 | 2-Pyrd | 3,4-diFPh | CO | single bond | 2 | O | $CH_2CH_2$ | sub. 27 |
| 3937 | 3-Pyrd | 3,4-diFPh | CO | single bond | 2 | O | $CH_2CH_2$ | sub. 27 |
| 3938 | 4-Oxa | 3,4-diFPh | CO | single bond | 2 | O | $CH_2CH_2$ | sub. 27 |
| 3939 | 5-Oxa | 3,4-diFPh | CO | single bond | 2 | O | $CH_2CH_2$ | sub. 27 |
| 3940 | 4-Thi | 3,4-diFPh | CO | single bond | 2 | O | $CH_2CH_2$ | sub. 27 |
| 3941 | 5-Thi | 3,4-diFPh | CO | single bond | 2 | O | $CH_2CH_2$ | sub. 27 |
| 3942 | 4-OOxa | 3,4-diFPh | CO | single bond | 2 | O | $CH_2CH_2$ | sub. 27 |
| 3943 | 5-OOxa | 3,4-diFPh | CO | single bond | 2 | O | $CH_2CH_2$ | sub. 27 |
| 3944 | 4-OThi | 3,4-diFPh | CO | single bond | 2 | O | $CH_2CH_2$ | sub. 27 |
| 3945 | 5-OThi | 3,4-diFPh | CO | single bond | 2 | O | $CH_2CH_2$ | sub. 27 |
| 3946 | 2-Pip | 3,4-diFPh | CO | single bond | 2 | O | $CH_2CH_2$ | sub. 27 |
| 3947 | 3-Pip | 3,4-diFPh | CO | single bond | 2 | O | $CH_2CH_2$ | sub. 27 |
| 3948 | 4-Pip | 3,4-diFPh | CO | single bond | 2 | O | $CH_2CH_2$ | sub. 27 |
| 3949 | 2-Mor | 3,4-diFPh | CO | single bond | 2 | O | $CH_2CH_2$ | sub. 27 |
| 3950 | 3-Mor | 3,4-diFPh | CO | single bond | 2 | O | $CH_2CH_2$ | sub. 27 |
| 3951 | 4-Mor | 3,4-diFPh | CO | single bond | 2 | O | $CH_2CH_2$ | sub. 27 |
| 3952 | 2-Thmor | 3,4-diFPh | CO | single bond | 2 | O | $CH_2CH_2$ | sub. 27 |
| 3953 | 3-Thmor | 3,4-diFPh | CO | single bond | 2 | O | $CH_2CH_2$ | sub. 27 |
| 3954 | 4-Thmor | 3,4-diFPh | CO | single bond | 2 | O | $CH_2CH_2$ | sub. 27 |
| 3955 | 2-Piz | 3,4-diFPh | CO | single bond | 2 | O | $CH_2CH_2$ | sub. 27 |
| 3956 | 3-Piz | 3,4-diFPh | CO | single bond | 2 | O | $CH_2CH_2$ | sub. 27 |
| 3957 | 4-Piz | 3,4-diFPh | CO | single bond | 2 | O | $CH_2CH_2$ | sub. 27 |
| 3958 | 2-Aze | 3,4-diFPh | CO | single bond | 2 | O | $CH_2CH_2$ | sub. 27 |
| 3959 | 3-Aze | 3,4-diFPh | CO | single bond | 2 | O | $CH_2CH_2$ | sub. 27 |
| 3960 | 4-Aze | 3,4-diFPh | CO | single bond | 2 | O | $CH_2CH_2$ | sub. 27 |
| 3961 | cPr | 3,4-diFPh | CO | single bond | 2 | O | $CH_2CH_2$ | sub. 28 |
| 3962 | cBu | 3,4-diFPh | CO | single bond | 2 | O | $CH_2CH_2$ | sub. 28 |
| 3963 | cPn | 3,4-diFPh | CO | single bond | 2 | O | $CH_2CH_2$ | sub. 28 |
| 3964 | cHex | 3,4-diFPh | CO | single bond | 2 | O | $CH_2CH_2$ | sub. 28 |
| 3965 | cHep | 3,4-diFPh | CO | single bond | 2 | O | $CH_2CH_2$ | sub. 28 |
| 3966 | 2-Pyrd | 3,4-diFPh | CO | single bond | 2 | O | $CH_2CH_2$ | sub. 28 |
| 3967 | 3-Pyrd | 3,4-diFPh | CO | single bond | 2 | O | $CH_2CH_2$ | sub. 28 |
| 3968 | 4-Oxa | 3,4-diFPh | CO | single bond | 2 | O | $CH_2CH_2$ | sub. 28 |
| 3969 | 5-Oxa | 3,4-diFPh | CO | single bond | 2 | O | $CH_2CH_2$ | sub. 28 |
| 3970 | 4-Thi | 3,4-diFPh | CO | single bond | 2 | O | $CH_2CH_2$ | sub. 28 |
| 3971 | 5-Thi | 3,4-diFPh | CO | single bond | 2 | O | $CH_2CH_2$ | sub. 28 |
| 3972 | 4-OOxa | 3,4-diFPh | CO | single bond | 2 | O | $CH_2CH_2$ | sub. 28 |
| 3973 | 5-OOxa | 3,4-diFPh | CO | single bond | 2 | O | $CH_2CH_2$ | sub. 28 |
| 3974 | 4-OThi | 3,4-diFPh | CO | single bond | 2 | O | $CH_2CH_2$ | sub. 28 |
| 3975 | 5-OThi | 3,4-diFPh | CO | single bond | 2 | O | $CH_2CH_2$ | sub. 28 |
| 3976 | 2-Pip | 3,4-diFPh | CO | single bond | 2 | O | $CH_2CH_2$ | sub. 28 |
| 3977 | 3-Pip | 3,4-diFPh | CO | single bond | 2 | O | $CH_2CH_2$ | sub. 28 |
| 3978 | 4-Pip | 3,4-diFPh | CO | single bond | 2 | O | $CH_2CH_2$ | sub. 28 |
| 3979 | 2-Mor | 3,4-diFPh | CO | single bond | 2 | O | $CH_2CH_2$ | sub. 28 |
| 3980 | 3-Mor | 3,4-diFPh | CO | single bond | 2 | O | $CH_2CH_2$ | sub. 28 |
| 3981 | 4-Mor | 3,4-diFPh | CO | single bond | 2 | O | $CH_2CH_2$ | sub. 28 |
| 3982 | 2-Thmor | 3,4-diFPh | CO | single bond | 2 | O | $CH_2CH_2$ | sub. 28 |
| 3983 | 3-Thmor | 3,4-diFPh | CO | single bond | 2 | O | $CH_2CH_2$ | sub. 28 |
| 3984 | 4-Thmor | 3,4-diFPh | CO | single bond | 2 | O | $CH_2CH_2$ | sub. 28 |
| 3985 | 2-Piz | 3,4-diFPh | CO | single bond | 2 | O | $CH_2CH_2$ | sub. 28 |
| 3986 | 3-Piz | 3,4-diFPh | CO | single bond | 2 | O | $CH_2CH_2$ | sub. 28 |
| 3987 | 4-Piz | 3,4-diFPh | CO | single bond | 2 | O | $CH_2CH_2$ | sub. 28 |
| 3988 | 2-Aze | 3,4-diFPh | CO | single bond | 2 | O | $CH_2CH_2$ | sub. 28 |
| 3989 | 3-Aze | 3,4-diFPh | CO | single bond | 2 | O | $CH_2CH_2$ | sub. 28 |
| 3990 | 4-Aze | 3,4-diFPh | CO | single bond | 2 | O | $CH_2CH_2$ | sub. 28 |
| 3991 | cPr | 3,4-diFPh | CO | single bond | 2 | O | $CH_2CH_2$ | sub. 29 |
| 3992 | cBu | 3,4-diFPh | CO | single bond | 2 | O | $CH_2CH_2$ | sub. 29 |
| 3993 | cPn | 3,4-diFPh | CO | single bond | 2 | O | $CH_2CH_2$ | sub. 29 |
| 3994 | cHex | 3,4-diFPh | CO | single bond | 2 | O | $CH_2CH_2$ | sub. 29 |
| 3995 | cHep | 3,4-diFPh | CO | single bond | 2 | O | $CH_2CH_2$ | sub. 29 |
| 3996 | 2-Pyrd | 3,4-diFPh | CO | single bond | 2 | O | $CH_2CH_2$ | sub. 29 |
| 3997 | 3-Pyrd | 3,4-diFPh | CO | single bond | 2 | O | $CH_2CH_2$ | sub. 29 |
| 3998 | 4-Oxa | 3,4-diFPh | CO | single bond | 2 | O | $CH_2CH_2$ | sub. 29 |
| 3999 | 5-Oxa | 3,4-diFPh | CO | single bond | 2 | O | $CH_2CH_2$ | sub. 29 |
| 4000 | 4-Thi | 3,4-diFPh | CO | single bond | 2 | O | $CH_2CH_2$ | sub. 29 |
| 4001 | 5-Thi | 3,4-diFPh | CO | single bond | 2 | O | $CH_2CH_2$ | sub. 29 |
| 4002 | 4-OOxa | 3,4-diFPh | CO | single bond | 2 | O | $CH_2CH_2$ | sub. 29 |
| 4003 | 5-OOxa | 3,4-diFPh | CO | single bond | 2 | O | $CH_2CH_2$ | sub. 29 |
| 4004 | 4-OThi | 3,4-diFPh | CO | single bond | 2 | O | $CH_2CH_2$ | sub. 29 |
| 4005 | 5-OThi | 3,4-diFPh | CO | single bond | 2 | O | $CH_2CH_2$ | sub. 29 |
| 4006 | 2-Pip | 3,4-diFPh | CO | single bond | 2 | O | $CH_2CH_2$ | sub. 29 |
| 4007 | 3-Pip | 3,4-diFPh | CO | single bond | 2 | O | $CH_2CH_2$ | sub. 29 |
| 4008 | 4-Pip | 3,4-diFPh | CO | single bond | 2 | O | $CH_2CH_2$ | sub. 29 |

TABLE 1-continued

| Exemplification compound number | R¹ | R² | A | B | N | D | G | Q |
|---|---|---|---|---|---|---|---|---|
| 4009 | 2-Mor | 3,4-diFPh | CO | single bond | 2 | O | $CH_2CH_2$ | sub. 29 |
| 4010 | 3-Mor | 3,4-diFPh | CO | single bond | 2 | O | $CH_2CH_2$ | sub. 29 |
| 4011 | 4-Mor | 3,4-diFPh | CO | single bond | 2 | O | $CH_2CH_2$ | sub. 29 |
| 4012 | 2-Thmor | 3,4-diFPh | CO | single bond | 2 | O | $CH_2CH_2$ | sub. 29 |
| 4013 | 3-Thmor | 3,4-diFPh | CO | single bond | 2 | O | $CH_2CH_2$ | sub. 29 |
| 4014 | 4-Thmor | 3,4-diFPh | CO | single bond | 2 | O | $CH_2CH_2$ | sub. 29 |
| 4015 | 2-Piz | 3,4-diFPh | CO | single bond | 2 | O | $CH_2CH_2$ | sub. 29 |
| 4016 | 3-Piz | 3,4-diFPh | CO | single bond | 2 | O | $CH_2CH_2$ | sub. 29 |
| 4017 | 4-Piz | 3,4-diFPh | CO | single bond | 2 | O | $CH_2CH_2$ | sub. 29 |
| 4018 | 2-Aze | 3,4-diFPh | CO | single bond | 2 | O | $CH_2CH_2$ | sub. 29 |
| 4019 | 3-Aze | 3,4-diFPh | CO | single bond | 2 | O | $CH_2CH_2$ | sub. 29 |
| 4020 | 4-Aze | 3,4-diFPh | CO | single bond | 2 | O | $CH_2CH_2$ | sub. 29 |
| 4021 | cPr | 3,4-diFPh | CO | single bond | 2 | O | $CH_2CH_2$ | sub. 30 |
| 4022 | cBu | 3,4-diFPh | CO | single bond | 2 | O | $CH_2CH_2$ | sub. 30 |
| 4023 | cPn | 3,4-diFPh | CO | single bond | 2 | O | $CH_2CH_2$ | sub. 30 |
| 4024 | cHex | 3,4-diFPh | CO | single bond | 2 | O | $CH_2CH_2$ | sub. 30 |
| 4025 | cHep | 3,4-diFPh | CO | single bond | 2 | O | $CH_2CH_2$ | sub. 30 |
| 4026 | 2-Pyrd | 3,4-diFPh | CO | single bond | 2 | O | $CH_2CH_2$ | sub. 30 |
| 4027 | 3-Pyrd | 3,4-diFPh | CO | single bond | 2 | O | $CH_2CH_2$ | sub. 30 |
| 4028 | 4-Oxa | 3,4-diFPh | CO | single bond | 2 | O | $CH_2CH_2$ | sub. 30 |
| 4029 | 5-Oxa | 3,4-diFPh | CO | single bond | 2 | O | $CH_2CH_2$ | sub. 30 |
| 4030 | 4-Thi | 3,4-diFPh | CO | single bond | 2 | O | $CH_2CH_2$ | sub. 30 |
| 4031 | 5-Thi | 3,4-diFPh | CO | single bond | 2 | O | $CH_2CH_2$ | sub. 30 |
| 4032 | 4-OOxa | 3,4-diFPh | CO | single bond | 2 | O | $CH_2CH_2$ | sub. 30 |
| 4033 | 5-OOxa | 3,4-diFPh | CO | single bond | 2 | O | $CH_2CH_2$ | sub. 30 |
| 4034 | 4-OThi | 3,4-diFPh | CO | single bond | 2 | O | $CH_2CH_2$ | sub. 30 |
| 4035 | 5-OThi | 3,4-diFPh | CO | single bond | 2 | O | $CH_2CH_2$ | sub. 30 |
| 4036 | 2-Pip | 3,4-diFPh | CO | single bond | 2 | O | $CH_2CH_2$ | sub. 30 |
| 4037 | 3-Pip | 3,4-diFPh | CO | single bond | 2 | O | $CH_2CH_2$ | sub. 30 |
| 4038 | 4-Pip | 3,4-diFPh | CO | single bond | 2 | O | $CH_2CH_2$ | sub. 30 |
| 4039 | 2-Mor | 3,4-diFPh | CO | single bond | 2 | O | $CH_2CH_2$ | sub. 30 |
| 4040 | 3-Mor | 3,4-diFPh | CO | single bond | 2 | O | $CH_2CH_2$ | sub. 30 |
| 4041 | 4-Mor | 3,4-diFPh | CO | single bond | 2 | O | $CH_2CH_2$ | sub. 30 |
| 4042 | 2-Thmor | 3,4-diFPh | CO | single bond | 2 | O | $CH_2CH_2$ | sub. 30 |
| 4043 | 3-Thmor | 3,4-diFPh | CO | single bond | 2 | O | $CH_2CH_2$ | sub. 30 |
| 4044 | 4-Thmor | 3,4-diFPh | CO | single bond | 2 | O | $CH_2CH_2$ | sub. 30 |
| 4045 | 2-Piz | 3,4-diFPh | CO | single bond | 2 | O | $CH_2CH_2$ | sub. 30 |
| 4046 | 3-Piz | 3,4-diFPh | CO | single bond | 2 | O | $CH_2CH_2$ | sub. 30 |
| 4047 | 4-Piz | 3,4-diFPh | CO | single bond | 2 | O | $CH_2CH_2$ | sub. 30 |
| 4048 | 2-Aze | 3,4-diFPh | CO | single bond | 2 | O | $CH_2CH_2$ | sub. 30 |
| 4049 | 3-Aze | 3,4-diFPh | CO | single bond | 2 | O | $CH_2CH_2$ | sub. 30 |
| 4050 | 4-Aze | 3,4-diFPh | CO | single bond | 2 | O | $CH_2CH_2$ | sub. 30 |
| 4051 | cPr | 3,4-diFPh | CO | single bond | 2 | O | $CH_2CH_2$ | sub. 31 |
| 4052 | cBu | 3,4-diFPh | CO | single bond | 2 | O | $CH_2CH_2$ | sub. 31 |
| 4053 | cPn | 3,4-diFPh | CO | single bond | 2 | O | $CH_2CH_2$ | sub. 31 |
| 4054 | cHex | 3,4-diFPh | CO | single bond | 2 | O | $CH_2CH_2$ | sub. 31 |
| 4055 | cHep | 3,4-diFPh | CO | single bond | 2 | O | $CH_2CH_2$ | sub. 31 |
| 4056 | 2-Pyrd | 3,4-diFPh | CO | single bond | 2 | O | $CH_2CH_2$ | sub. 31 |
| 4057 | 3-Pyrd | 3,4-diFPh | CO | single bond | 2 | O | $CH_2CH_2$ | sub. 31 |
| 4058 | 4-Oxa | 3,4-diFPh | CO | single bond | 2 | O | $CH_2CH_2$ | sub. 31 |
| 4059 | 5-Oxa | 3,4-diFPh | CO | single bond | 2 | O | $CH_2CH_2$ | sub. 31 |
| 4060 | 4-Thi | 3,4-diFPh | CO | single bond | 2 | O | $CH_2CH_2$ | sub. 31 |
| 4061 | 5-Thi | 3,4-diFPh | CO | single bond | 2 | O | $CH_2CH_2$ | sub. 31 |
| 4062 | 4-OOxa | 3,4-diFPh | CO | single bond | 2 | O | $CH_2CH_2$ | sub. 31 |
| 4063 | 5-OOxa | 3,4-diFPh | CO | single bond | 2 | O | $CH_2CH_2$ | sub. 31 |
| 4064 | 4-OThi | 3,4-diFPh | CO | single bond | 2 | O | $CH_2CH_2$ | sub. 31 |
| 4065 | 5-OThi | 3,4-diFPh | CO | single bond | 2 | O | $CH_2CH_2$ | sub. 31 |
| 4066 | 2-Pip | 3,4-diFPh | CO | single bond | 2 | O | $CH_2CH_2$ | sub. 31 |
| 4067 | 3-Pip | 3,4-diFPh | CO | single bond | 2 | O | $CH_2CH_2$ | sub. 31 |
| 4068 | 4-Pip | 3,4-diFPh | CO | single bond | 2 | O | $CH_2CH_2$ | sub. 31 |
| 4069 | 2-Mor | 3,4-diFPh | CO | single bond | 2 | O | $CH_2CH_2$ | sub. 31 |
| 4070 | 3-Mor | 3,4-diFPh | CO | single bond | 2 | O | $CH_2CH_2$ | sub. 31 |
| 4071 | 4-Mor | 3,4-diFPh | CO | single bond | 2 | O | $CH_2CH_2$ | sub. 31 |
| 4072 | 2-Thmor | 3,4-diFPh | CO | single bond | 2 | O | $CH_2CH_2$ | sub. 31 |
| 4073 | 3-Thmor | 3,4-diFPh | CO | single bond | 2 | O | $CH_2CH_2$ | sub. 31 |
| 4074 | 4-Thmor | 3,4-diFPh | CO | single bond | 2 | O | $CH_2CH_2$ | sub. 31 |
| 4075 | 2-Piz | 3,4-diFPh | CO | single bond | 2 | O | $CH_2CH_2$ | sub. 31 |
| 4076 | 3-Piz | 3,4-diFPh | CO | single bond | 2 | O | $CH_2CH_2$ | sub. 31 |
| 4077 | 4-Piz | 3,4-diFPh | CO | single bond | 2 | O | $CH_2CH_2$ | sub. 31 |
| 4078 | 2-Aze | 3,4-diFPh | CO | single bond | 2 | O | $CH_2CH_2$ | sub. 31 |
| 4079 | 3-Aze | 3,4-diFPh | CO | single bond | 2 | O | $CH_2CH_2$ | sub. 31 |
| 4080 | 4-Aze | 3,4-diFPh | CO | single bond | 2 | O | $CH_2CH_2$ | sub. 31 |
| 4081 | cPr | 3,4-diFPh | CO | single bond | 2 | O | $CH_2CH_2$ | sub. 32 |
| 4082 | cBu | 3,4-diFPh | CO | single bond | 2 | O | $CH_2CH_2$ | sub. 32 |
| 4083 | cPn | 3,4-diFPh | CO | single bond | 2 | O | $CH_2CH_2$ | sub. 32 |
| 4084 | cHex | 3,4-diFPh | CO | single bond | 2 | O | $CH_2CH_2$ | sub. 32 |

TABLE 1-continued

| Exemplification compound number | R¹ | R² | A | B | N | D | G | Q |
|---|---|---|---|---|---|---|---|---|
| 4085 | cHep | 3,4-diFPh | CO | single bond | 2 | O | $CH_2CH_2$ | sub. 32 |
| 4086 | 2-Pyrd | 3,4-diFPh | CO | single bond | 2 | O | $CH_2CH_2$ | sub. 32 |
| 4087 | 3-Pyrd | 3,4-diFPh | CO | single bond | 2 | O | $CH_2CH_2$ | sub. 32 |
| 4088 | 4-Oxa | 3,4-diFPh | CO | single bond | 2 | O | $CH_2CH_2$ | sub. 32 |
| 4089 | 5-Oxa | 3,4-diFPh | CO | single bond | 2 | O | $CH_2CH_2$ | sub. 32 |
| 4090 | 4-Thi | 3,4-diFPh | CO | single bond | 2 | O | $CH_2CH_2$ | sub. 32 |
| 4091 | 5-Thi | 3,4-diFPh | CO | single bond | 2 | O | $CH_2CH_2$ | sub. 32 |
| 4092 | 4-OOxa | 3,4-diFPh | CO | single bond | 2 | O | $CH_2CH_2$ | sub. 32 |
| 4093 | 5-OOxa | 3,4-diFPh | CO | single bond | 2 | O | $CH_2CH_2$ | sub. 32 |
| 4094 | 4-OThi | 3,4-diFPh | CO | single bond | 2 | O | $CH_2CH_2$ | sub. 32 |
| 4095 | 5-OThi | 3,4-diFPh | CO | single bond | 2 | O | $CH_2CH_2$ | sub. 32 |
| 4096 | 2-Pip | 3,4-diFPh | CO | single bond | 2 | O | $CH_2CH_2$ | sub. 32 |
| 4097 | 3-Pip | 3,4-diFPh | CO | single bond | 2 | O | $CH_2CH_2$ | sub. 32 |
| 4098 | 4-Pip | 3,4-diFPh | CO | single bond | 2 | O | $CH_2CH_2$ | sub. 32 |
| 4099 | 2-Mor | 3,4-diFPh | CO | single bond | 2 | O | $CH_2CH_2$ | sub. 32 |
| 4100 | 3-Mor | 3,4-diFPh | CO | single bond | 2 | O | $CH_2CH_2$ | sub. 32 |
| 4101 | 4-Mor | 3,4-diFPh | CO | single bond | 2 | O | $CH_2CH_2$ | sub. 32 |
| 4102 | 2-Thmor | 3,4-diFPh | CO | single bond | 2 | O | $CH_2CH_2$ | sub. 32 |
| 4103 | 3-Thmor | 3,4-diFPh | CO | single bond | 2 | O | $CH_2CH_2$ | sub. 32 |
| 4104 | 4-Thmor | 3,4-diFPh | CO | single bond | 2 | O | $CH_2CH_2$ | sub. 32 |
| 4105 | 2-Piz | 3,4-diFPh | CO | single bond | 2 | O | $CH_2CH_2$ | sub. 32 |
| 4106 | 3-Piz | 3,4-diFPh | CO | single bond | 2 | O | $CH_2CH_2$ | sub. 32 |
| 4107 | 4-Piz | 3,4-diFPh | CO | single bond | 2 | O | $CH_2CH_2$ | sub. 32 |
| 4108 | 2-Aze | 3,4-diFPh | CO | single bond | 2 | O | $CH_2CH_2$ | sub. 32 |
| 4109 | 3-Aze | 3,4-diFPh | CO | single bond | 2 | O | $CH_2CH_2$ | sub. 32 |
| 4110 | 4-Aze | 3,4-diFPh | CO | single bond | 2 | O | $CH_2CH_2$ | sub. 32 |
| 4111 | cPr | 3,4-diFPh | CO | single bond | 2 | O | $CH_2CH_2$ | sub. 33 |
| 4112 | cBu | 3,4-diFPh | CO | single bond | 2 | O | $CH_2CH_2$ | sub. 33 |
| 4113 | cPn | 3,4-diFPh | CO | single bond | 2 | O | $CH_2CH_2$ | sub. 33 |
| 4114 | cHex | 3,4-diFPh | CO | single bond | 2 | O | $CH_2CH_2$ | sub. 33 |
| 4115 | cHep | 3,4-diFPh | CO | single bond | 2 | O | $CH_2CH_2$ | sub. 33 |
| 4116 | 2-Pyrd | 3,4-diFPh | CO | single bond | 2 | O | $CH_2CH_2$ | sub. 33 |
| 4117 | 3-Pyrd | 3,4-diFPh | CO | single bond | 2 | O | $CH_2CH_2$ | sub. 33 |
| 4118 | 4-Oxa | 3,4-diFPh | CO | single bond | 2 | O | $CH_2CH_2$ | sub. 33 |
| 4119 | 5-Oxa | 3,4-diFPh | CO | single bond | 2 | O | $CH_2CH_2$ | sub. 33 |
| 4120 | 4-Thi | 3,4-diFPh | CO | single bond | 2 | O | $CH_2CH_2$ | sub. 33 |
| 4121 | 5-Thi | 3,4-diFPh | CO | single bond | 2 | O | $CH_2CH_2$ | sub. 33 |
| 4122 | 4-OOxa | 3,4-diFPh | CO | single bond | 2 | O | $CH_2CH_2$ | sub. 33 |
| 4123 | 5-OOxa | 3,4-diFPh | CO | single bond | 2 | O | $CH_2CH_2$ | sub. 33 |
| 4124 | 4-OThi | 3,4-diFPh | CO | single bond | 2 | O | $CH_2CH_2$ | sub. 33 |
| 4125 | 5-OThi | 3,4-diFPh | CO | single bond | 2 | O | $CH_2CH_2$ | sub. 33 |
| 4126 | 2-Pip | 3,4-diFPh | CO | single bond | 2 | O | $CH_2CH_2$ | sub. 33 |
| 4127 | 3-Pip | 3,4-diFPh | CO | single bond | 2 | O | $CH_2CH_2$ | sub. 33 |
| 4128 | 4-Pip | 3,4-diFPh | CO | single bond | 2 | O | $CH_2CH_2$ | sub. 33 |
| 4129 | 2-Mor | 3,4-diFPh | CO | single bond | 2 | O | $CH_2CH_2$ | sub. 33 |
| 4130 | 3-Mor | 3,4-diFPh | CO | single bond | 2 | O | $CH_2CH_2$ | sub. 33 |
| 4131 | 4-Mor | 3,4-diFPh | CO | single bond | 2 | O | $CH_2CH_2$ | sub. 33 |
| 4132 | 2-Thmor | 3,4-diFPh | CO | single bond | 2 | O | $CH_2CH_2$ | sub. 33 |
| 4133 | 3-Thmor | 3,4-diFPh | CO | single bond | 2 | O | $CH_2CH_2$ | sub. 33 |
| 4134 | 4-Thmor | 3,4-diFPh | CO | single bond | 2 | O | $CH_2CH_2$ | sub. 33 |
| 4135 | 2-Piz | 3,4-diFPh | CO | single bond | 2 | O | $CH_2CH_2$ | sub. 33 |
| 4136 | 3-Piz | 3,4-diFPh | CO | single bond | 2 | O | $CH_2CH_2$ | sub. 33 |
| 4137 | 4-Piz | 3,4-diFPh | CO | single bond | 2 | O | $CH_2CH_2$ | sub. 33 |
| 4138 | 2-Aze | 3,4-diFPh | CO | single bond | 2 | O | $CH_2CH_2$ | sub. 33 |
| 4139 | 3-Aze | 3,4-diFPh | CO | single bond | 2 | O | $CH_2CH_2$ | sub. 33 |
| 4140 | 4-Aze | 3,4-diFPh | CO | single bond | 2 | O | $CH_2CH_2$ | sub. 33 |
| 4141 | cPr | 4-FPh | CO | single bond | 2 | O | $CH_2CH_2$ | sub. 34 |
| 4142 | cBu | 4-FPh | CO | single bond | 2 | O | $CH_2CH_2$ | sub. 34 |
| 4143 | cPn | 4-FPh | CO | single bond | 2 | O | $CH_2CH_2$ | sub. 34 |
| 4144 | cHex | 4-FPh | CO | single bond | 2 | O | $CH_2CH_2$ | sub. 34 |
| 4145 | cHep | 4-FPh | CO | single bond | 2 | O | $CH_2CH_2$ | sub. 34 |
| 4146 | 2-Pyrd | 4-FPh | CO | single bond | 2 | O | $CH_2CH_2$ | sub. 34 |
| 4147 | 3-Pyrd | 4-FPh | CO | single bond | 2 | O | $CH_2CH_2$ | sub. 34 |
| 4148 | 4-Oxa | 4-FPh | CO | single bond | 2 | O | $CH_2CH_2$ | sub. 34 |
| 4149 | 5-Oxa | 4-FPh | CO | single bond | 2 | O | $CH_2CH_2$ | sub. 34 |
| 4150 | 4-Thi | 4-FPh | CO | single bond | 2 | O | $CH_2CH_2$ | sub. 34 |
| 4151 | 5-Thi | 4-FPh | CO | single bond | 2 | O | $CH_2CH_2$ | sub. 34 |
| 4152 | 4-OOxa | 4-FPh | CO | single bond | 2 | O | $CH_2CH_2$ | sub. 34 |
| 4153 | 5-OOxa | 4-FPh | CO | single bond | 2 | O | $CH_2CH_2$ | sub. 34 |
| 4154 | 4-OThi | 4-FPh | CO | single bond | 2 | O | $CH_2CH_2$ | sub. 34 |
| 4155 | 5-OThi | 4-FPh | CO | single bond | 2 | O | $CH_2CH_2$ | sub. 34 |
| 4156 | 2-Pip | 4-FPh | CO | single bond | 2 | O | $CH_2CH_2$ | sub. 34 |
| 4157 | 3-Pip | 4-FPh | CO | single bond | 2 | O | $CH_2CH_2$ | sub. 34 |
| 4158 | 4-Pip | 4-FPh | CO | single bond | 2 | O | $CH_2CH_2$ | sub. 34 |
| 4159 | 2-Mor | 4-FPh | CO | single bond | 2 | O | $CH_2CH_2$ | sub. 34 |
| 4160 | 3-Mor | 4-FPh | CO | single bond | 2 | O | $CH_2CH_2$ | sub. 34 |

TABLE 1-continued

| Exemplification compound number | R¹ | R² | A | B | N | D | G | Q |
|---|---|---|---|---|---|---|---|---|
| 4161 | 4-Mor | 4-FPh | CO | single bond | 2 | O | $CH_2CH_2$ | sub. 34 |
| 4162 | 2-Thmor | 4-FPh | CO | single bond | 2 | O | $CH_2CH_2$ | sub. 34 |
| 4163 | 3-Thmor | 4-FPh | CO | single bond | 2 | O | $CH_2CH_2$ | sub. 34 |
| 4164 | 4-Thmor | 4-FPh | CO | single bond | 2 | O | $CH_2CH_2$ | sub. 34 |
| 4165 | 2-Piz | 4-FPh | CO | single bond | 2 | O | $CH_2CH_2$ | sub. 34 |
| 4166 | 3-Piz | 4-FPh | CO | single bond | 2 | O | $CH_2CH_2$ | sub. 34 |
| 4167 | 4-Piz | 4-FPh | CO | single bond | 2 | O | $CH_2CH_2$ | sub. 34 |
| 4168 | 2-Aze | 4-FPh | CO | single bond | 2 | O | $CH_2CH_2$ | sub. 34 |
| 4169 | 3-Aze | 4-FPh | CO | single bond | 2 | O | $CH_2CH_2$ | sub. 34 |
| 4170 | 4-Aze | 4-FPh | CO | single bond | 2 | O | $CH_2CH_2$ | sub. 34 |
| 4171 | cPr | 4-FPh | CO | single bond | 2 | O | $CH_2CH_2$ | sub. 35 |
| 4172 | cBu | 4-FPh | CO | single bond | 2 | O | $CH_2CH_2$ | sub. 35 |
| 4173 | cPn | 4-FPh | CO | single bond | 2 | O | $CH_2CH_2$ | sub. 35 |
| 4174 | cHex | 4-FPh | CO | single bond | 2 | O | $CH_2CH_2$ | sub. 35 |
| 4175 | cHep | 4-FPh | CO | single bond | 2 | O | $CH_2CH_2$ | sub. 35 |
| 4176 | 2-Pyrd | 4-FPh | CO | single bond | 2 | O | $CH_2CH_2$ | sub. 35 |
| 4177 | 3-Pyrd | 4-FPh | CO | single bond | 2 | O | $CH_2CH_2$ | sub. 35 |
| 4178 | 4-Oxa | 4-FPh | CO | single bond | 2 | O | $CH_2CH_2$ | sub. 35 |
| 4179 | 5-Oxa | 4-FPh | CO | single bond | 2 | O | $CH_2CH_2$ | sub. 35 |
| 4180 | 4-Thi | 4-FPh | CO | single bond | 2 | O | $CH_2CH_2$ | sub. 35 |
| 4181 | 5-Thi | 4-FPh | CO | single bond | 2 | O | $CH_2CH_2$ | sub. 35 |
| 4182 | 4-OOxa | 4-FPh | CO | single bond | 2 | O | $CH_2CH_2$ | sub. 35 |
| 4183 | 5-OOxa | 4-FPh | CO | single bond | 2 | O | $CH_2CH_2$ | sub. 35 |
| 4184 | 4-OThi | 4-FPh | CO | single bond | 2 | O | $CH_2CH_2$ | sub. 35 |
| 4185 | 5-OThi | 4-FPh | CO | single bond | 2 | O | $CH_2CH_2$ | sub. 35 |
| 4186 | 2-Pip | 4-FPh | CO | single bond | 2 | O | $CH_2CH_2$ | sub. 35 |
| 4187 | 3-Pip | 4-FPh | CO | single bond | 2 | O | $CH_2CH_2$ | sub. 35 |
| 4188 | 4-Pip | 4-FPh | CO | single bond | 2 | O | $CH_2CH_2$ | sub. 35 |
| 4189 | 2-Mor | 4-FPh | CO | single bond | 2 | O | $CH_2CH_2$ | sub. 35 |
| 4190 | 3-Mor | 4-FPh | CO | single bond | 2 | O | $CH_2CH_2$ | sub. 35 |
| 4191 | 4-Mor | 4-FPh | CO | single bond | 2 | O | $CH_2CH_2$ | sub. 35 |
| 4192 | 2-Thmor | 4-FPh | CO | single bond | 2 | O | $CH_2CH_2$ | sub. 35 |
| 4193 | 3-Thmor | 4-FPh | CO | single bond | 2 | O | $CH_2CH_2$ | sub. 35 |
| 4194 | 4-Thmor | 4-FPh | CO | single bond | 2 | O | $CH_2CH_2$ | sub. 35 |
| 4195 | 2-Piz | 4-FPh | CO | single bond | 2 | O | $CH_2CH_2$ | sub. 35 |
| 4196 | 3-Piz | 4-FPh | CO | single bond | 2 | O | $CH_2CH_2$ | sub. 35 |
| 4197 | 4-Piz | 4-FPh | CO | single bond | 2 | O | $CH_2CH_2$ | sub. 35 |
| 4198 | 2-Aze | 4-FPh | CO | single bond | 2 | O | $CH_2CH_2$ | sub. 35 |
| 4199 | 3-Aze | 4-FPh | CO | single bond | 2 | O | $CH_2CH_2$ | sub. 35 |
| 4200 | 4-Aze | 4-FPh | CO | single bond | 2 | O | $CH_2CH_2$ | sub. 35 |
| 4201 | cPr | 4-FPh | CO | single bond | 2 | O | $CH_2CH_2$ | sub. 1 |
| 4202 | cBu | 4-FPh | CO | single bond | 2 | O | $CH_2CH_2$ | sub. 1 |
| 4203 | cPn | 4-FPh | CO | single bond | 2 | O | $CH_2CH_2$ | sub. 1 |
| 4204 | cHex | 4-FPh | CO | single bond | 2 | O | $CH_2CH_2$ | sub. 1 |
| 4205 | cHep | 4-FPh | CO | single bond | 2 | O | $CH_2CH_2$ | sub. 1 |
| 4206 | 2-Pyrd | 4-FPh | CO | single bond | 2 | O | $CH_2CH_2$ | sub. 1 |
| 4207 | 3-Pyrd | 4-FPh | CO | single bond | 2 | O | $CH_2CH_2$ | sub. 1 |
| 4208 | 4-Oxa | 4-FPh | CO | single bond | 2 | O | $CH_2CH_2$ | sub. 1 |
| 4209 | 5-Oxa | 4-FPh | CO | single bond | 2 | O | $CH_2CH_2$ | sub. 1 |
| 4210 | 4-Thi | 4-FPh | CO | single bond | 2 | O | $CH_2CH_2$ | sub. 1 |
| 4211 | 5-Thi | 4-FPh | CO | single bond | 2 | O | $CH_2CH_2$ | sub. 1 |
| 4212 | 4-OOxa | 4-FPh | CO | single bond | 2 | O | $CH_2CH_2$ | sub. 1 |
| 4213 | 5-OOxa | 4-FPh | CO | single bond | 2 | O | $CH_2CH_2$ | sub. 1 |
| 4214 | 4-OThi | 4-FPh | CO | single bond | 2 | O | $CH_2CH_2$ | sub. 1 |
| 4215 | 5-OThi | 4-FPh | CO | single bond | 2 | O | $CH_2CH_2$ | sub. 1 |
| 4216 | 2-Pip | 4-FPh | CO | single bond | 2 | O | $CH_2CH_2$ | sub. 1 |
| 4217 | 3-Pip | 4-FPh | CO | single bond | 2 | O | $CH_2CH_2$ | sub. 1 |
| 4218 | 4-Pip | 4-FPh | CO | single bond | 2 | O | $CH_2CH_2$ | sub. 1 |
| 4219 | 2-Mor | 4-FPh | CO | single bond | 2 | O | $CH_2CH_2$ | sub. 1 |
| 4220 | 3-Mor | 4-FPh | CO | single bond | 2 | O | $CH_2CH_2$ | sub. 1 |
| 4221 | 4-Mor | 4-FPh | CO | single bond | 2 | O | $CH_2CH_2$ | sub. 1 |
| 4222 | 2-Thmor | 4-FPh | CO | single bond | 2 | O | $CH_2CH_2$ | sub. 1 |
| 4223 | 3-Thmor | 4-FPh | CO | single bond | 2 | O | $CH_2CH_2$ | sub. 1 |
| 4224 | 4-Thmor | 4-FPh | CO | single bond | 2 | O | $CH_2CH_2$ | sub. 1 |
| 4225 | 2-Piz | 4-FPh | CO | single bond | 2 | O | $CH_2CH_2$ | sub. 1 |
| 4226 | 3-Piz | 4-FPh | CO | single bond | 2 | O | $CH_2CH_2$ | sub. 1 |
| 4227 | 4-Piz | 4-FPh | CO | single bond | 2 | O | $CH_2CH_2$ | sub. 1 |
| 4228 | 2-Aze | 4-FPh | CO | single bond | 2 | O | $CH_2CH_2$ | sub. 1 |
| 4229 | 3-Aze | 4-FPh | CO | single bond | 2 | O | $CH_2CH_2$ | sub. 1 |
| 4230 | 4-Aze | 4-FPh | CO | single bond | 2 | O | $CH_2CH_2$ | sub. 1 |
| 4231 | cPr | 4-FPh | CO | single bond | 2 | O | $CH_2CH_2$ | sub. 2 |
| 4232 | cBu | 4-FPh | CO | single bond | 2 | O | $CH_2CH_2$ | sub. 2 |
| 4233 | cPn | 4-FPh | CO | single bond | 2 | O | $CH_2CH_2$ | sub. 2 |
| 4234 | cHex | 4-FPh | CO | single bond | 2 | O | $CH_2CH_2$ | sub. 2 |
| 4235 | cHep | 4-FPh | CO | single bond | 2 | O | $CH_2CH_2$ | sub. 2 |
| 4236 | 2-Pyrd | 4-FPh | CO | single bond | 2 | O | $CH_2CH_2$ | sub. 2 |

TABLE 1-continued

| Exemplification compound number | R¹ | R² | A | B | N | D | G | Q |
|---|---|---|---|---|---|---|---|---|
| 4237 | 3-Pyrd | 4-FPh | CO | single bond | 2 | O | $CH_2CH_2$ | sub. 2 |
| 4238 | 4-Oxa | 4-FPh | CO | single bond | 2 | O | $CH_2CH_2$ | sub. 2 |
| 4239 | 5-Oxa | 4-FPh | CO | single bond | 2 | O | $CH_2CH_2$ | sub. 2 |
| 4240 | 4-Thi | 4-FPh | CO | single bond | 2 | O | $CH_2CH_2$ | sub. 2 |
| 4241 | 5-Thi | 4-FPh | CO | single bond | 2 | O | $CH_2CH_2$ | sub. 2 |
| 4242 | 4-OOxa | 4-FPh | CO | single bond | 2 | O | $CH_2CH_2$ | sub. 2 |
| 4243 | 5-OOxa | 4-FPh | CO | single bond | 2 | O | $CH_2CH_2$ | sub. 2 |
| 4244 | 4-OThi | 4-FPh | CO | single bond | 2 | O | $CH_2CH_2$ | sub. 2 |
| 4245 | 5-OThi | 4-FPh | CO | single bond | 2 | O | $CH_2CH_2$ | sub. 2 |
| 4246 | 2-Pip | 4-FPh | CO | single bond | 2 | O | $CH_2CH_2$ | sub. 2 |
| 4247 | 3-Pip | 4-FPh | CO | single bond | 2 | O | $CH_2CH_2$ | sub. 2 |
| 4248 | 4-Pip | 4-FPh | CO | single bond | 2 | O | $CH_2CH_2$ | sub. 2 |
| 4249 | 2-Mor | 4-FPh | CO | single bond | 2 | O | $CH_2CH_2$ | sub. 2 |
| 4250 | 3-Mor | 4-FPh | CO | single bond | 2 | O | $CH_2CH_2$ | sub. 2 |
| 4251 | 4-Mor | 4-FPh | CO | single bond | 2 | O | $CH_2CH_2$ | sub. 2 |
| 4252 | 2-Thmor | 4-FPh | CO | single bond | 2 | O | $CH_2CH_2$ | sub. 2 |
| 4253 | 3-Thmor | 4-FPh | CO | single bond | 2 | O | $CH_2CH_2$ | sub. 2 |
| 4254 | 4-Thmor | 4-FPh | CO | single bond | 2 | O | $CH_2CH_2$ | sub. 2 |
| 4255 | 2-Piz | 4-FPh | CO | single bond | 2 | O | $CH_2CH_2$ | sub. 2 |
| 4256 | 3-Piz | 4-FPh | CO | single bond | 2 | O | $CH_2CH_2$ | sub. 2 |
| 4257 | 4-Piz | 4-FPh | CO | single bond | 2 | O | $CH_2CH_2$ | sub. 2 |
| 4258 | 2-Aze | 4-FPh | CO | single bond | 2 | O | $CH_2CH_2$ | sub. 2 |
| 4259 | 3-Aze | 4-FPh | CO | single bond | 2 | O | $CH_2CH_2$ | sub. 2 |
| 4260 | 4-Aze | 4-FPh | CO | single bond | 2 | O | $CH_2CH_2$ | sub. 2 |
| 4261 | cPr | 4-FPh | CO | single bond | 2 | O | $CH_2CH_2$ | sub. 3 |
| 4262 | cBu | 4-FPh | CO | single bond | 2 | O | $CH_2CH_2$ | sub. 3 |
| 4263 | cPn | 4-FPh | CO | single bond | 2 | O | $CH_2CH_2$ | sub. 3 |
| 4264 | cHex | 4-FPh | CO | single bond | 2 | O | $CH_2CH_2$ | sub. 3 |
| 4265 | cHep | 4-FPh | CO | single bond | 2 | O | $CH_2CH_2$ | sub. 3 |
| 4266 | 2-Pyrd | 4-FPh | CO | single bond | 2 | O | $CH_2CH_2$ | sub. 3 |
| 4267 | 3-Pyrd | 4-FPh | CO | single bond | 2 | O | $CH_2CH_2$ | sub. 3 |
| 4268 | 4-Oxa | 4-FPh | CO | single bond | 2 | O | $CH_2CH_2$ | sub. 3 |
| 4269 | 5-Oxa | 4-FPh | CO | single bond | 2 | O | $CH_2CH_2$ | sub. 3 |
| 4270 | 4-Thi | 4-FPh | CO | single bond | 2 | O | $CH_2CH_2$ | sub. 3 |
| 4271 | 5-Thi | 4-FPh | CO | single bond | 2 | O | $CH_2CH_2$ | sub. 3 |
| 4272 | 4-OOxa | 4-FPh | CO | single bond | 2 | O | $CH_2CH_2$ | sub. 3 |
| 4273 | 5-OOxa | 4-FPh | CO | single bond | 2 | O | $CH_2CH_2$ | sub. 3 |
| 4274 | 4-OThi | 4-FPh | CO | single bond | 2 | O | $CH_2CH_2$ | sub. 3 |
| 4275 | 5-OThi | 4-FPh | CO | single bond | 2 | O | $CH_2CH_2$ | sub. 3 |
| 4276 | 2-Pip | 4-FPh | CO | single bond | 2 | O | $CH_2CH_2$ | sub. 3 |
| 4277 | 3-Pip | 4-FPh | CO | single bond | 2 | O | $CH_2CH_2$ | sub. 3 |
| 4278 | 4-Pip | 4-FPh | CO | single bond | 2 | O | $CH_2CH_2$ | sub. 3 |
| 4279 | 2-Mor | 4-FPh | CO | single bond | 2 | O | $CH_2CH_2$ | sub. 3 |
| 4280 | 3-Mor | 4-FPh | CO | single bond | 2 | O | $CH_2CH_2$ | sub. 3 |
| 4281 | 4-Mor | 4-FPh | CO | single bond | 2 | O | $CH_2CH_2$ | sub. 3 |
| 4282 | 2-Thmor | 4-FPh | CO | single bond | 2 | O | $CH_2CH_2$ | sub. 3 |
| 4283 | 3-Thmor | 4-FPh | CO | single bond | 2 | O | $CH_2CH_2$ | sub. 3 |
| 4284 | 4-Thmor | 4-FPh | CO | single bond | 2 | O | $CH_2CH_2$ | sub. 3 |
| 4285 | 2-Piz | 4-FPh | CO | single bond | 2 | O | $CH_2CH_2$ | sub. 3 |
| 4286 | 3-Piz | 4-FPh | CO | single bond | 2 | O | $CH_2CH_2$ | sub. 3 |
| 4287 | 4-Piz | 4-FPh | CO | single bond | 2 | O | $CH_2CH_2$ | sub. 3 |
| 4288 | 2-Aze | 4-FPh | CO | single bond | 2 | O | $CH_2CH_2$ | sub. 3 |
| 4289 | 3-Aze | 4-FPh | CO | single bond | 2 | O | $CH_2CH_2$ | sub. 3 |
| 4290 | 4-Aze | 4-FPh | CO | single bond | 2 | O | $CH_2CH_2$ | sub. 3 |
| 4291 | cPr | 4-FPh | CO | single bond | 2 | O | $CH_2CH_2$ | sub. 4 |
| 4292 | cBu | 4-FPh | CO | single bond | 2 | O | $CH_2CH_2$ | sub. 4 |
| 4293 | cPn | 4-FPh | CO | single bond | 2 | O | $CH_2CH_2$ | sub. 4 |
| 4294 | cHex | 4-FPh | CO | single bond | 2 | O | $CH_2CH_2$ | sub. 4 |
| 4295 | cHep | 4-FPh | CO | single bond | 2 | O | $CH_2CH_2$ | sub. 4 |
| 4296 | 2-Pyrd | 4-FPh | CO | single bond | 2 | O | $CH_2CH_2$ | sub. 4 |
| 4297 | 3-Pyrd | 4-FPh | CO | single bond | 2 | O | $CH_2CH_2$ | sub. 4 |
| 4298 | 4-Oxa | 4-FPh | CO | single bond | 2 | O | $CH_2CH_2$ | sub. 4 |
| 4299 | 5-Oxa | 4-FPh | CO | single bond | 2 | O | $CH_2CH_2$ | sub. 4 |
| 4300 | 4-Thi | 4-FPh | CO | single bond | 2 | O | $CH_2CH_2$ | sub. 4 |
| 4301 | 5-Thi | 4-FPh | CO | single bond | 2 | O | $CH_2CH_2$ | sub. 4 |
| 4302 | 4-OOxa | 4-FPh | CO | single bond | 2 | O | $CH_2CH_2$ | sub. 4 |
| 4303 | 5-OOxa | 4-FPh | CO | single bond | 2 | O | $CH_2CH_2$ | sub. 4 |
| 4304 | 4-OThi | 4-FPh | CO | single bond | 2 | O | $CH_2CH_2$ | sub. 4 |
| 4305 | 5-OThi | 4-FPh | CO | single bond | 2 | O | $CH_2CH_2$ | sub. 4 |
| 4306 | 2-Pip | 4-FPh | CO | single bond | 2 | O | $CH_2CH_2$ | sub. 4 |
| 4307 | 3-Pip | 4-FPh | CO | single bond | 2 | O | $CH_2CH_2$ | sub. 4 |
| 4308 | 4-Pip | 4-FPh | CO | single bond | 2 | O | $CH_2CH_2$ | sub. 4 |
| 4309 | 2-Mor | 4-FPh | CO | single bond | 2 | O | $CH_2CH_2$ | sub. 4 |
| 4310 | 3-Mor | 4-FPh | CO | single bond | 2 | O | $CH_2CH_2$ | sub. 4 |
| 4311 | 4-Mor | 4-FPh | CO | single bond | 2 | O | $CH_2CH_2$ | sub. 4 |
| 4312 | 2-Thmor | 4-FPh | CO | single bond | 2 | O | $CH_2CH_2$ | sub. 4 |

TABLE 1-continued

| Exemplification compound number | R¹ | R² | A | B | N | D | G | Q |
|---|---|---|---|---|---|---|---|---|
| 4313 | 3-Thmor | 4-FPh | CO | single bond | 2 | O | $CH_2CH_2$ | sub. 4 |
| 4314 | 4-Thmor | 4-FPh | CO | single bond | 2 | O | $CH_2CH_2$ | sub. 4 |
| 4315 | 2-Piz | 4-FPh | CO | single bond | 2 | O | $CH_2CH_2$ | sub. 4 |
| 4316 | 3-Piz | 4-FPh | CO | single bond | 2 | O | $CH_2CH_2$ | sub. 4 |
| 4317 | 4-Piz | 4-FPh | CO | single bond | 2 | O | $CH_2CH_2$ | sub. 4 |
| 4318 | 2-Aze | 4-FPh | CO | single bond | 2 | O | $CH_2CH_2$ | sub. 4 |
| 4319 | 3-Aze | 4-FPh | CO | single bond | 2 | O | $CH_2CH_2$ | sub. 4 |
| 4320 | 4-Aze | 4-FPh | CO | single bond | 2 | O | $CH_2CH_2$ | sub. 4 |
| 4321 | cPr | 4-FPh | CO | single bond | 2 | O | $CH_2CH_2$ | sub. 5 |
| 4322 | cBu | 4-FPh | CO | single bond | 2 | O | $CH_2CH_2$ | sub. 5 |
| 4323 | cPn | 4-FPh | CO | single bond | 2 | O | $CH_2CH_2$ | sub. 5 |
| 4324 | cHex | 4-FPh | CO | single bond | 2 | O | $CH_2CH_2$ | sub. 5 |
| 4325 | cHep | 4-FPh | CO | single bond | 2 | O | $CH_2CH_2$ | sub. 5 |
| 4326 | 2-Pyrd | 4-FPh | CO | single bond | 2 | O | $CH_2CH_2$ | sub. 5 |
| 4327 | 3-Pyrd | 4-FPh | CO | single bond | 2 | O | $CH_2CH_2$ | sub. 5 |
| 4328 | 4-Oxa | 4-FPh | CO | single bond | 2 | O | $CH_2CH_2$ | sub. 5 |
| 4329 | 5-Oxa | 4-FPh | CO | single bond | 2 | O | $CH_2CH_2$ | sub. 5 |
| 4330 | 4-Thi | 4-FPh | CO | single bond | 2 | O | $CH_2CH_2$ | sub. 5 |
| 4331 | 5-Thi | 4-FPh | CO | single bond | 2 | O | $CH_2CH_2$ | sub. 5 |
| 4332 | 4-OOxa | 4-FPh | CO | single bond | 2 | O | $CH_2CH_2$ | sub. 5 |
| 4333 | 5-OOxa | 4-FPh | CO | single bond | 2 | O | $CH_2CH_2$ | sub. 5 |
| 4334 | 4-OThi | 4-FPh | CO | single bond | 2 | O | $CH_2CH_2$ | sub. 5 |
| 4335 | 5-OThi | 4-FPh | CO | single bond | 2 | O | $CH_2CH_2$ | sub. 5 |
| 4336 | 2-Pip | 4-FPh | CO | single bond | 2 | O | $CH_2CH_2$ | sub. 5 |
| 4337 | 3-Pip | 4-FPh | CO | single bond | 2 | O | $CH_2CH_2$ | sub. 5 |
| 4338 | 4-Pip | 4-FPh | CO | single bond | 2 | O | $CH_2CH_2$ | sub. 5 |
| 4339 | 2-Mor | 4-FPh | CO | single bond | 2 | O | $CH_2CH_2$ | sub. 5 |
| 4340 | 3-Mor | 4-FPh | CO | single bond | 2 | O | $CH_2CH_2$ | sub. 5 |
| 4341 | 4-Mor | 4-FPh | CO | single bond | 2 | O | $CH_2CH_2$ | sub. 5 |
| 4342 | 2-Thmor | 4-FPh | CO | single bond | 2 | O | $CH_2CH_2$ | sub. 5 |
| 4343 | 3-Thmor | 4-FPh | CO | single bond | 2 | O | $CH_2CH_2$ | sub. 5 |
| 4344 | 4-Thmor | 4-FPh | CO | single bond | 2 | O | $CH_2CH_2$ | sub. 5 |
| 4345 | 2-Piz | 4-FPh | CO | single bond | 2 | O | $CH_2CH_2$ | sub. 5 |
| 4346 | 3-Piz | 4-FPh | CO | single bond | 2 | O | $CH_2CH_2$ | sub. 5 |
| 4347 | 4-Piz | 4-FPh | CO | single bond | 2 | O | $CH_2CH_2$ | sub. 5 |
| 4348 | 2-Aze | 4-FPh | CO | single bond | 2 | O | $CH_2CH_2$ | sub. 5 |
| 4349 | 3-Aze | 4-FPh | CO | single bond | 2 | O | $CH_2CH_2$ | sub. 5 |
| 4350 | 4-Aze | 4-FPh | CO | single bond | 2 | O | $CH_2CH_2$ | sub. 5 |
| 4351 | cPr | 4-FPh | CO | single bond | 2 | O | $CH_2CH_2$ | sub. 6 |
| 4352 | cBu | 4-FPh | CO | single bond | 2 | O | $CH_2CH_2$ | sub. 6 |
| 4353 | cPn | 4-FPh | CO | single bond | 2 | O | $CH_2CH_2$ | sub. 6 |
| 4354 | cHex | 4-FPh | CO | single bond | 2 | O | $CH_2CH_2$ | sub. 6 |
| 4355 | cHep | 4-FPh | CO | single bond | 2 | O | $CH_2CH_2$ | sub. 6 |
| 4356 | 2-Pyrd | 4-FPh | CO | single bond | 2 | O | $CH_2CH_2$ | sub. 6 |
| 4357 | 3-Pyrd | 4-FPh | CO | single bond | 2 | O | $CH_2CH_2$ | sub. 6 |
| 4358 | 4-Oxa | 4-FPh | CO | single bond | 2 | O | $CH_2CH_2$ | sub. 6 |
| 4359 | 5-Oxa | 4-FPh | CO | single bond | 2 | O | $CH_2CH_2$ | sub. 6 |
| 4360 | 4-Thi | 4-FPh | CO | single bond | 2 | O | $CH_2CH_2$ | sub. 6 |
| 4361 | 5-Thi | 4-FPh | CO | single bond | 2 | O | $CH_2CH_2$ | sub. 6 |
| 4362 | 4-OOxa | 4-FPh | CO | single bond | 2 | O | $CH_2CH_2$ | sub. 6 |
| 4363 | 5-OOxa | 4-FPh | CO | single bond | 2 | O | $CH_2CH_2$ | sub. 6 |
| 4364 | 4-OThi | 4-FPh | CO | single bond | 2 | O | $CH_2CH_2$ | sub. 6 |
| 4365 | 5-OThi | 4-FPh | CO | single bond | 2 | O | $CH_2CH_2$ | sub. 6 |
| 4366 | 2-Pip | 4-FPh | CO | single bond | 2 | O | $CH_2CH_2$ | sub. 6 |
| 4367 | 3-Pip | 4-FPh | CO | single bond | 2 | O | $CH_2CH_2$ | sub. 6 |
| 4368 | 4-Pip | 4-FPh | CO | single bond | 2 | O | $CH_2CH_2$ | sub. 6 |
| 4369 | 2-Mor | 4-FPh | CO | single bond | 2 | O | $CH_2CH_2$ | sub. 6 |
| 4370 | 3-Mor | 4-FPh | CO | single bond | 2 | O | $CH_2CH_2$ | sub. 6 |
| 4371 | 4-Mor | 4-FPh | CO | single bond | 2 | O | $CH_2CH_2$ | sub. 6 |
| 4372 | 2-Thmor | 4-FPh | CO | single bond | 2 | O | $CH_2CH_2$ | sub. 6 |
| 4373 | 3-Thmor | 4-FPh | CO | single bond | 2 | O | $CH_2CH_2$ | sub. 6 |
| 4374 | 4-Thmor | 4-FPh | CO | single bond | 2 | O | $CH_2CH_2$ | sub. 6 |
| 4375 | 2-Piz | 4-FPh | CO | single bond | 2 | O | $CH_2CH_2$ | sub. 6 |
| 4376 | 3-Piz | 4-FPh | CO | single bond | 2 | O | $CH_2CH_2$ | sub. 6 |
| 4377 | 4-Piz | 4-FPh | CO | single bond | 2 | O | $CH_2CH_2$ | sub. 6 |
| 4378 | 2-Aze | 4-FPh | CO | single bond | 2 | O | $CH_2CH_2$ | sub. 6 |
| 4379 | 3-Aze | 4-FPh | CO | single bond | 2 | O | $CH_2CH_2$ | sub. 6 |
| 4380 | 4-Aze | 4-FPh | CO | single bond | 2 | O | $CH_2CH_2$ | sub. 6 |
| 4381 | cPr | 4-FPh | CO | single bond | 2 | O | $CH_2CH_2$ | sub. 7 |
| 4382 | cBu | 4-FPh | CO | single bond | 2 | O | $CH_2CH_2$ | sub. 7 |
| 4383 | cPn | 4-FPh | CO | single bond | 2 | O | $CH_2CH_2$ | sub. 7 |
| 4384 | cHex | 4-FPh | CO | single bond | 2 | O | $CH_2CH_2$ | sub. 7 |
| 4385 | cHep | 4-FPh | CO | single bond | 2 | O | $CH_2CH_2$ | sub. 7 |
| 4386 | 2-Pyrd | 4-FPh | CO | single bond | 2 | O | $CH_2CH_2$ | sub. 7 |
| 4387 | 3-Pyrd | 4-FPh | CO | single bond | 2 | O | $CH_2CH_2$ | sub. 7 |
| 4388 | 4-Oxa | 4-FPh | CO | single bond | 2 | O | $CH_2CH_2$ | sub. 7 |

TABLE 1-continued

| Exemplification compound number | R¹ | R² | A | B | N | D | G | Q |
|---|---|---|---|---|---|---|---|---|
| 4389 | 5-Oxa | 4-FPh | CO | single bond | 2 | O | CH₂CH₂ | sub. 7 |
| 4390 | 4-Thi | 4-FPh | CO | single bond | 2 | O | CH₂CH₂ | sub. 7 |
| 4391 | 5-Thi | 4-FPh | CO | single bond | 2 | O | CH₂CH₂ | sub. 7 |
| 4392 | 4-OOxa | 4-FPh | CO | single bond | 2 | O | CH₂CH₂ | sub. 7 |
| 4393 | 5-OOxa | 4-FPh | CO | single bond | 2 | O | CH₂CH₂ | sub. 7 |
| 4394 | 4-OThi | 4-FPh | CO | single bond | 2 | O | CH₂CH₂ | sub. 7 |
| 4395 | 5-OThi | 4-FPh | CO | single bond | 2 | O | CH₂CH₂ | sub. 7 |
| 4396 | 2-Pip | 4-FPh | CO | single bond | 2 | O | CH₂CH₂ | sub. 7 |
| 4397 | 3-Pip | 4-FPh | CO | single bond | 2 | O | CH₂CH₂ | sub. 7 |
| 4398 | 4-Pip | 4-FPh | CO | single bond | 2 | O | CH₂CH₂ | sub. 7 |
| 4399 | 2-Mor | 4-FPh | CO | single bond | 2 | O | CH₂CH₂ | sub. 7 |
| 4400 | 3-Mor | 4-FPh | CO | single bond | 2 | O | CH₂CH₂ | sub. 7 |
| 4401 | 4-Mor | 4-FPh | CO | single bond | 2 | O | CH₂CH₂ | sub. 7 |
| 4402 | 2-Thmor | 4-FPh | CO | single bond | 2 | O | CH₂CH₂ | sub. 7 |
| 4403 | 3-Thmor | 4-FPh | CO | single bond | 2 | O | CH₂CH₂ | sub. 7 |
| 4404 | 4-Thmor | 4-FPh | CO | single bond | 2 | O | CH₂CH₂ | sub. 7 |
| 4405 | 2-Piz | 4-FPh | CO | single bond | 2 | O | CH₂CH₂ | sub. 7 |
| 4406 | 3-Piz | 4-FPh | CO | single bond | 2 | O | CH₂CH₂ | sub. 7 |
| 4407 | 4-Piz | 4-FPh | CO | single bond | 2 | O | CH₂CH₂ | sub. 7 |
| 4408 | 2-Aze | 4-FPh | CO | single bond | 2 | O | CH₂CH₂ | sub. 7 |
| 4409 | 3-Aze | 4-FPh | CO | single bond | 2 | O | CH₂CH₂ | sub. 7 |
| 4410 | 4-Aze | 4-FPh | CO | single bond | 2 | O | CH₂CH₂ | sub. 7 |
| 4411 | cPr | 4-FPh | CO | single bond | 2 | O | CH₂CH₂ | sub. 8 |
| 4412 | cBu | 4-FPh | CO | single bond | 2 | O | CH₂CH₂ | sub. 8 |
| 4413 | cPn | 4-FPh | CO | single bond | 2 | O | CH₂CH₂ | sub. 8 |
| 4414 | cHex | 4-FPh | CO | single bond | 2 | O | CH₂CH₂ | sub. 8 |
| 4415 | cHep | 4-FPh | CO | single bond | 2 | O | CH₂CH₂ | sub. 8 |
| 4416 | 2-Pyrd | 4-FPh | CO | single bond | 2 | O | CH₂CH₂ | sub. 8 |
| 4417 | 3-Pyrd | 4-FPh | CO | single bond | 2 | O | CH₂CH₂ | sub. 8 |
| 4418 | 4-Oxa | 4-FPh | CO | single bond | 2 | O | CH₂CH₂ | sub. 8 |
| 4419 | 5-Oxa | 4-FPh | CO | single bond | 2 | O | CH₂CH₂ | sub. 8 |
| 4420 | 4-Thi | 4-FPh | CO | single bond | 2 | O | CH₂CH₂ | sub. 8 |
| 4421 | 5-Thi | 4-FPh | CO | single bond | 2 | O | CH₂CH₂ | sub. 8 |
| 4422 | 4-OOxa | 4-FPh | CO | single bond | 2 | O | CH₂CH₂ | sub. 8 |
| 4423 | 5-OOxa | 4-FPh | CO | single bond | 2 | O | CH₂CH₂ | sub. 8 |
| 4424 | 4-OThi | 4-FPh | CO | single bond | 2 | O | CH₂CH₂ | sub. 8 |
| 4425 | 5-OThi | 4-FPh | CO | single bond | 2 | O | CH₂CH₂ | sub. 8 |
| 4426 | 2-Pip | 4-FPh | CO | single bond | 2 | O | CH₂CH₂ | sub. 8 |
| 4427 | 3-Pip | 4-FPh | CO | single bond | 2 | O | CH₂CH₂ | sub. 8 |
| 4428 | 4-Pip | 4-FPh | CO | single bond | 2 | O | CH₂CH₂ | sub. 8 |
| 4429 | 2-Mor | 4-FPh | CO | single bond | 2 | O | CH₂CH₂ | sub. 8 |
| 4430 | 3-Mor | 4-FPh | CO | single bond | 2 | O | CH₂CH₂ | sub. 8 |
| 4431 | 4-Mor | 4-FPh | CO | single bond | 2 | O | CH₂CH₂ | sub. 8 |
| 4432 | 2-Thmor | 4-FPh | CO | single bond | 2 | O | CH₂CH₂ | sub. 8 |
| 4433 | 3-Thmor | 4-FPh | CO | single bond | 2 | O | CH₂CH₂ | sub. 8 |
| 4434 | 4-Thmor | 4-FPh | CO | single bond | 2 | O | CH₂CH₂ | sub. 8 |
| 4435 | 2-Piz | 4-FPh | CO | single bond | 2 | O | CH₂CH₂ | sub. 8 |
| 4436 | 3-Piz | 4-FPh | CO | single bond | 2 | O | CH₂CH₂ | sub. 8 |
| 4437 | 4-Piz | 4-FPh | CO | single bond | 2 | O | CH₂CH₂ | sub. 8 |
| 4438 | 2-Aze | 4-FPh | CO | single bond | 2 | O | CH₂CH₂ | sub. 8 |
| 4439 | 3-Aze | 4-FPh | CO | single bond | 2 | O | CH₂CH₂ | sub. 8 |
| 4440 | 4-Aze | 4-FPh | CO | single bond | 2 | O | CH₂CH₂ | sub. 8 |
| 4441 | cPr | 4-FPh | CO | single bond | 2 | O | CH₂CH₂ | sub. 9 |
| 4442 | cBu | 4-FPh | CO | single bond | 2 | O | CH₂CH₂ | sub. 9 |
| 4443 | cPn | 4-FPh | CO | single bond | 2 | O | CH₂CH₂ | sub. 9 |
| 4444 | cHex | 4-FPh | CO | single bond | 2 | O | CH₂CH₂ | sub. 9 |
| 4445 | cHep | 4-FPh | CO | single bond | 2 | O | CH₂CH₂ | sub. 9 |
| 4446 | 2-Pyrd | 4-FPh | CO | single bond | 2 | O | CH₂CH₂ | sub. 9 |
| 4447 | 3-Pyrd | 4-FPh | CO | single bond | 2 | O | CH₂CH₂ | sub. 9 |
| 4448 | 4-Oxa | 4-FPh | CO | single bond | 2 | O | CH₂CH₂ | sub. 9 |
| 4449 | 5-Oxa | 4-FPh | CO | single bond | 2 | O | CH₂CH₂ | sub. 9 |
| 4450 | 4-Thi | 4-FPh | CO | single bond | 2 | O | CH₂CH₂ | sub. 9 |
| 4451 | 5-Thi | 4-FPh | CO | single bond | 2 | O | CH₂CH₂ | sub. 9 |
| 4452 | 4-OOxa | 4-FPh | CO | single bond | 2 | O | CH₂CH₂ | sub. 9 |
| 4453 | 5-OOxa | 4-FPh | CO | single bond | 2 | O | CH₂CH₂ | sub. 9 |
| 4454 | 4-OThi | 4-FPh | CO | single bond | 2 | O | CH₂CH₂ | sub. 9 |
| 4455 | 5-OThi | 4-FPh | CO | single bond | 2 | O | CH₂CH₂ | sub. 9 |
| 4456 | 2-Pip | 4-FPh | CO | single bond | 2 | O | CH₂CH₂ | sub. 9 |
| 4457 | 3-Pip | 4-FPh | CO | single bond | 2 | O | CH₂CH₂ | sub. 9 |
| 4458 | 4-Pip | 4-FPh | CO | single bond | 2 | O | CH₂CH₂ | sub. 9 |
| 4459 | 2-Mor | 4-FPh | CO | single bond | 2 | O | CH₂CH₂ | sub. 9 |
| 4460 | 3-Mor | 4-FPh | CO | single bond | 2 | O | CH₂CH₂ | sub. 9 |
| 4461 | 4-Mor | 4-FPh | CO | single bond | 2 | O | CH₂CH₂ | sub. 9 |
| 4462 | 2-Thmor | 4-FPh | CO | single bond | 2 | O | CH₂CH₂ | sub. 9 |
| 4463 | 3-Thmor | 4-FPh | CO | single bond | 2 | O | CH₂CH₂ | sub. 9 |
| 4464 | 4-Thmor | 4-FPh | CO | single bond | 2 | O | CH₂CH₂ | sub. 9 |

TABLE 1-continued

| Exemplification compound number | R¹ | R² | A | B | N | D | G | Q |
|---|---|---|---|---|---|---|---|---|
| 4465 | 2-Piz | 4-FPh | CO | single bond | 2 | O | $CH_2CH_2$ | sub. 9 |
| 4466 | 3-Piz | 4-FPh | CO | single bond | 2 | O | $CH_2CH_2$ | sub. 9 |
| 4467 | 4-Piz | 4-FPh | CO | single bond | 2 | O | $CH_2CH_2$ | sub. 9 |
| 4468 | 2-Aze | 4-FPh | CO | single bond | 2 | O | $CH_2CH_2$ | sub. 9 |
| 4469 | 3-Aze | 4-FPh | CO | single bond | 2 | O | $CH_2CH_2$ | sub. 9 |
| 4470 | 4-Aze | 4-FPh | CO | single bond | 2 | O | $CH_2CH_2$ | sub. 9 |
| 4471 | cPr | 4-FPh | CO | single bond | 2 | O | $CH_2CH_2$ | sub. 10 |
| 4472 | cBu | 4-FPh | CO | single bond | 2 | O | $CH_2CH_2$ | sub. 10 |
| 4473 | cPn | 4-FPh | CO | single bond | 2 | O | $CH_2CH_2$ | sub. 10 |
| 4474 | cHex | 4-FPh | CO | single bond | 2 | O | $CH_2CH_2$ | sub. 10 |
| 4475 | cHep | 4-FPh | CO | single bond | 2 | O | $CH_2CH_2$ | sub. 10 |
| 4476 | 2-Pyrd | 4-FPh | CO | single bond | 2 | O | $CH_2CH_2$ | sub. 10 |
| 4477 | 3-Pyrd | 4-FPh | CO | single bond | 2 | O | $CH_2CH_2$ | sub. 10 |
| 4478 | 4-Oxa | 4-FPh | CO | single bond | 2 | O | $CH_2CH_2$ | sub. 10 |
| 4479 | 5-Oxa | 4-FPh | CO | single bond | 2 | O | $CH_2CH_2$ | sub. 10 |
| 4480 | 4-Thi | 4-FPh | CO | single bond | 2 | O | $CH_2CH_2$ | sub. 10 |
| 4481 | 5-Thi | 4-FPh | CO | single bond | 2 | O | $CH_2CH_2$ | sub. 10 |
| 4482 | 4-OOxa | 4-FPh | CO | single bond | 2 | O | $CH_2CH_2$ | sub. 10 |
| 4483 | 5-OOxa | 4-FPh | CO | single bond | 2 | O | $CH_2CH_2$ | sub. 10 |
| 4484 | 4-OThi | 4-FPh | CO | single bond | 2 | O | $CH_2CH_2$ | sub. 10 |
| 4485 | 5-OThi | 4-FPh | CO | single bond | 2 | O | $CH_2CH_2$ | sub. 10 |
| 4486 | 2-Pip | 4-FPh | CO | single bond | 2 | O | $CH_2CH_2$ | sub. 10 |
| 4487 | 3-Pip | 4-FPh | CO | single bond | 2 | O | $CH_2CH_2$ | sub. 10 |
| 4488 | 4-Pip | 4-FPh | CO | single bond | 2 | O | $CH_2CH_2$ | sub. 10 |
| 4489 | 2-Mor | 4-FPh | CO | single bond | 2 | O | $CH_2CH_2$ | sub. 10 |
| 4490 | 3-Mor | 4-FPh | CO | single bond | 2 | O | $CH_2CH_2$ | sub. 10 |
| 4491 | 4-Mor | 4-FPh | CO | single bond | 2 | O | $CH_2CH_2$ | sub. 10 |
| 4492 | 2-Thmor | 4-FPh | CO | single bond | 2 | O | $CH_2CH_2$ | sub. 10 |
| 4493 | 3-Thmor | 4-FPh | CO | single bond | 2 | O | $CH_2CH_2$ | sub. 10 |
| 4494 | 4-Thmor | 4-FPh | CO | single bond | 2 | O | $CH_2CH_2$ | sub. 10 |
| 4495 | 2-Piz | 4-FPh | CO | single bond | 2 | O | $CH_2CH_2$ | sub. 10 |
| 4496 | 3-Piz | 4-FPh | CO | single bond | 2 | O | $CH_2CH_2$ | sub. 10 |
| 4497 | 4-Piz | 4-FPh | CO | single bond | 2 | O | $CH_2CH_2$ | sub. 10 |
| 4498 | 2-Aze | 4-FPh | CO | single bond | 2 | O | $CH_2CH_2$ | sub. 10 |
| 4499 | 3-Aze | 4-FPh | CO | single bond | 2 | O | $CH_2CH_2$ | sub. 10 |
| 4500 | 4-Aze | 4-FPh | CO | single bond | 2 | O | $CH_2CH_2$ | sub. 10 |
| 4501 | cPr | 4-FPh | CO | single bond | 2 | O | $CH_2CH_2$ | sub. 11 |
| 4502 | cBu | 4-FPh | CO | single bond | 2 | O | $CH_2CH_2$ | sub. 11 |
| 4503 | cPn | 4-FPh | CO | single bond | 2 | O | $CH_2CH_2$ | sub. 11 |
| 4504 | cHex | 4-FPh | CO | single bond | 2 | O | $CH_2CH_2$ | sub. 11 |
| 4505 | cHep | 4-FPh | CO | single bond | 2 | O | $CH_2CH_2$ | sub. 11 |
| 4506 | 2-Pyrd | 4-FPh | CO | single bond | 2 | O | $CH_2CH_2$ | sub. 11 |
| 4507 | 3-Pyrd | 4-FPh | CO | single bond | 2 | O | $CH_2CH_2$ | sub. 11 |
| 4508 | 4-Oxa | 4-FPh | CO | single bond | 2 | O | $CH_2CH_2$ | sub. 11 |
| 4509 | 5-Oxa | 4-FPh | CO | single bond | 2 | O | $CH_2CH_2$ | sub. 11 |
| 4510 | 4-Thi | 4-FPh | CO | single bond | 2 | O | $CH_2CH_2$ | sub. 11 |
| 4511 | 5-Thi | 4-FPh | CO | single bond | 2 | O | $CH_2CH_2$ | sub. 11 |
| 4512 | 4-OOxa | 4-FPh | CO | single bond | 2 | O | $CH_2CH_2$ | sub. 11 |
| 4513 | 5-OOxa | 4-FPh | CO | single bond | 2 | O | $CH_2CH_2$ | sub. 11 |
| 4514 | 4-OThi | 4-FPh | CO | single bond | 2 | O | $CH_2CH_2$ | sub. 11 |
| 4515 | 5-OThi | 4-FPh | CO | single bond | 2 | O | $CH_2CH_2$ | sub. 11 |
| 4516 | 2-Pip | 4-FPh | CO | single bond | 2 | O | $CH_2CH_2$ | sub. 11 |
| 4517 | 3-Pip | 4-FPh | CO | single bond | 2 | O | $CH_2CH_2$ | sub. 11 |
| 4518 | 4-Pip | 4-FPh | CO | single bond | 2 | O | $CH_2CH_2$ | sub. 11 |
| 4519 | 2-Mor | 4-FPh | CO | single bond | 2 | O | $CH_2CH_2$ | sub. 11 |
| 4520 | 3-Mor | 4-FPh | CO | single bond | 2 | O | $CH_2CH_2$ | sub. 11 |
| 4521 | 4-Mor | 4-FPh | CO | single bond | 2 | O | $CH_2CH_2$ | sub. 11 |
| 4522 | 2-Thmor | 4-FPh | CO | single bond | 2 | O | $CH_2CH_2$ | sub. 11 |
| 4523 | 3-Thmor | 4-FPh | CO | single bond | 2 | O | $CH_2CH_2$ | sub. 11 |
| 4524 | 4-Thmor | 4-FPh | CO | single bond | 2 | O | $CH_2CH_2$ | sub. 11 |
| 4525 | 2-Piz | 4-FPh | CO | single bond | 2 | O | $CH_2CH_2$ | sub. 11 |
| 4526 | 3-Piz | 4-FPh | CO | single bond | 2 | O | $CH_2CH_2$ | sub. 11 |
| 4527 | 4-Piz | 4-FPh | CO | single bond | 2 | O | $CH_2CH_2$ | sub. 11 |
| 4528 | 2-Aze | 4-FPh | CO | single bond | 2 | O | $CH_2CH_2$ | sub. 11 |
| 4529 | 3-Aze | 4-FPh | CO | single bond | 2 | O | $CH_2CH_2$ | sub. 11 |
| 4530 | 4-Aze | 4-FPh | CO | single bond | 2 | O | $CH_2CH_2$ | sub. 11 |
| 4531 | cPr | 4-FPh | CO | single bond | 2 | O | $CH_2CH_2$ | sub. 12 |
| 4532 | cBu | 4-FPh | CO | single bond | 2 | O | $CH_2CH_2$ | sub. 12 |
| 4533 | cPn | 4-FPh | CO | single bond | 2 | O | $CH_2CH_2$ | sub. 12 |
| 4534 | cHex | 4-FPh | CO | single bond | 2 | O | $CH_2CH_2$ | sub. 12 |
| 4535 | cHep | 4-FPh | CO | single bond | 2 | O | $CH_2CH_2$ | sub. 12 |
| 4536 | 2-Pyrd | 4-FPh | CO | single bond | 2 | O | $CH_2CH_2$ | sub. 12 |
| 4537 | 3-Pyrd | 4-FPh | CO | single bond | 2 | O | $CH_2CH_2$ | sub. 12 |
| 4538 | 4-Oxa | 4-FPh | CO | single bond | 2 | O | $CH_2CH_2$ | sub. 12 |
| 4539 | 5-Oxa | 4-FPh | CO | single bond | 2 | O | $CH_2CH_2$ | sub. 12 |
| 4540 | 4-Thi | 4-FPh | CO | single bond | 2 | O | $CH_2CH_2$ | sub. 12 |

TABLE 1-continued

| Exemplification compound number | R¹ | R² | A | B | N | D | G | Q |
|---|---|---|---|---|---|---|---|---|
| 4541 | 5-Thi | 4-FPh | CO | single bond | 2 | O | $CH_2CH_2$ | sub. 12 |
| 4542 | 4-OOxa | 4-FPh | CO | single bond | 2 | O | $CH_2CH_2$ | sub. 12 |
| 4543 | 5-OOxa | 4-FPh | CO | single bond | 2 | O | $CH_2CH_2$ | sub. 12 |
| 4544 | 4-OThi | 4-FPh | CO | single bond | 2 | O | $CH_2CH_2$ | sub. 12 |
| 4545 | 5-OThi | 4-FPh | CO | single bond | 2 | O | $CH_2CH_2$ | sub. 12 |
| 4546 | 2-Pip | 4-FPh | CO | single bond | 2 | O | $CH_2CH_2$ | sub. 12 |
| 4547 | 3-Pip | 4-FPh | CO | single bond | 2 | O | $CH_2CH_2$ | sub. 12 |
| 4548 | 4-Pip | 4-FPh | CO | single bond | 2 | O | $CH_2CH_2$ | sub. 12 |
| 4549 | 2-Mor | 4-FPh | CO | single bond | 2 | O | $CH_2CH_2$ | sub. 12 |
| 4550 | 3-Mor | 4-FPh | CO | single bond | 2 | O | $CH_2CH_2$ | sub. 12 |
| 4551 | 4-Mor | 4-FPh | CO | single bond | 2 | O | $CH_2CH_2$ | sub. 12 |
| 4552 | 2-Thmor | 4-FPh | CO | single bond | 2 | O | $CH_2CH_2$ | sub. 12 |
| 4553 | 3-Thmor | 4-FPh | CO | single bond | 2 | O | $CH_2CH_2$ | sub. 12 |
| 4554 | 4-Thmor | 4-FPh | CO | single bond | 2 | O | $CH_2CH_2$ | sub. 12 |
| 4555 | 2-Piz | 4-FPh | CO | single bond | 2 | O | $CH_2CH_2$ | sub. 12 |
| 4556 | 3-Piz | 4-FPh | CO | single bond | 2 | O | $CH_2CH_2$ | sub. 12 |
| 4557 | 4-Piz | 4-FPh | CO | single bond | 2 | O | $CH_2CH_2$ | sub. 12 |
| 4558 | 2-Aze | 4-FPh | CO | single bond | 2 | O | $CH_2CH_2$ | sub. 12 |
| 4559 | 3-Aze | 4-FPh | CO | single bond | 2 | O | $CH_2CH_2$ | sub. 12 |
| 4560 | 4-Aze | 4-FPh | CO | single bond | 2 | O | $CH_2CH_2$ | sub. 12 |
| 4561 | cPr | 4-FPh | CO | single bond | 2 | O | $CH_2CH_2$ | sub. 13 |
| 4562 | cBu | 4-FPh | CO | single bond | 2 | O | $CH_2CH_2$ | sub. 13 |
| 4563 | cPn | 4-FPh | CO | single bond | 2 | O | $CH_2CH_2$ | sub. 13 |
| 4564 | cHex | 4-FPh | CO | single bond | 2 | O | $CH_2CH_2$ | sub. 13 |
| 4565 | cHep | 4-FPh | CO | single bond | 2 | O | $CH_2CH_2$ | sub. 13 |
| 4566 | 2-Pyrd | 4-FPh | CO | single bond | 2 | O | $CH_2CH_2$ | sub. 13 |
| 4567 | 3-Pyrd | 4-FPh | CO | single bond | 2 | O | $CH_2CH_2$ | sub. 13 |
| 4568 | 4-Oxa | 4-FPh | CO | single bond | 2 | O | $CH_2CH_2$ | sub. 13 |
| 4569 | 5-Oxa | 4-FPh | CO | single bond | 2 | O | $CH_2CH_2$ | sub. 13 |
| 4570 | 4-Thi | 4-FPh | CO | single bond | 2 | O | $CH_2CH_2$ | sub. 13 |
| 4571 | 5-Thi | 4-FPh | CO | single bond | 2 | O | $CH_2CH_2$ | sub. 13 |
| 4572 | 4-OOxa | 4-FPh | CO | single bond | 2 | O | $CH_2CH_2$ | sub. 13 |
| 4573 | 5-OOxa | 4-FPh | CO | single bond | 2 | O | $CH_2CH_2$ | sub. 13 |
| 4574 | 4-OThi | 4-FPh | CO | single bond | 2 | O | $CH_2CH_2$ | sub. 13 |
| 4575 | 5-OThi | 4-FPh | CO | single bond | 2 | O | $CH_2CH_2$ | sub. 13 |
| 4576 | 2-Pip | 4-FPh | CO | single bond | 2 | O | $CH_2CH_2$ | sub. 13 |
| 4577 | 3-Pip | 4-FPh | CO | single bond | 2 | O | $CH_2CH_2$ | sub. 13 |
| 4578 | 4-Pip | 4-FPh | CO | single bond | 2 | O | $CH_2CH_2$ | sub. 13 |
| 4579 | 2-Mor | 4-FPh | CO | single bond | 2 | O | $CH_2CH_2$ | sub. 13 |
| 4580 | 3-Mor | 4-FPh | CO | single bond | 2 | O | $CH_2CH_2$ | sub. 13 |
| 4581 | 4-Mor | 4-FPh | CO | single bond | 2 | O | $CH_2CH_2$ | sub. 13 |
| 4582 | 2-Thmor | 4-FPh | CO | single bond | 2 | O | $CH_2CH_2$ | sub. 13 |
| 4583 | 3-Thmor | 4-FPh | CO | single bond | 2 | O | $CH_2CH_2$ | sub. 13 |
| 4584 | 4-Thmor | 4-FPh | CO | single bond | 2 | O | $CH_2CH_2$ | sub. 13 |
| 4585 | 2-Piz | 4-FPh | CO | single bond | 2 | O | $CH_2CH_2$ | sub. 13 |
| 4586 | 3-Piz | 4-FPh | CO | single bond | 2 | O | $CH_2CH_2$ | sub. 13 |
| 4587 | 4-Piz | 4-FPh | CO | single bond | 2 | O | $CH_2CH_2$ | sub. 13 |
| 4588 | 2-Aze | 4-FPh | CO | single bond | 2 | O | $CH_2CH_2$ | sub. 13 |
| 4589 | 3-Aze | 4-FPh | CO | single bond | 2 | O | $CH_2CH_2$ | sub. 13 |
| 4590 | 4-Aze | 4-FPh | CO | single bond | 2 | O | $CH_2CH_2$ | sub. 13 |
| 4591 | cPr | 4-FPh | CO | single bond | 2 | O | $CH_2CH_2$ | sub. 14 |
| 4592 | cBu | 4-FPh | CO | single bond | 2 | O | $CH_2CH_2$ | sub. 14 |
| 4593 | cPn | 4-FPh | CO | single bond | 2 | O | $CH_2CH_2$ | sub. 14 |
| 4594 | cHex | 4-FPh | CO | single bond | 2 | O | $CH_2CH_2$ | sub. 14 |
| 4595 | cHep | 4-FPh | CO | single bond | 2 | O | $CH_2CH_2$ | sub. 14 |
| 4596 | 2-Pyrd | 4-FPh | CO | single bond | 2 | O | $CH_2CH_2$ | sub. 14 |
| 4597 | 3-Pyrd | 4-FPh | CO | single bond | 2 | O | $CH_2CH_2$ | sub. 14 |
| 4598 | 4-Oxa | 4-FPh | CO | single bond | 2 | O | $CH_2CH_2$ | sub. 14 |
| 4599 | 5-Oxa | 4-FPh | CO | single bond | 2 | O | $CH_2CH_2$ | sub. 14 |
| 4600 | 4-Thi | 4-FPh | CO | single bond | 2 | O | $CH_2CH_2$ | sub. 14 |
| 4601 | 5-Thi | 4-FPh | CO | single bond | 2 | O | $CH_2CH_2$ | sub. 14 |
| 4602 | 4-OOxa | 4-FPh | CO | single bond | 2 | O | $CH_2CH_2$ | sub. 14 |
| 4603 | 5-OOxa | 4-FPh | CO | single bond | 2 | O | $CH_2CH_2$ | sub. 14 |
| 4604 | 4-OThi | 4-FPh | CO | single bond | 2 | O | $CH_2CH_2$ | sub. 14 |
| 4605 | 5-OThi | 4-FPh | CO | single bond | 2 | O | $CH_2CH_2$ | sub. 14 |
| 4606 | 2-Pip | 4-FPh | CO | single bond | 2 | O | $CH_2CH_2$ | sub. 14 |
| 4607 | 3-Pip | 4-FPh | CO | single bond | 2 | O | $CH_2CH_2$ | sub. 14 |
| 4608 | 4-Pip | 4-FPh | CO | single bond | 2 | O | $CH_2CH_2$ | sub. 14 |
| 4609 | 2-Mor | 4-FPh | CO | single bond | 2 | O | $CH_2CH_2$ | sub. 14 |
| 4610 | 3-Mor | 4-FPh | CO | single bond | 2 | O | $CH_2CH_2$ | sub. 14 |
| 4611 | 4-Mor | 4-FPh | CO | single bond | 2 | O | $CH_2CH_2$ | sub. 14 |
| 4612 | 2-Thmor | 4-FPh | CO | single bond | 2 | O | $CH_2CH_2$ | sub. 14 |
| 4613 | 3-Thmor | 4-FPh | CO | single bond | 2 | O | $CH_2CH_2$ | sub. 14 |
| 4614 | 4-Thmor | 4-FPh | CO | single bond | 2 | O | $CH_2CH_2$ | sub. 14 |
| 4615 | 2-Piz | 4-FPh | CO | single bond | 2 | O | $CH_2CH_2$ | sub. 14 |
| 4616 | 3-Piz | 4-FPh | CO | single bond | 2 | O | $CH_2CH_2$ | sub. 14 |

TABLE 1-continued

| Exemplification compound number | R¹ | R² | A | B | N | D | G | Q |
|---|---|---|---|---|---|---|---|---|
| 4617 | 4-Piz | 4-FPh | CO | single bond | 2 | O | $CH_2CH_2$ | sub. 14 |
| 4618 | 2-Aze | 4-FPh | CO | single bond | 2 | O | $CH_2CH_2$ | sub. 14 |
| 4619 | 3-Aze | 4-FPh | CO | single bond | 2 | O | $CH_2CH_2$ | sub. 14 |
| 4620 | 4-Aze | 4-FPh | CO | single bond | 2 | O | $CH_2CH_2$ | sub. 14 |
| 4621 | cPr | 4-FPh | CO | single bond | 2 | O | $CH_2CH_2$ | sub. 15 |
| 4622 | cBu | 4-FPh | CO | single bond | 2 | O | $CH_2CH_2$ | sub. 15 |
| 4623 | cPn | 4-FPh | CO | single bond | 2 | O | $CH_2CH_2$ | sub. 15 |
| 4624 | cHex | 4-FPh | CO | single bond | 2 | O | $CH_2CH_2$ | sub. 15 |
| 4625 | cHep | 4-FPh | CO | single bond | 2 | O | $CH_2CH_2$ | sub. 15 |
| 4626 | 2-Pyrd | 4-FPh | CO | single bond | 2 | O | $CH_2CH_2$ | sub. 15 |
| 4627 | 3-Pyrd | 4-FPh | CO | single bond | 2 | O | $CH_2CH_2$ | sub. 15 |
| 4628 | 4-Oxa | 4-FPh | CO | single bond | 2 | O | $CH_2CH_2$ | sub. 15 |
| 4629 | 5-Oxa | 4-FPh | CO | single bond | 2 | O | $CH_2CH_2$ | sub. 15 |
| 4630 | 4-Thi | 4-FPh | CO | single bond | 2 | O | $CH_2CH_2$ | sub. 15 |
| 4631 | 5-Thi | 4-FPh | CO | single bond | 2 | O | $CH_2CH_2$ | sub. 15 |
| 4632 | 4-OOxa | 4-FPh | CO | single bond | 2 | O | $CH_2CH_2$ | sub. 15 |
| 4633 | 5-OOxa | 4-FPh | CO | single bond | 2 | O | $CH_2CH_2$ | sub. 15 |
| 4634 | 4-OThi | 4-FPh | CO | single bond | 2 | O | $CH_2CH_2$ | sub. 15 |
| 4635 | 5-OThi | 4-FPh | CO | single bond | 2 | O | $CH_2CH_2$ | sub. 15 |
| 4636 | 2-Pip | 4-FPh | CO | single bond | 2 | O | $CH_2CH_2$ | sub. 15 |
| 4637 | 3-Pip | 4-FPh | CO | single bond | 2 | O | $CH_2CH_2$ | sub. 15 |
| 4638 | 4-Pip | 4-FPh | CO | single bond | 2 | O | $CH_2CH_2$ | sub. 15 |
| 4639 | 2-Mor | 4-FPh | CO | single bond | 2 | O | $CH_2CH_2$ | sub. 15 |
| 4640 | 3-Mor | 4-FPh | CO | single bond | 2 | O | $CH_2CH_2$ | sub. 15 |
| 4641 | 4-Mor | 4-FPh | CO | single bond | 2 | O | $CH_2CH_2$ | sub. 15 |
| 4642 | 2-Thmor | 4-FPh | CO | single bond | 2 | O | $CH_2CH_2$ | sub. 15 |
| 4643 | 3-Thmor | 4-FPh | CO | single bond | 2 | O | $CH_2CH_2$ | sub. 15 |
| 4644 | 4-Thmor | 4-FPh | CO | single bond | 2 | O | $CH_2CH_2$ | sub. 15 |
| 4645 | 2-Piz | 4-FPh | CO | single bond | 2 | O | $CH_2CH_2$ | sub. 15 |
| 4646 | 3-Piz | 4-FPh | CO | single bond | 2 | O | $CH_2CH_2$ | sub. 15 |
| 4647 | 4-Piz | 4-FPh | CO | single bond | 2 | O | $CH_2CH_2$ | sub. 15 |
| 4648 | 2-Aze | 4-FPh | CO | single bond | 2 | O | $CH_2CH_2$ | sub. 15 |
| 4649 | 3-Aze | 4-FPh | CO | single bond | 2 | O | $CH_2CH_2$ | sub. 15 |
| 4650 | 4-Aze | 4-FPh | CO | single bond | 2 | O | $CH_2CH_2$ | sub. 15 |
| 4651 | cPr | 4-FPh | CO | single bond | 2 | O | $CH_2CH_2$ | sub. 16 |
| 4652 | cBu | 4-FPh | CO | single bond | 2 | O | $CH_2CH_2$ | sub. 16 |
| 4653 | cPn | 4-FPh | CO | single bond | 2 | O | $CH_2CH_2$ | sub. 16 |
| 4654 | cHex | 4-FPh | CO | single bond | 2 | O | $CH_2CH_2$ | sub. 16 |
| 4655 | cHep | 4-FPh | CO | single bond | 2 | O | $CH_2CH_2$ | sub. 16 |
| 4656 | 2-Pyrd | 4-FPh | CO | single bond | 2 | O | $CH_2CH_2$ | sub. 16 |
| 4657 | 3-Pyrd | 4-FPh | CO | single bond | 2 | O | $CH_2CH_2$ | sub. 16 |
| 4658 | 4-Oxa | 4-FPh | CO | single bond | 2 | O | $CH_2CH_2$ | sub. 16 |
| 4659 | 5-Oxa | 4-FPh | CO | single bond | 2 | O | $CH_2CH_2$ | sub. 16 |
| 4660 | 4-Thi | 4-FPh | CO | single bond | 2 | O | $CH_2CH_2$ | sub. 16 |
| 4661 | 5-Thi | 4-FPh | CO | single bond | 2 | O | $CH_2CH_2$ | sub. 16 |
| 4662 | 4-OOxa | 4-FPh | CO | single bond | 2 | O | $CH_2CH_2$ | sub. 16 |
| 4663 | 5-OOxa | 4-FPh | CO | single bond | 2 | O | $CH_2CH_2$ | sub. 16 |
| 4664 | 4-OThi | 4-FPh | CO | single bond | 2 | O | $CH_2CH_2$ | sub. 16 |
| 4665 | 5-OThi | 4-FPh | CO | single bond | 2 | O | $CH_2CH_2$ | sub. 16 |
| 4666 | 2-Pip | 4-FPh | CO | single bond | 2 | O | $CH_2CH_2$ | sub. 16 |
| 4667 | 3-Pip | 4-FPh | CO | single bond | 2 | O | $CH_2CH_2$ | sub. 16 |
| 4668 | 4-Pip | 4-FPh | CO | single bond | 2 | O | $CH_2CH_2$ | sub. 16 |
| 4669 | 2-Mor | 4-FPh | CO | single bond | 2 | O | $CH_2CH_2$ | sub. 16 |
| 4670 | 3-Mor | 4-FPh | CO | single bond | 2 | O | $CH_2CH_2$ | sub. 16 |
| 4671 | 4-Mor | 4-FPh | CO | single bond | 2 | O | $CH_2CH_2$ | sub. 16 |
| 4672 | 2-Thmor | 4-FPh | CO | single bond | 2 | O | $CH_2CH_2$ | sub. 16 |
| 4673 | 3-Thmor | 4-FPh | CO | single bond | 2 | O | $CH_2CH_2$ | sub. 16 |
| 4674 | 4-Thmor | 4-FPh | CO | single bond | 2 | O | $CH_2CH_2$ | sub. 16 |
| 4675 | 2-Piz | 4-FPh | CO | single bond | 2 | O | $CH_2CH_2$ | sub. 16 |
| 4676 | 3-Piz | 4-FPh | CO | single bond | 2 | O | $CH_2CH_2$ | sub. 16 |
| 4677 | 4-Piz | 4-FPh | CO | single bond | 2 | O | $CH_2CH_2$ | sub. 16 |
| 4678 | 2-Aze | 4-FPh | CO | single bond | 2 | O | $CH_2CH_2$ | sub. 16 |
| 4679 | 3-Aze | 4-FPh | CO | single bond | 2 | O | $CH_2CH_2$ | sub. 16 |
| 4680 | 4-Aze | 4-FPh | CO | single bond | 2 | O | $CH_2CH_2$ | sub. 16 |
| 4681 | cPr | 4-FPh | CO | single bond | 2 | O | $CH_2CH_2$ | sub. 17 |
| 4682 | cBu | 4-FPh | CO | single bond | 2 | O | $CH_2CH_2$ | sub. 17 |
| 4683 | cPn | 4-FPh | CO | single bond | 2 | O | $CH_2CH_2$ | sub. 17 |
| 4684 | cHex | 4-FPh | CO | single bond | 2 | O | $CH_2CH_2$ | sub. 17 |
| 4685 | cHep | 4-FPh | CO | single bond | 2 | O | $CH_2CH_2$ | sub. 17 |
| 4686 | 2-Pyrd | 4-FPh | CO | single bond | 2 | O | $CH_2CH_2$ | sub. 17 |
| 4687 | 3-Pyrd | 4-FPh | CO | single bond | 2 | O | $CH_2CH_2$ | sub. 17 |
| 4688 | 4-Oxa | 4-FPh | CO | single bond | 2 | O | $CH_2CH_2$ | sub. 17 |
| 4689 | 5-Oxa | 4-FPh | CO | single bond | 2 | O | $CH_2CH_2$ | sub. 17 |
| 4690 | 4-Thi | 4-FPh | CO | single bond | 2 | O | $CH_2CH_2$ | sub. 17 |
| 4691 | 5-Thi | 4-FPh | CO | single bond | 2 | O | $CH_2CH_2$ | sub. 17 |
| 4692 | 4-OOxa | 4-FPh | CO | single bond | 2 | O | $CH_2CH_2$ | sub. 17 |

TABLE 1-continued

| Exemplification compound number | R¹ | R² | A | B | N | D | G | Q |
|---|---|---|---|---|---|---|---|---|
| 4693 | 5-OOxa | 4-FPh | CO | single bond | 2 | O | CH₂CH₂ | sub. 17 |
| 4694 | 4-OThi | 4-FPh | CO | single bond | 2 | O | CH₂CH₂ | sub. 17 |
| 4695 | 5-OThi | 4-FPh | CO | single bond | 2 | O | CH₂CH₂ | sub. 17 |
| 4696 | 2-Pip | 4-FPh | CO | single bond | 2 | O | CH₂CH₂ | sub. 17 |
| 4697 | 3-Pip | 4-FPh | CO | single bond | 2 | O | CH₂CH₂ | sub. 17 |
| 4698 | 4-Pip | 4-FPh | CO | single bond | 2 | O | CH₂CH₂ | sub. 17 |
| 4699 | 2-Mor | 4-FPh | CO | single bond | 2 | O | CH₂CH₂ | sub. 17 |
| 4700 | 3-Mor | 4-FPh | CO | single bond | 2 | O | CH₂CH₂ | sub. 17 |
| 4701 | 4-Mor | 4-FPh | CO | single bond | 2 | O | CH₂CH₂ | sub. 17 |
| 4702 | 2-Thmor | 4-FPh | CO | single bond | 2 | O | CH₂CH₂ | sub. 17 |
| 4703 | 3-Thmor | 4-FPh | CO | single bond | 2 | O | CH₂CH₂ | sub. 17 |
| 4704 | 4-Thmor | 4-FPh | CO | single bond | 2 | O | CH₂CH₂ | sub. 17 |
| 4705 | 2-Piz | 4-FPh | CO | single bond | 2 | O | CH₂CH₂ | sub. 17 |
| 4706 | 3-Piz | 4-FPh | CO | single bond | 2 | O | CH₂CH₂ | sub. 17 |
| 4707 | 4-Piz | 4-FPh | CO | single bond | 2 | O | CH₂CH₂ | sub. 17 |
| 4708 | 2-Aze | 4-FPh | CO | single bond | 2 | O | CH₂CH₂ | sub. 17 |
| 4709 | 3-Aze | 4-FPh | CO | single bond | 2 | O | CH₂CH₂ | sub. 17 |
| 4710 | 4-Aze | 4-FPh | CO | single bond | 2 | O | CH₂CH₂ | sub. 17 |
| 4711 | cPr | 4-FPh | CO | single bond | 2 | O | CH₂CH₂ | sub. 18 |
| 4712 | cBu | 4-FPh | CO | single bond | 2 | O | CH₂CH₂ | sub. 18 |
| 4713 | cPn | 4-FPh | CO | single bond | 2 | O | CH₂CH₂ | sub. 18 |
| 4714 | cHex | 4-FPh | CO | single bond | 2 | O | CH₂CH₂ | sub. 18 |
| 4715 | cHep | 4-FPh | CO | single bond | 2 | O | CH₂CH₂ | sub. 18 |
| 4716 | 2-Pyrd | 4-FPh | CO | single bond | 2 | O | CH₂CH₂ | sub. 18 |
| 4717 | 3-Pyrd | 4-FPh | CO | single bond | 2 | O | CH₂CH₂ | sub. 18 |
| 4718 | 4-Oxa | 4-FPh | CO | single bond | 2 | O | CH₂CH₂ | sub. 18 |
| 4719 | 5-Oxa | 4-FPh | CO | single bond | 2 | O | CH₂CH₂ | sub. 18 |
| 4720 | 4-Thi | 4-FPh | CO | single bond | 2 | O | CH₂CH₂ | sub. 18 |
| 4721 | 5-Thi | 4-FPh | CO | single bond | 2 | O | CH₂CH₂ | sub. 18 |
| 4722 | 4-OOxa | 4-FPh | CO | single bond | 2 | O | CH₂CH₂ | sub. 18 |
| 4723 | 5-OOxa | 4-FPh | CO | single bond | 2 | O | CH₂CH₂ | sub. 18 |
| 4724 | 4-OThi | 4-FPh | CO | single bond | 2 | O | CH₂CH₂ | sub. 18 |
| 4725 | 5-OThi | 4-FPh | CO | single bond | 2 | O | CH₂CH₂ | sub. 18 |
| 4726 | 2-Pip | 4-FPh | CO | single bond | 2 | O | CH₂CH₂ | sub. 18 |
| 4727 | 3-Pip | 4-FPh | CO | single bond | 2 | O | CH₂CH₂ | sub. 18 |
| 4728 | 4-Pip | 4-FPh | CO | single bond | 2 | O | CH₂CH₂ | sub. 18 |
| 4729 | 2-Mor | 4-FPh | CO | single bond | 2 | O | CH₂CH₂ | sub. 18 |
| 4730 | 3-Mor | 4-FPh | CO | single bond | 2 | O | CH₂CH₂ | sub. 18 |
| 4731 | 4-Mor | 4-FPh | CO | single bond | 2 | O | CH₂CH₂ | sub. 18 |
| 4732 | 2-Thmor | 4-FPh | CO | single bond | 2 | O | CH₂CH₂ | sub. 18 |
| 4733 | 3-Thmor | 4-FPh | CO | single bond | 2 | O | CH₂CH₂ | sub. 18 |
| 4734 | 4-Thmor | 4-FPh | CO | single bond | 2 | O | CH₂CH₂ | sub. 18 |
| 4735 | 2-Piz | 4-FPh | CO | single bond | 2 | O | CH₂CH₂ | sub. 18 |
| 4736 | 3-Piz | 4-FPh | CO | single bond | 2 | O | CH₂CH₂ | sub. 18 |
| 4737 | 4-Piz | 4-FPh | CO | single bond | 2 | O | CH₂CH₂ | sub. 18 |
| 4738 | 2-Aze | 4-FPh | CO | single bond | 2 | O | CH₂CH₂ | sub. 18 |
| 4739 | 3-Aze | 4-FPh | CO | single bond | 2 | O | CH₂CH₂ | sub. 18 |
| 4740 | 4-Aze | 4-FPh | CO | single bond | 2 | O | CH₂CH₂ | sub. 18 |
| 4741 | cPr | 4-FPh | CO | single bond | 2 | O | CH₂CH₂ | sub. 19 |
| 4742 | cBu | 4-FPh | CO | single bond | 2 | O | CH₂CH₂ | sub. 19 |
| 4743 | cPn | 4-FPh | CO | single bond | 2 | O | CH₂CH₂ | sub. 19 |
| 4744 | cHex | 4-FPh | CO | single bond | 2 | O | CH₂CH₂ | sub. 19 |
| 4745 | cHep | 4-FPh | CO | single bond | 2 | O | CH₂CH₂ | sub. 19 |
| 4746 | 2-Pyrd | 4-FPh | CO | single bond | 2 | O | CH₂CH₂ | sub. 19 |
| 4747 | 3-Pyrd | 4-FPh | CO | single bond | 2 | O | CH₂CH₂ | sub. 19 |
| 4748 | 4-Oxa | 4-FPh | CO | single bond | 2 | O | CH₂CH₂ | sub. 19 |
| 4749 | 5-Oxa | 4-FPh | CO | single bond | 2 | O | CH₂CH₂ | sub. 19 |
| 4750 | 4-Thi | 4-FPh | CO | single bond | 2 | O | CH₂CH₂ | sub. 19 |
| 4751 | 5-Thi | 4-FPh | CO | single bond | 2 | O | CH₂CH₂ | sub. 19 |
| 4752 | 4-OOxa | 4-FPh | CO | single bond | 2 | O | CH₂CH₂ | sub. 19 |
| 4753 | 5-OOxa | 4-FPh | CO | single bond | 2 | O | CH₂CH₂ | sub. 19 |
| 4754 | 4-OThi | 4-FPh | CO | single bond | 2 | O | CH₂CH₂ | sub. 19 |
| 4755 | 5-OThi | 4-FPh | CO | single bond | 2 | O | CH₂CH₂ | sub. 19 |
| 4756 | 2-Pip | 4-FPh | CO | single bond | 2 | O | CH₂CH₂ | sub. 19 |
| 4757 | 3-Pip | 4-FPh | CO | single bond | 2 | O | CH₂CH₂ | sub. 19 |
| 4758 | 4-Pip | 4-FPh | CO | single bond | 2 | O | CH₂CH₂ | sub. 19 |
| 4759 | 2-Mor | 4-FPh | CO | single bond | 2 | O | CH₂CH₂ | sub. 19 |
| 4760 | 3-Mor | 4-FPh | CO | single bond | 2 | O | CH₂CH₂ | sub. 19 |
| 4761 | 4-Mor | 4-FPh | CO | single bond | 2 | O | CH₂CH₂ | sub. 19 |
| 4762 | 2-Thmor | 4-FPh | CO | single bond | 2 | O | CH₂CH₂ | sub. 19 |
| 4763 | 3-Thmor | 4-FPh | CO | single bond | 2 | O | CH₂CH₂ | sub. 19 |
| 4764 | 4-Thmor | 4-FPh | CO | single bond | 2 | O | CH₂CH₂ | sub. 19 |
| 4765 | 2-Piz | 4-FPh | CO | single bond | 2 | O | CH₂CH₂ | sub. 19 |
| 4766 | 3-Piz | 4-FPh | CO | single bond | 2 | O | CH₂CH₂ | sub. 19 |
| 4767 | 4-Piz | 4-FPh | CO | single bond | 2 | O | CH₂CH₂ | sub. 19 |
| 4768 | 2-Aze | 4-FPh | CO | single bond | 2 | O | CH₂CH₂ | sub. 19 |

TABLE 1-continued

| Exemplification compound number | R¹ | R² | A | B | N | D | G | Q |
|---|---|---|---|---|---|---|---|---|
| 4769 | 3-Aze | 4-FPh | CO | single bond | 2 | O | CH₂CH₂ | sub. 19 |
| 4770 | 4-Aze | 4-FPh | CO | single bond | 2 | O | CH₂CH₂ | sub. 19 |
| 4771 | cPr | 4-FPh | CO | single bond | 2 | O | CH₂CH₂ | sub. 20 |
| 4772 | cBu | 4-FPh | CO | single bond | 2 | O | CH₂CH₂ | sub. 20 |
| 4773 | cPn | 4-FPh | CO | single bond | 2 | O | CH₂CH₂ | sub. 20 |
| 4774 | cHex | 4-FPh | CO | single bond | 2 | O | CH₂CH₂ | sub. 20 |
| 4775 | cHep | 4-FPh | CO | single bond | 2 | O | CH₂CH₂ | sub. 20 |
| 4776 | 2-Pyrd | 4-FPh | CO | single bond | 2 | O | CH₂CH₂ | sub. 20 |
| 4777 | 3-Pyrd | 4-FPh | CO | single bond | 2 | O | CH₂CH₂ | sub. 20 |
| 4778 | 4-Oxa | 4-FPh | CO | single bond | 2 | O | CH₂CH₂ | sub. 20 |
| 4779 | 5-Oxa | 4-FPh | CO | single bond | 2 | O | CH₂CH₂ | sub. 20 |
| 4780 | 4-Thi | 4-FPh | CO | single bond | 2 | O | CH₂CH₂ | sub. 20 |
| 4781 | 5-Thi | 4-FPh | CO | single bond | 2 | O | CH₂CH₂ | sub. 20 |
| 4782 | 4-OOxa | 4-FPh | CO | single bond | 2 | O | CH₂CH₂ | sub. 20 |
| 4783 | 5-OOxa | 4-FPh | CO | single bond | 2 | O | CH₂CH₂ | sub. 20 |
| 4784 | 4-OThi | 4-FPh | CO | single bond | 2 | O | CH₂CH₂ | sub. 20 |
| 4785 | 5-OThi | 4-FPh | CO | single bond | 2 | O | CH₂CH₂ | sub. 20 |
| 4786 | 2-Pip | 4-FPh | CO | single bond | 2 | O | CH₂CH₂ | sub. 20 |
| 4787 | 3-Pip | 4-FPh | CO | single bond | 2 | O | CH₂CH₂ | sub. 20 |
| 4788 | 4-Pip | 4-FPh | CO | single bond | 2 | O | CH₂CH₂ | sub. 20 |
| 4789 | 2-Mor | 4-FPh | CO | single bond | 2 | O | CH₂CH₂ | sub. 20 |
| 4790 | 3-Mor | 4-FPh | CO | single bond | 2 | O | CH₂CH₂ | sub. 20 |
| 4791 | 4-Mor | 4-FPh | CO | single bond | 2 | O | CH₂CH₂ | sub. 20 |
| 4792 | 2-Thmor | 4-FPh | CO | single bond | 2 | O | CH₂CH₂ | sub. 20 |
| 4793 | 3-Thmor | 4-FPh | CO | single bond | 2 | O | CH₂CH₂ | sub. 20 |
| 4794 | 4-Thmor | 4-FPh | CO | single bond | 2 | O | CH₂CH₂ | sub. 20 |
| 4795 | 2-Piz | 4-FPh | CO | single bond | 2 | O | CH₂CH₂ | sub. 20 |
| 4796 | 3-Piz | 4-FPh | CO | single bond | 2 | O | CH₂CH₂ | sub. 20 |
| 4797 | 4-Piz | 4-FPh | CO | single bond | 2 | O | CH₂CH₂ | sub. 20 |
| 4798 | 2-Aze | 4-FPh | CO | single bond | 2 | O | CH₂CH₂ | sub. 20 |
| 4799 | 3-Aze | 4-FPh | CO | single bond | 2 | O | CH₂CH₂ | sub. 20 |
| 4800 | 4-Aze | 4-FPh | CO | single bond | 2 | O | CH₂CH₂ | sub. 20 |
| 4801 | cPr | 4-FPh | CO | single bond | 2 | O | CH₂CH₂ | sub. 21 |
| 4802 | cBu | 4-FPh | CO | single bond | 2 | O | CH₂CH₂ | sub. 21 |
| 4803 | cPn | 4-FPh | CO | single bond | 2 | O | CH₂CH₂ | sub. 21 |
| 4804 | cHex | 4-FPh | CO | single bond | 2 | O | CH₂CH₂ | sub. 21 |
| 4805 | cHep | 4-FPh | CO | single bond | 2 | O | CH₂CH₂ | sub. 21 |
| 4806 | 2-Pyrd | 4-FPh | CO | single bond | 2 | O | CH₂CH₂ | sub. 21 |
| 4807 | 3-Pyrd | 4-FPh | CO | single bond | 2 | O | CH₂CH₂ | sub. 21 |
| 4808 | 4-Oxa | 4-FPh | CO | single bond | 2 | O | CH₂CH₂ | sub. 21 |
| 4809 | 5-Oxa | 4-FPh | CO | single bond | 2 | O | CH₂CH₂ | sub. 21 |
| 4810 | 4-Thi | 4-FPh | CO | single bond | 2 | O | CH₂CH₂ | sub. 21 |
| 4811 | 5-Thi | 4-FPh | CO | single bond | 2 | O | CH₂CH₂ | sub. 21 |
| 4812 | 4-OOxa | 4-FPh | CO | single bond | 2 | O | CH₂CH₂ | sub. 21 |
| 4813 | 5-OOxa | 4-FPh | CO | single bond | 2 | O | CH₂CH₂ | sub. 21 |
| 4814 | 4-OThi | 4-FPh | CO | single bond | 2 | O | CH₂CH₂ | sub. 21 |
| 4815 | 5-OThi | 4-FPh | CO | single bond | 2 | O | CH₂CH₂ | sub. 21 |
| 4816 | 2-Pip | 4-FPh | CO | single bond | 2 | O | CH₂CH₂ | sub. 21 |
| 4817 | 3-Pip | 4-FPh | CO | single bond | 2 | O | CH₂CH₂ | sub. 21 |
| 4818 | 4-Pip | 4-FPh | CO | single bond | 2 | O | CH₂CH₂ | sub. 21 |
| 4819 | 2-Mor | 4-FPh | CO | single bond | 2 | O | CH₂CH₂ | sub. 21 |
| 4820 | 3-Mor | 4-FPh | CO | single bond | 2 | O | CH₂CH₂ | sub. 21 |
| 4821 | 4-Mor | 4-FPh | CO | single bond | 2 | O | CH₂CH₂ | sub. 21 |
| 4822 | 2-Thmor | 4-FPh | CO | single bond | 2 | O | CH₂CH₂ | sub. 21 |
| 4823 | 3-Thmor | 4-FPh | CO | single bond | 2 | O | CH₂CH₂ | sub. 21 |
| 4824 | 4-Thmor | 4-FPh | CO | single bond | 2 | O | CH₂CH₂ | sub. 21 |
| 4825 | 2-Piz | 4-FPh | CO | single bond | 2 | O | CH₂CH₂ | sub. 21 |
| 4826 | 3-Piz | 4-FPh | CO | single bond | 2 | O | CH₂CH₂ | sub. 21 |
| 4827 | 4-Piz | 4-FPh | CO | single bond | 2 | O | CH₂CH₂ | sub. 21 |
| 4828 | 2-Aze | 4-FPh | CO | single bond | 2 | O | CH₂CH₂ | sub. 21 |
| 4829 | 3-Aze | 4-FPh | CO | single bond | 2 | O | CH₂CH₂ | sub. 21 |
| 4830 | 4-Aze | 4-FPh | CO | single bond | 2 | O | CH₂CH₂ | sub. 21 |
| 4831 | cPr | 4-FPh | CO | single bond | 2 | O | CH₂CH₂ | sub. 22 |
| 4832 | cBu | 4-FPh | CO | single bond | 2 | O | CH₂CH₂ | sub. 22 |
| 4833 | cPn | 4-FPh | CO | single bond | 2 | O | CH₂CH₂ | sub. 22 |
| 4834 | cHex | 4-FPh | CO | single bond | 2 | O | CH₂CH₂ | sub. 22 |
| 4835 | cHep | 4-FPh | CO | single bond | 2 | O | CH₂CH₂ | sub. 22 |
| 4836 | 2-Pyrd | 4-FPh | CO | single bond | 2 | O | CH₂CH₂ | sub. 22 |
| 4837 | 3-Pyrd | 4-FPh | CO | single bond | 2 | O | CH₂CH₂ | sub. 22 |
| 4838 | 4-Oxa | 4-FPh | CO | single bond | 2 | O | CH₂CH₂ | sub. 22 |
| 4839 | 5-Oxa | 4-FPh | CO | single bond | 2 | O | CH₂CH₂ | sub. 22 |
| 4840 | 4-Thi | 4-FPh | CO | single bond | 2 | O | CH₂CH₂ | sub. 22 |
| 4841 | 5-Thi | 4-FPh | CO | single bond | 2 | O | CH₂CH₂ | sub. 22 |
| 4842 | 4-OOxa | 4-FPh | CO | single bond | 2 | O | CH₂CH₂ | sub. 22 |
| 4843 | 5-OOxa | 4-FPh | CO | single bond | 2 | O | CH₂CH₂ | sub. 22 |
| 4844 | 4-OThi | 4-FPh | CO | single bond | 2 | O | CH₂CH₂ | sub. 22 |

TABLE 1-continued

| Exemplification compound number | R¹ | R² | A | B | N | D | G | Q |
|---|---|---|---|---|---|---|---|---|
| 4845 | 5-OThi | 4-FPh | CO | single bond | 2 | O | $CH_2CH_2$ | sub. 22 |
| 4846 | 2-Pip | 4-FPh | CO | single bond | 2 | O | $CH_2CH_2$ | sub. 22 |
| 4847 | 3-Pip | 4-FPh | CO | single bond | 2 | O | $CH_2CH_2$ | sub. 22 |
| 4848 | 4-Pip | 4-FPh | CO | single bond | 2 | O | $CH_2CH_2$ | sub. 22 |
| 4849 | 2-Mor | 4-FPh | CO | single bond | 2 | O | $CH_2CH_2$ | sub. 22 |
| 4850 | 3-Mor | 4-FPh | CO | single bond | 2 | O | $CH_2CH_2$ | sub. 22 |
| 4851 | 4-Mor | 4-FPh | CO | single bond | 2 | O | $CH_2CH_2$ | sub. 22 |
| 4852 | 2-Thmor | 4-FPh | CO | single bond | 2 | O | $CH_2CH_2$ | sub. 22 |
| 4853 | 3-Thmor | 4-FPh | CO | single bond | 2 | O | $CH_2CH_2$ | sub. 22 |
| 4854 | 4-Thmor | 4-FPh | CO | single bond | 2 | O | $CH_2CH_2$ | sub. 22 |
| 4855 | 2-Piz | 4-FPh | CO | single bond | 2 | O | $CH_2CH_2$ | sub. 22 |
| 4856 | 3-Piz | 4-FPh | CO | single bond | 2 | O | $CH_2CH_2$ | sub. 22 |
| 4857 | 4-Piz | 4-FPh | CO | single bond | 2 | O | $CH_2CH_2$ | sub. 22 |
| 4858 | 2-Aze | 4-FPh | CO | single bond | 2 | O | $CH_2CH_2$ | sub. 22 |
| 4859 | 3-Aze | 4-FPh | CO | single bond | 2 | O | $CH_2CH_2$ | sub. 22 |
| 4860 | 4-Aze | 4-FPh | CO | single bond | 2 | O | $CH_2CH_2$ | sub. 22 |
| 4861 | cPr | 4-FPh | CO | single bond | 2 | O | $CH_2CH_2$ | sub. 23 |
| 4862 | cBu | 4-FPh | CO | single bond | 2 | O | $CH_2CH_2$ | sub. 23 |
| 4863 | cPn | 4-FPh | CO | single bond | 2 | O | $CH_2CH_2$ | sub. 23 |
| 4864 | cHex | 4-FPh | CO | single bond | 2 | O | $CH_2CH_2$ | sub. 23 |
| 4865 | cHep | 4-FPh | CO | single bond | 2 | O | $CH_2CH_2$ | sub. 23 |
| 4866 | 2-Pyrd | 4-FPh | CO | single bond | 2 | O | $CH_2CH_2$ | sub. 23 |
| 4867 | 3-Pyrd | 4-FPh | CO | single bond | 2 | O | $CH_2CH_2$ | sub. 23 |
| 4868 | 4-Oxa | 4-FPh | CO | single bond | 2 | O | $CH_2CH_2$ | sub. 23 |
| 4869 | 5-Oxa | 4-FPh | CO | single bond | 2 | O | $CH_2CH_2$ | sub. 23 |
| 4870 | 4-Thi | 4-FPh | CO | single bond | 2 | O | $CH_2CH_2$ | sub. 23 |
| 4871 | 5-Thi | 4-FPh | CO | single bond | 2 | O | $CH_2CH_2$ | sub. 23 |
| 4872 | 4-OOxa | 4-FPh | CO | single bond | 2 | O | $CH_2CH_2$ | sub. 23 |
| 4873 | 5-OOxa | 4-FPh | CO | single bond | 2 | O | $CH_2CH_2$ | sub. 23 |
| 4874 | 4-OThi | 4-FPh | CO | single bond | 2 | O | $CH_2CH_2$ | sub. 23 |
| 4875 | 5-OThi | 4-FPh | CO | single bond | 2 | O | $CH_2CH_2$ | sub. 23 |
| 4876 | 2-Pip | 4-FPh | CO | single bond | 2 | O | $CH_2CH_2$ | sub. 23 |
| 4877 | 3-Pip | 4-FPh | CO | single bond | 2 | O | $CH_2CH_2$ | sub. 23 |
| 4878 | 4-Pip | 4-FPh | CO | single bond | 2 | O | $CH_2CH_2$ | sub. 23 |
| 4879 | 2-Mor | 4-FPh | CO | single bond | 2 | O | $CH_2CH_2$ | sub. 23 |
| 4880 | 3-Mor | 4-FPh | CO | single bond | 2 | O | $CH_2CH_2$ | sub. 23 |
| 4881 | 4-Mor | 4-FPh | CO | single bond | 2 | O | $CH_2CH_2$ | sub. 23 |
| 4882 | 2-Thmor | 4-FPh | CO | single bond | 2 | O | $CH_2CH_2$ | sub. 23 |
| 4883 | 3-Thmor | 4-FPh | CO | single bond | 2 | O | $CH_2CH_2$ | sub. 23 |
| 4884 | 4-Thmor | 4-FPh | CO | single bond | 2 | O | $CH_2CH_2$ | sub. 23 |
| 4885 | 2-Piz | 4-FPh | CO | single bond | 2 | O | $CH_2CH_2$ | sub. 23 |
| 4886 | 3-Piz | 4-FPh | CO | single bond | 2 | O | $CH_2CH_2$ | sub. 23 |
| 4887 | 4-Piz | 4-FPh | CO | single bond | 2 | O | $CH_2CH_2$ | sub. 23 |
| 4888 | 2-Aze | 4-FPh | CO | single bond | 2 | O | $CH_2CH_2$ | sub. 23 |
| 4889 | 3-Aze | 4-FPh | CO | single bond | 2 | O | $CH_2CH_2$ | sub. 23 |
| 4890 | 4-Aze | 4-FPh | CO | single bond | 2 | O | $CH_2CH_2$ | sub. 23 |
| 4891 | cPr | 4-FPh | CO | single bond | 2 | O | $CH_2CH_2$ | sub. 24 |
| 4892 | cBu | 4-FPh | CO | single bond | 2 | O | $CH_2CH_2$ | sub. 24 |
| 4893 | cPn | 4-FPh | CO | single bond | 2 | O | $CH_2CH_2$ | sub. 24 |
| 4894 | cHex | 4-FPh | CO | single bond | 2 | O | $CH_2CH_2$ | sub. 24 |
| 4895 | cHep | 4-FPh | CO | single bond | 2 | O | $CH_2CH_2$ | sub. 24 |
| 4896 | 2-Pyrd | 4-FPh | CO | single bond | 2 | O | $CH_2CH_2$ | sub. 24 |
| 4897 | 3-Pyrd | 4-FPh | CO | single bond | 2 | O | $CH_2CH_2$ | sub. 24 |
| 4898 | 4-Oxa | 4-FPh | CO | single bond | 2 | O | $CH_2CH_2$ | sub. 24 |
| 4899 | 5-Oxa | 4-FPh | CO | single bond | 2 | O | $CH_2CH_2$ | sub. 24 |
| 4900 | 4-Thi | 4-FPh | CO | single bond | 2 | O | $CH_2CH_2$ | sub. 24 |
| 4901 | 5-Thi | 4-FPh | CO | single bond | 2 | O | $CH_2CH_2$ | sub. 24 |
| 4902 | 4-OOxa | 4-FPh | CO | single bond | 2 | O | $CH_2CH_2$ | sub. 24 |
| 4903 | 5-OOxa | 4-FPh | CO | single bond | 2 | O | $CH_2CH_2$ | sub. 24 |
| 4904 | 4-OThi | 4-FPh | CO | single bond | 2 | O | $CH_2CH_2$ | sub. 24 |
| 4905 | 5-OThi | 4-FPh | CO | single bond | 2 | O | $CH_2CH_2$ | sub. 24 |
| 4906 | 2-Pip | 4-FPh | CO | single bond | 2 | O | $CH_2CH_2$ | sub. 24 |
| 4907 | 3-Pip | 4-FPh | CO | single bond | 2 | O | $CH_2CH_2$ | sub. 24 |
| 4908 | 4-Pip | 4-FPh | CO | single bond | 2 | O | $CH_2CH_2$ | sub. 24 |
| 4909 | 2-Mor | 4-FPh | CO | single bond | 2 | O | $CH_2CH_2$ | sub. 24 |
| 4910 | 3-Mor | 4-FPh | CO | single bond | 2 | O | $CH_2CH_2$ | sub. 24 |
| 4911 | 4-Mor | 4-FPh | CO | single bond | 2 | O | $CH_2CH_2$ | sub. 24 |
| 4912 | 2-Thmor | 4-FPh | CO | single bond | 2 | O | $CH_2CH_2$ | sub. 24 |
| 4913 | 3-Thmor | 4-FPh | CO | single bond | 2 | O | $CH_2CH_2$ | sub. 24 |
| 4914 | 4-Thmor | 4-FPh | CO | single bond | 2 | O | $CH_2CH_2$ | sub. 24 |
| 4915 | 2-Piz | 4-FPh | CO | single bond | 2 | O | $CH_2CH_2$ | sub. 24 |
| 4916 | 3-Piz | 4-FPh | CO | single bond | 2 | O | $CH_2CH_2$ | sub. 24 |
| 4917 | 4-Piz | 4-FPh | CO | single bond | 2 | O | $CH_2CH_2$ | sub. 24 |
| 4918 | 2-Aze | 4-FPh | CO | single bond | 2 | O | $CH_2CH_2$ | sub. 24 |
| 4919 | 3-Aze | 4-FPh | CO | single bond | 2 | O | $CH_2CH_2$ | sub. 24 |
| 4920 | 4-Aze | 4-FPh | CO | single bond | 2 | O | $CH_2CH_2$ | sub. 24 |

TABLE 1-continued

| Exemplification compound number | R¹ | R² | A | B | N | D | G | Q |
|---|---|---|---|---|---|---|---|---|
| 4921 | cPr | 4-FPh | CO | single bond | 2 | O | $CH_2CH_2$ | sub. 25 |
| 4922 | cBu | 4-FPh | CO | single bond | 2 | O | $CH_2CH_2$ | sub. 25 |
| 4923 | cPn | 4-FPh | CO | single bond | 2 | O | $CH_2CH_2$ | sub. 25 |
| 4924 | cHex | 4-FPh | CO | single bond | 2 | O | $CH_2CH_2$ | sub. 25 |
| 4925 | cHep | 4-FPh | CO | single bond | 2 | O | $CH_2CH_2$ | sub. 25 |
| 4926 | 2-Pyrd | 4-FPh | CO | single bond | 2 | O | $CH_2CH_2$ | sub. 25 |
| 4927 | 3-Pyrd | 4-FPh | CO | single bond | 2 | O | $CH_2CH_2$ | sub. 25 |
| 4928 | 4-Oxa | 4-FPh | CO | single bond | 2 | O | $CH_2CH_2$ | sub. 25 |
| 4929 | 5-Oxa | 4-FPh | CO | single bond | 2 | O | $CH_2CH_2$ | sub. 25 |
| 4930 | 4-Thi | 4-FPh | CO | single bond | 2 | O | $CH_2CH_2$ | sub. 25 |
| 4931 | 5-Thi | 4-FPh | CO | single bond | 2 | O | $CH_2CH_2$ | sub. 25 |
| 4932 | 4-OOxa | 4-FPh | CO | single bond | 2 | O | $CH_2CH_2$ | sub. 25 |
| 4933 | 5-OOxa | 4-FPh | CO | single bond | 2 | O | $CH_2CH_2$ | sub. 25 |
| 4934 | 4-OThi | 4-FPh | CO | single bond | 2 | O | $CH_2CH_2$ | sub. 25 |
| 4935 | 5-OThi | 4-FPh | CO | single bond | 2 | O | $CH_2CH_2$ | sub. 25 |
| 4936 | 2-Pip | 4-FPh | CO | single bond | 2 | O | $CH_2CH_2$ | sub. 25 |
| 4937 | 3-Pip | 4-FPh | CO | single bond | 2 | O | $CH_2CH_2$ | sub. 25 |
| 4938 | 4-Pip | 4-FPh | CO | single bond | 2 | O | $CH_2CH_2$ | sub. 25 |
| 4939 | 2-Mor | 4-FPh | CO | single bond | 2 | O | $CH_2CH_2$ | sub. 25 |
| 4940 | 3-Mor | 4-FPh | CO | single bond | 2 | O | $CH_2CH_2$ | sub. 25 |
| 4941 | 4-Mor | 4-FPh | CO | single bond | 2 | O | $CH_2CH_2$ | sub. 25 |
| 4942 | 2-Thmor | 4-FPh | CO | single bond | 2 | O | $CH_2CH_2$ | sub. 25 |
| 4943 | 3-Thmor | 4-FPh | CO | single bond | 2 | O | $CH_2CH_2$ | sub. 25 |
| 4944 | 4-Thmor | 4-FPh | CO | single bond | 2 | O | $CH_2CH_2$ | sub. 25 |
| 4945 | 2-Piz | 4-FPh | CO | single bond | 2 | O | $CH_2CH_2$ | sub. 25 |
| 4946 | 3-Piz | 4-FPh | CO | single bond | 2 | O | $CH_2CH_2$ | sub. 25 |
| 4947 | 4-Piz | 4-FPh | CO | single bond | 2 | O | $CH_2CH_2$ | sub. 25 |
| 4948 | 2-Aze | 4-FPh | CO | single bond | 2 | O | $CH_2CH_2$ | sub. 25 |
| 4949 | 3-Aze | 4-FPh | CO | single bond | 2 | O | $CH_2CH_2$ | sub. 25 |
| 4950 | 4-Aze | 4-FPh | CO | single bond | 2 | O | $CH_2CH_2$ | sub. 25 |
| 4951 | cPr | 4-FPh | CO | single bond | 2 | O | $CH_2CH_2$ | sub. 26 |
| 4952 | cBu | 4-FPh | CO | single bond | 2 | O | $CH_2CH_2$ | sub. 26 |
| 4953 | cPn | 4-FPh | CO | single bond | 2 | O | $CH_2CH_2$ | sub. 26 |
| 4954 | cHex | 4-FPh | CO | single bond | 2 | O | $CH_2CH_2$ | sub. 26 |
| 4955 | cHep | 4-FPh | CO | single bond | 2 | O | $CH_2CH_2$ | sub. 26 |
| 4956 | 2-Pyrd | 4-FPh | CO | single bond | 2 | O | $CH_2CH_2$ | sub. 26 |
| 4957 | 3-Pyrd | 4-FPh | CO | single bond | 2 | O | $CH_2CH_2$ | sub. 26 |
| 4958 | 4-Oxa | 4-FPh | CO | single bond | 2 | O | $CH_2CH_2$ | sub. 26 |
| 4959 | 5-Oxa | 4-FPh | CO | single bond | 2 | O | $CH_2CH_2$ | sub. 26 |
| 4960 | 4-Thi | 4-FPh | CO | single bond | 2 | O | $CH_2CH_2$ | sub. 26 |
| 4961 | 5-Thi | 4-FPh | CO | single bond | 2 | O | $CH_2CH_2$ | sub. 26 |
| 4962 | 4-OOxa | 4-FPh | CO | single bond | 2 | O | $CH_2CH_2$ | sub. 26 |
| 4963 | 5-OOxa | 4-FPh | CO | single bond | 2 | O | $CH_2CH_2$ | sub. 26 |
| 4964 | 4-OThi | 4-FPh | CO | single bond | 2 | O | $CH_2CH_2$ | sub. 26 |
| 4965 | 5-OThi | 4-FPh | CO | single bond | 2 | O | $CH_2CH_2$ | sub. 26 |
| 4966 | 2-Pip | 4-FPh | CO | single bond | 2 | O | $CH_2CH_2$ | sub. 26 |
| 4967 | 3-Pip | 4-FPh | CO | single bond | 2 | O | $CH_2CH_2$ | sub. 26 |
| 4968 | 4-Pip | 4-FPh | CO | single bond | 2 | O | $CH_2CH_2$ | sub. 26 |
| 4969 | 2-Mor | 4-FPh | CO | single bond | 2 | O | $CH_2CH_2$ | sub. 26 |
| 4970 | 3-Mor | 4-FPh | CO | single bond | 2 | O | $CH_2CH_2$ | sub. 26 |
| 4971 | 4-Mor | 4-FPh | CO | single bond | 2 | O | $CH_2CH_2$ | sub. 26 |
| 4972 | 2-Thmor | 4-FPh | CO | single bond | 2 | O | $CH_2CH_2$ | sub. 26 |
| 4973 | 3-Thmor | 4-FPh | CO | single bond | 2 | O | $CH_2CH_2$ | sub. 26 |
| 4974 | 4-Thmor | 4-FPh | CO | single bond | 2 | O | $CH_2CH_2$ | sub. 26 |
| 4975 | 2-Piz | 4-FPh | CO | single bond | 2 | O | $CH_2CH_2$ | sub. 26 |
| 4976 | 3-Piz | 4-FPh | CO | single bond | 2 | O | $CH_2CH_2$ | sub. 26 |
| 4977 | 4-Piz | 4-FPh | CO | single bond | 2 | O | $CH_2CH_2$ | sub. 26 |
| 4978 | 2-Aze | 4-FPh | CO | single bond | 2 | O | $CH_2CH_2$ | sub. 26 |
| 4979 | 3-Aze | 4-FPh | CO | single bond | 2 | O | $CH_2CH_2$ | sub. 26 |
| 4980 | 4-Aze | 4-FPh | CO | single bond | 2 | O | $CH_2CH_2$ | sub. 26 |
| 4981 | cPr | 4-FPh | CO | single bond | 2 | O | $CH_2CH_2$ | sub. 27 |
| 4982 | cBu | 4-FPh | CO | single bond | 2 | O | $CH_2CH_2$ | sub. 27 |
| 4983 | cPn | 4-FPh | CO | single bond | 2 | O | $CH_2CH_2$ | sub. 27 |
| 4984 | cHex | 4-FPh | CO | single bond | 2 | O | $CH_2CH_2$ | sub. 27 |
| 4985 | cHep | 4-FPh | CO | single bond | 2 | O | $CH_2CH_2$ | sub. 27 |
| 4986 | 2-Pyrd | 4-FPh | CO | single bond | 2 | O | $CH_2CH_2$ | sub. 27 |
| 4987 | 3-Pyrd | 4-FPh | CO | single bond | 2 | O | $CH_2CH_2$ | sub. 27 |
| 4988 | 4-Oxa | 4-FPh | CO | single bond | 2 | O | $CH_2CH_2$ | sub. 27 |
| 4989 | 5-Oxa | 4-FPh | CO | single bond | 2 | O | $CH_2CH_2$ | sub. 27 |
| 4990 | 4-Thi | 4-FPh | CO | single bond | 2 | O | $CH_2CH_2$ | sub. 27 |
| 4991 | 5-Thi | 4-FPh | CO | single bond | 2 | O | $CH_2CH_2$ | sub. 27 |
| 4992 | 4-OOxa | 4-FPh | CO | single bond | 2 | O | $CH_2CH_2$ | sub. 27 |
| 4993 | 5-OOxa | 4-FPh | CO | single bond | 2 | O | $CH_2CH_2$ | sub. 27 |
| 4994 | 4-OThi | 4-FPh | CO | single bond | 2 | O | $CH_2CH_2$ | sub. 27 |
| 4995 | 5-OThi | 4-FPh | CO | single bond | 2 | O | $CH_2CH_2$ | sub. 27 |
| 4996 | 2-Pip | 4-FPh | CO | single bond | 2 | O | $CH_2CH_2$ | sub. 27 |

TABLE 1-continued

| Exemplification compound number | R¹ | R² | A | B | N | D | G | Q |
|---|---|---|---|---|---|---|---|---|
| 4997 | 3-Pip | 4-FPh | CO | single bond | 2 | O | $CH_2CH_2$ | sub. 27 |
| 4998 | 4-Pip | 4-FPh | CO | single bond | 2 | O | $CH_2CH_2$ | sub. 27 |
| 4999 | 2-Mor | 4-FPh | CO | single bond | 2 | O | $CH_2CH_2$ | sub. 27 |
| 5000 | 3-Mor | 4-FPh | CO | single bond | 2 | O | $CH_2CH_2$ | sub. 27 |
| 5001 | 4-Mor | 4-FPh | CO | single bond | 2 | O | $CH_2CH_2$ | sub. 27 |
| 5002 | 2-Thmor | 4-FPh | CO | single bond | 2 | O | $CH_2CH_2$ | sub. 27 |
| 5003 | 3-Thmor | 4-FPh | CO | single bond | 2 | O | $CH_2CH_2$ | sub. 27 |
| 5004 | 4-Thmor | 4-FPh | CO | single bond | 2 | O | $CH_2CH_2$ | sub. 27 |
| 5005 | 2-Piz | 4-FPh | CO | single bond | 2 | O | $CH_2CH_2$ | sub. 27 |
| 5006 | 3-Piz | 4-FPh | CO | single bond | 2 | O | $CH_2CH_2$ | sub. 27 |
| 5007 | 4-Piz | 4-FPh | CO | single bond | 2 | O | $CH_2CH_2$ | sub. 27 |
| 5008 | 2-Aze | 4-FPh | CO | single bond | 2 | O | $CH_2CH_2$ | sub. 27 |
| 5009 | 3-Aze | 4-FPh | CO | single bond | 2 | O | $CH_2CH_2$ | sub. 27 |
| 5010 | 4-Aze | 4-FPh | CO | single bond | 2 | O | $CH_2CH_2$ | sub. 27 |
| 5011 | cPr | 4-FPh | CO | single bond | 2 | O | $CH_2CH_2$ | sub. 28 |
| 5012 | cBu | 4-FPh | CO | single bond | 2 | O | $CH_2CH_2$ | sub. 28 |
| 5013 | cPn | 4-FPh | CO | single bond | 2 | O | $CH_2CH_2$ | sub. 28 |
| 5014 | cHex | 4-FPh | CO | single bond | 2 | O | $CH_2CH_2$ | sub. 28 |
| 5015 | cHep | 4-FPh | CO | single bond | 2 | O | $CH_2CH_2$ | sub. 28 |
| 5016 | 2-Pyrd | 4-FPh | CO | single bond | 2 | O | $CH_2CH_2$ | sub. 28 |
| 5017 | 3-Pyrd | 4-FPh | CO | single bond | 2 | O | $CH_2CH_2$ | sub. 28 |
| 5018 | 4-Oxa | 4-FPh | CO | single bond | 2 | O | $CH_2CH_2$ | sub. 28 |
| 5019 | 5-Oxa | 4-FPh | CO | single bond | 2 | O | $CH_2CH_2$ | sub. 28 |
| 5020 | 4-Thi | 4-FPh | CO | single bond | 2 | O | $CH_2CH_2$ | sub. 28 |
| 5021 | 5-Thi | 4-FPh | CO | single bond | 2 | O | $CH_2CH_2$ | sub. 28 |
| 5022 | 4-OOxa | 4-FPh | CO | single bond | 2 | O | $CH_2CH_2$ | sub. 28 |
| 5023 | 5-OOxa | 4-FPh | CO | single bond | 2 | O | $CH_2CH_2$ | sub. 28 |
| 5024 | 4-OThi | 4-FPh | CO | single bond | 2 | O | $CH_2CH_2$ | sub. 28 |
| 5025 | 5-OThi | 4-FPh | CO | single bond | 2 | O | $CH_2CH_2$ | sub. 28 |
| 5026 | 2-Pip | 4-FPh | CO | single bond | 2 | O | $CH_2CH_2$ | sub. 28 |
| 5027 | 3-Pip | 4-FPh | CO | single bond | 2 | O | $CH_2CH_2$ | sub. 28 |
| 5028 | 4-Pip | 4-FPh | CO | single bond | 2 | O | $CH_2CH_2$ | sub. 28 |
| 5029 | 2-Mor | 4-FPh | CO | single bond | 2 | O | $CH_2CH_2$ | sub. 28 |
| 5030 | 3-Mor | 4-FPh | CO | single bond | 2 | O | $CH_2CH_2$ | sub. 28 |
| 5031 | 4-Mor | 4-FPh | CO | single bond | 2 | O | $CH_2CH_2$ | sub. 28 |
| 5032 | 2-Thmor | 4-FPh | CO | single bond | 2 | O | $CH_2CH_2$ | sub. 28 |
| 5033 | 3-Thmor | 4-FPh | CO | single bond | 2 | O | $CH_2CH_2$ | sub. 28 |
| 5034 | 4-Thmor | 4-FPh | CO | single bond | 2 | O | $CH_2CH_2$ | sub. 28 |
| 5035 | 2-Piz | 4-FPh | CO | single bond | 2 | O | $CH_2CH_2$ | sub. 28 |
| 5036 | 3-Piz | 4-FPh | CO | single bond | 2 | O | $CH_2CH_2$ | sub. 28 |
| 5037 | 4-Piz | 4-FPh | CO | single bond | 2 | O | $CH_2CH_2$ | sub. 28 |
| 5038 | 2-Aze | 4-FPh | CO | single bond | 2 | O | $CH_2CH_2$ | sub. 28 |
| 5039 | 3-Aze | 4-FPh | CO | single bond | 2 | O | $CH_2CH_2$ | sub. 28 |
| 5040 | 4-Aze | 4-FPh | CO | single bond | 2 | O | $CH_2CH_2$ | sub. 28 |
| 5041 | cPr | 4-FPh | CO | single bond | 2 | O | $CH_2CH_2$ | sub. 29 |
| 5042 | cBu | 4-FPh | CO | single bond | 2 | O | $CH_2CH_2$ | sub. 29 |
| 5043 | cPn | 4-FPh | CO | single bond | 2 | O | $CH_2CH_2$ | sub. 29 |
| 5044 | cHex | 4-FPh | CO | single bond | 2 | O | $CH_2CH_2$ | sub. 29 |
| 5045 | cHep | 4-FPh | CO | single bond | 2 | O | $CH_2CH_2$ | sub. 29 |
| 5046 | 2-Pyrd | 4-FPh | CO | single bond | 2 | O | $CH_2CH_2$ | sub. 29 |
| 5047 | 3-Pyrd | 4-FPh | CO | single bond | 2 | O | $CH_2CH_2$ | sub. 29 |
| 5048 | 4-Oxa | 4-FPh | CO | single bond | 2 | O | $CH_2CH_2$ | sub. 29 |
| 5049 | 5-Oxa | 4-FPh | CO | single bond | 2 | O | $CH_2CH_2$ | sub. 29 |
| 5050 | 4-Thi | 4-FPh | CO | single bond | 2 | O | $CH_2CH_2$ | sub. 29 |
| 5051 | 5-Thi | 4-FPh | CO | single bond | 2 | O | $CH_2CH_2$ | sub. 29 |
| 5052 | 4-OOxa | 4-FPh | CO | single bond | 2 | O | $CH_2CH_2$ | sub. 29 |
| 5053 | 5-OOxa | 4-FPh | CO | single bond | 2 | O | $CH_2CH_2$ | sub. 29 |
| 5054 | 4-OThi | 4-FPh | CO | single bond | 2 | O | $CH_2CH_2$ | sub. 29 |
| 5055 | 5-OThi | 4-FPh | CO | single bond | 2 | O | $CH_2CH_2$ | sub. 29 |
| 5056 | 2-Pip | 4-FPh | CO | single bond | 2 | O | $CH_2CH_2$ | sub. 29 |
| 5057 | 3-Pip | 4-FPh | CO | single bond | 2 | O | $CH_2CH_2$ | sub. 29 |
| 5058 | 4-Pip | 4-FPh | CO | single bond | 2 | O | $CH_2CH_2$ | sub. 29 |
| 5059 | 2-Mor | 4-FPh | CO | single bond | 2 | O | $CH_2CH_2$ | sub. 29 |
| 5060 | 3-Mor | 4-FPh | CO | single bond | 2 | O | $CH_2CH_2$ | sub. 29 |
| 5061 | 4-Mor | 4-FPh | CO | single bond | 2 | O | $CH_2CH_2$ | sub. 29 |
| 5062 | 2-Thmor | 4-FPh | CO | single bond | 2 | O | $CH_2CH_2$ | sub. 29 |
| 5063 | 3-Thmor | 4-FPh | CO | single bond | 2 | O | $CH_2CH_2$ | sub. 29 |
| 5064 | 4-Thmor | 4-FPh | CO | single bond | 2 | O | $CH_2CH_2$ | sub. 29 |
| 5065 | 2-Piz | 4-FPh | CO | single bond | 2 | O | $CH_2CH_2$ | sub. 29 |
| 5066 | 3-Piz | 4-FPh | CO | single bond | 2 | O | $CH_2CH_2$ | sub. 29 |
| 5067 | 4-Piz | 4-FPh | CO | single bond | 2 | O | $CH_2CH_2$ | sub. 29 |
| 5068 | 2-Aze | 4-FPh | CO | single bond | 2 | O | $CH_2CH_2$ | sub. 29 |
| 5069 | 3-Aze | 4-FPh | CO | single bond | 2 | O | $CH_2CH_2$ | sub. 29 |
| 5070 | 4-Aze | 4-FPh | CO | single bond | 2 | O | $CH_2CH_2$ | sub. 29 |
| 5071 | cPr | 4-FPh | CO | single bond | 2 | O | $CH_2CH_2$ | sub. 30 |
| 5072 | cBu | 4-FPh | CO | single bond | 2 | O | $CH_2CH_2$ | sub. 30 |

TABLE 1-continued

| Exemplification compound number | R¹ | R² | A | B | N | D | G | Q |
|---|---|---|---|---|---|---|---|---|
| 5073 | cPn | 4-FPh | CO | single bond | 2 | O | $CH_2CH_2$ | sub. 30 |
| 5074 | cHex | 4-FPh | CO | single bond | 2 | O | $CH_2CH_2$ | sub. 30 |
| 5075 | cHep | 4-FPh | CO | single bond | 2 | O | $CH_2CH_2$ | sub. 30 |
| 5076 | 2-Pyrd | 4-FPh | CO | single bond | 2 | O | $CH_2CH_2$ | sub. 30 |
| 5077 | 3-Pyrd | 4-FPh | CO | single bond | 2 | O | $CH_2CH_2$ | sub. 30 |
| 5078 | 4-Oxa | 4-FPh | CO | single bond | 2 | O | $CH_2CH_2$ | sub. 30 |
| 5079 | 5-Oxa | 4-FPh | CO | single bond | 2 | O | $CH_2CH_2$ | sub. 30 |
| 5080 | 4-Thi | 4-FPh | CO | single bond | 2 | O | $CH_2CH_2$ | sub. 30 |
| 5081 | 5-Thi | 4-FPh | CO | single bond | 2 | O | $CH_2CH_2$ | sub. 30 |
| 5082 | 4-OOxa | 4-FPh | CO | single bond | 2 | O | $CH_2CH_2$ | sub. 30 |
| 5083 | 5-OOxa | 4-FPh | CO | single bond | 2 | O | $CH_2CH_2$ | sub. 30 |
| 5084 | 4-OThi | 4-FPh | CO | single bond | 2 | O | $CH_2CH_2$ | sub. 30 |
| 5085 | 5-OThi | 4-FPh | CO | single bond | 2 | O | $CH_2CH_2$ | sub. 30 |
| 5086 | 2-Pip | 4-FPh | CO | single bond | 2 | O | $CH_2CH_2$ | sub. 30 |
| 5087 | 3-Pip | 4-FPh | CO | single bond | 2 | O | $CH_2CH_2$ | sub. 30 |
| 5088 | 4-Pip | 4-FPh | CO | single bond | 2 | O | $CH_2CH_2$ | sub. 30 |
| 5089 | 2-Mor | 4-FPh | CO | single bond | 2 | O | $CH_2CH_2$ | sub. 30 |
| 5090 | 3-Mor | 4-FPh | CO | single bond | 2 | O | $CH_2CH_2$ | sub. 30 |
| 5091 | 4-Mor | 4-FPh | CO | single bond | 2 | O | $CH_2CH_2$ | sub. 30 |
| 5092 | 2-Thmor | 4-FPh | CO | single bond | 2 | O | $CH_2CH_2$ | sub. 30 |
| 5093 | 3-Thmor | 4-FPh | CO | single bond | 2 | O | $CH_2CH_2$ | sub. 30 |
| 5094 | 4-Thmor | 4-FPh | CO | single bond | 2 | O | $CH_2CH_2$ | sub. 30 |
| 5095 | 2-Piz | 4-FPh | CO | single bond | 2 | O | $CH_2CH_2$ | sub. 30 |
| 5096 | 3-Piz | 4-FPh | CO | single bond | 2 | O | $CH_2CH_2$ | sub. 30 |
| 5097 | 4-Piz | 4-FPh | CO | single bond | 2 | O | $CH_2CH_2$ | sub. 30 |
| 5098 | 2-Aze | 4-FPh | CO | single bond | 2 | O | $CH_2CH_2$ | sub. 30 |
| 5099 | 3-Aze | 4-FPh | CO | single bond | 2 | O | $CH_2CH_2$ | sub. 30 |
| 5100 | 4-Aze | 4-FPh | CO | single bond | 2 | O | $CH_2CH_2$ | sub. 30 |
| 5101 | cPr | 4-FPh | CO | single bond | 2 | O | $CH_2CH_2$ | sub. 31 |
| 5102 | cBu | 4-FPh | CO | single bond | 2 | O | $CH_2CH_2$ | sub. 31 |
| 5103 | cPn | 4-FPh | CO | single bond | 2 | O | $CH_2CH_2$ | sub. 31 |
| 5104 | cHex | 4-FPh | CO | single bond | 2 | O | $CH_2CH_2$ | sub. 31 |
| 5105 | cHep | 4-FPh | CO | single bond | 2 | O | $CH_2CH_2$ | sub. 31 |
| 5106 | 2-Pyrd | 4-FPh | CO | single bond | 2 | O | $CH_2CH_2$ | sub. 31 |
| 5107 | 3-Pyrd | 4-FPh | CO | single bond | 2 | O | $CH_2CH_2$ | sub. 31 |
| 5108 | 4-Oxa | 4-FPh | CO | single bond | 2 | O | $CH_2CH_2$ | sub. 31 |
| 5109 | 5-Oxa | 4-FPh | CO | single bond | 2 | O | $CH_2CH_2$ | sub. 31 |
| 5110 | 4-Thi | 4-FPh | CO | single bond | 2 | O | $CH_2CH_2$ | sub. 31 |
| 5111 | 5-Thi | 4-FPh | CO | single bond | 2 | O | $CH_2CH_2$ | sub. 31 |
| 5112 | 4-OOxa | 4-FPh | CO | single bond | 2 | O | $CH_2CH_2$ | sub. 31 |
| 5113 | 5-OOxa | 4-FPh | CO | single bond | 2 | O | $CH_2CH_2$ | sub. 31 |
| 5114 | 4-OThi | 4-FPh | CO | single bond | 2 | O | $CH_2CH_2$ | sub. 31 |
| 5115 | 5-OThi | 4-FPh | CO | single bond | 2 | O | $CH_2CH_2$ | sub. 31 |
| 5116 | 2-Pip | 4-FPh | CO | single bond | 2 | O | $CH_2CH_2$ | sub. 31 |
| 5117 | 3-Pip | 4-FPh | CO | single bond | 2 | O | $CH_2CH_2$ | sub. 31 |
| 5118 | 4-Pip | 4-FPh | CO | single bond | 2 | O | $CH_2CH_2$ | sub. 31 |
| 5119 | 2-Mor | 4-FPh | CO | single bond | 2 | O | $CH_2CH_2$ | sub. 31 |
| 5120 | 3-Mor | 4-FPh | CO | single bond | 2 | O | $CH_2CH_2$ | sub. 31 |
| 5121 | 4-Mor | 4-FPh | CO | single bond | 2 | O | $CH_2CH_2$ | sub. 31 |
| 5122 | 2-Thmor | 4-FPh | CO | single bond | 2 | O | $CH_2CH_2$ | sub. 31 |
| 5123 | 3-Thmor | 4-FPh | CO | single bond | 2 | O | $CH_2CH_2$ | sub. 31 |
| 5124 | 4-Thmor | 4-FPh | CO | single bond | 2 | O | $CH_2CH_2$ | sub. 31 |
| 5125 | 2-Piz | 4-FPh | CO | single bond | 2 | O | $CH_2CH_2$ | sub. 31 |
| 5126 | 3-Piz | 4-FPh | CO | single bond | 2 | O | $CH_2CH_2$ | sub. 31 |
| 5127 | 4-Piz | 4-FPh | CO | single bond | 2 | O | $CH_2CH_2$ | sub. 31 |
| 5128 | 2-Aze | 4-FPh | CO | single bond | 2 | O | $CH_2CH_2$ | sub. 31 |
| 5129 | 3-Aze | 4-FPh | CO | single bond | 2 | O | $CH_2CH_2$ | sub. 31 |
| 5130 | 4-Aze | 4-FPh | CO | single bond | 2 | O | $CH_2CH_2$ | sub. 31 |
| 5131 | cPr | 4-FPh | CO | single bond | 2 | O | $CH_2CH_2$ | sub. 32 |
| 5132 | cBu | 4-FPh | CO | single bond | 2 | O | $CH_2CH_2$ | sub. 32 |
| 5133 | cPn | 4-FPh | CO | single bond | 2 | O | $CH_2CH_2$ | sub. 32 |
| 5134 | cHex | 4-FPh | CO | single bond | 2 | O | $CH_2CH_2$ | sub. 32 |
| 5135 | cHep | 4-FPh | CO | single bond | 2 | O | $CH_2CH_2$ | sub. 32 |
| 5136 | 2-Pyrd | 4-FPh | CO | single bond | 2 | O | $CH_2CH_2$ | sub. 32 |
| 5137 | 3-Pyrd | 4-FPh | CO | single bond | 2 | O | $CH_2CH_2$ | sub. 32 |
| 5138 | 4-Oxa | 4-FPh | CO | single bond | 2 | O | $CH_2CH_2$ | sub. 32 |
| 5139 | 5-Oxa | 4-FPh | CO | single bond | 2 | O | $CH_2CH_2$ | sub. 32 |
| 5140 | 4-Thi | 4-FPh | CO | single bond | 2 | O | $CH_2CH_2$ | sub. 32 |
| 5141 | 5-Thi | 4-FPh | CO | single bond | 2 | O | $CH_2CH_2$ | sub. 32 |
| 5142 | 4-OOxa | 4-FPh | CO | single bond | 2 | O | $CH_2CH_2$ | sub. 32 |
| 5143 | 5-OOxa | 4-FPh | CO | single bond | 2 | O | $CH_2CH_2$ | sub. 32 |
| 5144 | 4-OThi | 4-FPh | CO | single bond | 2 | O | $CH_2CH_2$ | sub. 32 |
| 5145 | 5-OThi | 4-FPh | CO | single bond | 2 | O | $CH_2CH_2$ | sub. 32 |
| 5146 | 2-Pip | 4-FPh | CO | single bond | 2 | O | $CH_2CH_2$ | sub. 32 |
| 5147 | 3-Pip | 4-FPh | CO | single bond | 2 | O | $CH_2CH_2$ | sub. 32 |
| 5148 | 4-Pip | 4-FPh | CO | single bond | 2 | O | $CH_2CH_2$ | sub. 32 |

TABLE 1-continued

| Exemplification compound number | R¹ | R² | A | B | N | D | G | Q |
|---|---|---|---|---|---|---|---|---|
| 5149 | 2-Mor | 4-FPh | CO | single bond | 2 | O | CH₂CH₂ | sub. 32 |
| 5150 | 3-Mor | 4-FPh | CO | single bond | 2 | O | CH₂CH₂ | sub. 32 |
| 5151 | 4-Mor | 4-FPh | CO | single bond | 2 | O | CH₂CH₂ | sub. 32 |
| 5152 | 2-Thmor | 4-FPh | CO | single bond | 2 | O | CH₂CH₂ | sub. 32 |
| 5153 | 3-Thmor | 4-FPh | CO | single bond | 2 | O | CH₂CH₂ | sub. 32 |
| 5154 | 4-Thmor | 4-FPh | CO | single bond | 2 | O | CH₂CH₂ | sub. 32 |
| 5155 | 2-Piz | 4-FPh | CO | single bond | 2 | O | CH₂CH₂ | sub. 32 |
| 5156 | 3-Piz | 4-FPh | CO | single bond | 2 | O | CH₂CH₂ | sub. 32 |
| 5157 | 4-Piz | 4-FPh | CO | single bond | 2 | O | CH₂CH₂ | sub. 32 |
| 5158 | 2-Aze | 4-FPh | CO | single bond | 2 | O | CH₂CH₂ | sub. 32 |
| 5159 | 3-Aze | 4-FPh | CO | single bond | 2 | O | CH₂CH₂ | sub. 32 |
| 5160 | 4-Aze | 4-FPh | CO | single bond | 2 | O | CH₂CH₂ | sub. 32 |
| 5161 | cPr | 4-FPh | CO | single bond | 2 | O | CH₂CH₂ | sub. 33 |
| 5162 | cBu | 4-FPh | CO | single bond | 2 | O | CH₂CH₂ | sub. 33 |
| 5163 | cPn | 4-FPh | CO | single bond | 2 | O | CH₂CH₂ | sub. 33 |
| 5164 | cHex | 4-FPh | CO | single bond | 2 | O | CH₂CH₂ | sub. 33 |
| 5165 | cHep | 4-FPh | CO | single bond | 2 | O | CH₂CH₂ | sub. 33 |
| 5166 | 2-Pyrd | 4-FPh | CO | single bond | 2 | O | CH₂CH₂ | sub. 33 |
| 5167 | 3-Pyrd | 4-FPh | CO | single bond | 2 | O | CH₂CH₂ | sub. 33 |
| 5168 | 4-Oxa | 4-FPh | CO | single bond | 2 | O | CH₂CH₂ | sub. 33 |
| 5169 | 5-Oxa | 4-FPh | CO | single bond | 2 | O | CH₂CH₂ | sub. 33 |
| 5170 | 4-Thi | 4-FPh | CO | single bond | 2 | O | CH₂CH₂ | sub. 33 |
| 5171 | 5-Thi | 4-FPh | CO | single bond | 2 | O | CH₂CH₂ | sub. 33 |
| 5172 | 4-OOxa | 4-FPh | CO | single bond | 2 | O | CH₂CH₂ | sub. 33 |
| 5173 | 5-OOxa | 4-FPh | CO | single bond | 2 | O | CH₂CH₂ | sub. 33 |
| 5174 | 4-OThi | 4-FPh | CO | single bond | 2 | O | CH₂CH₂ | sub. 33 |
| 5175 | 5-OThi | 4-FPh | CO | single bond | 2 | O | CH₂CH₂ | sub. 33 |
| 5176 | 2-Pip | 4-FPh | CO | single bond | 2 | O | CH₂CH₂ | sub. 33 |
| 5177 | 3-Pip | 4-FPh | CO | single bond | 2 | O | CH₂CH₂ | sub. 33 |
| 5178 | 4-Pip | 4-FPh | CO | single bond | 2 | O | CH₂CH₂ | sub. 33 |
| 5179 | 2-Mor | 4-FPh | CO | single bond | 2 | O | CH₂CH₂ | sub. 33 |
| 5180 | 3-Mor | 4-FPh | CO | single bond | 2 | O | CH₂CH₂ | sub. 33 |
| 5181 | 4-Mor | 4-FPh | CO | single bond | 2 | O | CH₂CH₂ | sub. 33 |
| 5182 | 2-Thmor | 4-FPh | CO | single bond | 2 | O | CH₂CH₂ | sub. 33 |
| 5183 | 3-Thmor | 4-FPh | CO | single bond | 2 | O | CH₂CH₂ | sub. 33 |
| 5184 | 4-Thmor | 4-FPh | CO | single bond | 2 | O | CH₂CH₂ | sub. 33 |
| 5185 | 2-Piz | 4-FPh | CO | single bond | 2 | O | CH₂CH₂ | sub. 33 |
| 5186 | 3-Piz | 4-FPh | CO | single bond | 2 | O | CH₂CH₂ | sub. 33 |
| 5187 | 4-Piz | 4-FPh | CO | single bond | 2 | O | CH₂CH₂ | sub. 33 |
| 5188 | 2-Aze | 4-FPh | CO | single bond | 2 | O | CH₂CH₂ | sub. 33 |
| 5189 | 3-Aze | 4-FPh | CO | single bond | 2 | O | CH₂CH₂ | sub. 33 |
| 5190 | 4-Aze | 4-FPh | CO | single bond | 2 | O | CH₂CH₂ | sub. 33 |
| 5191 | cPr | 4-FPh | CO | single bond | 2 | O | CH₂CH₂ | sub. 34 |
| 5192 | cBu | 4-FPh | CO | single bond | 2 | O | CH₂CH₂ | sub. 34 |
| 5193 | cPn | 4-FPh | CO | single bond | 2 | O | CH₂CH₂ | sub. 34 |
| 5194 | cHex | 4-FPh | CO | single bond | 2 | O | CH₂CH₂ | sub. 34 |
| 5195 | cHep | 4-FPh | CO | single bond | 2 | O | CH₂CH₂ | sub. 34 |
| 5196 | 2-Pyrd | 4-FPh | CO | single bond | 2 | O | CH₂CH₂ | sub. 34 |
| 5197 | 3-Pyrd | 4-FPh | CO | single bond | 2 | O | CH₂CH₂ | sub. 34 |
| 5198 | 4-Oxa | 4-FPh | CO | single bond | 2 | O | CH₂CH₂ | sub. 34 |
| 5199 | 5-Oxa | 4-FPh | CO | single bond | 2 | O | CH₂CH₂ | sub. 34 |
| 5200 | 4-Thi | 4-FPh | CO | single bond | 2 | O | CH₂CH₂ | sub. 34 |
| 5201 | 5-Thi | 4-FPh | CO | single bond | 2 | O | CH₂CH₂ | sub. 34 |
| 5202 | 4-OOxa | 4-FPh | CO | single bond | 2 | O | CH₂CH₂ | sub. 34 |
| 5203 | 5-OOxa | 4-FPh | CO | single bond | 2 | O | CH₂CH₂ | sub. 34 |
| 5204 | 4-OThi | 4-FPh | CO | single bond | 2 | O | CH₂CH₂ | sub. 34 |
| 5205 | 5-OThi | 4-FPh | CO | single bond | 2 | O | CH₂CH₂ | sub. 34 |
| 5206 | 2-Pip | 4-FPh | CO | single bond | 2 | O | CH₂CH₂ | sub. 34 |
| 5207 | 3-Pip | 4-FPh | CO | single bond | 2 | O | CH₂CH₂ | sub. 34 |
| 5208 | 4-Pip | 4-FPh | CO | single bond | 2 | O | CH₂CH₂ | sub. 34 |
| 5209 | 2-Mor | 4-FPh | CO | single bond | 2 | O | CH₂CH₂ | sub. 34 |
| 5210 | 3-Mor | 4-FPh | CO | single bond | 2 | O | CH₂CH₂ | sub. 34 |
| 5211 | 4-Mor | 4-FPh | CO | single bond | 2 | O | CH₂CH₂ | sub. 34 |
| 5212 | 2-Thmor | 4-FPh | CO | single bond | 2 | O | CH₂CH₂ | sub. 34 |
| 5213 | 3-Thmor | 4-FPh | CO | single bond | 2 | O | CH₂CH₂ | sub. 34 |
| 5214 | 4-Thmor | 4-FPh | CO | single bond | 2 | O | CH₂CH₂ | sub. 34 |
| 5215 | 2-Piz | 4-FPh | CO | single bond | 2 | O | CH₂CH₂ | sub. 34 |
| 5216 | 3-Piz | 4-FPh | CO | single bond | 2 | O | CH₂CH₂ | sub. 34 |
| 5217 | 4-Piz | 4-FPh | CO | single bond | 2 | O | CH₂CH₂ | sub. 34 |
| 5218 | 2-Aze | 4-FPh | CO | single bond | 2 | O | CH₂CH₂ | sub. 34 |
| 5219 | 3-Aze | 4-FPh | CO | single bond | 2 | O | CH₂CH₂ | sub. 34 |
| 5220 | 4-Aze | 4-FPh | CO | single bond | 2 | O | CH₂CH₂ | sub. 34 |
| 5221 | cPr | 4-FPh | CO | single bond | 2 | O | CH₂CH₂ | sub. 35 |
| 5222 | cBu | 4-FPh | CO | single bond | 2 | O | CH₂CH₂ | sub. 35 |
| 5223 | cPn | 4-FPh | CO | single bond | 2 | O | CH₂CH₂ | sub. 35 |
| 5224 | cHex | 4-FPh | CO | single bond | 2 | O | CH₂CH₂ | sub. 35 |

TABLE 1-continued

| Exemplification compound number | R$^1$ | R$^2$ | A | B | N | D | G | Q |
|---|---|---|---|---|---|---|---|---|
| 5225 | cHep | 4-FPh | CO | single bond | 2 | O | CH$_2$CH$_2$ | sub. 35 |
| 5226 | 2-Pyrd | 4-FPh | CO | single bond | 2 | O | CH$_2$CH$_2$ | sub. 35 |
| 5227 | 3-Pyrd | 4-FPh | CO | single bond | 2 | O | CH$_2$CH$_2$ | sub. 35 |
| 5228 | 4-Oxa | 4-FPh | CO | single bond | 2 | O | CH$_2$CH$_2$ | sub. 35 |
| 5229 | 5-Oxa | 4-FPh | CO | single bond | 2 | O | CH$_2$CH$_2$ | sub. 35 |
| 5230 | 4-Thi | 4-FPh | CO | single bond | 2 | O | CH$_2$CH$_2$ | sub. 35 |
| 5231 | 5-Thi | 4-FPh | CO | single bond | 2 | O | CH$_2$CH$_2$ | sub. 35 |
| 5232 | 4-OOxa | 4-FPh | CO | single bond | 2 | O | CH$_2$CH$_2$ | sub. 35 |
| 5233 | 5-OOxa | 4-FPh | CO | single bond | 2 | O | CH$_2$CH$_2$ | sub. 35 |
| 5234 | 4-OThi | 4-FPh | CO | single bond | 2 | O | CH$_2$CH$_2$ | sub. 35 |
| 5235 | 5-OThi | 4-FPh | CO | single bond | 2 | O | CH$_2$CH$_2$ | sub. 35 |
| 5236 | 2-Pip | 4-FPh | CO | single bond | 2 | O | CH$_2$CH$_2$ | sub. 35 |
| 5237 | 3-Pip | 4-FPh | CO | single bond | 2 | O | CH$_2$CH$_2$ | sub. 35 |
| 5238 | 4-Pip | 4-FPh | CO | single bond | 2 | O | CH$_2$CH$_2$ | sub. 35 |
| 5239 | 2-Mor | 4-FPh | CO | single bond | 2 | O | CH$_2$CH$_2$ | sub. 35 |
| 5240 | 3-Mor | 4-FPh | CO | single bond | 2 | O | CH$_2$CH$_2$ | sub. 35 |
| 5241 | 4-Mor | 4-FPh | CO | single bond | 2 | O | CH$_2$CH$_2$ | sub. 35 |
| 5242 | 2-Thmor | 4-FPh | CO | single bond | 2 | O | CH$_2$CH$_2$ | sub. 35 |
| 5243 | 3-Thmor | 4-FPh | CO | single bond | 2 | O | CH$_2$CH$_2$ | sub. 35 |
| 5244 | 4-Thmor | 4-FPh | CO | single bond | 2 | O | CH$_2$CH$_2$ | sub. 35 |
| 5245 | 2-Piz | 4-FPh | CO | single bond | 2 | O | CH$_2$CH$_2$ | sub. 35 |
| 5246 | 3-Piz | 4-FPh | CO | single bond | 2 | O | CH$_2$CH$_2$ | sub. 35 |
| 5247 | 4-Piz | 4-FPh | CO | single bond | 2 | O | CH$_2$CH$_2$ | sub. 35 |
| 5248 | 2-Aze | 4-FPh | CO | single bond | 2 | O | CH$_2$CH$_2$ | sub. 35 |
| 5249 | 3-Aze | 4-FPh | CO | single bond | 2 | O | CH$_2$CH$_2$ | sub. 35 |
| 5250 | 4-Aze | 4-FPh | CO | single bond | 2 | O | CH$_2$CH$_2$ | sub. 35 |

Among the compounds listed above, preferred compounds are compounds of exemplification compound number 1 to 180,631 to 1230, 1681 to 2100, 3151 to 3330 and 3781 to 4200. More preferred compounds are compounds of exemplification compound number 1051 to 1230, 1681 to 2100, and 3871 to 3874. Most preferred compounds are compounds of exemplification compound number 1051 to 1054, 1081 to 1084, 1111 to 1114, 1141 to 1144, 1171 to 1174, 1201 to 1204, 1171 to 1174, 1921 to 1924, 1951 to 1954, and 3871 to 3874.

The present invention is explained below by Reference example.

Reference Example

Reference Example 1

2-[(2R)-(3,4-dichlorophenyl)morpholin-2-yl]ethanol

Adioxane solution of hydrogen chloride (4N, 500 ml) containing 2-[4-tert-butoxycarbonyl-(2R)-(3,4-dichlorophenyl)morpholin-2-yl]ethanol tert-butydimethylsilyl ether (38.6 g, 78.7 mmol) was stirred at 60° C. for 3 hours. The solvent was distilled off under reduced pressure. The residue was dissolved in 1N hydrochloric acid, and this was washed with diethyl ether. The water layer was made alkaline with a 2N aqueous solution of sodium hydroxide and then extracted with methylene chloride. After the organic layer was washed with a saturated aqueous solution of sodium chloride, it was dried over anhydrous magnesium sulfate and the solvent was distilled off under reduced pressure. The residue was recrystalized from a mixture of n-hexane (210 ml) and ethyl acetate (175 ml) to give the title compound (18.0 g, 83%) as a white crystalline solid.

Melting point: 90–91 ° C.

$[\alpha]_D^{24}$+19.2° C. (c=0.51, Methanol)

Infrared spectrum ν max cm$^{-1}$(KBr): 3261, 3098, 2940, 1471, 1085, 1047.

Mass spectrometric analysis (EI) m/z: 275(M$^+$).

Formulation Example

Formulation Example 1 Powders

Powders can be obtained by mixing the compound of Example 1 (5 g), lactose (895 g) and corn starch (100 g) in a blender.

Formulation Example 2 Granules

Granules can be prepered by mixing the compound of Example 2 (5 g), lactose (865 g) and low-substituted hydroxypropylcellulose (100 g), adding 300 g of a 10% aqueous solution of hydroxypropylcellulose to the mixture, kneading the mixture, granulating the kneaded mass using an extrusion granulator and then drying the granulated product.

Formulation Example 3 Capsules

Capsules can be obtained by mixing the compound of example 3(5 g), lactose (115 g), corn starch (58 g) and magnesium stearate (2 g) in a V-shaped mixer and then filling the resulting mixture, in 180 mg portions, into No. 3 capsules.

Formulation Example 4 Tablets

Tablets can be obtained by mixing the compound of example 4 (5 g), lactose (90 g), corn starch (34 g), crystalline cellulose (20 g) and magnesium stearate (1 g) in a blender and then tableting the resulting mixture using a tableting machine.

Test Example

Text Example 1 NK$_1$ Receptor Binding Test (a) Preparation of crude lung membrane fraction Crude membrane fraction was prepared from the lungs of male Hartley guinea pigs. Namely, the guinea pigs were bled from the cava abdominalis under chloroform anaesthesia and pulmonary airway tissue was extracted immediately.

The extracted lungs were perfused with a buffer (1) (5OmM Tris-HCl, pH 7.4), thinly cut in the buffer, and then homogenized in a buffer (2) [buffer (1) containing 120 mM sodium chloride and 5 mM potassium chloride] using a Polytron homogenizer.

The tissue mass was removed from the homogenate by filtration with a nylon mesh (50 μm) and the supernatant was centrifuged (30,000×g, 30 minutes, 4° C.).

The resultant pellet was resuspended in an ice-cooled buffer (3) [buffer (1) containing 10 mM EDTA and 300 mM potassium chloride), allowed to stand at 4° C. for 60 minutes and then washed centrifugally twice (30,000×g, 15 minutes, 4° C.).

The crude membrane fraction was preserved at −80° C. before use.

(b) Receptor Binding Test

To a mixed solution (250 μl) of the test compound and [$^3$H]-Substance P (final concentration: 1 nM) (50 mM Tris-HCl, pH 7.4, 6 mM manganese chloride, 800 μg/ml BSA, 8 μg/ml chymostatin, 8 μg/ml leupeptin, 80 μg/ml bacitracin. 20 μg/ml phosphoramidon) was added the crude lung membrane fraction solution (250 μl), followed by incubation at room temperature for 30 minutes.

After the reaction, a membrane ingredient was recovered on a GF/B glass fiber filter (Whatman Co.) using an automatic filtering device (Brandel Co.).

The glass filter was used after being pre-treated with a 0.1% polyethyleneimine solution for about 4 hours so as to inhibit non-specific binding as much as possible.

The membrane ingredient-recovered filter was transferred to a mini-plastic vial containing a pico flow (4 ml) and the radioactivity was measured using a liquid scintillation counter (Beckman Co., LSC3500) to determine the 50% binding drug concentration ($IC_{50}$).

The $IC_{50}$ values of the compounds of the present invention were 1000 ng/ml or more.

Test Example 2 $NK_2$ Receptor Binding Test (a) Preparation of crude ileum membrane fraction A crude membrane fraction was prepared from the ileum of male Hartley guinea pigs. Namely, the guinea pigs were bled from the cava abdominalis under chloroform anaesthesia and the ileum was extracted immediately.

After the contents secreta and epithelium of the ilium had been scraped off using a glass slide, the extracted ileum was thinly cut in a buffer (1) (50 mM Tris-HCl, pH 7.4) and then homogenized in a buffer (2) [buffer (1) containing 120 mM sodium chloride and 5 mM potassium chloride] using a Polytron homogenizer.

The tissue mass was removed from the homogenate by filtration with a nylon mesh (50 μm) and the supernatant was centrifuged (30,000×g, 30 minutes, 4° C.).

The resultant pellet was resuspended in an ice-cooled buffer (3) [buffer (1) containing 10 mM EDTA and 300 mM potassium chloride], allowed to stand at 4° C. for 60 minutes and then washed centrifugally twice (30,000×g, 15 minutes, 4° C.).

The crude membrane fraction was preserved at −80° C. before use.

(b) Receptor Binding Test

To a mixed solution (250 μl) of the test compound and [$^3$H]-SR.-48968 (Amasham Co., final concentration: 1 nM) (50 mM Tris-HCl, pH 7.4; 6 mM manganese chloride, 800 μg/ml BSA, 8 μg/ml chymostatin, 8 μg/ml leupeptin, 80 μg/ml bacitracin, 20 μg/ml phosphoramidon) was added the crude ileum membrane fraction solution (250 μl), followed by incubation at room temperature for 30 minutes.

After the reaction, a membrane ingredient was recovered on a GF/B glass fiber filter (Whatman Co.) using an automatic filtering device (Brandel Co.).

The glass filter was used after pretreatment with a 10% of polyethyleneimine solution for about 4 hours so as to inhibit non-specific binding as much as possible.

The membrane ingredient-recovered filter was transferred to a mini-plastic vial containing a pico flow (4 ml) and the radioactivity was measured using a liquid scintillation counter (Beckman Co., LSC3500) to determine the 50% binding drug concentration ($IC_{50}$).

TABLE 2

Results of $NK_2$ Receptor Binding Test

| Test Compound | $IC_{50}$ (ng/ml) |
|---|---|
| Compound of Example 1 | 0.94 |
| Compound of Example 2 | 0.76 |
| Compound of Example 3 | 0.91 |

As is shown in Table 2 the compounds of the present invention demonstrated potent $NK_2$ receptor binding activity.

The compound of present invention has excellent $NK_2$-selective antagonistic action and has low toxicity, and thus it is useful as a medicament. For example, it is useful as a preventive and therapeutic agent for diseases of the central nervous system such as anxiety, depression, psychosis and schizophrenia; neurodegenerative diseases such as dementia of AIDS, Alzheimer's senile dementia, Alzheimer's disease, Down's syndrome, demyelinating disease, amyotrophic lateral sclerosis, neuropathy, peripheral neuropathy and neuralgia; respiratory diseases such as chronic obstructive pulmonary disease, bronchitis, pneumonia, bronchoconstriction, asthma and coughs; inflammatory diseases such as inflammatory bowel disease (IBD), psoriasis, fibrosis, arthrosteitis, degenerative arthritis and rheumatoid arthritis; eczema; allergic diseases such as rhinitis; hypersensitivity diseases such as hypersensitivity to vines; ophthalmological diseases such as conjunctivitis, vernal conjunctivitis, vernal cetarrh, destruction of the blood-aqueous humor barrier caused by various inflammatory eye diseases, elevated intraocular pressure and miosis; skin diseases such as contact dermatitis, atopic dermatitis, urticaria and other eczematoid dermatitis; addictions such as alcohol dependency; somatic diseases caused by stress; sympathetic reflex dystrophy such as hand and shoulder syndrome; dysthymia; undesirable immune reactions such as rejection of grafts, diseases relating to immunopotentiation such as systemic lupus erythematosus or immunosuppression; digestive diseases such as diseases caused by abnormalities in nerves regulating the organs, colitis, ulcerative colitis and Crohn's disease; emesis such as emesis induced by adverse effects of X-ray irradiation and chemotherapy, poisons, toxins, pregnancy, vestibular disorders, postoperative illness, gastrointestinal occlusion, reduced gastrointestinal movement, visceral pain, migraine headaches, increased intracranial pressure, reduced intracranial pressure or adverse reactions induced by administration of various medicaments; urinary bladder functional diseases such as cystitis and urinary incontinence, eosinophilia caused by collagen diseases, scleriasis or Fasciola hepatica infection; diseases caused by abnormal blood flow due to vasodilation or vasoconstriction such as angina pectoris, migraine headaches and Reynauds's disease; and pain of pain nociceptive reception such as migraine headaches, headaches and toothache; and sleep apnea.

What is claimed is:
1. A compound of formula (I)

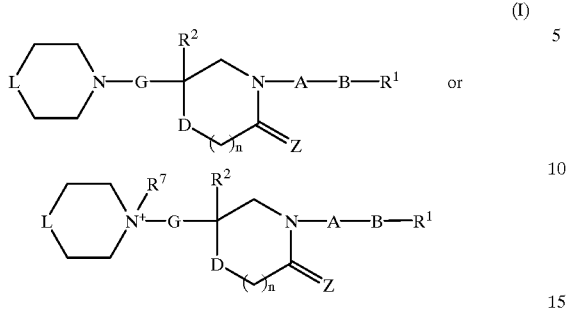

wherein:
- $R^1$ is selected from the group consisting of $(C_3-C_7)$ cycloalkyl groups which may optionally be substituted with 1 to 3 substituents selected from Substituent group A defined below and Substituent group B defined below, said $(C_3-C_7)$cycloalkyl groups further optionally being fused with an aryl ring defined below which may optionally be substituted with 1 to 3 substituents selected from Substituent group A defined below or a heteroaryl ring defined below which may optionally be substituted with 1 to 3 substituents selected from Substituent group A defined below, and 3- to 7-membered saturated heterocyclic groups defined below which may optionally be substituted with 1 or 2 substituents selected from Substituent group A defined below and Substituent group B defined below, said 5- to 7-membered saturated heterocyclic group further optionally being fused with an aryl ring defined below which may optionally be substituted with 1 to 3 substituents selected from Substituent group A defined below or a heteroaryl ring defined below which may optionally be substituted with 1 to 3 substituents selected from Substituent group A defined below;
- $R^2$ is selected from the group consisting of aryl groups defined below which may optionally be substituted with 1 to 3 substituents selected from Substituent group A defined below, or heteroaryl groups defined below which may optionally be substituted with 1 to 3 substituents selected from Substituent group A defined below;
- A is selected from the group consisting of methylene groups, carbonyl groups and sulfonyl groups;
- B is selected from the group consisting of single bonds, $(C_1-C_4)$alkylene groups and $(C_2-C_4)$alkenylene groups;
- D is selected from the group consisting of oxygen atoms and sulfur atoms;
- G is selected from the group consisting of $(C_1-C_4)$ alkylene groups and $(C_2-C_4)$alkenylene groups;
- L is selected from the group consisting of groups of formula —N($R^3$)— and groups of formula —C($R^4$)($R^5$)—, wherein
  - $R^3$ is selected from the group consisting of aryl groups defined below which may optionally be substituted with 1 to 3 substituents selected from Substituent group A defined below, and heteroaryl groups defined below which may optionally be substituted with 1 to 3 substituents selected from Substituent group A defined below,
  - $R^4$ is selected from the group consisting of hydrogen atoms, aryl groups defined below which may optionally be substituted with 1 to 3 substituents selected from Substituent group A defined below, heteroaryl groups defined below which may optionally be substituted with 1 to 3 substituents selected from Substituent group A defined below, $(C_3-C_7)$cycloalkyl groups which may optionally be substituted with 1 to 3 substituents selected from Substituent group A defined below and Substituent group B defined below, said $(C_3-C_7)$cycloalkyl groups further optionally being fused with an aryl ring defined below which may optionally be substituted with 1 to 3 substituents selected from Substituent group A defined below or a heteroaryl ring defined below which may optionally be substituted with 1 to 3 substituents selected from Substituent group A defined below, and 3- to 7-membered saturated heterocyclic groups which may optionally be substituted with 1 to 3 substituents selected from Substituent group A defined below and Substituent group B defined below, said 5- to 7-membered saturated heterocyclic groups further optionally being fused with an aryl ring defined below which may optionally be substituted with 1 to 3 substituents selected from Substituent group A defined below or a heteroaryl ring defined below which may optionally be substituted with 1 to 3 substituents selected from Substituent group A defined below,
  - $R^5$ is selected from the group consisting of lower alkyl groups defined below, amino groups, acylamino groups defined below wherein the nitrogen atom of said acylamino groups may optionally be substituted with a lower alkyl group defined below, acylamino lower alkyl groups comprising a lower alkyl moiety as defined below which is substituted with an acylamino group defined above, hydroxy groups, hydroxy lower alkyl groups wherein the lower alkyl moiety is as defined below and the oxygen atom is optionally substituted with an aralkyl group defined below, lower alkoxy groups defined below, and groups of formula —CO—$R^6$ (wherein $R^6$ is selected from the group consisting of lower alkyl groups defined below, lower alkoxy groups defined below, amine residues defined below, aryl groups defined below which are substituted with 1 to 3 substituents selected from Substituent group A defined below, and heteroaryl groups defined below which are substituted with 1 to 3 substituents selected from Substituent group A defined below), or $R^4$ and $R^5$, together with the carbon atom to which they are attached, form a ring selected from the group consisting of $(C_5-C_8)$cycloalkane rings, $(C_5-C_8)$cycloalkene rings and 5- to 8-membered saturated heterocyclic rings defined below (each of said cycloalkane, cycloalkene and heterocyclic rings may optionally be substituted with 1 or 2 substituents selected from Substituent group A defined below and Substituent group B defined below, and said rings may also be optionally fused with an aryl ring defined below which may optionally be substituted with 1 to 3 substituents selected from Substituent group A defined below or a heteroaryl ring which may optionally be substituted with 1 to 3 substituents selected from Substituent group A defined below);
- $R^7$ represents a lower alkyl group defined below;
- Z represents two hydrogen atoms or an oxygen atom; and
- n represents 0, 1 or 2;

or a pharmaceutically acceptable salt, or ester thereof;

Substituent group A comprises halogen atoms, lower alkyl groups defined below, halogeno lower alkyl groups comprising a lower alkyl group defined below substituted with one or more halogen atoms, lower alkoxy groups defined below, lower alkoxycarbonyl groups comprising a carbonyl group substituted with an alkoxy group defined below, carboxyl groups, hydroxy groups, lower aliphatic acyl groups defined below, lower aliphatic acylamino groups comprising an amino group substituted by a lower aliphatic acyl group defined above, amino groups, and cyano groups;

Substituent group B comprises oxo groups and thiol groups, and as substituents on a nitrogen atom present in said 3- to 7-membered saturated heterocyclic groups in the definitions of substituents $R^1$ and $R^4$, lower alkyl groups defined below, aryl groups defined below and aralkyl groups defined below, in which said alkyl, aryl and aralkyl groups may optionally be substituted with a substituent selected from Substituent group A defined above, lower alkanesulfonyl groups comprising a sulfonyl group which is substituted with a lower alkyl group defined below and acyl groups defined below;

said 3- to 7- membered saturated heterocyclic groups referred to in the definition of substituents $R^1$ and $R^4$ are 3- to 7-membered non-aromatic heterocyclic groups containing 1 to 3 sulfur, oxygen and/or nitrogen atoms;

said aryl groups referred to in the definition of substituents $R^2$, $R^3$, $R^4$ and $R^6$ and in the definition of Substituent group B are ($C_5$–$C_{14}$) aromatic hydrocarbon groups which may optionally be fused with a ($C_3$–$C_{10}$) cycloalkyl group;

said heteroaryl groups referred to in the definition of substituents $R^2$, $R^3$, $R^4$ and $R^6$ are 5- to 7-membered heteroaryl groups containing 1 to 3 oxygen, sulfur and/or nitrogen atoms which may optionally be fused with another ring system;

said lower alkyl groups referred to in the definition of substituents $R^5$, $R^6$, and $R^7$, in the definition of Substituent groups A and, as the lower alkyl moieties of said acylamino lower alkyl groups and hydroxy lower alkyl groups in the definition of $R^5$, as the optional lower alkyl substituent on the nitrogen atom of said acylamino groups in the definition of substituent $R^5$, and as the lower alkyl moiety of said lower alkanesulfonyl groups in the definition of Substituent group B are straight or branched ($C_1$–$C_6$)alkyl groups;

said aryl rings which may optionally be fused with said optionally substituted ($C_3$–$C_7$)cycloalkyl groups and said optionally substituted 3- to 7-membered saturated heterocyclic groups in the definition of substituents $R^1$ and $R^4$ and with said optionally substituted ($C_5$–$C_8$) cycloalkane rings, ($C_5$–$C_8$)cycloalkene rings and 5- to 8-membered saturated heterocyclic rings in the definition of the rings obtainable by the combination of substituents $R^4$ and $R^5$ and the carbon atom to which they are attached are $C_6$–$C_{14}$ aromatic hydrocarbon rings;

said heteroaryl rings which may optionally be fused with said optionally substituted ($C_3$–$C_7$)cycloalkyl groups and said optionally substituted 3- to 7-membered saturated heterocyclic groups in definition of substituents $R^1$ and $R^4$ and with said optionally substituted ($C_5$–$C_8$) cycloalkane rings, ($C_5$–$C_8$)cycloalkene rings and 5- to 8-membered saturated heterocyclic rings in the definition of the rings obtainable by the combination of substituents $R^4$ and $R^5$ and the carbon atom to which they are attached are 5- to 7-membered heteroaryl rings containing 1 to 3 sulfur, oxygen and/or nitrogen atoms;

said acyl groups referred to in the definition of Substituent group B and the acyl moieties of said optionally substituted acylamino groups and said acylamino lower alkyl groups in the definition of substituent $R^5$ are selected from the group consisting of alkylcarbonyl groups, halogenated alkylcarbonyl groups, lower alkoxyalkylcarbonyl groups, unsaturated alkylcarbonyl groups, arylcarbonyl groups, halogenated arylcarbonyl groups, lower alkylated arylcarbonyl groups, nitrated arylcarbonyl groups, lower alkoxycarbonylated aryl carbonyl groups, lower alkoxycarbonyl groups, lower alkoxycarbonyl groups which are substituted with halogen atoms or a tri(lower alkyl)silyl group, akenylcarbonyl groups, aralkylcarbonyl groups in which the aryl moiety may optionally be substituted with 1 or 2 lower alkoxy or nitro groups, lower alkanesulfonyl groups, fluorinated lower alkanesulfonyl groups and arylsulfonyl groups;

said aralkyl groups referred to in the definition of Substituent group B and as the optional substituent on the oxygen atom of said hydroxy lower alkyl group in the definition of substituent $R^5$ consist of a lower alkyl group as defined above which is substituted with an aryl group as defined above;

said lower alkoxy groups referred to in the definition of substituents $R^5$ and $R^6$ and Substituent group A and as the alkoxy moiety of the lower alkoxycarbonyl groups in the definition of Substituent group A are lower alkyl groups as defined above which are attached to an oxygen atom;

said 5- to 8-membered saturated heterocyclic rings referred to in the definition of said rings obtainable by the combination of substituents $R^4$ and $R^5$ and the carbon atom to which they are attached are 5- to 8-membered saturated heterocyclic rings containing 1 to 3 sulfur, oxygen and/or nitrogen atoms;

said lower aliphatic acyl groups referred to in the definition of Substituent group A and as the lower aliphatic acyl moiety of said lower aliphatic acylamino groups in the definition of said Substituent group A defined above are $C_2$–$C_7$ lower aliphatic acyl groups;

said halogeno lower alkyl groups referred to in the definition of Substituent group A are lower alkyl groups as defined above which are substituted by 1 or more halogen atoms; and said amine residues referred to in the definition of substituent $R^6$ are selected from the group consisting of amino groups, amino groups substituted with 1 or 2 lower alkyl groups as defined above, amino groups substituted with 1 or 2 ($C_5$–$C_7$) cycloalkyl groups, saturated cyclic amine residues, arylamino groups which may optionally be substituted on the nitrogen atom thereof with a lower alkyl group as defined above, aralkylamino which may optionally be substituted on the nitrogen atom thereof with a lower alkyl group as defined above, and heteroarylamino groups which may optionally be substituted on the nitrogen atom thereof with a lower alkyl group as defined above.

2. A compound as defined in claim 1, wherein $R^1$ is selected from the group consisting of ($C_3$–$C_6$)cycloalkyl groups, 5- or 6-membered saturated heterocyclic groups, ($C_3$–$C_6$)cycloalkyl groups substituted with 1 to 3 substituents selected from Substituent group A and Substituent group B, and 5- or 6-membered saturated heterocyclic groups substituted with 1 or 2 substituents selected from Substituent group A and Substituent group B, or a pharmaceutically acceptable salt or ester thereof.

3. A compound as defined in claim 1, wherein $R^1$ is selected from the group consisting of $(C_3-C_6)$cycloalkyl groups, 5- or 6-membered saturated heterocyclic groups and 5- or 6-membered saturated heterocyclic groups substituted with 1 or 2 substituents selected from Substituent group A and Substituent group B, or a pharmaceutically acceptable salt or ester thereof.

4. A compound as defined in claim 1, wherein $R^2$ is selected from the group consisting of aryl groups and aryl groups substituted with 1 to 3 substituents selected from Substituent group A, or a pharmaceutically acceptable salt or ester thereof.

5. A compound as defined in claim 1, wherein $R^2$ is an aryl group substituted with 1 to 3 halogen atoms, or a pharmaceutically acceptable salt or ester thereof.

6. A compound as defined in claim 1, wherein A is selected from the group consisting of methylene groups and carbonyl groups, or a pharmaceutically acceptable salt or ester thereof.

7. A compound as defined in claim 1, wherein A is a carbonyl group and Z is two hydrogen atoms; or A is a methylene group and Z is an oxygen atom, or a pharmaceutically acceptable salt or ester thereof.

8. A compound as defined in claim 1, wherein A is a carbonyl group, or a pharmaceutically acceptable salt or ester thereof.

9. A compound as defined in claim 1, wherein B is a single bond, or a pharmaceutically acceptable salt or ester thereof.

10. A compound as defined in claim 1, wherein D is an oxygen n a tom, or a pharmaceutically acceptable salt or ester thereof.

11. A compound as defined in claim 1, wherein G is a $(C_1-C_4)$alkylene group, or a pharmaceutically acceptable salt or ester thereof.

12. A compound as defined in claim 1, wherein G is a $(C_2-C_3)$alkylene group, or a pharmaceutically acceptable salt or ester thereof.

13. A compound as defined in claim 1, wherein $R^3$ is selected from the group consisting of beteroaryl group a and aryl groups substituted with 1 to 3substituents selected from Substituent group A, or a pharmaceutically acceptable salt or ester thereof.

14. A compound as defined in claim 1, wherein L is a group of formula —C($R^4$)($R^5$)—, or a pharmaceutically acceptable salt or ester thereof.

15. A compound as defined in claim 1, wherein $R^4$ and $R^5$, together with the carbon atom to which they are attached, form a ring selected from the group consisting of $(C_5-C_8)$cycloalkane rings, $(C_5-C_8)$cycloalkene rings and 5- to 8-membered saturated heterocyclic rings (each of said cycloalkane, cycloalkene and saturated heterocyclic rings may be optionally substituted with 1 or 2 substituents selected from Substituent group A and Substituent group B, and said rings may also be optionally fused with a ring selected from the group consisting of aryl rings, heteroaryl rings, aryl rings substituted with 1 to 3 substituents selected from Substituent group A and heteroaryl rings substituted with 1 to 3 substituents selected from Substituent group A), or a pharmaceutically acceptable salt or ester thereof.

16. A compound as defined in claim 1, wherein $R^4$ and $R^5$, together with the carbon atom to which they are attached, form a ring selected from the group consisting of $(C_5-C_6)$cycloalkane rings, $(C_5-C_6)$cycloalkene rings and 5- or 6-membered saturated heterocyclic rings (each of said cycloalkane, cycloalkene and saturated heterocyclic rings may be optionally substituted with 1 or 2 substituents selected from Substituent group A and Substituent group B, and said rings may also be optionally fused with a ring selected from the group consisting of aryl rings, heteroaryl rings, aryl rings substituted with 1 to 3 substituents selected from Substituent group A and heteroaryl rings substituted with 1 to 3 substituents selected from Substituent group A), or a pharmaceutically acceptable salt or ester thereof.

17. A compound as defined in claim 1, wherein $R^4$ and $R^5$, together with the carbon atom to which they are attached, form a ring selected from the group consisting of a cyclopentane ring, a cyclopentene ring, a tetrahydrothiophene ring, a tetrahydrothiophenesulfoxide ring, a tetrahydrothiophenesulfone ring and a piperidine ring (each of said rings may be optionally substituted with 1 or 2 substituents selected from Substituent group A and Substituent group B, and said rings may also be optionally fused with a ring selected from the group consisting of aryl rings, heteroaryl rings, aryl rings substituted with 1 to 3 substituents selected from Substituent group A and heteroaryl rings substituted with 1 to 3 substituents selected from Substituent group A), or a pharmaceutically acceptable salt or ester thereof.

18. A compound as defined in claim 1, wherein z is two hydrogen atoms, or a pharmaceutically acceptable salt or ester thereof.

19. A compound as defined in claim 1, wherein n is 0 or 1, or a pharmaceutically acceptable salt or ester thereof.

20. A compound as defined in claim 1, wherein n is 1, or a pharmaceutically acceptable salt or ester thereof.

21. A compound as defined in claim 1, wherein:

$R^1$ is selected from the group consisting of $(C_3-C_6)$ cycloalkyl groups, 5- or 6-membered saturated heterocyclic groups, $(C_3-C_6)$cycloalkyl groups substituted with 1 to 3 substituents selected from Substituent group A and Substituent group B and 5- or 6-membered saturated heterocyclic groups substituted with 1 or 2 substituents selected from Substituent group A and Substituent group B;

$R^2$ is selected from the group consisting of aryl groups and aryl groups substituted with 1 to 3 substituents selected from Substituent group A;

A is a carbonyl group;

B is a single bond;

D is an oxygen atom;

G is a $(C_1-C_4)$alkylene group;

L is a group of formula —C($R^4$)($R^5$)—, wherein $R^4$ and $R^5$, together with the carbon atom to which they are attached, form a ring selected from the group consisting of $(C_5-C_8)$cycloalkane rings, $(C_5-C_8)$cycloalkene rings and 5- to 8-membered saturated heterocyclic rings (each of said cycloalkane, cycloalkene and saturated heterocyclic rings may be optionally substituted with 1 or 2 substituents selected from Substituent group A and Substituent group B, and said rings may also be optionally fused with a ring selected from the group consisting of aryl rings, heteroaryl rings, aryl rings substituted with 1 to 3 substituents selected from Substituent group A and heteroaryl rings substituted with 1 to 3 substituents selected from Substituent group A);

z is two hydrogen atoms; and n is 0 or 1;

or a pharmaceutically acceptable salt or ester thereof.

22. A compound as defined in claim 1, wherein:

$R^1$ is selected from the group consisting of $(C_3-C_6)$ cycloalkyl groups, 5- or 6-membered saturated heterocyclic groups and 5- or 6-membered saturated heterocyclic groups substituted with 1 or 2 substituents selected from Substituent group A and Substituent group B;

R² is an aryl group substituted with 1 to 3 halogen atoms;
A is a carbonyl group;
B is a single bond;
D is an oxygen atom;
G is a (C₂–C₃)alkylene group;
L is a group of formula —C(R⁴)(R⁵)—, wherein R⁴ and R⁵, together with the carbon atom to which they are attached, form a ring selected from the group consisting of (C₅–C₆)cycloalkane rings, (C₅–C₆)cycloalkene rings and 5- or 6-membered saturated heterocyclic rings (each of said cycloalkane, cycloalkene and saturated heterocyclic rings may be optionally substituted with 1 or 2 substituents selected from Substituent group A and Substituent group B, and said rings may also be optionally fused with a ring selected from the group consisting of aryl rings, heteroaryl rings, aryl rings substituted with 1 to 3 substituents selected from Substituent group A and heteroaryl rings substituted with 1 to 3 substituents selected from Substituent group A);
z is two hydrogen atoms; and
n is 0 or 1;
or a pharmaceutically acceptable salt or ester thereof.

23. A compound as defined in claim 1, wherein:
R¹ is selected from the group consisting of (C₃–C₆) cycloalkyl groups, 5- or 6-membered saturated heterocyclic groups and 5- or 6-membered saturated heterocyclic groups substituted with 1 or 2 substituents selected from Substituent group A and Substituent group B;
R² is an aryl group substituted with 1 to 3 halogen atoms;
A is a carbonyl group;
B is a single bond;
D is an oxygen atom;
G is a (C₂–C₃)alkylene group;
L is a group of formula —C(R⁴)(R⁵)—, wherein R⁴ and R⁵, together with the carbon atom to which they are attached, form a ring selected from the group consisting of a cyclopentane ring, a cyclopentene ring, a tetrahydrothiophene ring, a tetrahydrothiophenesulfoxide ring, a tetrahydrothiophenesulfone ring or a piperidine ring (each of said rings may be optionally substituted with 1 or 2 substituents selected from Substituent group A and Substituent group B, and said rings may also be optionally fused with a ring selected from the group consisting of aryl rings, heteroaryl rings, aryl rings substituted with 1 to 3 substituents selected from Substituent group A and heteroaryl rings substituted with 1 to 3 substituents selected from Substituent group A);
Z is two hydrogen atoms; and
n is 0 or 1;
or a pharmaceutically acceptable salt or ester thereof.

24. A compound according to claim 1, wherein the compound is selected from the group consisting of the following compounds, and the pharmaceutically acceptable salts or esters thereof:
1-{2-[(2R)-(3,4-dichlorophenyl)-4-(cyclopropanecarbonyl)morpholin-2-yl]ethyl}spiro[benzo[c]thiophene-1(3H),4'-piperidine]-(2S)-oxide,
1-{2-[(2R)-(3,4-dichlorophenyl)-4-(cyclobutanecarbonyl)morpholin-2-yl]ethyl}spiro[benzo[c]thiophene-1(3H),4'-piperidine]-(2S)-oxide,
1-{2-[(2R)-(3,4-dichlorophenyl)-4-(cyclopentanecarbonyl)morpholin-2-yl]ethyl}spiro[benzo[c]thiophene-1(3H),4'-piperidine]-(2S)-oxide,
1-{2-[(2R)-(3,4-dichlorophenyl)-4-(cyclohexanecarbonyl)morpholin-2-yl]ethyl}spiro[benzo[c]thiophene-1(3H),4'-piperidine]-(2S)-oxide,
1-{2-[(2R)-(3,4-difluorophenyl)-4-(cyclopropanecarbonyl)morpholin-2-yl]ethyl}spiro[benzo[c]thiophene-1(3H),4'-piperidine]-(2S)-oxide,
1-{2-[(2R)-(3,4-difluorophenyl)-4-(cyclobutanecarbonyl)morpholin-2-yl]ethyl}spiro[benzo[c]thiophene-1(3H),4'-piperidine]-(2S)-oxide,
1-{2-[(2R)-(3,4-difluorophenyl)-4-(cyclopentanecarbonyl)morpholin-2-yl]ethyl}spiro[benzo[c]thiophene-1(3H),4'-piperidine]-(2S)-oxide,
1-{2-[(2R)-(3,4-difluorophenyl)-4-(cyclohexanecarbonyl)morpholin-2-yl]ethyl}spiro[benzo[c]thiophene-1(3H),4'-piperidine]-(2S)-oxide,
1-{2-[(2R)-(3,4-dichlorophenyl)-4-(cyclopropanecarbonyl)morpholin-2-yl]ethyl}spiro[((2S)-hydroxy)indane-1,4'-piperidine],
1-{2-[(2R)-(3,4-dichlorophenyl)-4-(cyclobutanecarbonyl)morpholin-2-yl]ethyl}spiro[((2S)-hydroxy)indane-1,4'-piperidine],
1-{2-[(2R)-(3,4-dichlorophenyl)-4-(cyclopentanecarbonyl)morpholin-2-yl]ethyl}spiro[((2S)-hydroxy)indane-1,4'-piperidine],
1-{2-[(2R)-(3,4-dichlorophenyl)-4-(cyclohexanecarbonyl)morpholin-2-yl]ethyl}spiro[((2S)-hydroxy)indane-1,4'-piperidine],
1-{2-[(2R)-(3,4-difluorophenyl)-4-(cyclopropanecarbonyl)morpholin-2-yl]ethyl}spiro[((2S)-hydroxy)indane-1,4'-piperidine],
1-{2-[(2R)-(3,4-difluorophenyl)-4-(cyclobutanecarbonyl)morpholin-2-yl]ethyl}spiro[((2S)-hydroxy)indane-1,4'-piperidine],
1-{2-[(2R)-(3,4-difluorophenyl)-4-(cyclopentanecarbonyl)morpholin-2-yl]ethyl}spiro[((2S)-hydroxy)indane-1,4'-piperidine],
1-{2-[(2R)-(3,4-difluorophenyl)-4-(cyclohexanecarbonyl)morpholin-2-yl]ethyl}spiro[((2S)-hydroxy)indane-1,4'-piperidine],
1-{2-[(2R)-(3,4-dichlorophenyl)-4-(cyclopropanecarbonyl)morpholin-2-yl]ethyl}-4-phenylpiperidine-4-carboxamide, and
1-{2-[(2R)-(3,4-dichlorophenyl)-4-(cyclopentanecarbonyl)morpholin-2-yl]ethyl}-4-(2-pyridyl)piperidine-4-carboxamide.

25. A compound according to claim 24, wherein said compound is
1-{2-[(2R)-(3,4-dichlorophenyl)-4-(cyclopropanecarbonyl)morpholin-2-yl]ethyl}spiro[benzo[c]thiophene-1(3H),4'-piperidine]-(2S)-oxide.

26. A compound according to claim 24, wherein said compound is
1-{2-[(2R)-(3,4-dichlorophenyl)-4-(cyclobutanecarbonyl)morpholin-2-yl]ethyl}spiro[benzo[c]thiophene-1(3H),4'-piperidine]-(2S)-oxide.

27. A compound according to claim 24, wherein said compound is
1-{2-[(2R)-(3,4-dichlorophenyl)-4-(cyclopentanecarbonyl)morpholin-2-yl]ethyl}spiro[benzo[c]thiophene-1(3H),4'-piperidine]-(2S)-oxide.

28. A compound according to claim 24, wherein said compound is
1-{2-[(2R)-(3,4-dichlorophenyl)-4-(cyclohexanecarbonyl)morpholin-2-yl]ethyl}spiro[benzo[c]thiophene-1(3H),4'-piperidine]-(2S)-oxide.

29. A compound according to claim 24, wherein said compound is
1-{2-[(2R)-(3,4-difluorophenyl)-4-(cyclopropanecarbonyl)morpholin-2-yl]ethyl}spiro[benzo[c]thiophene-1(3H),4'-piperidine)-(2S)-oxide.

30. A compound according to claim 24, wherein said compound is
1-{2-[(2R)-(3,4-difluorophenyl)-4-(cyclobutanecarbonyl)morpholin-2-yl]ethyl}spiro[benzo[c]thiophene-1(3H),4'-piperidine]-(2S)-oxide.

31. A compound according to claim 24, wherein said compound is
1-{2-[(2R)-(3,4-difluorophenyl)-4-(cyclopentanecarbonyl)morpholin-2-yl]ethyl}spiro[benzo[c]thiophene-1(3H),4'-piperidine]-(2S)-oxide.

32. A compound according to claim 24, wherein said compound is
1-{2-[(2R)-(3,4-difluorophenyl)-4-(cyclohexanecarbonyl)morpholin-2-yl]ethyl}spiro[benzo[c]thiophene-1(3H),4'-piperidine]-(2S)-oxide.

33. A compound according to claim 24, wherein said compound is
1-{2-[(2R)-(3,4-dichlorophenyl)-4-(cyclopropanecarbonyl)morpholin-2-yl]ethyl}spiro[((2S)-hydroxy)indane-1,4'-piperidine].

34. A compound according to claim 24, wherein said compound is
1-{2-[(2R)-(3,4-dichlorophenyl)-4-(cyclobutanecarbonyl)morpholin-2-yl]ethyl}spiro[((2S)-hydroxy)indane-1,4'-piperidine].

35. A compound according to claim 24, wherein said compound is
1-{2-[(2R)-(3,4-dichlorophenyl)-4-(cyclopentanecarbonyl)morpholin-2-yl]ethyl}spiro[((2S)-hydroxy)indane-1,4'-piperidine].

36. A compound according to claim 24, wherein said compound is
1-{2-[(2R)-(3,4-dichlorophenyl)-4-(cyclohexanecarbonyl)morpholin-2-yl]ethyl}spiro[((2S)-hydroxy)indane-1,4'-piperidine].

37. A compound according to claim 24, wherein said compound is
1-{2-[(2R)-(3,4-difluorophenyl)-4-(cyclopropanecarbonyl)morpholin-2-yl]ethyl}spiro[((2S)-hydroxy)indane-1,4'-piperidine].

38. A compound according to claim 24, wherein said compound is
1-{2-[(2R)-(3,4-difluorophenyl)-4-(cyclobutanecarbonyl)morpholin-2-yl]ethyl}spiro[((2S)-hydroxy)indane-1,4'-piperidine].

39. A compound according to claim 24, wherein said compound is
1-{2-[(2R)-(3,4-difluorophenyl)-4-(cyclopentanecarbonyl)morpholin-2-yl]ethyl}spiro[((2S)-hydroxy)indane-1,4'-piperidine].

40. A compound according to claim 24, wherein said compound is
1-{2-[(2R)-(3,4-difluorophenyl)-4-(cyclohexanecarbonyl)morpholin-2-yl]ethyl}spiro[((2S)-hydroxy)indane-1,4'-piperidine].

41. A compound according to claim 24, where in said compound is
1-{2-[(2R)-(3,4-dichlorophenyl)-4-(cyclopropanecarbonyl)morpholin-2-yl]ethyl}-4-phenylpiperidine-4-carboxamide.

42. A compound according to claim 24, wherein said compound is
1-{2-[(2R)-(3,4-dichlorophenyl)-4-(cyclopentanecarbonyl)morpholin-2-yl]ethyl}-4-(2-pyridyl)piperidine-4-carboxamide.

43. A pharmaceutical composition comprising an effective amount of a pharmacologically active compound together with a carrier therefore, wherein said pharmacologically active compound is a compound of formula (I) according to claim 1 or a pharmaceutically acceptable salt or ester thereof.

44. A pharmaceutical composition comprising an effective amount of a pharmacologically active compound together with a carrier therefore, wherein said pharmacologically active compound is a compound of formula (I) according to claim 24 or a pharmaceutically acceptable salt or ester thereof.

45. A method for the prevention or treatment of asthma and/or bronchitis in a human, which comprises administering to said human an effective amount of a compound according to claim 1, or a pharmaceutically acceptable salt or ester thereof.

46. A method for the prevention or treatment of rhinitis in a human, which comprises administering to said human an effective amount of a compound according to claim 1, or a pharmaceutically acceptable salt or ester thereof.

47. A method for the prevention or treatment of allergic diseases in a human, which comprises administering to said human an effective amount of a compound according to claim 1, or a pharmaceutically acceptable salt or ester thereof.

48. A method for the prevention or treatment of urinary incontinence in a human, which comprises administering to said human an effective amount of a compound according to claim 1, or a pharmaceutically acceptable salt or ester thereof.

49. A method for the prevention or treatment of respiratory diseases in a human, which comprises administering to said human an effective amount of a compound according to claim 1, or a pharmaceutically acceptable salt or ester thereof.

50. A method for the prevention or treatment of diseases of the central nervous system in a human, which comprises administering to said human an effective amount of a compound according to claim 1, or a pharmaceutically acceptable salt or ester thereof.

51. A method for the prevention or treatment of inflammatory bowel disease in a human, which comprises administering to said human an effective amount of a compound according to claim 1, or a pharmaceutically acceptable salt or ester thereof.

52. A compound as defined in claim 1, wherein $R^1$ is a ($C_3$–$C_6$) cycloalkyl group;

$R^2$ is a phenyl group substituted with 1 to 3 halogen atoms;

A is a carbonyl group;

B is a single bond;

D is an oxygen atom;

G is a ($C_2$–$C_3$) alkylene group;

L is a group of the formula —C($R^4$) ($R^5$), wherein $R^4$ and $R^5$, together with the carbon ring to which they are attached, form a ring selected from the group consisting of

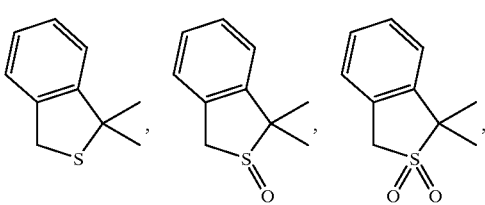
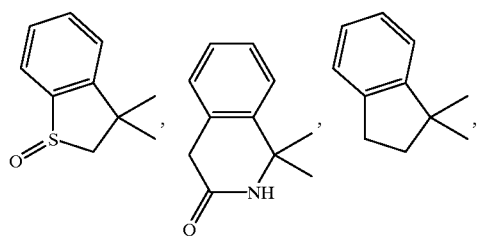
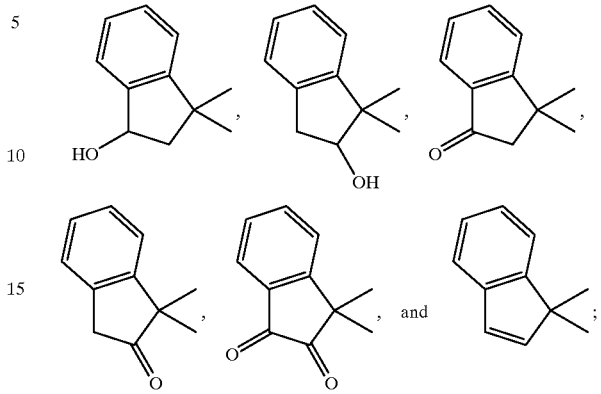
Z is two hydrogen atoms;
n is 0 or 1; and
a pharmaceutically acceptable salt, or ester thereof.
* * * * *